(12) United States Patent
Freskos et al.

(10) Patent No.: US 6,689,794 B2
(45) Date of Patent: Feb. 10, 2004

(54) AROMATIC SULFONE HYDROXAMATES AND THEIR USE AS PROTEASE INHIBITORS

(75) Inventors: John N. Freskos, Clayton, MO (US); Yvette M. Fobian, Wildwood, MO (US); Thomas E. Barta, Evanston, IL (US); Daniel P. Becker, Glenview, IL (US); Louis J. Bedell, Mt. Prospect, IL (US); Terri L. Boehm, Ballwin, MO (US); Jeffery N. Carroll, Columbia, IL (US); Gary A. DeCrescenzo, St. Charles, MO (US); Susan L. Hockerman, Chicago, IL (US); Darren J. Kassab, Wildwood, MO (US); Steve A. Kolodziej, Ballwin, MO (US); Joseph McDonald, Wildwood, MO (US); Deborah A. Mischke, Defiance, MO (US); Monica B. Norton, St. Louis, MO (US); Joseph G. Rico, Ballwin, MO (US); John J. Talley, Boston, MA (US); Clara I. Villamil, Glenview, IL (US); Lijuan Jane Wang, Wildwood, MO (US)

(73) Assignee: Pharmacia Corporation, St. Louis, MO (US)

(*) Notice: Subject to any disclaimer, the term of this patent is extended or adjusted under 35 U.S.C. 154(b) by 51 days.

(21) Appl. No.: 10/142,737

(22) Filed: May 10, 2002

(65) Prior Publication Data

US 2004/0010019 A1 Jan. 2, 2003

Related U.S. Application Data

(60) Provisional application No. 60/290,375, filed on May 11, 2001.

(51) Int. Cl.[7] ............... A61K 31/445; A61K 31/35; C07D 401/02
(52) U.S. Cl. ............... 514/318; 514/317; 514/321; 514/326; 514/336; 514/364; 514/365; 514/374; 514/376; 514/382; 514/389; 514/392; 514/422; 514/444; 546/187; 546/194; 546/197; 546/207; 546/209; 546/210; 546/211; 546/213; 546/282.1; 546/281.7; 548/131; 548/143; 548/204; 548/229; 548/236; 548/253; 548/311.1; 548/517; 549/60
(58) Field of Search ............... 546/281.7, 187, 546/194, 197, 207, 209, 210, 211, 213, 282.1; 514/317, 336, 318, 321, 326, 364, 365, 374, 376, 382, 369, 392, 422, 444; 548/131, 143, 204, 229, 236, 253, 311.1, 517; 549/60

(56) References Cited

U.S. PATENT DOCUMENTS

| | | | |
|---|---|---|---|
| 4,595,700 A | 6/1986 | Donald et al. | 514/616 |
| 5,932,595 A | 8/1999 | Bender et al. | 514/317 |
| 6,013,649 A | 1/2000 | Freskos et al. | 514/237.8 |
| 6,300,514 B1 | 10/2001 | Takahashi et al. | 560/17 |

FOREIGN PATENT DOCUMENTS

| | | | |
|---|---|---|---|
| EP | 0 266 182 | 5/1988 | C07D/307/32 |
| EP | 0 606 046 | 7/1994 | C07D/213/42 |
| EP | 0 780 386 | 6/1997 | C07D/309/08 |
| EP | 0 930 067 | 7/1999 | A61K/31/40 |
| EP | 1 081 137 | 3/2001 | C07D/211/96 |
| JP | 4-338331 | 11/1992 | A61K/31/365 |
| JP | WO 97/49679 | 12/1997 | C07C/317/44 |
| WO | WO 90/05719 | 5/1990 | C07C/323/62 |
| WO | WO 93/20047 | 10/1993 | C07C/317/44 |
| WO | WO 94/02466 | 2/1994 | C07D/221/14 |
| WO | WO 94/24140 | 10/1994 | C07H/13/04 |
| WO | WO 95/09841 | 4/1995 | C07C/323/60 |
| WO | WO 95/13289 | 5/1995 | C07K/5/062 |
| WO | WO 95/29892 | 11/1995 | C07D/207/327 |
| WO | WO 96/06074 | 2/1996 | C07C/259/06 |
| WO | WO 96/11209 | 4/1996 | C07K/5/06 |
| WO | WO 97/20824 | 6/1997 | C07D/241/04 |
| WO | WO 97/24117 | 7/1997 | A61K/31/19 |
| WO | WO 98/37877 | 9/1998 | A61K/31/16 |
| WO | WO 98/38163 | 9/1998 | C07C/323/60 |
| WO | WO 99/09000 | 2/1999 | C07C/235/00 |
| WO | WO 99/25687 | 5/1999 | C07D/211/66 |
| WO | WO 99/42436 | 8/1999 | C07C/239/14 |
| WO | WO 00/46221 | 8/2000 | C07D/405/12 |
| WO | WO 00/50396 | 8/2000 | C07D/211/66 |
| WO | WO 00/59874 | 10/2000 | C07C/259/06 |
| WO | WO 00/69821 | 11/2000 | C07D/211/66 |

OTHER PUBLICATIONS

Dack et al. "Preparation of N–hydroxytetrahydro . . . " CA 131:44740 (1999).

Denis et al., *Matrix metalloproteinase inhibitors: Present achievements and future prospects*, Invest, NEW DRUGS, 15:175–185 (1997).

Gearing et al., *Processing of tumour necrosis factor–αα precursor by metalloproteinases*, NATURE, 370:555–557 (1994).

Kenyon, BM, et al., *A Model of Angiogenesis in the Mouse Cornea*; Investigative Ophthalmology & Visual Science, vol. 37, No. 8 (Jul. 1996).

Knight et al., *A novel coumarin–labelled peptide for sensitive continuous assays of the matrix metalloproteinases*, FEBS LETT. 296(3):263–266 (1992).

(List continued on next page.)

*Primary Examiner*—Zinna Northington Davis
(74) *Attorney, Agent, or Firm*—Harness, Dickey & Pierce, P.L.C.

(57) ABSTRACT

This invention is directed to aromatic sulfone hydroxamates (also known as "aromatic sulfone hydroxamic acids") and salts thereof that, inter alia, inhibit matrix metalloproteinase (also known as "matrix metalloprotease" or "MMP") activity and/or aggrecanase activity. This invention also is directed to a prevention or treatment method that comprises administering such a compound or salt in an MMP-inhibiting and/or aggrecanase-inhibiting effective amount to an animal, particularly a mammal having (or disposed to having) a pathological condition associated with MMP and/or aggrecanase activity.

90 Claims, No Drawings

OTHER PUBLICATIONS

Luckow et al., *Efficient generation of infectious recombinant baculoviruses by site–specific transposon–mediated insertion of foreign genes into a baculovirus genome propagated in escherihia coli*, J. Virol. 67:4566–4579 (1993).

McClure et al., *Matrix metalloprotease (MMP)–13 selective inhibitors for treatment of arthritis deformans and other MMP–related diseases*, CA 131:125454 (1999) [CA Plus Accession No. 1999:468334].

McGeehan et al., *Regulation of tumour necrosis factor–α processing by a metalloproteinase inhibitor*; NATURE, 370:558–561 (1994).

Mitchell et al., *Cloning, expression, and type II collagenolytic activity of matrix metalloproteinase–13 from human osteoarthritic cartilage*, J. Clin. Invest., 97(3):761–768 (1996).

Rasmussen et al., *Matrix metalloproteinase inhibition as a novel anticancer strategy: a review with special focus on batimastat and marimastat*, Pharmacol. Ther., 75(1):69–75 (1997).

Reboul et al., *The new collagenase, collagnease–3, is expressed and synthesized by human chondrocytes but not by synoviocytes*, J. Clin. Invest., 97(9):2011–2019 (1996).

Schwartz et al., *Synthetic inhibitors of bacterial and mammalian interstitial collagenases*, Prog. in Med. Chem., 29:271–334 (1992).

Tang, *ADAMTS: a novel family of extracellular matrix proteases*, The International Journal of Biochemistry & Cell Biology 33 (2001) pp. 33–44.

Woessner, "The Matrix Metalloproteinase Family", *Matrix Metalloproteinases*, (1999) pp. 1–14.

Brown, "Synthetic Inhibitors of Matrix Metalloproteinases"; *Matrix Metalloproteinases*, pp. 243–261 (Academic Press, Eds Parks, W.C., & Mecham, R.P., 1998).

AROMATIC SULFONE HYDROXAMATES AND THEIR USE AS PROTEASE INHIBITORS

PRIORITY CLAIM TO RELATED PATENT APPLICATION

This patent claims priority to U.S. Provisional Patent Application Serial No. 60/290,375 (filed May 11, 2001). The entire text of U.S. Provisional Patent Application Ser. No. 60/290,375 is incorporated by reference into this patent.

FIELD OF THE INVENTION

This invention is directed generally to proteinase (also known as "protease") inhibitors, and, more particularly, to aromatic sulfone hydroxamates (also known as "aromatic sulfone hydroxamic acids") that, inter alia, inhibit matrix metalloproteinase (also known as "matrix metalloprotease" or "MMP") activity and/or aggrecanase activity. This invention also is directed to compositions of such inhibitors, intermediates for the syntheses of such inhibitors, methods for making such inhibitors, and methods for preventing or treating conditions associated with MMP activity and/or aggrecanase activity, particularly pathological conditions.

BACKGROUND OF THE INVENTION

Connective tissue is a required component of all mammals. It provides rigidity, differentiation, attachments, and, in some cases, elasticity. Connective tissue components include, for example, collagen, elastin, proteoglycans, fibronectin, and laminin. These biochemicals make up (or are components of) structures, such as skin, bone, teeth, tendon, cartilage, basement membrane, blood vessels, cornea, and vitreous humor.

Under normal conditions, connective tissue turnover and/or repair processes are in equilibrium with connective tissue production. Degradation of connective tissue is carried out by the action of proteinases released from resident tissue cells and/or invading inflammatory or tumor cells.

Matrix metalloproteinases, a family of zinc-dependent proteinases, make up a major class of enzymes involved in degrading connective tissue. Matrix metalloproteinases are divided into classes, with some members having several different names in common use. Examples are: MMP-1 (also known as collagenase 1, fibroblast collagenase, or EC 3.4.24.3); MMP-2 (also known as gelatinase A, 72 kDa gelatinase, basement membrane collagenase, or EC 3.4.24.24), MMP-3 (also known as stromelysin 1 or EC 3.4.24.17), proteoglycanase, MMP-7 (also known as matrilysin), MMP-8 (also known as collagenase II, neutrophil collagenase, or EC 3.4.24.34), MMP-9 (also known as gelatinase B, 92 kDa gelatinase, or EC 3.4.24.35), MMP-10 (also known as stromelysin 2 or EC 3.4.24.22), MMP-1 I (also known as stromelysin 3), MMP-12 (also known as metalloelastase, human macrophage elastase or HME), MMP-13 (also known as collagenase 111), and MMP-14 (also known as MT1-MMP or membrane MMP). See, generally, Woessner, J. F., "The Matrix Metalloprotease Family" in *Matrix Metalloproteinases*, pp.1–14 (Edited by Parks, W. C. & Mecharn, R. P., Academic Press, San Diego, Calif. 1998).

Excessive breakdown of connective tissue by MMPs is a feature of many pathological conditions. Inhibition of MMPs therefore provides a control mechanism for tissue decomposition to prevent and/or treat these pathological conditions. Such pathological conditions generally include, for example, tissue destruction, fibrotic diseases, pathological matrix weakening, defective injury repair, cardiovascular diseases, pulmonary diseases, kidney diseases, liver diseases, ophthalmologic diseases, and diseases of the central nervous system. Specific examples of such conditions include, for example, rheumatoid arthritis, osteoarthritis, septic arthritis, multiple sclerosis, a decubitis ulcer, corneal ulceration, epidermal ulceration, gastric ulceration, tumor metastasis, tumor invasion, tumor angiogenesis, periodontal disease, liver cirrhosis, fibrotic lung disease, emphysema, otosclerosis, atherosclerosis, proteinuria, coronary thrombosis, dilated cardiomyopathy, congestive heart failure, aortic aneurysm, epidermolysis bullosa, bone disease, Alzheimer's disease, defective injury repair (e.g., weak repairs, adhesions such as post-surgical adhesions, and scarring), post-myocardial infarction, bone disease, and chronic obstructive pulmonary disease.

Matrix metalloproteinases also are involved in the biosynthesis of tumor necrosis factors (TNFs). Tumor necrosis factors are implicated in many pathological conditions. TNF-α, for example, is a cytokine that is presently thought to be produced initially as a 28 kD cell-associated molecule. It is released as an active, 17 kD form that can mediate a large number of deleterious effects in vitro and in vivo. TNF-α can cause and/or contribute to the effects of inflammation (e.g., rheumatoid arthritis), autoimmune disease, graft rejection, multiple sclerosis, fibrotic diseases, cancer, infectious diseases (e.g., malaria, mycobacterial infection, meningitis, etc.), fever, psoriasis, cardiovascular diseases (e.g., post-ischemic reperfusion injury and congestive heart failure), pulmonary diseases, hemorrhage, coagulation, hyperoxic alveolar injury, radiation damage, and acute phase responses like those seen with infections and sepsis and during shock (e.g., septic shock and hemodynamic shock). Chronic release of active TNF-α can cause cachexia and anorexia. TNF-α also can be lethal.

Inhibiting TNF (and related compounds) production and action is an important clinical disease treatment. Matrix metalloproteinase inhibition is one mechanism that can be used. MMP (e.g., collagenase, stromelysin, and gelatinase) inhibitors, for example, have been reported to inhibit TNF-α release. See, e.g., Gearing et al. *Nature* 376, 555–557 (1994). See also, McGeehan et al. See also, *Nature* 376, 558–561 (1994). MMP inhibitors also have been reported to inhibit TNF-α convertase, a metalloproteinase involved in forming active TNF-α. See, e.g., WIPO Int'l Pub. No. WO 94/24140. See also, WIPO Int'l Pub. No. WO 94/02466. See also, WIPO Int'l Pub. No. WO 97/20824.

Matrix metalloproteinases also are involved in other biochemical processes in mammals. These include control of ovulation, post-partum uterine involution, possibly implantation, cleavage of APP (β-amyloid precursor protein) to the amyloid plaque, and inactivation of ($α_1$-protease inhibitor ($α_1$-PI). Inhibiting MMPs therefore may be a mechanism that may be used to control of fertility. In addition, increasing and maintaining the levels of an endogenous or administered serine protease inhibitor (e.g., $α_1$-PI) supports the treatment and prevention of pathological conditions such as emphysema, pulmonary diseases, inflammatory diseases, and diseases of aging (e.g., loss of skin or organ stretch and resiliency).

Numerous metalloproteinase inhibitors are known. See, generally, Brown, P.D., "Synthetic Inhibitors of Matrix Metalloproteinases," in *Matrix Metalloproteinases*, pp. 243–61 (Edited by Parks, W. C. & Mecham, R. P., Academic Press, San Diego, Calif. 1998).

Metalloproteinase inhibitors include, for example, natural biochemicals, such as tissue inhibitor of metalloproteinase (TIMP), α2-macroglobulin, and their analogs and derivatives. These are high-molecular-weight protein molecules that form inactive complexes with metalloproteinases.

A number of smaller peptide-like compounds also have been reported to inhibit metalloproteinases. Mercaptoamide peptidyl derivatives, for example, have been reported to inhibit angiotensin converting enzyme (also known as ACE) in vitro and in vivo. ACE aids in the production of angiotensin II, a potent pressor substance in mammals. Inhibiting ACE leads to lowering of blood pressure.

A wide variety of thiol compounds have been reported to inhibit MMPs. See, e.g., WO95/12389. See also, WO96/11209. See also, U.S. Pat. No. 4,595,700. See also, U.S. Pat. No. 6,013,649.

A wide variety of hydroxamate compounds also have been reported to inhibit MMP's. Such compounds reportedly include hydroxamates having a carbon backbone. See, e.g., WIPO Int'l Pub. No. WO 95/29892. See also, WIPO Int'l Pub. No. WO 97/24117. See also, WIPO Int'l Pub. No. WO 97/49679. See also, European Patent No. EP 0 780 386. Such compounds also reportedly include hydroxamates having peptidyl backbones or peptidomimetic backbones. See, e.g, WIPO Int'l Pub. No. WO 90/05719. See also, WIPO Int'l Pub. No. WO 93/20047. See also, WIPO Int'l Pub. No. WO 95/09841. See also, WIPO Int'l Pub. No. WO 96/06074. See also, Schwartz et al., Progr. Med. Chem., 29:271–334(1992). See also, Rasmussen et al., PharmacoL Ther., 75(1): 69–75 (1997). See also, Denis et al., Invest New Drugs, 15(3): 175–185 (1997). Various piperazinylsulfonyl-methyl hydroxamates and piperidinylsulfonylmethyl hydroxamates have additionally been reported to inhibit MMPs. See, WIPO Int'l Pub. No. WO 00/46221. And various aromatic sulfone hydroxamates have been reported to inhibit MMPs. See, WIPO Int'l Pub. No. WO 99/25687. See also, WIPO Int'l Pub. No. WO 00/50396. See also, WIPO Int'l Pub. No. WO 00/69821.

It is often advantageous for an MMP inhibitor drug to target a certain MMP(s) over another MMP(s). For example, it is typically preferred to inhibit MMP-2, MMP-3, MMP-9, and/or MMP-13 (particularly MMP-13) when treating and/or preventing cancer, inhibiting of metastasis, and inhibiting angiogenesis. It also is typically preferred to inhibit MMP-13 when preventing and/or treating osteoarthritis. See, e.g., Mitchell et al., J Clin. Invest., 97:761–768 (1996). See also, Reboul et al., J Clin. Invest., 97:2011–2019 (1996). Normally, however, it is preferred to use a drug that has little or no inhibitory effect on MMP-1 and MMP-14. This preference stems from the fact that both MMP-1 and MMP-14 are involved in several homeostatic processes, and inhibition of MMP-1 and/or MMP-14 consequently tends to interfere with such processes.

Many known MMP inhibitors exhibit the same or similar inhibitory effects against each of the MMPs. For example, batimastat (a peptidomimetic hydroxamate) has been reported to exhibit $IC_{50}$ values of from about 1 to about 20 nM against each of MMP-1, MMP-2, MMP-3, MMP-7, and MMP-9. Marimastat (another peptidomimetic hydroxamate) has been reported to be another broad-spectrum MMP inhibitor with an enzyme inhibitory spectrum similar to batimastat, except that Marimastat reportedly exhibited an $IC_{50}$ value against MMP-3 of 230 nM. See Rasmussen et al., Pharmacol. Ther., 75(1): 69–75 (1997).

Meta analysis of data from Phase I/II studies using Marimastat in patients with advanced, rapidly progressive, treatment-refractory solid tumor cancers (colorectal, pancreatic, ovarian, and prostate) indicated a dose-related reduction in the rise of cancer-specific antigens used as surrogate markers for biological activity. Although Marimastat exhibited some measure of efficacy via these markers, toxic side effects reportedly were observed. The most common drug-related toxicity of Marimastat in those clinical trials was musculoskeletal pain and stiffness, often commencing in the small joints in the hands, and then spreading to the arms and shoulder. A short dosing holiday of 1–3 weeks-followed by dosage reduction reportedly permits treatment to continue. See Rasmussen et al., Pharmacol. Ther., 75(1): 69–75 (1997). It is thought that the lack of specificity of inhibitory effect among the MMPs may be the cause of that effect.

Another enzyme implicated in pathological conditions associated with excessive degradation of connective tissue is aggrecanase, particularly aggrecanase-1 (also known as ADAMTSA-4). Specifically, articular cartilage contains large amounts of the proteoglycan aggrecan. Proteoglycan aggrecan provides mechanical properties that help articular cartilage in withstanding compressive deformation during joint articulation. The loss of aggrecan fragments and their release into synovial fluid caused by proteolytic cleavages is a central pathophysiological event in osteoarthritis and rheumatoid arthritis. It has been reported that two major cleavage sites exist in the proteolytically sensitive interglobular domains at the N-terminal region of the aggrecan core protein. One of those sites has been reported to be cleaved by several matrix metalloproteases. The other site, however, has been reported to be cleaved by aggrecanase-1. Thus, inhibiting excessive aggrecanase activity provides an additional and/or alternative prevention or treatment method for inflammatory conditions. See generally, Tang, B. L., "ADAMTS: A Novel Family of Extracellular Matrix Proteases," Int'l Journal of Biochemistry & Cell Biology, 33, pp. 33–44 (2001). Such diseases reportedly include, for example, osteoarthritis, rheumatoid arthritis, joint injury, reactive arthritis, acute pyrophosphate arthritis, and psoriatic arthritis. See, e.g., European Patent Application Publ. No. EP 1 081 137 A1.

In addition to inflammatory conditions, there also is evidence that inhibiting aggrecanase may be used for preventing or treating cancer. For example, excessive levels of aggrecanase-1 reportedly have been observed with a ghoma cell line. It also has been postulated that the enzymatic nature of aggrecanase and its similarities with the MPs would support tumor invasion, metastasis, and angiogenesis. See Tang, Int'l Journal of Biochemistry & Cell Biology, 33, pp. 33–44 (2001).

Various hydroxamate compounds have been reported to inhibit aggrecanase-1. Such compounds include, for example, those described in European Patent Application Publ. No. EP 1 081 137 A1. Such compounds also include, for example, those described in WIPO PCT Int'l Publ. No. WO 00/09000. Such compounds further include, for example, those described in WIPO PCT Int'l Publ. No. WO 00/59874.

In view of the importance of hydroxamate compounds in the prevention or treatment of several pathological conditions and the lack of enzyme specificity exhibited by two of the more potent MMP-inhibitor drugs that have been in clinical trials, there continues to be a need for hydroxamates having greater enzyme specificity (preferably toward MMP-2, MMP-9, MMP-13, and/or aggrecanase (particularly toward MMP-13 in some instances, toward both MMP-2 and MMP-9 in other instances, and aggrecanase in yet other instances), while exhibiting little or no inhibition of MMP-1 and/or MMP-14. The following disclosure describes hydroxamate compounds that tend to exhibit such desirable activities.

SUMMARY OF THE INVENTION

This invention is directed to hydroxamate compounds (and salts thereof) that inhibit pathological protease activity (particularly compounds that inhibit MMP-2, MMP-9, MMP-13, and/or aggrecanase activity), while generally exhibiting relatively little or no inhibition against MMP-1 and MMP-14 activity. This invention also is directed to a method for inhibiting MMP activity and/or aggrecanase activity, particularly pathological MMP and/or aggrecanase activity. Such a method is particularly suitable to be used with mammals, such as humans, other primates (e.g., monkeys, chimpanzees. etc.), companion animals (e.g., dogs, cats, horses. etc.), farm animals (e.g. goats, sheep, pigs, cattle, etc.), laboratory animals (e.g., mice, rats, etc.), and wild and zoo animals (e.g., wolves, bears, deer, etc.).

Briefly, therefore, the invention is directed in part to a compound or salt thereof. The compound has a structure corresponding to Formula I:

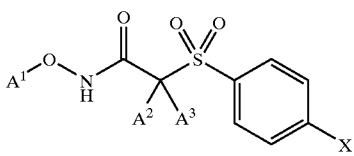

Here:

$A^1$ is —H, alkylcarbonyl, alkoxycarbonyl, carbocyclylcarbonyl, carbocyclylalkylcarbonyl, heterocyclylcarbonyl, heterocyclylalkylcarbonyl, carbocyclyloxycarbonyl, carbocyclylalkoxycarbonyl, aminoalkylcarbonyl, alkyl(thiocarbonyl), alkoxy (thiocarbonyl), carbocyclyl(thiocarbonyl), carbocyclylalkyl (thiocarbonyl), heterocyclyl(thiocarbonyl), heterocyclylalkyl(thiocarbonyl), carbocyclyloxy (thiocarbonyl), carbocyclylalkoxy(thiocarbonyl), or aminoalkyl(thiocarbonyl). Except where $A^1$ is —H, any member of this group optionally is substituted (i.e., it may be either unsubstituted or substituted).

$A^2$ and $A^3$, together with the carbon atom to which they are both attached, form an optionally-substituted heterocyclyl containing from 5 to 8 ring members.

In a preferred embodiment of the invention, X is —$E^1$—$E^2$—$E^3$—$E^4$—$E^5$. In this embodiment:

$E^1$ is —O—, —S(O)$_2$—, —S(O)—, —S—, —N(R$^1$)—, —C(O)—N(R$^1$)—, —N(R$^1$)—C(O)—, or —C(R$^1$)(R$^2$)—.

$E^2$ forms a link of at least 2 carbon atoms between $E^1$ and $E^3$. $E^2$ is alkyl, cycloalkyl, alkylcycloalkyl, cycloalkylalkyl, or alkylcycloalkylalkyl. Any member of this group optionally is substituted.

$E^3$ is —C(O)—, —O—(CO)—, —C(O)—O—, —C(NR$^3$)—, —N(R$^4$)—, —C(O)—N(R$^4$)—, —N($^4$)—C(O)—, —N(R$^4$)—C(O)—N(R$^5$)—, —S—, —S(O)—, —N(R$^4$)—S(O)$_2$—, —S(O)$_2$—N(R$^4$)—, —C(O)—N(R$^4$)—N(R$^5$)—C(O)—, —C(R$^4$)(R$^6$)—C(O)—, or —C(R$^7$)(R$^8$)—.

$E^4$ is a bond, alkyl, or alkenyl. The alkyl and alkenyl optionally are substituted.

$E^5$ is —H, —OH, alkyl, alkenyl, alkynyl, alkoxy, alkoxyalkyl, carbocyclyl, or heterocyclyl. Except where $E^5$ is except —H or —OH, any member of this group optionally is substituted. $E^5$ is not —H when both $E^3$ is —C(R$^7$)(R$^8$)— and $E^4$ is a bond.

$R^1$ and $R^2$ are independently selected from the group consisting of —H and alkyl. The alkyl optionally is substituted. Neither $R^1$ nor $R^2$ forms a ring structure with $E^2$, $E^3$, $E^4$, or $E^5$.

$R^3$ is —H or —OH.

$R^4$ and $R^5$ are independently selected from the group consisting of —H, alkyl, carbocyclyl, carbocyclylalkyl, heterocyclyl, and heterocyclylalkyl. Except for —H, any member of this group optionally is substituted. Neither $R^4$ nor $R^5$ forms a ring structure with $E^2$, $E^4$, or $E^5$.

$R^6$ is —CN or —OH.

$R^7$ is —H, halogen, —OH, alkyl, alkoxy, or alkoxyalkyl. The alkyl, alkoxy, and alkoxyalkyl optionally are substituted.

$R^8$ is —OH or alkoxy. The alkoxy optionally is substituted.

In another preferred embodiment of the invention, X is —$E^1$—$E^2$—$E^3$—$E^4$—$E^5$. In this embodiment:

$E^1$ is —O—, —S(O)$_2$—, —S(O)—, —S—, —N(R$^1$), —C(O)—N(R$^1$)—, —N(R$^2$)—C(O)—, or —C(R$^1$)(R$^2$)—.

$E^2$ forms a link of at least 2 carbon atoms between $E^1$ and $E^3$. $E^2$ is alkyl, cycloalkyl, alkylcycloalkyl, cycloalkylalkyl, or alkylcycloalkylalkyl. Any member of this group optionally is substituted.

$E^3$ is carbocyclyl or heterocyclyl. The carbocyclyl and heterocyclyl have 5 or 6 ring members and optionally are substituted.

$E^4$ is a bond, alkyl, alkenyl, —O—, or —N(R$^3$)—. The alkyl and alkenyl optionally are substituted.

$E^5$ is carbocyclyl or heterocyclyl. The carbocyclyl and heterocyclyl optionally are substituted.

$R^1$ and $R^2$ are independently selected from the group consisting of —H and alkyl. The alkyl optionally is substituted. Neither $R^1$ nor $R^2$ forms a ring structure with $E^2$, $E^3$, $E^4$, or $E^5$.

$R^3$ is —H or alkyl. The alkyl optionally is substituted.

In another preferred embodiment of the invention, X is —$E^1$—$E^2$—C($E^6$)═C($^7$)—$E^3$—$E^4$—$E^5$. In this embodiment:

$E^1$ is —O—, —S(O)$_2$—, —S(O)—, —N(R)—, —C(O)—N(R$^1$)—, —N(R$^1$)C(O)—, or —C(R$^1$)(R$^2$)—.

$E^2$ is alkyl, cycloalkyl, alkylcycloalkyl, cycloalkylalkyl, or alkylcycloalkylalkyl. Any member of this group optionally is substituted.

$E^4$ is a bond or alkyl. The alkyl optionally is substituted.

$E^5$ is alkyl, alkenyl, alkynyl, alkoxy, alkoxyalkyl, carbocyclyl, or heterocyclyl. Any member of this group optionally is substituted.

$E^6$ is —H, halogen, or alkyl. The alkyl optionally is substituted.

$E^7$ is —H, alkyl, alkenyl, alkynyl, —S(O)$_2$—R$^3$, —NO$_2$, —C(O)—N(R$^3$)(R$^4$), —(C)(OR$^3$), carbocyclyl, carbocyclylalkyl, alkoxycarbocyclyl, —CN, —C═N—OH, or —C═NH. The alkyl, alkenyl, alkynyl, carbocyclyl, carbocycylalkyl, and alkoxycarbocyclyl optionally are substituted.

$R^1$ and $R^2$ are independently selected from the group consisting of —H and alkyl. The alkyl optionally is substituted. Neither $R^1$ nor $R^2$ forms a ring structure with $E^2$, $E^4$, $E^5$, $E^6$, or $E^7$.

$R^3$ and $R^4$ are independently selected from the group consisting of —H, alkyl, carbocyclyl, carbocyclylalkyl, heterocyclyl, heterocyclylalkyl. Except where the member is —H, any member of this group optionally is substituted.

In another preferred embodiment of the invention, X is —$E^1$—$E^2$—$E^3$—$E^4$—$E^5$. In this embodiment:

$E^1$ is —O—, —S(O)$_2$—, —S(O)—, —N(R$^3$)—, —C(O)—N(R$^3$)—, —N(R$^3$)—C(O)—, or —C(R$^1$)(R$^2$)—.

$E^2$ is a bond, alkyl, cycloalkyl, alkylcycloalkyl, cycloalkylalkyl, or alkylcycloalkylalkyl. Except where the member is a bond, any member of such group optionally is substituted.

$E^3$ is carbonylpyrrollidinyl. The carbonylpyrrollidinyl optionally is substituted.

$E^4$ is a bond, alkyl, or alkenyl. The alkyl and alkenyl optionally and substituted.

$E^5$ is alkyl, alkenyl, alkynyl, alkoxy, alkoxyalkyl, carbocyclyl, or heterocyclyl. Any member of this group optionally is substituted.

$R^1$ and $R^2$ are independently selected from the group consisting of —H and alkyl. The alkyl optionally is substituted. Neither $R^1$ nor $R^2$ forms a ring structure with $E^2$, $E^3$, $E^4$, or $E^5$.

In another preferred embodiment of the invention, X is —$E^1$—$E^2$—$E^5$. In this embodiment:

$E^1$ is —O—, —S(O)$_2$—, —S(O)—, —N($R^1$)—, —C(O)—N($R^1$)—, —N($R^1$)—C(O)—, or —C($R^1$)($R^2$)—.

$E^2$ is alkyl, cycloalkyl, alkylcycloalkyl, cycloalkylalkyl, or alkylcycloalkylalkyl. Any member of this group optionally is substituted with one or more substituents independently selected from the group consisting of halogen, alkyl, and haloalkyl.

$E^5$ is alkyl, alkenyl, alkynyl, cycloalkyl, cyclopentenyl, cyclopentadienyl, cyclohexenyl, or cyclohexadienyl. The cycloalkyl, cyclopentenyl, cyclopentadienyl, cyclohexenyl, and cyclohexadienyl optionally are substituted. The alkyl, alkenyl, and alkynyl (a) contain at least 4 carbon atoms, and (b) optionally are substituted with one or more substituents selected from the group consisting of —OH, —NO$_2$, —CN, and halogen.

$R^1$ and $R^2$ are independently selected from the group consisting of —H and alkyl. The alkyl optionally is substituted. Neither $R^1$ nor $R^2$ forms a ring structure with $E^5$.

In another preferred embodiment of the invention, X is —$E^1$—$E^2$—$E^3$—$E^4$—$E^5$. In this embodiment:

$E^1$ is —O—, —S(O)$_2$—, —S(O)—, —N($R^1$)—, —C(O)—N($R^1$)—, —N($R^1$)—C(O)—, or —C($R^1$)($R^2$)—.

$E^2$ is alkyl, cycloalkyl, alkylcycloalkyl, cycloalkylalkyl, or alkylcycloalkylalkyl. Any member of this group optionally is substituted.

$E^3$ is carbonylpiperidinyl. The carbonylpiperidinyl optionally is substituted.

$E^4$ is a bond, alkyl, or alkenyl. The alkyl and alkenyl optionally are substituted.

$E^5$ is alkyl, alkenyl, alkynyl, alkoxy, alkoxyalkyl, carbocyclyl, or heterocyclyl. Any member of this group optionally is substituted.

$R^1$ and $R^2$ are independently selected from the group consisting of —H and alkyl. The alkyl optionally is substituted. Neither $R^1$ nor $R^2$ forms a ring structure with $E^2$, $E^3$, $E^4$, or $E^5$.

In another preferred embodiment of the invention, X is —$E^1$—$E^2$—$E^5$. In this embodiment:

$E^1$ is —O—, —S(O)$_2$—, —S(O)—, —N($R^1$)—, —C(O)—N($R^1$)—, —N($R^1$)—C(O)—, or —C($R^1$)($R^2$)—.

$E^2$ forms a link of at least 3 carbon atoms between $E^1$ and $E^5$. $E^2$ is alkyl, cycloalkyl, alkylcycloalkyl, cycloalkylalkyl, or alkylcycloalkylalkyl. Any member of this group optionally is substituted.

$E^5$ is optionally-substituted heterocyclyl, optionally-substituted fused-ring carbocyclyl, or substituted single-ring carbocyclyl.

$R^1$ and $R^2$ are independently selected from the group consisting of —H and alkyl. The alkyl optionally is substituted. Neither $R^1$ nor $R^2$ forms a ring structure with $E^5$.

In another preferred embodiment of the invention, X is —$E^1$—$E^2$—$E^5$. In this embodiment:

$E^1$ is —O—, —S(O)$_2$—, —S(O)—, —N($R^1$)—, —C(O)—N($R^1$)—, —N($R^1$)—C(O)—, or —C($R^1$)($R^2$).

$E^2$ forms a link of at least 4 carbon atoms between $E^1$ and $E^5$. $E^2$ is alkyl, cycloalkyl, alkylcycloalkyl, cycloalkylalkyl, or alkylcycloalkylalkyl. Any member of this group optionally is substituted.

$E^5$ is —OH or optionally-substituted carbocyclyl.

$R^1$ and $R^2$ are independently selected from the group consisting of —H and alkyl. The alkyl optionally is substituted. Neither $R^1$ nor $R^2$ forms a ring structure with $E^5$.

In another preferred embodiment of the invention, X is —$E^1$—$E^2$—O—$E^4$—$E^5$. In this embodiment:

$E^1$ is —S(O)$_2$—, —S(O)—, —N($R^1$)—, —C(O)—N($R^1$)—, —N($R^1$)—C(O)—, or —C($R^1$)($R^2$)—.

$E^2$ is alkyl, cycloalkyl, alkylcycloalkyl, cycloalkylalkyl, or alkylcycloalkylalkyl. Any member of this group optionally is substituted.

$E^4$ is a bond, alkyl, or alkenyl. The alkyl and alkenyl optionally are substituted.

$E^5$ is alkyl, alkenyl, alkynyl, alkoxy, alkoxyalkyl, carbocyclyl, or heterocyclyl. Any member of this group optionally is substituted.

$R^1$ and $R^2$ are independently selected from the group consisting of —H and alkyl. The alkyl optionally is substituted. Neither $R^1$ nor $R^2$ forms a ring structure with $E^2$, $E^4$, or $E^5$.

In another preferred embodiment of the invention, X is —O—$E^2$—O—$E^5$. In this embodiment:

$E^2$ comprises at least 3 carbon atoms. $E^2$ is alkyl, cycloalkyl, alkylcycloalkyl, cycloalkylalkyl, or alkylcycloalkylalkyl. Any member of this group optionally is substituted.

$E^5$ is —H, alkyl, alkenyl, alkynyl, alkoxyalkyl, carbocyclyl, carbocyclylalkoxyalkyl, heterocyclyl, heterocyclylalkyl, or heterocyclylalkoxyalkyl. The alkyl, alkenyl, alkynyl, and alkoxyalkyl optionally are substituted with one or more substituents independently selected from the group consisting of halogen, —OH, —NO$_2$, and —CN, the carbocyclyl, carbocyclylalkoxyalkyl, heterocyclyl, heterocyclylalkyl, and heterocyclylalkoxyalkyl optionally are substituted with one or more substituents independently selected from the group consisting of halogen, —OH, —NO$_2$, —CN, alkyl, haloalkyl, alkoxy, haloalkoxy, alkoxyalkyl, halogen-substituted alkoxyalkyl, —N($R^3$)($R^4$), —C(O)($^5$), —S—$R^3$, —S(O)$_2$—$R^3$, carbocyclyl, halocarbocyclyl, carbocyclylalkyl, and halogen-substituted carbocyclylalkyl.

$R^1$ and $R^2$ are independently selected from the group consisting of —H, alkyl, carbocyclyl, carbocyclylalkyl, heterocyclyl, and heterocyclylalkyl. Except where the member is —H, any member of this group optionally is substituted with one or more halogen.

$R^3$ is —H, alkyl, —O—$R^4$, —N($R^4$)($R^5$), carbocyclylalkyl, or heterocyclylalkyl. The alkyl, carbocyclylalkyl, and heterocyclylalkyl optionally are substituted with one or more halogen.

$R^4$ and $R^5$ are independently selected from the group consisting of —H, alkyl, carbocyclyl, carbocyclylalkyl, heterocyclyl, and heterocyclylalkyl. Except where the member is —H, any member of this group optionally is substituted with one or more halogen.

In another preferred embodiment of the invention, X is —O—$E^2$—O—$E^4$—$E^5$. In this embodiment:

$E^2$ is alkyl, cycloalkyl, alkylcycloalkyl, cycloalkylalkyl, or alkylcycloalkylalkyl. Any member of this group optionally is substituted. An atom in $E^2$ optionally is bound to an atom in $E^5$ to form a ring.

$E^4$ is a bond, alkyl, or alkenyl. The alkyl and alkenyl optionally are substituted.

$E^5$ is:
an optionally-substituted radical selected from the group consisting of alkenyl, alkynyl, alkoxy, alkoxyalkyl, fused-ring carbocyclyl, and heterocyclyl;
single-ring carbocyclyl substituted with one or more substituents independently selected from the group consisting of —OH, —NO$_2$, —CN, —N(R$^5$)(R$^6$), —C(O)(R$^7$), —S—R$^5$, —S(O)$_2$—R$^5$, carbocyclyl, halocarbocyclyl, carbocyclylalkyl, halogen-substituted carbocyclylalkyl, heterocyclyl, haloheterocyclyl, heterocyclylalkyl, and halogen-substituted heterocyclylalkyl; or
single-ring carbocyclyl having multiple substitutions.

$R^1$ and $R^2$ are independently selected from the group consisting of —H, alkyl, carbocyclyl, carbocyclylalkyl, heterocyclyl, and heterocyclylalkyl. Except where the member is —H, any member of this group optionally is substituted with one or more halogen.

$R^3$ is —H, alkyl, —O—R$^4$, —N(R$^4$)(R$^5$), carbocyclylalkyl, or heterocyclylalkyl. The alkyl, carbocyclylalkyl, and heterocyclylalkyl optionally are substituted with one or more halogen.

$R^4$ and $R^5$ are independently selected from the group consisting of—H, alkyl, carbocyclyl, carbocyclylalkyl, heterocyclyl, and heterocyclylalkyl. Except where the member is —H, any member of this group optionally is substituted with one or more halogen.

In another preferred embodiment of the invention, X is —E$^1$—E$^2$—S(O)$_2$—E$^4$—E$^5$. In this embodiment:
$E^1$ is —S(O)$_2$—, —S(O)—, —N(R$^1$)—, —C(O)—N(R$^1$)—, —N(R$^1$)C(O)—, or —C(R$^1$)(R$^2$)—.

$E^2$ is alkyl, cycloalkyl, alkylcycloalkyl, cycloalkylalkyl, or alkylcycloalkylalkyl. Any member of this group optionally is substituted.

$E^4$ is a bond, alkyl, or alkenyl. The alkyl and alkenyl optionally are substituted.

$E^5$ is alkyl, alkenyl, alkynyl, alkoxy, alkoxyalkyl, carbocyclyl, or heterocyclyl. Any member of this group optionally is substituted.

$R^1$ and $R^2$ are independently selected from the group consisting of —H and alkyl. The alkyl optionally is substituted. Neither $R^1$ nor $R^2$ forms a ring structure with E$^2$, E$^4$, or E$^5$.

In another preferred embodiment of the invention, X is —O—E$^2$—S(O)$_2$—E$^4$—E$^5$. In this embodiment:
$E^2$ is alkyl, cycloalkyl, alkylcycloalkyl, cycloalkylalkyl, or alkylcycloalkylalkyl. Any member of this group optionally is substituted.

$E^4$ is alkyl or alkenyl. The alkyl and alkenyl optionally are substituted.

$E^5$ is —H, alkyl, alkenyl, alkynyl, alkoxy, carbocyclyl, or heterocyclyl. Any member of this group optionally is substituted.

In another preferred embodiment of the invention, X is —O—E$^2$—S(O)$_2$—E$^5$. In this embodiment:
$E^2$ comprises less than 5 carbon atoms. E$^2$ is alkyl, cycloalkyl, alkylcycloalkyl, cycloalkylalkyl, or alkylcycloalkylalkyl. Any member of this group optionally is substituted.

$E^5$ is alkyl, alkenyl, alkynyl, alkoxyalkyl, carbocyclyl, or heterocyclyl. Any member of this group optionally is substituted.

In another preferred embodiment of the invention, X is —O—E$^2$—S(O)$_2$—E$^5$. In this embodiment:
$E^2$ is alkyl, cycloalkyl, alkylcycloalkyl, cycloalkylalkyl, or alkylcycloalkylalkyl. Any member of this group optionally is substituted.

$E^5$ is alkyl, alkenyl, alkynyl, alkoxyalkyl, saturated carbocyclyl, partially saturated carbocyclyl, or heterocyclyl. Any member of this group optionally is substituted.

In another preferred embodiment of the invention, X is:

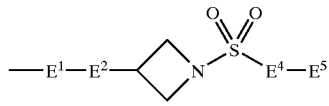

In this embodiment:
$E^1$—S(O)$_2$—, —S(O)—, —N(R$^1$)—, —C(O)—N(R$^1$)—, —N(R$^1$)—C(O), or —C(R)(R$^2$)—.

$E^2$ is alkyl, cycloalkyl, alkylcycloalkyl, cycloalkylalkyl, or alkylcycloalkylalkyl. Any member of this group optionally is substituted.

$E^4$ is a bond, alkyl, or alkenyl, The alkyl and alkenyl optionally are substituted.

$E^5$ is alkyl, alkenyl, alkynyl, alkoxy, alkoxyalkyl, carbocyclyl, or heterocyclyl. Any member of this group optionally is substituted.

$R^1$ and $R^2$ are independently selected from the group consisting of —H and alkyl. The alkyl optionally is substituted. Neither $R^1$ nor $R^2$ forms a ring structure with E$^2$, E$^4$, or E$^5$.

In another preferred embodiment of the invention, X is:

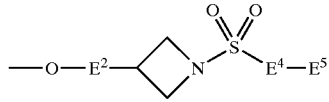

In this embodiment:
$E^2$ is a bond, alkyl, cycloalkyl, alkylcycloalkyl, cycloalkylalkyl, or alkylcycloalkylalkyl. Any member of this group optionally is substituted.

$E^4$ is a bond, alkyl, or alkenyl. The alkyl and alkenyl optionally are substituted.

$E^5$ is substituted carbocyclyl or optionally-substituted heterocyclyl. The carbocyclyl is substituted with:
two or more substituents independently selected from the group consisting of halogen, —OH, —NO$_2$, —CN, alkyl, haloalkyl, alkoxy, haloalkoxy, alkoxyalkyl, halogen-substituted alkoxyalkyl, —N(R$^3$)(R$^4$), —C(O)(R$^5$), —S—R$^3$, —S(O)$_2$—R$^3$, carbocyclyl, halocarbocyclyl, carbocyclylalkyl, and halogen-substituted carbocyclylalkyl; or
a substituent selected from the group consisting of halogen, —OH, —NO$_2$, —CN, —C(O)O—R$^3$, —S—R$^3$, —S(O)$_2$—R$^3$, carbocyclyl, halocarbocyclyl, carbocyclylalkyl, and halogen-substituted carbocyclylalkyl.

The heterocyclyl, on the other hand, optionally is substituted with one or more substituents independently selected from the group consisting of halogen, —OH, —NO$_2$, —CN, alkyl, haloalkyl, alkoxy, haloalkoxy, alkoxyalkyl, halogen-substituted alkoxyalkyl, —N(R$^3$)(R$^4$), —C(O)(R$^5$), —S—R$^3$, —S(O)$_2$—R$^3$, carbocyclyl, halocarbocyclyl, carbocyclylalkyl, and halogen-substituted carbocyclylalkyl.

$R^3$ and $R^4$ are independently selected from the group consisting of —H, alkyl, carbocyclyl, carbocyclylalkyl, heterocyclyl, and heterocyclylalkyl. Except where the member is —H, any member of this group optionally is substituted with one or more halogen.

$R^5$ is —H, alkyl, —O—R$^6$, —N(R$^6$)(R$^7$), carbocyclylalkyl, or heterocyclylalkyl. The alkyl, carbocyclylalkyl, and heterocyclylalkyl optionally are substituted with one or more halogen.

$R^6$ and $R^7$ are independently selected from the group consisting of —H, alkyl, carbocyclyl, carbocyclylalkyl, heterocyclyl, and heterocyclylalkyl. Except where the member is —H, any member of this group optionally is substituted with one or more halogen.

In another preferred embodiment of the invention, X is —$E^1$—$E^2$—$E^5$. In this embodiment:

$E^1$ is —O—, —S(O)$_2$—, —S(O)—, —S—, —N(R$^1$)—, —C(O)N(R$^1$)—, —N(R$^1$)—C(O)—, or —C(R$^1$)(R$^2$)—.

$E^1$ is alkyl, cycloalkyl, alkylcycloalkyl, cycloalkylalkyl, or alkylcycloalkylalkyl. Any member of such group optionally is substituted.

$E^5$ is substituted heterocyclyl.

$R^1$ and $R^2$ are independently selected from the group consisting of—H and alkyl. The alkyl optionally is substituted.

Neither $R^1$ nor $R^2$ forms a ring structure with $E^5$.

In another preferred embodiment of the invention, X is —$E^1$—$E^2$—$E^5$. In this embodiment:

$E^1$ is —O—, —S(O)$_2$—, —S(O)—, —N(R$^1$)—, —C(O)—N(R$^1$)—, —N(R$^1$)—C(O)—, or —C(R$^1$)(R$^2$)—.

$E^2$ is alkyl, cycloalkyl, alkylcycloalkyl, cycloalkylalkyl, or alkylcycloalkylalkyl. Any member of such group optionally is substituted. In addition, $E^2$ comprises at least two carbon atoms.

$E^5$ is optionally-substituted heterocyclyl.

$R^1$ and $R^2$ are independently selected from the group consisting of —H and alkyl. The alkyl optionally is substitute.

Neither $R^1$ nor $R^2$ forms a ring structure with $E^5$.

In another preferred embodiment of the invention, X is —$E^1$—$E^2$—$E^3$—$E^4$—$E^5$. In this embodiment:

$E^1$ is —O—, —S(O)$_2$—, —S(O)—, —S—, —N(R$^1$)—, —C(O)—N(R$^1$)—, —N(R$^1$)—C(O)—, or —C(R$^1$)(R$^2$)—.

$E^2$ is alkyl, cycloalkyl, alkylcycloalkyl, cycloalkylalkyl, or alkylcycloalkylalkyl. Any member of such group optionally is substituted.

$E^3$ is —C(O)—, —O—(CO)—, —C(O)O—, —C(NR$^3$)—, —N(R$^4$)—, —N(R$^4$)—C(NR$^3$)—, —C(NR$^3$)—N(R$^4$)—, —C(O)—N(R$^4$)—, —N(R$^4$)—C(O)—, —N(R$^4$)—C(O)—N(R$^5$)—, —S—, —S(O)—, —N(R$^4$)—S(O)$_2$—, —S(O)$_2$—N(R$^4$)—, —C(O)—N(R$^4$)—N(R$^5$)—C(O)—, —C(R$^4$)(R$^6$)—C(O)—, or —C(R$^7$)(R$^8$)—.

$E^4$ is a bond, alkyl, or alkenyl. The alkyl and alkenyl optionally are substituted.

$E^5$ is carbocyclyl or heterocyclyl. The carbocyclyl and heterocyclyl are:

substituted with a substituent selected from the group consisting of optionally-substituted carbocyclyl, optionally-substituted carbocyclylalkyl, optionally-substituted heterocyclyl, and optionally-substituted heterocyclylalkyl; and optionally substituted with one or more substituents independently selected from the group consisting of halogen, —OH, —NO$_2$, —CN, alkyl, alkoxy, alkoxyalkyl, —N(R$^{11}$)(R$^{12}$), —C(O)(R$^{13}$), —S—R$^{11}$, —S(O)$_2$—R$^{11}$, carbocyclyl, carbocyclylalkyl, haloalkyl, haloalkoxy, halogen-substituted alkoxyalkyl, halocarbocyclyl, halogen-substituted carbocyclylalkyl, hydroxycarbocyclyl, and heteroaryl.

$R^1$ and $R^2$ are independently selected from the group consisting of —H and alkyl, wherein the alkyl optionally is substituted.

$R^3$ is —H or —OH.

$R^4$ and $R^5$ are independently selected from the group consisting of —H, alkyl, carbocyclyl, carbocyclylalkyl, heterocyclyl, and heterocyclylalkyl, wherein any member (except —H) of such group optionally is substituted.

$R^6$ is —CN or —OH.

$R^7$ is —H, halogen, —OH, alkyl, alkoxy, or alkoxyalkyl. The alkyl, alkoxy, and alkoxyalkyl optionally are substituted.

$R^8$ is —OH or alkoxy. The alkoxy optionally is substituted.

$R^{11}$ and $R^{12}$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Any member (except —H) of such group optionally is substituted with one or more halogen.

$R^{13}$ is —H, $C_1$–$C_8$-alkyl, —O—R$^{14}$, —N(R$^{14}$)(R$^{15}$), carbocyclyl-$C_1$–$C_8$-alkyl, heterocyclyl-$C_1$–$C_8$-alkyl, halo-$C_1$–$C_8$-alkyl, halogen-substituted carbocyclyl-$C_1$–$C_8$-alkyl, or halogen-substituted heterocyclyl-$C_1$–$C_8$-alkyl.

$R^{14}$ and $R^{15}$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Any member (except —H) of such group optionally is substituted with one or more halogen.

Neither $R^1$ nor $R^2$ forms a ring structure with $E^2$, $E^3$, $E^4$, or $E^5$.

Neither $R^4$ nor $R^5$ forms a ring structure with $E^2$, $E^3$, $E^4$, or $E^5$.

This invention also is directed, in part, to a method for preventing or treating a condition associated with pathological matrix metalloprotease activity in a mammal having the condition or predisposed to having the condition. The method comprises administering an above-described compound or a pharmaceutically acceptable salt thereof to the mammal in an amount that is therapeutically-effective to prevent or treat the condition.

This invention also is directed, in part, to a method for preventing or treating a pathological condition in a mammal having the condition or predisposed to having the condition. The method comprises administering an above-described compound or a pharmaceutically acceptable salt thereof to the mammal in an amount that is therapeutically-effective to prevent or treat the condition. In this embodiment, the pathological condition comprises tissue destruction, a fibrotic disease, pathological matrix weakening, defective injury repair, a cardiovascular disease, a pulmonary disease, a kidney disease, a liver disease, an ophthalmologic disease, and a central nervous system disease.

This invention also is directed, in part, to a method for preventing or treating a pathological condition in a mammal having the condition or predisposed to having the condition. The method comprises administering an above-described compound or a pharmaceutically acceptable salt thereof to the mammal in an amount that is therapeutically-effective to prevent or treat the condition. In this embodiment, the pathological condition comprises osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermal ulceration, epidermolysis bullosa, aortic aneurysm, defective injury repair, an adhesion, scarring, congestive heart failure, post myocardial infarction, coronary thrombosis, emphysema, proteinuria, Alzheimer's disease, bone disease, and chronic obstructive pulmonary disease.

This invention also is directed, in part, to a method for preventing or treating a condition associated with pathological TNF-α convertase activity in a mammal having the condition or predisposed to having the condition. The method comprises administering an above-described compound or a pharmaceutically acceptable salt thereof to the mammal in an amount that is therapeutically-effective to prevent or treat the condition.

This invention also is directed, in part, to a method for preventing or treating a condition associated with pathological aggrecanase activity in a mammal having the condition or predisposed to having the condition. The method comprises administering an above-described compound or a pharmaceutically acceptable salt thereof to the mammal in an amount that is therapeutically-effective to prevent or treat the condition.

This invention also is directed, in part, to pharmaceutical compositions comprising a therapeutically-effective amount of an above-described compound or a pharmaceutically-acceptable salt thereof.

This invention also is directed, in part, to a use of an above-described compound or a pharmaceutically acceptable salt thereof to prepare a medicament for treating a condition associated with pathological matrix metalloprotease activity.

This invention also is directed, in part, to a use of an above-described compound or a pharmaceutically acceptable salt thereof to prepare a medicament for treating a condition associated with pathological TNF-α convertase activity.

This invention also is directed, in part, to a use of an above-described compound or a pharmaceutically acceptable salt thereof to prepare a medicament for treating a condition associated with pathological aggrecanase activity.

Further benefits of Applicants' invention will be apparent to one skilled in the art from reading this patent.

DETAILED DESCRIPTION OF THE PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this patent, and may be variously modified.

A. Compounds of this Invention

In accordance with this invention, it has been found that certain aromatic sulfone hydroxamates tend to be effective for inhibiting MMPs, particularly those associated with excessive (or otherwise pathological) breakdown of connective tissue. Specifically, Applicants have found that these hydroxamates tend to be effective for inhibiting proteases (particularly MMP-2, MMP-9, MMP-13, other MMP's associated with pathological conditions, and/or aggrecanase) that are often particularly destructive to tissue if present or generated in abnormally excessive quantities or concentrations. Moreover, Applicants have discovered that these hydroxamates tend to be selective toward inhibiting pathological protease activity, while avoiding excessive inhibition of other proteases (particularly MMP-1 and/or MMP-14) that are typically essential to normal bodily function (e.g., tissue turnover and repair).

A-1. Preferred Compound Structures

As noted above, the compound of this invention generally has a structure corresponding to Formula I:

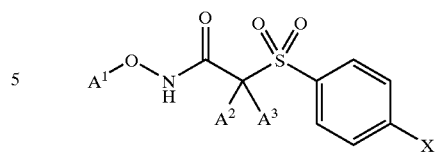

I.

$A^1$ is —H, alkylcarbonyl, alkoxycarbonyl, carbocyclylcarbonyl, carbocyclylalkylcarbonyl, heterocyclylcarbonyl, heterocyclylalkylcarbonyl, carbocyclyloxycarbonyl, carbocyclylalkoxycarbonyl, aminoalkylcarbonyl, alkyl(thiocarbonyl), alkoxy(thiocarbonyl), carbocyclyl(thiocarbonyl), carbocyclylalkyl(thiocarbonyl), heterocyclyl(thiocarbonyl), heterocyclylalkyl(thiocarbonyl), carbocyclyloxy(thiocarbonyl), carbocyclylalkoxy(thiocarbonyl), or aminoalkyl(thiocarbonyl). Except where the member is —H, any member of this group optionally is substituted.

In some preferred embodiments, $A^1$ is —H, $C_1$–$C_8$-alkylcarbonyl, $C_1$–$C_8$-alkoxycarbonyl, carbocyclylcarbonyl, carbocyclyl-$C_1$–$C_8$-alkylcarbonyl, heterocyclylcarbonyl, heterocyclyl-$C_1$–$C_8$-alkylcarbonyl, carbocyclyloxycarbonyl, carbocyclyl-$C_1$–$C_8$-alkoxycarbonyl, $N(R^A)(R^B)$—$C_1$–$C_8$-alkylcarbonyl, $C_1$–$C_8$-alkyl(thiocarbonyl), $C_1$–$C_8$-alkoxy(thiocarbonyl), carbocyclyl(thiocarbonyl), carbocyclyl-$C_1$–$C_8$-alkyl(thiocarbonyl), heterocyclyl(thiocarbonyl), heterocyclyl-$C_1$–$C_8$-alkyl(thiocarbonyl), carbocyclyloxy(thiocarbonyl), carbocyclyl-$C_1$–$C_8$-alkoxy(thiocarbonyl), or $N(R^A)(R^B)$—$C_1$–$C_8$-alkyl(thiocarbonyl). $R^A$ and $R^B$ are independently selected from the group consisting of —H, $C_1$–$C_8$-alkyl, $C_1$–$C_8$-alkoxycarbonyl, $C_1$–$C_8$-alkylcarbonyl, carbocyclyl-$C_1$–$C_8$-alkyl, and carbocyclyl-$C_1$–$C_8$-alkoxycarbonyl.

In generally more preferred embodiments, $A^1$ is —H.

$A^2$ and $A^3$, together with the carbon atom to which they are both attached, form an optionally-substituted heterocyclyl containing from 5 to 8 ring members (i.e., from 5 to 8 atoms are bound together to form the ring (or rings) of the heterocyclyl).

In some preferred embodiments, $A^2$ and $A^3$, together with the carbon atom to which they both are attached, form an optionally-substituted heterocyclyl containing either 5 or 6 ring members.

In some preferred embodiments, the compound corresponds in structure to one of the following formulas:

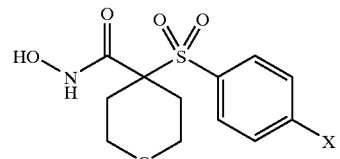

I-A

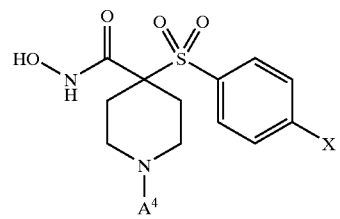

I-B $A^4$ is —H, alkyl, alkylcarbonyl, alkylcarbonylalkyl, alkylcarbonylalkylcarbonyl, alkoxycarbonyl, alkoxycarbonylalkyl, alkoxycarbonylalkylcarbonyl, alkylsulfonyl, alkyliminocarbonyl, alkenyl, alkynyl, alkoxyalkyl, alkylthioalkyl, alkylsulfonylalkyl, alkylsulfoxidoalkyl, alkylthioalkenyl, alkylsulfoxidoalkenyl, alkylsulfonylalkenyl, carbocyclyl, carbocyclylalkyl, carbocyclylalkoxyalkyl, carbocyclylcarbonyl, carbocyclylsulfonyl, carbocyclyliminocarbonyl, carbocyclyloxycarbonyl, carbocyclylthioalkyl, carbocyclylsulfoxidoalkyl, carbocyclylsulfonylalkyl, carbocyclylthioalkenyl, carbocyclylsulfoxidoalkenyl, carbocyclylsulfonylalkenyl, heterocyclyl, heterocyclylalkyl, heterocyclylalkoxyalkyl, heterocyclylcarbonyl, heterocyclylthioalkyl, heterocyclylsulfoxidoalkyl, heterocyclylsulfonylalkyl, heterocyclylthioalkenyl, heterocyclylsulfoxidoalkenyl, heterocyclylsulfonylalkenyl, heterocyclylsulfonyl, heterocyclyliminocarbonyl, heterocyclylalkylcarbonyl, heterocyclylcarbonylalkylcarbonyl, heterocyclylsulfonyl, heterocyclylcarbonylalkyl, aminoalkylcarbonyl, aminocarbonyl, aminocarbonylalkylcarbonyl, aminosulfonyl, aminosulfonylalkyl, aminoalkyl, aminocarbonylalkyl, or aminoalkylsulfonyl. Except where the member is —H, any member of this group optionally is substituted.

In some preferred embodiments, $A^4$ is —H, $C_1$–$C_8$-alkyl, $C_1$–$C_8$-alkylcarbonyl, $C_1$–$C_8$-alkylcarbonyl-$C_1$–$C_8$-alkyl, $C_1$–$C_8$-alkylcarbonyl-$C_1$–$C_8$-alkylcarbonyl, $C_1$–$C_8$-alkoxycarbonyl, $C_1$–$C_8$-alkoxycarbonyl-$C_1$–$C_8$-alkyl, $C_1$–$C_8$-alkoxycarbonyl-$C_1$–$C_8$-alkylcarbonyl, $C_1$–$C_8$-alkylsulfonyl, $C_1$–$C_8$-alkylaminocarbonyl, $C_2$–$C_8$-alkenyl, $C_2$–$C_8$-alkynyl, $C_1$–$C_8$-alkoxy-$C_1$–$C_8$-alkyl, $C_1$–$C_8$-alkylthio-$C_1$–$C_8$-alkyl, $C_1$–$C_8$-alkylthio-$C_2$–$C_8$-alkenyl, $C_1$–$C_8$-alkylsulfoxido-$C_1$–$C_8$-alkyl, $C_1$–$C_8$-alkylsulfoxido-$C_2$–$C_8$-alkenyl, $C_1$–$C_8$-alkylsulfonyl-$C_1$–$C_8$-alkyl, $C_1$–$C_8$-alkylsulfonyl-$C_2$–$C_8$-alkenyl, carbocyclyl, carbocyclyl-$C_1$–$C_8$-alkyl, carbocyclyl-$C_1$–$C_8$-alkoxy-$C_1$–$C_8$-alkyl, carbocyclylcarbonyl, carbocyclylsulfonyl, carbocyclyliminocarbonyl, carbocyclyloxycarbonyl, carbocyclylthio-$C_1$–$C_8$-alkyl, carbocyclylthio-$C_2$–$C_8$-alkenyl, carbocyclylsulfoxido-$C_1$–$C_8$-alkyl, carbocyclylsulfoxido-$C_2$–$C_8$-alkenyl, carbocyclylsulfonyl-$C_1$–$C_8$-alkyl, carbocyclylsulfonyl-$C_2$–$C_8$-alkenyl, heterocyclyl, heterocyclyl-$C_1$–$C_8$-alkyl, heterocyclyl-$C_1$–$C_8$-alkoxy-$C_1$–$C_8$-alkyl, heterocyclylcarbonyl, heterocyclylthio-$C_1$–$C_8$-alkyl, heterocyclylsulfoxido-$C_1$–$C_8$-alkyl, heterocyclylsulfonyl-$C_1$–$C_8$-alkyl, heterocyclylthio-$C_2$–$C_8$-alkenyl, heterocyclylsulfoxido-$C_2$–$C_8$-alkenyl, heterocyclylsulfonyl-$C_2$–$C_8$-alkenyl, heterocyclylsulfonyl, heterocyclyliminocarbonyl, heterocyclyl-$C_1$–$C_8$-alkylcarbonyl, heterocyclylcarbonyl-$C_1$–$C_8$-alkylcarbonyl, heterocyclylsulfonyl, heterocyclylcarbonyl-$C_1$–$C_8$-alkyl, $N(R^C)(R^D)$—$C_1$–$C_8$-alkylcarbonyl, $N(R^C)(R^D)$-carbonyl, $N(R^C)(R^D)$-carbonyl-$C_1$–$C_8$-alkylcarbonyl, $N(R^C)(R^D)$-sulfonyl, $N(R^C)(R^D)$-sulfonyl-$C_1$–$C_8$-alkyl, $N(R^C)(R^D)$—$C_1$–$C_8$-alkyl, $N(R^C)(R^D)$carbonyl-$C_1$–C-alkyl, or $N(R^C)(R^D)$—$C_1$–$C_8$-alkylsulfonyl. Any substitutable member of this group optionally is substituted with one or more substituents independently selected from the group consisting of halogen, —OH, —CN, —C(O)—OH, —SH, —$SO_3H$, and $NO_2$.

$R^C$ and $R^D$ are independently selected from the group consisting of —H, —OH, $C_1$–$C_8$-alkyl, $C_1$–$C_8$-alkylcarbonyl, $C_1$–$C_8$-alkoxy-$C_1$–$C_8$-alkyl, $C_2$–$C_8$-alkenyl, $C_2$–$C_8$-alkynyl, $C_1$–$C_8$-alkyl-thio-$C_1$–$C_8$-alkyl, $C_1$–$C_8$-alkyl-sulfoxido-$C_1$–$C_8$-alkyl, $C_1$–$C_8$-alkyl-sulfonyl-$C_1$–$C_8$-alkyl, carbocyclyl, carbocyclyl-$C_1$–$C_8$-alkyl, carbocyclylcarbonyl, carbocyclyl-$C_1$–$C_8$-alkoxy-$C_1$–$C_8$-alkyl, carbocyclylthio-$C_1$–$C_8$-alkyl, carbocyclylsulfoxido-$C_1$–$C_8$-alkyl, carbocyclylsulfonyl-$C_1$–$C_8$-alkyl, heterocyclyl, heterocyclyl-$C_1$–$C_8$-alkyl, heterocyclyl-$C_1$–$C_8$-alkoxy-$C_1$–$C_8$-alkyl, heterocyclylcarbonyl, heterocyclylthio-$C_1$–$C_8$-alkyl, heterocyclylsulfoxido-$C_1$–$C_8$-alkyl, heterocyclylsulfonyl-$C_1$–$C_8$-alkyl, aminocarbonyl-$C_1$–$C_8$-alkyl, $C_1$–$C_8$-alkyloxycarbonylamino-$C_1$–$C_8$-alkyl, and amino-$C_1$–$C_8$-alkyl. Except where the member is —H or OH, any member of this group optionally is substituted with one or more substituents independently selected from the group consisting of halogen, —OH, —CN, —C(O)—OH, —SH, —$SO_3H$, and $NO_2$. The nitrogen of the amino-$C_1$–$C_8$-alkyl optionally is substituted with 1 or 2 substituents independently selected from the group consisting of $C_1$–$C_8$-alkyl, $C_1$–$C_8$-alkylcarbonyl, carbocyclyl, and carbocyclyl-$C_1$–$C_8$-alkyl. No greater than one of $R^C$ or $R^D$ is —OH.

In some preferred embodiments, $A^4$ is —H, $C_1$–$C_6$-alkyl (often preferably $C_1$–$C_4$-alkyl, and more preferably ethyl), $C_1$–$C_6$-alkoxy-$C_1$–$C_6$-alkyl (often preferably $C_1$–$C_2$-alkoxy-$C_1$–$C_3$-alkyl, and more preferably methoxyethyl), carbocyclyl (often preferably $C_3$–$C_6$-cycloalkyl or phenyl, and more preferably cyclopropyl), carbocyclyl-$C_1$–$C_6$-alkyl (often preferably $C_3$–$C_6$-cycloalkyl-$C_1$–$C_3$-alkyl or phenyl-$C_1$–$C_3$-alkyl, and more preferably cyclopropylmethyl or benzyl), $C_1$–$C_6$-alkylsulfonyl (often preferably $C_1$–$C_2$-alkylsulfonyl, and more preferably methylsulfonyl), $C_3$–$C_6$-alkenyl (often preferably $C_3$–$C_4$-alkenyl, and more preferably $C_3$-alkenyl), $C_3$–$C_6$-alkynyl (often preferably $C_3$–$C_4$-alkynyl, and more preferably $C_3$-alkynyl). Except where the member is —H, any member of these groups optionally is substituted with halogen, but more typically is preferably not substituted with halogen.

In some preferred embodiments, $A^4$ is —H, ethyl, methoxyethyl, cyclopropyl, cyclopropylmethyl, or benzyl.

X may be selected from a wide range of substituents. The following discussion describes several specific preferred embodiments encompassing the substituents that Applicants have found to be generally preferred.

Preferred Embodiment No. 1

In some embodiments of this invention, the compound has a structure corresponding to Formula II:

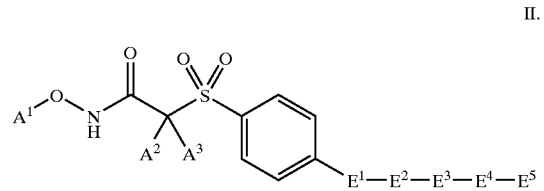

II.

$A^1$, $A^2$, and $A^3$ are as defined above for Formula I.

$E^1$ is —O—, —$S(O)_2$—, —S(O), —$N(R^1)$—, —C(O)—$N(R^1)$—, —$N(R^1)$—C(O)—, or —$C(R^1)(R^2)$—. $E^1$ alternatively may be —S—.

$E^2$ forms a link of at least 2 carbon atoms between $E^1$ and $E^3$. $E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_2$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$-alkyl.

In some preferred embodiments, $E^2$ is $C_2$–$C_6$-alkyl optionally substituted with one or more halogen.

In some preferred embodiments, $E^2$ is $C_2$–$C_6$-alkyl.

In some preferred embodiments, $E^2$ is $C_2$–$C_6$-alkyl.

$E^3$ is —C(O)—, —O—(CO)—, —C(O)—O—, —C(NR$^3$)—, —N(R$^4$)—, —C(O)—N(R$^4$)—, —N(R$^4$)—C(O)—, —N(R$^4$)—C(O)—N(R$^5$)—, —S—, —S(O)—, —N(R$^4$)—S(O)$_2$—, —S(O)$_2$—N(R$^4$)—, —C(O)—N(R$^4$)—N(R$^5$)—C(O)—, —C(R$^4$)(R$^6$)—C(O)—, or —C(R$^7$)(R$^8$)—.

$E^4$ is a bond, alkyl, or alkenyl. The alkyl and alkenyl optionally are substituted.

In some preferred embodiments, $E^4$ is a bond, $C_1$–$C_{20}$-alkyl, or $C_2$–$C_{20}$-alkenyl. The $C_1$–$C_{20}$-alkyl and $C_2$–$C_{20}$-alkenyl optionally are substituted with one or more substituents independently selected from the group consisting of halogen and carbocyclyl. This carbocyclyl, in turn, optionally is substituted with one or more substituents independently selected from the group consisting of halogen, —OH, —NO$_2$, —CN, $C_1$–$C_8$-alkyl, $C_1$–$C_8$-alkoxy, $C_1$–$C_8$-alkoxy-$C_1$–$C_8$-alkyl, carbocyclyl, carbocyclyl-$C_1$–$C_8$-alkyl, halo-$C_1$–$C_8$-alkyl, halo-$C_1$–$C_8$-alkoxy, halogen-substituted $C_1$–$C_8$-alkoxy-$C_1$–$C_8$-alkyl, halocarbocyclyl, and halogen-substituted carbocyclyl-$C_1$–$C_8$-alkyl.

In some preferred embodiments, $E^4$ a bond, $C_1$–$C_3$-alkyl, or $C_2$–$C_3$-alkenyl. The $C_1$–$C_3$-alkyl, and $C_2$–$C_3$-alkenyl optionally are substituted with one or more substituents independently selected from the group consisting of halogen and carbocyclyl. This carbocyclyl, in turn, optionally is substituted with one or more substituents independently selected from the group consisting of halogen, —OH, —NO$_2$, —CN, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halocarbocyclyl, and halogen-substituted carbocyclyl-$C_1$–$C_6$-alkyl.

In some preferred embodiments, $E^4$ is a bond, $C_1$–$C_3$-alkyl, or $C_2$–$C_3$-alkenyl.

$E^5$ is —H, —OH, alkyl, alkenyl, alkynyl, alkoxy, alkoxyalkyl, carbocyclyl, or heterocyclyl. Except where $E^5$ is —H or —OH, any member of this group optionally is substituted. $E^5$ is not —H when both $E^3$ is —C(R$^7$)(R$^8$)— and $E^4$ is a bond.

In some preferred embodiments, $E^5$ is —H, —OH, $C_1$–$C_{20}$-alkyl, $C_2$–$C_{20}$-alkenyl, $C_2$–$C_{20}$-alkynyl, $C_1$–$C_{20}$-alkoxy, $C_1$–$C_{20}$-alkoxy-$C_1$–$C_{20}$-alkyl, carbocyclyl, or heterocyclyl. The $C_1$–$C_{20}$-alkyl, $C_2$–$C_{20}$-alkenyl, $C_2$–$C_{20}$-alkynyl, $C_1$–$C_{20}$-alkoxy, and $C_1$–$C_{20}$-alkoxy-$C_1$–$C_{20}$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, $C_1$–$C_8$-alkyl, $C_1$–$C_8$-alkoxy, $C_1$–$C_8$-alkoxy-$C_1$–$C_8$-alkyl, —N(R$^{11}$)(R$^{12}$), —C(O)(R$^{13}$), —S—R$^{11}$, —S(O)$_2$—R$^{11}$, carbocyclyl, carbocyclyl-$C_1$–$C_8$-alkyl, halo-$C_1$–$C_8$-alkyl, halo-$C_1$–$C_8$-alkoxy, halogen-substituted $C_1$–$C_8$-alkoxy-$C_1$–$C_8$-alkyl, halocarbocyclyl, and halogen-substituted carbocyclyl-$C_1$–$C_8$-alkyl. The carbocyclyl and heterocyclyl also optionally are substituted with one or more substituents independently selected from the group consisting of $C_1$–$C_8$-alkylcarbocyclyl, halogen-substituted $C_1$–$C_8$-alkylcarbocyclyl, hydroxycarbocyclyl, and heterocyclyl.

In some preferred embodiments, $E^5$ is —H, —OH, $C_1$–$C_8$-alkyl, $C_2$–$C_8$-alkenyl, $C_2$–$C_8$-alkynyl, $C_1$–$C_8$-alkoxy, $C_1$–$C_8$-alkoxy-$C_1$–$C_8$-alkyl, carbocyclyl, or heterocyclyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, $C_1$–$C_6$-alkyl, $C_1$–$C_6$-alkoxy, $C_1$–$C_6$-alkoxy-$C_1$–$C_6$-alkyl, —N(R$^{11}$)(R$^{12}$), —C(O)(R$^{13}$), —S—R$^{11}$, —S(O)$_2$—R$^{11}$, carbocyclyl, carbocyclyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halocarbocyclyl, halogen-substituted carbocyclyl-$C_1$–$C_6$-alkyl, $C_1$–$C_6$-alkylcarbocyclyl, halogen-substituted $C_1$–$C_6$-alkylcarbocyclyl, hydroxycarbocyclyl, and heteroaryl.

In some preferred embodiments, $E^5$ is furanyl, tetrahydropyranyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, dioxazolyl, oxathiazolyl, oxathiolyl, oxathiolanyl, pyranyl, dihydropyranyl, pyridinyl, piperidinyl, diazinyl, piperazinyl, triazinyl, oxazinyl, isoxazinyl, oxathiazinyl, oxadiazinyl, morpholinyl, azepinyl, oxepinyl, thiepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofilranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, or acridinyl. Such substituent optionally is substituted with one or more substituents independently selected from the group consisting of halogen, —OH, —NO$_2$, —CN, $C_1$–$C_6$-alkyl, $C_1$–$C_6$-alkoxy, $C_1$–$C_6$-alkoxy-$C_1$–$C_6$-alkyl, —N(R$^{11}$)(R$^{12}$), —C(O)(R$^{13}$), —S—R$^{11}$, —S(O)$_2$—R$^{11}$, aryl, aryl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, haloaryl, and halogen-substituted aryl-$C_1$–$C_6$-alkyl. Any member of such group also optionally is substituted with one or more substituent independent selected from the group consisting of $C_1$–$C_6$-alkylaryl, halogen-substituted $C_1$–$C_6$-alkylaryl, hydroxyaryl, and heteroaryl.

In some preferred embodiments, $E^5$ is indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, or pyridofuranyl. Such substituent optionally is substituted with one or more substituents independently selected from the group consisting of halogen, —OH, —NO$_2$, —CN, C$_1$–C$_6$-alkyl, C$_1$–C$_6$-alkoxy, C$_1$–C$_6$-alkoxy-C$_1$–C$_6$-alkyl, —N(R$^{11}$)(R$^{12}$), —C(O)(R$^{13}$), —S—R$^{11}$, —S(O)$_2$—R$^{11}$, aryl, aryl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, haloaryl, halogen-substituted aryl-C$_1$–C$_6$-alkyl. Such substituent also optionally is substituted with one or more substituents independently selected from the group consisting of C$_1$–C$_6$-alkylaryl, halogen-substituted C$_1$–C$_6$-alkylaryl, hydroxyaryl, and heteroaryl.

In some preferred embodiments, E$^5$ is benzazinyl, benzofuranyl, or tetrahydroisoquinolinyl. Such substituent optionally is substituted with one or more substituents independently selected from the group consisting of halogen, —OH, —NO$_2$, —CN, C$_1$–C$_6$-alkyl, C$_1$–C$_6$-alkoxy, C$_1$–C$_6$-alkoxy-C$_1$–C$_6$-alkyl, —N(R$^{11}$)(R$^{12}$), —C(O)(R$^{13}$), —S—R$^{11}$, —S(O)$_2$—R$^{11}$, aryl, aryl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, haloaryl, and halogen-substituted aryl-C$_1$–C$_6$-alkyl. Such substituent also optionally is substituted with one or more substituents independently selected from the group consisting of C$_1$–C$_6$-alkylaryl, halogen-substituted C$_1$–C$_6$-alkylaryl, hydroxyaryl, and heteroaryl.

In some preferred embodiments, E$^5$ is indolyl, benzoxazolyl, benzothienyl, benzothiazolyl, or pyridofuranyl. Such substituent any member of such group optionally is substituted with one or more substituents independently selected from the group consisting of halogen, —OH, —NO$_2$, —CN, C$_1$–C$_6$-alkyl, C$_1$–C$_6$-alkoxy, C$_1$–C$_6$-alkoxy-C$_1$–C$_6$-alkyl, —N(R$^{11}$)(R$^{12}$), —C(O)(R$^{13}$), —S—R$^{11}$, —S(O)$_2$—R$^{11}$, aryl, aryl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, haloaryl, and halogen-substituted aryl-C$_1$–C$_6$-alkyl. Such substituent also optionally is substituted with one or more substituents independently selected from the group consisting of C$_1$–C$_6$-alkylaryl, halogen-substituted C$_1$–C$_6$-alkylaryl, hydroxyaryl, and heteroaryl.

R$^1$ and R$^2$ are independently selected from the group consisting of —H and alkyl. The alkyl optionally is substituted. Neither R$^1$ nor R$^2$ forms a ring structure with E$^2$, E$^3$, or E$^5$.

In some preferred embodiments, R$^1$ and R$^2$ are independently selected from the group consisting of —H, C$_1$–C$_8$-alkyl, and halo-C$_1$–C$_8$-alkyl.

In some preferred embodiments, R$^1$ and R$^2$ are independently selected from the group consisting of —H, C$_1$–C$_6$-alkyl, and halo-C$_1$–C$_6$-alkyl.

In some preferred embodiments, R$^1$ and R$^2$ are independently selected from the group consisting of —H, and C$_1$–C$_6$-alkyl.

R$^3$ is —H or —OH.

R$^4$ and R$^5$ are independently selected from the group consisting of —H, alkyl, carbocyclyl, carbocyclylalkyl, heterocyclyl, and heterocyclylalkyl. Except for —H, any member of this group optionally is substituted. Neither R$^4$ nor R$^5$ forms a ring structure with E$^2$, E$^4$, or E$^5$.

In some preferred embodiments, R$^4$ and R$^5$ are independently selected from the group consisting of —H, C$_1$–C$_8$-alkyl, carbocyclyl, carbocyclyl-C$_1$–C$_8$-alkyl, heterocyclyl, and heterocyclyl-C$_1$–C$_8$-alkyl. Except where the member is —H, any member of this group may be substituted with one or more halogen, but more typically is preferably not substituted with halogen.

In some preferred embodiments, R$^4$ and R$^5$ are independently selected from the group consisting of —H, C$_1$–C$_6$-alkyl, carbocyclyl, carbocyclyl-C$_1$–C$_6$-alkyl, heterocyclyl, and heterocyclyl-C$_1$–C$_6$-alkyl. Except where the member is —H, any member of this group optionally is substituted with one or more halogen, but more typically is preferably not substituted with halogen.

R$^6$ is —CN or —OH.

R$^7$ is —H, halogen, —OH, alkyl, alkoxy, or alkoxyalkyl. The alkyl, alkoxy, and alkoxyalkyl optionally are substituted.

In some preferred embodiments, R$^7$ is —H, halogen, —OH, C$_1$–C$_8$-alkyl, C$_1$–C$_8$-alkoxy, C$_1$–C$_8$-alkoxy-C$_1$–C$_8$-alkyl, halo-C$_1$–C$_8$-alkyl, halo-C$_1$–C$_8$-alkoxy, or halogen-substituted C$_1$–C$_8$-alkoxy-C$_1$–C$_8$-alkyl.

In some preferred embodiments, R$^7$ is —H, halogen, —OH, C$_1$–C$_6$-alkyl, C$_1$–C$_6$-alkoxy, C$_1$C$_6$-alkoxy-C$_1$–C$_6$-alkyl, halo-C$_1$–C$_6$-alkyl, halo-C$_1$–C$_6$-alkoxy, or halogen-substituted C$_1$–C$_6$-alkoxy-C$_1$–C$_6$-alkyl.

In some preferred embodiments, R$^7$ is —H, halogen, —OH, C$_1$–C$_6$-alkyl, C$_1$–C$_6$-alkoxy, or C$_1$–C$_6$-alkoxy-C$_1$–C$_6$-alkyl.

R$^8$ is —OH or alkoxy. The alkoxy optionally is substituted.

In some preferred embodiments, R$^8$ is —OH, C$_1$–C$_8$-alkoxy, or halo-C$_1$–C$_8$-alkoxy.

In some preferred embodiments, R$^8$ is —OH, C$_1$–C$_6$-alkoxy, or halo-C$_1$–C$_6$-alkoxy.

In some preferred embodiments, R$^8$ is —OH or C$_1$–C$_6$-alkoxy.

R$^{11}$ and R$^{12}$ are independently selected from the group consistingof —H. C$_1$–C$_8$-alkyl, carbocyclyl, carbocyclyl-C$_1$–C$_8$-alkyl, heterocyclyl, and heterocyclyl-C$_1$–C$_8$-alkyl. Except where the member is —H, any member of this group may be substituted with one or more halogen, but more typically is preferably not substituted with halogen.

In some preferred embodiments, R$^{11}$ and R$^{12}$ are independently selected from the group consisting of —H, C$_1$–C$_6$-alkyl, carbocyclyl, carbocyclyl-C$_1$–C$_6$-alkyl, heterocyclyl, and heterocyclyl-C$_1$–C$_6$-alkyl. Except where the member is —H, any member of this group may be substituted with one or more halogen, but more typically is preferably not substituted with halogen.

R$^{13}$ is —H, C$_1$–C$_8$-alkyl, —O—R$^{14}$, —N(R$^{14}$)(R$^{15}$), carbocyclyl-C$_1$–C$_8$-alkyl, heterocyclyl-C$_1$–C$_8$-alkyl, halo-C$_1$–C$_8$-alkyl, halogen-substituted carbocyclyl-C$_1$–C$_8$-alkyl, or halogen-substituted heterocyclyl-C$_1$–C$_8$-alkyl.

In some preferred embodiments, R$^{13}$ is —H, C$_1$–C$_6$-alkyl, —O—R$^{14}$, —N(R$^{14}$)(R$^{15}$), carbocyclyl-C$_1$–C$_6$-alkyl, heterocyclyl-C$_1$–C$_6$-alkyl, halo-C$_1$–C$_6$-alkyl, halogen-substituted carbocyclyl-C$_1$–C$_6$-alkyl, or halogen-substituted heterocyclyl-C$_1$–C$_6$-alkyl.

In some preferred embodiments, R$^{13}$ is —H, C$_1$–C$_6$-alkyl, —O—R$^{14}$, —N(R$^{14}$)(R$^{15}$), carbocyclyl-C$_1$–C$_6$-alkyl, or heterocyclyl-C$_1$–C$_6$-alkyl.

R$^{14}$ and R$^{15}$ are independently selected from the group consisting of —H, C$_1$–C$_8$-alkyl, carbocyclyl, carbocyclyl-C$_1$–C$_8$-alkyl, heterocyclyl, and heterocyclyl-C$_1$–C$_8$-alkyl. Except where the member is —H, any member of this group may be substituted with one or more halogen, but typically is preferably not substituted with halogen.

In some preferred embodiments, R$^{14}$ and R$^{15}$ are independently selected from the group consisting of —H, C$_1$–C$_6$-alkyl, carbocyclyl, carbocyclyl-C$_1$–C$_6$-allyl, heterocyclyl, and heterocyclyl-C$_1$–C$_6$-alkyl. Except where the member is —H, any member of this group may be substituted with one or more halogen, but typically is preferably not substituted with halogen.

Preferred Embodiment No. 1a: E$^3$ is —C(O)—

In some embodiments, E$^3$ is —C(O)—.

In some such embodiments, E$^5$ is optionally-substituted carbocyclyl, and often preferably optionally-substituted cycloalkyl or optionally-substituted aryl.

In some preferred embodiments, for example, E$^5$ is optionally-substituted phenyl. Such compounds include, for example:

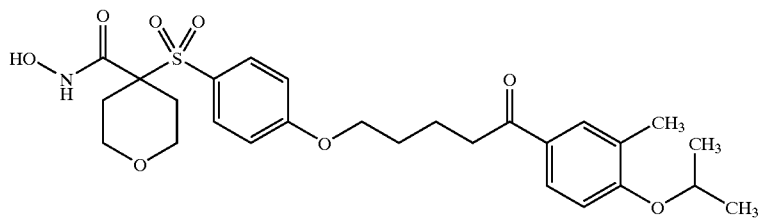
IIA-1
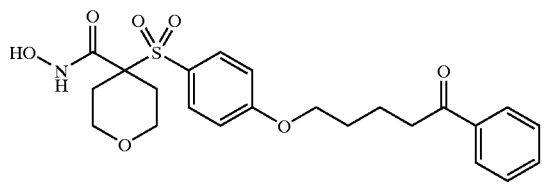
IIA-2
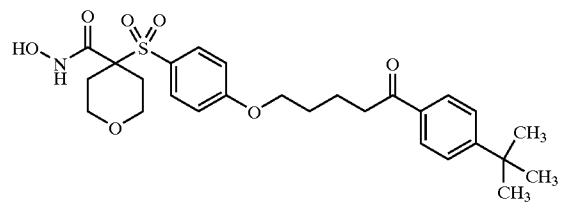
IIA-3
IIA-4
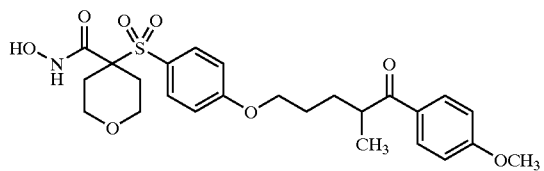
IIA-5
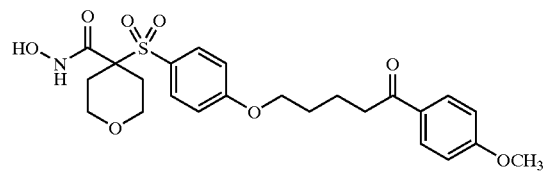
IIA-6
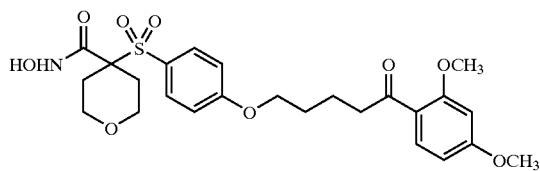
IIA-7
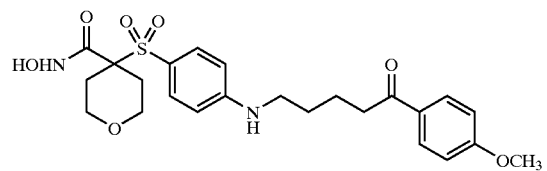
IIA-8
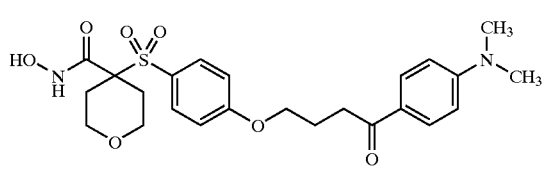
IIA-9
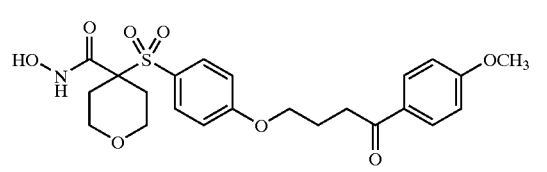
IIA-10
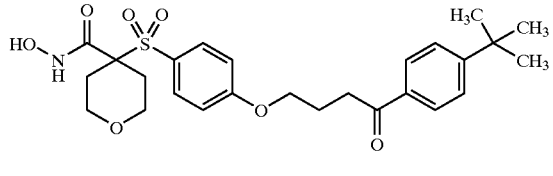
IIA-11
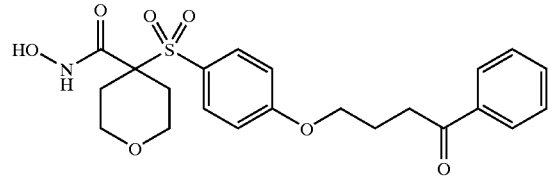
IIA-12

-continued
IIA-13
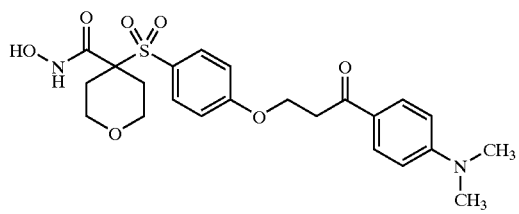
IIA-14
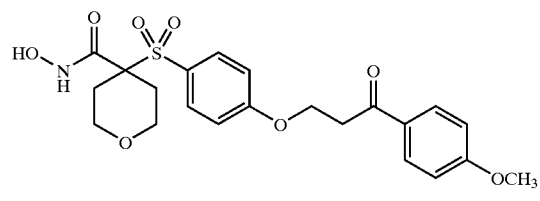
IIA-15
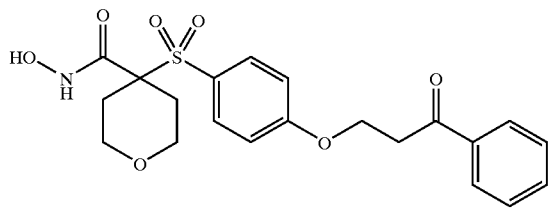
IIA-16
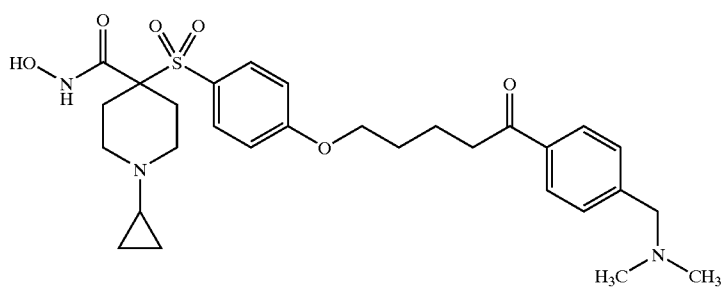
IIA-17
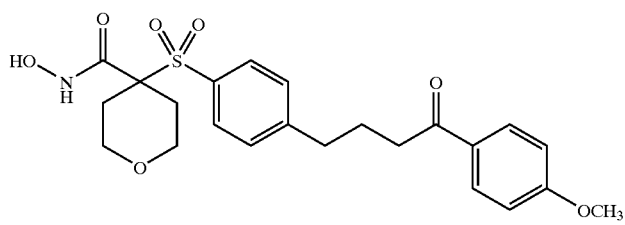
IIA-18
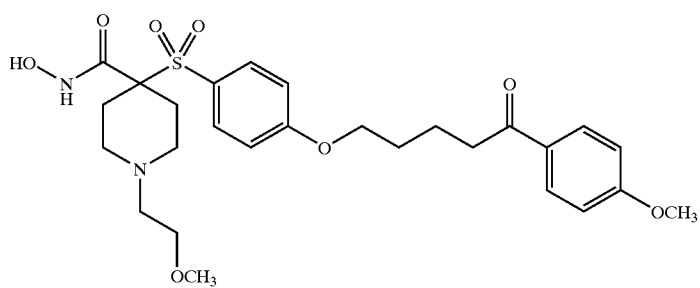
IIA-19
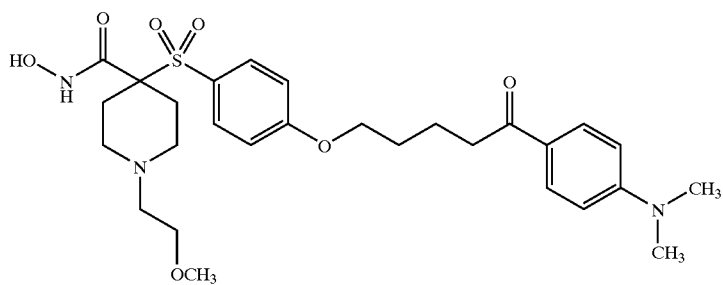

IIA-20
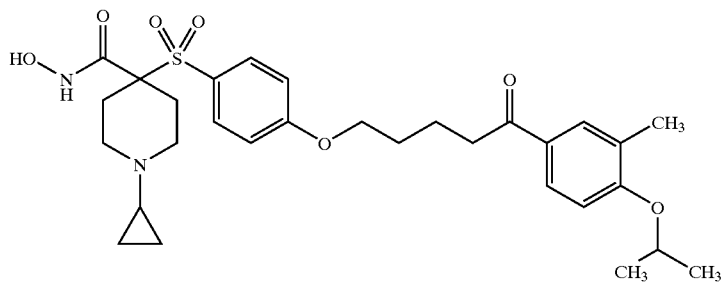
IIA-21
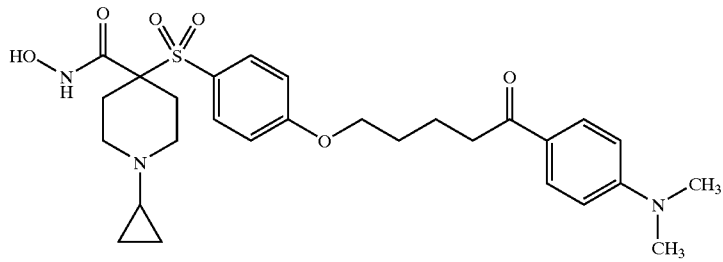
IIA-22
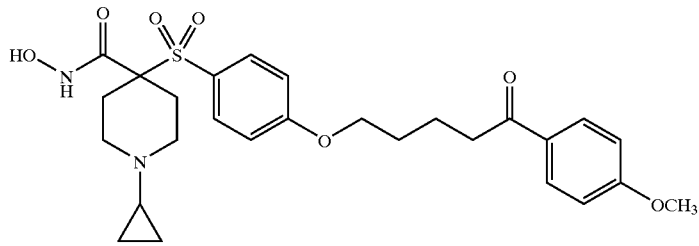
IIA-23
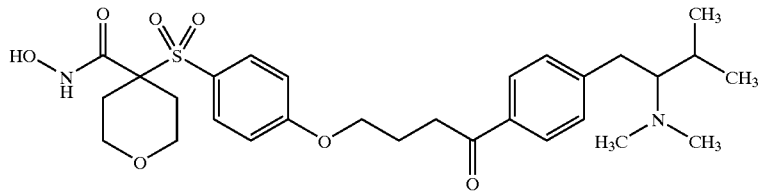
IIA-24
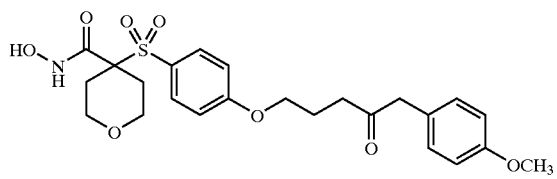
IIA-25
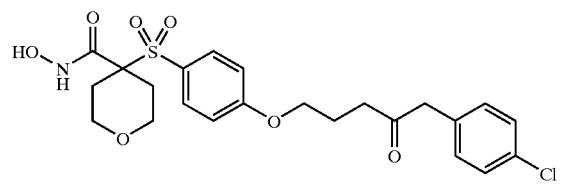
IIA-26
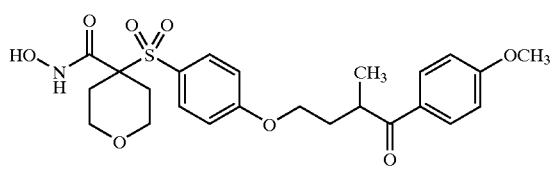
IIA-27
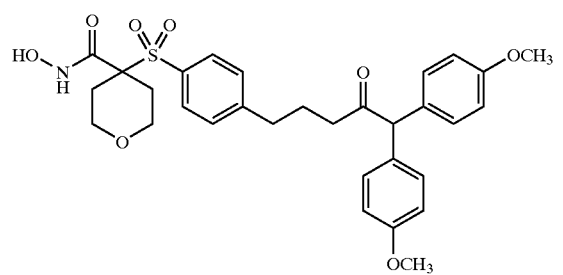

IIA-28

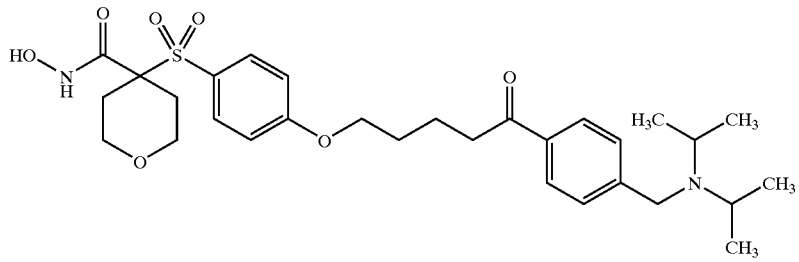

Such compounds also include compounds wherein $E^5$ is phenyl substituted with one or more substituents independently selected from the group consisting of aryl, haloaryl, aryl-$C_1$–$C_6$-alkyl, and halogen-substituted aryl-$C_1$–$C_6$-alkyl. Here, the phenyl also optionally is substituted with one or more substituents independently selected from the group consisting of halogen, —OH, —$NO_2$, —CN, $C_1$–$C_6$-alkyl, $C_1$–$C_6$-alkoxy, $C_1$–$C_6$-alkoxy-$C_1$–$C_6$-alkyl, $N(R^{11})(R^{12})$, —$C(O)(R^{13})$, —S—$R^{11}$, —$S(O)_2$—$R^{11}$, aryl, aryl-$C_1$–$C_6$-alkyl, halo-$C_{1-6}$-alkyl, halo-$C_1$–$C_6$-alkoxy, halogen-substituted $C_1$–$C_6$-alkoxy-$C_1$–$C_6$-alkyl, haloaryl, halogen-substituted aryl-$C_1$–$C_6$-alkyl, $C_1$–$C_6$-alkylaryl, halogen-substituted $C_1$–$C_6$-alkylaryl, hydroxyaryl, and heteroaryl. Such compounds include, for example:

IIA-29

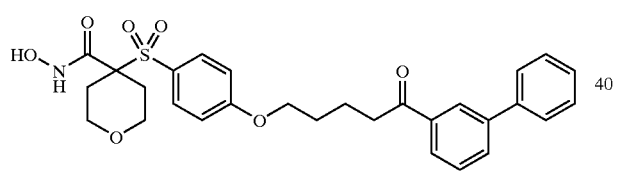

IIA-30

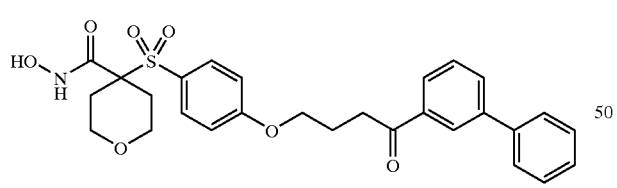

IIA-31

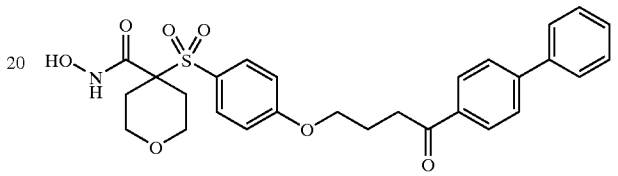

IIA-32

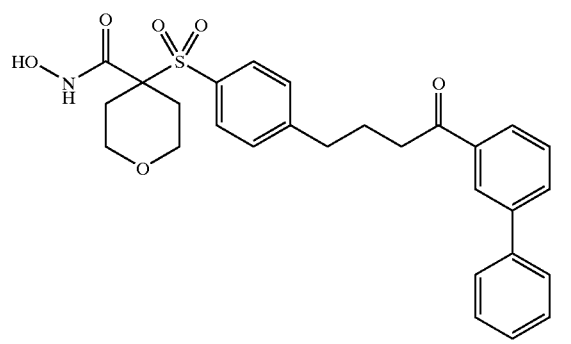

IIA-33

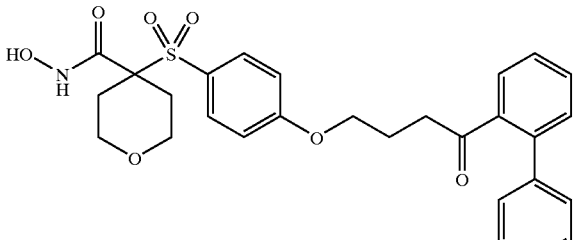

In other preferred embodiments, $E^5$ is optionally-substituted naphthalenyl. Such compounds include, for example:

IIA-34

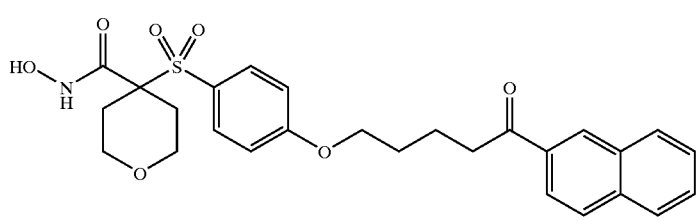

IIA-35
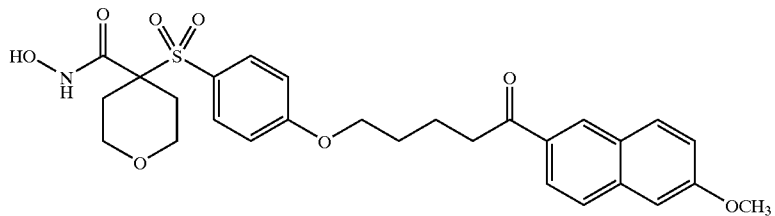
IIA-36
IIA-37
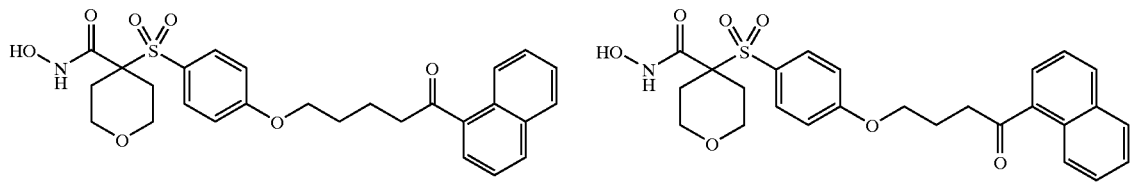
IIA-38
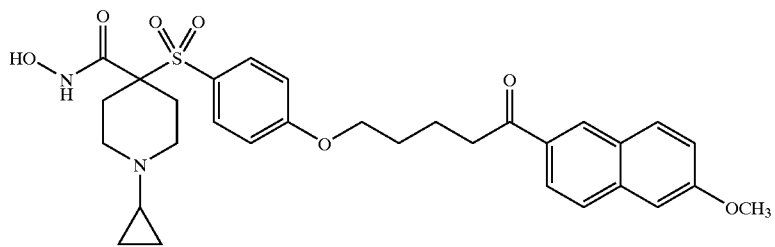
IIA-39
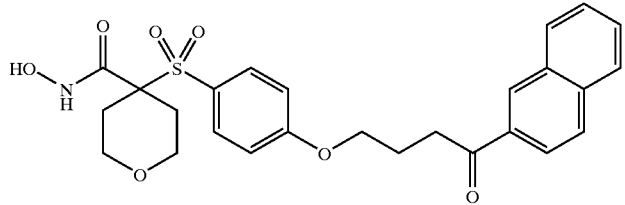
IIA-40
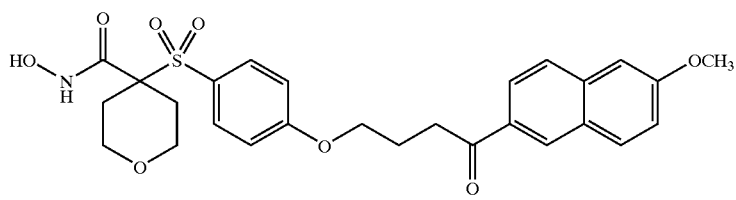

In yet other preferred embodiments, $E^5$ is optionally-substituted $C_5$–$C_6$-cycloalkyl. Such compounds include, for example:

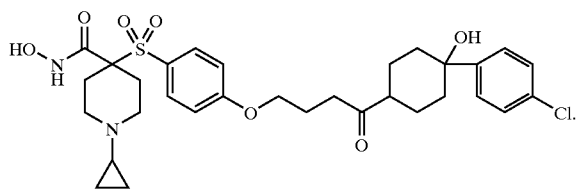

IIA-41

In some preferred embodiments, $E^5$ is —H, —OH, $C_1$–$C_6$-alkyl, $C_2$–$C_6$-alkenyl, $C_2$–$C_6$-alkynyl, $C_1$–$C_6$-alkoxy, or $C_1$–$C_6$-alkoxy-$C_1$–$C_6$-alkyl. The $C_1$–$C_6$-alkyl, $C_2$–$C_6$-alkenyl, $C_2$–$C_6$-alkynyl, $C_1$–$C_6$-alkoxy, and $C_1$–$C_6$-alkoxy-$C_1$–$C_6$-alkyl optionally are substituted with one or more substituents independently selected from the group consisting of halogen, —OH, —NO$_2$, and —CN. Such compounds include, for example:

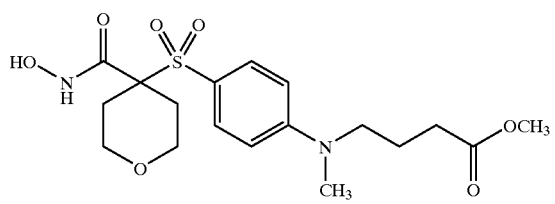

IIA-42

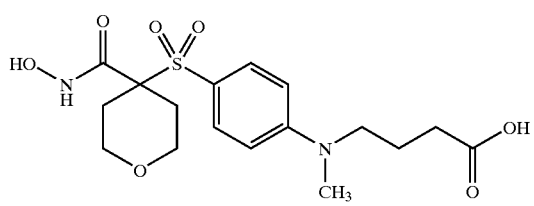

IIA-43

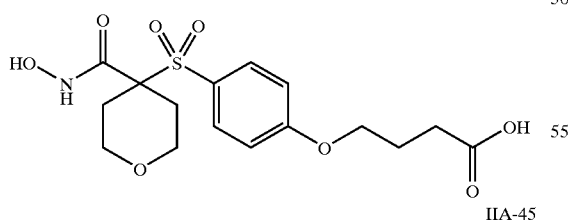

IIA-44

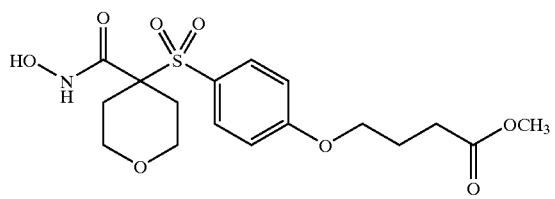

IIA-45

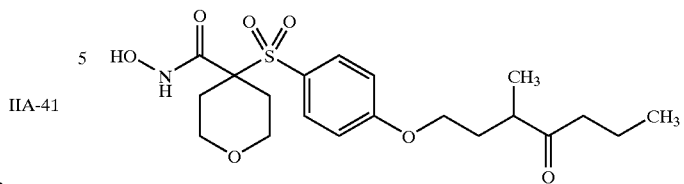

IIA-46

Other such compounds include, for example:

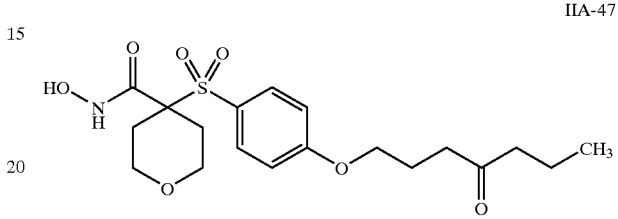

IIA-47

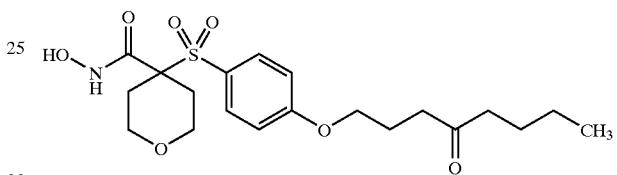

IIA-48

In other preferred embodiments, $E^5$ is optionally-substituted heterocyclyl. In one such embodiment, $E^5$ is optionally-substituted thiophenyl. Such compounds include, for example:

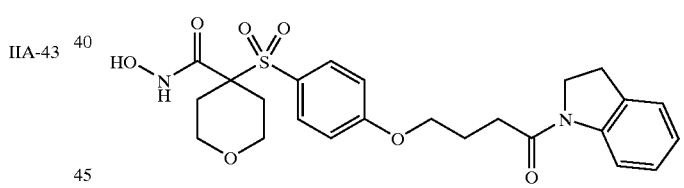

IIA-49

Other such compounds include, for example:

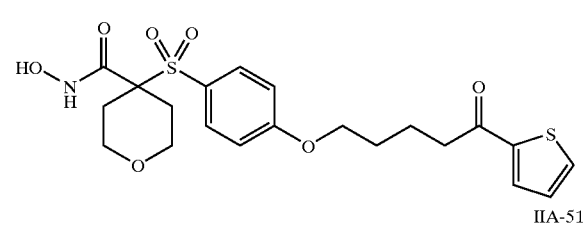

IIA-50

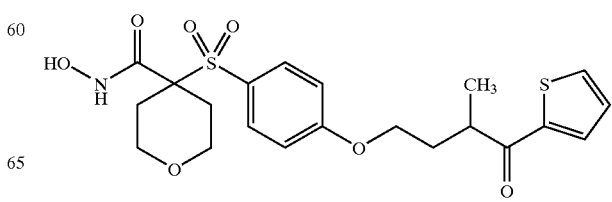

IIA-51

IIA-52

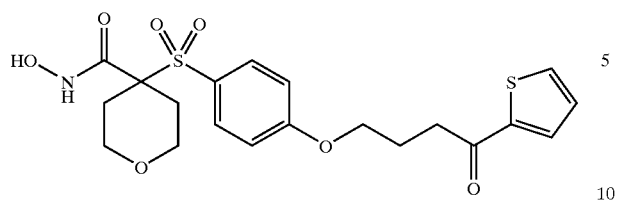

IIB-5

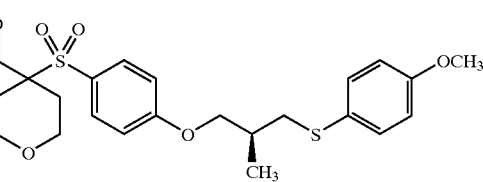

Preferred Embodiment No. 1-b: $E^3$ is —S—

In some embodiments, $E^3$ is —S—.

In some such embodiments, $E^5$ is —H, —OH, $C_1$–$C_8$-alkyl, $C_2$–$C_8$-alkenyl, $C_2$–$C_8$-alkynyl, $C_1$–$C_8$-alkoxy, or $C_1$–$C_8$-alkoxy-$C_1$–$C_8$-alkyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —$NO_2$, and —CN. Such compounds include, for example:

IIB-6

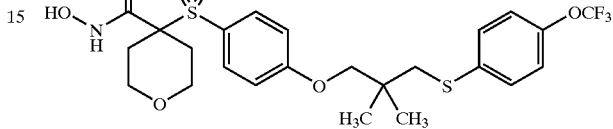

IIB-7

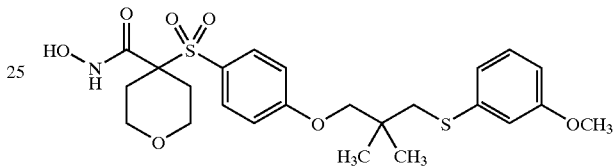

IIB-1

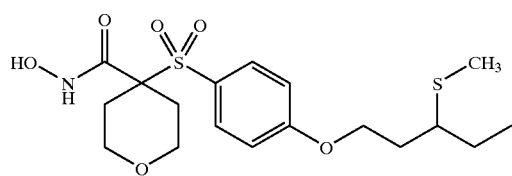

In some preferred embodiments, $E^5$ is optionally-substituted carbocyclyl, often preferably optionally-substituted aryl, and more preferably optionally-substituted phenyl. Such compounds include, for example:

IIB-8

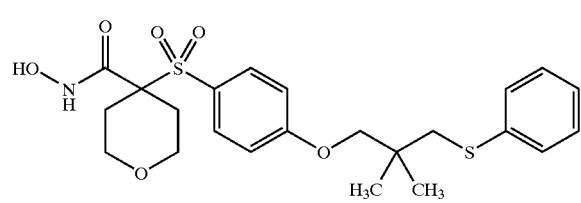

IIB-2

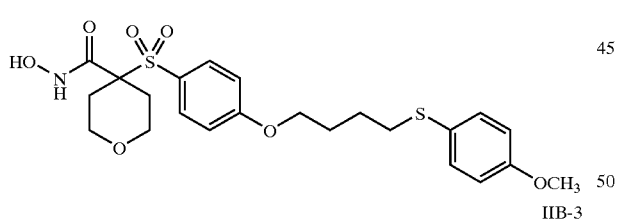

IIB-9

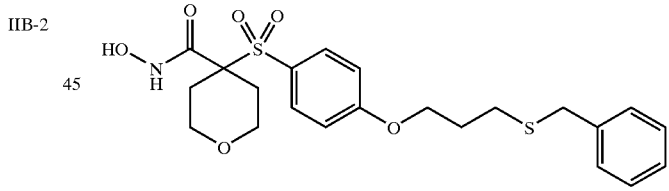

IIB-3

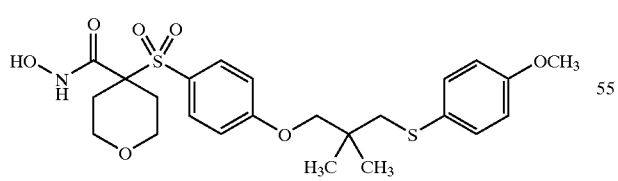

IIB-10

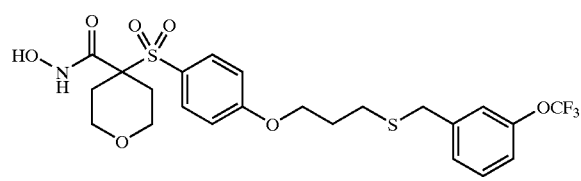

IIB-4

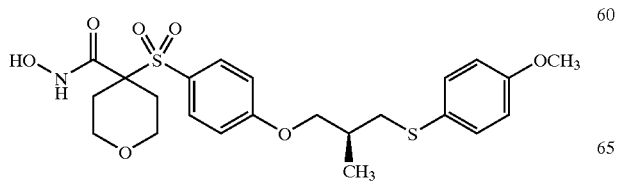

In some preferred embodiments, $E^5$ is optionally-substituted heterocyclyl. In one such embodiment, $E^5$ is optionally-substituted pyrimidinyl. Such compounds include, for example:

IIB-11
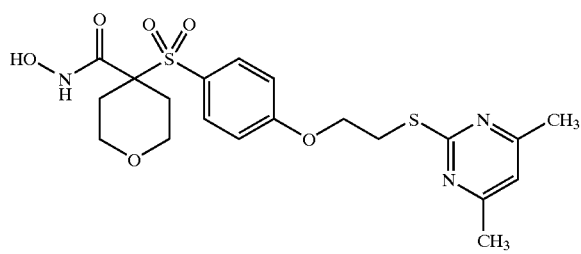
IIB-12
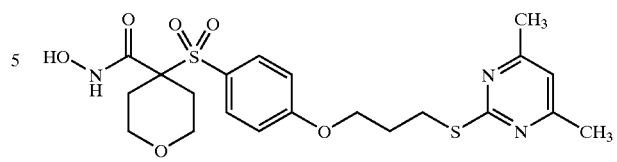
In another such embodiment, $E^5$ is optionally-substituted 2-fused-ring heterocyclyl. In some preferred embodiments, $E^5$ is optionally-substituted benzoxazolyl or optionally-substituted benzothiazolyl. Such compounds include, for example:
IIB-13
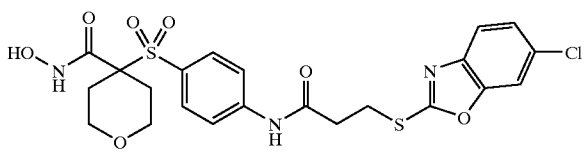
IIB-14
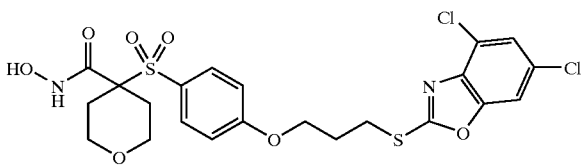
IIB-15
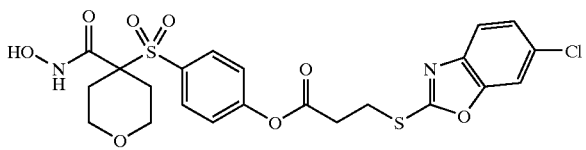
IIB-16
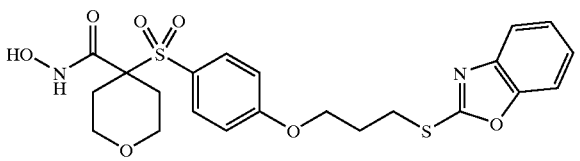
IIB-17
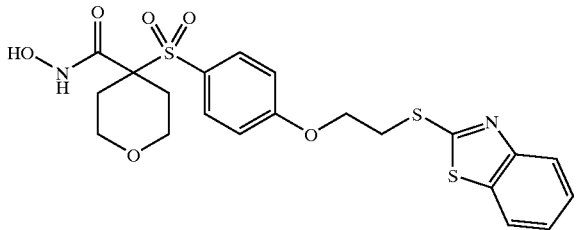
IIB-18
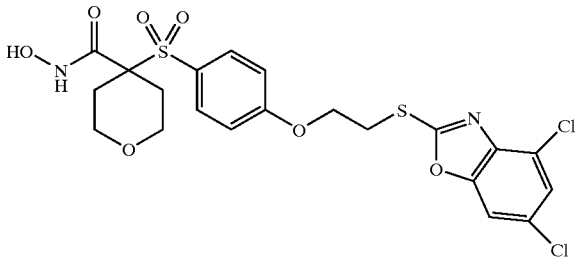
IIB-19
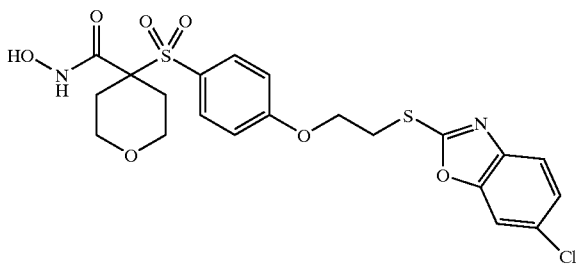
IIB-20
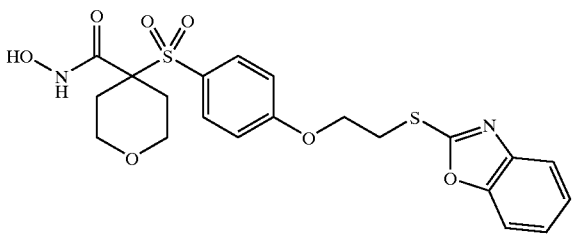
IIB-21
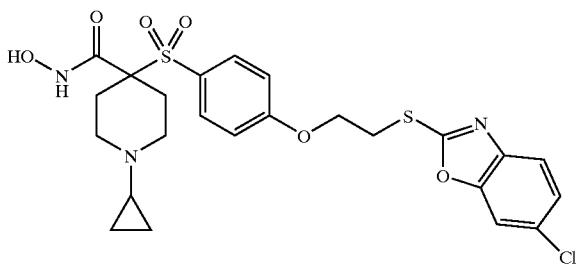
IIB-22
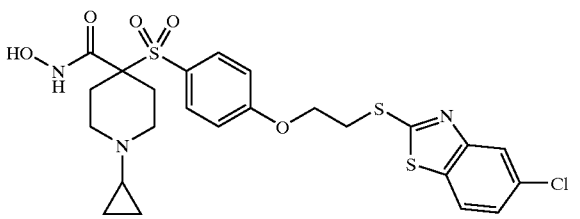

-continued
IIB-23
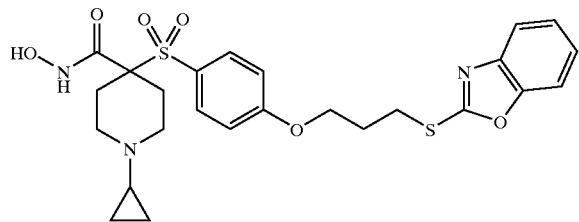
IIB-24
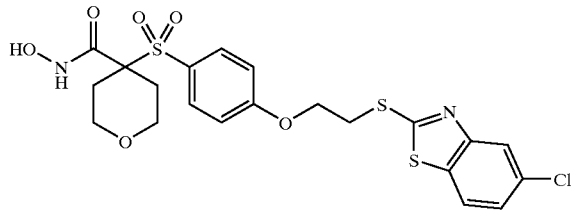
IIB-25
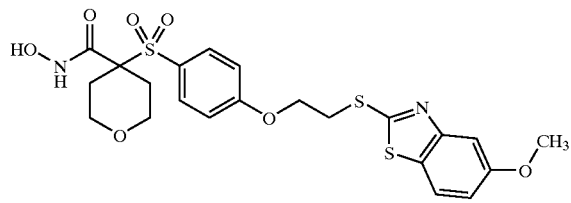
IIB-26
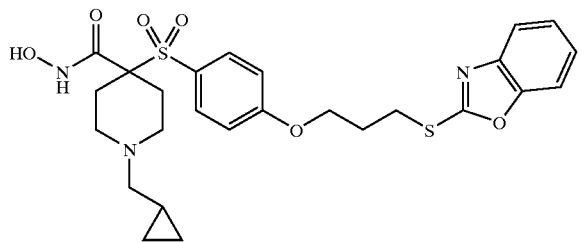
IIB-27
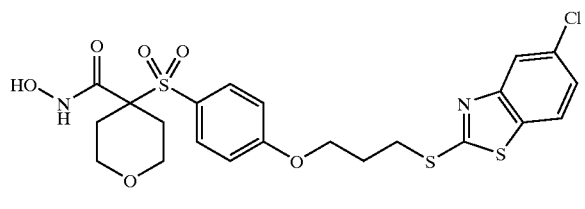
IIB-28
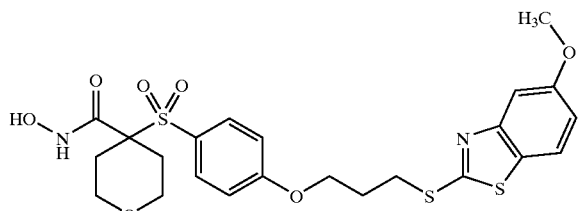
IIB-29
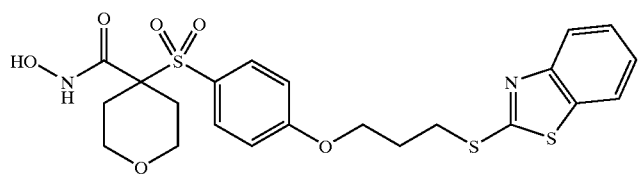
IIB-30
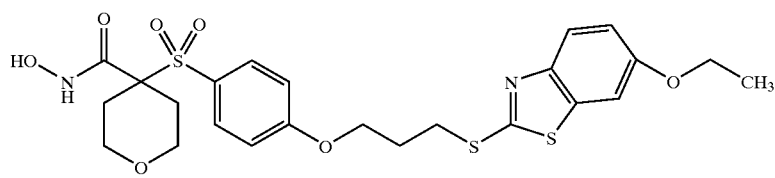
IIB-31
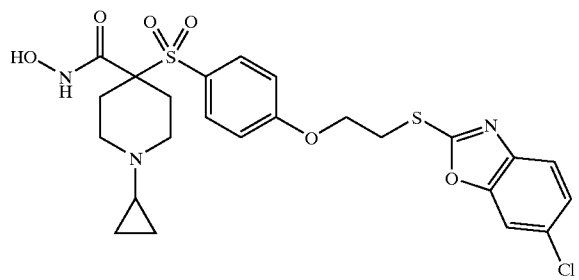
IIB-32
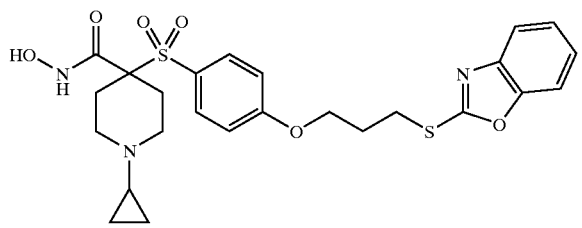

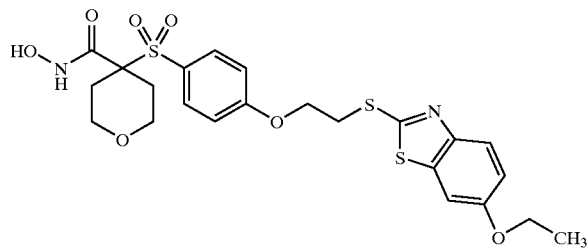
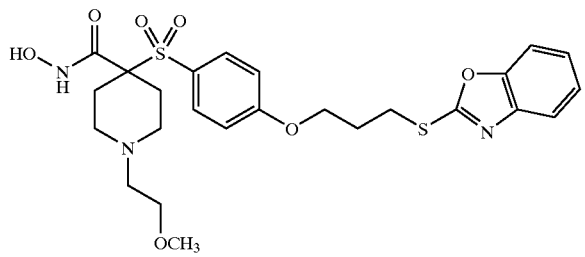
Other such compounds include, for example:
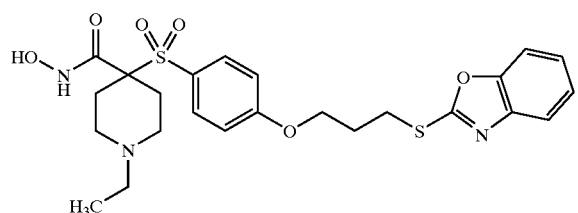
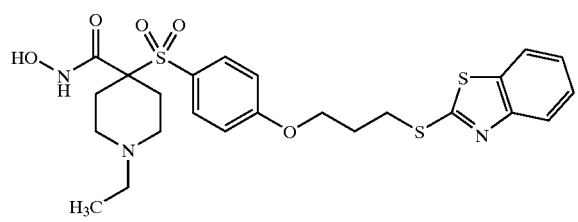
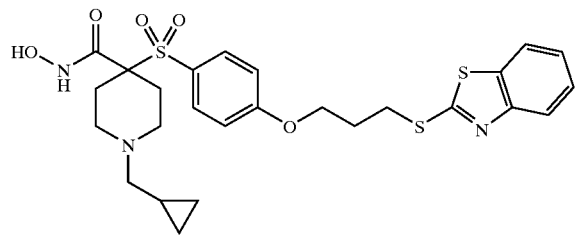
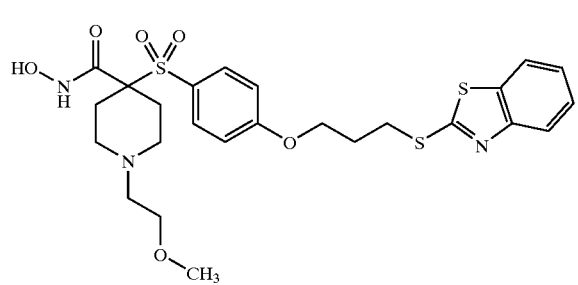
Preferred Embodiment No. 1-c: $E^3$ is —N($R^4$)—C(O)—
In some embodiments, $E^3$ is —N($R^4$)—C(O)—.
In some such embodiments, $E^5$ is optionally-substituted carbocyclyl. In some preferred embodiments, $E^5$ is optionally-substituted phenyl. Such compounds include, for example:
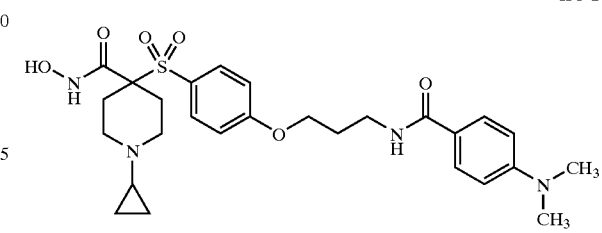
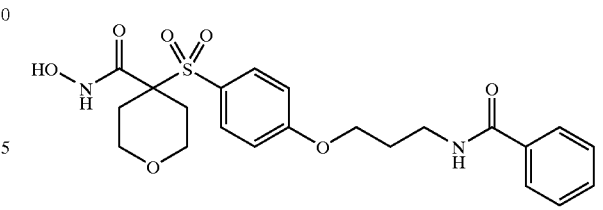
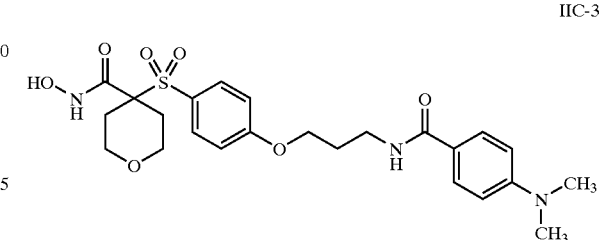
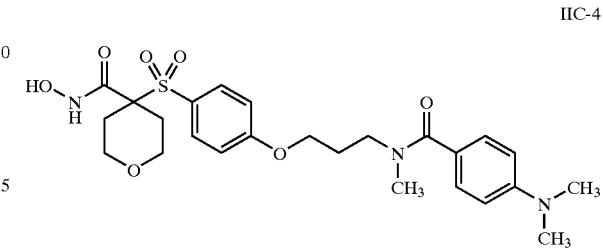
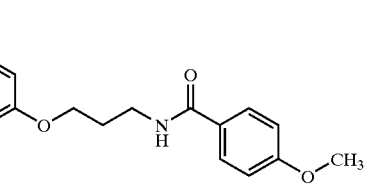

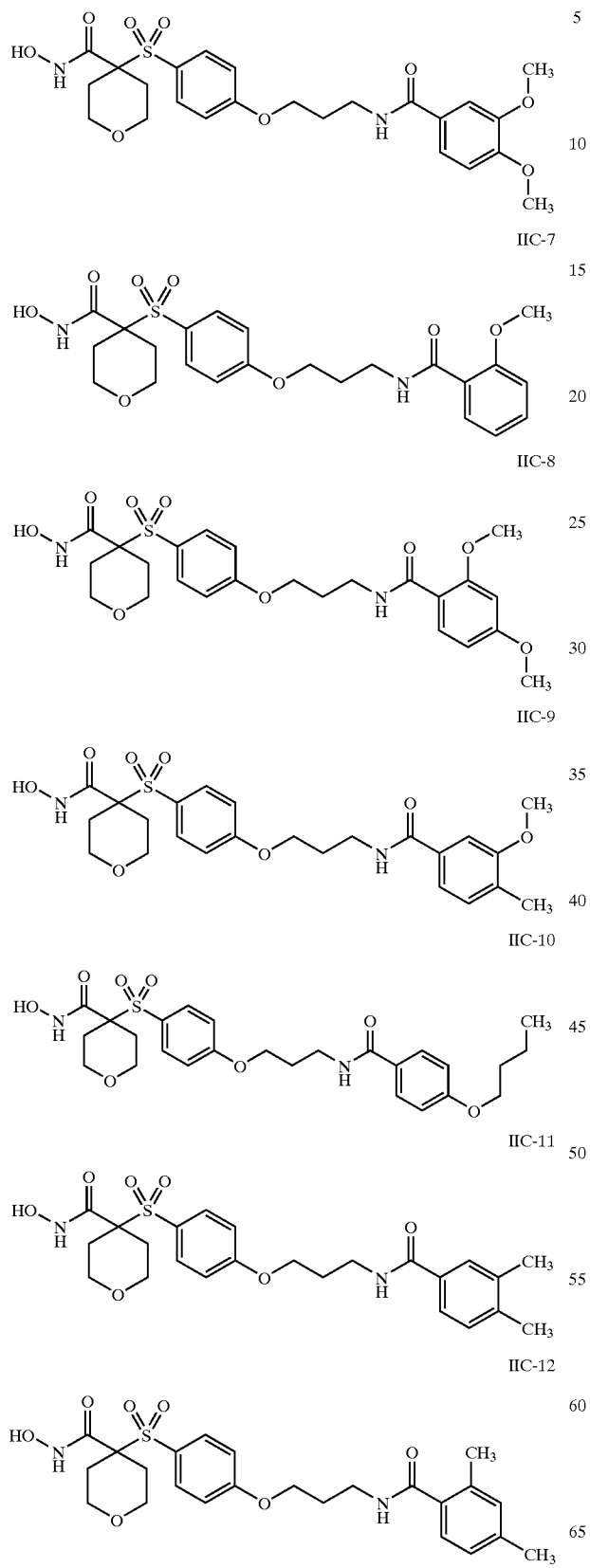
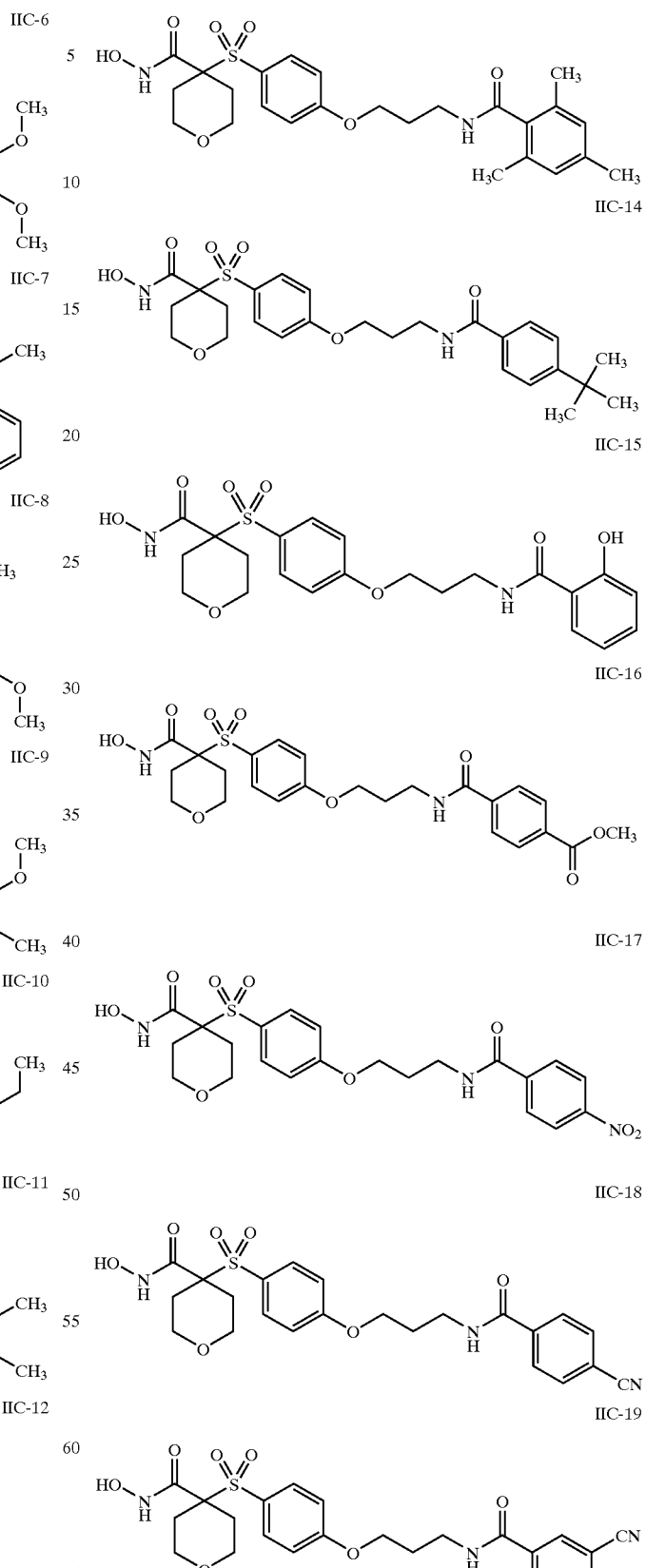

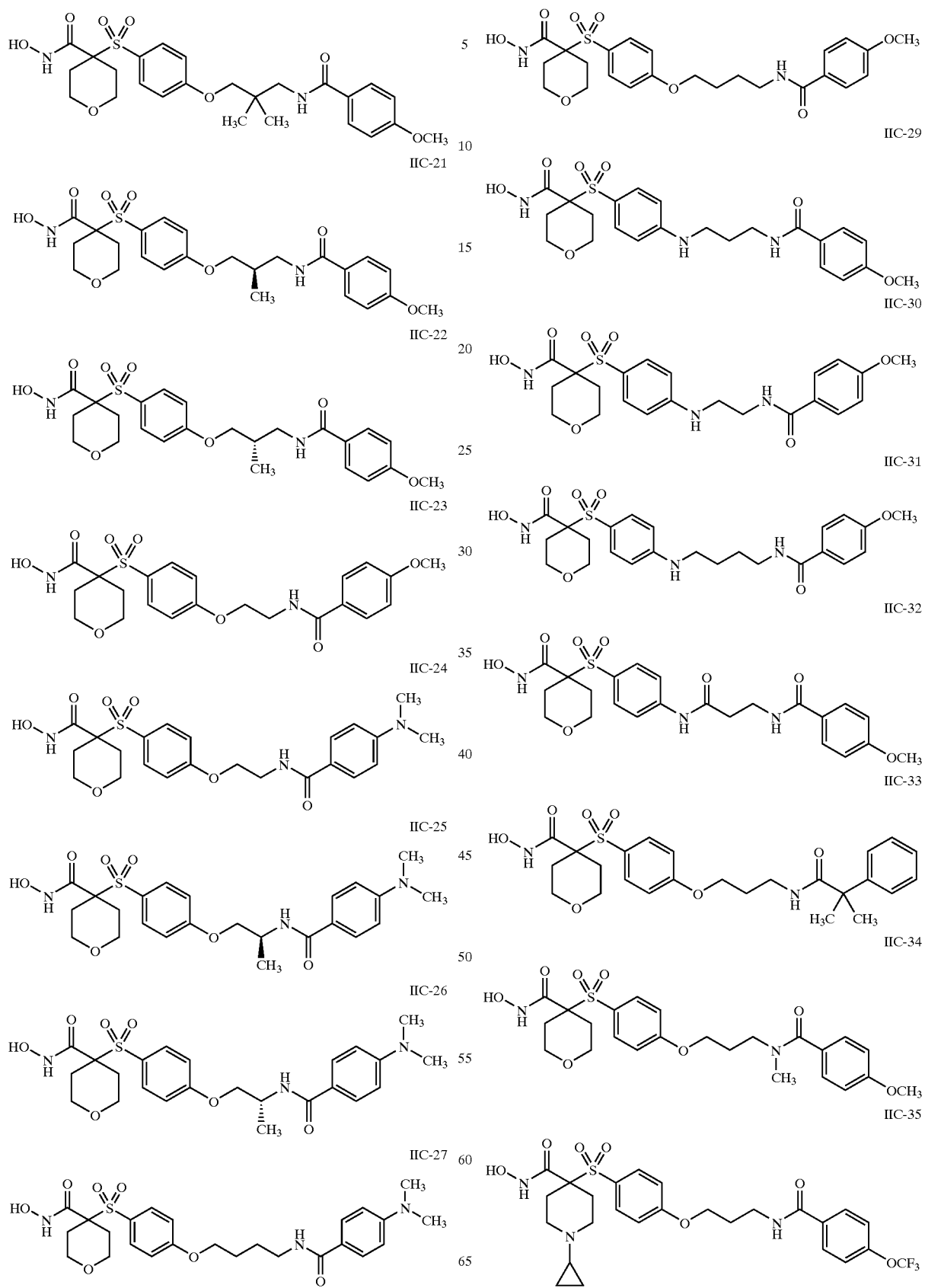

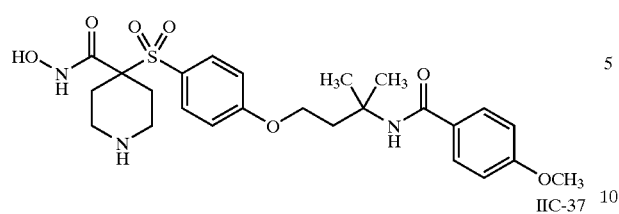
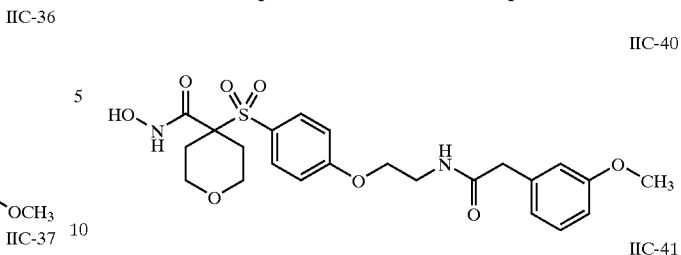
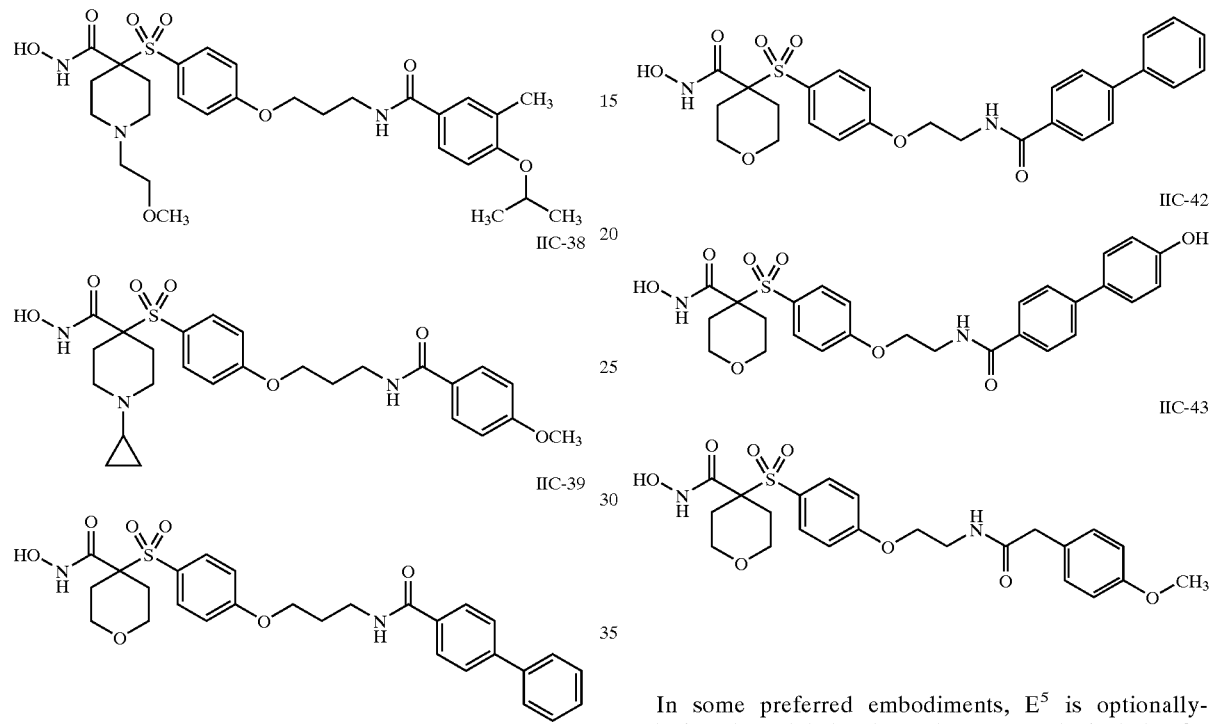
In some preferred embodiments, $E^5$ is optionally-substituted naphthalenyl. Such compounds include, for example:
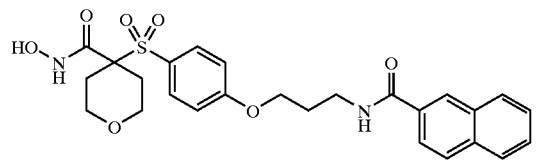
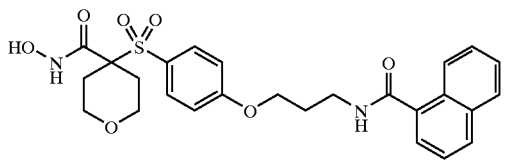
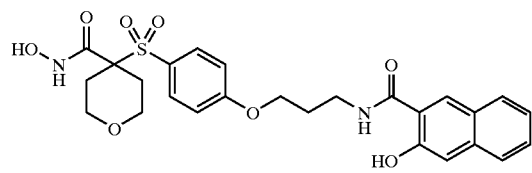
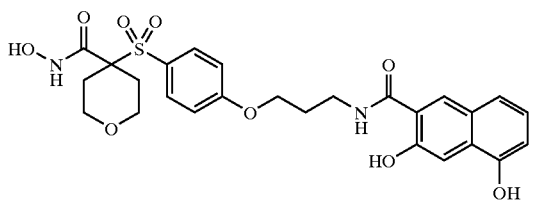

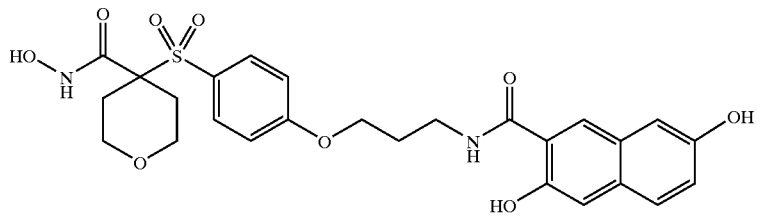
IIC-48
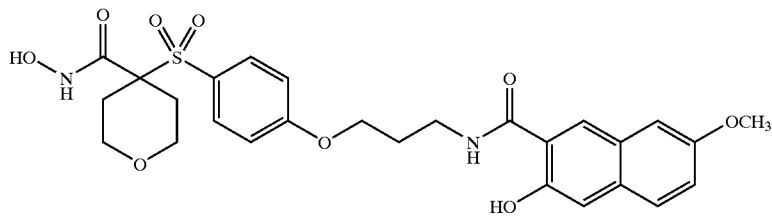
IIC-49
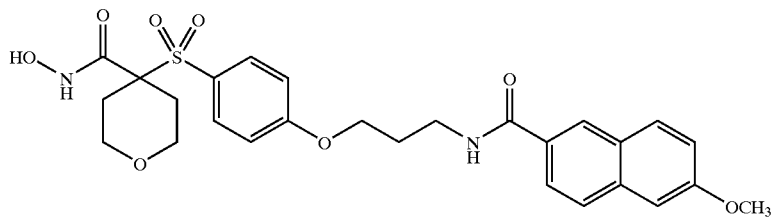
IIC-50
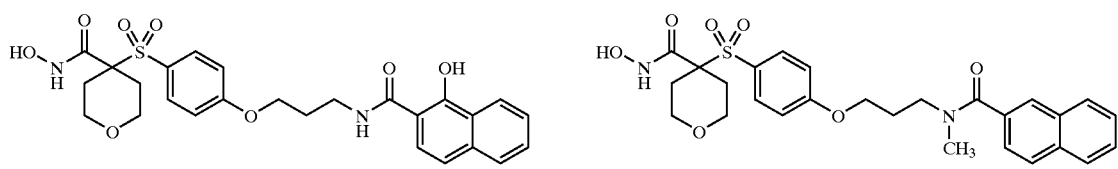
IIC-51                                   IIC-52
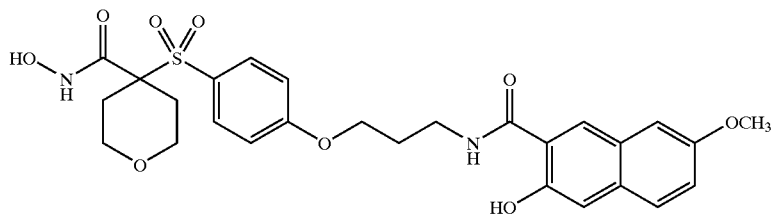
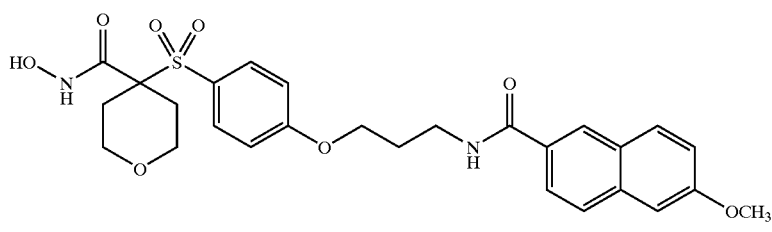
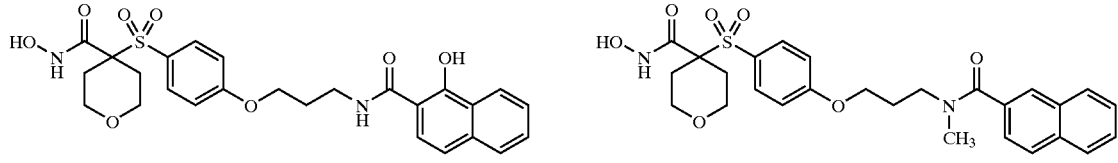

In some preferred embodiments, $E^5$ is optionally-substituted cycloalkyl. Such compounds include, for example, fused-ring cycloalkyls. These compounds include, for example:

IIC-53

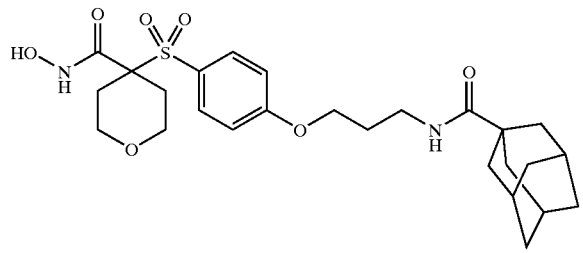

These compounds also include, for example:

IIC-54

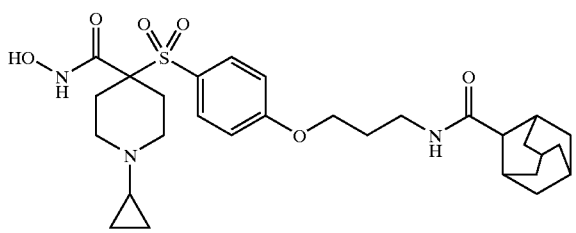

IIC-55

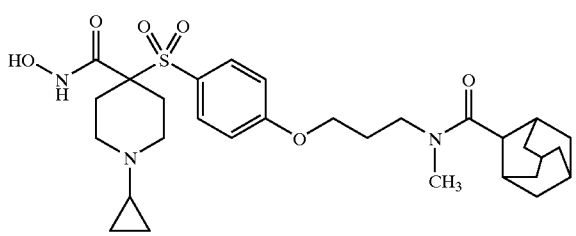

In some preferred embodiments, $E^5$ is optionally-substituted $C_1$–$C_6$-cycloalkyl. These compounds include, for example:

IIC-56

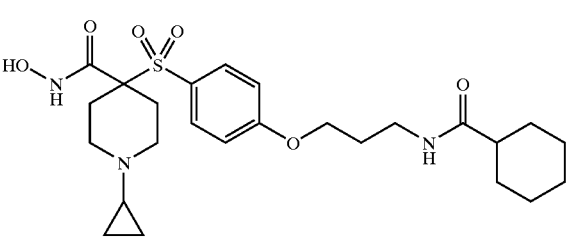

IIC-57

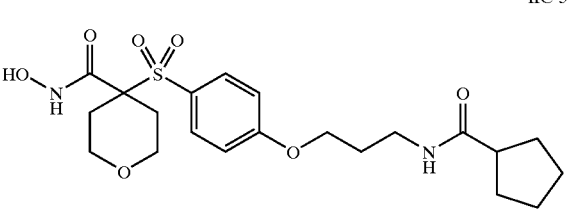

In some preferred embodiments, $E^5$ is optionally-substituted heterocyclyl. In one such embodiment, $E^5$ is an optionally-substituted heterocyclyl selected from the group consisting of pyridinyl, pyrrolyl, isopyrrolyl, oxazolyl, isoxazole, thiazolyl, furanyl, and morpholinyl. In another such embodiment, $E^5$ is an optionally-substituted heterocyclyl selected from the group consisting of tetrazolyl, imidazolyl, and thienyl. Compounds of these embodiments include, for example:

IIC-58

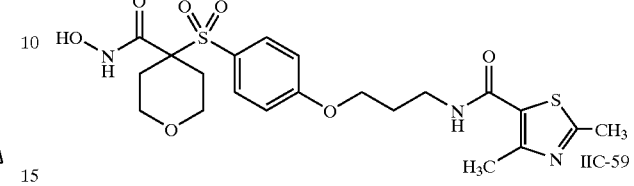

IIC-59

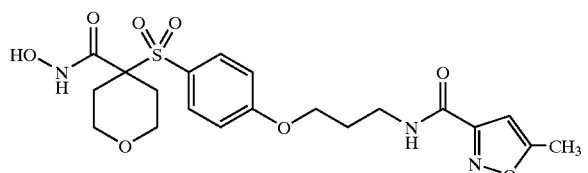

IIC-60

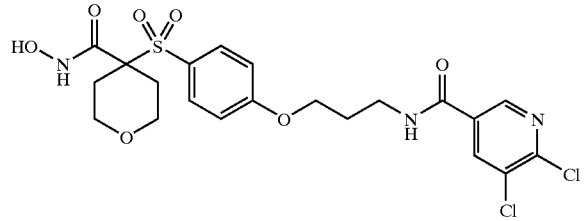

IIC-61

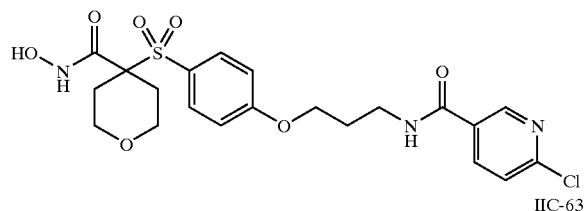

IIC-62

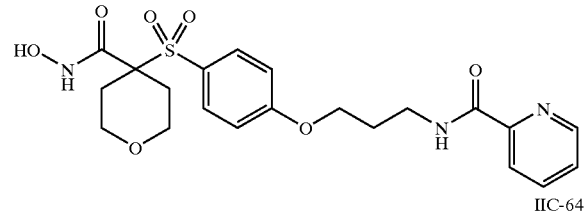

IIC-63

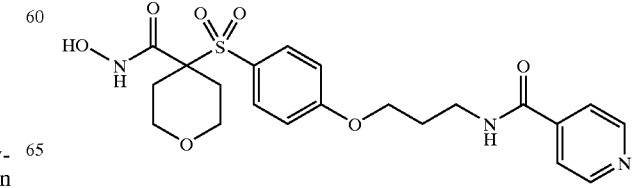

IIC-64

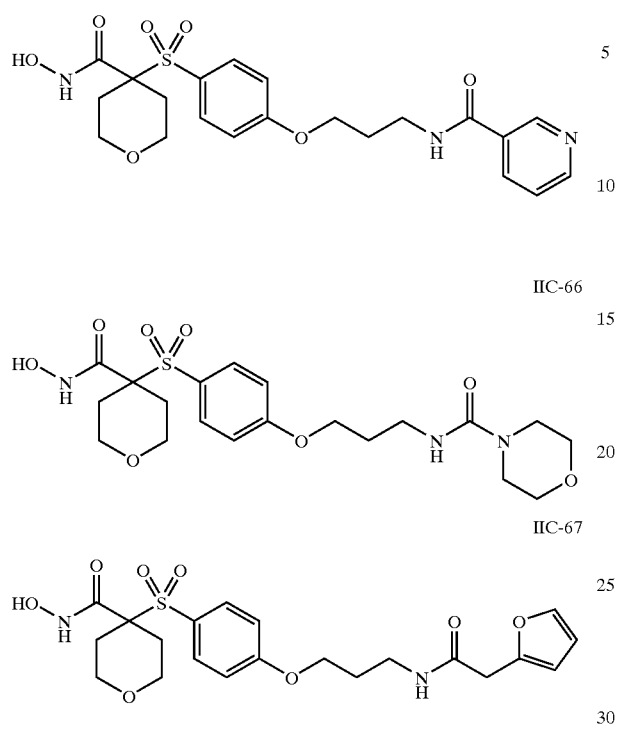

Such compounds also include, for example:

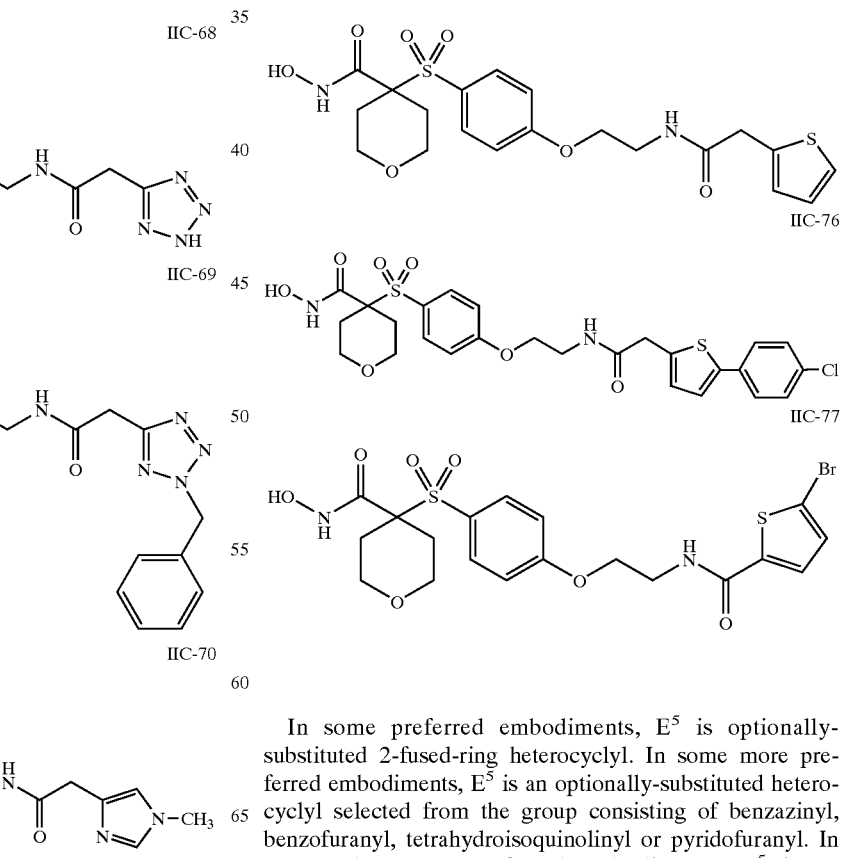

In some preferred embodiments, $E^5$ is optionally-substituted 2-fused-ring heterocyclyl. In some more preferred embodiments, $E^5$ is an optionally-substituted heterocyclyl selected from the group consisting of benzazinyl, benzofuranyl, tetrahydroisoquinolinyl or pyridofuranyl. In some other more preferred embodiments, $E^5$ is an optionally-substituted heterocyclyl selected from the group consisting of indolyl, benzoxazolyl, benzothienyl, and benzothiazolyl. Compounds of such embodiments include, for example:
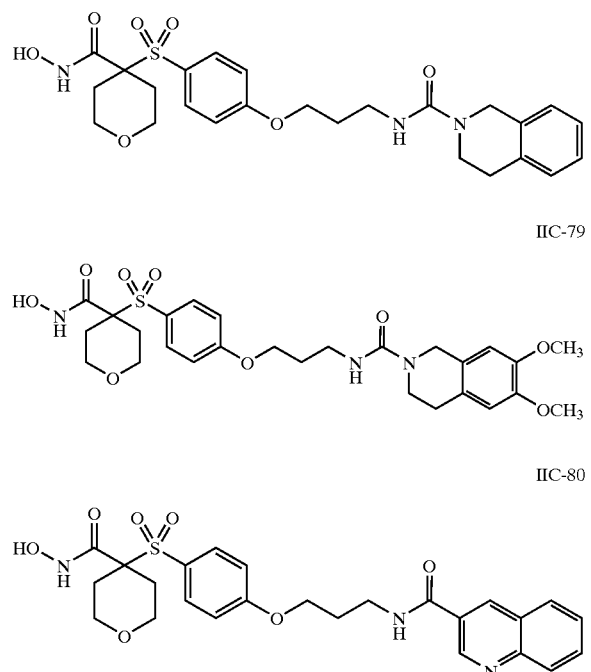
Other such compounds include, for example:
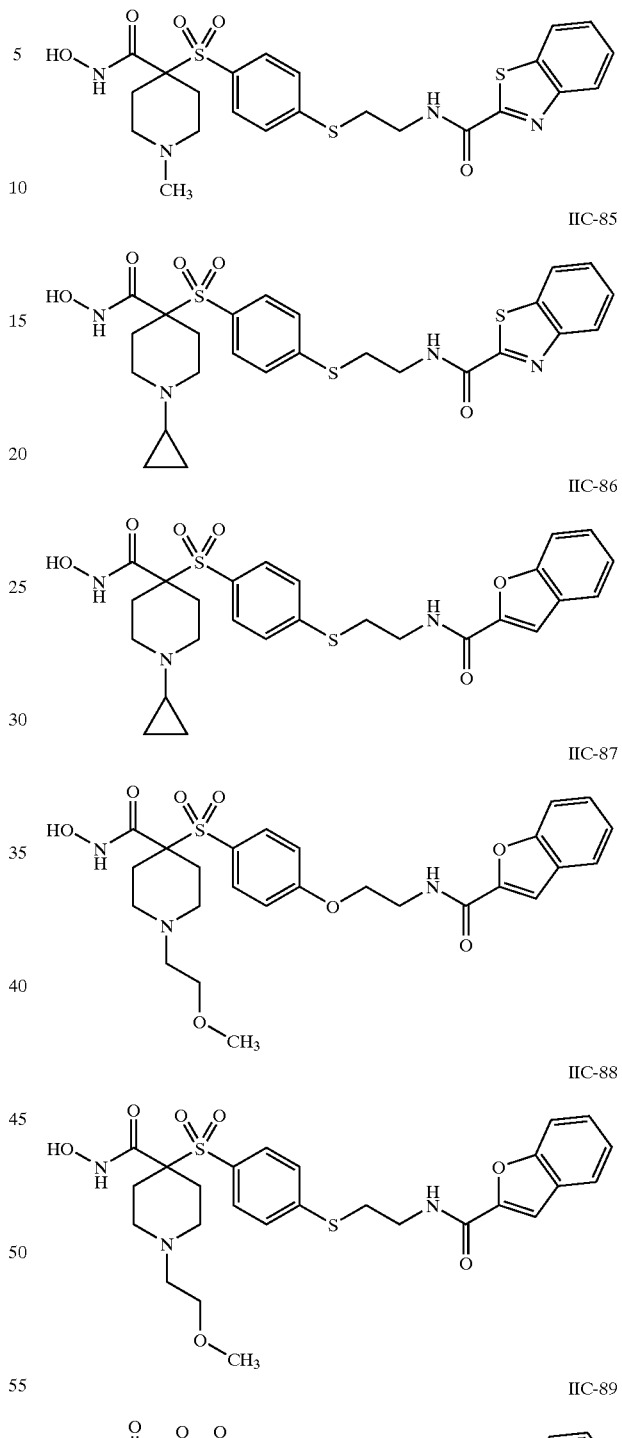
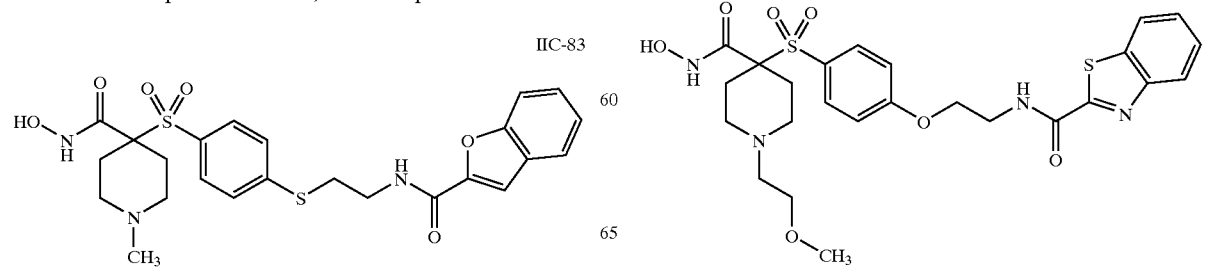

-continued

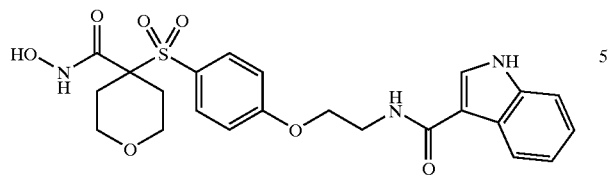
IIC-90

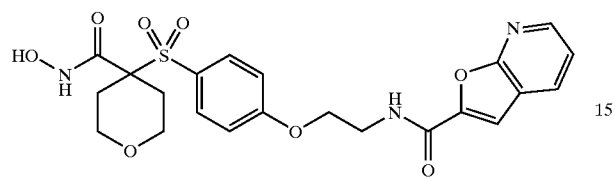
IIC-91

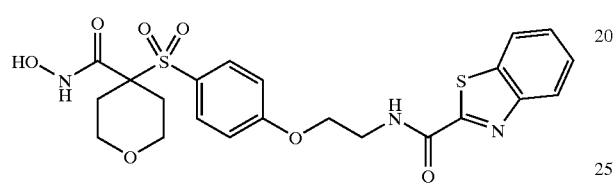
IIC-92

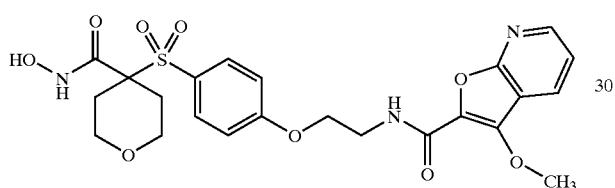
IIC-93

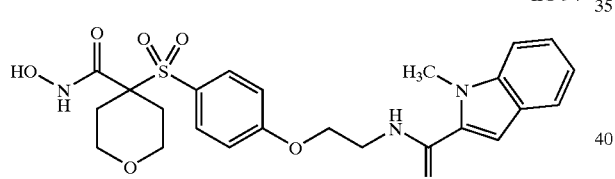
IIC-94

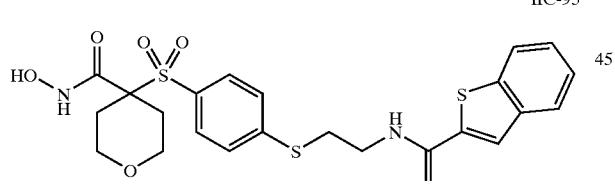
IIC-95

IIC-96

-continued

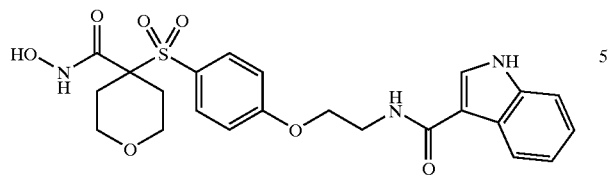
IIC-97

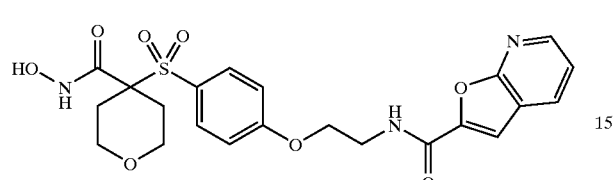
IIC-98

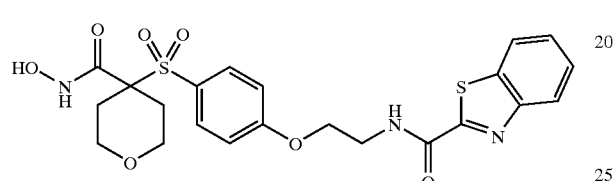
IIC-99

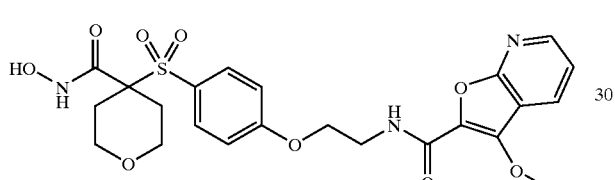
IIC-100

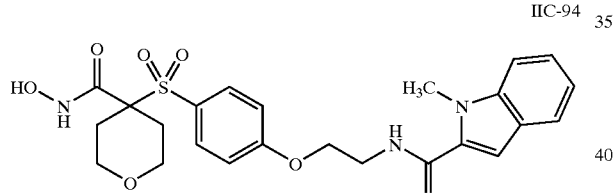
IIC-101

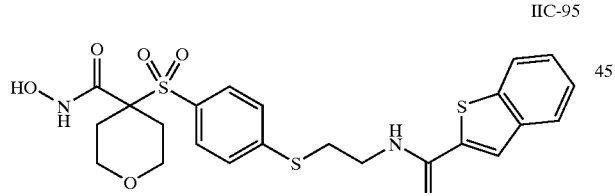
IIC-102

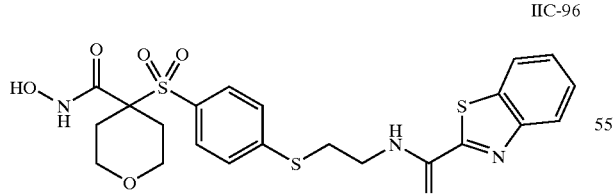
IIC-103

In some preferred embodiments, $E^5$ is —OH, $C_1$–$C_6$-alkyl, $C_2$–$C_6$-alkenyl, $C_2$–$C_6$-alkynyl, $C_1$–$C_6$-alkoxy, or $C_1$–$C_6$-alkoxy-$C_1$–$C_6$-alkyl. Except where the member is —OH, any member of this group optionally is substituted with one or more substituents independently selected from the group consisting of halogen, —OH, —NO$_2$, and —CN. Such compounds include, for example:


IIC-105

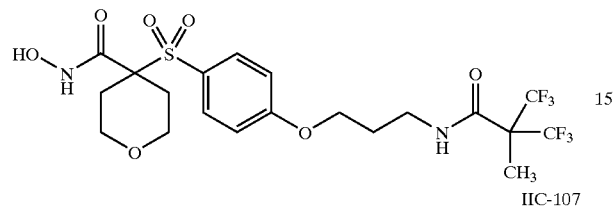

IIC-106

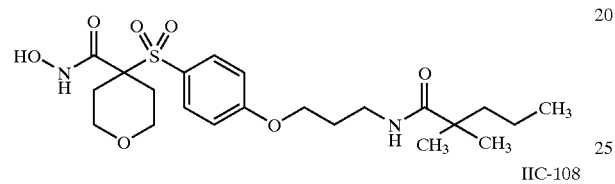

IIC-107

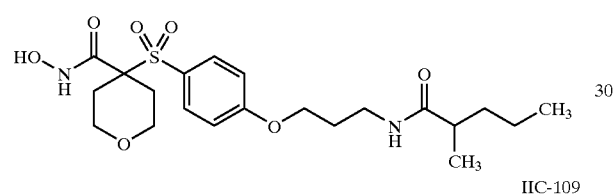

IIC-108

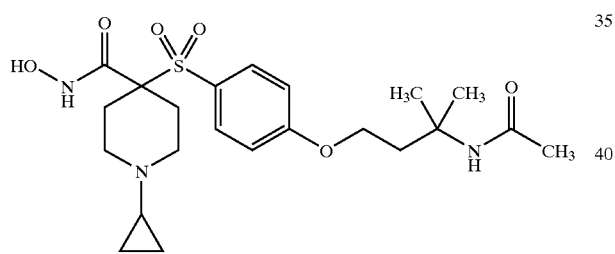

IIC-109

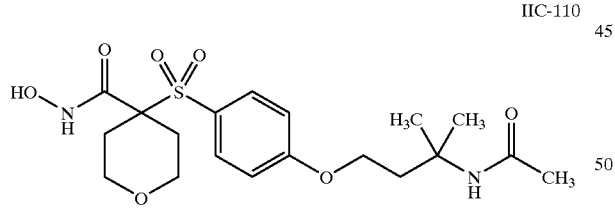

IIC-110

Preferred Embodiment No. 1-d: $E^3$ is —C(O)—N($R^4$)—

In some embodiments, $E^3$ is —C(O)—N($R^{14}$)—.

In some such embodiments, for example, $E^5$ is optionally-substituted carbocyclyl, often preferably optionally-substituted aryl.

In some preferred embodiments, $E^5$ is optionally-substituted phenyl. Such compounds include, for example:

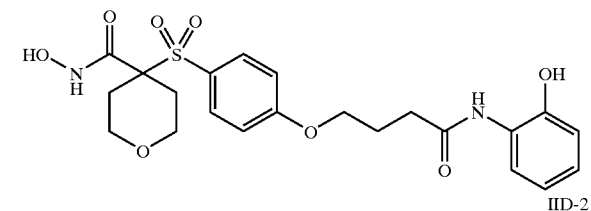

IID-1

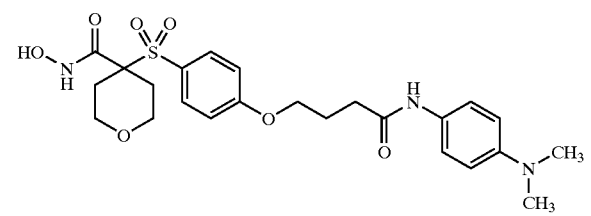

IID-2

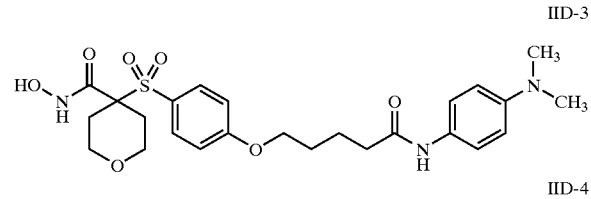

IID-3

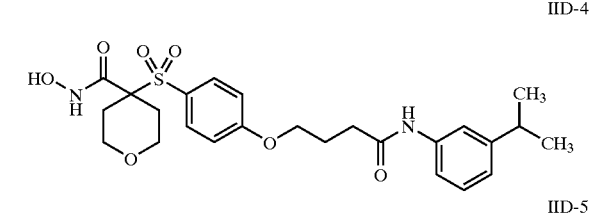

IID-4

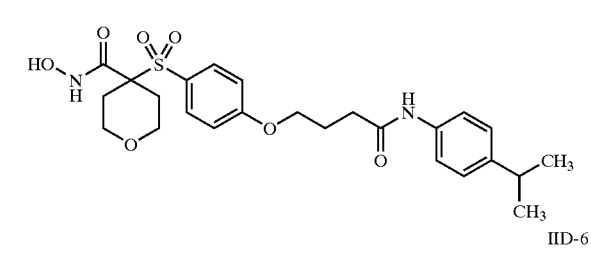

IID-5

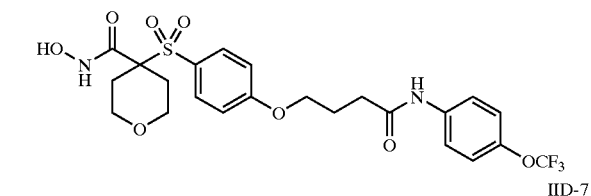

IID-6

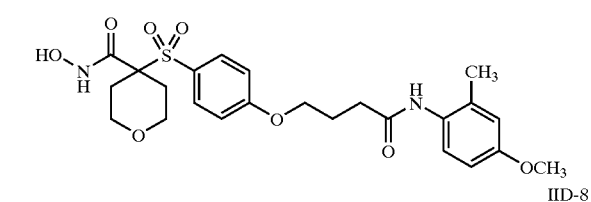

IID-7

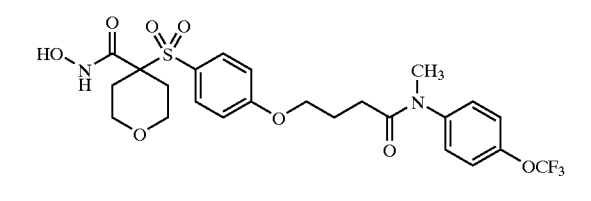

IID-8

-continued

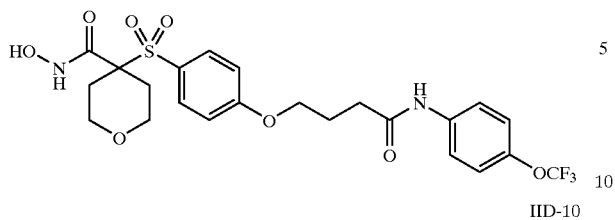
IID-9

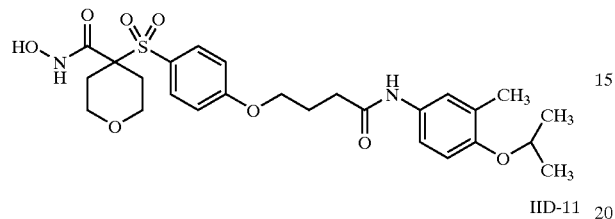
IID-10

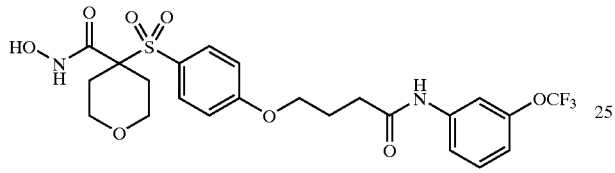
IID-11

Other such compounds include, for example:

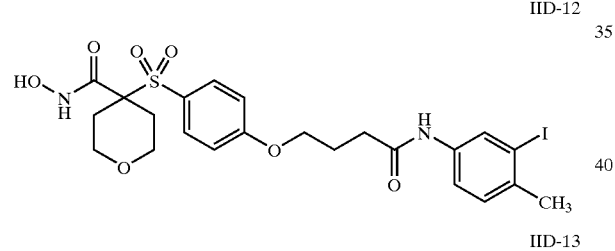
IID-12

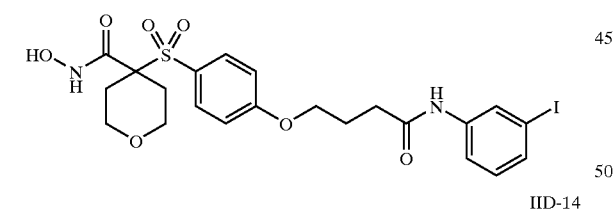
IID-13

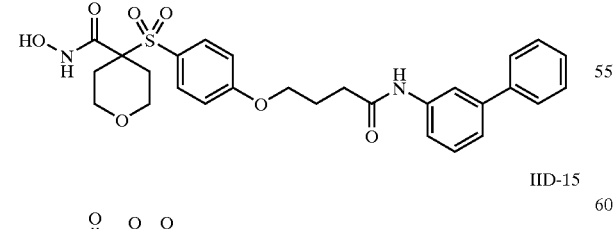
IID-14

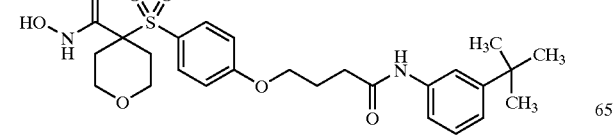
IID-15

-continued

IID-16

In some preferred embodiments, $E^5$ is optionally-substituted naphthalenyl. These compounds include, for example:

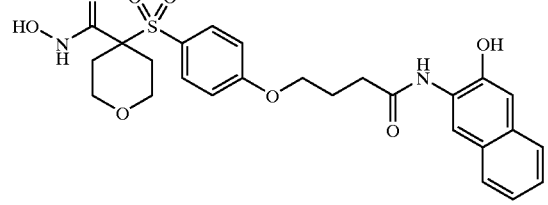
IID-17

In some preferred embodiments, $E^5$ is —OH, $C_1$–$C_6$-alkyl, $C_2$–$C_6$-alkenyl, $C_2$–$C_6$-alkynyl, $C_1$–$C_6$-alkoxy, or $C_1$–$C_6$-alkoxy-$C_1$–$C_6$-alkyl. Except where the member is —OH, any member of this group optionally is substituted with one or more substituents independently selected from the group consisting of halogen, —OH, —NO$_2$, and —CN. Such compounds include, for example:

IID-18

Preferred Embodiment No. 1-e: $E^3$ is —N(R$^4$)—C(O)—N(R$^5$)—

In some embodiments, $E^3$ is —N(R$^4$)—C(O)—N(R$^5$)—. In some such embodiments, for example, $E^5$ is optionally-substituted carbocyclyl, often preferably optionally-substituted aryl, and more preferably optionally-substituted phenyl. Such compounds include, for example:

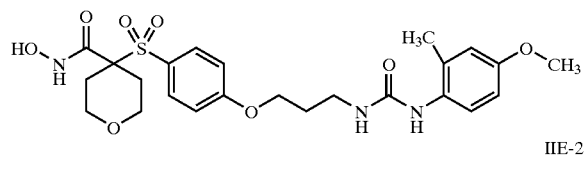
IIE-1

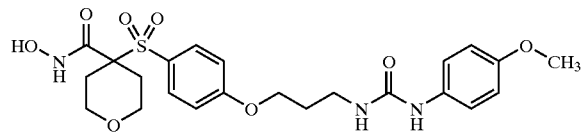
IIE-2

IIE-3

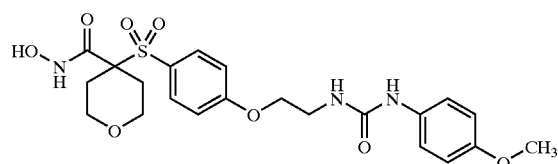

Preferred Embodiment No. 1-f: $E^3$ is $-S(O)_2-N(R^4)-$

In some embodiments, $E^3$ is $-S(O-NR^4)-$.

In some such embodiments, $E^5$ is optionally-substituted carbocyclyl. The carbocyclyl may be, for example, cycloalkyl. Such compounds include, for example:

IIF-1

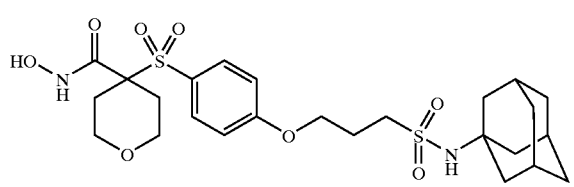

In some preferred embodiments, the carbocyclyl is aryl (preferably phenyl). Such compounds include, for example:

IIF-2


IIF-3


IIF-4

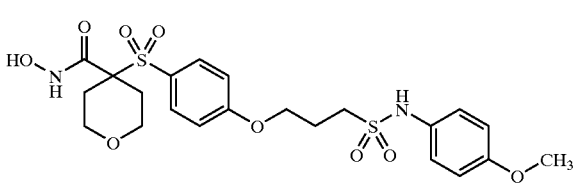

IIF-5

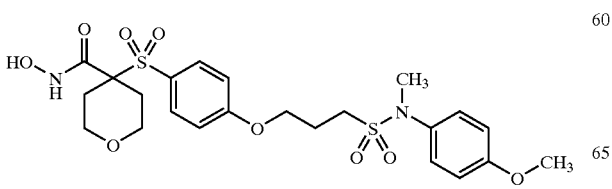

IIF-6

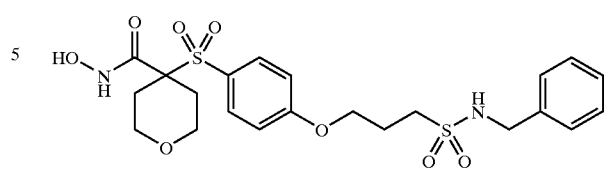

IIF-7

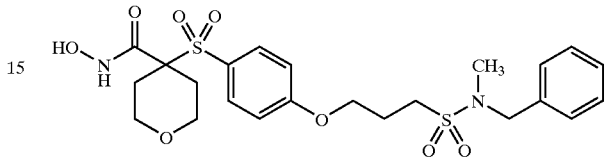

IIF-8

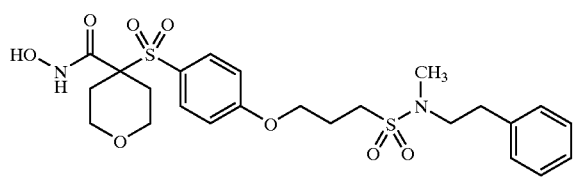

In some preferred embodiments, $E^5$ is $-H$, $-OH$, $C_1-C_6$-alkyl, $C_2-C_6$-alkenyl, $C_2-C_6$-alkynyl, $C_1-C_6$-alkoxy, or $C_1-C_6$-alkoxy-$C_1-C_6$-alkyl. Except where the member is $-H$ or $-OH$, any member of this group optionally is substituted with one or more substituents independently selected from the group consisting of halogen, $-OH$, $-NO_2$, and $-CN$. Such compounds include, for example:

IIF-9

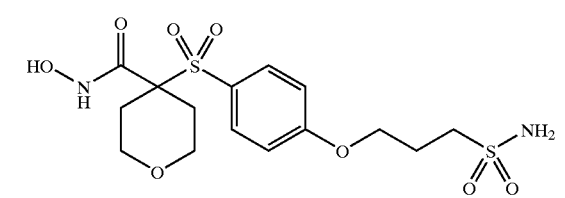

IIF-10

IIF-11

Preferred Embodiment No. 1-g $E^3$ is —N($R^4$)—S(O)$_2$—

In some embodiments, $E^3$ is —N($R^4$)—S(O)$_2$. In some such embodiments, $E^5$ is optionally-substituted carbocyclyl, often preferably optionally-substituted aryl, and more preferably optionally-substituted phenyl. Such compounds include, for example:

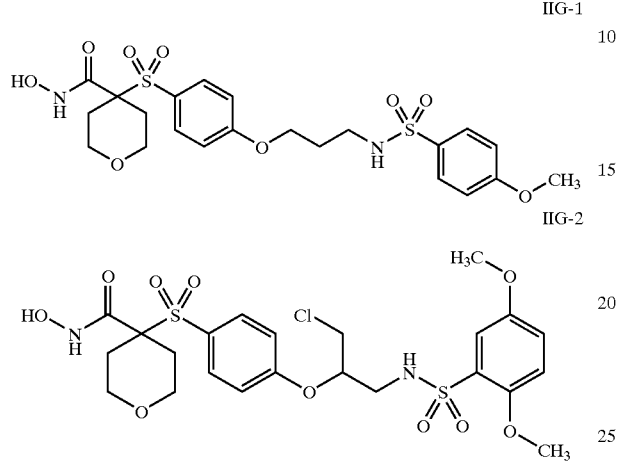

IIG-1

IIG-2

Other such compounds include, for example:

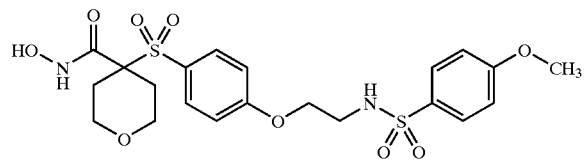

IIG-3

Preferred Embodiment No. 1-h: $E^3$ is —C(O)—N($R^4$)—N($R^5$)—C(O)—

In some embodiments, $E^3$ is —C(O)—N($R^4$)—N($R^5$)—C(O)—. In some such embodiments, $E^5$ is optionally-substituted carbocyclyl, often preferably optionally-substituted aryl, and more preferably optionally-substituted phenyl. Such compounds include, for example:

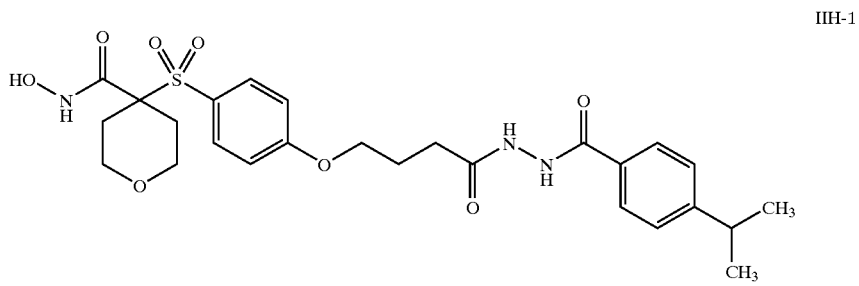

IIH-1

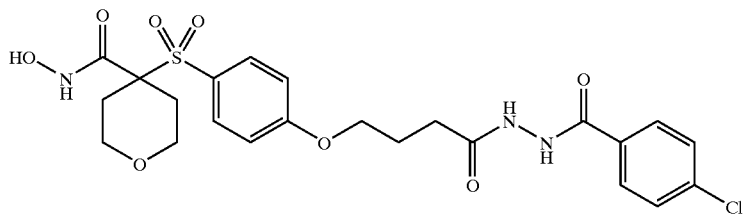

IIH-2

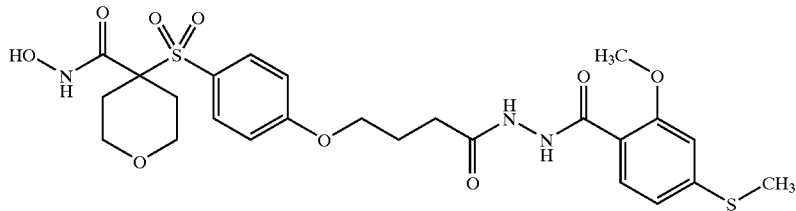

IIH-3

Preferred Embodiment No. 1-i: $E^3$ is —C($R^4$)($R^6$)—C(O)—

In some embodiments, $E^3$ is —C($R^4$)($R^6$)—C(O)—. In some such embodiments, $E^5$ is optionally-substituted carbocyclyl, often preferably optionally-substituted aryl, and more preferably optionally-substituted phenyl. Such compounds include, for example:

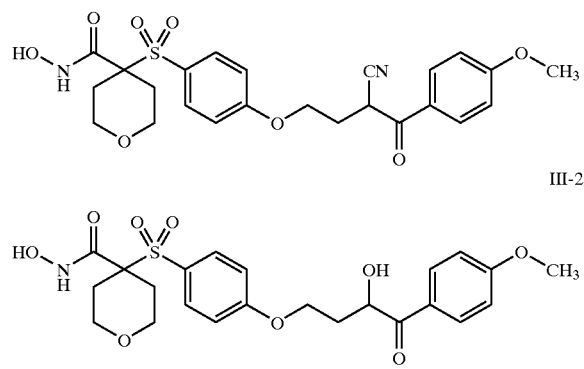

III-1

III-2

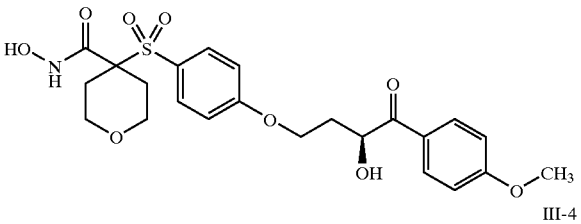

III-3

III-4

Preferred Embodiment No. 1-j: $E^3$ is —O—C(O)—

In some embodiments, $E^3$ is —C(O)—. In some such embodiments, $E^5$ is optionally-substituted heterocyclyl. In some preferred embodiments, $E^5$ is an optionally-substituted 2-fused-ring heterocyclyl. In some embodiments, for example, $E^5$ is optionally-substituted tetrahydroisoquinolinyl. Such compounds include, for example:

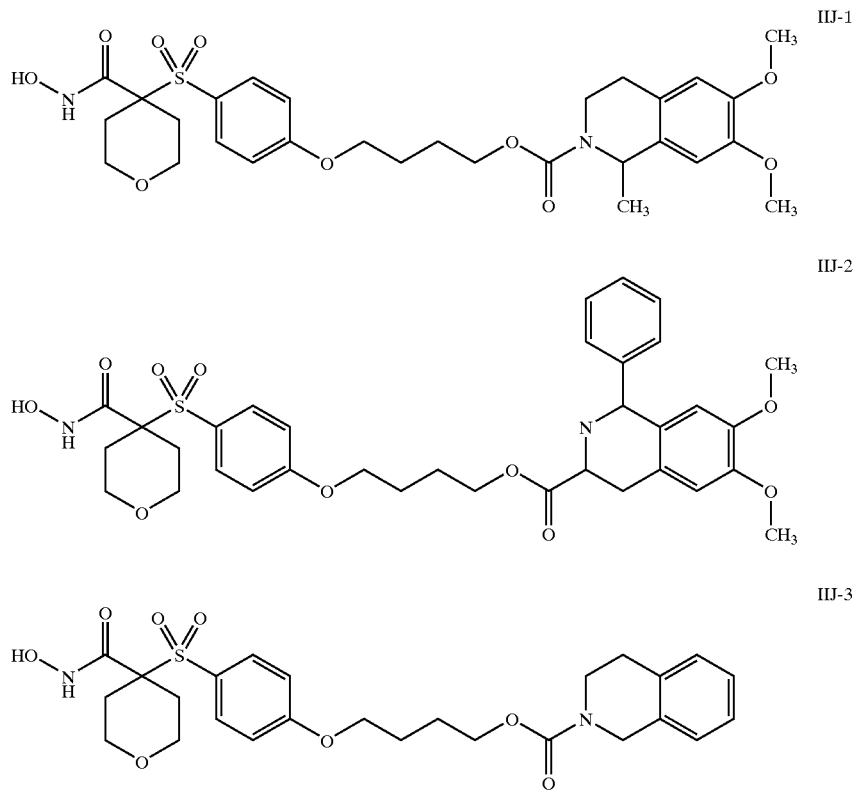

IIJ-1

IIJ-2

IIJ-3

Preferred Embodiment No. 1-k: $E^3$ is —N($R^4$)—

In some embodiments, $E^3$ is —N($R^4$)—. In some such embodiments, $E^5$ is optionally-substituted heterocyclyl. In some preferred embodiments, $E^5$ is optionally-substituted 2-fused-ring heterocyclyl. In some embodiments, for example, $E^5$ is optionally-substituted benzoxazolyl, benzothiazolyl, or benzimidazolyl. Such compounds include, for example:

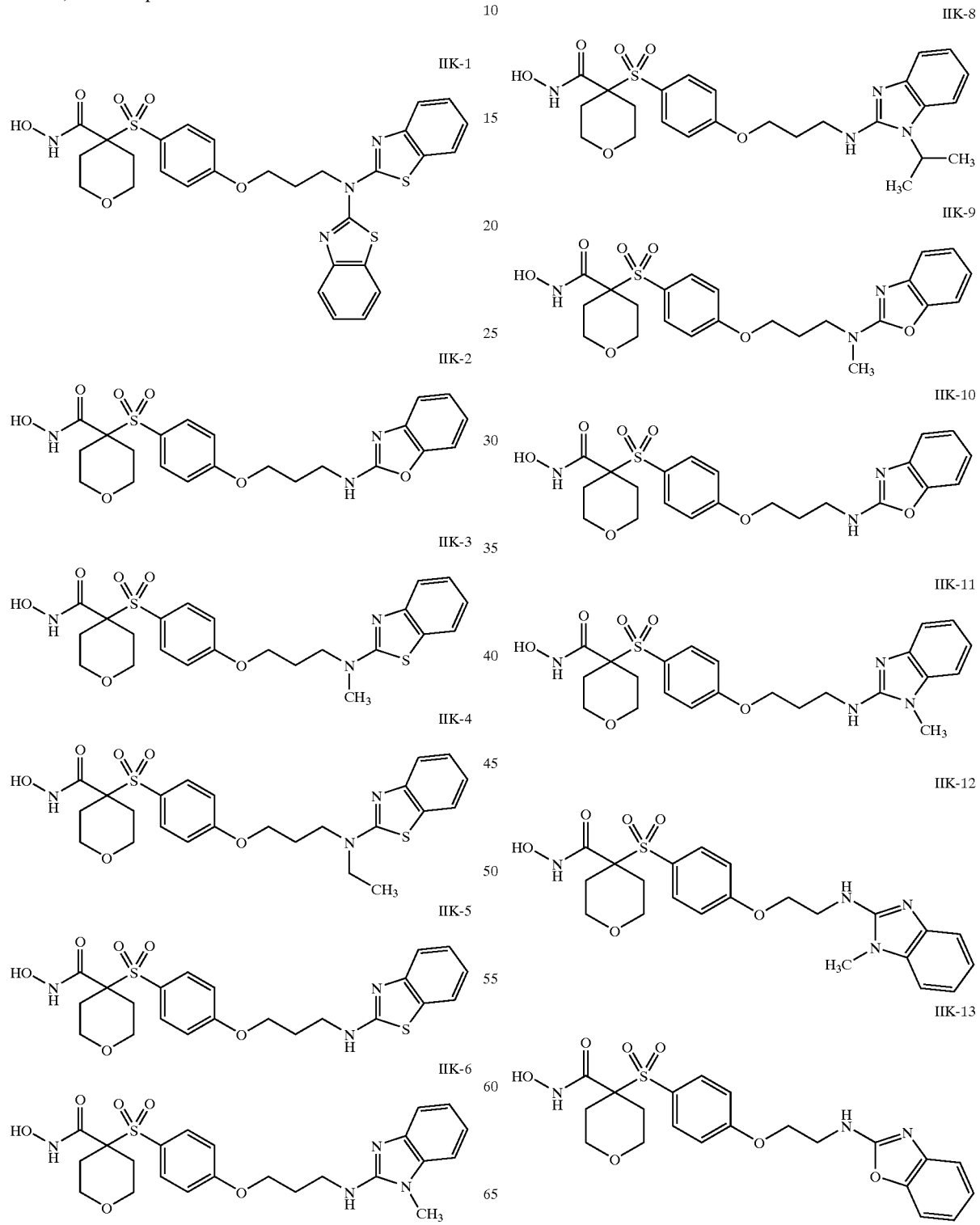

-continued

IIK-14

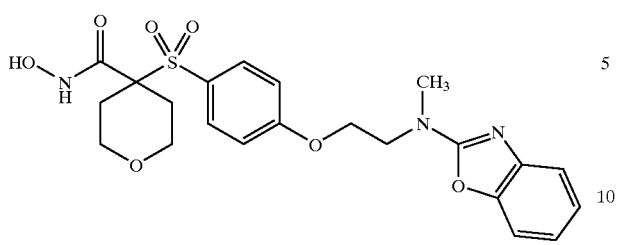

Preferred Embodiment No. 1-i: $E^3$ is —C(NR$^3$)—

In some embodiments, $E^3$ is —C(NR$^3$)—. In some such embodiments, $E^5$ is optionally-substituted carbocyclyl, often preferably optionally-substituted aryl, and more preferably optionally-substituted phenyl. Such compounds include, for example:

IIL-1

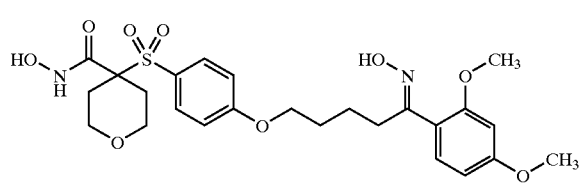

Preferred Embodiment No. 1-m: $E^3$ is —C(R$^7$)(R$^8$)—

In some embodiments, $E^3$ is —C(R$^7$)(R$^8$)—. In some such embodiments, $E^5$ is optionally-substituted carbocyclyl, often preferably optionally-substituted aryl, and more preferably optionally-substituted phenyl. Such compounds include, for example:

IIM-1

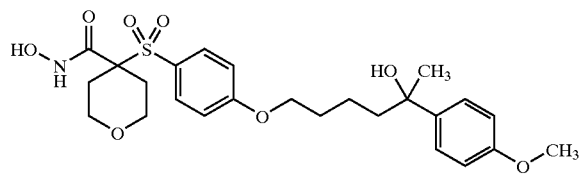

IIM-2

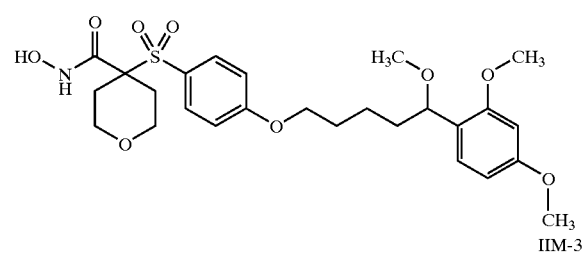

IIM-3

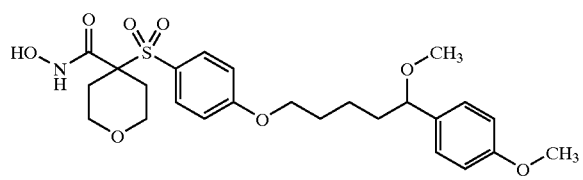

-continued

IIM-4

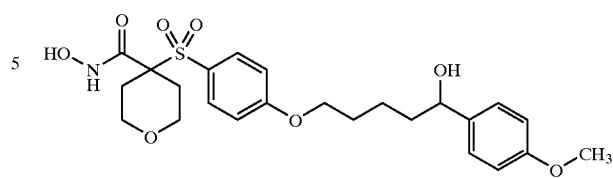

Preferred Embodiment No. 1-n: $E^3$ is —N(R$^4$)—C(NR$^3$)—

In some embodiments, $E^3$ is —N(R$^4$)—C(NR$^3$)—. In some such embodiments, $E^5$ is optionally-substituted carbocyclyl, often preferably optionally-substituted aryl, and more preferably optionally-substituted phenyl. Such compounds include, for example:

IIN-1

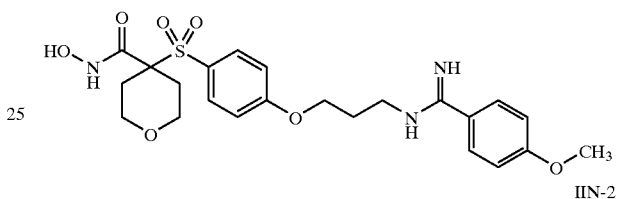

IIN-2

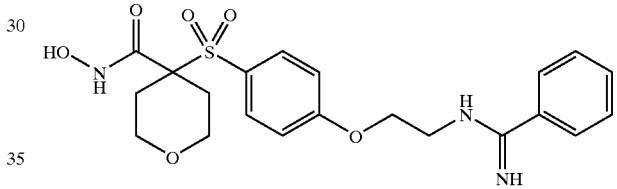

Preferred Embodiment No. 2

In some embodiments of this invention, the compound has a structure to Formula III:

III

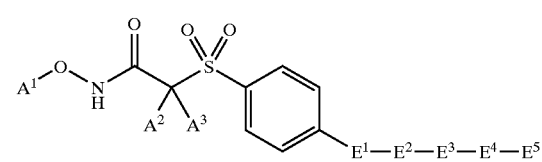

$A^1$, $A^2$, and $A^3$ are as defined above for Formula I.

$E^1$ is —O—, —S(O)$_2$—, —S(O)—, —N(R$^1$)—, —C(O)—N(R$^1$)—, —N(R$^1$)—C(O)—, or —C(R$^1$)(R$^2$)—.

$E^1$ alternatively maybe —S—.

$E^2$ forms a link of at least 2 carbon atoms between $E^1$ and $E^3$. $E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_2$–$C_{20}$-alkyl, cycloalkyl, $C_1$–$C_{10}$-alkylcyloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$-alkyl.

In some preferred embodiments, $E^2$ is $C_2$–$C_6$-alkyl optionally substituted with one or more halogen.

In some preferred embodiments, $E^2$ is $C_2$–$C_5$-alkyl optionally substituted with one or more halogen.

In some preferred embodiments, $E^2$ is $C_2$–$C_5$-alkyl.

In some preferred embodiments, $E^2$ is —(CH$_2$)$_m$—, wherein m is from 2 to 5.

$E^3$ is carbocyclyl or heterocyclyl. This carbocyclyl and heterocyclyl have 5 or 6 ring members and optionally are substituted.

In some preferred embodiments, $E^3$ is carbocyclyl or heterocyclyl wherein the carbocyclyl and heterocyclyl have 5 or 6 ring members and optionally are substituted with one or more substituents independently selected from the group consisting of halogen, —OH, keto, $C_1$–$C_8$-alkyl, $C_1$–$C_8$-alkoxy, $C_1$–$C_8$-alkoxy-$C_1$–$C_8$-alkyl, carbocyclyl, carbocyclyl-$C_1$–$C_8$-alkyl, heterocyclyl, and heterocyclyl-$C_1$–$C_8$-alkyl. Except where the substituent is halogen, —OH, or keto, any of these substituents optionally is substituted with one or more substituents independently selected from the group consisting of halogen, —OH, $C_1$–$C_8$-alkyl, $C_1$–$C_8$-alkoxy, $C_1$–$C_8$-alkoxy-$C_1$–$C_8$-alkyl, $C_1$–$C_8$-alkylthio, halo-$C_1$–$C_8$-alkyl, halo-$C_1$–$C_8$-alkoxy, halo-$C_1$–$C_8$-alkylthio, and halogen-substituted $C_1$–$C_8$-alkoxy-$C_1$–$C_8$-alkyl.

In some preferred embodiments, $E^3$ is carbocyclyl or heterocyclyl wherein the carbocyclyl and heterocyclyl have 5 or 6 ring members and optionally are substituted with one or more substituents independently selected from the group consisting of halogen, —OH, keto, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl. Except where the substituent is halogen, —OH, or keto, any substituent of this group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio.

$E^4$ is a bond, alkyl, alkenyl, —O—, or —N($R^3$)—. The alkyl and alkenyl optionally are substituted.

In some preferred embodiments, $E^4$ is a bond, —O—, —N($R^3$)—, $C_1$–$C_{20}$-alkyl, or $C_2$–$C_{20}$-alkenyl. The $C_1$–$C_{20}$-alkyl and $C_2$–$C_{20}$-alkenyl optionally are substituted with one or more substituents independently selected from the group consisting of halogen and carbocyclyl optionally substituted with one or more substituents independently selected from the group consisting of halogen, —OH, —NO$_2$, —CN, $C_1$–$C_8$-alkyl, $C_1$–$C_8$-alkoxy, $C_1$–$C_8$-alkoxy-$C_1$–$C_8$-alkyl, carbocyclyl, carbocyclyl-$C_1$–$C_8$-alkyl, halo-$C_1$–$C_8$-alkyl, halo-$C_1$–$C_8$-alkoxy, halocarbocyclyl, halogen-substituted carbocyclyl-$C_1$–$C_8$-alkyl, and halogen-substituted $C_1$–$C_8$-alkoxy-$C_1$–$C_8$-alkyl.

In some preferred embodiments, $E^4$ is a bond, —O—, —N($R^3$)—, $C_1$–$C_3$-alkyl, or $C_2$–$C_3$-alkenyl. The $C_1$–$C_3$-alkyl and $C_2$–$C_3$-alkenyl optionally are substituted with one or more substituents independently selected from the group consisting of halogen and carbocyclyl optionally substituted with one or more substituents independently selected from the group consisting of halogen, —OH, —NO$_2$, —CN, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halocarbocyclyl, and halogen-substituted carbocyclyl-$C_1$–$C_6$-alkyl.

In some preferred embodiments, $E^4$ is a bond, —O—, —N($R^3$)—, $C_1$–$C_3$-alkyl, or $C_2$–$C_3$-alkenyl.

In some preferred embodiments, $E^4$ is a bond.

$E^5$ is carbocyclyl or heterocyclyl. The carbocyclyl and heterocyclyl optionally are substituted. In some preferred embodiments, the carbocyclyl and heterocyclyl optionally are substituted with one or more substituents independently selected from the group consisting of halogen, —OH, —NO$_2$, —CN, keto, $C_1$–$C_8$-alkyl, $C_1$–$C_8$-alkoxy, $C_1$–$C_8$-alkoxy-$C_1$–$C_8$-alkyl, —N(R)($R^7$), —C(O)($R^8$), —S—$R^6$, —S(O)$_2$—$R^6$, carbocyclyl, carbocyclyl-$C_1$–$C_8$-alkyl, halo-$C_1$–$C_8$-alkyl, halo-$C_1$–$C_8$-alkoxy, halogen-substituted $C_1$–$C_8$-alkoxy-$C_1$–$C_8$-alkyl, halocarbocyclyl, and halogen-substituted carbocyclyl-$C_1$–$C_8$-alkyl. The carbocyclyl and heterocyclyl also optionally are substituted with one or more substituents independently selected from the group consisting of $C_2$–$C_8$-alkenyl and $C_2$–$C_8$-alkenyl.

In some preferred embodiments, $E^5$ is pyridinyl optionally substituted with one or more substituents independently selected from the group consisting of halogen, —OH, —NO$_2$, —CN, $C_1$–$C_6$-alkyl, $C_1$–$C_6$-alkoxy, $C_1$–$C_6$-alkoxy-$C_1$–$C_6$-alkyl, —N(R)($R^7$), —C(O)($R^8$), —S—$R^6$, —S(O)$_2$—$R^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl. The pyridinyl also is optionally substituted with one or more substituents independently selected from the group consisting of $C_2$–$C_6$-alkenyl and $C_2$–$C_6$-alkynyl.

In some preferred embodiments, $E^5$ is piperidinyl, piperazinyl, imidazolyl, furanyl, thienyl, pyrimidyl, benzodioxolyl, benzodioxanyl, benzofuryl, or benzothienyl. Such substituent optionally is substituted with one or more substituents independently selected from the group consisting of halogen, —OH, —NO$_2$, —CN, $C_1$–$C_6$-alkyl, $C_{1-C6}$-alkoxy, $C_1$–$C_6$-alkoxy-$C_1$–$C_6$-alkyl, —N($R^6$)($R^7$), —C(O)($R^8$), —S—$R^6$, —S(O)$_2$—$R^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl. Such substituent also optionally is substituted with one or more substituents independently selected from the group consisting of $C_2$–$C_6$-alkenyl and $C_2$–$C_6$-alkynyl.

In some preferred embodiments, $E^5$ is phenyl optionally substituted with one or more substituents independently selected from the group consisting of halogen, —OH, —NO$_2$, —CN, $C_1$–$C_6$-alkyl, $C_1$–$C_6$-alkoxy, $C_1$–$C_6$-alkoxy-$C_1$–$C_6$-alkyl, —N($R^6$)($R^7$), —C(O)($R^8$), —S—$R^6$, —S(O)$_2$—$R^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl. The phenyl also is optionally substituted with one or more substituents independently selected from the group consisting of $C_2$–$C_6$-alkenyl and $C_2$–$C_6$-alkynyl.

In some preferred embodiments, $E^5$ is naphthalenyl optionally substituted with one or more substituents independently selected from the group consisting of halogen, —OH, —NO$_2$, —CN, $C_1$–$C_6$-alkyl, $C_1$–$C_6$-alkoxy, $C_1$–$C_6$-alkoxy-$C_1$–$C_6$-alkyl, —N($R^6$)($R^7$), —C(O)($R^8$), —S—$R^6$, —S(O)$_2$—$R^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl. The naphthalenyl also is optionally substituted with one or more substituents independently selected from the group consisting of $C_2$–$C_6$-alkenyl and $C_2$–$C_6$-alkynyl.

$R^1$ and $R^2$ are independently selected from the group consisting of —H and alkyl. The alkyl optionally is substituted. Neither $R^1$ nor $R^2$ forms a ring structure with $E^2$, $E^3$, $E^4$, or $E^5$.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^3$ is —H or alkyl. The alkyl optionally is substituted.

In some preferred embodiments, $R^3$ is —H, $C_1$–$C_8$-alkyl, or halo-$C_1$–$C_8$-alkyl.

In some preferred embodiments, $R^3$ is —H, $C_1$–$C_6$-alkyl, or halo-$C_1$–$C_6$-alkyl.

In some preferred embodiments, $R^3$ is —H or $C_1$–$C_8$-alkyl.

$R^6$ and $R^7$ are independently selected from the group consisting of —H, $C_1$–$C_8$-alkyl, carbocyclyl, carbocyclyl-$C_1$–$C_8$-alkyl, heterocyclyl, heterocyclyl-$C_1$–$C_8$-alkyl, halo-$C_1$–$C_8$-alkyl, halocarbocyclyl, halogen-substituted carbocyclyl-$C_1$–$C_6$-alkyl, haloheterocyclyl and halogen-substituted heterocyclyl-$C_1$–$C_8$-alkyl.

In some preferred embodiments, $R^6$ and $R^7$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^8$ is —H, $C_1$–$C_8$-alkyl, —O—$R^9$, —N($R^9$)($R^{10}$), carbocyclyl-$C_1$–$C_8$-alkyl, heterocyclyl-$C_1$–$C_8$-alkyl, halo-$C_1$–$C_8$-alkyl, halogen-substituted carbocyclyl-$C_1$–$C_8$-alkyl, or halogen-substituted heterocyclyl-$C_1$–$C_8$-alkyl.

In some preferred embodiments, $R^8$ is —H, $C_1$–$C_6$-alkyl, —O—$R^9$, —N($R^9$)($R^{10}$), carbocyclyl-$C_1$–$C_6$-alkyl, heterocyclyl-$C_1$–$C_6$-alkyl, halo-$C_1$–$C_6$-alkyl, halogen-substituted carbocyclyl-$C_1$–$C_6$-alkyl, or halogen-substituted heterocyclyl-$C_1$–$C_6$-alkyl.

In some preferred embodiments, $R^8$ is —H, $C_1$–$C_6$-alkyl, —O—$R^9$, —N($R^9$)($R^{10}$), carbocyclyl-$C_1$–$C_6$-alkyl, or heterocyclyl-$C_1$–$C_6$-alkyl.

$R^9$ and $R^{10}$ are independently selected from the group consisting of —H, $C_1$–$C_8$-alkyl, carbocyclyl, carbocyclyl-$C_1$–$C_8$-alkyl, heterocyclyl, heterocyclyl-$C_1$–$C_8$-alkyl, halo-$C_1$–$C_8$-alkyl, halocarbocyclyl, halogen-substituted carbocyclyl-$C_1$–$C_8$-alkyl, haloheterocyclyl, and halogen-substituted heterocyclyl-$C_1$–$C_8$-alkyl.

In some preferred embodiments, $R^9$ and $R^{10}$ are independently selected from the group consisting of —H, $C_1$–$C_6$-alkyl, carbocyclyl, carbocyclyl-$C_1$–$C_6$-alkyl, heterocyclyl, heterocyclyl-$C_1$–$C_6$-alkyl, halo-$C_1$–$C_6$-alkyl, halocarbocyclyl, halogen-substituted carbocyclyl-$C_1$–$C_6$-alkyl, haloheterocyclyl, and halogen-substituted heterocyclyl-$C_1$–$C_6$-alkyl.

In some preferred embodiments, $R^9$ and $R^{10}$ are independently selected from the group consisting of —H, $C_1$–$C_6$-alkyl, carbocyclyl, carbocyclyl-$C_1$–$C_6$-alkyl, heterocyclyl, heterocyclyl-$C_1$–$C_6$-alkyl.

Preferred Embodiment No. 2-a: E3 is Optionally-substituted Heterocyclyl

In some embodiments, $E^3$ is optionally-substituted heterocyclyl.

In some preferred embodiments $E^3$ is an optionally-substituted heterocyclyl that contains only one heteroatom ring member. Examples of often suitable heterocyclyls include furanyl, tetrahydropyranyl, dihydrofuranyl, tetrahydrofuranyl, thiophenyl, dihydrothiophenyl, tetrahydrothiophenyl, pyrrolinyl, pyrrolyl, isopyrrolyl, pyrrolidinyl, pyridinyl, piperidinyl, pyranyl, dihydropyranyl, and tetrahydropyranyl.

In some preferred embodiments, $E^3$ is optionally-substituted pyridinyl. In some such embodiments, $E^5$ is optionally-substituted phenyl. Such compounds include, for example:

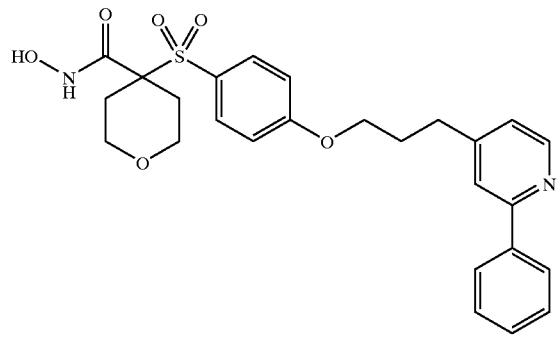

IIIA-1

Such compounds also include, for example:

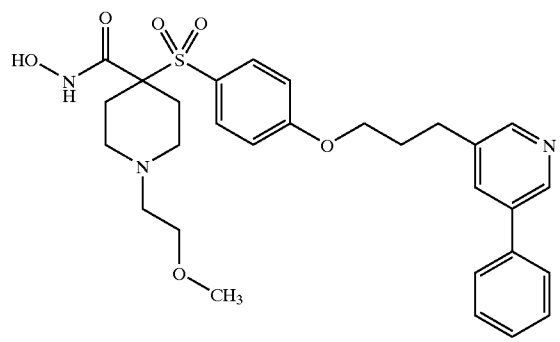

IIIA-2

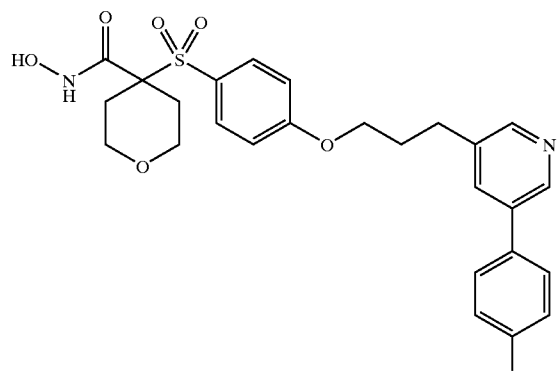

IIIA-3

IIIA-4

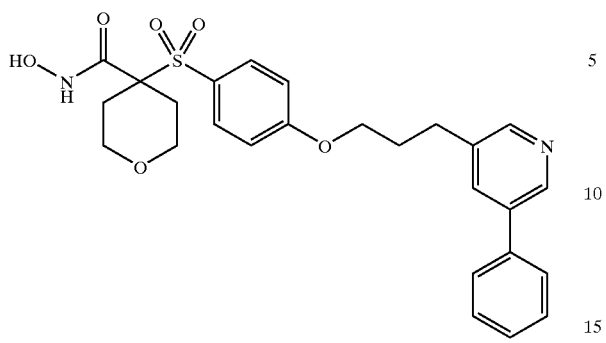

In some preferred embodiments, $E^3$ is an optionally-substituted heterocyclyl selected from the group consisting of:

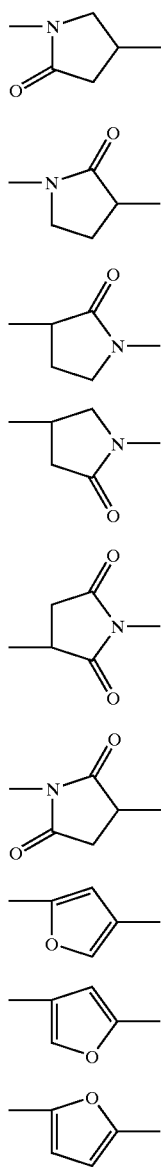

E-1
E-2
E-3
E-4
E-5
E-6
E-7
E-8
E-9

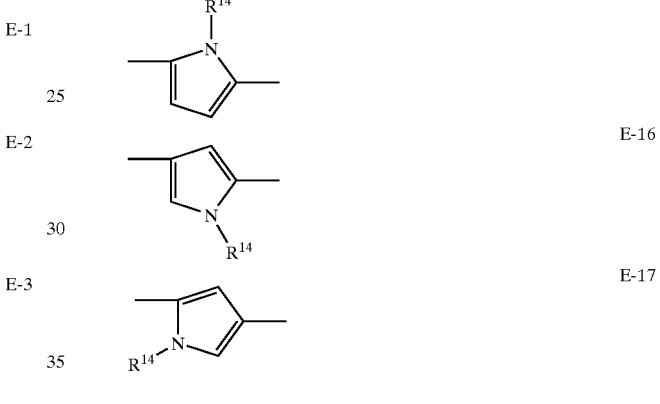

E-10
E-11
E-12
E-13
E-14
E-15
E-16
E-17

Any member of this group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl. Except where the substituent is halogen or —OH, any substituent of this group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio. $R^{14}$ is selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl. Except where the member is halogen or —OH, any member of this group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio.

In some preferred embodiments, $E^3$ is optionally-substituted furanyl. In one such embodiment, for example, $E^5$ is optionally-substituted phenyl. Such compounds include, for example:

IIIA-5

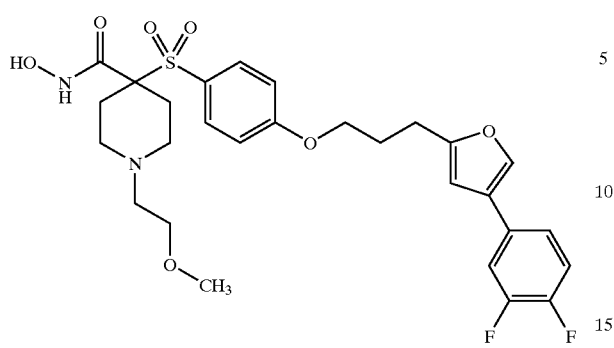

In some preferred embodiments, $E^3$ is optionally-substituted thienyl. In some such embodiments, $E^5$ is optionally-substituted phenyl. Such compounds include, for example:

IIIA-6

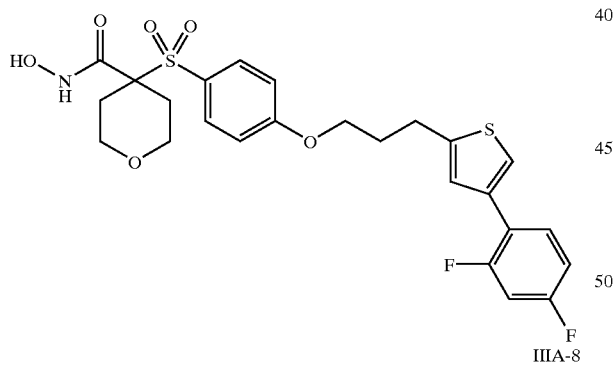

IIIA-7

IIIA-8

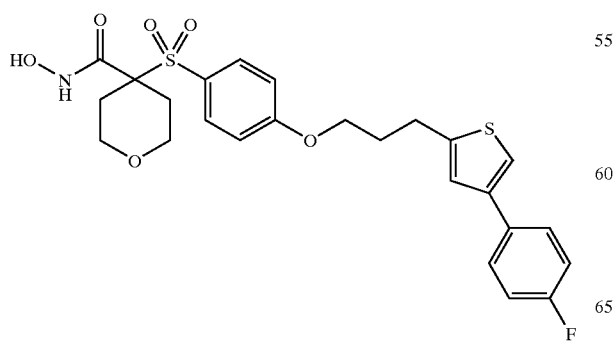

Such compounds also include, for example:

IIIA-9

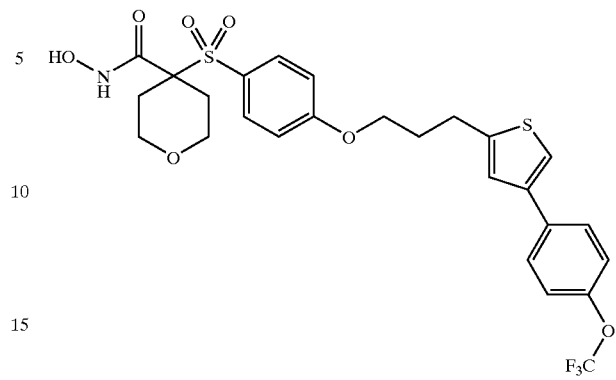

IIIA-10

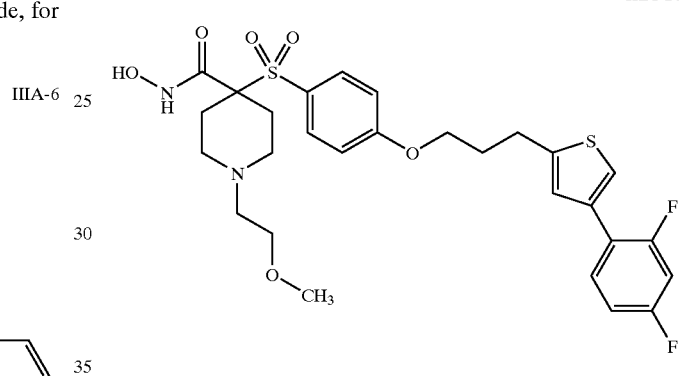

In some preferred embodiments, $E^3$ is optionally-substituted pyrrolidinyl. In some such embodiments, for example, $E^5$ is optionally-substituted phenyl. Such compounds include, for example:

IIIA-11

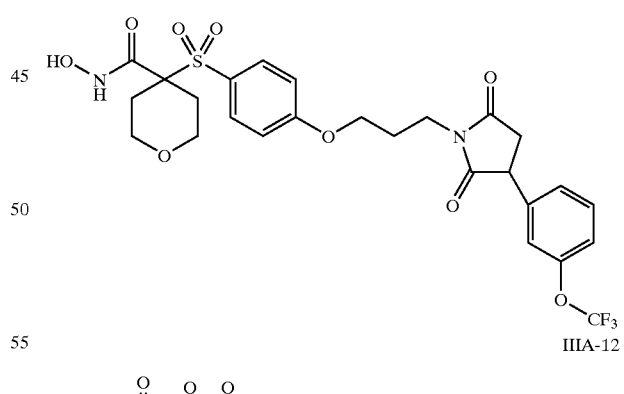

IIIA-12

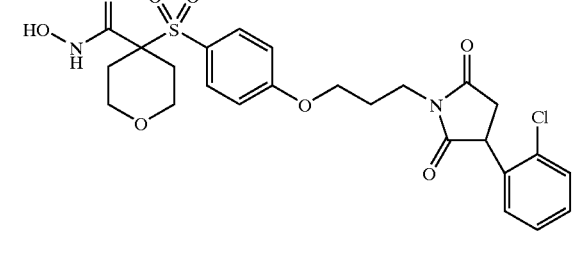

$E^3$ also may be, for example, an optionally-substituted heterocyclyl that contains no greater and no less than two heteroatom ring members. Suitable heterocyclyls include, for example, pyrazolyl, pyrazolinyl, pyrazolidinyl, imidazolyl, isoimidazolyl, imidazolinyl, imidazolidinyl, dithiolyl, thiazolyl, isothiazolyl, thiazolinyl, isothiazolinyl, thiazolidinyl, isothiazolidinyl, oxathiolyl, oxathiolanyl, oxazolyl, isoxazolyl, oxazolidinyl, isoxazolidinyl, pyrazinyl, piperazinyl, pyrimidinyl, pyridazinyl, oxazinyl, and morpholinyl.

In some preferred embodiments, $E^3$ is an optionally-substituted heterocyclyl selected from the group consisting of:

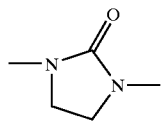
E-18

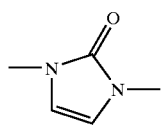
E-19

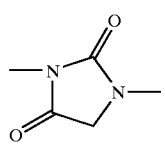
E-20

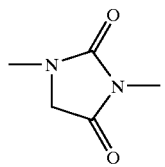
E-21

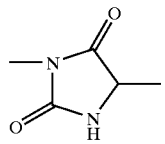
E-22

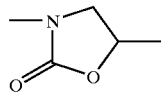
E-23

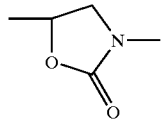
E-24

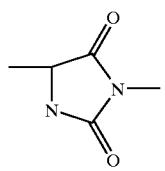
E-25

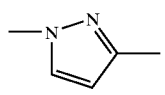
E-1

-continued

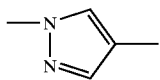
E-1

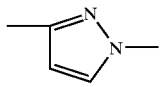
E-1

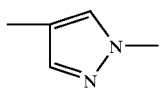
E-1

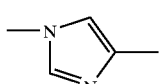
E-26

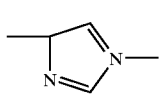
E-27

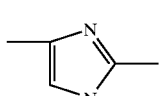
E-28

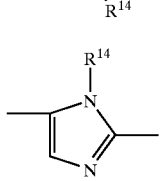
E-29

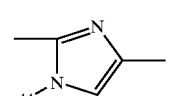
E30

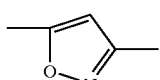
E-31

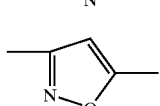
E-32

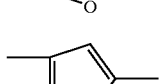
E-33

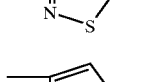
E-34

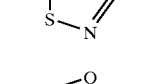
E-35

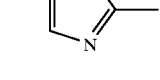
E-36

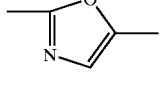
E-37

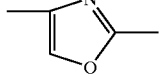

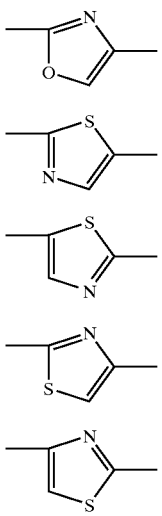

E-38
E-39
E-40
E-41
E-42

Any member of this group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl. Except where the substituent is halogen or —OH, any substituent of this group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio. Such substituents also optionally are substituted with one or more substituents independently selected from the group consisting of $C_2$–$C_6$-alkenyl and $C_2$–$C_6$-alkynyl. $R^{14}$ is as defined above where $E^3$ contains only one heteroatom in its ring.

In some particularly preferred embodiments, $E^3$ is an optionally-substituted heterocyclyl selected from the group consisting of oxazolyl and isoxazolyl. In some such embodiment, for example, $E^5$ is optionally-substituted carbocyclyl, often preferably optionally-substituted aryl, and more preferably optionally-substituted phenyl. Such compounds include, for example:

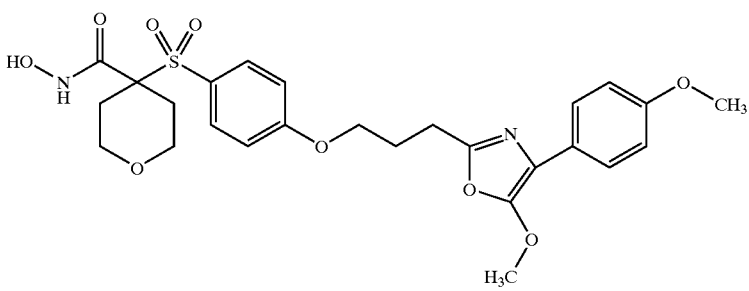

IIIA-13

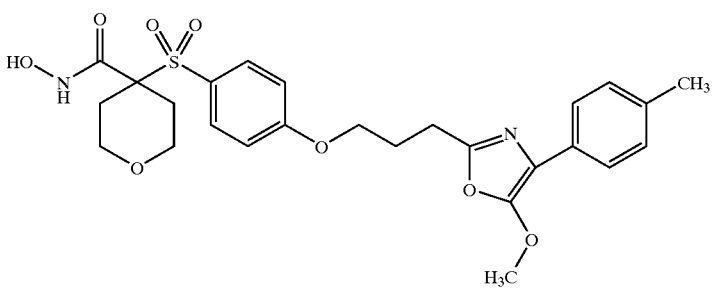

IIIA-14

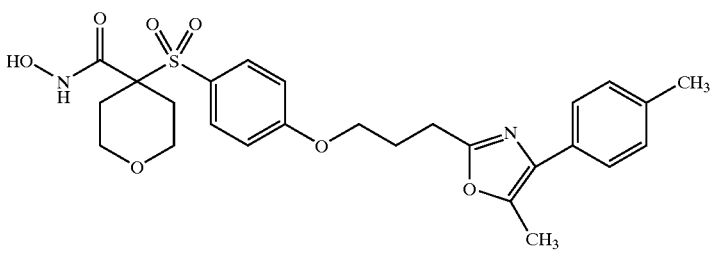

IIIA-15

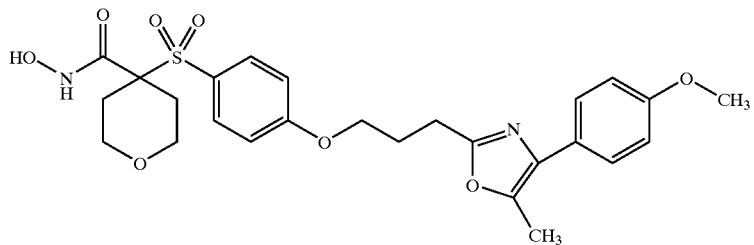
IIIA-16
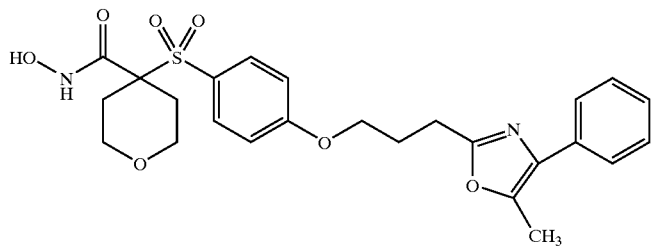
IIIA-17
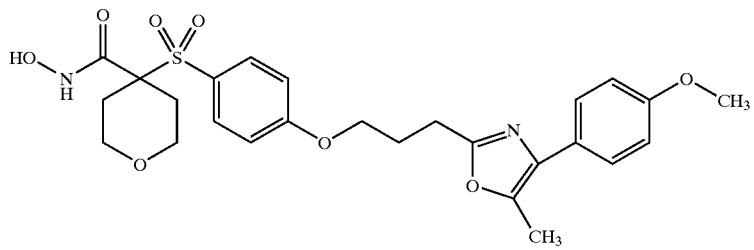
IIIA-18
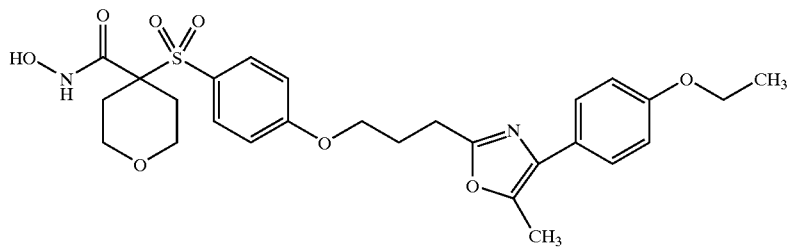
IIIA-19
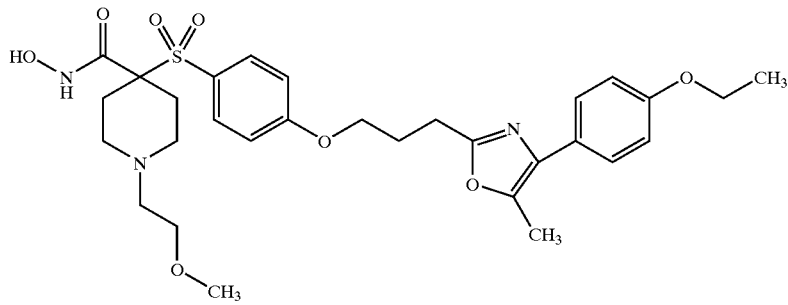
IIIA-20
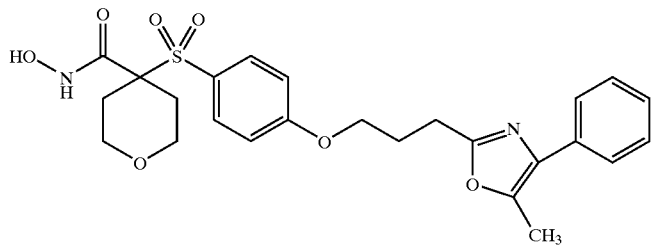
IIIA-21

In some preferred embodiments, $E^3$ is an optionally-substituted heteroaryl selected from the group consisting of pyrazolyl and isoimidazolyl. In some such embodiments, $E^5$ is optionally-substituted carbocyclyl, often preferably optionally-substituted aryl, and more preferably optionally-substituted phenyl. Such compounds include, for example:

IIIA-22

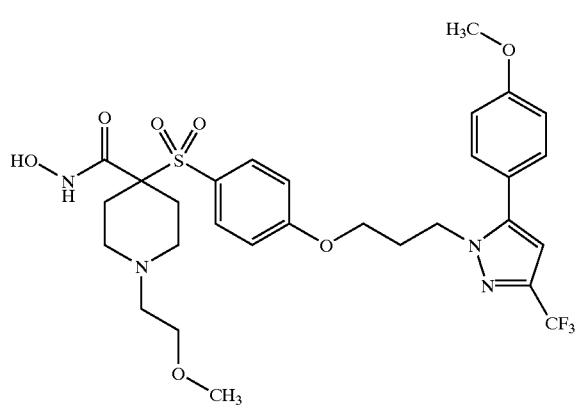

IIIA-23

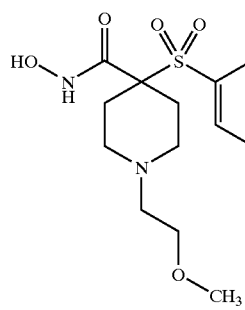

IIIA-24

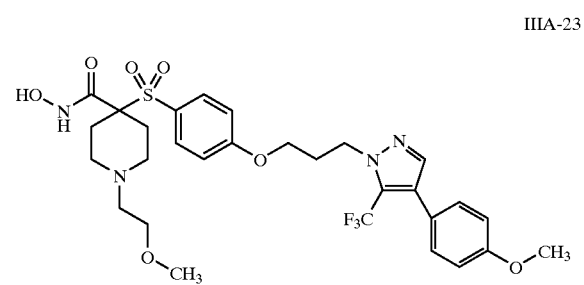

IIIA-25

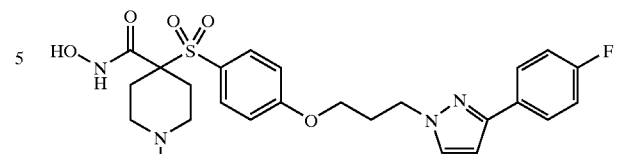

IIIA-26

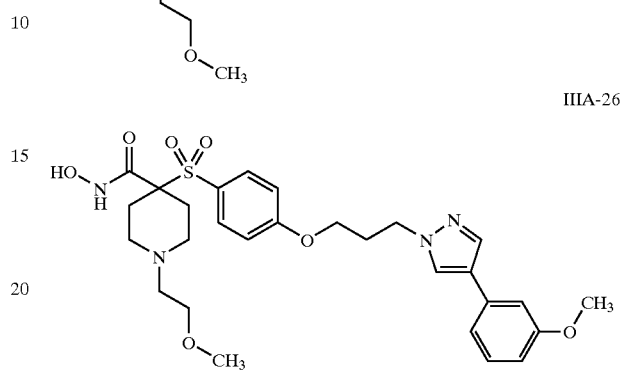

In some preferred embodiments, $E^3$ is an optionally-substituted heteroaryl selected from the group consisting of thiazolyl and isothiazolyl. In one such embodiment, for example, $E^5$ is optionally-substituted carbocyclyl, often preferably optionally-substituted aryl, and more preferably optionally-substituted phenyl. Such compounds include, for example:

IIIA-27

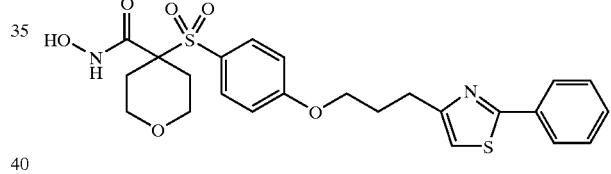

In some preferred embodiments, $E^3$ is an optionally-substituted heteroaryl selected from the group consisting of pyrazolidinyl and imidazolidinyl. In some such embodiments, $E^5$ is optionally-substituted carbocyclyl. In some preferred embodiments, $E^5$ is optionally-substituted aryl, often preferably optionally-substituted phenyl. Such compounds include, for example:

IIIA-28

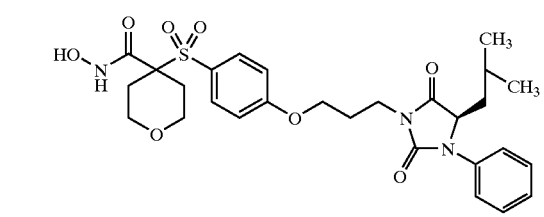

IIIA-29

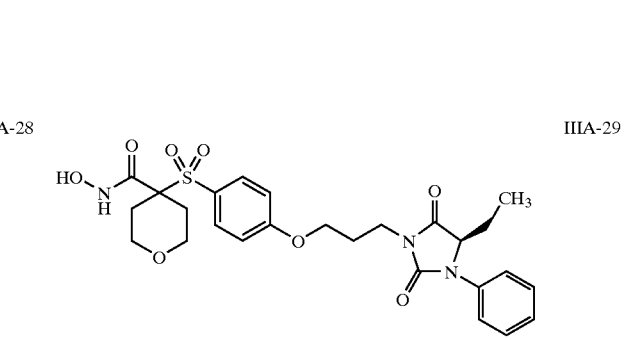

-continued
IIIA-30
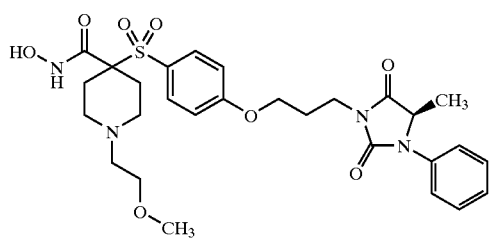
IIIA-31
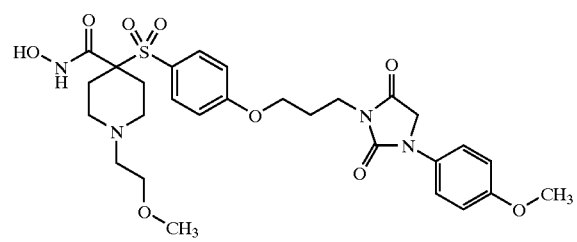
IIIA-32
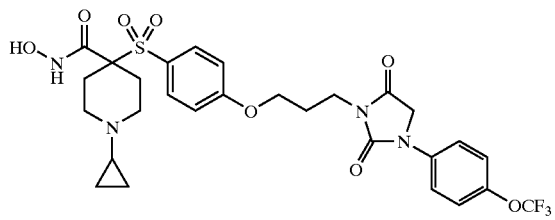
IIIA-33
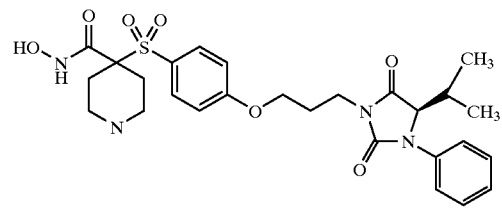
IIIA-34
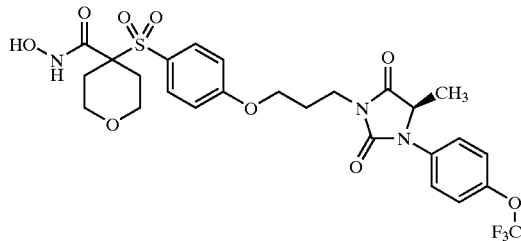
IIIA-35
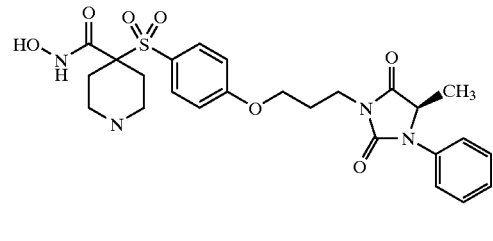
IIIA-36
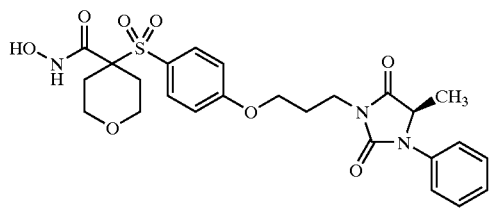
IIIA-37
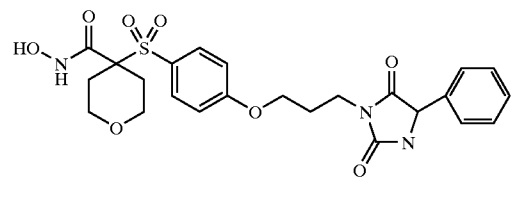
IIIA-38
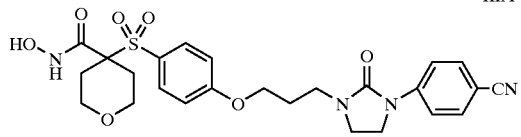
IIIA-39
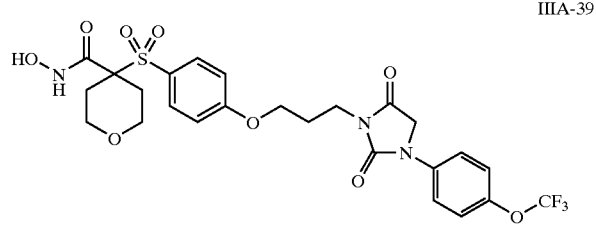
IIIA-40
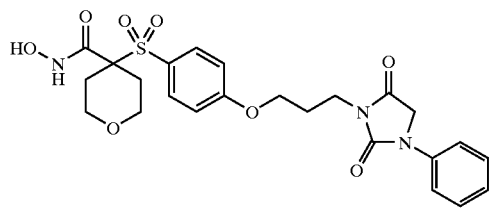
IIIA-41
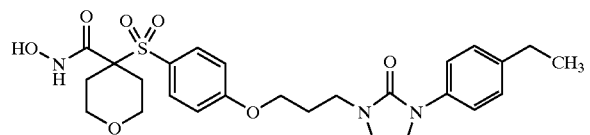

IIIA-42
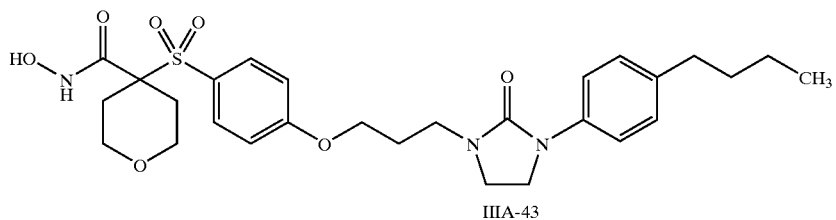
IIIA-43
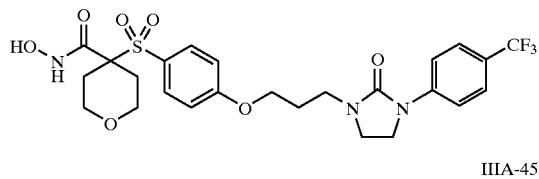
IIIA-44
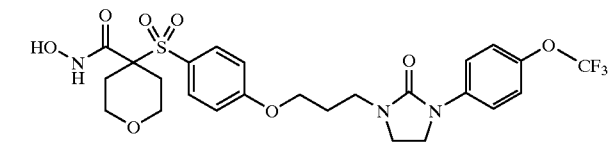
IIIA-45
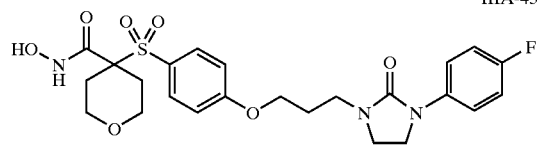
IIIA-46
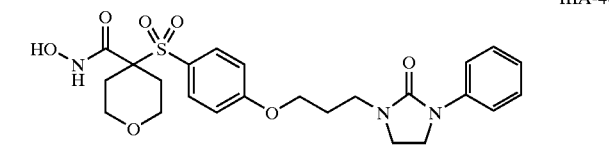
IIIA-47
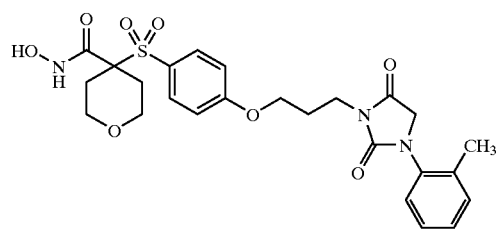
IIIA-48
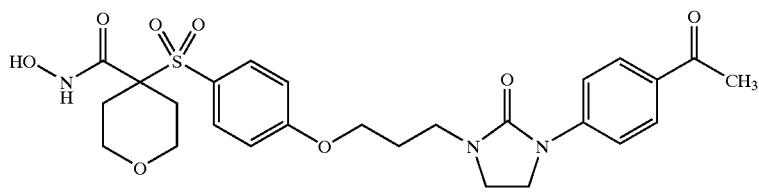
IIIA-49
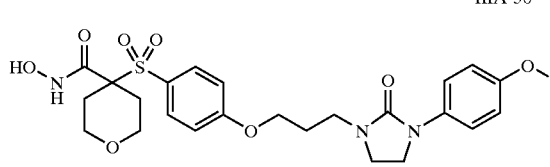
IIIA-50
IIIA-51
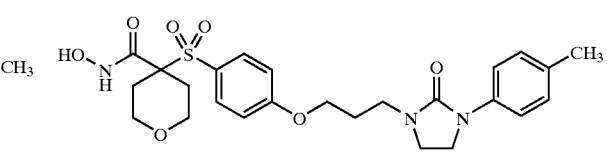
IIIA-52
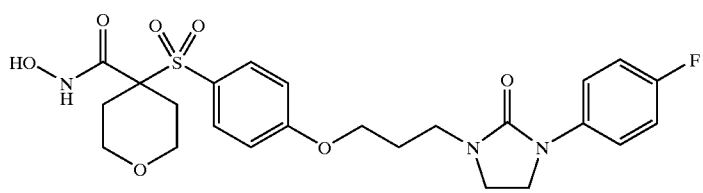

-continued

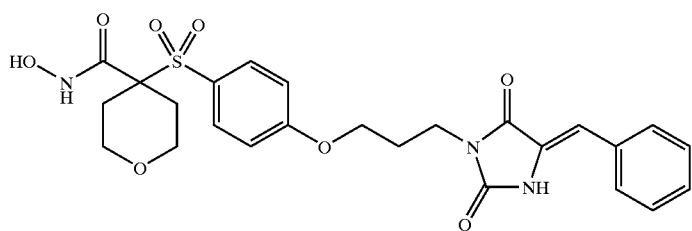

IIIA-53

In other preferred embodiments, $E^5$ is optionally substituted $C_5$–$C_6$-cycloalkyl. Such compounds include, for example:

IIIA-54

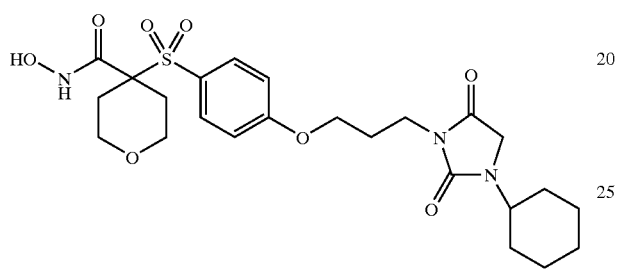

In some preferred embodiments, $E^3$ is optionally-substituted oxazolidinyl. In some such embodiments, $E^5$ is optionally-substituted carbocyclyl, often preferably optionally-substituted aryl, and more preferably optionally-substituted phenyl. Such compounds include, for example:

IIIA-55

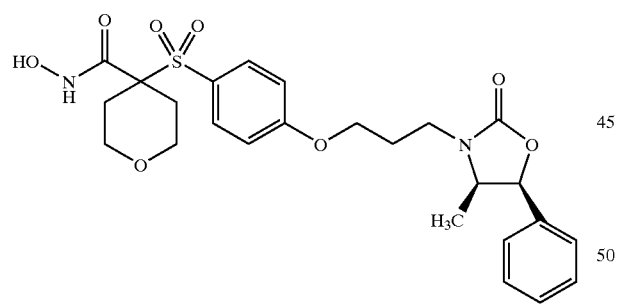

IIIA-56

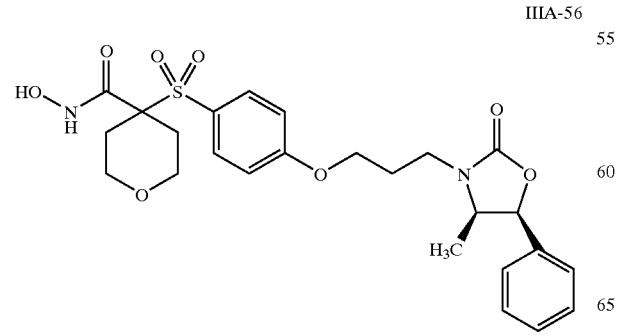

-continued

IIIA-57

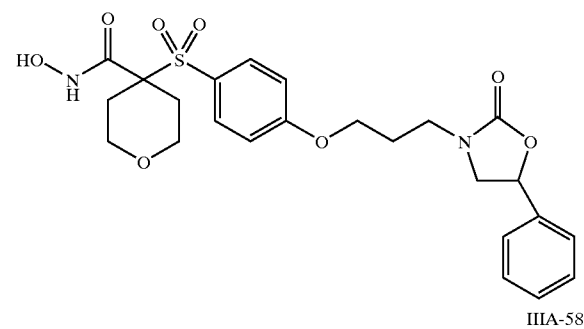

IIIA-58

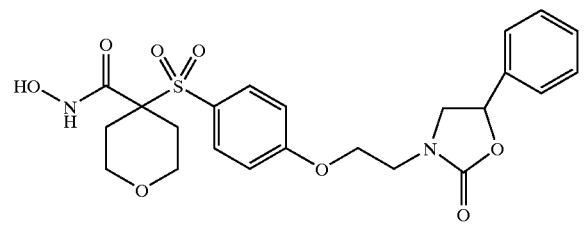

IIIA-59

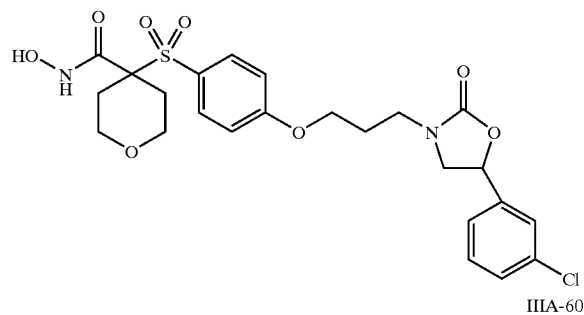

IIIA-60

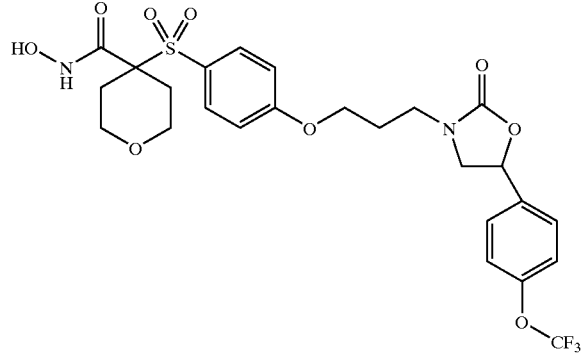

$E^3$ also may be, for example, an optionally-substituted heterocyclyl that contains no greater and no less than 3 heteroatom ring members. Often suitable heterocyclyls include, for example, oxadiazolyl, thiadiazolyl, and triazolyl. Here, the triazolyl optionally is substituted.

In some preferred embodiments, $E^3$ is an optionally-substituted heteroaryl selected from the group consisting of:

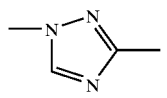
E-43

E-44

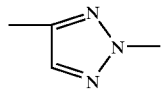
E-45

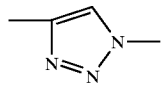
E-46

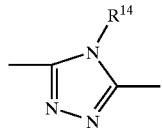
E-47

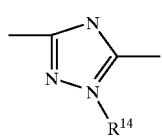
E-48

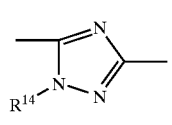
E-49

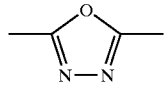
E-50

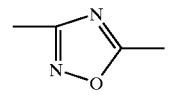
E-51

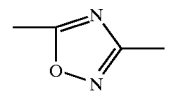
E-52

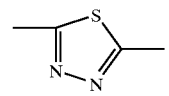
E-53

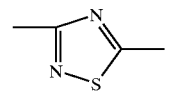
E-54

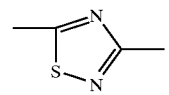
E-55

Any member of this group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl. Except where the substituent is halogen or —OH, any substituent of this group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio. $R^{14}$ is as defined above for heterocyclyls containing 1 or 2 heteroatom ring members.

In some preferred embodiments, $E^3$ is oxadiazolyl.

In some such embodiments, $E^5$ is optionally-substituted phenyl. Such compounds include, for example:

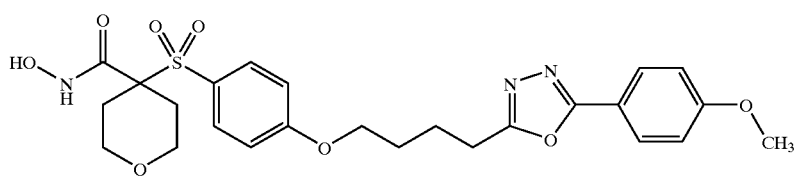
IIIA-61

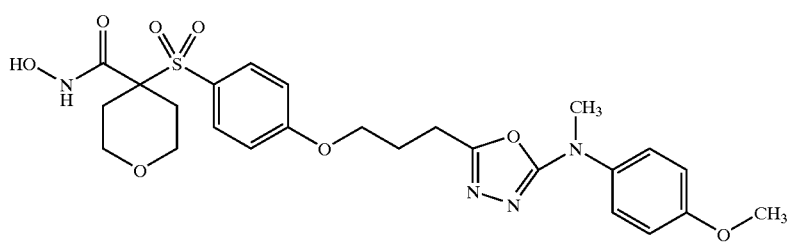
IIIA-62

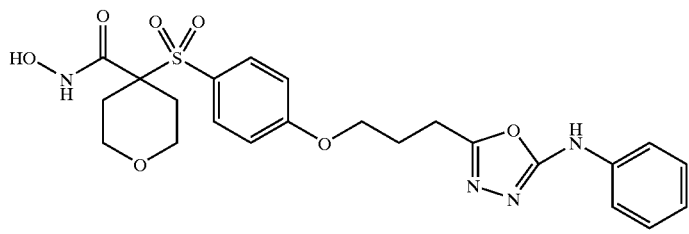
IIIA-63
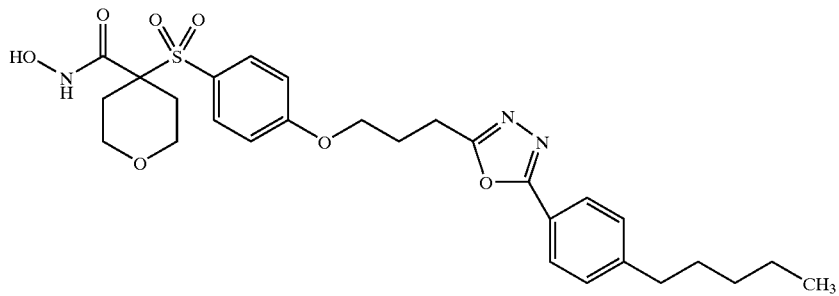
IIIA-64
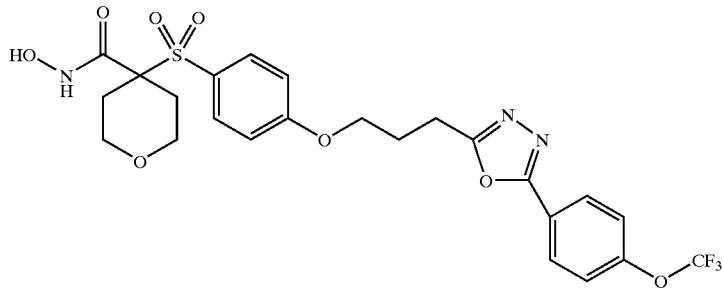
IIIA-65
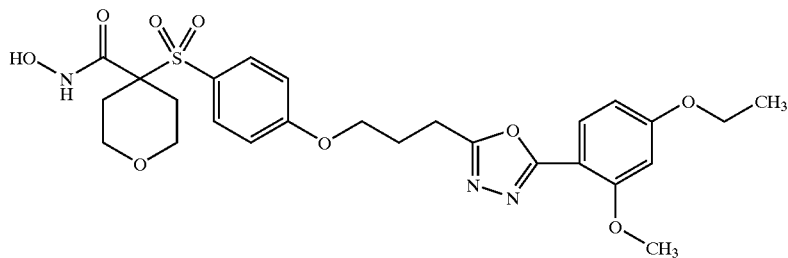
IIIA-66
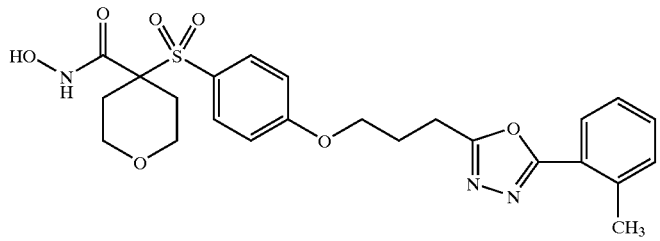
IIIA-67
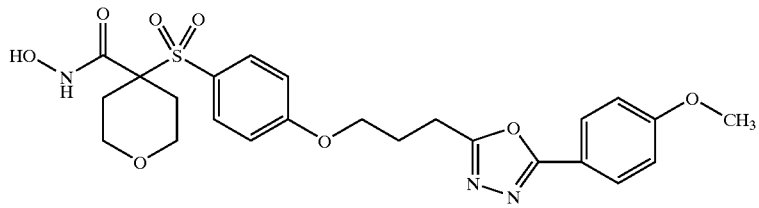
IIIA-68

-continued
IIIA-69
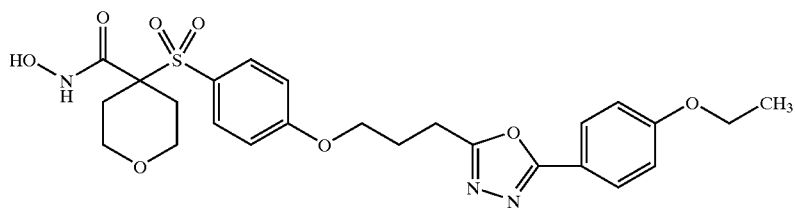
IIIA-70
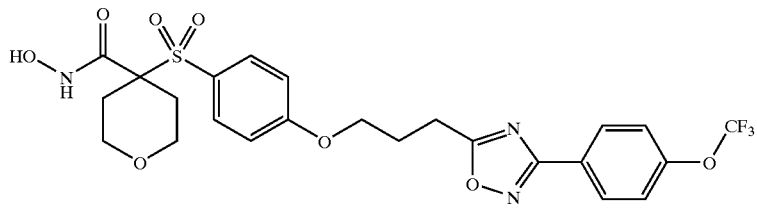
IIIA-71
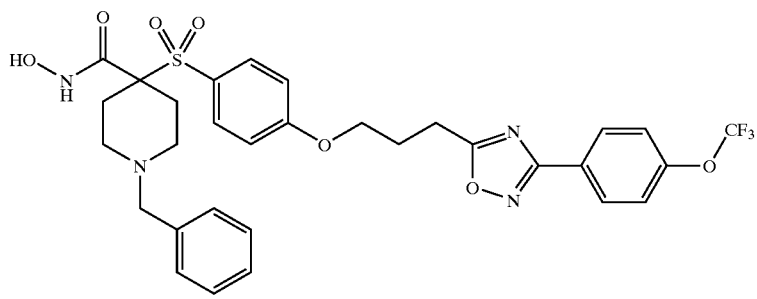
IIIA-72
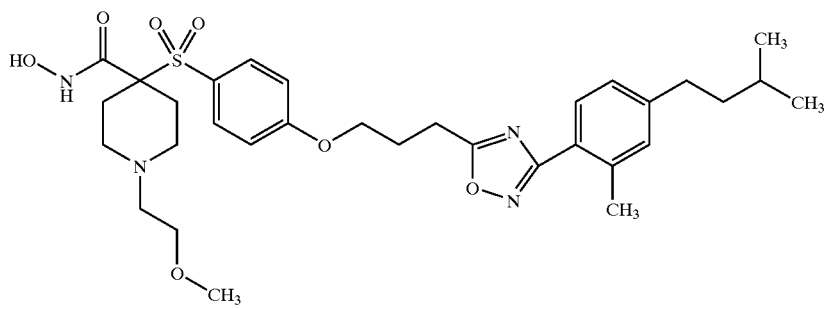
IIIA-73
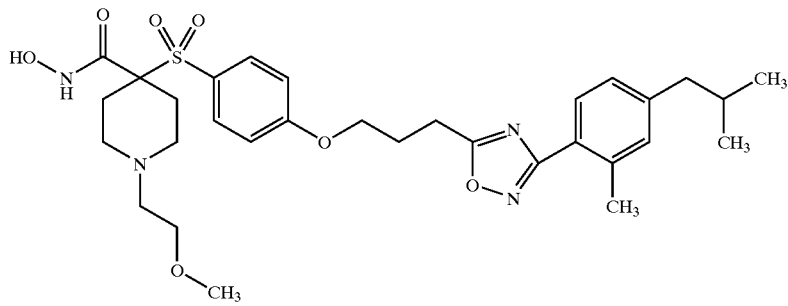
IIIA-74
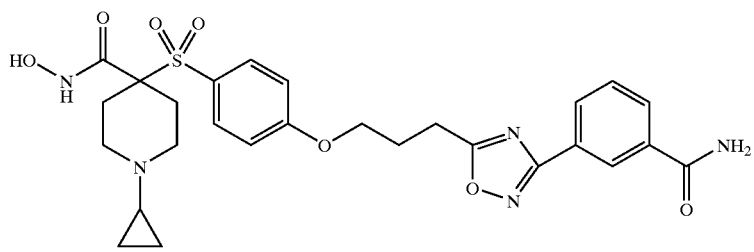

IIIA-75
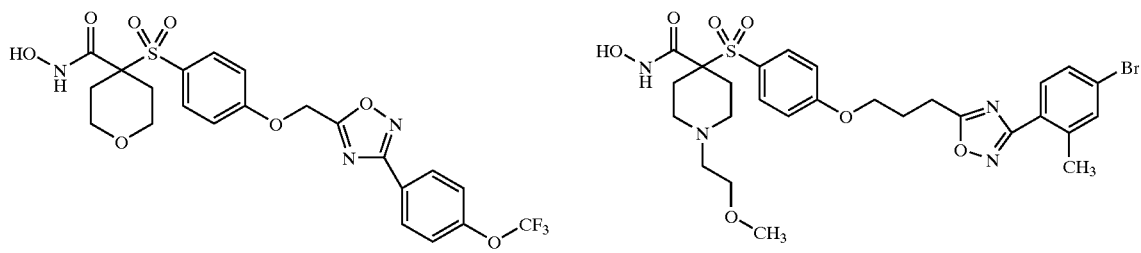
IIIA-76
IIIA-77
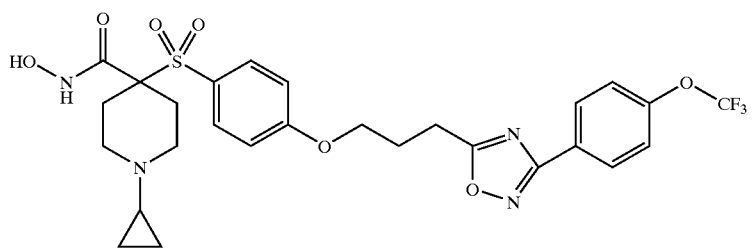
IIIA-78
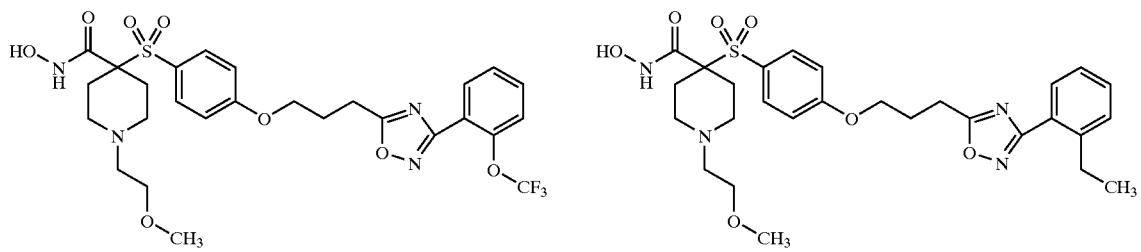
IIIA-79
IIIA-80
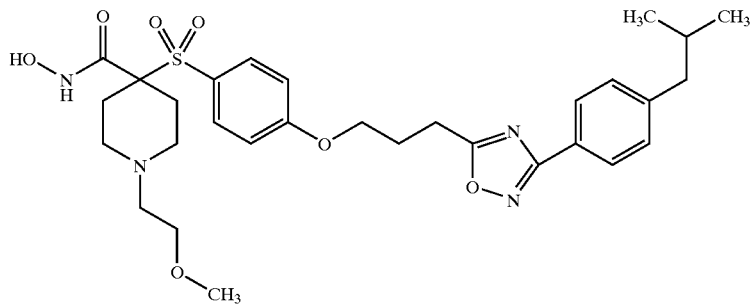
IIIA-81
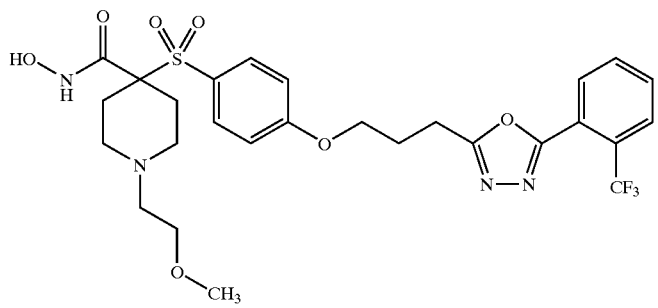
IIIA-82
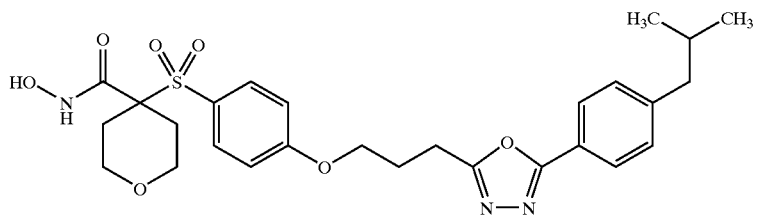

-continued
IIIA-83
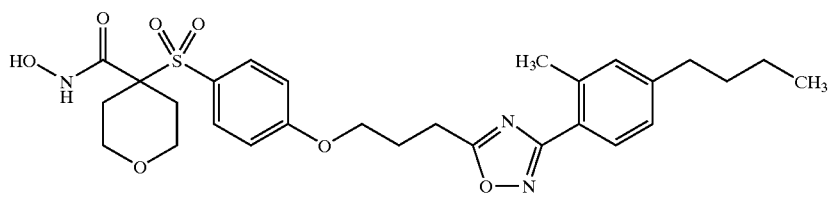
IIIA-84
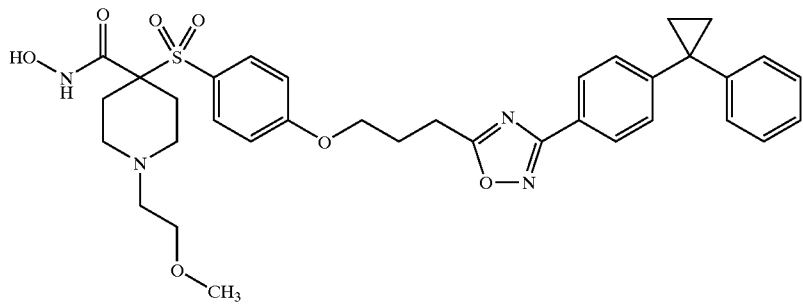
IIIA-85
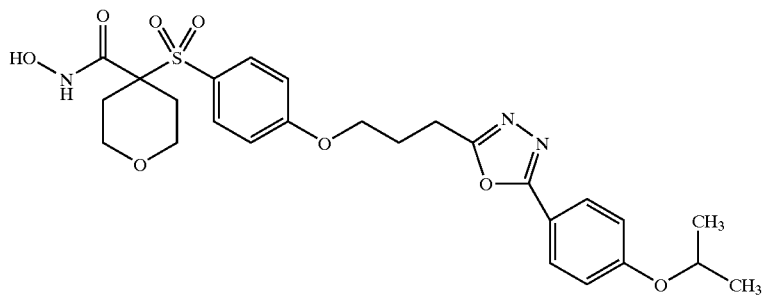
IIIA-86
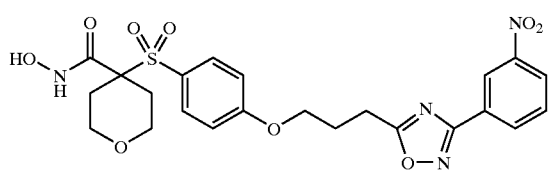
IIIA-87
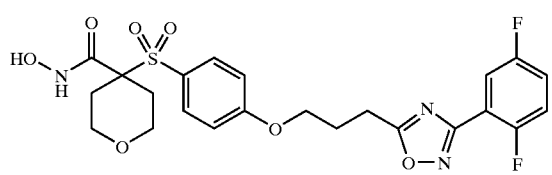
IIIA-88
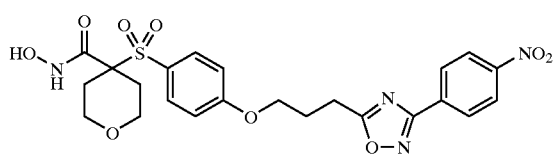
IIIA-89
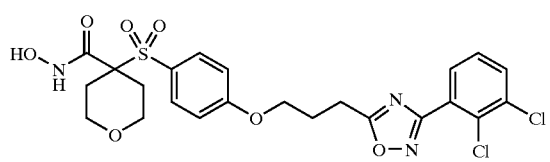
IIIA-90
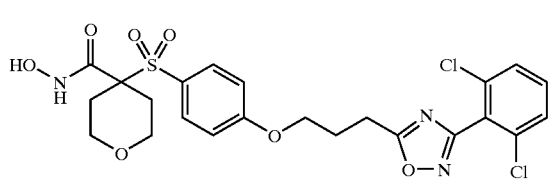
IIIA-91
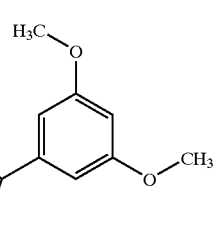
IIIA-92
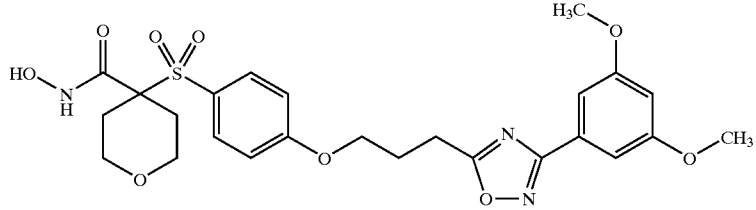

IIIA-93
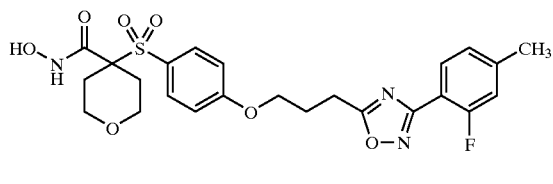
IIIA-94
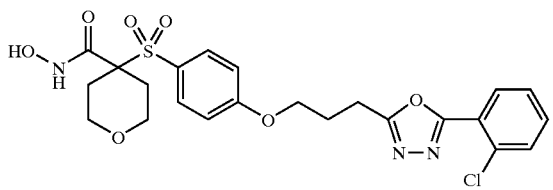
IIIA-95
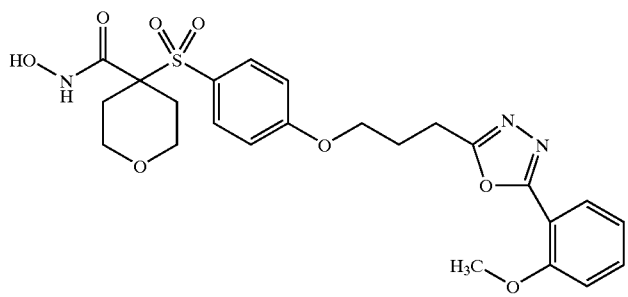
IIIA-96
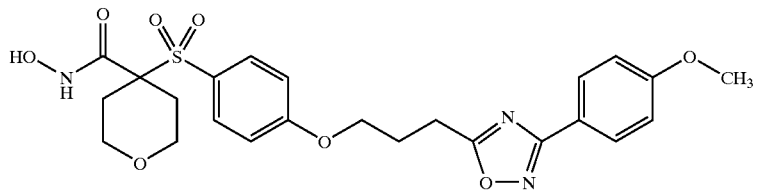
IIIA-97
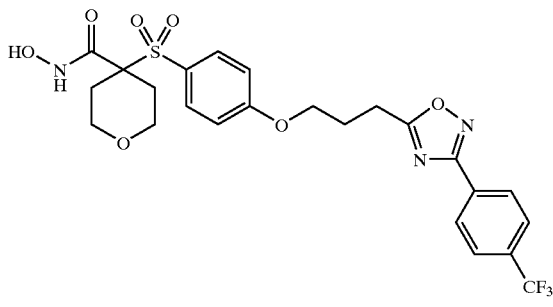
IIIA-98
IIIA-99
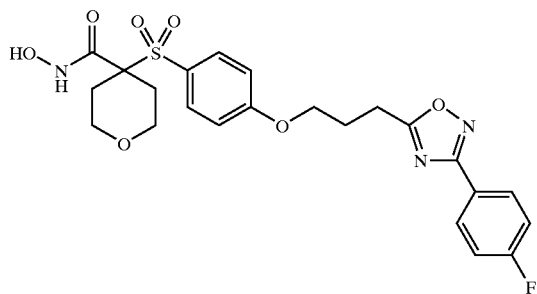
IIIA-100
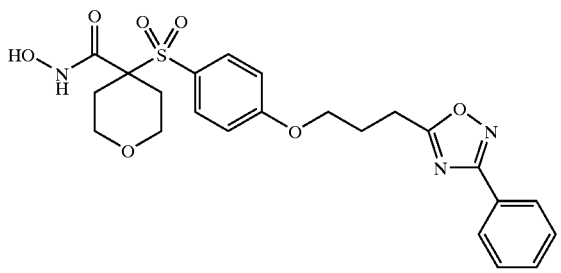

-continued
IIIA-101
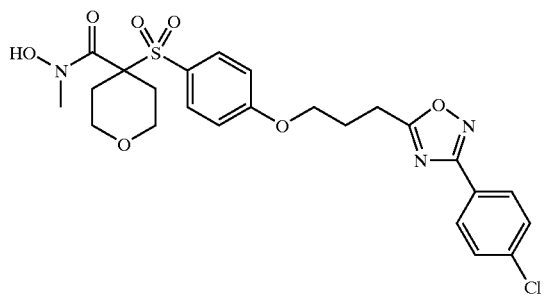
IIIA-102
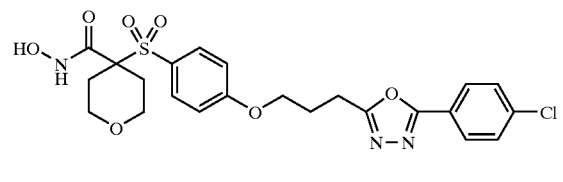
IIIA-103
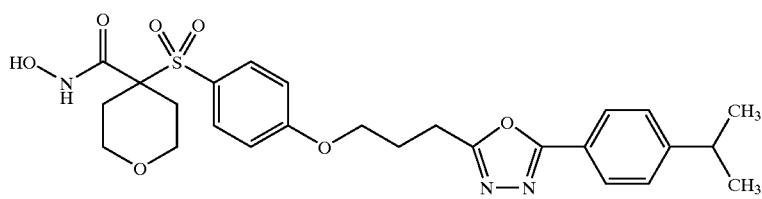
IIIA-104
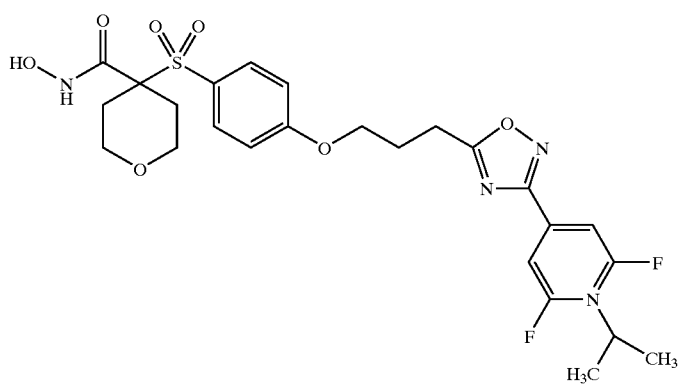
IIIA-105
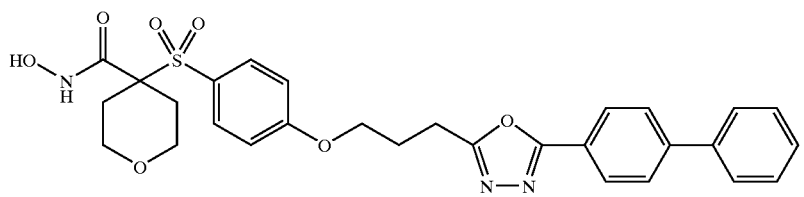
IIIA-106
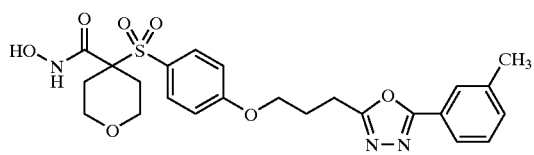
IIIA-107
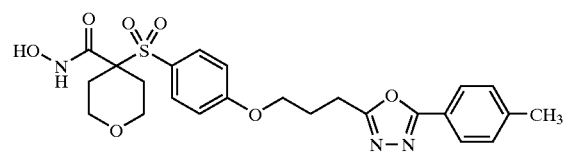
IIIA-108
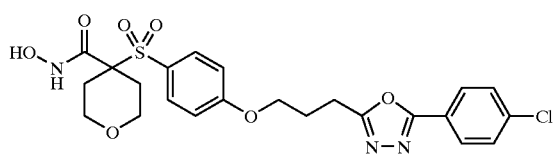
IIIA-109
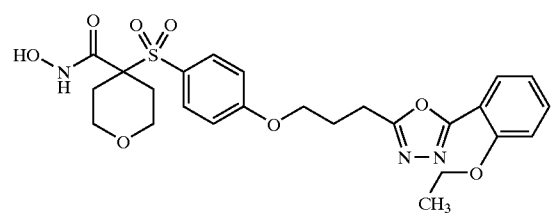

-continued
IIIA-110
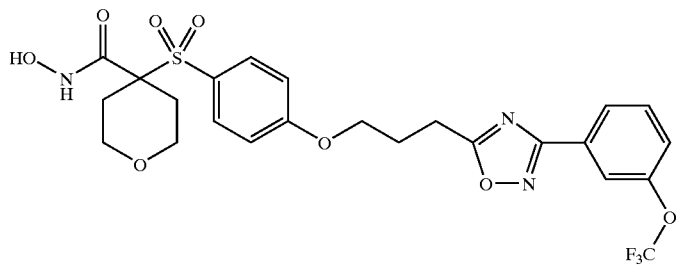
IIIA-111
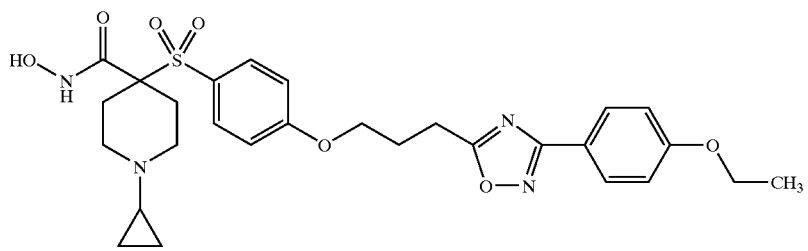
IIIA-112
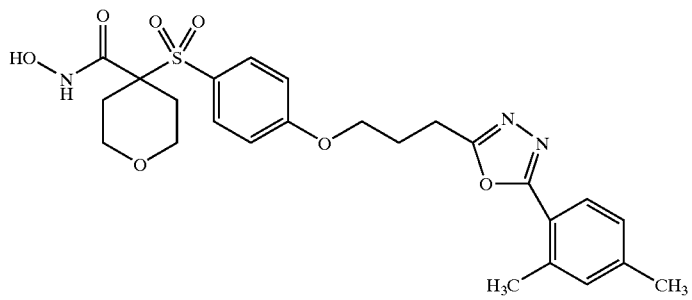
IIIA-113
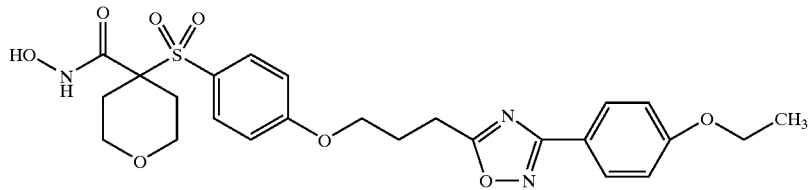
IIIA-114
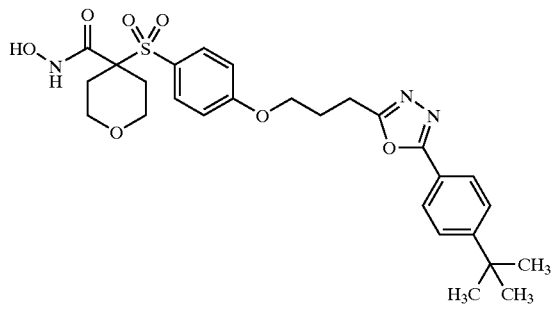
IIIA-115
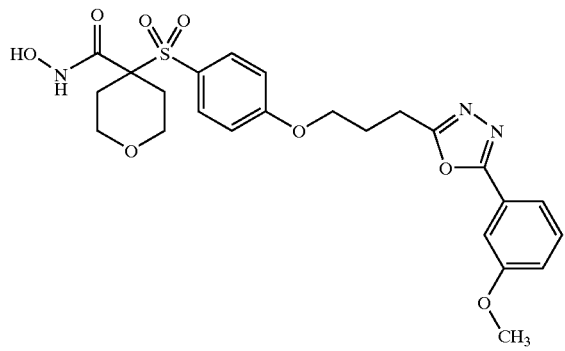

IIIA-116
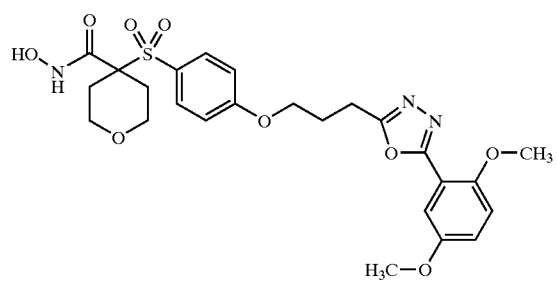
IIIA-117
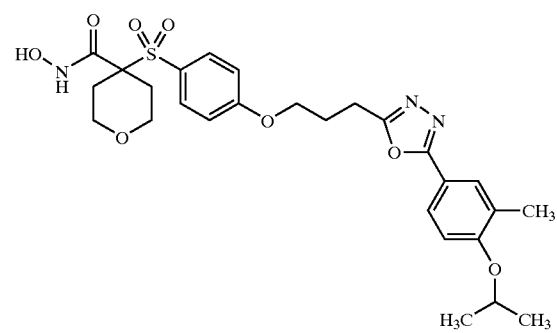
IIIA-118
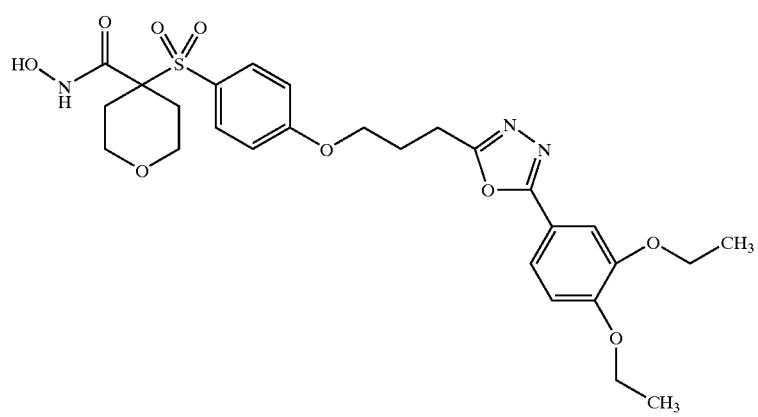
IIIA-119
IIIA-120
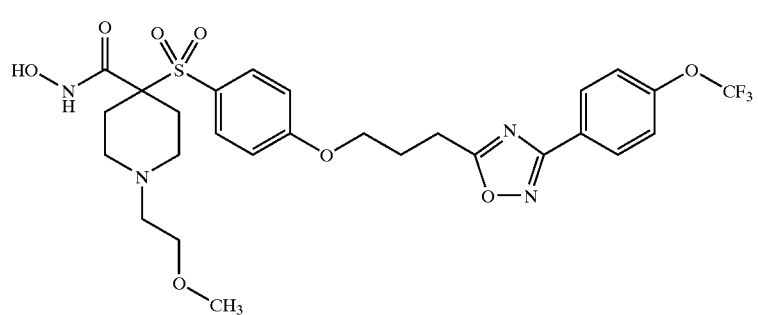

Such compounds also include, for example:

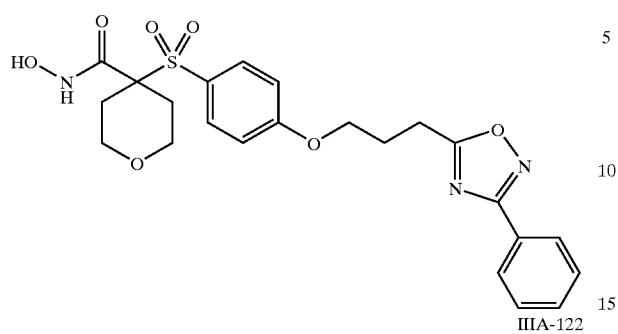

IIIA-121

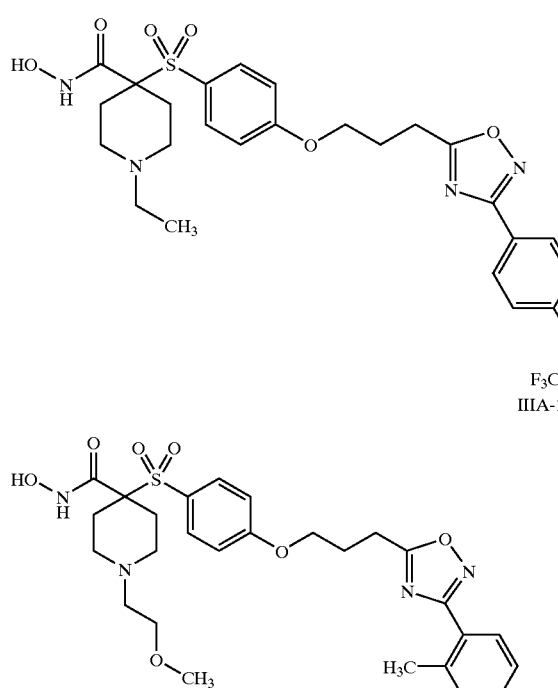

IIIA-122

IIIA-123

In other embodiments, $E^5$ is optionally-substituted naphthalenyl. Such compounds include, for example:

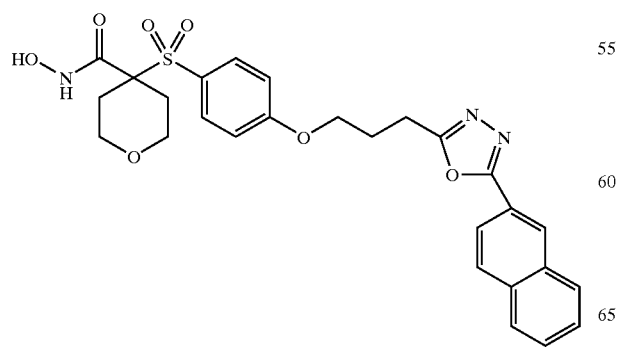

IIIA-124

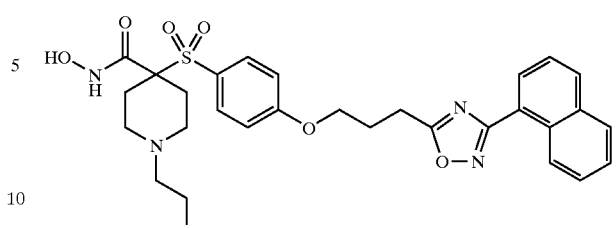

IIIA-125

In other embodiments, $E^5$ is optionally-substituted $C_5$–$C_6$-cycloalkyl. Such compounds include, for example:

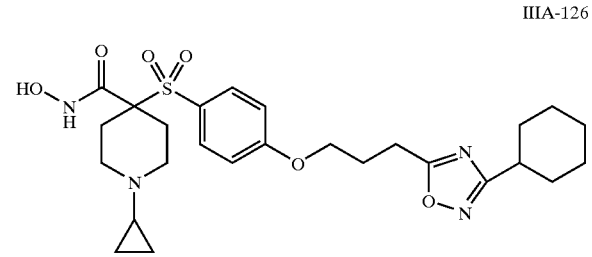

IIIA-126

IIIA-127

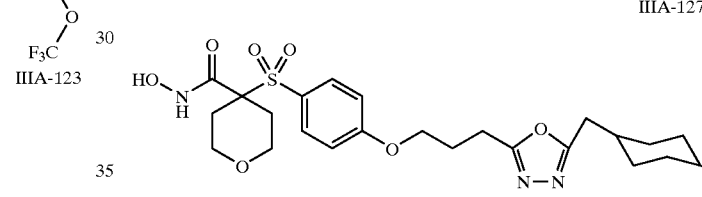

In yet other embodiments, $E^5$ is optionally-substituted heterocyclyl. Such compounds include, for example:

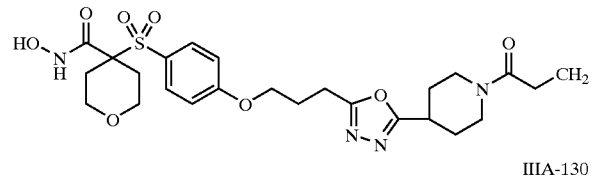

IIIA-128

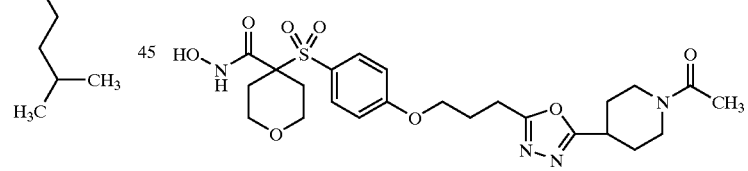

IIIA-129

IIIA-130

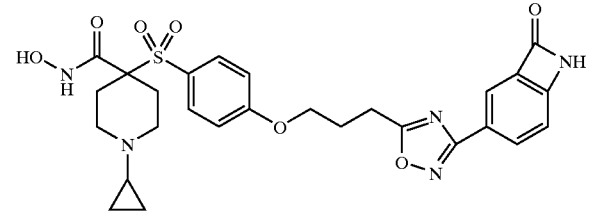

-continued

IIIA-131
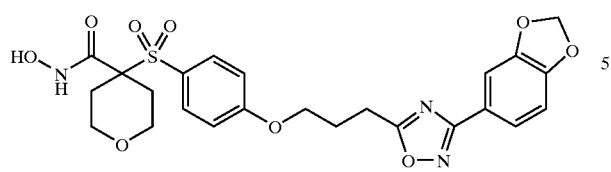

Such compounds also include, for example:

IIIA-132
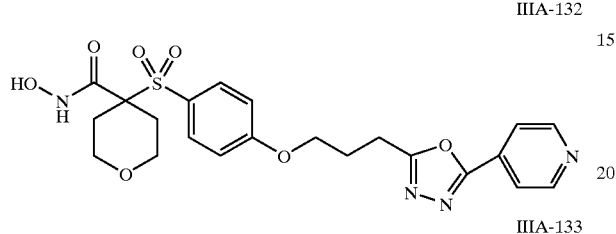

IIIA-133
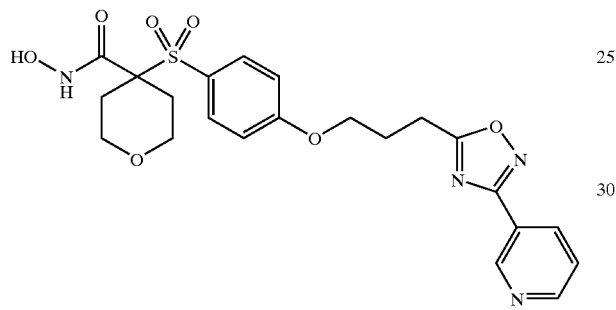

$E^3$ also may be, for example, an optionally-substituted heterocyclyl that contains at least 4 heteroatom ring members.

In some preferred embodiments, $E^3$ is selected from the group consisting of:

E-56
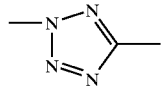

E-57
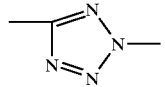

E-58
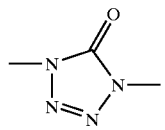

In some such embodiments, $E^5$ is optionally-substituted carbocyclyl, often preferably optionally-substituted aryl, and more preferably optionally-substituted phenyl. Such compounds include, for example:

IIIA-134
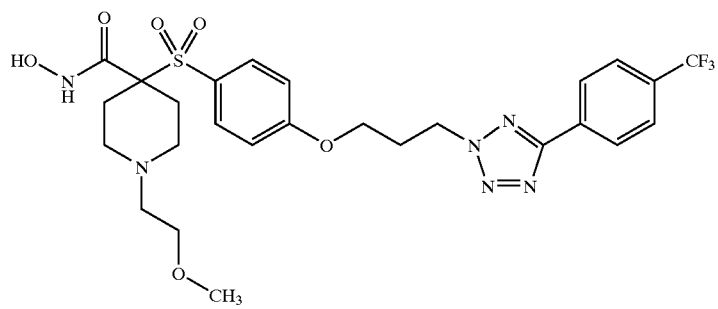

IIIA-135
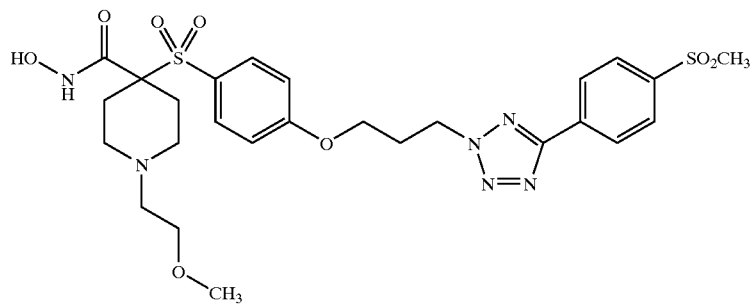

-continued
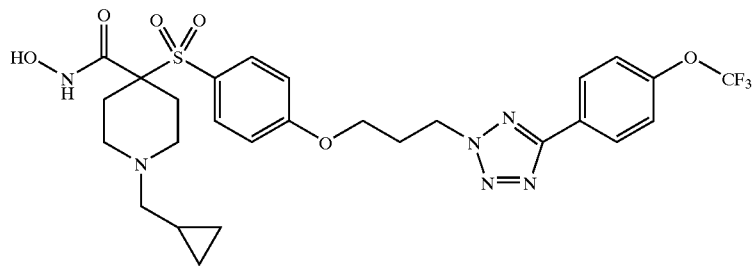
IIIA-136
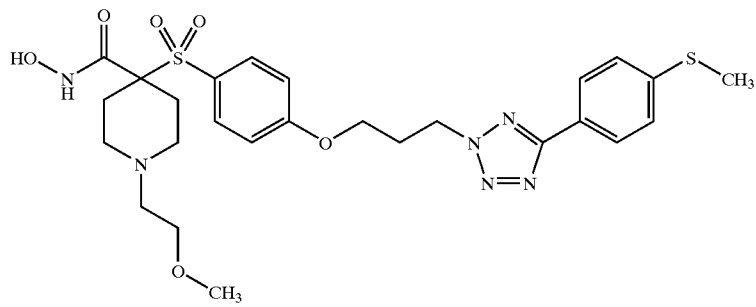
IIIA-137
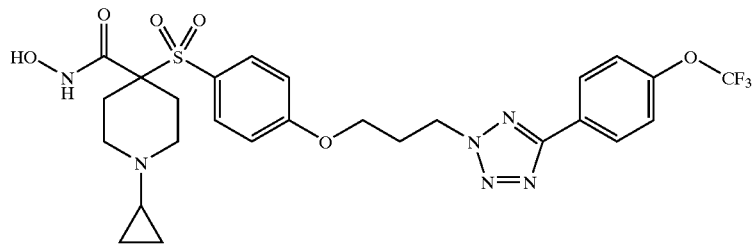
IIIA-138
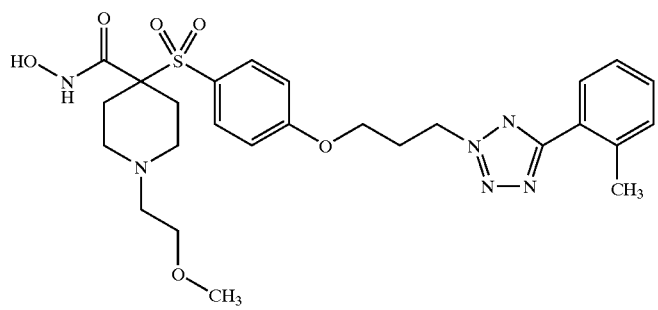
IIIA-139
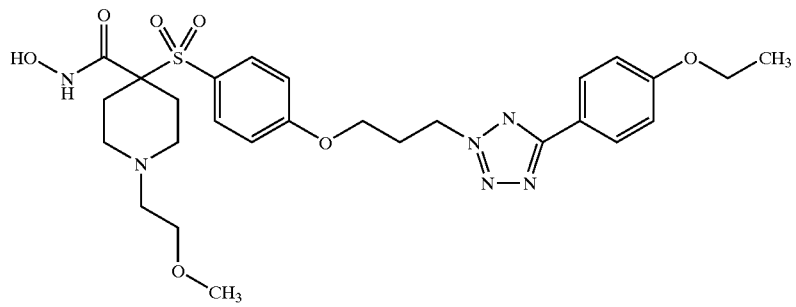
IIIA-140

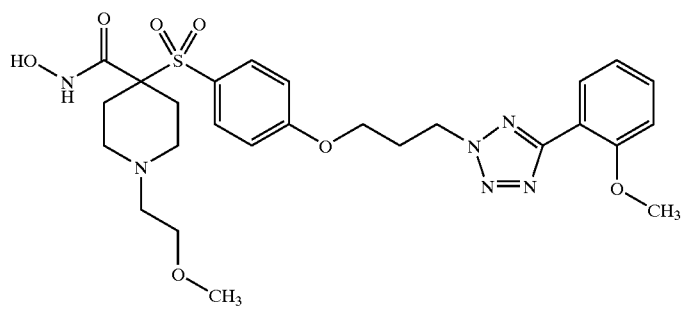
IIIA-141
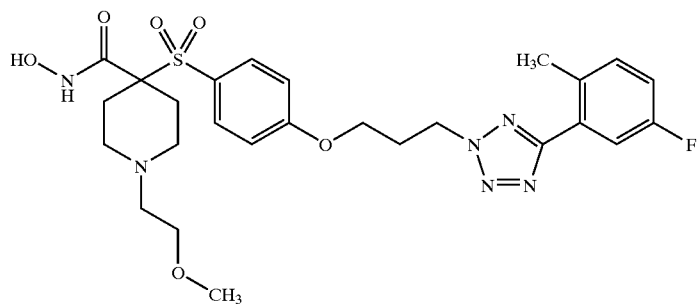
IIIA-142
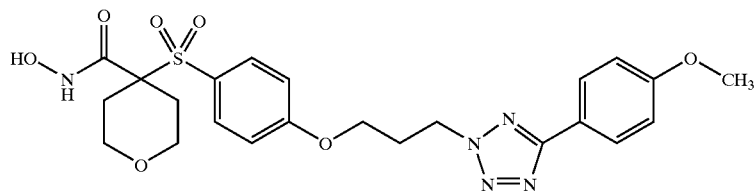
IIIA-143
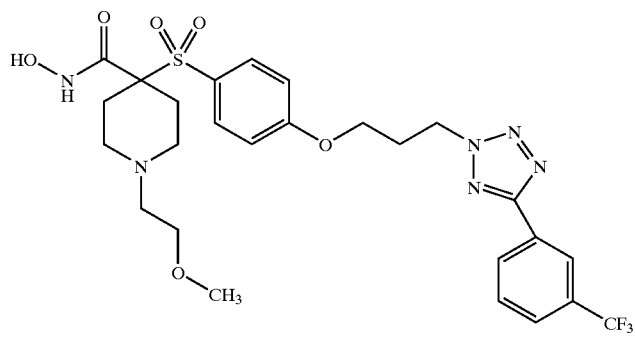
IIIA-148
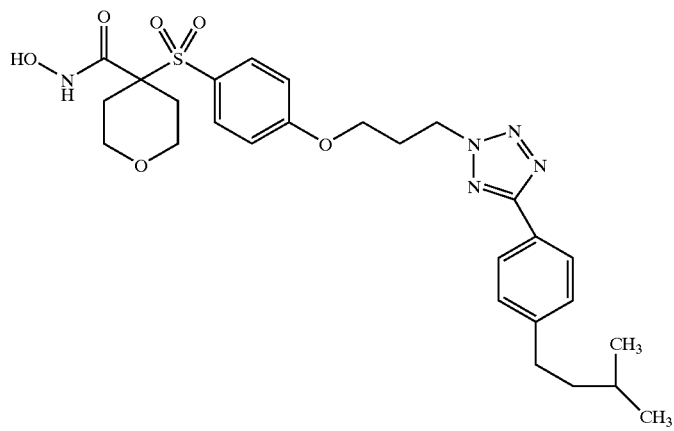
IIIA-149

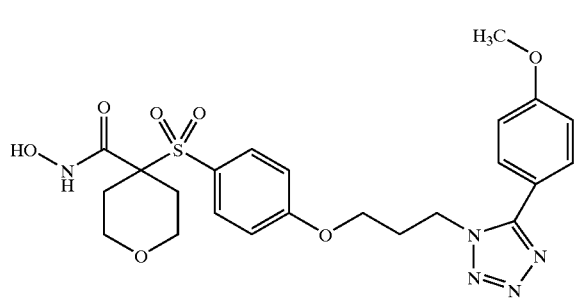
IIIA-150
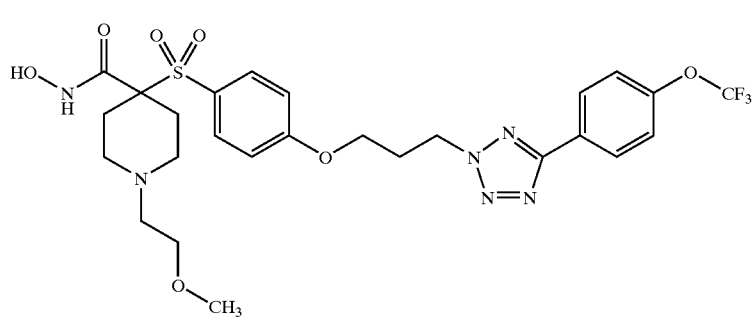
IIIA-151
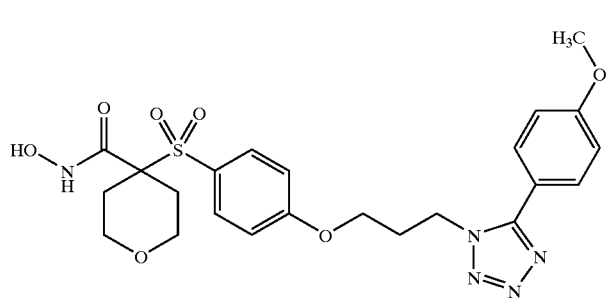
IIIA-144
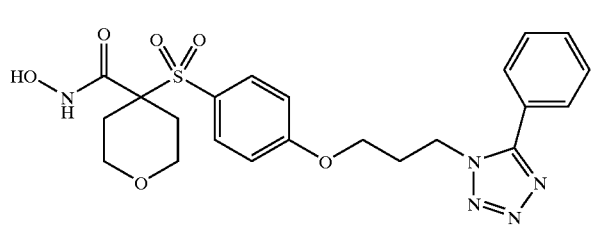
IIIA-145
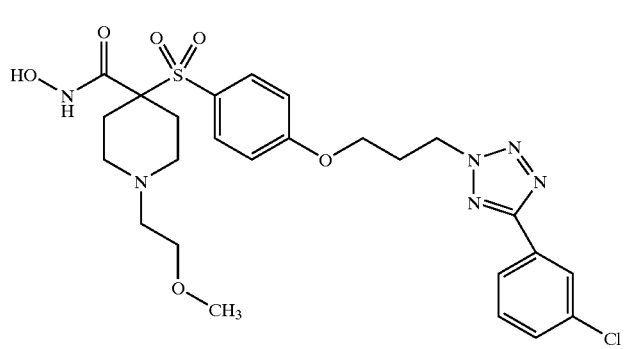
IIIA-146

-continued

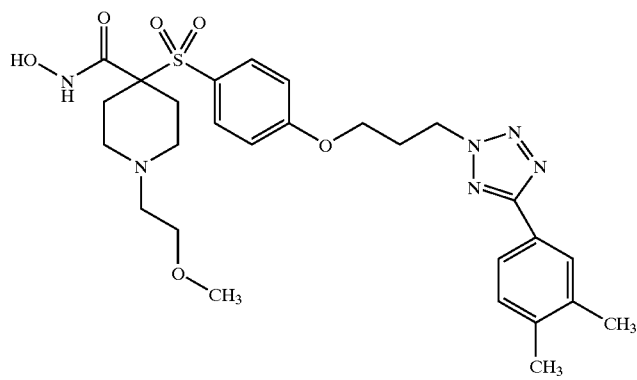
IIIA-147

In other such embodiments, $E^5$ is optionally-substituted heterocyclyl. Such compounds include, for example:

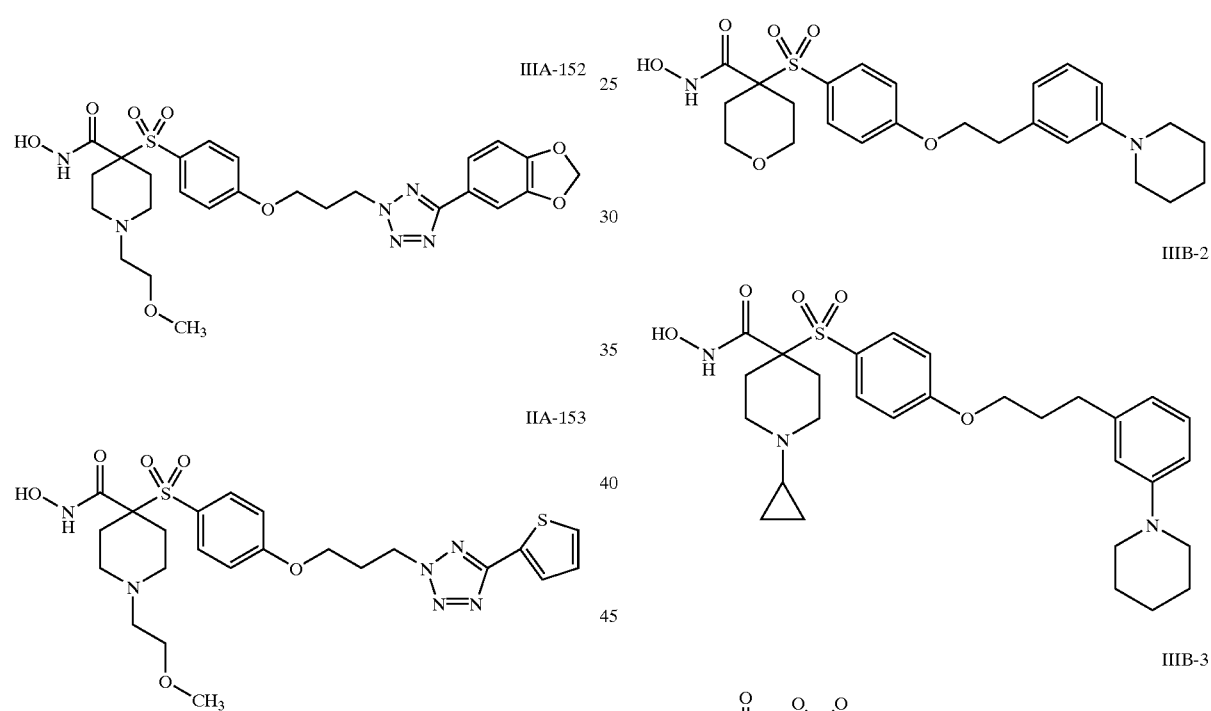

Preferred Embodiment No. 2-b: $E^3$ is Optionally Substituted Carbocyclyl

In some embodiments, $E^3$ is an optionally-substituted carbocyclyl. $E^3$ may be, for example, an optionally-substituted carbocyclyl selected from the group consisting of cyclopropyl, cyclobutyl, cyclopentyl, cyclopentenyl, cyclopentadienyl, cyclohexyl, cyclohexenyl, cyclohexadienyl, phenyl, naphthalenyl, tetrahydronaphthalenyl, indenyl, isoindenyl, indanyl, bicyclodecanyl, anthracenyl, phenanthrene, benzonaphthenyl, fluoreneyl, decalinyl, and norpinanyl.

In some preferred embodiments, $E^3$ is optionally-substituted phenyl. In one such embodiment, for example, $E^5$ is optionally-substituted heterocyclyl.

In some such embodiments, $E^5$ is optionally-substituted heterocycloalkyl. Examples of such compounds include, for example:

In other preferred embodiments, $E^5$ is optionally-substituted, 5-member heteroaryl. Examples of such compounds include, for example:

IIIB-4
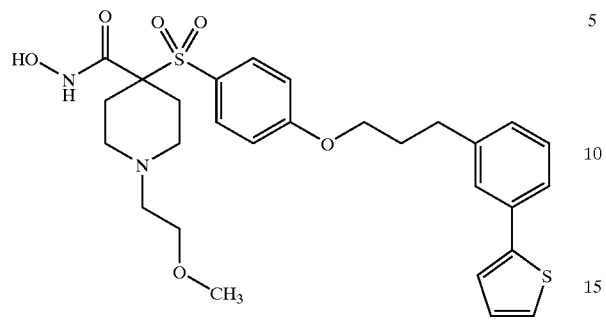
IIIB-5
IIIB-6
IIIB-7
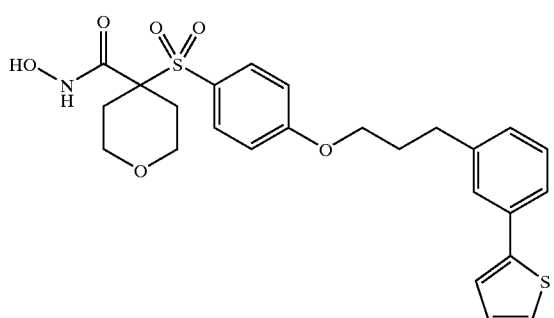
IIIB-8
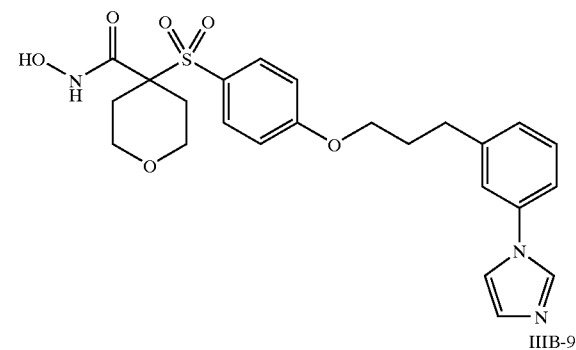
IIIB-9
IIIB-10
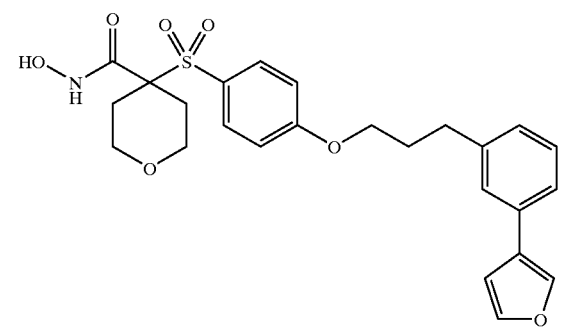
Such compounds also include, for example:
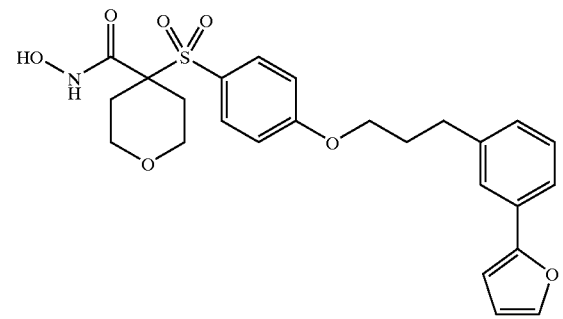
In other preferred embodiments, $E^5$ is optionally-substituted, 6-member heteroaryl.
In other preferred embodiments, $E^5$ is optionally-substituted pyridinyl. Such compounds include, for example:
IIIB-11
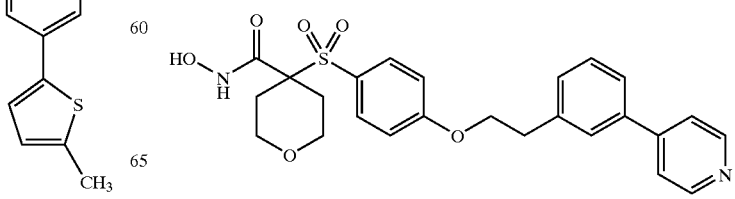

Such compounds also include, for example:
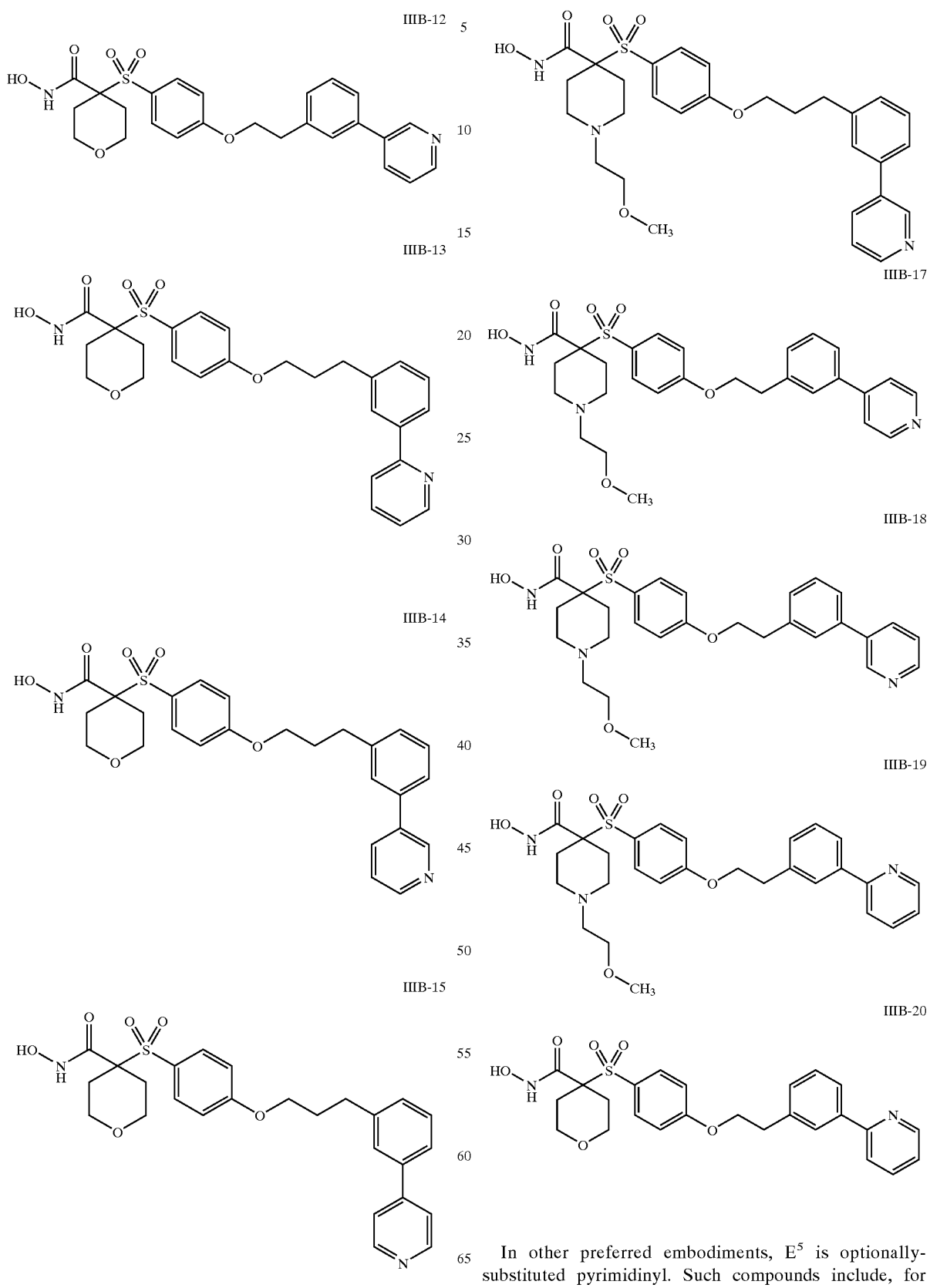
In other preferred embodiments, $E^5$ is optionally-substituted pyrimidinyl. Such compounds include, for example:

IIIB-21

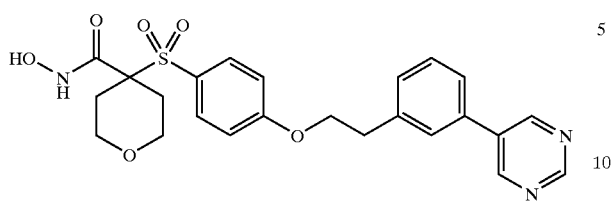

In other preferred embodiments, $E^5$ is optionally-substituted, multi-ring heterocyclyl. Such compounds include, for example:

IIIB-22

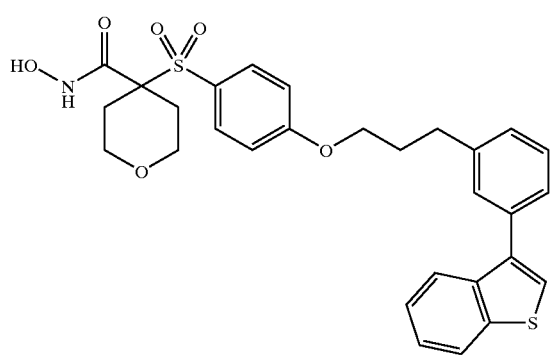

IIIB-23

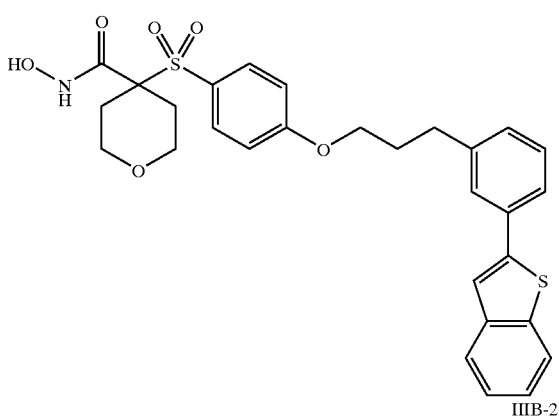

IIIB-24

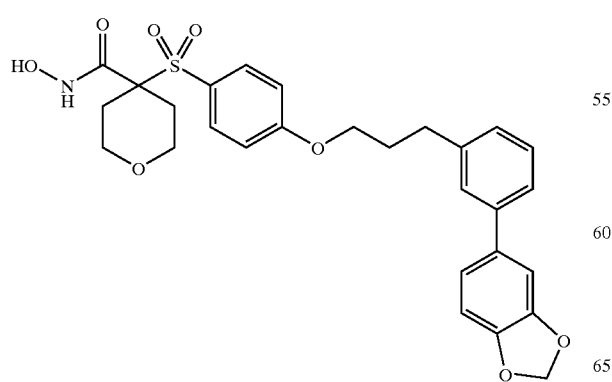

IIIB-25

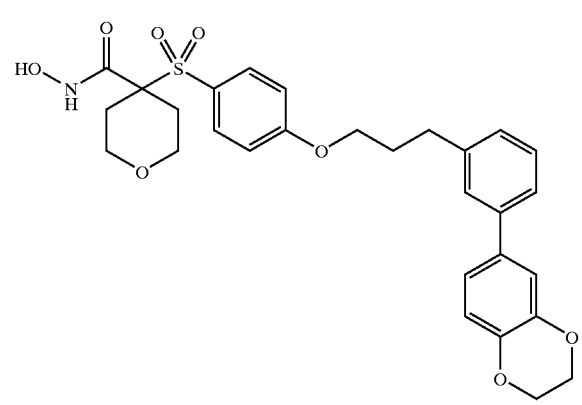

IIIB-26

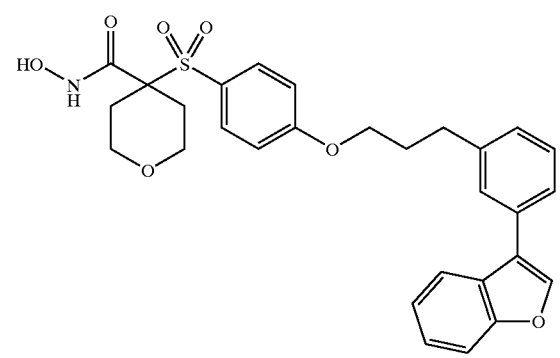

In some preferred embodiments, for example, $E^5$ is optionally-substituted carbocyclyl, often preferably optionally-substituted aryl, In some preferred embodiments, $E^5$ is optionally-substituted phenyl. Such compounds include, for example:

IIIB-27

IIIB-28

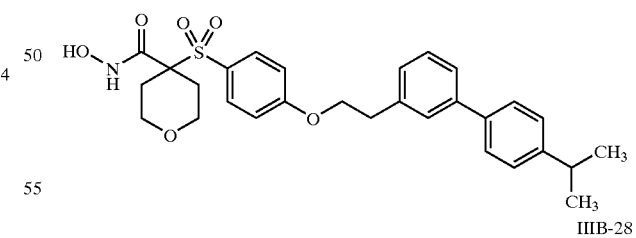

-continued
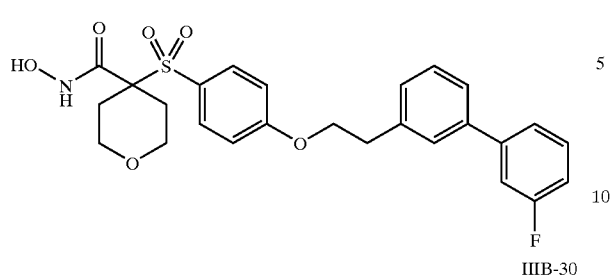
IIIB-29
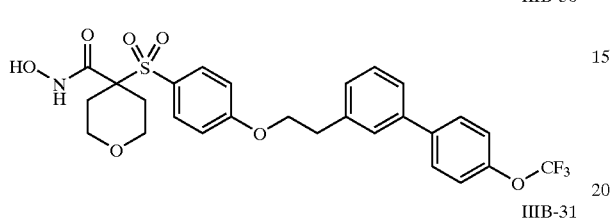
IIIB-30
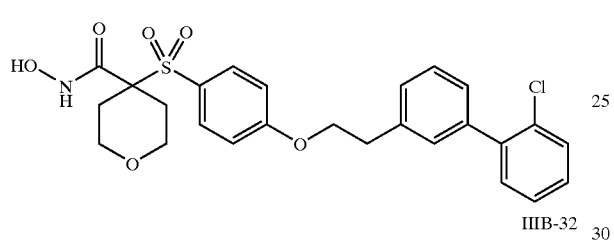
IIIB-31
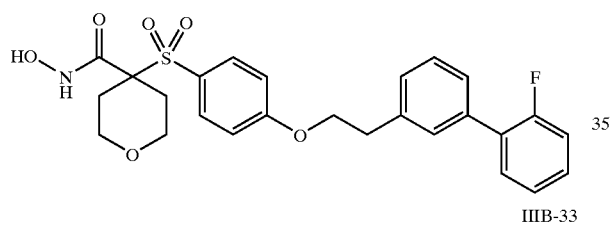
IIIB-32
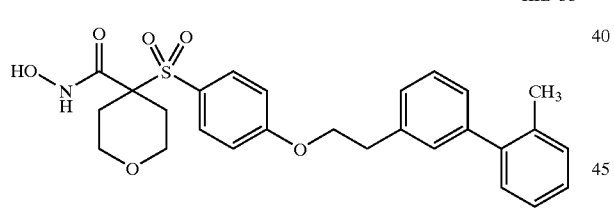
IIIB-33
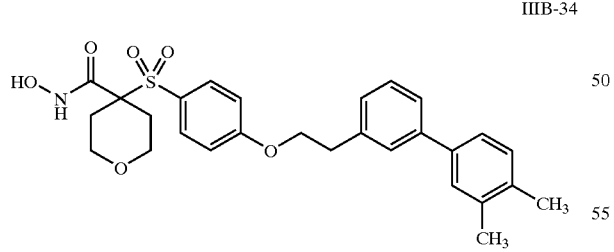
IIIB-34
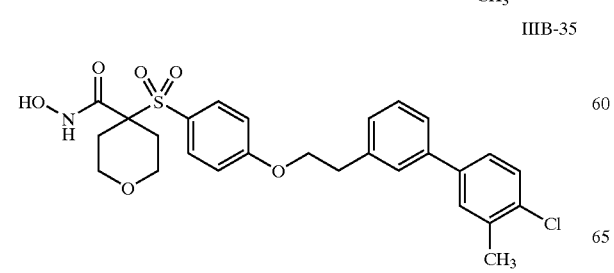
IIIB-35
-continued
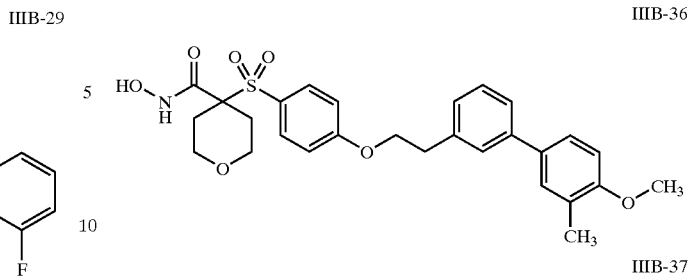
IIIB-36
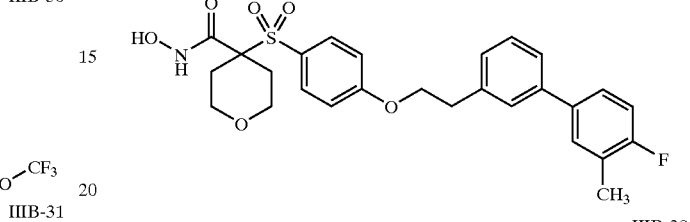
IIIB-37
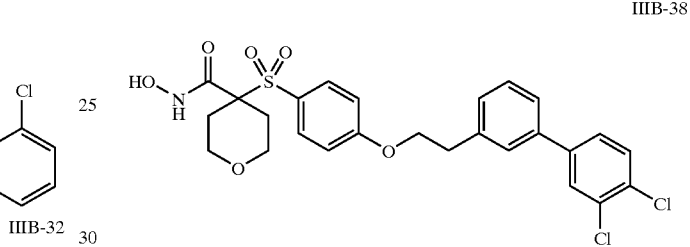
IIIB-38
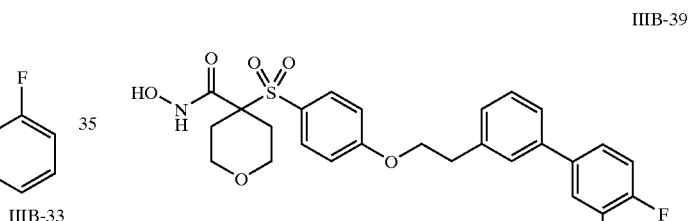
IIIB-39
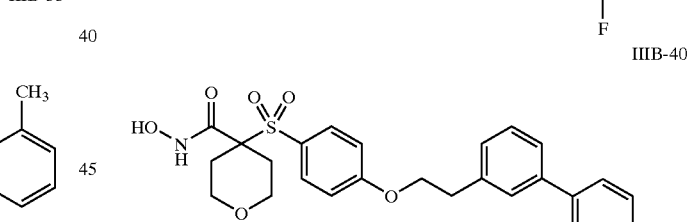
IIIB-40
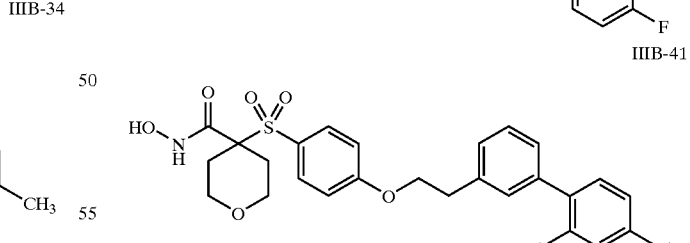
IIIB-41
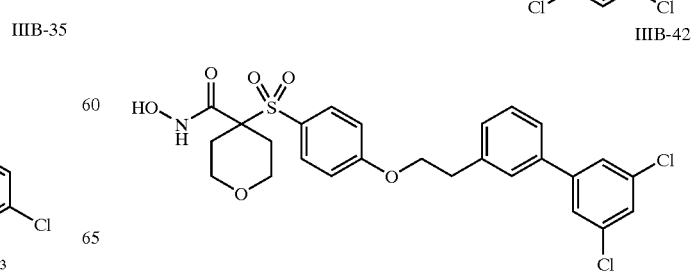
IIIB-42

IIIB-43
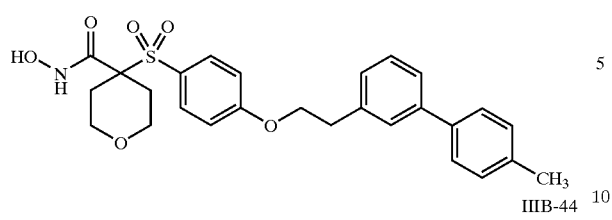
IIIB-44
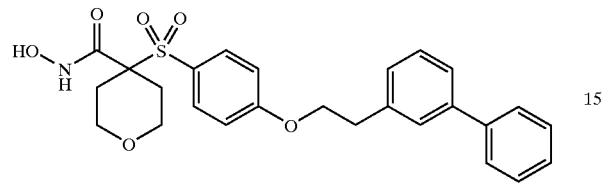
IIIB-45
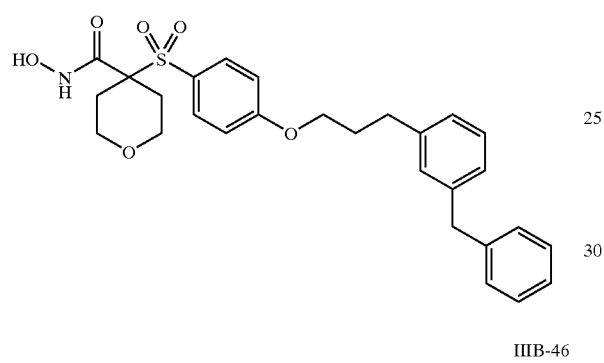
IIIB-46
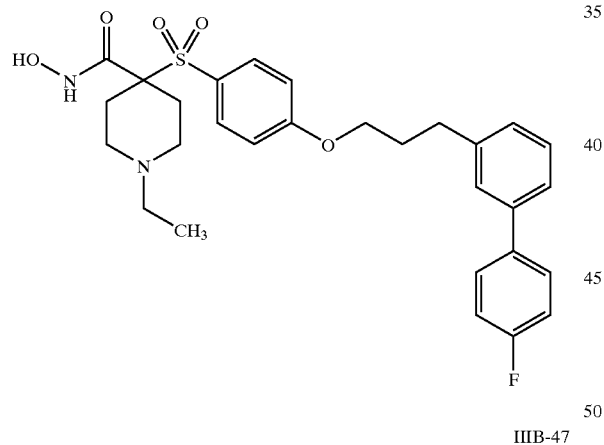
IIIB-47
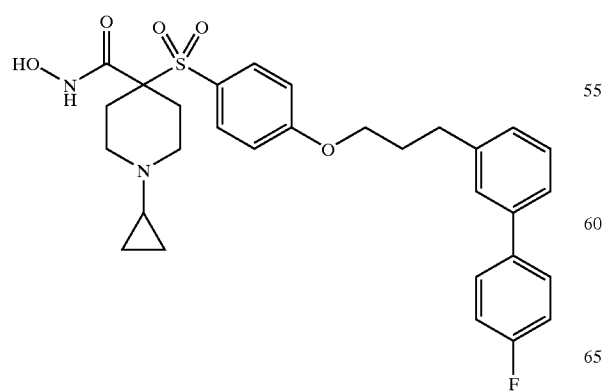
IIIB-48
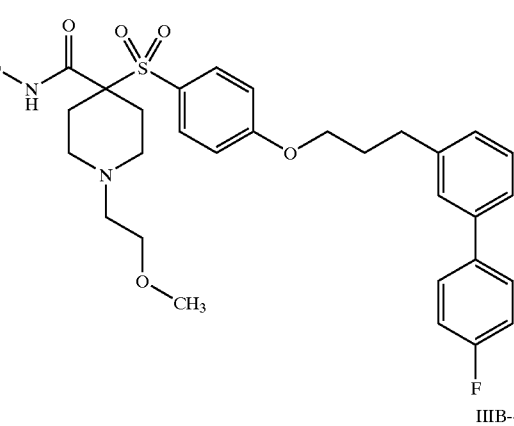
IIIB-49
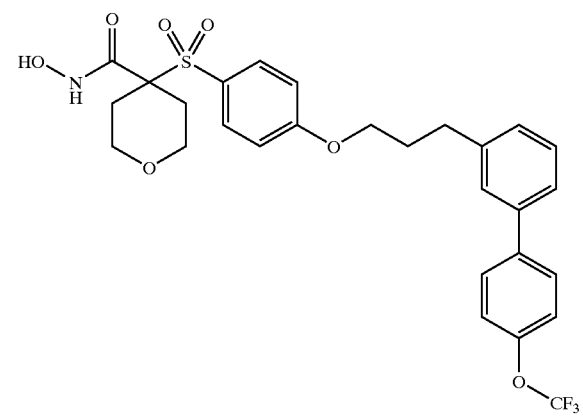
IIIB-50
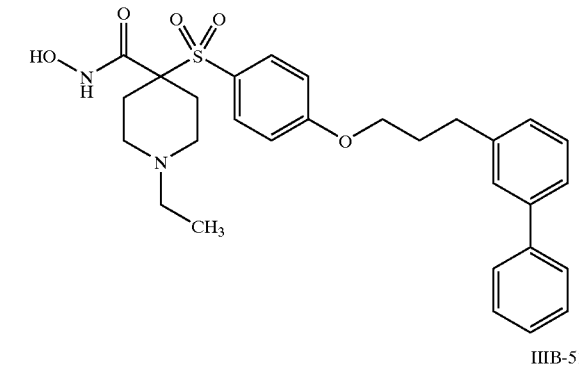
IIIB-51
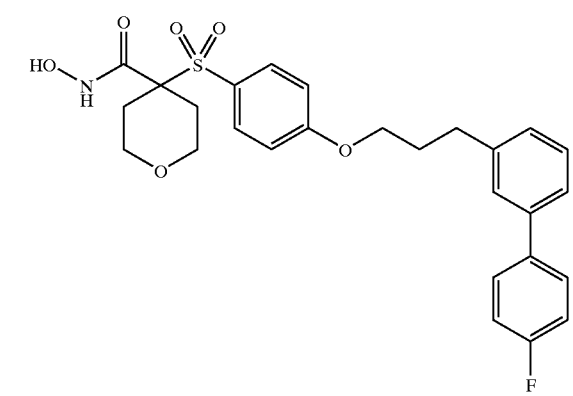

IIIB-52
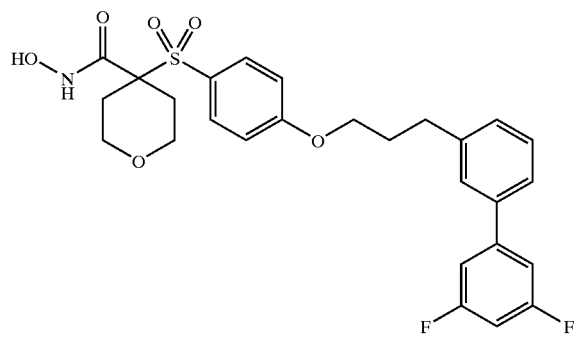
IIIB-56
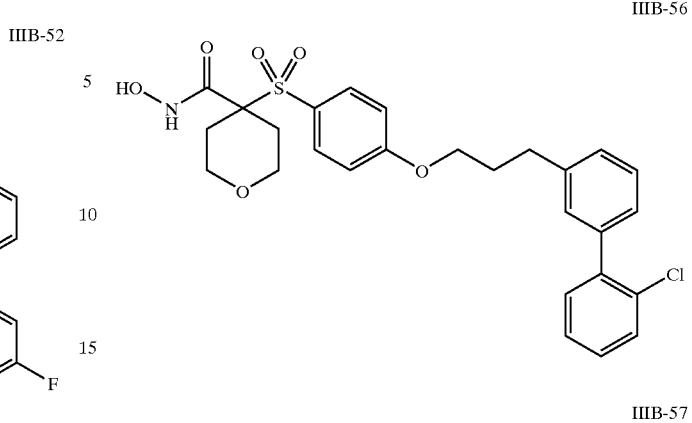
IIIB-53
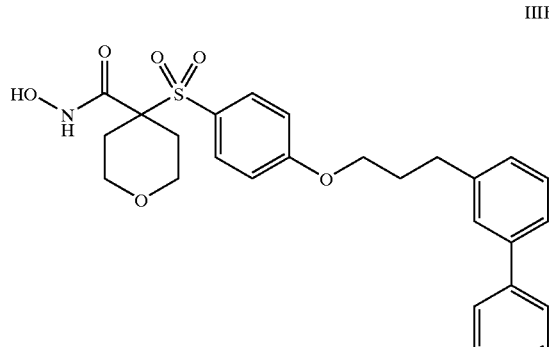
IIIB-57
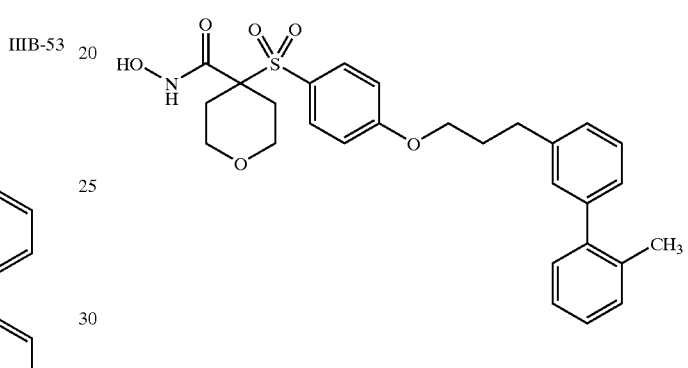
IIIB-54
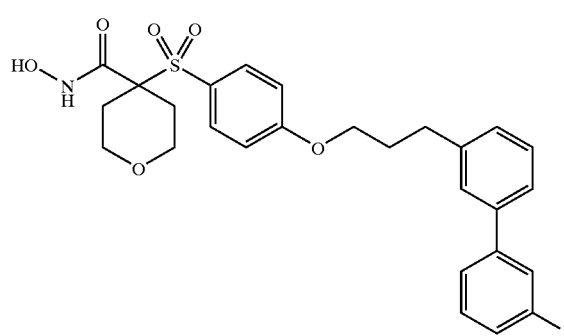
IIIB-58
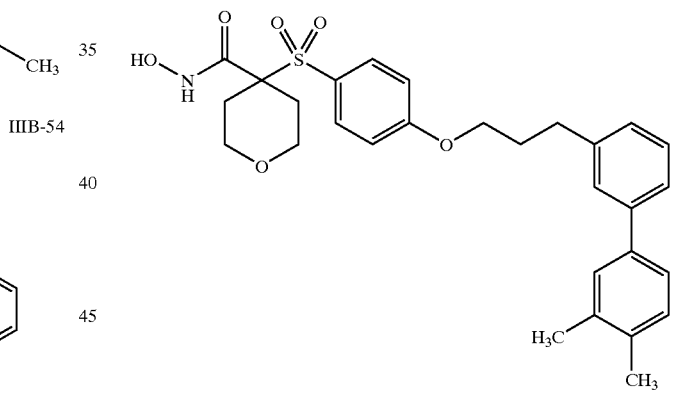
IIIB-55
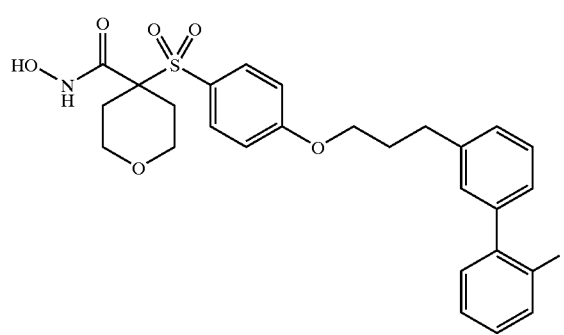
IIIB-59
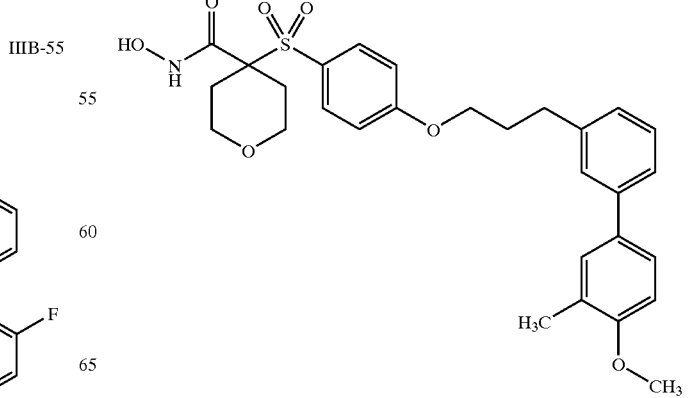

-continued
IIIB-60
IIIB-61
IIIB-62
IIIB-63
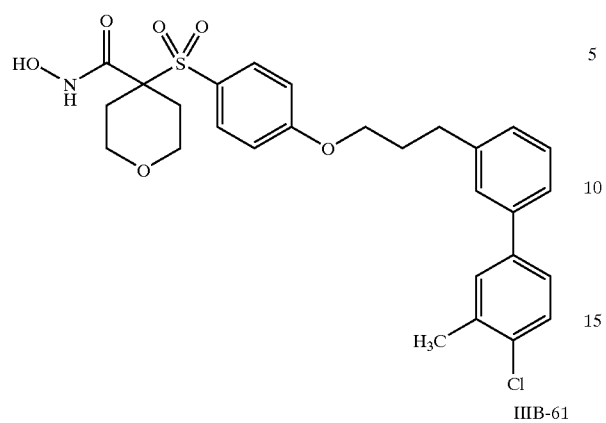
-continued
IIIB-64
IIIB-65
IIIB-66
IIIB-67
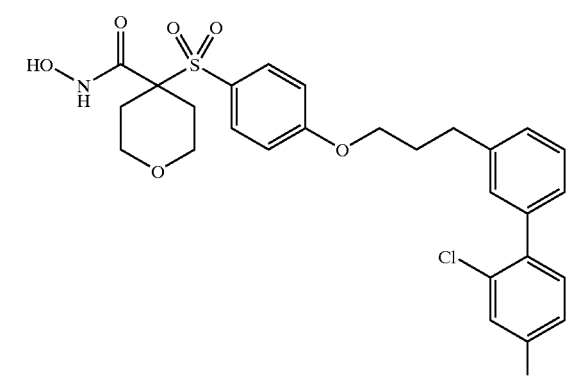
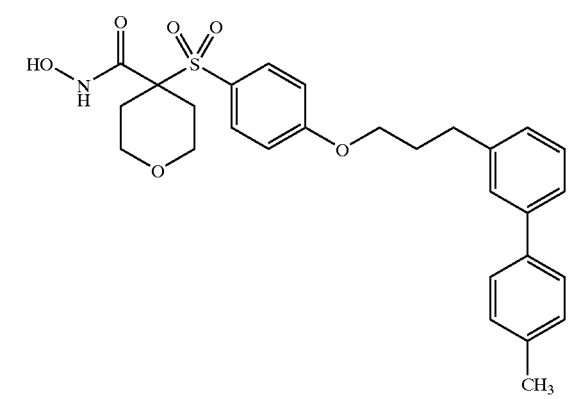
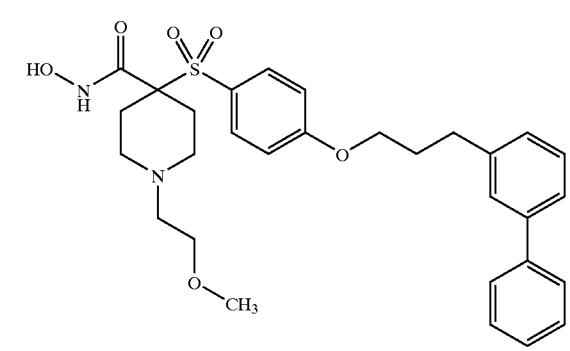

-continued
IIIB-68
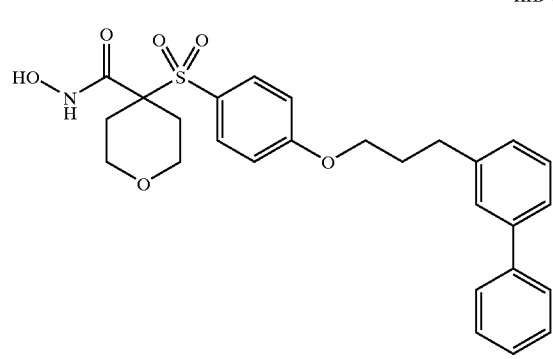
IIIB-69
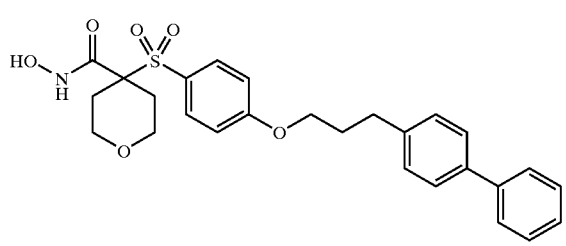
IIIB-70
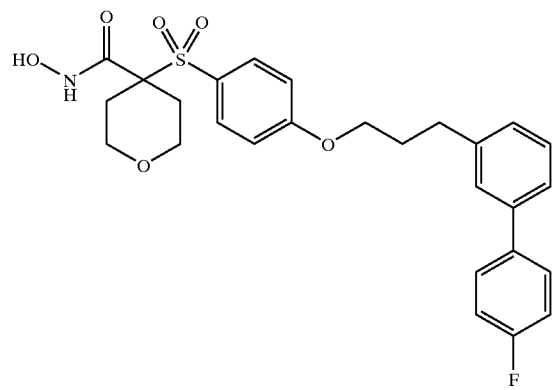
IIIB-71
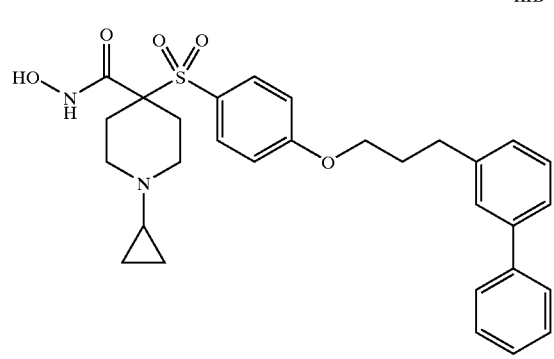
Other such compounds include, for example:
IIIB-72
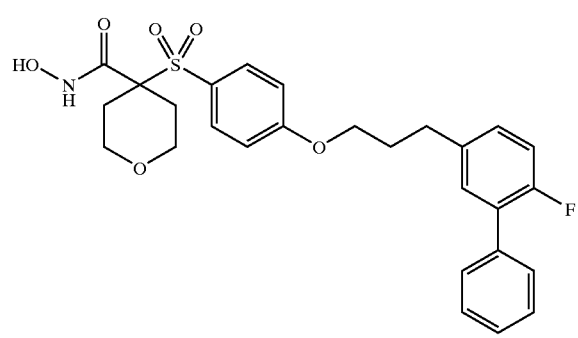
IIIB-73
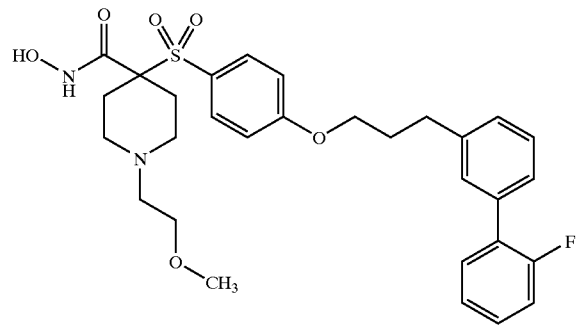
IIIB-74
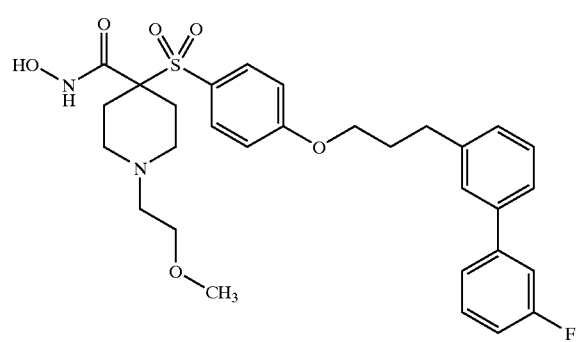
IIIB-75
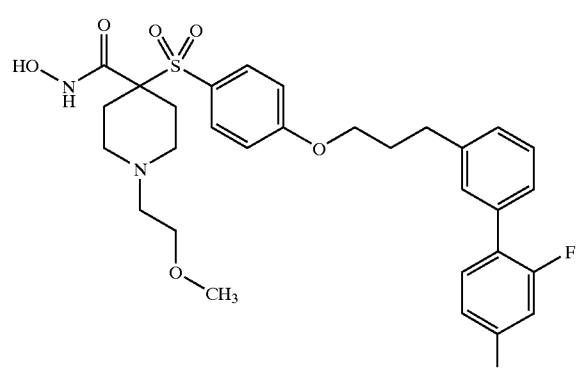

IIIB-76
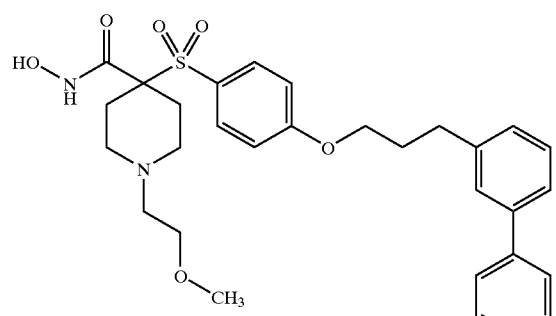
IIIB-77
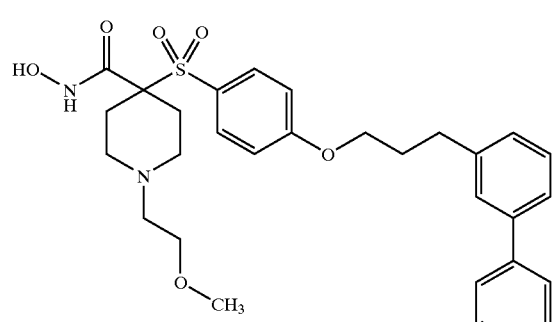
IIIB-78
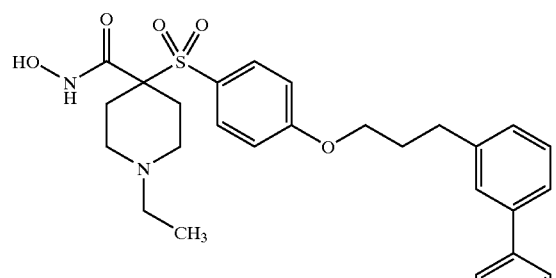
IIIB-79
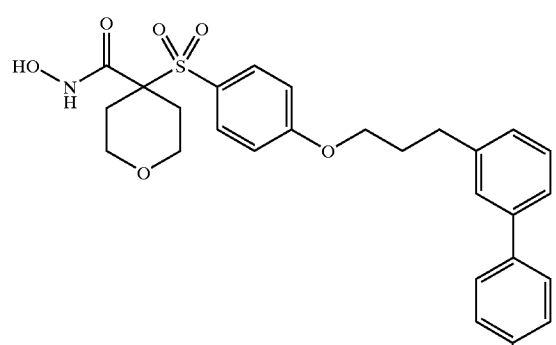
IIIB-80
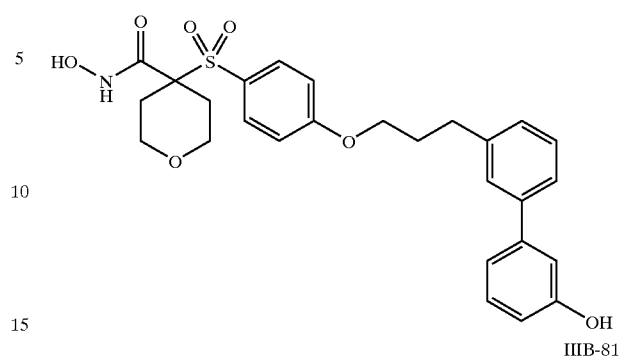
IIIB-81
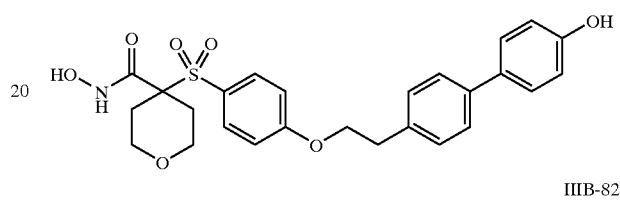
IIIB-82
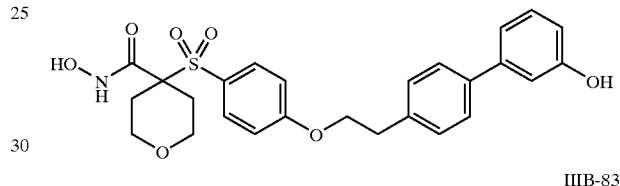
IIIB-83
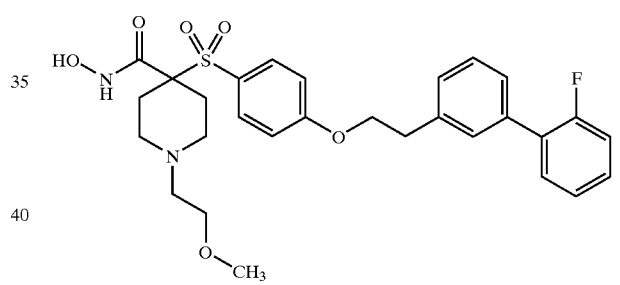
IIIB-84
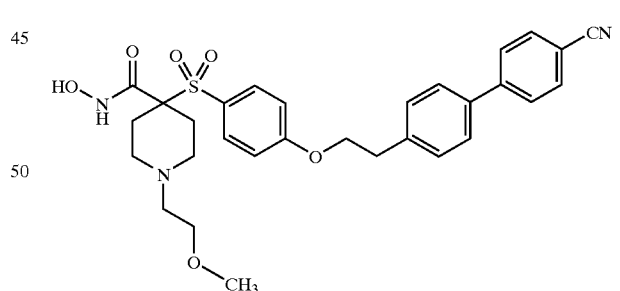
IIIB-85
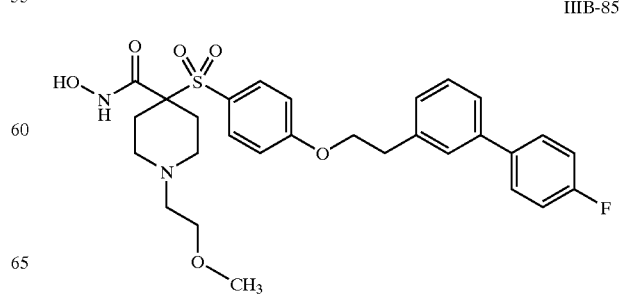

IIIB-86
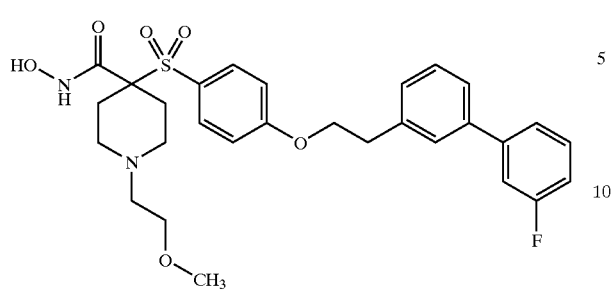
IIIB-87
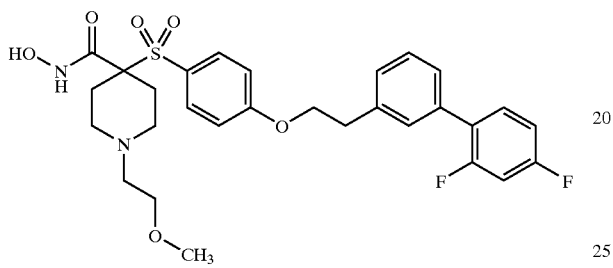
IIIB-88
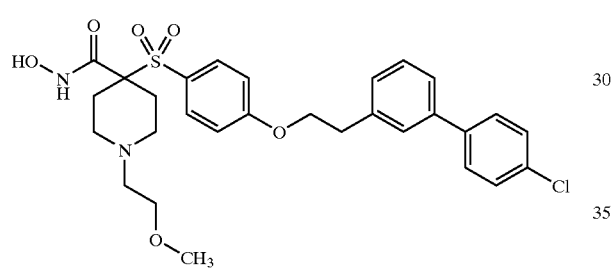
IIIB-89
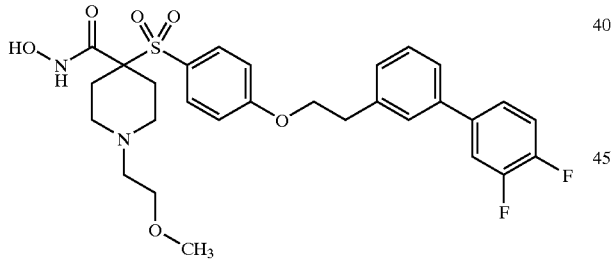
IIIB-90
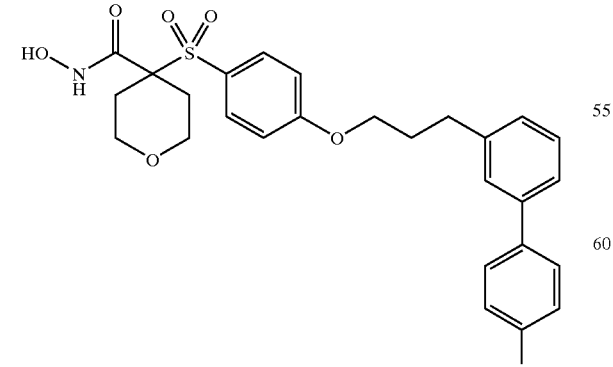
IIIB-91
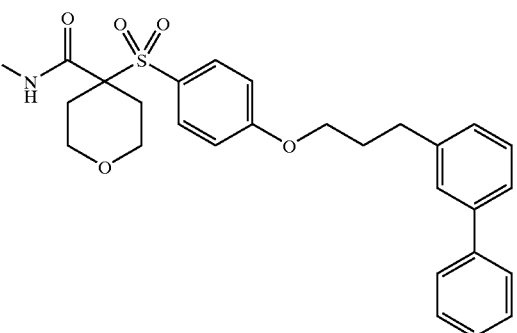
IIIB-92
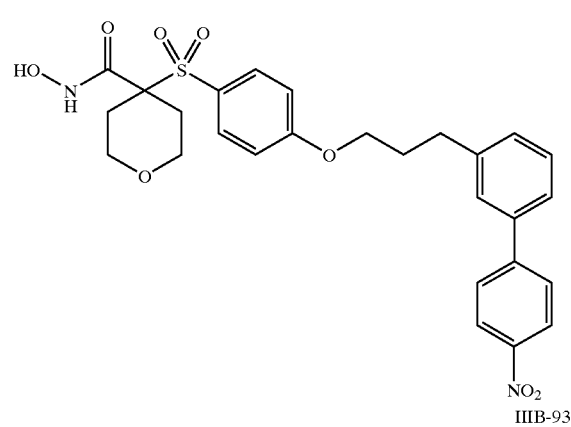
IIIB-93
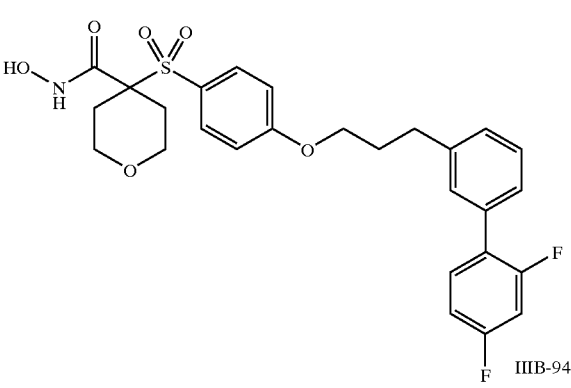
IIIB-94
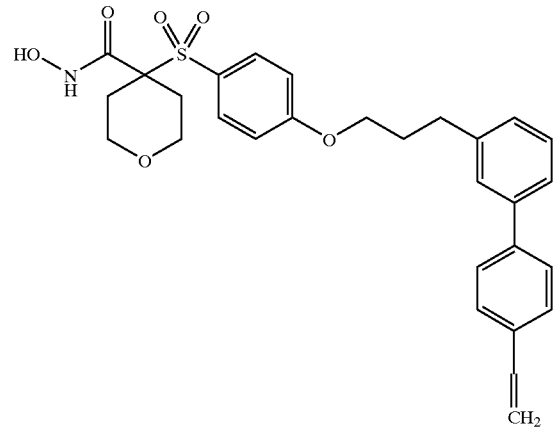

IIIB-95
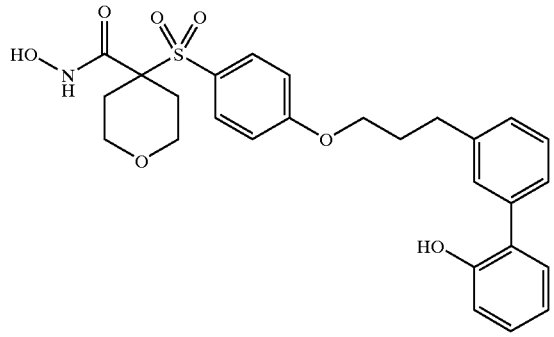
IIIB-96
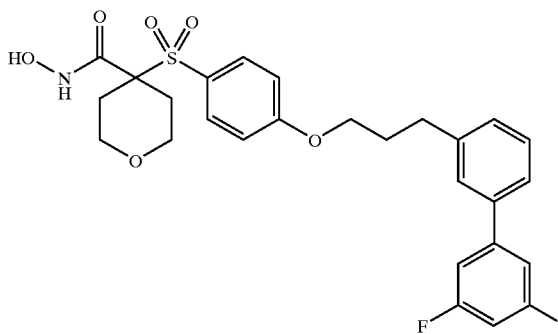
IIIB-97
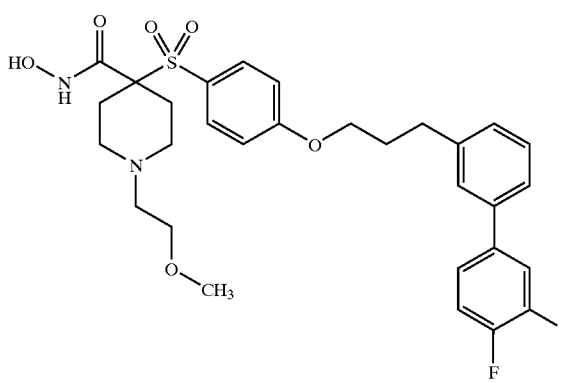
IIIB-98
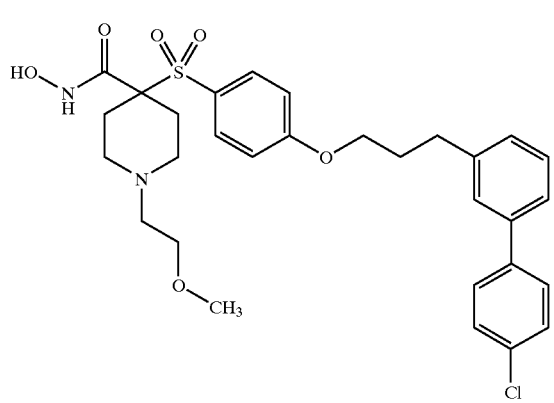
IIIB-99
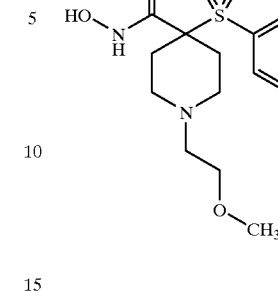
In other preferred embodiments, $E^5$ is optionally-substituted naphthalenyl. Such compounds include, for example:
IIIB-100
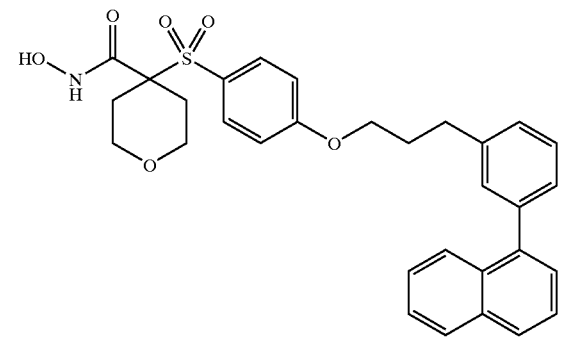
IIIB-101
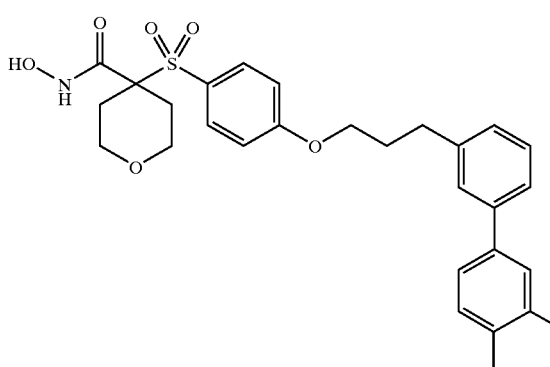
Preferred Embodiment No. 3
In some embodiments of this invention, the compound has a structure to Formula IV:
IV
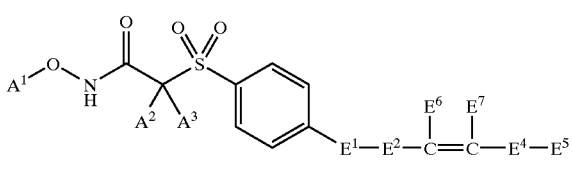

$A^1$, $A^2$, and $A^3$ are as defined above for Formula I.

$E^1$ is s —O—, —S(O)$_2$—, —S(O)—, —N(R$^1$)—, —C(O)—N(R$^1$)—, —N(R$^1$)—C(O)—, or —C(R$^1$)(R$^2$)—.

$E^2$ is alkyl, cycloalkyl, alkylcycloaklyl, cycloalkylalkyl, or alkylcycloalkylalkyl. Any member of this group optionally is substituted.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$alkyl.

In some preferred embodiments, $E^2$ is $C_1$–$C_6$-alkyl, cycloalkyl, $C_1$–$C_6$alkylcycloalkyl, cycloalkyl-$C_1$–$C_6$-alkyl, or $C_1$–$C_6$-alkylcycloalkyl-$C_1$–$C_6$-alkyl. Any member of this group optionally is substituted with one or more substituents independently selected from the group consisting of halogen, $C_1$–$C_2$-alkyl, and halo-$C_1$–$C_2$-alkyl.

In some preferred embodiments, $E^2$ is $C_1$–$C_6$-alkyl, cycloalkyl, $C_1$–$C_6$-alkylcycloalkyl, cycloalkyl-$C_1$–$C_6$-alkyl, or $C_1$–$C_6$-alkylcycloalkyl-$C_1$–$C_6$-alkyl. Any member of this group optionally is substituted with one or more $C_1$–$C_2$-alkyl.

$E^4$ is a bond or alkyl. The alkyl optionally is substituted.

In some preferred embodiments, $E^4$ is a bond, $C_1$–$C_{20}$-alkyl, or halo-$C_1$–$C_{20}$-alkyl.

In some preferred embodiments, $E^4$ is a bond, $C_1$–$C_3$-alkyl, or halo-$C_1$–$C_3$-alkyl.

In some preferred embodiments, $E^4$ is a bond or $C_1$–$C_3$-alkyl.

In some preferred embodiments, $E^4$ is a bond.

$E^5$ is alkyl, alkenyl, alkynyl, alkoxy, alkoxyalkyl, carbocyclyl, or heterocyclyl. Any member of this group optionally is substituted.

In some preferred embodiments, $E^5$ is $C_1$–$C_{20}$-alkyl, $C_2$–$C_{20}$-alkenyl, $C_2$–$C_{20}$-alkynyl, $C_1$–$C_{20}$-alkoxy, $C_1$–$C_{20}$-alkoxy-$C_1$–$C_{20}$-alkyl, carbocyclyl, or heterocyclyl. The $C_1$–$C_{20}$-alkyl, $C_2$–$C_{20}$-alkenyl, $C_2$–$C_{20}$-alkynyl, $C_1$–$C_{20}$-alkoxy, and $C_1$–$C_{20}$-alkoxy-$C_1$–$C_{20}$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, keto, $C_1$–$C_8$-alkyl, halo-$C_1$–$C_8$-alkyl, $C_1$–$C_8$-alkoxy, $C_1$–$C_8$-alkoxy-$C_1$–$C_8$-alkyl, halo-$C_1$–$C_8$-alkoxy, —N(R$^7$)(R$^8$), —C(O)(R$^9$), —S—R$^7$, —S(O)$_2$—R$^7$, carbocyclyl, halocarbocyclyl, carbocyclyl-$C_1$–$C_8$-alkyl, and halogen-substituted $C_1$–$C_8$-alkoxy-$C_1$–$C_8$alkyl.

In some preferred embodiments, $E^5$ is $C_1$–$C_8$-alkyl, $C_2$–$C_8$-alkenyl, $C_2$–$C_8$-alkynyl, $C_1$–$C_8$-alkoxy, $C_1$–$C_8$-alkoxy-$C_1$–$C_8$-alkyl, carbocyclyl, or heterocyclyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, keto, $C_1$–$C_6$-alkyl, halo-$C_1$–$C_6$-alkyl, $C_1$–$C_6$-alkoxy, $C_1$–$C_6$-alkoxy-$C_1$–$C_6$-alkyl, halo-$C_1$–$C_6$-alkoxy, —N(R$^7$)(R$^8$), —C(O)(R$^9$), —S—R$^7$, —S(O)$_2$—R$^7$, carbocyclyl, halocarbocyclyl, carbocyclyl-$C_1$–$C_6$-alkyl, and halogen-substituented $C_1$–$C_6$-alkoxy-$C_1$–$C_6$-alkyl.

$E^6$ is —H, halogen, or alkyl. The alkyl optionally is substituted.

In some preferred embodiments, $E^6$ is —H, halogen, or $C_1$–$C_8$-alkyl. The $C_1$–$C_8$-alkyl may be substituted with one or more halogen, but more typically is preferably not substituted with halogen.

In some preferred embodiments, $E^6$ is —H, halogen, or $C_1$–$C_6$-alkyl. The $C_1$–$C_6$-alkyl may be substituted with one or more halogen, but more typically is preferably not substituted with halogen.

$E^7$ is —H, alkyl, alkenyl, alkynyl, —S(O)$_2$—R$^3$, —NO$_2$, —C(O)—N(R$^3$)(R$^4$), —(C)(OR$^3$), carbocyclyl, carbocyclylalkyl, alkoxycarbocyclyl, —CN, —C=N—OH, or —C=NH. The alkyl, alkenyl, alkynyl, carbocyclyl, carbocyclylalkyl, and alkoxycarbocyclyl optionally are substituted.

In some preferred embodiments, $E^7$ is —H, $C_1$–$C_8$-alkyl, $C_1$–$C_8$-alkenyl, $C_1$–$C_8$-alkynyl, —S(O)$_2$—R$^3$, —NO$_2$, —C(O)—N(R$^3$)(R$^4$), —(C)(OR$^3$), carbocyclyl, carbocyclyl-$C_1$–$C_8$-alkyl, $C_1$–$C_8$-alkoxycarbocyclyl, —CN, —C=N—OH, or —C=NH. The $C_1$–$C_6$-alkyl, $C_1$–$C_6$-alkenyl, $C_1$–$C_8$-alkynyl, carbocyclyl, carbocycyl-$C_1$–$C_8$-alkyl, or $C_1$–$C_8$-alkoxycarbocyclyl may be substituted with one or more halogen, but more typically is preferably not substituted with halogen.

In some preferred embodiments, $E^7$ is —H, $C_1$–$C_6$-alkyl, $C_1$–$C_6$-alkenyl, $C_1$–$C_6$-alkynyl, —S(O)$_2$—R$^3$, —NO$_2$, —C(O)—N(R$^3$)(R$^4$), —(C)(OR$^3$), carbocyclyl, carbocycly-$C_1$–$C_6$-alkyl, $C_1$–$C_6$-alkoxycarbocycyly, —CN, —C=N—OH, or —C=NH. The $C_1$–$C_6$-alkyl, $C_1$–$C_6$-alkenyl, $C_1$–$C_6$-alkynyl, carbocyclyl, carbocycyl-$C_1$–$C_6$-alkyl, or $C_1$–$C_6$-alkoxycarbocyclyl may be substituted with one or more halogen, but more typically is preferably not substituted with halogen.

$R^1$ and $R^2$ are independently selected from the group consisting of —H and alkyl. The alkyl optionally is substituted. Neither $R^1$ nor $R^2$ forms a ring structure with $E^2$, $E^4$, $E^5$, $E^6$, or $E^7$.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^3$ and $R^4$ are independently selected from the group consisting of —H, alkyl, carbocyclyl, carbocyclylalkyl, heterocyclyl, and heterocyclylalkyl. Except where the member is —H, any member of this group optionally is substituted.

In some preferred embodiments, $R^3$ and $R^4$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^3$ and $R^4$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ and $R^8$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^7$ and $R^8$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^9$ is —H, $C_1$–$C_8$-alkyl, —O—$R^{10}$, —N($R^{10}$)($R^{11}$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^9$ is —H, $C_1$–$C_6$-alkyl, —O—$R^{10}$, —N($R^{10}$)($R^{11}$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^{10}$ and $R^{11}$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^{10}$ and $R^{11}$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferred not substituted with halogen.

In some preferred embodiments, $E^5$ is optionally-substituted carbocyclyl or optionally-substituted heterocyclyl. For example, in some such embodiments, $E^5$ is optionally-substituted carbocyclyl, often preferably optionally-substituted aryl, and more preferred optionally-substituted phenyl. Such compounds include, for example:

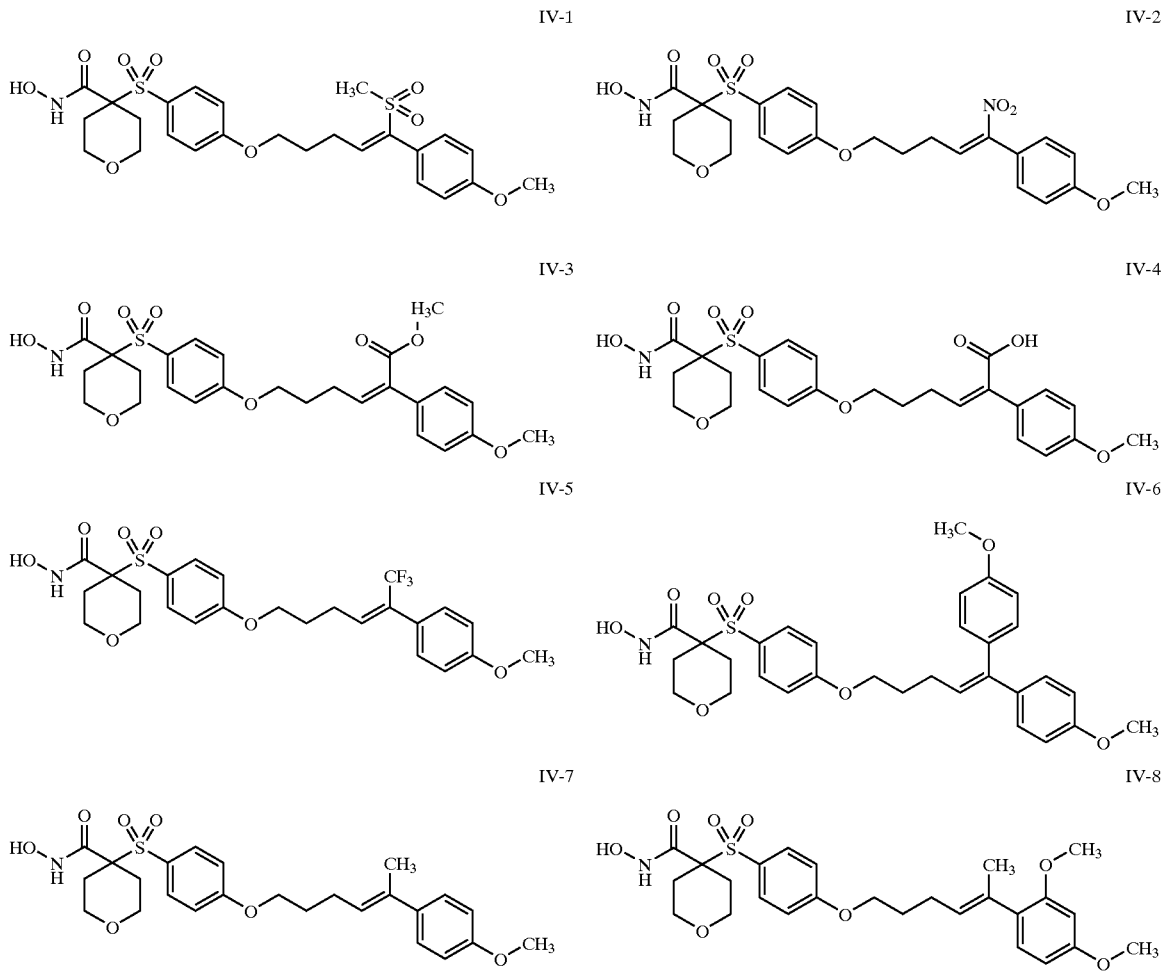

-continued
IV-9
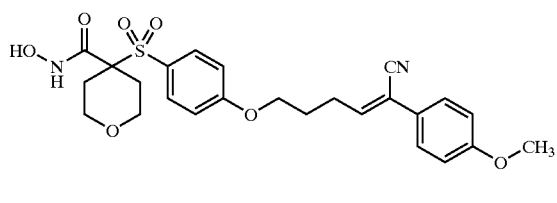
IV-10
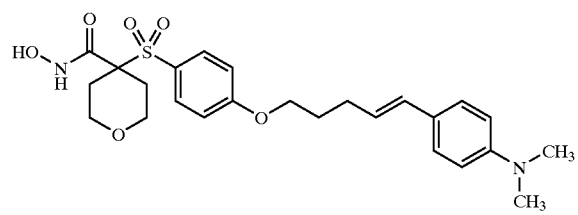
IV-11
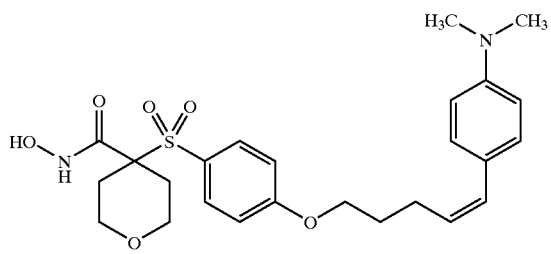
IV-12
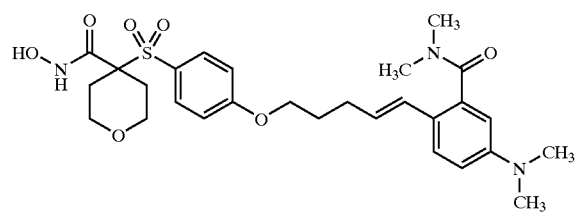
IV-13
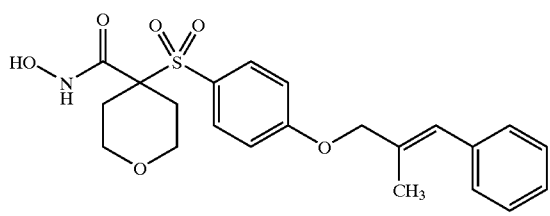
IV-14
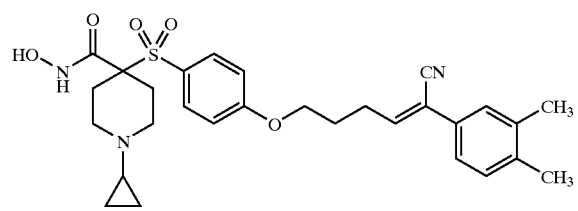
IV-15
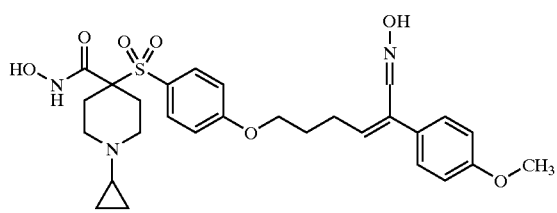
IV-16
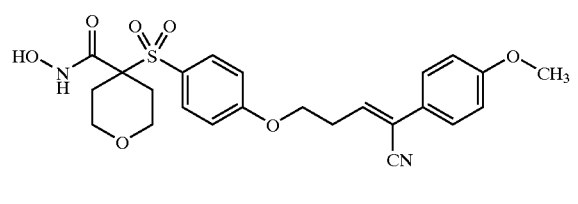
IV-17
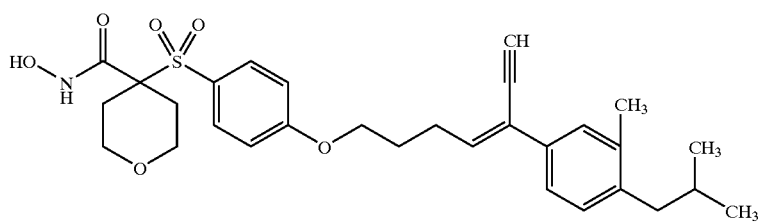
IV-18
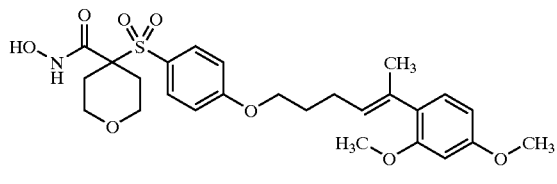
IV-19
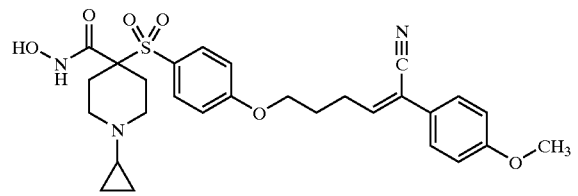

In some preferred embodiments $E^5$ is $C_1$–$C_6$-alkyl, $C_2$–$C_6$-alkenyl, $C_2$–$C_6$-alkynyl, $C_1$–$C_6$-alkoxy, or $C_1$–$C_6$-alkoxy-$C_1$–$C_6$-alkyl. Any member of this group optionally is substituted with one or more substituents independently selected from the group consisting of halogen, —OH, —NO$_2$, and —CN.

In some preferred embodiments, $E^5$ is optionally-substituted $C_1$–$C_6$-alkyl, with the $C_1$–$C_6$-alkyl often being more preferably unsubstituted. Such compounds include, for example:

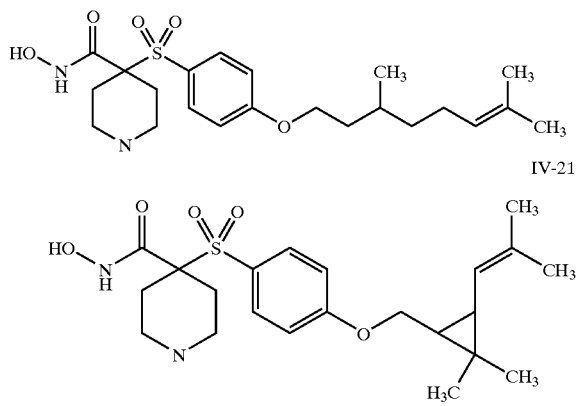

IV-20

IV-21

Preferred Embodiment No. 4

In some embodiments of this invention, the compound has a structure corresponding to Formula V:

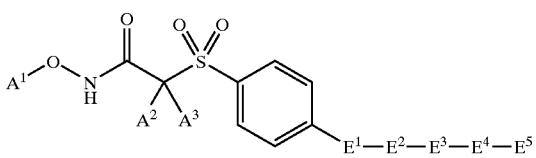

V $A^1$, $A^2$, and $A^3$ are as defined above for Formula I.

$E^1$ is —O—, —S(O)$_2$—, —S(O)—, —N(R$^3$)—, —C(O)—N(R$^3$)—, —N(R$^3$)—C(O)—, or —C(R$^1$)(R$^2$)—.

$E^2$ is a bond, alkyl, cycloalkyl, alkylcycloalkyl, cycloalkylalkyl, or alkylcycloalkylalkyl. Except where the member is a bond, any member of such group optionally is substituted.

In some preferred embodiments, $E^2$ is a bond, $C_{-C20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group (except for the bond) optionally is substituted with one or more substituents independently selected from the group consisting of halogen, $C_1$–$C_6$-alkyl, and halo-$C_1$–$C_6$-alkyl.

In some preferred embodiments, $E^2$ is a bond, $C_1$–$C_6$-alkyl, or halo-$C_1$–$C_6$-alkyl.

In some preferred embodiments $E^2$ is a bond or $C_1$–$C_6$-alkyl.

$E^3$ is carbonylpyrrollidinyl. The carbonylpyrrollidinyl optionally is substituted.

In some preferred embodiments, $E^3$ is carbonylpyrrollidinyl wherein the carbonylpyrrollidinyl may be substituted with one or more halogen, but more typically is preferably not substituted with halogen.

$E^4$ is a bond, alkyl, or alkenyl. The alkyl and alkenyl optionally are substituted.

In some preferred embodiments, $E^4$ is a bond, $C_1$–$C_{20}$-alkyl, halo-$C_1$–$C_{20}$-alkyl, $C_2$–$C_{20}$-alkenyl, or halo-$C_2$–$C_{20}$-alkenyl.

In some preferred embodiments, $E^4$ is a bond, $C_1$–$C_3$-alkyl, halo-$C_1$–$C_3$-alkyl, $C_2$–$C_3$-alkenyl, or balo-$C_2$–$C_3$-alkenyl.

In some preferred embodiments, $E^4$ is a bond, $C_1$–$C_3$-alkyl, or $C_2$–$C_3$-alkenyl.

In some preferred embodiments, $E^4$ is a bond.

$E^5$ is alkyl, alkenyl, alkynyl, alkoxy, alkoxyalkyl, carbocyclyl, or heterocyclyl. Any member of this group optionally is substituted.

In some preferred embodiments, $E^5$ is $C_1$–$C_{20}$-alkyl, $C_2$–$C_{20}$-alkenyl, $C_2$–$C_{20}$-alkynyl, $C_1$–$C_{20}$-alkoxy, $C_1$–$C_{20}$-alkoxy-$C_1$–$C_{20}$-alkyl, carbocyclyl, or heterocyclyl. The $C_1$–$C_{20}$-alkyl, $C_2$–$C_{20}$-alkenyl, $C_2$–$C_{20}$-alkynyl, $C_1$–$C_{20}$-alkoxy, and $C_1$–$C_{20}$-alkoxy-$C_1$–$C_{20}$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, keto, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_6$-alkyl, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_8$-alkyl, and halogen-substituted carbocyclyl-$C_1$–$C_8$-alkyl.

In some preferred embodiments, $E^5$ is $C_1$–$C_8$-alkyl, $C_2$–$C_8$-alkenyl, $C_2$–$C_8$-alkynyl, $C_1$–$C_8$-alkoxy, $C_1$–$C_8$-alkoxy-$C_1$–$C_8$-alkyl, carbocyclyl, or heterocyclyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl.

$R^1$ and $R^2$ are independently selected from group —H and alkyl. The alkyl optionally is substituted. Neither $R^1$ nor $R^2$ forms a ring structure with $E^2$, $E^3$, $E^4$, or $E^5$.

In some preferred embodiments, $R^1$ and $R^2$ are independently selected from the group consisting of —H, $C_1$–$C_8$-alkyl, and halo-$C_1$–$C_6$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^5$ and $R^6$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ is —H, $C_1$–$C_8$-alkyl, —O—$R^8$, —N($R^8$)($R^9$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^7$ is —H, $C_1$–$C_6$-alkyl, —O—$R^8$, —N($R^8$)($R^9$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^8$ and $R^9$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, the compound has a structure corresponding to Formula V-A:

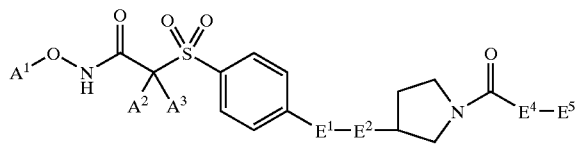

V-A

In some preferred embodiments, $E^5$ is optionally-substituted carbocyclyl or optionally substituted heterocyclyl. For example, in some such embodiments, $E^5$ is optionally substituted carbocyclyl, often preferably optionally-substituted aryl, and more preferably optionally-substituted phenyl. Such compounds include, for example:

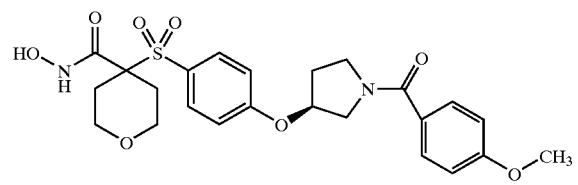

V-1

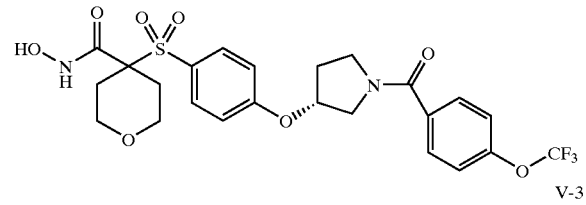

V-2

V-3

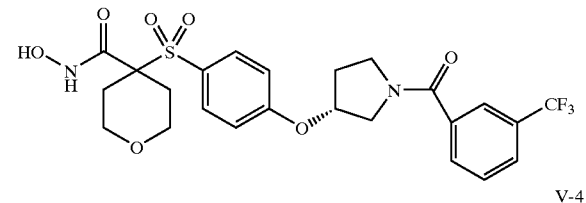

V-4

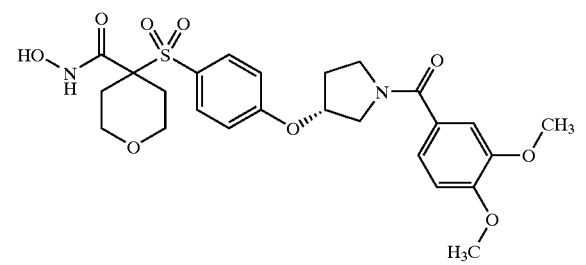

V-5

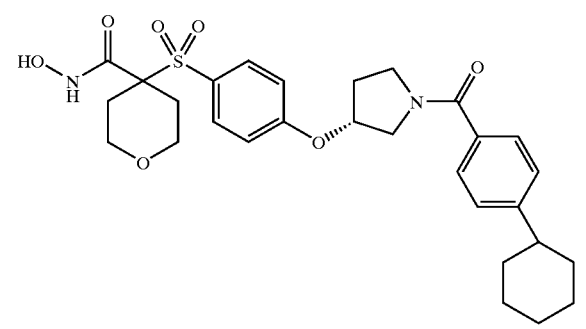

In some preferred embodiments, $E^5$ is optionally-substituted $C_5$–$C_6$-cycloalkyl. Such compounds include, for example:

V-6

In some preferred embodiments, $E^5$ is $C_1$–$C_8$-alkyl, $C_2$–$C_8$-alkenyl, $C_2$–$C_8$-alkynyl, $C_1$–$C_8$-alkoxy, or $C_1$–$C_8$-alkoxy-$C_1$–$C_8$-alkyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —NO$_2$, and —CN.

In some preferred embodiments, $E^5$ is optionally-substituted $C_1$–$C_8$-alkyl, with $C_1$–$C_8$-alkyl often being more preferred. Such compounds include, for example:

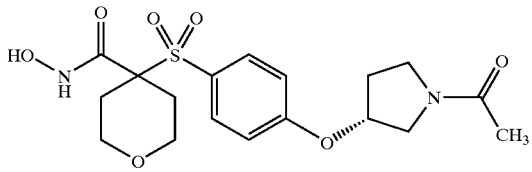

V-7

Preferred Embodiment No. 5

In some embodiments of this invention, the compound has a structure corresponding to Formula VI:

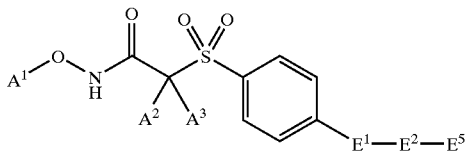

VI $A^1$, $A^2$, and $A^3$ are as defined above for Formula I.

$E^1$ is —O—, —S(O)$_2$—, —S(O)—, —N(R$^1$)—, —C(O)—N(R$^1$)—, —N(R$^1$)—C(O)—, or —C(R$^1$)(R$^2$)—.

$E^2$ is alkyl, cycloalkyl, alkylcycloalkyl, cycloalkylalkyl, or alkylcycloalkylalkyl. Any member of this group optionally is substituted with one or more substituents independently selected from the group consisting of halogen, alkyl, and haloalkyl.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$-alkyl.

In some preferred embodiments, $E^2$ is $C_1$–$C_6$-alkyl, cycloalkyl, $C_1$–$C_6$-alkylcycloalkyl, cycloalkyl-$C_1$–$C_6$-alkyl, or $C_1$–$C_6$-alkylcycloalkyl-$C_1$–$C_6$-alkyl. Any member of this group optionally is substituted with one or more substituents independently selected from the group consisting of halogen, $C_1$–$C_2$-alkyl, and halo-$C_1$–$C_2$-alkyl.

In some preferred embodiments, $E^2$ is $C_1$–$C_6$-alkyl, cycloalkyl, $C_1$–$C_6$-alkylcycloalkyl, cycloalkyl-$C_1$–$C_6$-alkyl, or $C_1$–$C_6$-alkylcycloalkyl-$C_1$–$C_6$-alkyl. Any member of this group optionally is substituted with one or more $C_1$–$C_2$-alkyl.

$E^5$ is alkyl, alkenyl, alkynyl, cycloalkyl, cyclopentenyl, cyclopentadienyl, cyclohexenyl, or cyclohexadienyl. Here, the cycloalkyl, cyclopentenyl, cyclopentadienyl, cyclohexenyl, and cyclohexadienyl optionally are substituted. The alkyl, alkenyl, and alkynyl (a) contain at least 4 carbon atoms, and (b) optionally are substituted with one or more substituents selected from the group consisting of —OH, —NO$_2$, —CN, and halogen.

In some preferred embodiments, $E^5$ is $C_4$–$C_{20}$-alkyl, $C_4$–$C_{20}$-alkenyl, $C_4$–$C_{20}$-alkynyl, cycloalkyl, cyclopentenyl, cyclopentadienyl, cyclohexenyl, or cyclohexadienyl. The $C_4$–$C_{20}$-alkyl, $C_4$–$C_{20}$-alkenyl, and $C_4$–$C_{20}$-alkynyl optionally are substituted with one or more substituents independently selected from the group consisting of —OH, —NO$_2$, —CN, and halogen. The cycloalkyl, cyclopentenyl, cyclopentadienyl, cyclohexenyl, and cyclohexadienyl optionally are substituted with one or more substituents independently selected from the group consisting of halogen, —OH, —NO$_2$, —CN, keto, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_8$-alkyl, and halogen-substituted carbocyclyl-$C_1$–$C_8$-alkyl.

In some preferred embodiments, $E^5$ is $C_4$–$C_8$-alkyl, $C_4$–$C_8$-alkenyl, $C_4$–$C_8$-alkynyl, cycloalkyl, cyclopentenyl, cyclopentadienyl, cyclohexenyl, or cyclohexadienyl. The $C_4$–$C_8$-alkyl, $C_4$–$C_8$-alkenyl, and $C_4$–$C_8$-alkynyl optionally are substituted with one or more substituents independently selected from the group consisting of —OH, —NO$_2$, —CN, and halogen. The cycloalkyl, cyclopentenyl, cyclopentadienyl, cyclohexenyl, and cyclohexadienyl optionally are substituted with one or more substituents independently selected from the group consisting of halogen, —OH, —NO$_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substitute carbocyclyl-$C_1$–$C_6$-alkyl.

$R^1$ and $R^2$ are independently selected from the group consisting of —H and alkyl. The alkyl optionally is substituted. Neither $R^1$ nor $R^2$ forms a ring structure with $E^5$.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^5$ and $R^6$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ is —H, $C_1$–$C_8$-alkyl, —O—R$^8$, —N(R$^8$)(R$^9$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^7$ is —H, $C_1$–$C_6$-alkyl, —O—R$^8$, —N(R$^8$)(R$^9$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^8$ and $R^9$ are independently selected from the group consisting of —H, $C_1$–$C_8$-alkyl, carbocyclyl, carbocyclyl- $C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^5$ is $C_4$–$C_8$-alkyl, $C_4$–$C_8$-alkenyl, or $C_4$–$C_8$-alkynyl. The $C_4$–$C_8$-alkyl, $C_4$–$C_8$-alkenyl, and $C_4$–$C_8$-alkynyl optionally are substituted with one or more substituents independently selected from the group consisting of —OH, —$NO_2$, —CN, and halogen. Such compounds include, for example:

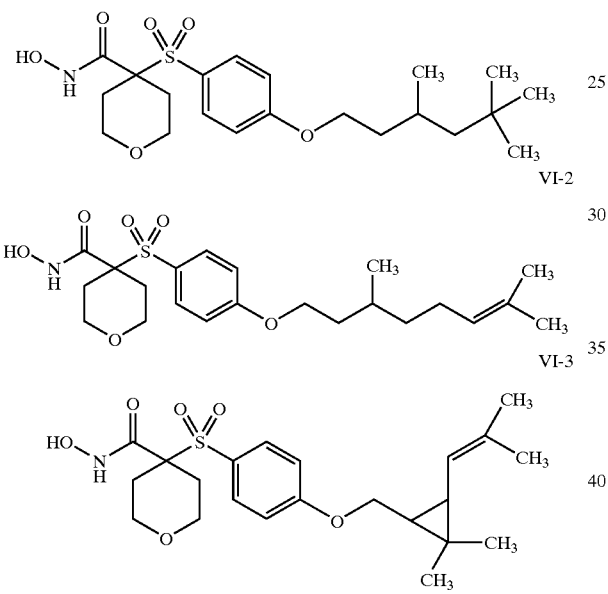

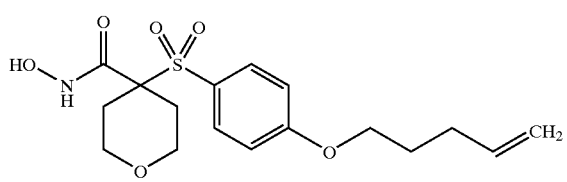

In some preferred embodiments, $E^5$ is optionally-substituted carbocyclyl. In some such embodiments, $E^5$ is optionally-substituted $C_5$–$C_6$-cycloalkyl. Such compounds include, for example:

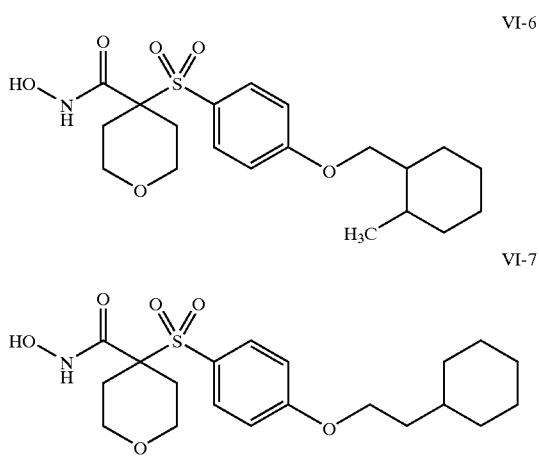

In other embodiments, $E^5$ is an optionally-substituted, partially-saturated carbocyclyl selected from the group consisting of cyclopentenyl, cyclopentadienyl, cyclohexenyl, and cyclohexadienyl. Such compounds include, for example:

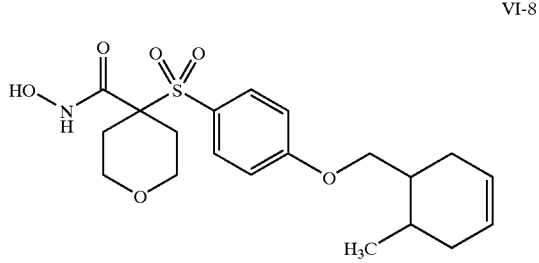

Preferred Embodiment No. 6

In some embodiments of this invention, the compound has a structure to Formula VII:

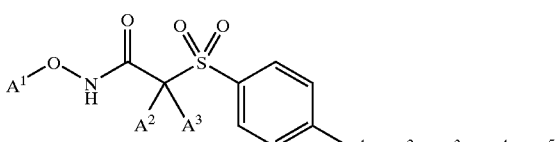

$A^1$, $A^2$, and $A^3$ are as defined above for Formula I.

$E^2$ is —O—, —S(O)$_2$—, —S(O)—, —N($R^1$)—, —C(O)—N($R^1$)—, —N($R^1$)—C(O)—, or —C($R^1$)($R^2$)—.

$E^2$ is alkyl, cycloalkyl, alkylcycloalkyl, cycloalkylalkyl, or alkylcycloalkyl. Any member of this group optionally is substituted.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$-alkyl.

In some preferred embodiments, $E^2$ is $C_1$–$C_6$-alkyl optionally substituted with one or more halogen.

In some preferred embodiments, $E^2$ is $C_1$–$C_6$-alkyl.

$E^3$ is carbonylpiperidinyl. The carbonylpiperidinyl optionally is substituted.

In some preferred embodiments, $E^3$ is carbonylpiperidinyl wherein the carbonylpiperidinyl may be substituted with one or more halogen, but more typically is preferably not substituted with halogen.

In some preferred embodiments, the compound has a structure corresponding to one of the following formulas:

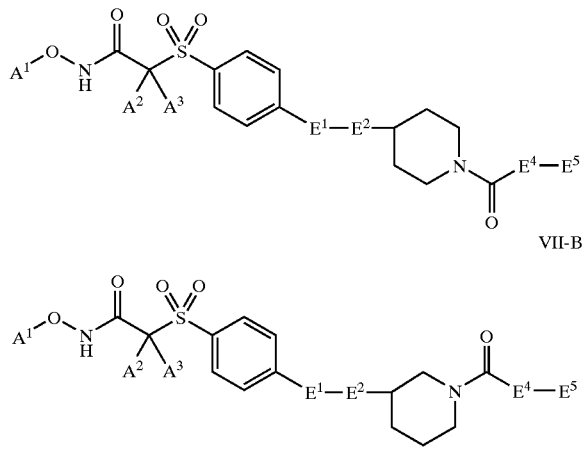

VII-A

VII-B $E^4$ is a bond, alkyl, or alkenyl. The alkyl and alkenyl optionally are substituted.

In some preferred embodiments, $E^4$ is a bond, $C_1$–$C_{20}$-alkyl, halo-$C_1$–$C_{20}$alkyl, $C_2$–$C_{20}$-alkenyl, or halo-$C_2$–$C_{20}$-alkenyl.

In some preferred embodiments, $E^4$ is a bond, $C_1$–$C_3$-alkyl, halo-$C_1$–$C_3$-alkyl, $C_2$–$C_3$-alkenyl, or halo-$C_2$–$C_3$-alkenyl.

In some preferred embodiments, $E^4$ is a bond, $C_1$–$C_3$-alkyl, or $C_2$–$C_3$-alkenyl.

In some preferred embodiments, $E^4$ is a bond.

$E^5$ is alkyl, alkenyl, alkynyl, alkoxy, alkoxyalkyl, carbocyclyl, or heterocyclyl. Any member of this group optionally is substituted.

In some preferred embodiments, $E^5$ is $C_1$–$C_{20}$-alkyl, $C_2$–$C_{20}$-alkenyl, $C_2$–$C_{20}$-alkynyl, $C_1$–$C_{20}$-alkoxy, $C_1$–$C_{20}$-alkoxy-$C_1$–$C_{20}$-alkyl, carbocyclyl, or heterocyclyl. The $C_1$–$C_{20}$-alkyl, $C_2$–$C_{20}$-alkenyl, $C_2$–$C_{20}$-alkynyl, $C_1$–$C_{20}$-alkoxy, and $C_1$–$C_{20}$-alkoxy-$C_1$–$C_{20}$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, keto, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, carbocyclyl, halocarbocyclyl, and carbocyclyl-$C_1$–$C_8$-alkyl.

In some preferred embodiments, $E^5$ is $C_1$–$C_8$-alkyl, $C_2$–$C_8$-alkenyl, $C_2$–$C_8$-alkynyl, $C_1$–$C_8$-alkoxy, $C_1$–$C_8$-alkoxy-$C_1$–$C_8$-alkyl, carbocyclyl, or heterocyclyl. Here, the $C_1$–$C_8$-alkyl, $C_2$–$C_8$-alkenyl, $C_2$–$C_8$-alkynyl, $C_1$–$C_8$-alkoxy, and $C_1$–$C_6$-alkoxy-$C_1$–$C_6$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S—R$_5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl.

$R^1$ and $R^2$ are independently selected from the group consisting of —H, and alkyl. The alkyl optionally is substituted. Neither $R^1$ nor $R^2$ forms a ring structure with $E^2$, $E^3$, $E^4$, or $E^5$.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^5$ and $R^6$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ is —H, $C_1$–$C_6$-alkyl, —O—R$^8$, —N(R$^8$)(R$^9$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^7$ is —H, $C_1$–$C_6$-alkyl, —O—R$^8$, —N(R$^8$)(R$^9$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^8$ and $R^9$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^5$ is optionally-substituted carbocyclyl or optionally substituted heterocyclyl. In some such embodiments, $E^5$ is optionally-substituted aryl, often preferably optionally-substituted phenyl. Such compounds include, for example:

VII-1

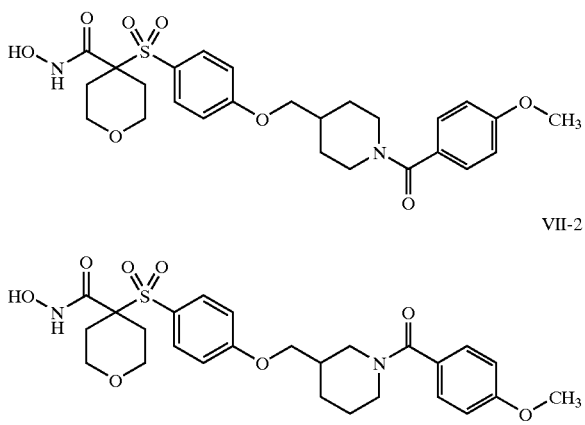

VII-2

Preferred Embodiment No. 7

In some embodiments of this invention, the compound has a structure corresponding to Formula VIII:

VIII

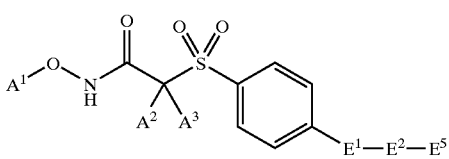

$A^1$, $A^2$, and $A^3$ are as defined above for Formula I.

$E^1$ is —O—, —S(O)$_2$—, —S(O)—, —N(R$^1$)—, —C(O)—N(R$^1$)—, —N(R$^1$)—C(O)—, or —C(R$^1$)(R$^2$)—.

$E^2$ forms a link of at least 3 carbon atoms between $E^1$ and $E^5$. $E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_3$–$C_{20}$-alkyl, cycloalkyl, $C_1$–$C_{10}$-alkyl-cycloalkyl, cycloalkyl-$C_1$–$C_{10}$-alkyl, or $C_1$–$C_{10}$-alkyl-cycloalkyl-$C_1$–$C_{10}$-alkyl. Any member of this group may be substituted with one or more halogen, but more typically is preferably not substituted with halogen.

In some preferred embodiments, $E^2$ is $C_3$–$C_6$-alkyl optionally substituted with one or more halogen.

In some preferred embodiments, $E^2$ is $C_3$–$C_6$-alkyl.

$E^5$ is optionally-substituted heterocyclyl, optionally-substituted fused-ring carbocyclyl, or substituted single-ring carbocyclyl.

In some preferred embodiments, $E^5$ is single-ring carbocyclyl, fused-ring carbocyclyl, or heterocyclyl.

Here, the single-ring carbocyclyl is substituted with one or more substituents independently selected from the group consisting of halogen, —OH, —NO$_2$, —CN, keto, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_8$-alkyl, halogen-substituted carbocyclyl-$C_1$–$C_8$-alkyl. The single-ring carbocyclyl also optionally is substituted on the same atom with two substituents independently selected from the group consisting of alkyl and haloalkyl, the two substituents together forming $C_5$–$C_6$-cycloalkyl or halo-$C_5$–$C_6$-cycloalkyl.

In some preferred embodiments, the single-ring carbocyclyl is substituted with one or more substituents independently selected from the group consisting of and halogen, —OH, —NO$_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S-R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl. The single-ring carbocyclyl also optionally is substituted on the same atom with two substituents independently selected from the group consisting of alkyl and haloalkyl, the two substituents together forming $C_5$–$C_6$-cycloalkyl or halo-$C_5$–$C_6$-cycloalkyl.

The heterocyclyl and fused-ring carbocyclyl optionally are substituted with one or more substituents independently selected from the group consisting of and halogen, —OH, —NO$_2$, —CN, keto, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, carbocyclyl, halocarbocyclyl, and carbocyclyl-$C_1$–$C_6$-alkyl. The heterocyclyl and fused-ring carbocyclyl also optionally are substituted on the same atom with two substituents independently selected from the group consisting of alkyl and haloalkyl, the two substituents together forming $C_5$–$C_6$-cycloalkyl or halo-$C_5$–$C_6$-cycloalkyl.

In some preferred embodiments, the heterocyclyl and fused-ring carbocyclyl optionally are substituted with one or more substituents independently selected from the group consisting of and halogen, —OH, —NO$_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl. The heterocyclyl and fused-ring carbocyclyl also optionally are substituted the same atom with two substituents independently selected from the group consisting of alkyl and haloalkyl, the two substituents together forming $C_5$–$C_6$-cycloalkyl or halo-$C_5$–$C_6$cycloalkyl.

$R^1$ and $R^2$ are independently selected from the group consisting of —H and alkyl. The alkyl optionally is substituted. Neither $R^1$ nor $R^2$ forms a ring structure with $E^5$.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^5$ and $R^6$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ is —H, $C_1$–$C_8$-alkyl, —O—$R^8$, —N($R^8$)($R^9$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^7$ is —H, $C_1$–$C_6$-alkyl, —O—$R^8$, —N($R^8$)($R^9$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^8$ and $R^9$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^5$ is a substituted single-ring carbocyclyl. $E^5$ may be, for example a substituted single-ring carbocyclyl selected from the group consisting of cyclopropyl, cyclobutyl, cyclopentyl, cyclopentenyl, cyclopentadienyl, cyclohexyl, cyclohexenyl, cyclohexadienyl, and phenyl.

In some preferred embodiments, $E^5$ is substituted phenyl. Such compounds include, for example:

VIII-1

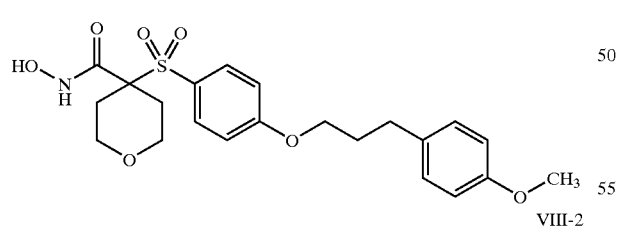

VIII-2

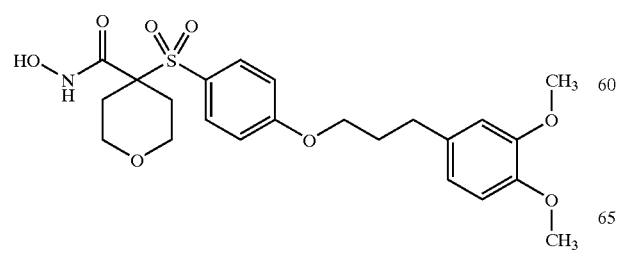

VIII-3

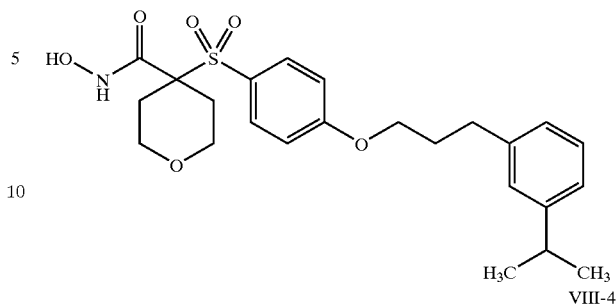

VIII-4

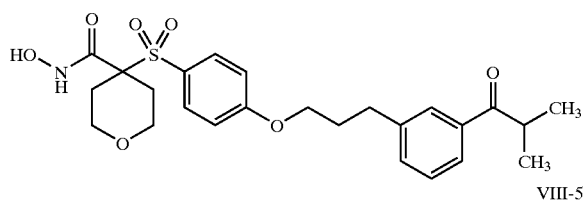

VIII-5

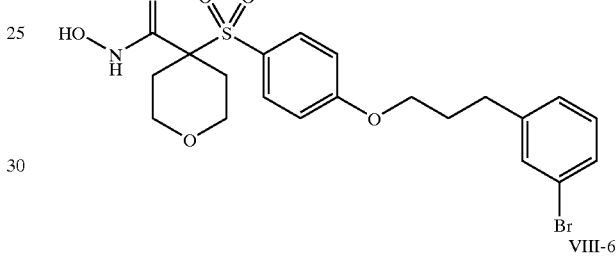

VIII-6

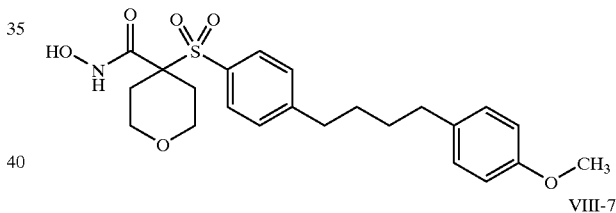

VIII-7

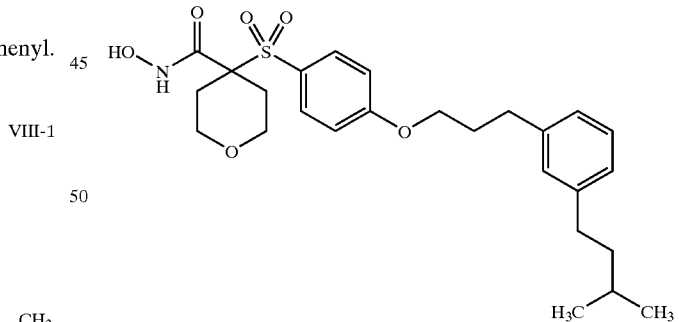

Such compounds also include, for example:

VIII-8

VIII-9
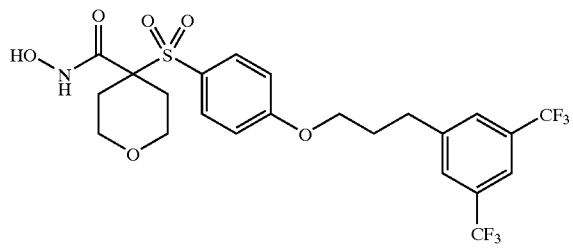

VIII-10
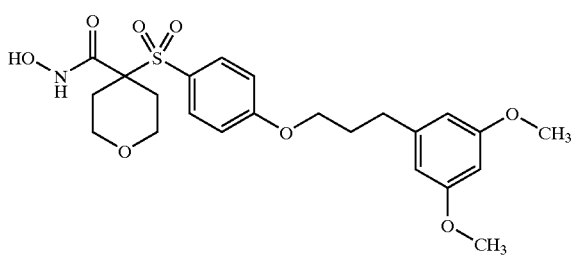

VIII-11
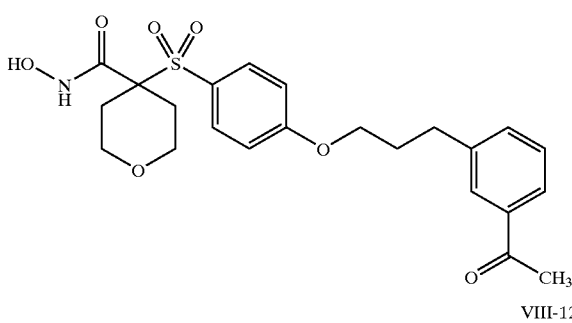

VIII-12
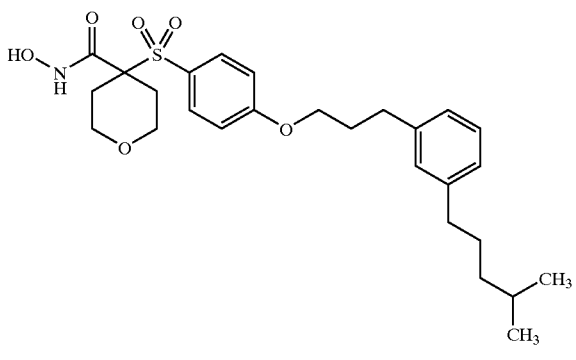

VIII-13
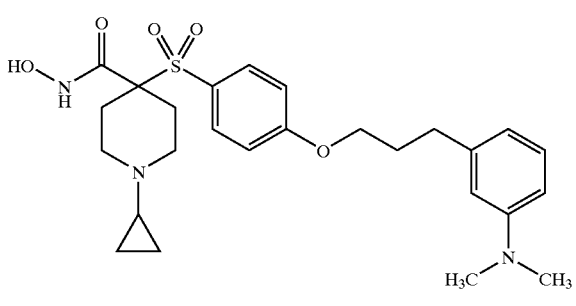

VIII-14
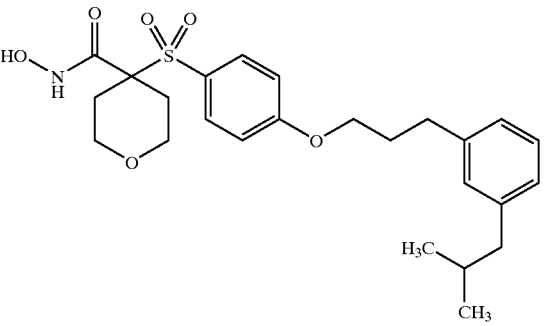

In some preferred embodiments, $E^5$ is optionally-substituted fused-ring carbocyclyl. $E^5$ may be, for example, optionally-substituted fused-ring carbocyclyl selected from the group consisting of naphthalenyl, tetrahydronaphthalenyl, indenyl, isoindenyl, indanyl, bicyclodecanyl, anthracenyl, phenanthrene, benzonaphthenyl, fluroreneyl, decalinyl, and norpinanyl.

In some preferred embodiments, $E^5$ is optionally-substituted naphthalenyl. Such compounds include, for example:

VIII-15
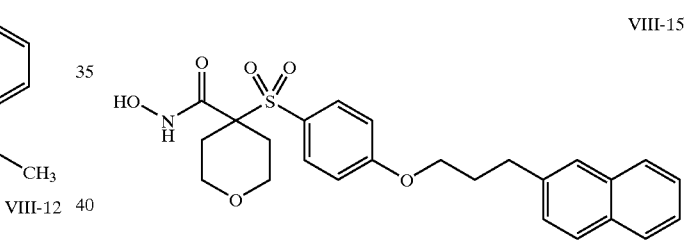

VIII-16

VIII-17
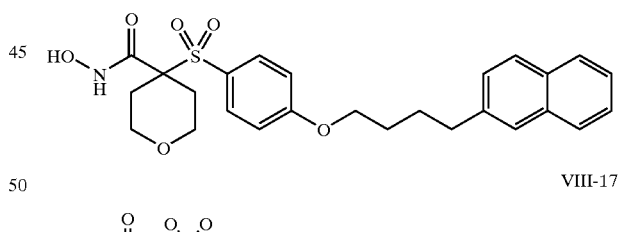

In some preferred embodiments, $E^5$ is optionally-substituted, single-ring heterocyclyl.

In some preferred embodiments, $E^5$ is an optionally-substituted pyridinyl. Such compounds include, for example:

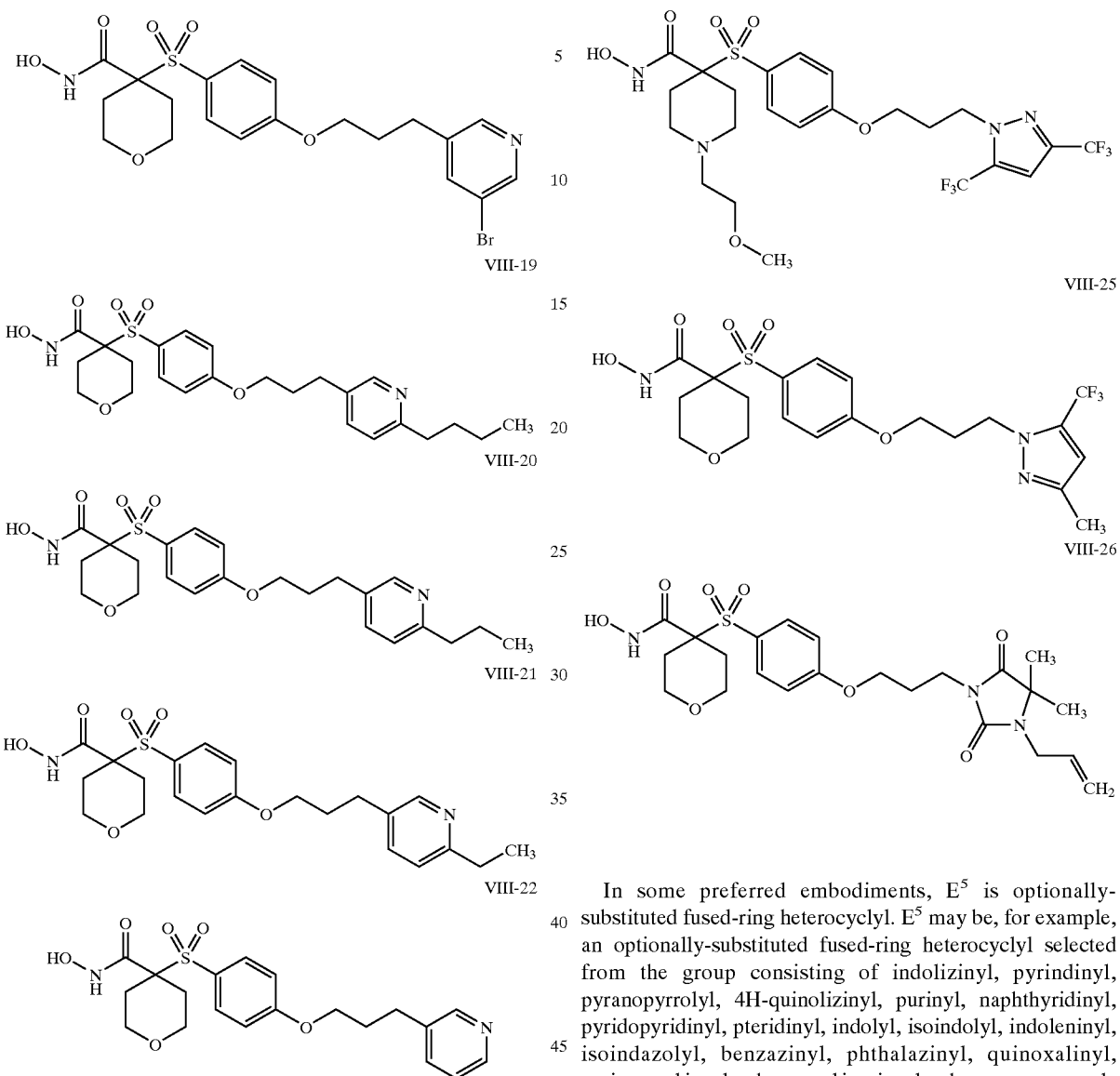

In some preferred embodiments, $E^5$ is an optionally-substituted heterocyclyl selected from the group consisting of imidazolyl, imidazolinyl, imidazolidinyl, pyrazolyl, pyrazolinyl, and pyrazolidinyl. Such compounds include, for example:

In some preferred embodiments, $E^5$ is optionally-substituted fused-ring heterocyclyl. $E^5$ may be, for example, an optionally-substituted fused-ring heterocyclyl selected from the group consisting of indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofiranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl. Compounds wherein $E^5$ is an optionally-substituted fused-ring heterocyclyl include, for example:

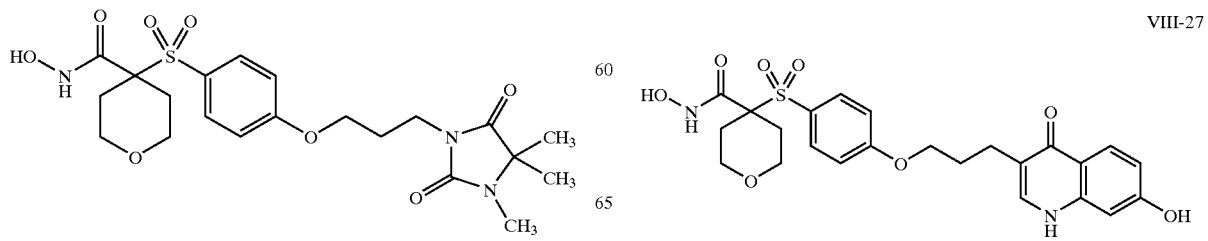

-continued
VIII-28
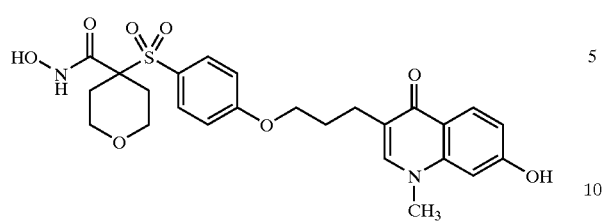
VIII-29
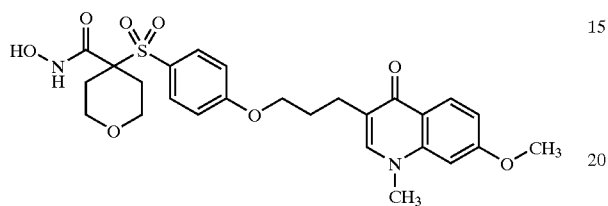
VIII-30
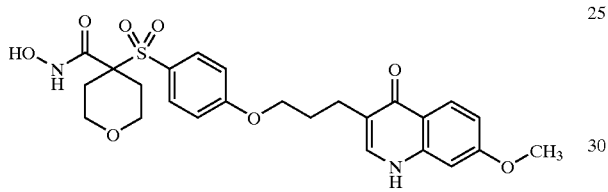
VIII-31
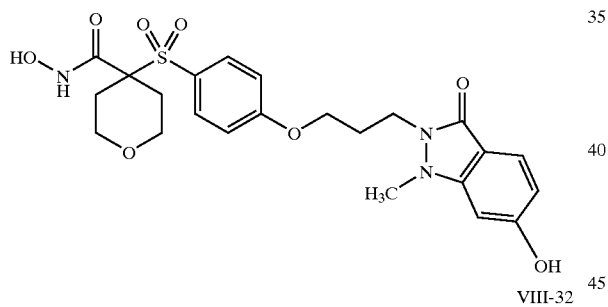
VIII-32
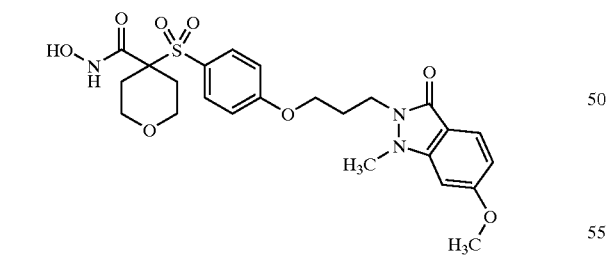
VIII-33
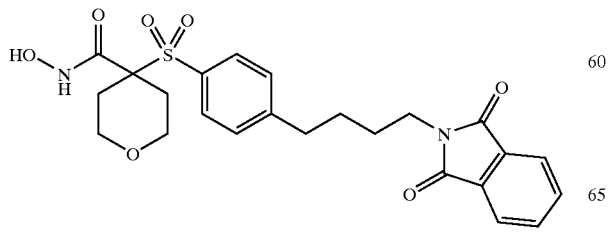
-continued
VIII-34
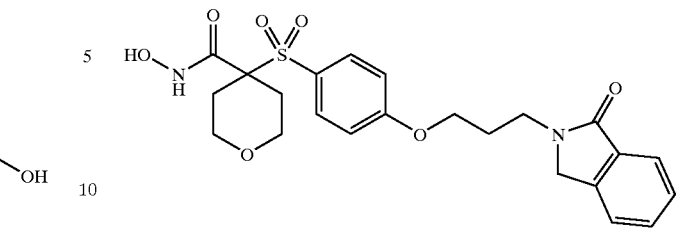
VIII-35
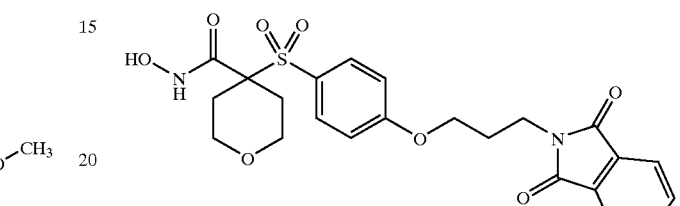
VIII-36
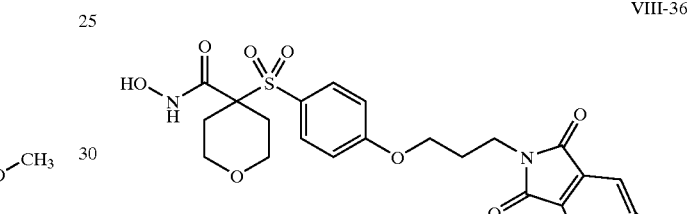
VIII-37
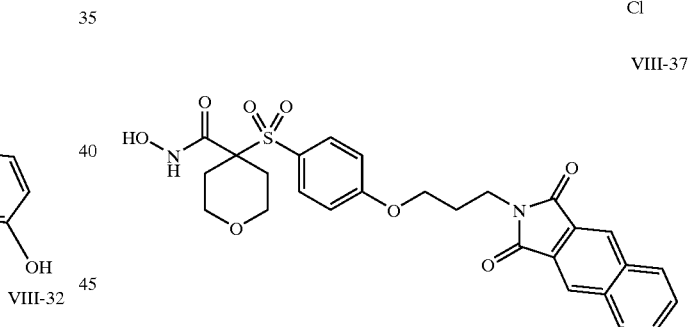
VIII-38
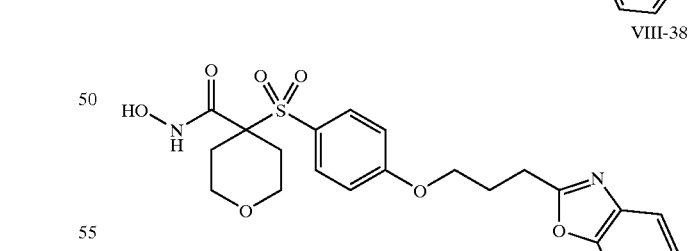
VIII-39
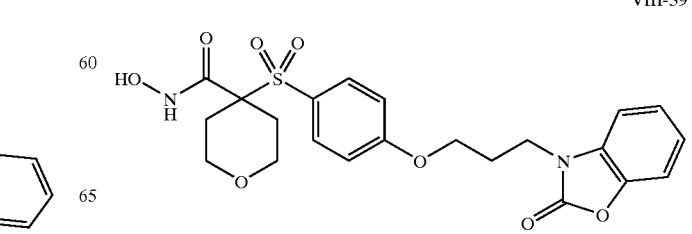

VIII-40
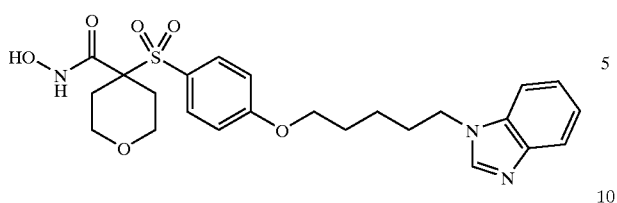

In some preferred embodiments, $E^5$ is optionally-substituted tetrahydroisoquinolinyl. Such compounds include, for example:

VIII-41
VIII-42
VIII-43
VIII-44
VIII-45
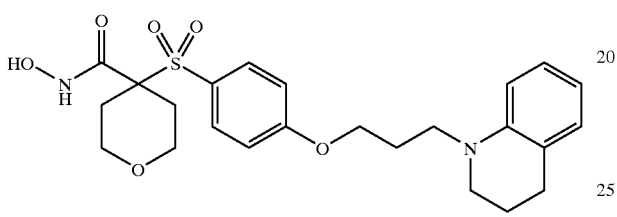
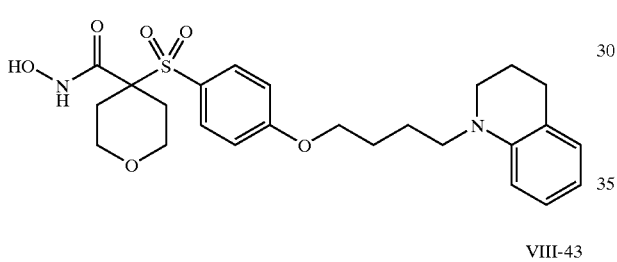
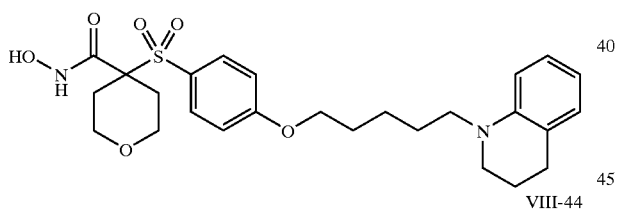
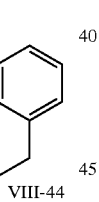
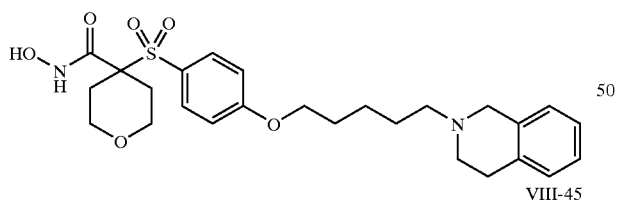
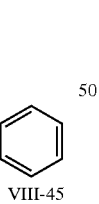

VIII-46
VIII-47
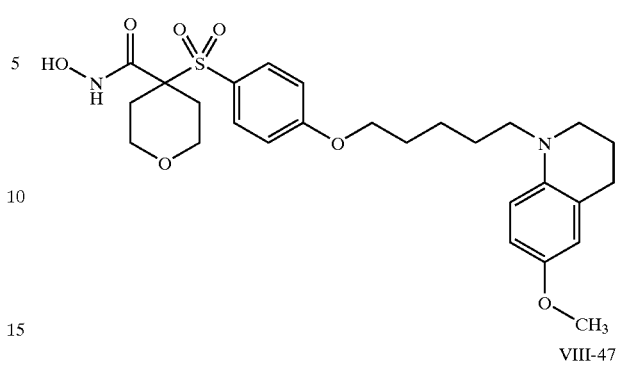

VIII-48
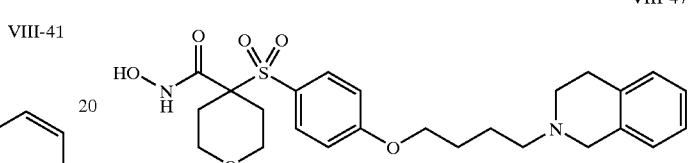

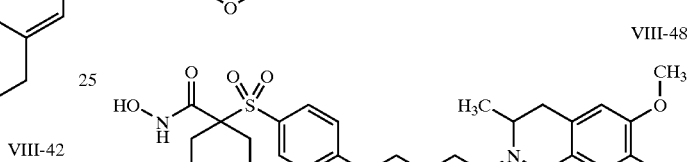
VIII-49
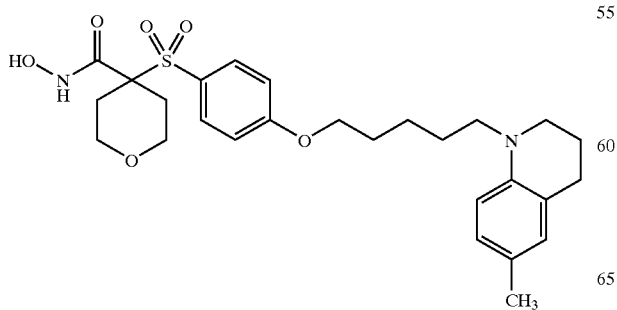

In some preferred embodiments, $E^5$ is heterocyclyl that is substituted on the same atom with two substituents independently selected from the group consisting of alkyl and haloalkyl, the two substituents together forming $C_5$–$C_6$-cycloalkyl or halo-$C_5$–$C_6$-cycloalkyl. This heterocyclyl also optionally is substituted with one or more substituents independently selected from the group consisting of and halogen, —OH, —NO₂, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N($R^5$)($R^6$), —C(O)($R^7$), —S—$R^5$, —S(O)₂—$R^5$, carbocyclyl, halocarbocyclyl, carbocyclyl-$C_1$–$C_6$-alkyl, and halogen-substituted carbocycly-$C_1$–$C_6$-alkyl. The heterocyclyl that is substituted may be, for example, selected from the group consisting of dihydrofuranyl, tetrahydrofuranyl dihydrothiophenyl, tetrahydrothiophenyl, pyrrolinyl, pyrrolidinyl, imidazolinyl, imidazolidinyl, pyrazolinyl, pyrazolidinyl, dithiolyl, oxathiolyl, thiazolinyl, isothiazolinyl, thiazolidinyl, isothiazolidinyl, oxathiolanyl, pyranyl, dihydropyranyl, piperidinyl, piperazinyl, and morpholinyl. Such compounds include, for example:

VIII-50

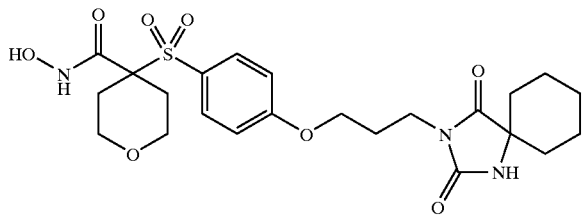

Preferred Embodiment No. 8

In some embodiments of this invention, the compound has a structure corresponding to Formula IX:

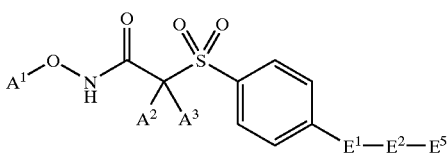

IX $A^1$, $A^2$, and $A^3$ are as defined above for Formula I.

$E^1$ is —O—, —S(O)$_2$—, —S(O)—, —N(R$^1$)—, —C(O)—N(R$^1$)—, —N(R$^1$)—C(O)—, or —C(R$^1$)(R$^2$)—.

$E^2$ forms a link of at least 4 carbon atoms between $E^1$ and $E^5$. $E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_4$–$C_{20}$-alkyl, cycloalkyl, $C_1$–$C_{10}$-alkyl-cycloalkyl, cycloalkyl-$C_1$–$C_{10}$-alkyl, or $C_1$–$C_{10}$-alkyl-cycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$-alkyl.

In some preferred embodiments, $E^2$ is $C_4$–$C_6$-alkyl optionally substituted with one or more halogen.

In some preferred embodiments, $E^2$ is $C_4$–$C_6$-alkyl.

$E^5$ is —OH or optionally-substituted carbocyclyl.

In some preferred embodiments, $E^5$ is —OH or carbocyclyl wherein the carbocyclyl optionally is substituted with one or more substituents independently selected from the group consisting of and halogen, —OH, —NO$_2$, —CN, keto, $C_1$–$C_8$-alkyl, halo-$C_1$–$C_{alkyl}$, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_8$-alkyl. The carbocyclyl also optionally is substituted with two $C_1$–$C_8$-alkyl or halo-$C_1$–$C_8$-alkyl groups on the same atom that form a $C_5$–$C_6$-cycloalkyl or $C_5$–$C_6$-halocycloalkyl.

In some preferred embodiments, $E^5$ is —OH or carbocyclyl wherein the carbocyclyl optionally is substituted with one or more substituents independently selected from the group consisting of and halogen, —OH, —NO$_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl.

$R^1$ and $R^2$ are independently selected from the group consisting of —H and alkyl. The alkyl optionally is substituted. Neither $R^1$ nor $R^2$ forms a ring structure with $E^5$.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^5$ and $R^6$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ is —H, $C_1$–$C_8$-alkyl, —O—R$^8$, —N(R$^8$)(R$^9$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^7$ is —H, $C_1$–$C_6$-alkyl, —O—R$^8$, —N(R$^8$)(R$^9$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^8$ and $R^9$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen. Such compounds include, for example:

In some preferred embodiments, $E^5$ is optionally-substituted carbocyclyl, often preferably optionally-substituted aryl, and more preferably optionally-substituted phenyl. Such compounds include, for example:

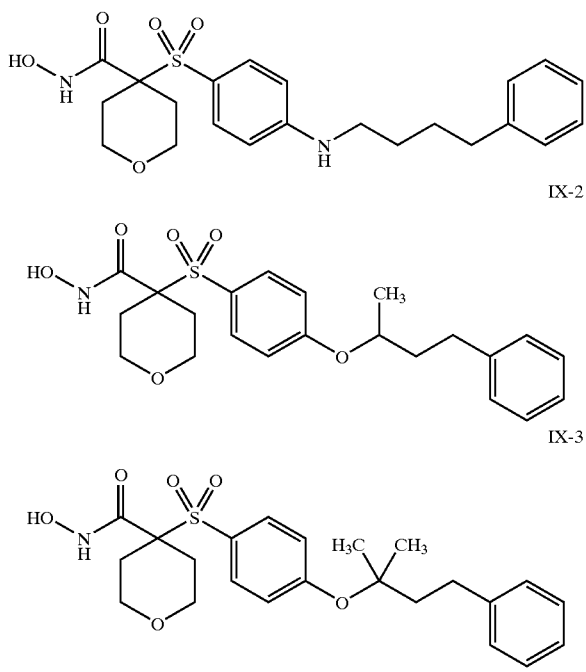

In some preferred embodiments, $E^5$ is —OH. Such compounds include, for example:

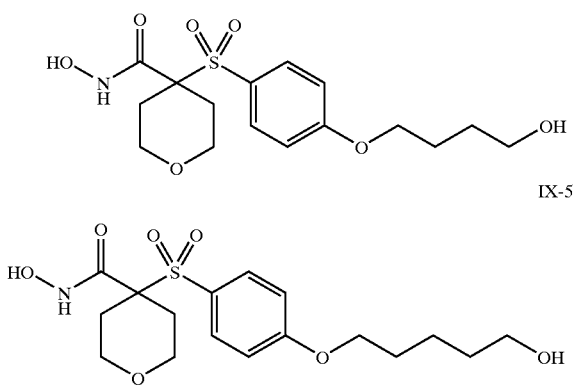

Preferred Embodiment No. 9

In some embodiments of this invention, the compound has a structure corresponding to Formula X:

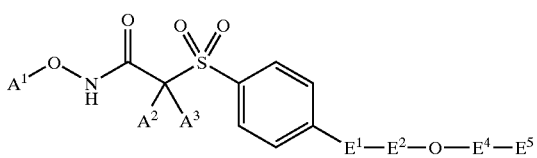

$A^1$, $A^2$, and $A^3$ are as defined above for Formula I.

$E^1$ is —S(O)$_2$—, —S(O)—, —N(R$^1$)—, —C(O)—N(R$^1$)—, —N(R$^1$)—C(O)—, or —C(R$^1$)(R$^2$)—.

$E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, $C_1$–$C_6$-alkyl.

In some preferred embodiments, $E^2$ is $C_2$–$C_6$-alkyl optionally substituted with one or more halogen.

In some preferred embodiments, $E^2$ is $C_2$–$C_6$-alkyl.

$E^4$ is a bond, alkyl, or alkenyl. The alkyl and alkenyl optionally are substituted.

In some preferred embodiments, $E^4$ is a bond, $C_1$–$C_{20}$-alkyl, halo-$C_1C_{20}$-alkyl, $C_2$–$C_{20}$-alkenyl, or halo-$C_2$–$C_{20}$-alkenyl.

In some preferred embodiments $E^4$ is a bond, $C_1$–$C_3$-alkyl, halo-$C_1$–$C_3$-alkyl, $C_2$–$C_3$-alkenyl, or halo-$C_2$–$C_3$-alkenyl.

In some preferred embodiments, $E^4$ is a bond, $C_1$–$C_3$-alkyl, or $C_2$–$C_3$-alkenyl.

$E^5$ is alkyl, alkenyl, alkynyl, alkoxy, alkoxyalkyl, carbocyclyl, or heterocyclyl. Any member of this group optionally is substituted.

In some preferred embodiments, $E^5$ is $C_1$–$C_{20}$-alkyl, $C_2$–$C_{20}$-alkenyl, $C_2$–$C_{20}$-alkynyl, $C_1$–$C_{20}$-alkoxy, $C_1$–$C_{20}$-alkoxy-$C_1$–$C_{20}$-alkyl, carbocyclyl, or heterocyclyl. The $C_1$–$C_{20}$-alkyl, $C_2$–$C_{20}$-alkenyl, $C_2$–$C_{20}$-alkynyl, $C_1$–$C_{20}$-alkoxy, and $C_1$–$C_{20}$-alkoxy-$C_1$–$C_{20}$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, keto, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_8$-alkyl, and halogen-substituted carbocyclyl-$C_1$–$C_8$-alkyl.

In some preferred embodiments, $E^5$ is $C_1$–$C_8$-alkyl, $C_2$–$C_8$-alkenyl, $C_2$–$C_8$-alkynyl, $C_1$–$C_8$-alkoxy, $C_1$–$C_8$-alkoxy-$C_1$–$C_8$-alkyl, carbocyclyl, or heterocyclyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl.

$R^1$ and $R^2$ are independently selected from the group consisting of —H and alkyl. The alkyl optionally is substituted. Neither $R^1$ nor $R^2$ forms a ring structure with $E^2$, $E^4$, or $E^5$.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^5$ and $R^6$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ is —H, $C_1$–$C_6$-alkyl, —O—$R^8$, —N($R^8$)($R^9$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^7$ is —H, $C_1$–$C_6$-alkyl, —O—$R^8$, —N($R^8$)($R^9$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^8$ and $R^9$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^5$ is $C_1$–$C_8$-alkyl, $C_2$–$C_8$-alkenyl, $C_2$–$C_8$-alkynyl, $C_1$–$C_8$-alkoxy, or $C_1$–$C_8$-alkoxy-$C_1$–$C_8$-alkyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —$NO_2$, and —CN.

In some preferred embodiments, $E^5$ is $C_1$–$C_8$-alkyl. Such compounds include, for example:

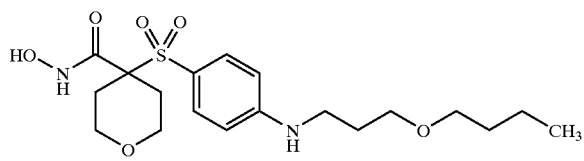

X-1

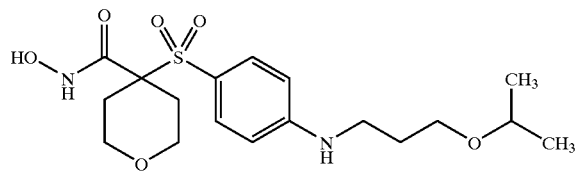

X-2

Preferred Embodiment No. 10

In some embodiments of this invention, the compound has a structure to Formula XI:

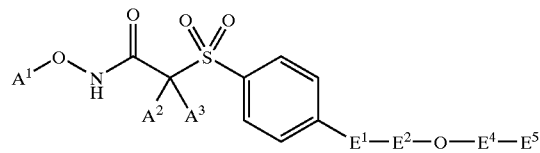

XI $A^1$, $A^2$, and $A^3$ are as defined above for Formula I.

$E^2$ comprises at least 3 carbon atoms. $E^2$ is alkyl, cycloalkyl, alkylcycloalkyl, cycloalkylalkyl, or alkylcycloalkylalkyl. Any member of this group optionally substituted.

In some preferred embodiments, $E^2$ is $C_3$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$-alkyl.

In some preferred embodiments, $E^2$ is $C_3$–$C_{10}$-alkyl optionally is substituted with one or more halogen.

In some preferred embodiments, $E^2$ is $C_3$–$C_{10}$-alkyl.

In some preferred embodiments, $E^2$ is $C_3$–$C_5$-alkyl.

$E^5$ is —H, alkyl, alkenyl, alkynyl, alkoxyalkyl, carbocyclyl, carbocyclylalkoxyalkyl, heterocyclyl, heterocyclylalkyl, or heterocyclylalkoxyalkyl. The alkyl, alkenyl, alkynyl, and alkoxyalkyl optionally are substituted with one or more substituents independently selected from the group consisting of halogen, —OH, —$NO_2$, and —CN. The carbocyclyl, carbocyclylalkoxyalkyl, heterocyclyl, heterocyclylalkyl, and heterocyclylalkoxyalkyl optionally are substituted with one or more substituents independently selected from the group consisting of halogen, —OH, —$NO_2$, —CN, alkyl, haloalkyl, alkoxy, haloalkoxy, alkoxyalkyl, halogen-substituted alkoxyalkyl, —N($R^3$)($R^4$), —C(O)($R^5$), —S—$R^3$, —S(O)$_2$—$R^3$, carbocyclyl, halocarbocyclyl, carbocyclylalkyl, and halogen-substituted carbocyclylalkyl.

In some preferred embodiments, $E^5$ is —H, $C_1$–$C_{20}$-alkyl, $C_2$–$C_{20}$-alkenyl, $C_2$–$C_{20}$-alkynyl, $C_1$–$C_{20}$-alkoxy-$C_1$–$C_{20}$-alkyl, carbocyclyl, carbocyclyl-$C_1$–$C_{10}$-alkoxy-$C_1$–$C_{10}$-alkyl, heterocyclyl, heterocyclyl-$C_1$–$C_{10}$-alkyl, or heterocyclyl-$C_1$–$C_{10}$-alkoxy-$C_1$–$C_{10}$alkyl. The $C_2$–$C_{20}$-alkyl, $C_2$–$C_{20}$-alkenyl, $C_2$–$C_{20}$-alkynyl, and $C_1$–$C_{20}$-alkoxy-$C_1$–$C_{20}$-alkyl optionally are substituted with one or more substituents independently selected from the group consisting of halogen, —OH, —$NO_2$, and —CN. The carbocyclyl, carbocyclyl-$C_1$–$C_{10}$-alkoxy-$C_1$–$C_{10}$-alkyl, heterocyclyl, heterocyclyl-$C_1$–$C_{10}$-alkyl, and heterocyclyl-$C_1$–$C_{10}$- alkoxy-$C_1$–$C_{10}$-alkyl optionally are substituted with one or more substituents independently selected from the group consisting of halogen, —OH, —$NO_2$, —CN, keto, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N($R^3$)($R^4$), —C(O)($R^5$), —S—$R^3$, —S(O)$_2$—$R^3$, carbocyclyl, halocarbocyclyl, carbocyclyl-$C_1$–$C_8$-alkyl, and halogen-substituted carbocyclyl-$C_1$–$C_8$-alkyl.

In some preferred embodiments, $E^5$ is —H, $C_1$–$C_8$-alkyl, $C_2$–$C_8$-alkenyl, $C_2$–$C_8$-alkynyl, $C_1$–$C_8$-alkoxy-$C_1$–$C_8$-alkyl, carbocyclyl, carbocyclyl-$C_1$–$C_8$-alkoxy-$C_1$–$C_8$-alkyl, heterocyclyl, heterocyclyl-$C_1$–$C_8$-alkyl, or heterocyclyl-$C_1$–$C_8$-alkyl, or heterocyclyl-$C_1$–$C_8$-alkoxy-$C_1$–$C_8$-alkyl. The $C_1$–$C_8$-alkyl, $C_2$–$C_8$-alkenyl, $C_2$–$C_8$-alkynyl, and $C_1$–$C_8$-alkoxy-$C_1$–$C_8$-alkyl optionally are substituted with one or more substituents independently selected from the group consisting of halogen, —OH, —$NO_2$, and —CN. The carbocyclyl, carbocyclyl-$C_1$–$C_8$-alkoxy-$C_1$–$C_8$-alkyl, heterocyclyl, heterocyclyl-$C_1$–$C_8$-alkyl, and heterocyclyl-$C_1$–$C_8$-alkoxy-$C_1$–$C_8$-alkyl optionally are substituted with one or more substituents independently selected from the group consisting of halogen, —OH, —$NO_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N($R^3$)($R^4$), —C(O)($R^5$), —S—$R^3$, —S(O)$_2$—$R^3$, carbocyclyl, halocarbocyclyl, carbocyclyl-$C_1$–$C_6$-alkyl, and halogen-substituted carbocyclyl-$C_1$–$C_6$-alkyl.

$R^1$ and $R^2$ are independently selected from the group consisting of —H, alkyl, carbocyclyl, carbocyclylalkyl, heterocyclyl, and heterocyclylalkyl. Except where the member is —H, any member of this group may be substituted with one or more halogen, but more typically is preferably not substituted with halogen.

In some preferred embodiments, $R^1$ and $R^2$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^1$ and $R^2$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^3$ is —H, alkyl, —O—$R^4$, —N($R^4$)($R^5$), carbocyclylalkyl, or heterocyclylalkyl. The alkyl, carbocyclylalkyl, or heterocyclylalkyl may be substituted with one or more halogen, but more typically is preferably not substituted with halogen.

In some preferred embodiments, $R^3$ is —H, $C_1$–$C_8$-alkyl, —O—$R^4$, —N($R^4$)($R^5$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^3$ is —H, $C_1$–$C_6$-alkyl, —O—$R^4$, —N($R^4$)($R^5$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^4$ and $R^5$ are independently selected from the group consisting of —H, alkyl, carbocyclyl, carbocyclylalkyl, heterocyclyl, and heterocyclylalkyl. Except where the member is —H, any member of this group may be substituted with one or more halogen, but more typically is preferably not substituted with halogen.

In some preferred embodiments, $R^4$ and $R^5$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^4$ and $R^5$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^5$ is —H, $C_1$–$C_8$-alkyl, $C_2$–$C_8$-alkenyl, $C_2$–$C_8$-alkynyl, or $C_1$–$C_8$-alkoxy-$C_1$–$C_8$-alkyl. The $C_1$–$C_8$-alkyl, $C_2$–$C_8$-alkenyl, $C_2$–$C_8$-alkynyl, and $C_1$–$C_8$-alkoxy-$C_1$–$C_8$-alkyl optionally are substituted with one or more substituents independently selected from the group consisting of halogen, —OH, —$NO_2$, and —CN. Such compounds include, for example:

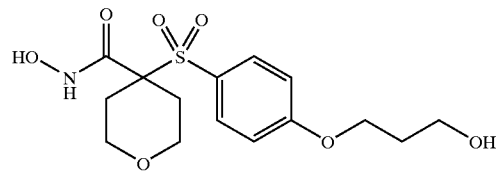

XI-1

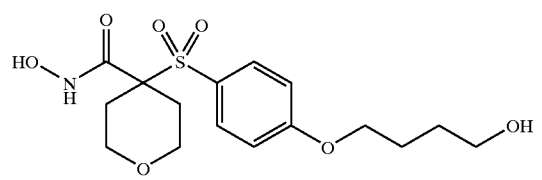

XI-2

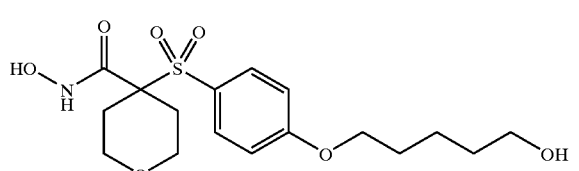

XI-3

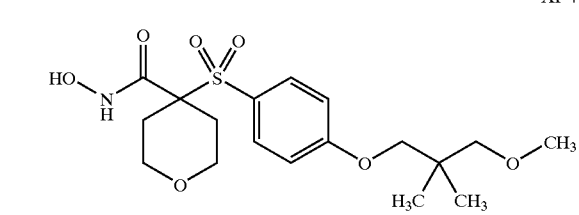

XI-4

XI-5
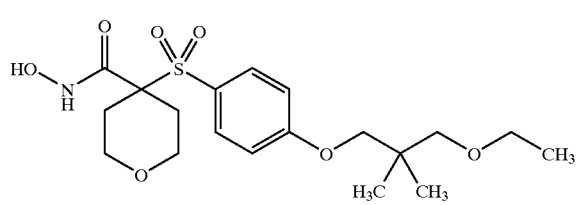

XI-9
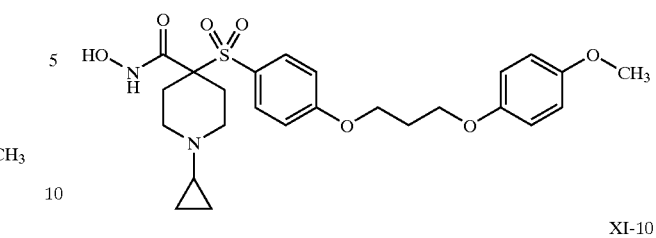

XI-6
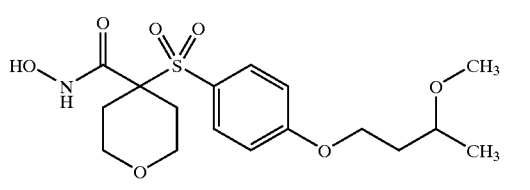

XI-10
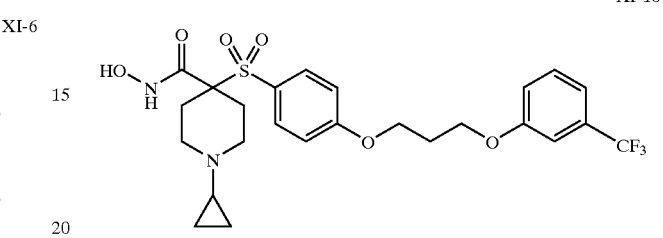

XI-7
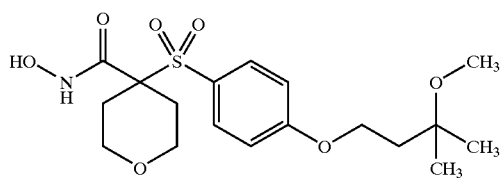

XI-11
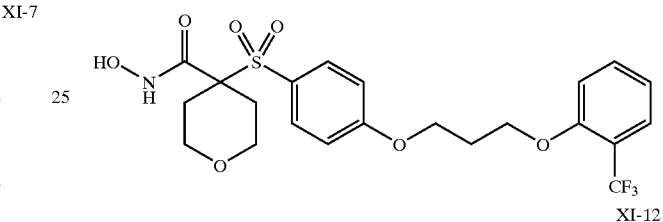

XI-8
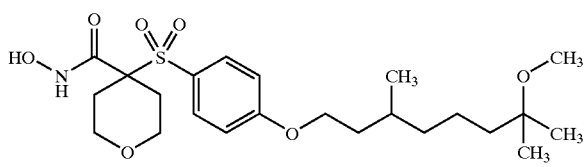

XI-12
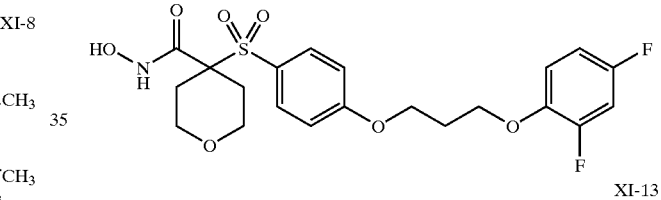

In some preferred embodiments, $E^5$ is carbocyclyl, carbocyclyl-$C_1$–$C_8$-alkoxy-$C_1$–$C_8$-alkyl, heterocyclyl, heterocyclyl-$C_1$–$C_8$-alkyl, or heterocyclyl-$C_1$–$C_8$-alkoxy-$C_1$–$C_8$-alkyl, the carbocyclyl, carbocyclyl-$C_1$–$C_8$-alkoxy-$C_1$–$C_8$-alkyl, heterocyclyl, heterocyclyl-$C_1$–$C_8$-alkyl, and heterocyclyl-$C_1$–$C_8$-alkoxy-$C_1$–$C_8$-alkyl optionally are substituted with one or more substituents independently selected from the group consisting of halogen, —OH, —$NO_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N($R^3$)($R^4$), —C(O)($R^5$), —S—$R^3$, —S(O)$_2$—$R^3$, carbocyclyl, halocarbocyclyl, carbocyclyl-$C_1$–$C_6$-alkyl, and halogen-substituted carbocyclyl-$C_1$–$C_6$-alkyl.

In some preferred embodiments, $E^5$ is optionally-substituted carbocyclyl.

In some preferred embodiments, $E^5$ is optionally-substituted phenyl. Such compounds include, for example:

XI-13
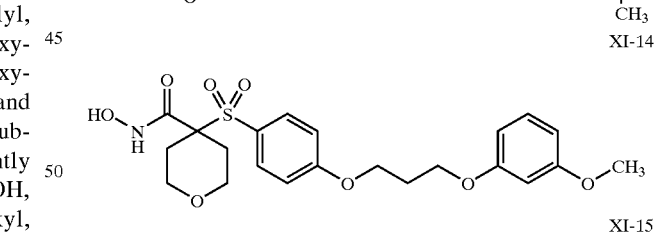

XI-14
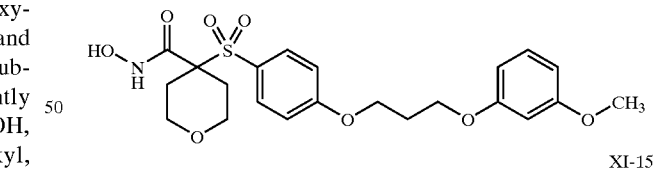

XI-15
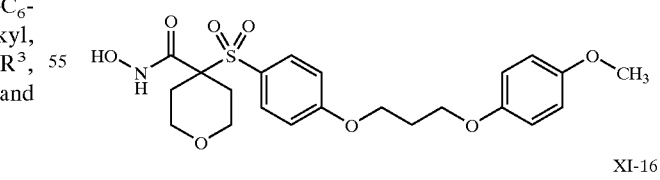

XI-16
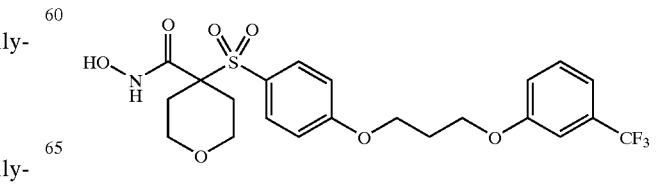

XI-17

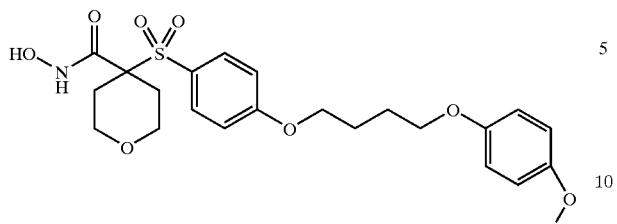

XI-18

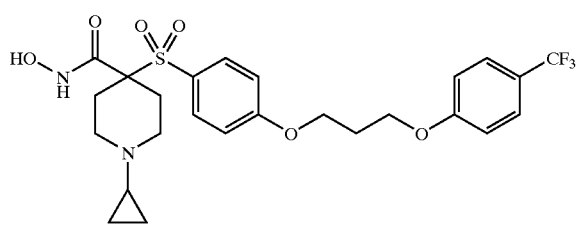

In some preferred embodiments, E⁵ is optionally-substituted naphthalenyl. Such compounds include, for example:

XI-19

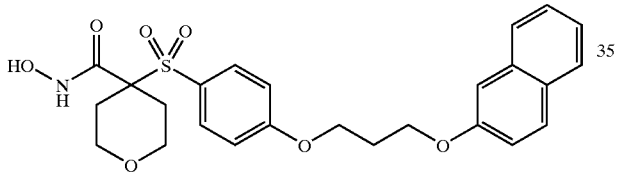

In some preferred embodiments, E⁵ is heterocyclyl or heterocyclyl-$C_1$–$C_8$-alkyl. Such compounds include, for example:

XI-20

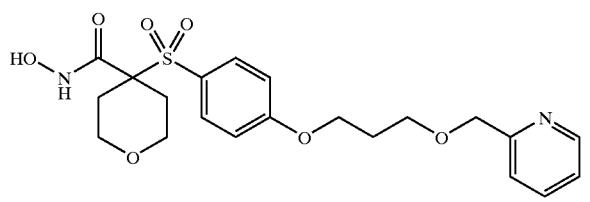

XI-21

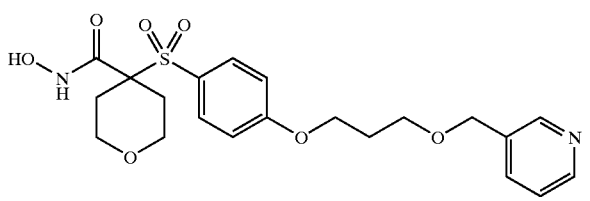

XI-22

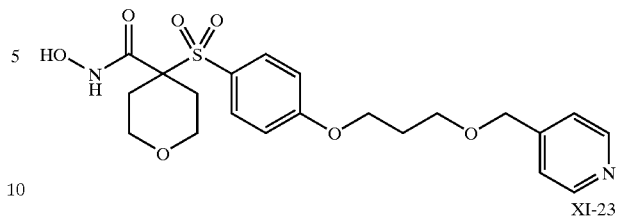

XI-23

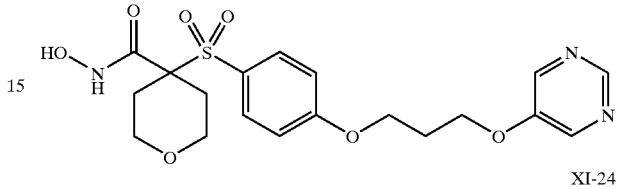

XI-24

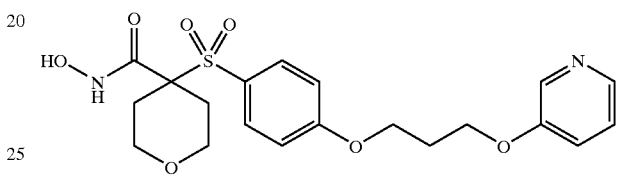

XI-24

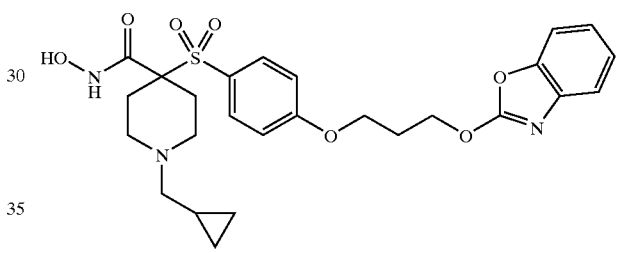

Preferred Embodiment No. 11

In some embodiments of this invention, the compound has a structure to Formula XII:

XII

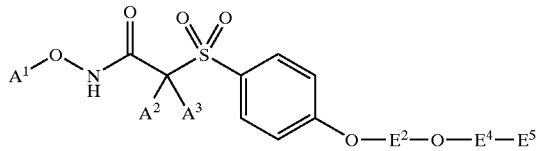

$A^1$, $A^2$, and $A^3$ are as defined above for Formula I.

$E^2$ is alkyl, cycloalkyl, alkylcycloalkyl, cycloalkylalkyl, or alkylcycloalkyl. Any member of this group optionally is substituted. An atom in $E^2$ optionally is bound to an atom in $E^5$ to form a ring.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents selected from the group consisting of halogen, $C_1$–$C_6$-alkyl, halo-$C_1$–$C_6$-alkyl.

In some preferred embodiments, $E^2$ is $C_2$–$C_6$-alkyl optionally substituted with one or more halogen.

In some preferred embodiments, $E^2$ is $C_2$–$C_6$-alkyl.

$E^4$ is a bond, alkyl, or alkenyl. The alkyl and alkenyl optionally are substituted.

In some preferred embodiments, $E^4$ is a bond, $C_1$–$C_{20}$-alkyl, halo-$C_1$–$C_{20}$-alkyl, $C_2$–$C_{20}$-alkenyl, or halo-$C_2$–$C_{20}$-alkenyl.

In some preferred embodiments, $E^4$ is a bond, $C_1$–$C_3$-alkyl, halo-$C_1$–$C_3$-alkyl, $C_2$–$C_3$-alkenyl, or halo-$C_2$–$C_3$-alkenyl.

In some preferred embodiments, $E^4$ is a bond, $C_1$–$C_3$-alkyl, or $C_2$–$C_3$-alkenyl.

In some preferred embodiments, $E^4$ is methyl.

In some preferred embodiments, $E^4$ is a bond.

$E^5$ is:

an optionally-substituted radical selected from the group consisting of alkenyl, alkynyl, alkoxy, alkoxyalkyl, fused-ring carbocyclyl, and heterocyclyl; or single-ring carbocyclyl substituted with one or more substituents independently selected from the group consisting of —OH, —$NO_2$, —CN, —N($R^5$)($R^6$), —C(O)($R^7$), —S—$R^5$, —S(O)$_2$—$R^5$, carbocyclyl, halocarbocyclyl, carbocyclylalkyl, halogen-substituted carbocyclylalkyl, heterocyclyl, haloheterocyclyl, heterocyclylalkyl, and halogen-substituted heterocyclylalkyl; or single-ring carbocyclyl having multiple substitutions.

In some preferred embodiments, $E^5$ is $C_2$–$C_{20}$-alkenyl, $C_2$–$C_{20}$-alkynyl, $C_1$–$C_{20}$-alkoxy, $C_1$–$C_{20}$-alkoxy-$C_1$–$C_{20}$-alkyl, heterocyclyl, single-ring carbocyclyl, or fused-ring carbocyclyl. The $C_2$–$C_{20}$-alkenyl, $C_2$–$C_{20}$-alkynyl, $C_1$–$C_{20}$-alkoxy, and $C_1$–$C_{20}$-alkoxy-$C_1$–$C_{20}$-alkyl optionally are substituted with one or more substituents independently selected from the group consisting of halogen, —OH, —$NO_2$, and —CN. The heterocyclyl and fused-ring carbocyclyl optionally are substituted with one or more substituents independently selected from the group consisting of halogen, —OH, —$NO_2$, —CN, $C_1$–$C_6$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N($R^5$)($R^6$), —C(O)($R^7$), —S—$R^5$, —S(O)$_2$—$R^5$, carbocyclyl, halocarbocyclyl, carbocyclyl-$C_1$–$C_6$-alkyl, halogen-substituted carbocyclyl-$C_1$–$C_8$-alkyl, heterocyclyl, haloheterocyclyl, heterocyclyl-$C_1$–$C_8$-alkyl, and halogen-substituted heterocyclyl-$C_1$–$C_8$-alkyl. The single-ring carbocyclyl is either:

substituted with one or more substituents independently selected from the group consisting of —OH, —$NO_2$, —CN, —N($R^5$)($R^6$), —C(O)($R^7$), —S—$R^5$, —S(O)$_2$—$R^5$, carbocyclyl, halocarbocyclyl, carbocyclyl-$C_1$–$C_8$-alkyl, halogen-substituted carbocyclyl-$C_1$–$C_8$-alkyl, heterocyclyl, haloheterocyclyl, heterocyclyl-$C_1$–$C_8$-alkyl, and halogen-substituted heterocyclyl-$C_1$–$C_8$-alkyl, or substituted with 2 or more substituents independently selected from the group consisting of halogen, —OH, —$NO_2$, —CN, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N($R^5$)($R^6$), —C(O)($R^7$), —S—$R^5$, —S(O)$_2$—$R^5$, carbocyclyl, halocarbocyclyl, carbocyclyl-$C_1$–$C_8$-alkyl, halogen-substituted carbocyclyl-$C_1$–$C_8$-alkyl, heterocyclyl, haloheterocyclyl, heterocyclyl-$C_1$–$C_8$-alkyl, and halogen-substituted heterocyclyl-$C_1$–$C_8$-alkyl.

In some preferred embodiments, $E^5$ is $C_2$–$C_8$-alkenyl, $C_2$–$C_8$-alkynyl, $C_1$–$C_8$-alkoxy, $C_1$–$C_8$-alkoxy-$C_2$–$C_8$-alkyl, heterocyclyl, single-ring carbocyclyl, or fused-ring carbocyclyl. The $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —$NO_2$, and —CN. The heterocyclyl and fused-ring carbocyclyl optionally are substituted with one or more substituents independently selected from the group consisting of halogen, —OH, —$NO_2$, —CN, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N($R^5$)($R^6$), —C(O)($R^7$), —S—$R^5$, —S(O)$_2$—$R^5$, carbocyclyl, halocarbocyclyl, carbocyclyl-$C_1$–$C_6$-alkyl, halogen-substituted carbocyclyl-$C_1$–$C_6$-alkyl, heterocyclyl, haloheterocyclyl, heterocyclyl-$C_1$–$C_6$-alkyl, and halogen-substituted heterocyclyl-$C_1$–$C_6$-alkyl. The single-ring carbocyclyl is either:

substituted with one or more substituents independently selected from the group consisting of —OH, —$NO_2$, —CN, —N($R^5$)($R^6$), —C(O)($R^7$), —S—$R^5$, —S(O)$_2$—$R^5$, carbocyclyl, halocarbocyclyl, carbocyclyl-$C_1$–$C_6$-alkyl, halogen-substituted carbocyclyl-$C_1$–$C_6$-alkyl, heterocyclyl, haloheterocyclyl, heterocyclyl-$C_1$–$C_6$alkyl, and halogen-substituted heterocyclyl-$C_1$–$C_6$-alkyl; or substituted with 2 or more substituents independently selected from the group consisting of halogen, —OH, —$NO_2$, —CN, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N($R^5$)($R^6$), —C(O)($R^7$), —S—$R^5$, —S(O)$_2$—$R^5$, carbocyclyl, halocarbocyclyl, carbocyclyl-$C_1$–$C_6$-alkyl, halogen-substituted carbocyclyl-$C_1$–$C_6$-alkyl, heterocyclyl, haloheterocyclyl, heterocyclyl-$C_1$–$C_6$-alkyl, and halogen-substituted heterocyclyl-$C_1$–$C_6$-alkyl.

$R^1$ and $R^2$ are independently selected from the group consisting of —H, alkyl, carbocyclyl, carbocyclylalkyl, heterocyclyl, and heterocyclylalkyl. Except where the member is —H, any member of this group may be substituted with one or more halogen, but more typically is preferably not substituted with halogen.

In some preferred embodiments, $R^1$ and $R^2$ are independently selected from the group consisting of —H, $C_1$–$C_8$-alkyl, carbocyclyl, carbocyclyl-$C_1$–$C_6$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^1$ and $R^2$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^3$ is —H, alkyl, —O—$R^4$, —N($R^4$)($R^5$), carbocyclylalkyl, or heterocyclylalkyl. The alkyl, carbocyclylalkyl, or heterocyclylalkyl may be substituted with one or more halogen, but more typically is preferably not substituted with halogen.

In some preferred embodiments, $R^3$ is —H, $C_1$–$C_8$-alkyl, —O—$R^4$, —N($R^4$)($R^5$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^3$ is —H, $C_1$–$C_6$-alkyl, —O—$R^4$, —N($R^4$)($R^5$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with hyalogen.

In some preferred embodiments, $R^3$ is —H, $C_1$–$C_6$-alkyl, —O—$R^4$, —N($R^4$)($R^5$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^4$ and $R^5$ are independently selected from the group consisting of —H, alkyl, carbocyclyl, carbocyclylalkyl, heterocyclyl, and heterocyclylalkyl. Except where the member is —H, any member of this group may be substituted with one or more halogen, but more typically is preferably not substituted with halogen.

In some preferred embodiments, $R^4$ and $R^5$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^4$ and $R^5$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^2$ is bound to an atom of $E^5$ to form a ring. Such compounds include, for example:

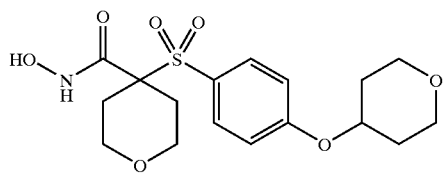

XII-1

In some preferred embodiments, $E^2$ is not bound to an atom of $E^5$ to form a ring.

In some such preferred embodiments, $E^5$ is a single-ring carbocyclyl (preferably phenyl) substituted with one or more substituents independently selected from the group consisting of —OH, —NO$_2$, —CN, —N($R^5$)($R^6$), —C(O)($R^7$), —S—$R^5$, —S(O)$_2$—$R^5$, carbocyl, halocarbocyclyl, carbocyclyl-$C_1$–$C_6$-alkyl, halogen-substituted carbocyclyl-$C_1$–$C_6$-alkyl, heterocyclyl, haloheterocyclyl, heterocyclyl-$C_1$–$C_6$-alkyl, and halogen-substituted heterocyclyl-$C_1$–$C_6$-alkyl. Such compounds include, for example:

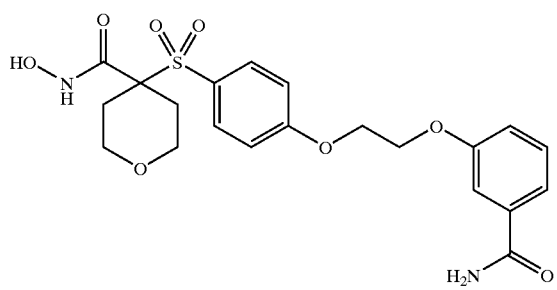

XII-2

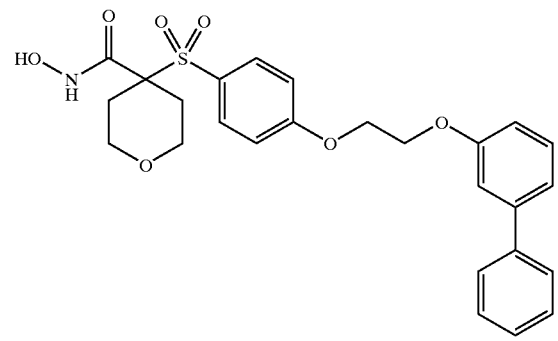

XII-3

In some preferred embodiments, $E^5$ is single-ring carbocyclyl (preferably phenyl) substituted with 2 or more substituents independently selected from the group consisting of halogen, —OH, —NO$_2$, —CN, $C_1$–$C_6$-alkyl, halo-$C_1$–$C_6$-alkyl, $C_1$–$C_6$-alkoxy, halo-$C_1$–$C_6$-alkoxy, —N($R^5$)($R^6$), —C(O)($R^7$), —S—$R^5$, —S(O)$_2$—$R^5$, carbocyclyl, halocarbocyclyl, carbocyclyl-$C_1$–$C_6$-alkyl, and halogen-substituted carbocyclyl-$C_1$–$C_6$-alkyl, heterocyclyl, haloheterocyclyl, heterocyclyl-$C_1$–$C_6$-alkyl, and halogen-substituted heterocyclyl-$C_1$–$C_6$-alkyl. Such compounds include, for example:

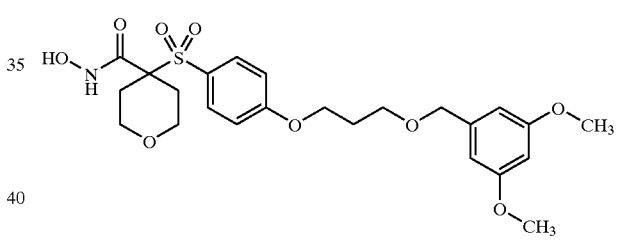

XII-4

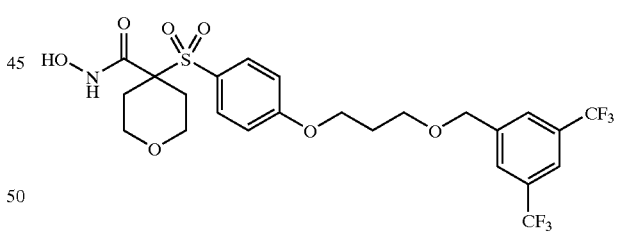

XII-5

In some preferred embodiments, $E^5$ is heterocyclyl optionally substituted with one or more substituents independently selected from the group consisting of halogen, —OH, —NO$_2$, —CN, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N($R^5$)($R^6$), —C(O)($R^7$), —S—$R^5$, —S(O)$_2$—$R^5$, carbocyclyl, halocarbocyclyl, carbocyclyl-$C_1$–$C_6$-alkyl, halogen-substituted carbocyclyl-$C_1$–$C_6$-alkyl, heterocyclyl, haloheterocyclyl, heterocyclyl-$C_1$–$C_6$-alkyl, and halogen-substituted heterocyclyl-$C_1$–$C_6$-alkyl. Such compounds include, for example:

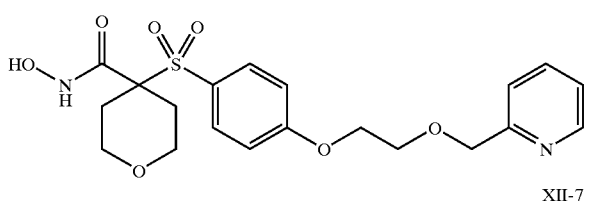

XII-6
XII-7
XII-8
XII-9
XII-10

Preferred Embodiment No. 12

In some embodiments of this invention, the compound has a structure corresponding to Formula XIII:

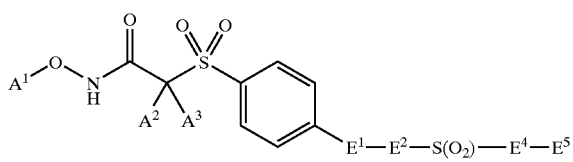

XIII $A^1$, $A^2$, and $A^3$ are as defined above for Formula I.

$E^1$ is —S(O)$_2$—, —S(O)—, —N(R$^1$)—, —C(O)—N(R$^1$)—, —N(R$^1$)—C(O)—, or —C(R$^1$)(R$^2$)—.

$E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents selected from the group consisting of halogen, $C_1$–$C_6$-alkyl, and halo-$C_1$–$C_6$-alkyl.

In some preferred embodiments, $E^2$ is $C_1$–$C_6$-alkyl, cycloalkyl, $C_1$–$C_6$-alkylcycloalkyl, cycloalkyl-$C_1$–$C_6$-alkyl, or $C_1$–$C_6$-alkylcycloalkyl-$C_1$–$C_6$-alkyl. Any member of this group optionally is substituted with one or more halogen, although such substituent typically is preferably not substituted with halogen.

$E^4$ is a bond, alkyl, or alkenyl. The alkyl and alkenyl optionally are substituted.

In some preferred embodiments, $E^4$ is a bond, $C_1$–$C_{20}$-alkyl, halo-$C_1$–$C_{20}$-alkyl, $C_2$–$C_{20}$-alkenyl, or halo-$C_2$–$C_{20}$-alkenyl.

In some preferred embodiments, $E^4$ is a bond, $C_1$–$C_3$-alkyl, halo-$C_1$–$C_3$-alkyl, $C_2$–$C_3$-alkenyl, or halo-$C_2$–$C_3$-alkenyl.

In some preferred embodiments, $E^4$ is a bond, $C_1$–$C_3$-alkyl, or $C_2$–$C_3$-alkenyl.

$E^5$ is alkyl, alkenyl, alkynyl, alkoxy, alkoxyalkyl, carbocyclyl, or heterocyclyl. Any member of this group optionally is substituted.

In some preferred embodiments, $E^5$ is $C_1$–$C_{20}$-alkyl, $C_2$–$C_{20}$-alkenyl, $C_2$–$C_{20}$-alkynyl, $C_1$–$C_{20}$-alkoxy, $C_1$–$C_{20}$-alkoxy-$C_1$–$C_{20}$-alkyl, carbocyclyl, or heterocyclyl. The $C_1$–$C_{20}$-alkyl, $C_2$–$C_{20}$-alkenyl, $C_2$–$C_{20}$-alkynyl, $C_1$–$C_{20}$-alkoxy, and $C_1$–$C_{20}$-alkoxy-$C_1$–$C_{20}$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, $C_1$–$C_8$-alkyl, halo-$C_1$–$C_8$-alkyl, $C_1$–$C_8$-alkoxy, halo-$C_1$–$C_8$-alkoxy, —N$^5$)(R$^6$), —C(O)(R$^7$), —S—R$^5$, —S(O)$_2$—R$^5$, carbocyclyl, halocarbocyclyl, carbocyclyl-$C_1$–$C_8$-alkyl, and halogen-substituted carbocyclyl-$C_1$–$C_8$-alkyl.

In some preferred embodiments, $E^5$ is $C_1$–$C_8$-alkyl, $C_2$–$C_8$-alkenyl, $C_2$–$C_8$-alkynyl, $C_1$–$C_8$-alkoxy, $C_1$–$C_8$-alkoxy-$C_1$–$C_8$-alkyl, carbocyclyl, or heterocyclyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, $C_1$–$C_6$-alkyl, halo-$C_1$–$C_6$-alkyl, $C_1$–$C_6$-alkoxy, halo-$C_1$–$C_6$-alkoxy, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl.

$R^1$ and $R^2$ are independently selected from the group consisting of —H and alkyl. The alkyl optionally is substituted. Neither $R^1$ nor $R^2$ forms a ring structure with $E^2$, $E^4$, or $E^5$.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ is —H, $C_1$–$C_6$-alkyl, —O—$R^8$, —N($R^8$)($R^9$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^7$ is —H, $C_1$–$C_6$-alkyl, —O—$R^8$, —N($R^8$)($R^9$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^8$ and $R^9$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

Preferred Embodiment No. 13

In some embodiments of this invention, the compound has a structure corresponding to Formula XIV:

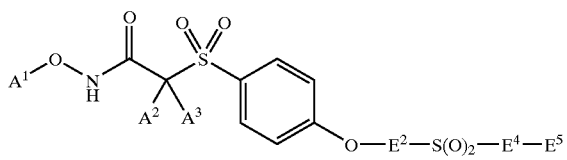

XIV $A^1$, $A^2$, and $A^3$ are as defined above for Formula I.

$E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl; or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$-alkyl.

In some preferred embodiments, $E^2$ is $C_1$–$C_6$-alkyl optionally substituted with one or more halogen.

In some preferred embodiments, $E^2$ is $C_1$–$C_6$-alkyl.

$E^4$ is alkyl or alkenyl. The alkyl and alkenyl optionally are substituted.

In some preferred embodiments, $E^4$ is $C_1$–$C_{20}$-alkyl, halo-$C_1$–$C_{20}$-alkyl, $C_2$–$C_{20}$-alkenyl, or halo-$C_2$–$C_{20}$-alkenyl.

In some preferred embodiments, $E^4$ is $C_1$–$C_3$-alkyl, halo-$C_1$–$C_3$-alkyl, $C_2$–$C_3$-alkenyl, or halo-$C_2$–$C_3$-alkenyl.

In some preferred embodiments, $E^4$ is $C_1$–$C_3$-alkyl or $C_2$–$C_3$-alkenyl.

$E^5$ is —H, alkyl, alkenyl, alkynyl, alkoxy, carbocyclyl, or heterocyclyl. Any member of this group optionally is substituted.

In some preferred embodiments, $E^5$ is —H, $C_1$–$C_{20}$-alkyl, $C_2$–$C_{20}$-alkenyl, $C_2$–$C_{20}$-alkynyl, $C_1$–$C_{20}$-alkoxy, carbocyclyl, or heterocyclyl. The $C_1$–$C_{20}$-alkyl, $C_2$–$C_{20}$-alkenyl, $C_2$–$C_{20}$-alkynyl, and $C_1$–$C_{20}$-alkoxy optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, $C_1$–$C_8$-alkyl, halo-$C_1$–$C_8$-alkyl, $C_1$–$C_8$-alkoxy, halo-$C_1$–$C_8$-alkoxy, —N($R^3$)($R^4$), —C(O)($R^5$), —S—$R^3$, —S(O)$_2$—$R^3$, carbocyclyl, halocarbocyclyl, carbocyclyl-$C_1$–$C_8$-alkyl, and halogen-substituted carbocyclyl-$C_1$–$C_8$-alkyl.

In some preferred embodiments, $E^5$ is —H, $C_1$–$C_8$-alkyl, $C_2$–$C_8$-alkenyl, $C_2$–$C_8$-alkynyl, $C_1$–$C_8$-alkoxy, carbocyclyl, or heterocyclyl. The $C_1$–$C_8$-alkyl, $C_2$–$C_8$-alkenyl, $C_2$–$C_8$-alkynyl, and $C_1$–$C_8$-alkoxy optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, $C_1$–$C_6$-alkyl, halo-$C_1$–$C_6$-alkyl, $C_1$–$C_6$-alkoxy, halo-$C_1$–$C_6$-alkoxy, —N($R^3$)($R^4$), —C(O)($R^5$), —S—$R^3$, —S(O)$_2$—$R^3$, carbocyclyl, halocarbocyclyl, carbocyclyl-$C_1$–$C_6$-alkyl, and halogen-substituted carbocyclyl-$C_1$–$C_6$-alkyl.

$R^3$ and $R^4$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^3$ and $R^4$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^5$ is —H, $C_1$–$C_8$-alkyl, —O—$R^6$, —N($R^6$)($R^7$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^5$ is —H, $C_1$–$C_6$-alkyl, —O—$R^6$, —N($R^6$)($R^7$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^6$ and $R^7$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^6$ and $R^7$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^5$ is —H, $C_1$–$C_8$-alkyl, $C_2$–$C_8$-alkenyl, $C_2$–$C_8$-alkynyl, or $C_1$–$C_8$-alkoxy. The $C_1$–$C_8$-alkyl, $C_2$–$C_8$-alkenyl, $C_2$–$C_8$-alkynyl, and $C_1$–$C_8$-alkoxy optionally are substituted with one or more substituents independently selected from the group consisting of halogen, —OH, —$NO_2$, and —CN. In one such embodiment, $E^5$ is $C_1$–$C_8$-alkyl optionally substituted with one or more substituents independently selected from the group consisting of halogen, —OH, —$NO_2$, and —CN. Such compounds include, for example:

XIV-1

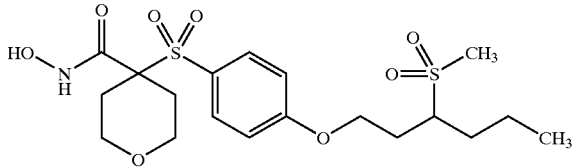

In some preferred embodiments, $E^5$ is optionally-substituted carbocyclyl and optionally-substituted heterocyclyl.

In some preferred embodiments, $E^5$ is optionally-substituted aryl, often preferably optionally-substituted phenyl. Such compounds include, for example:

XIV-2

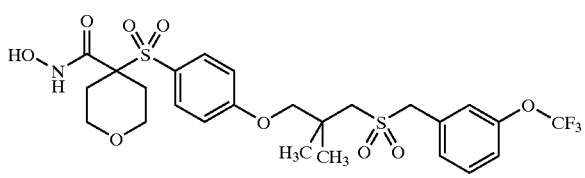

XIV-3

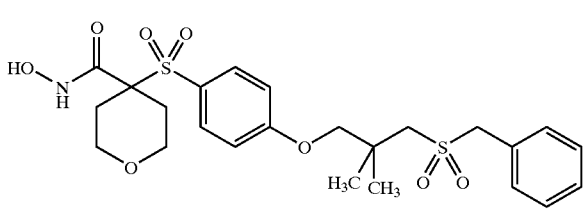

Preferred Embodiment No. 14

In some embodiments of this invention, the compound has a structure corresponding to Formula XV:

XV

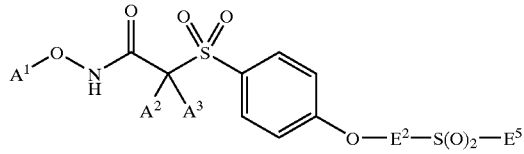

$A^1$, $A^2$, and $A^3$ are as defined above for Formula I.

$E^2$ comprises less than 5 carbon atoms. $E^2$ is alkyl, cycloalkyl, alkylcycloalkyl, cycloalkylalkyl, or alkylcycloalkylalkyl. Any member of this group optionally is substituted, but preferably is not substituted.

$E^5$ is alkyl, alkenyl, alkynyl, alkoxyalkyl, carbocyclyl, or heterocyclyl. Any member of this group optionally is substituted.

In some preferred embodiments, $E^5$ is $C_1$–$C_{20}$-alkyl, $C_2$–$C_{20}$-alkenyl, $C_2$–$C_{20}$-alkynyl, $C_1$–$C_{20}$-alkoxy-$C_1$–$C_{20}$-alkyl, carbocyclyl, or heterocyclyl. The $C_1$–$C_{20}$-alkyl, $C_2$–$C_{20}$-alkenyl, $C_2$–$C_{20}$-alkynyl, and $C_1$–$C_{20}$-alkoxy-$C_1$–$C_{20}$-alkyl optionally are substituted with one or more substituents independently selected from the group consisting of halogen, —OH, —$NO_2$, and —CN. The carbocyclyl and heterocyclyl optionally are substituted with one or more substituents independently selected from the group consisting of halogen, —OH, —$NO_2$, —CN, keto, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_{1-C8}$-alkoxy-$C_1$–$C_8$-alkyl, —$N(R^3)(R^4)$, —$C(O)(R^5)$, —S—$R^3$, —$S(O)_2$—$R^3$, carbocyclyl, halocarbocyclyl, carbocyclyl-$C_1$–$C_8$-alkyl, halogen-substituted carbocyclyl-$C_1$–$C_8$-alkyl, $C_1$–$C_8$-alkylcarbocyclyloxy, and halogen-substituted $C_1$–$C_8$-alkylcarbocyclyloxy.

In some preferred embodiments, $E^5$ is $C_1$–$C_8$-alkyl, $C_2$–$C_8$-alkenyl, $C_2$–$C_8$-alkynyl, $C_1$–$C_8$-alkoxy-$C_1$–$C_8$-alkyl, carbocyclyl, or heterocyclyl. The $C_1$–$C_8$-alkyl, $C_2$–$C_8$-alkenyl, $C_2$–$C_8$-alkynyl, and $C_1$–$C_8$-alkoxy-$C_1$–$C_8$-alkyl optionally are substituted with one or more substituents independently selected from the group consisting of halogen, —OH, —$NO_2$, and —CN. The carbocyclyl and heterocyclyl optionally are substituted with one or more substituents independently selected from the group consisting of halogen, —OH, —$NO_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —$N(R^3)(R^4)$, —$C(O)(R^5)$, —S—$R^3$, —$S(O)_2$—$R^3$, carbocyclyl, halocarbocyclyl, carbocyclyl-$C_1$–$C_6$-alkyl, halogen-substituted carbocyclyl-$C_1$–$C_6$-alkyl, $C_1$–$C_6$-alkylcarbocyclyloxy, and halogen-substituted $C_1$–$C_6$-alkylcarbocyclyloxy.

$R^3$ and $R^4$ are independently selected from the group consisting of —H, $C_1$–$C_8$-alkyl carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^3$ and $R^4$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^5$ is —H, $C_1$–$C_8$-alkyl, —O—$R^6$, —N($R^6$)($R^7$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^5$ is —H, $C_1$–$C_6$-alkyl, —O—$R^6$, —N($R^6$)($R^7$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^6$ and $R^7$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^6$ and $R^7$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^5$ is $C_1$–$C_8$-alkyl, $C_2$–$C_8$-alkenyl, $C_2$–$C_8$-alkynyl, or $C_1$–$C_8$-alkoxy-$C_1$–$C_8$-alkyl. The $C_1$–$C_8$-alkyl, $C_2$–$C_8$-alkenyl, $C_2$–$C_8$-alkynyl, and $C_1$–$C_8$-alkoxy-$C_1$–$C_8$-alkyl optionally are substituted with one or more substituents independently selected from the group consisting of halogen, —OH, —NO$_2$, and —CN.

In some preferred embodiments, $E^5$ is optionally-substituted carbocyclyl.

In some preferred embodiments, $E^5$ is optionally-substituted $C_5$–$C_6$-cycloalkyl. Such compounds include, for example:

XV-1

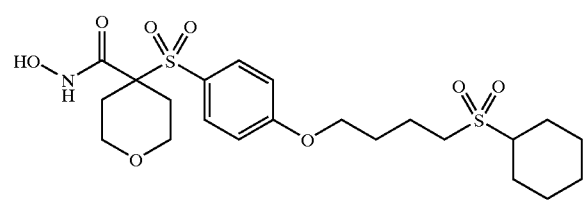

XV-2

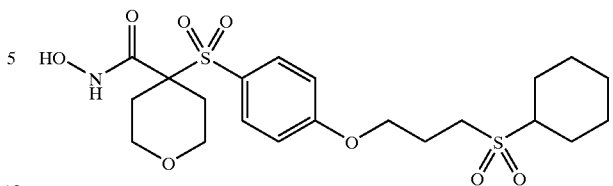

XV-3

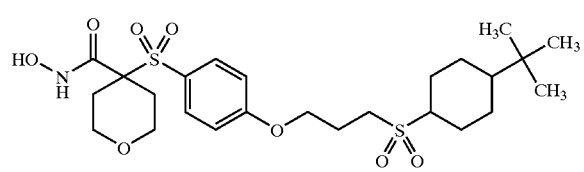

In some preferred embodiments, $E^5$ is optionally-substituted phenyl. Such compounds include, for example:

XV-4

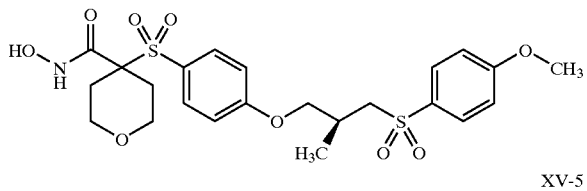

XV-5

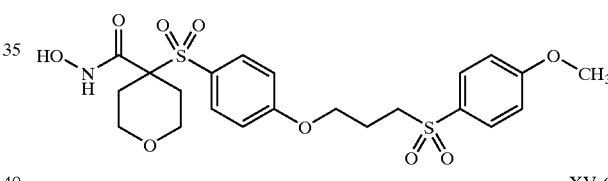

XV-6

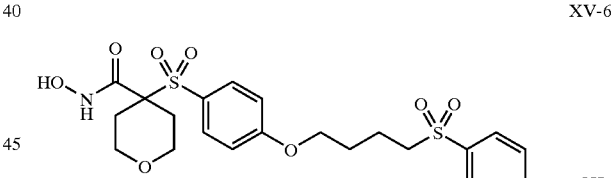

XV-7

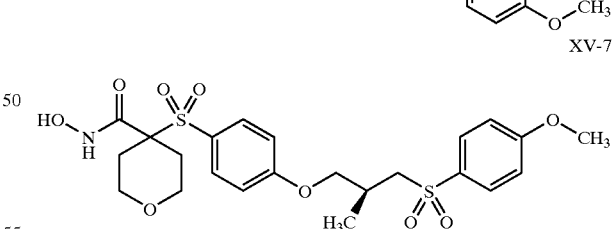

In some preferred embodiments, $E^5$ is optionally-substituted heterocyclyl.

In some preferred embodiments, $E^5$ is optionally-substituted heterocyclyl selected from the group consisting of piperidinyl, morpholinyl, and tetrahydroisoquinolinyl. Such compounds include, for example:

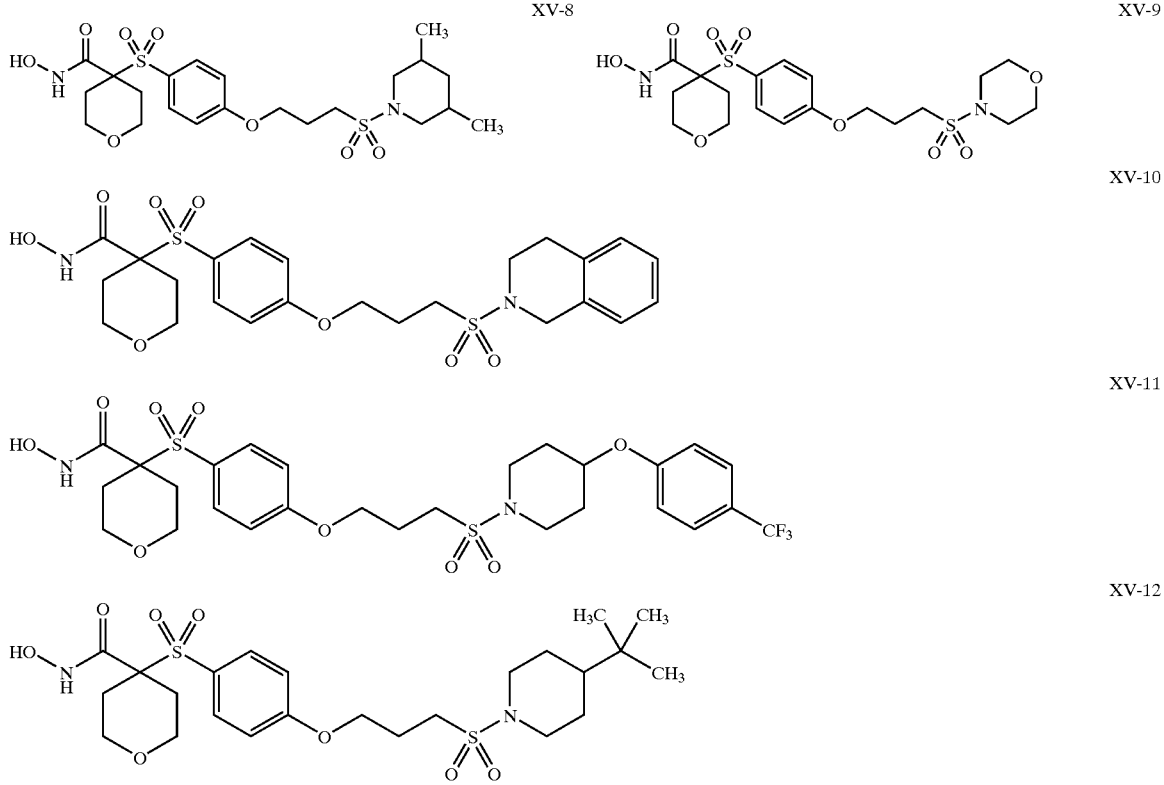

Preferred Embodiment No. 15

In some embodiments of this invention, the compound has a structure corresponding to Formula XVI:

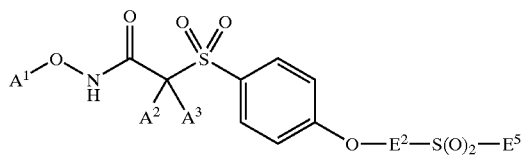

XVI $A^1$, $A^2$, and $A^3$ are as defined above for Formula I.

$E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, halo-$C_1$–$C_6$-alkyl.

In some preferred embodiments, $E^2$ is $C_1$–$C_6$-alkyl optionally substituted with one or more halogen.

In some preferred embodiments, $E^2$ is $C_1$–$C_6$-alkyl.

$E^5$ is alkyl, alkenyl, alkynyl, alkoxyalkyl, saturated carbocyclyl, partially saturated carbocyclyl, or heterocyclyl. Any member of this group optionally is substituted.

In some preferred embodiments, $E^5$ is $C_1$–$C_{20}$-alkyl, $C_2$–$C_{20}$-alkenyl, $C_2$–$C_{20}$-alkynyl, $C_1$–$C_{20}$-alkoxy-$C_1$–$C_{20}$-alkyl, saturated carbocyclyl, partially saturated carbocyclyl, or heterocyclyl. The $C_1$–$C_{20}$-alkyl, $C_2$–$C_{20}$-alkenyl, $C_2$–$C_{20}$-alkynyl, and $C_1$–$C_{20}$-alkoxy-$C_1$–$C_{20}$-alkyl optionally are substituted with one or more substituents independently selected from the group consisting of halogen, —OH, —$NO_2$, and —CN. The saturated carbocyclyl, partially saturated carbocyclyl, and heterocyclyl optionally are substituted with one or more substituents independently selected from the group consisting of halogen, —OH, —$NO_2$, —CN, $C_1$–$C_6$-alkyl, halo-$C_1$–$C_6$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N($R^3$)($R^4$), —C(O)($R^5$), —S—$R^3$, —S(O)$_2$—$R^3$, carbocyclyl, halocarbocyclyl, carbocyclyl-$C_1$–$C_6$-alkyl, halogen-substituted carbocyclyl-$C_1$–$C_8$-alkyl, $C_1$–$C_8$-alkylcarbocyclyloxy, and halogen-substituted $C_1$–$C_8$-alkylcarbocyclyloxy.

In some preferred embodiments, $E^5$ is $C_1$–$C_8$-alkyl, $C_2$–$C_8$-alkenyl, $C_2$–$C_8$-alkynyl, $C_1$–$C_8$-alkoxy-$C_1$–$C_8$-alkyl, saturated carbocyclyl, partially saturated carbocyclyl, or heterocyclyl. The $C_1$–$C_8$-alkyl, $C_2$–$C_8$-alkenyl, $C_2$–$C_8$-alkynyl, and $C_1$–$C_8$-alkoxy-$C_1$–$C_8$-alkyl optionally are substituted with one or more substituents independently selected from the group consisting of halogen, —OH, —$NO_2$, and —CN. The saturated carbocyclyl, partially saturated carbocyclyl, and heterocyclyl optionally are substituted with one or more substituents independently selected from the group consisting of halogen, —OH, —$NO_2$, —CN, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N($R^3$)($R^4$), —C(O)($R^5$), —S—$R^3$, —S(O)$_2$—$R^3$, carbocyclyl, halocarbocyclyl, carbocyclyl-$C_1$–$C_6$-alkyl, halogen-substituted carbocyclyl-$C_1$–$C_6$-alkyl, $C_1$–$C_6$-alkylcarbocyclyloxy, and halogen-substituted $C_1$–$C_6$-alkylcarbocyclyloxy.

$R^3$ and $R^4$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^3$ and $R^4$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^5$ is s —H, $C_1$–$C_8$-alkyl, —O—$R^6$, —N($R^6$)($R^7$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^5$ is —H, $C_1$–$C_6$-alkyl, —O—$R^6$, —N($R^6$)($R^7$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^6$ and $R^7$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^6$ and $R^7$ are independently selected from the group consisting of —H, $C_1$ . $C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

In some preferred embodiments, $E^5$ is $C_1$–$C_8$-alkyl, $C_2$–$C_8$-alkenyl, $C_2$–$C_8$-alkynyl, or $C_1$–$C_8$-alkoxy-$C_1$–$C_8$-alkyl. The $C_{-C8}$-alkyl, $C_2$–$C_8$-alkenyl, $C_2$–$C_8$-alkynyl, and $C_1$–$C_8$-alkoxy-$C_1$–$C_8$-alkyl optionally are substituted with one or more substituents independently selected from the group consisting of halogen, —OH, —NO$_2$, and —CN.

In some preferred embodiments, $E^5$ is optionally-substituted, partially-saturated carbocyclyl.

In some preferred embodiments, $E^5$ is optionally-substituted, saturated carbocyclyl (preferably optionally-substituted $C_5$–$C_6$ cycloalkyl). Such compounds include, for example:

XVI-1

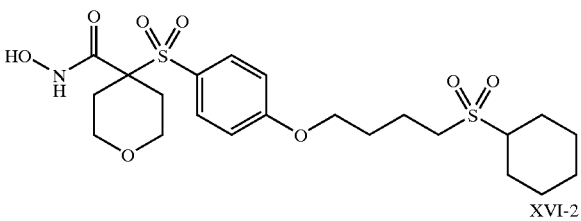

XVI-2

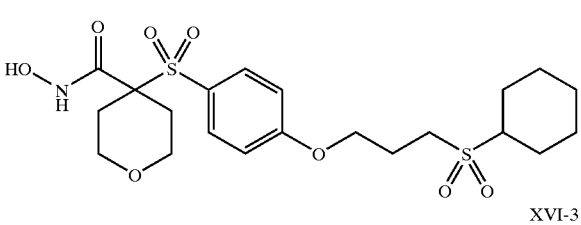

XVI-3

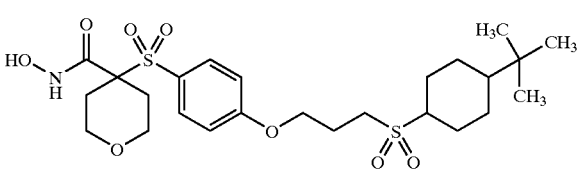

In some preferred embodiments, $E^5$ is optionally-substituted heterocyclyl. Such compounds include, for example:

XVI-4

XVI-5

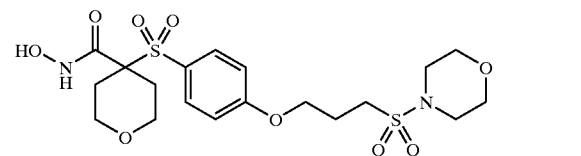

XVI-6

XV-7

-continued

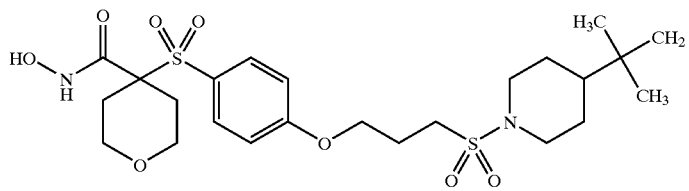

XVI-8

Preferred Embodiment No. 16

In some embodiments of this invention, the compound has a structure corresponding to Formula XVII:

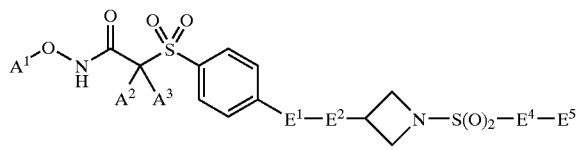

XVII $A^1$, $A^2$, and $A^3$ are as defined above for Formula I.

$E^1$ is —S(O)$_2$—, —S(O)—, —N(R$^1$)—, —C(O)—N(R$^1$)—, —N(R$^1$)—C(O)—, or —C(R$^1$)(R$^2$)—.

$E^2$ is alkyl, carbocyclyl, alkylcycloalkyl, cycloalkyl, or alkylcycloalkylalkyl. Any member of this group optionally is substituted.

In some preferred embodiments, $E^2$ is $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group may be substituted with one or more halogen, but more typically is preferably not substituted with halogen.

In some preferred embodiments, $E^2$ is $C_1$–$C_6$-alkyl optionally substituted with one or more halogen.

In some preferred embodiments, $E^2$ is $C_1$–$C_6$-alkyl.

$E^4$ is a bond, alkyl, or alkenyl, The alkyl and alkenyl optionally are substituted.

In some preferred embodiments, $E^4$ is a bond, $C_1$–$C_{20}$-alkyl, halo-$C_1$–$C_{20}$-alkyl, $C_2$–$C_{20}$-alkenyl, or halo-$C_2$–$C_{20}$-alkenyl.

In some preferred embodiments, $E^4$ is a bond, $C_1$–$C_3$-alkyl, halo-$C_1$–$C_3$-alkyl, $C_2$–$C_3$-alkenyl, or halo-$C_2$–$C_3$-alkenyl.

In some preferred embodiments, $E^4$ is a bond, $C_1$–$C_3$-alkyl, or $C_2$–$C_3$-alkenyl.

$E^5$ is alkyl, alkenyl, alkynyl, alkoxy, alkoxyalkyl, carbocyclyl, or heterocyclyl. Any member of this group optionally is substituted.

In some preferred embodiments, $E^5$ is $C_1$–$C_{20}$-alkyl, $C_2$–$C_{20}$-alkenyl, $C_2$–$C_{20}$-alkynyl, $C_1$–$C_{20}$-alkoxy, $C_1$–$C_{20}$-alkoxy-$C_1$–$C_{20}$-alkyl, carbocyclyl, or heterocyclyl. The $C_1$–$C_{20}$-alkyl, $C_2$–$C_{20}$-alkenyl, $C_2$–$C_{20}$-alkynyl, $C_1$–$C_{20}$-alkoxy, and $C_1$–$C_{20}$-alkoxy-$C_1$–$C_{20}$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —N(R$^5$)(R$^6$), —C(O)(R$^7$), —S—R$^5$, —S(O)$_2$—R$^5$, carbocyclyl, balocarbocyclyl, carbocyclyl-$C_1$–$C_8$-alkyl, and halogen-substituted carbocyclyl-$C_1$–$C_8$-alkyl.

In some preferred embodiments, $E^5$ is $C_1$–$C_8$-alkyl, $C_2$–$C_8$-alkenyl, $C_2$–$C_8$-alkynyl, $C_1$–$C_8$-alkoxy, $C_1$–$C_8$-alkoxy-$C_1$–$C_8$-alkyl, carbocyclyl, or heterocyclyl. The $C_1$–$C_8$-alkyl, $C_2$–$C_8$-alkenyl, $C_2$–$C_8$-alkynyl, $C_1$–$C_8$-alkoxy, and $C_1$–$C_8$-alkoxy-$C_1$–$C_8$-alkyl optionally are substituted with one or more substituents independently selected from the group consisting of halogen, —OH, —NO$_2$, and —CN. The carbocyclyl and heterocyclyl optionally are substituted with one or more substituents independently selected from the group consisting of halogen, —OH, —NO$_2$, —CN, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl.

$R^1$ and $R^2$ are independently selected from the group consisting of —H and alkyl. The alkyl optionally is substituted. Neither $R^1$ nor $R^2$ forms a ring structure with $E^2$, $E^4$, or $E^5$.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

In some preferred embodiments, $R^1$ and $R^2$ are independently selected from the group consisting of —H and $C_1$–$C_6$-alkyl.

$R^5$ and $R^6$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

$R^7$ is —H, $C_1$–$C_6$-alkyl, —O—R$^8$, —N(R$^8$)(R$^9$), carbocyclyl-$C_1$–$C_8$-alkyl, or heterocyclyl-$C_1$–$C_8$-alkyl. The $C_1$–$C_8$-alkyl, carbocyclyl-$C_1$–$C_8$-alkyl, or heterocyclyl-$C_1$–$C_8$-alkyl may be substituted with one or more halogen, but more typically is preferably not substituted with halogen.

In some preferred embodiments, $R^7$ is —H, $C_1$–$C_6$-alkyl, —O—R$^8$, —N(R$^8$)(R$^9$), carbocyclyl-$C_1$–$C_6$-alkyl, or heterocyclyl-$C_1$–$C_6$-alkyl. The $C_1$–$C_6$-alkyl, carbocyclyl-$C_1$–$C_6$-alkyl, or heterocyclyl-$C_1$–$C_6$-alkyl may be substituted with one or more halogen, but more typically is preferably not substituted with halogen.

$R^8$ and $R^9$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group may be substituted with one or more halogen, but more typically is preferably not substituted with halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group may be substituted with one or more halogen, but more typically is preferably not substituted with halogen.

Preferred Embodiment No. 17

In some embodiments of this invention, the compound has a structure corresponding to Formula XVII:

XVIII

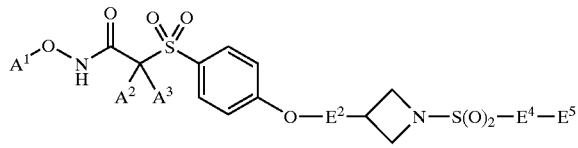

$A^1$, $A^2$, and $A^3$ are as defined above for Formula I.

$E^2$ is a bond, alkyl, cycloalkyl, alkylcycloalkyl, cycloalkylalkyl, or alkylcycloalkylalkyl. Any member of this group optionally is substituted.

In some preferred embodiments, $E^2$ is a bond, $C_1$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group may be substituted with one or more halogen, but more typically is preferably not substituted with halogen.

In some preferred embodiments, $E^2$ is a bond, $C_1$–$C_6$-alkyl, or halo-$C_1$–$C_6$-alkyl.

In some preferred embodiments, $E^2$ is a bond or $C_1$–$C_6$-alkyl.

In some preferred embodiments, $E^2$ is a bond.

$E^4$ is a bond, alkyl, or alkenyl. The alkyl and alkenyl optionally are substituted.

In some preferred embodiments, $E^4$ is a bond, $C_1$–$C_{20}$-alkyl, halo-$C_1$–$C_{20}$-alkyl, $C_2$–$C_{20}$-alkenyl, or halo-$C_2$–$C_{20}$-alkenyl.

In some preferred embodiments, $E^4$ is a bond, $C_1$–$C_3$-alkyl, halo-$C_1$–$C_3$-alkyl, $C_2$–$C_3$-alkenyl, or halo-$C_2$–$C_3$-alkenyl.

In some preferred embodiments, $E^4$ is a bond, $C_1$–$C_3$-alkyl, or $C_2$–$C_3$-alkenyl.

In some preferred embodiments, $E^4$ is a bond.

$E^5$ is optionally-substituted heterocyclyl or substituted carbocyclyl.

The $E^5$ heterocyclyl optionally is substituted with one or more substituents independently selected from the group consisting of halogen, —OH, —$NO_2$, —CN, alkyl, haloalkyl, alkoxy, haloalkoxy, alkoxyalkyl, halogen-substituted alkoxyalkyl, —$N(R^3)(R^4)$, —$C(O)(R^5)$, —S—$R^3$, —$S(O)_2$—$R^3$, carbocyclyl, halocarbocyclyl, carbocyclylalkyl, and halogen-substituted carbocyclylalkyl.

In some preferred embodiments, $E^5$ is heterocyclyl optionally substituted with one or more substituents independently selected from the group consisting of halogen, —OH, —$NO_2$, —CN, $C_1$–$C_8$-alkyl, halo-$C_1$–$C_8$-alkyl, $C_1$–$C_8$-alkoxy, halo-$C_1$–$C_8$-alkoxy, $C_1$–$C_6$-alkoxy-$C_1$–$C_6$-alkyl, halogen-substituted $C_1$–$C_8$-alkoxy-$C_1$–$C_6$-alkyl, —$N(R^3)(R^4)$, —$C(O)(R^5)$, —S—$R^3$, —$S(O)_2$—$R^3$, carbocyclyl, halocarbocyclyl, carbocyclyl-$C_1$–$C_6$-alkyl, and halogen-substituted carbocyclyl-$C_1$–$C_8$-alkyl.

In some preferred embodiments, $E^5$ is heterocyclyl optionally substituted with one or more substituents independently selected from the group consisting of halogen, —OH, —$NO_2$, —CN, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —$N(R^3)(R^4)$, —$C(O)(R^5)$, —S—$R^3$, —$S(O)_2$—$R^3$, carbocyclyl, halocarbocyclyl, carbocyclyl-$C_1$–$C_6$-alkyl, and halogen-substituted carbocyclyl-$C_1$–$C_6$-alkyl.

The $E^5$ carbocyclyl is substituted with:

2 or more substituents independently selected from the group consisting of halogen, —OH, —$NO_2$, —CN, alkyl, haloalkyl, alkoxy, haloalkoxy, alkoxyalkyl, halogen-substituted alkoxyalkyl, —$N(R^3)(R^4)$, —$C(O)(R^5)$, —S—$R^3$, —$S(O)_2$—$R^3$, carbocyclyl, halocarbocyclyl, carbocyclylalkyl, and halogen-substituted carbocyclylalkyl; or a substituent selected from the group consisting of halogen, —OH, —$NO_2$, —CN, —C(O)—O—$R^3$, —S—$R^3$, —$S(O)_2$—$R^3$, carbocyclyl, halocarbocyclyl, carbocyclylalkyl, and halogen-substituted carbocyclylalkyl.

In some preferred embodiments, $E^5$ is carbocyclyl substituted with:

2 or more substituents independently selected from the group consisting of halogen, —OH, —$NO_2$, —CN, $C_1$–$C_8$-alkyl, halo-$C_1$–$C_8$-alkyl, $C_1$–$C_8$-alkoxy, halo-$C_1$–$C_8$-alkoxy, $C_1$–$C_8$-alkoxy-$C_1$–$C_8$-alkyl, halogen-substituted $C_1$–$C_8$-alkoxy-$C_1$–$C_8$-alkyl, —$N(R^3)(R^4)$, —$C(O)(R^5)$, —S—$R^3$, —$S(O)_2$—$R^3$, carbocyclyl, halocarbocyclyl, carbocyclyl-$C_1$–$C_8$-alkyl, and halogen-substituted carbocyclyl-$C_1$–$C_8$-alkyl, or a substituent selected from the group consisting of halogen, —OH, —$NO_2$, —CN, —C(O)—O—$R^3$, —S—$R^3$, —$S(O)_2$—$R^3$, carbocyclyl, halocarbocyclyl, carbocyclyl-$C_1$–$C_8$-alkyl, and halogen-substituted carbocyclyl-$C_1$–$C_8$alkyl.

In some preferred embodiments, $E^5$ is carbocyclyl substituted with:

2 or more substituents independently selected from the group consisting of halogen, —OH, —$NO_2$, —CN, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —$N(R^3)(R^4)$, —$C(O)(R^5)$, —S—$R^3$, —$S(O)_2$—$R^3$, carbocyclyl, halocarbocyclyl, carbocyclyl-$C_1$–$C_6$-alkyl, and halogen-substituted carbocyclyl-$C_1$–$C_6$-alkyl, or a substituent selected from the group consisting of halogen, —OH, —$NO_2$, —CN, —C(O)—O—$R^3$, —S—$R^3$, —$S(O)_2$—$R^3$, carbocyclyl, halocarbocyclyl, carbocyclyl-$C_1$–$C_6$-alkyl, and halogen-substituted carbocyclyl-$C_1$–$C_6$-alkyl.

$R^3$ and $R^4$ are independently selected from the group consisting of —H, alkyl, carbocyclyl, carbocyclylalkyl, heterocyclyl, and heterocyclylalkyl. Except where the member is —H, any member of this group may be substituted with one or more halogen, but more typically is preferably not substituted with halogen.

In some preferred embodiments, $R^3$ and $R^4$ are independently selected from the group consisting of —H, $C_1$–$C_8$- alkyl, carbocyclyl, carbocyclyl-$C_1$-$C_8$-alkyl, heterocyclyl, and heterocyclyl-$C_1$-$C_8$-alkyl. Except where the member is —H, any member of this group may be substituted with one or more halogen, but more typically is preferably not substituted with halogen.

In some preferred embodiments, $R^3$ and $R^4$ are independently selected from the group consisting of —H, $C_1$-$C_6$-alkyl, carbocyclyl, carbocyclyl-$C_1$-$C_6$-alkyl, heterocyclyl, and heterocyclyl-$C_1$-$C_6$-alkyl. Except where the member is —H, any member of this group may be substituted with one or more halogen, but more typically is preferably not substituted with halogen.

$R^5$ is —H, alkyl, —O—$R^6$, —N($R^6$)($R^7$), carbocyclylalkyl, or heterocyclylalkyl. The alkyl, carbocyclylalkyl, or heterocyclylalkyl may be substituted with one or more halogen, but more typically is preferably not substituted with halogen.

In some preferred embodiments, $R^5$ is —H, $C_1$-$C_8$-alkyl, —O—$R^6$, —N($R^6$)($R^7$), carbocyclyl-$C_1$-$C_8$-alkyl, or heterocyclyl-$C_1$-$C_8$-alkyl. The $C_1$-$C_8$-alkyl, carbocyclyl-$C_1$-$C_8$-alkyl, or heterocyclyl-$C_1$-$C_8$-alkyl may be substituted with one or more halogen, but more typically is preferably not substituted with halogen.

In some preferred embodiments, $R^5$ is —H, $C_1$-$C_6$-alkyl, —O—$R^6$, —N($R^6$)($R^7$), carbocyclyl-$C_1$-$C_6$-alkyl, or heterocyclyl-$C_1$-$C_6$-alkyl. The $C_1$-$C_6$-alkyl, carbocyclyl-$C_1$-$C_6$-alkyl, or heterocyclyl-$C_1$-$C_6$-alkyl may be substituted with one or more halogen, but more typically is preferably not substituted with halogen.

$R^6$ and $R^7$ are independently selected from the group consisting of —H, alkyl, carbocyclyl, carbocyclylalkyl, heterocyclyl, and heterocyclylalkyl. Except where the member is —H, any member of this group may be substituted with one or more halogen, but more typically is preferably not substituted with halogen.

In some preferred embodiments, $R^6$ and $R^7$ are independently selected from the group consisting of —H, $C_1$-$C_8$-alkyl, carbocyclyl, carbocyclyl-$C_1$-$C_8$-alkyl, heterocyclyl, and heterocyclyl-$C_1$-$C_8$-alkyl. Except where the member is —H, any member of this group may be substituted with one or more halogen, but more typically is preferably not substituted with halogen.

In some preferred embodiments, $R^6$ and $R^7$ are independently selected from the group consisting of —H, $C_1$-$C_6$-alkyl, carbocyclyl, carbocyclyl-$C_1$-$C_6$-alkyl, heterocyclyl, and heterocyclyl-$C_1$-$C_6$-alkyl. Except where the member is —H, any member of this group may be substituted with one or more halogen, but more typically is preferably not substituted with halogen.

In some preferred embodiments, $E^5$ is optionally-substituted heterocyclyl.

In some preferred embodiments, $E^5$ is substituted carbocyclyl (preferably substituted phenyl). Such compounds include, for example:

XVIII-1

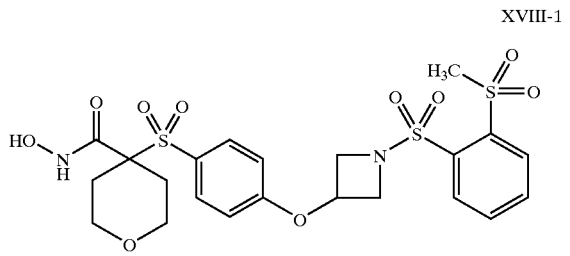

-continued

XVIII-2

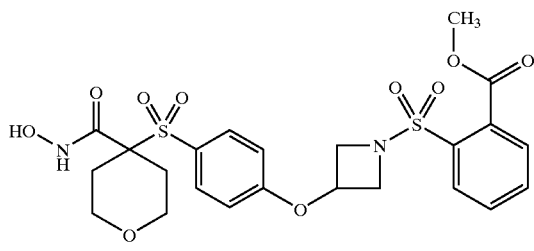

XVIII-3

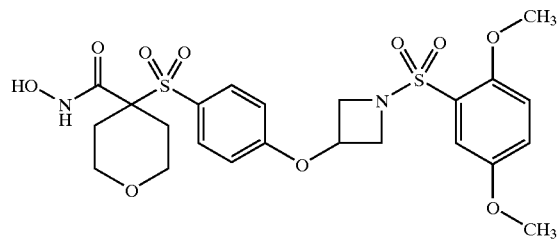

Preferred Embodiment No. 18

In some embodiments of this invention, the compound has a structure corresponding to Formula XVIII:

XIX

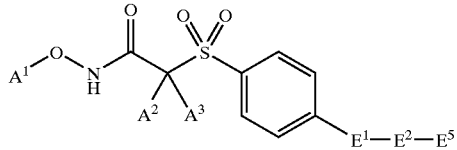

$A^1$, $A^2$ and $A^3$ are as defined above for Formula I.

$E^1$ is —O—, —S(O)$_2$—, —S(O)—, —S—, —N($R^1$)—, —C(O)—N($R^1$)—, —N($R^1$)—C(O)—, or —C($R^1$)($R^2$)—.

$E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_1$-$C_{20}$-alkyl, cycloalkyl, $C_1$-$C_{10}$-alkyl-cycloalkyl, cycloalkyl-$C_1$-$C_{10}$-alkyl, or $C_1$-$C_{10}$-alkyl-cycloalkyl-$C_1$-$C_{10}$-alkyl. Any member of this group optionally is substituted with one or more halogen.

In some preferred embodiments, $E^2$ is $C_1$-$C_6$-alkyl. The alkyl optionally is substituted with one or more halogen.

$E^5$ is substituted heterocyclyl.

In some preferred embodiments, $E^5$ is heterocyclyl that is:
substituted with one or more substituents independently selected from the group consisting of halogen, —OH, —NO$_2$, —CN, keto, $C_1$-$C_8$-alkyl, halo-$C_1$-$C_8$-alkyl, $C_1$-$C_8$-alkoxy, halo-$C_1$-$C_8$-alkoxy, $C_1$-$C_8$-alkoxy-$C_1$-$C_8$-alkyl, halogen-substituted $C_1$-$C_8$-alkoxy-$C_1$-$C_8$-alkyl, —N($R^5$)($R^6$), —C(O)($R^7$), —S—$R^5$, —S(O)$_2$—$R^5$, carbocyclyl, halocarbocyclyl, and carbocyclyl-$C_1$-$C_6$-alkyl, and/or
substituted on the same atom with two substituents independently selected from the group consisting of alkyl and haloalkyl, the two substituents together forming $C_5$-$C_6$-cycloalkyl or halo-$C_5$-$C_6$-cycloalkyl.

In some preferred embodiments, $E^5$ is heterocyclyl that is:
substituted with one or more substituents independently selected from the group consisting of halogen, —OH, —NO$_2$, —CN, keto, C$_1$–C$_6$-alkyl, halo-C$_1$–C$_6$-alkyl, C$_1$–C$_6$-alkoxy, halo-C$_1$–C$_6$-alkoxy, C$_1$–C$_6$-alkoxy-C$_1$C$_6$-alkyl, halogen-substituted C$_1$–C$_6$-alkoxy-C$_1$–C$_6$-alkyl, —N(R$^5$)(R$^6$), —C(O)(R$^7$), —S—R$^5$, —S(O)$_2$—R$^5$, carbocyclyl, halocarbocyclyl, carbocyclyl-C$_1$–C$_6$, and halogen-substituted carbocyclyl-C$_1$–C$_6$-alkyl, and/or substituted on the same atom with two substituents independently selected from the group consisting of alkyl and haloalkyl, the two substituents together forming C$_5$–C$_6$-cycloalkyl or halo-C$_5$–C$_6$-cycloalkyl.

R$^1$ and R$^2$ are independently selected from the group consisting of —H and alkyl. The alkyl optionally is substituted.

In some preferred embodiments, R$^1$ and R$^2$ are independently selected from the group consisting of —H, C$_1$–C$_8$-alkyl, and halo-C$_1$–C$_8$-alkyl.

R$^3$ and R$^4$ are independently selected from the group consisting of —H, C$_1$–C$_8$-alkyl, C$_1$–C$_8$-alkoxycarbonyl, C$_1$–C$_8$-alkylcarbonyl, carbocyclyl-C$_1$–C$_8$-alkyl, and carbocyclyl-C$_1$–C$_8$-alkoxycarbonyl.

R$^5$ and R$^6$ are independently selected from the group consisting of —H, C$_1$–C$_8$-allyl, carbocyclyl, carbocyclyl-C$_1$–C$_8$-alkyl, heterocyclyl, and heterocyclyl-C$_1$–C$_8$-alkyl. Except where the member is —H, any member of this group optionally is substituted with one or more halogen.

In some preferred embodiments, R$^5$ and R$^6$ are independently selected from the group consisting of —H, C$_1$–C$_6$-alkyl, carbocyclyl, carbocyclyl-C$_1$–C$_6$-alkyl, heterocyclyl, and heterocyclyl-C$_1$–C$_6$-alkyl. Except where the member is —H, any member of this group optionally is substituted with one or more halogen.

R$^7$ is —H, C$_1$C$_8$-alkyl, —O—R$^8$, —N(R$^8$)(R$^9$), carbocyclyl-C$_1$–C$_8$-alkyl, or heterocyclyl-C$_1$–C$_8$-alkyl. The alkyl, carbocyclylalkyl, or heterocyclylalkyl may be substituted with one or more halogen.

In some preferred embodiments, R$^7$ is —H, C$_1$–C$_6$-alkyl, —O—R$^8$, —N(R$^8$)(R$^9$), carbocyclyl-C$_1$–C$_6$-alkyl, or heterocyclyl-C$_1$–C$_6$-alkyl. The alkyl, carbocyclylalkyl, and heterocyclylalkyl optionally are substituted with one or more halogen.

R$^8$ and R$^9$ are independently selected from the group consisting of —H, C$_1$–C$_8$-alkyl, carbocyclyl, carbocyclyl-C$_1$–C$_8$-alkyl, heterocyclyl, and heterocyclyl-C$_1$–C$_8$-alkyl. Except where the member is —H, any member of this group optionally is substituted with one or more halogen.

In some preferred embodiments, R$^8$ and R$^9$ are independently selected from the group consisting of —H, C$_1$–C$_6$-alkyl, carbocyclyl, carbocyclyl-C$_1$–C$_6$-alkyl, heterocyclyl, and heterocyclyl-C$_1$–C$_6$-alkyl. Except where the member is —H, any member of this group optionally is substituted with one or more halogen.

Compounds of this embodiment include, for example:

XIX-1

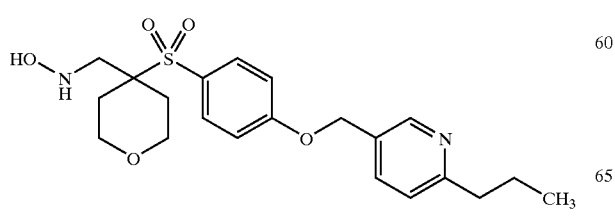

XIX-2

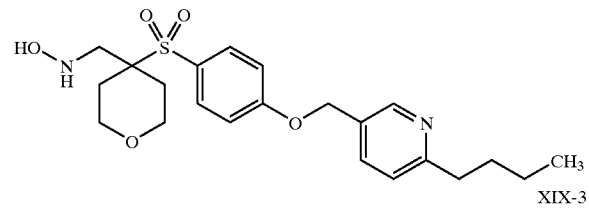

XIX-3

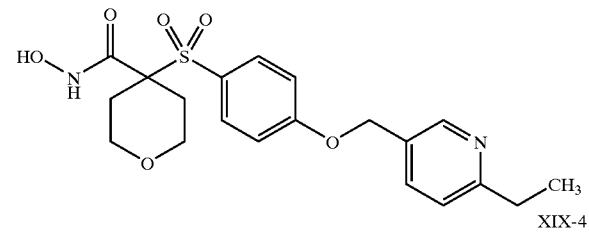

XIX-4

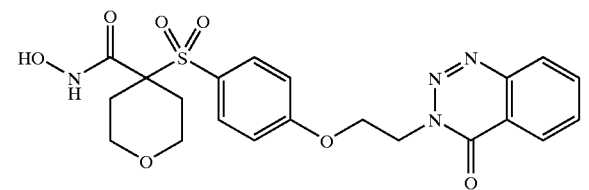

Preferred Embodiment No. 19

In some embodiments of this invention, the compound has a structure corresponding to Formula XIX:

XX

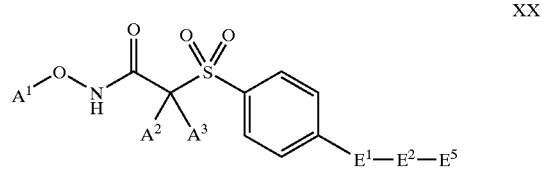

A$^1$, A$^2$, and A$^3$ are as defined above for Formula I.

E$^1$ is —O—, —S(O)$_2$—, —S(O)—, —N(R$^1$)—, —C(O)—N(R$^1$)—, —N(R$^1$)—C(O)—, or —C(R$^1$)(R$^2$)—.

E$^2$ comprises at least two carbon atoms. E$^2$ is alkyl, cycloalkyl, alkylcycloalkyl, cycloalkylalkyl, or alkylcycloalkylalkyl. Any member of this group optionally is substituted.

In some preferred embodiments, E$^2$ is C$_2$–C$_{20}$-alkyl, cycloalkyl, C$_1$–C$_{10}$-cycloalkyl, cycloalkyl-C$_1$–C$_{10}$-alkyl, or C$_1$–C$_{10}$-alkyl-cycloalkyl-C$_1$–C$_{10}$-alkyl. Any member of this group optionally is substituted with one or more halogen.

In some preferred embodiments, E$^2$ is C$_2$–C$_6$-alkyl. The alkyl may optionally be substituted with one or more halogen.

E$^5$ is optionally-substituted heterocyclyl.

In some preferred embodiments, E$^5$ is heterocyclyl that is:

optionally substituted with one or more substituents independently selected from the group consisting of halogen, —OH, —NO$_2$, —CN, keto, C$_1$–C$_8$-alkyl, halo-C$_1$–C$_8$-alkyl, C$_1$–C$_8$-alkoxy, halo-C$_1$–C$_8$-alkoxy, C$_1$–C$_8$-alkoxy-C$_1$–C$_8$-alkyl, halogen-substituted C$_1$–C$_8$-alkoxy-C$_1$–C$_8$-alkyl, —N(R$^5$)(R$^6$), —C(O)(R$^7$), —S—R$^5$, —S(O)$_2$—R$^5$, carbocyclyl, halocarbocyclyl, and carbocyclyl-C$_1$–C$_6$-alkyl, and/or optionally substituted on the same atom with two substituents independently selected from the group consisting of alkyl and haloalkyl, the two substituents together forming $C_5$–$C_6$-cycloalkyl or halo-$C_5$–$C_6$-cycloalkyl.

In some preferred embodiments, $E^5$ is heterocyclyl that is:

optionally substituted with one or more substituents independently selected from the group consisting of halogen, —OH, —NO$_2$, —CN, keto, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkoxy-$C_1$–$C_6$-alkyl, halogen-substituted $C_1$–$C_6$-alkoxy-$C_1$–$C_6$-alkyl, —N(R$^5$)(R$^6$), —C(O)(R$^7$), —S—R$^5$, —S(O)$_2$—R$^5$, carbocyclyl, halocarbocyclyl, carbocyclyl-$C_1$–$C_6$-alkyl, and halogen-substituted carbocyclyl-$C_1$–$C_6$-alkyl, and optionally substituted on the same atom with two substituents independently selected from the group consisting of alkyl and haloalkyl, the two substituents together forming $C_5$–$C_6$-cycloalkyl or halo-$C_5$–$C_6$-cycloalkyl.

$R^1$ and $R^2$ are independently selected from the group consisting of —H and alkyl. The alkyl optionally is substituted.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

$R^3$ and $R^4$ are independently selected from the group consisting of —H, $C_1$–$C_8$-alkyl, $C_1$–$C_8$-alkoxycarbonyl, $C_1$–$C_8$-alkylcarbonyl, carbocyclyl-$C_1C_8$-alkyl, and carbocyclyl-$C_1$–$C_8$-alkoxycarbonyl.

$R^5$ and $R^6$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group optionally is substituted with one or more halogen.

In some preferred embodiments, $R^5$ and $R^6$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group optionally is substituted with one or more halogen.

$R^7$ is —H, $C_1$–$C_8$-alkyl, —O—R$^8$, —N(R$^8$)(R$^9$), carbocyclyl-$C_1$–$C_8$-alkyl, or heterocyclyl-$C_1$–$C_8$-alkyl. The alkyl, carbocyclylalkyl, and heterocyclylalkyl optionally are substituted with one or more halogen.

In some preferred embodiments, $R^7$ is —H, $C_1$–$C_6$-alkyl, —O—R$^8$, —N(R$^8$)(R$^9$), carbocyclyl-$C_1$–$C_6$-alkyl, or heterocyclyl-$C_1$–$C_6$-alkyl. The alkyl, carbocyclylalkyl, and heterocyclylalkyl optionally are substituted with one or more halogen.

$R^8$ and $R^9$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group optionally is substituted with one or more halogen.

In some preferred embodiments, $R^8$ and $R^9$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group optionally is substituted with one or more halogen.

Some particularly preferred compounds include:

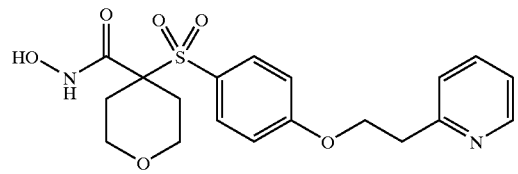

XX-1

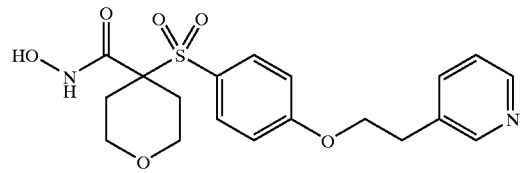

XX-2

Preferred Embodiment No. 20

In some embodiments of this invention, the compound has a structure corresponding to Formula XX:

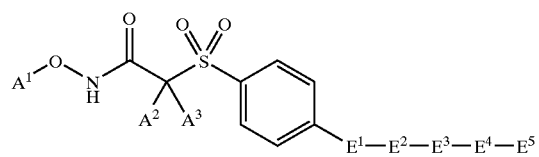

XXI $A^1$, $A^2$, and $A^3$ are as defined above for Formula I.

$E^1$ is —O—, —S(O)$_2$—, —S(O)—, —S—, —N(R$^1$)—, —C(O)—N(R$^1$)—, —N(R$^1$)—C(O)—, or —(R$^1$)(R$^2$)—.

$E^2$ is alkyl, cycloalkyl, alkylcycloalkyl, cycloalkylalkyl, or alkylcycloalkylalkyl. Any member of this group optionally is substituted.

In some preferred embodiments, $E^2$ is $C_2$–$C_{20}$-alkyl, cycloalkyl, $C_1$–$C_{10}$-alkylcycloalkyl, cycloalkyl-$C_1$–$C_{10}$-alkyl, or $C_1$–$C_{10}$-alkylcycloalkyl-$C_1$–$C_{10}$-alkyl. Any member of this group optionally is substituted with one or more substituents independently selected from the group consisting of halogen, $C_1$–$C_6$-alkyl, and halo-$C_1$–$C_6$-alkyl.

In some preferred embodiments, $E^2$ is $C_2$–$C_6$-alkyl. The alkyl may optionally be substituted with one or more halogen.

$E^3$ is —C(O)—, —O—(CO)—, —C(O)—O—, —C(NR$^3$)—, —N(R$^4$)—, —N(R$^4$)—C(NR$^3$)—, —C(NR$^3$)—N(R$^4$)—, —C(O)—N(R$^4$)—, —N(R$^4$)—C(O), —N(R$^4$)—C(O)—N(R$^5$)—, —S—, —S(O)—, —N(R$^4$)—S(O)$_2$—, —S(O)$_2$—N(R$^4$)—, —C(O)—N(R$^4$)—N(R$^5$)—C(O)—, —C(R$^4$)(R$^6$)—C(O)—, or —C(R$^7$)(R$^8$)—.

$E^4$ is a bond, alkyl, or alkenyl. The alkyl and alkenyl optionally are substituted.

In some preferred embodiments, $E^4$ is a bond, $C_1$–$C_{20}$-alkyl, or $C_2$–$C_{20}$-alkenyl. The alkyl and alkenyl optionally are substituted with one or more substituents independently selected from the group consisting of halogen, and carbocyclyl. The carbocyclyl, in turn, optionally is substituted with one or more substituents independently selected from the group consisting of halogen, —OH, —NO$_2$, —CN, $C_1$–$C_8$-alkyl, $C_1$–$C_8$-alkoxy, $C_1$–$C_8$-alkoxy-$C_1$–$C_8$-alkyl, carbocyclyl, carbocyclyl-$C_1$–$C_8$-alkyl, halo-$C_1$–$C_8$-alkyl, halo-$C_1$–$C_8$-alkoxy, halogen-substituted $C_1$–$C_8$-alkoxy-$C_1$–$C_8$-alkyl, halocarbocyclyl, and halogen-substituted carbocyclyl-$C_1$–$C_8$-alkyl.

In some preferred embodiments, $E^4$ is a bond, $C_1$–$C_3$-alkyl, or $C_2$–$C_3$-alkenyl. The alkyl and alkenyl optionally are substituted with one or more substituents independently selected from the group consisting of halogen and carbocyclyl. The carbocyclyl, in turn, optionally is substituted with one or more substituents independently selected from the group consisting of halogen, —OH, —$NO_2$, —CN, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halocarbocyclyl, and halogen-substituted carbocyclyl-$C_1$–$C_6$-alkyl.

$E^5$ is carbocyclyl or heterocyclyl. The carbocyclyl and heterocyclyl are:

substituted with a substituent selected from the group consisting of optionally-substituted carbocyclyl, optionally-substituted carbocyclylalkyl, optionally-substituted heterocyclyl, and optionally-substituted heterocyclylalkyl, and optionally substituted with one or more substituents independently selected from the group consisting of halogen, —OH, —$NO_2$, —CN, alkyl, alkoxy, alkoxyalkyl, —N($R^{11}$)($R^{12}$), —C(O)($R^{13}$), —S—$R^{11}$, —S(O)$_2$—$R^{11}$, carbocyclyl, carbocyclylalkyl, haloalkyl, haloalkoxy, halogen-substituted alkoxyalkyl, halocarbocyclyl, halogen-substituted carbocyclylalkyl, hydroxycarbocyclyl, and heteroaryl.

In some preferred embodiments, $E^5$ is carbocyclyl or heterocyclyl. The carbocyclyl and heterocyclyl are:

substituted with a substituent selected from the group consisting of optionally-substituted carbocyclyl, optionally-substituted carbocyclyl-$C_1$–$C_8$-alkyl, optionally-substituted heterocyclyl, and optionally-substituted heterocyclyl-$C_1$–$C_8$-alkyl, and optionally substituted with one or more substituents independently selected from the group consisting of halogen, —OH, —$NO_2$, —CN, $C_1$–$C_8$-alkyl, $C_1$–$C_8$-alkoxy, $C_1$–$C_8$-alkoxy-$C_1$–$C_8$-alkyl, —N($R^{11}$)($R^{12}$), —C(O)($R^{13}$), —S—$R^{11}$, —S(O)$_2$—$R^{11}$, carbocyclyl, carbocyclyl-$C_1$–$C_8$-alkyl, halo-$C_1$–$C_8$-alkyl, halo-$C_1$–$C_8$-alkoxy, halogen-substituted $C_1$–$C_8$-alkoxy-$C_1$–$C_8$-alkyl, halocarbocyclyl, halogen-substituted carbocyclyl-$C_1$–$C_8$-alkyl, hydroxycarbocyclyl, and heteroaryl.

In some preferred embodiments, $E^5$ is carbocyclyl or heterocyclyl, wherein the carbocyclyl and heterocyclyl are:

substituted with a substituent selected from the group consisting of optionally-substituted carbocyclyl, optionally-substituted carbocyclyl-$C_1$–$C_6$-alkyl, optionally-substituted heterocyclyl, and optionally-substituted heterocyclyl-$C_1$–$C_6$-alkyl, and optionally substituted with one or more substituents independently selected from the group consisting of halogen, —OH, —$NO_2$, —CN, $C_1$–$C_6$-alkyl, $C_1$–$C_6$-alkoxy, $C_1$–$C_6$-alkoxy-$C_1$–$C_6$-alkyl, —N($R^{11}$)($R^{12}$), —C(O)($R^{13}$), —S—$R^{11}$, —S(O)$_2$—$R^{11}$, carbocyclyl, carbocyclyl-$C_1$–$C_6$-alkyl, halo-$C_1$–$C_6$-alkoxy, halogen-substituted $C_1$–$C_6$-alkoxy-$C_1$–$C_6$-alkyl, halocarbocyclyl, halogen-substituted carbocyclyl-$C_1$–$C_6$-alkyl, hydroxycarbocyclyl, and heteroaryl.

$R^1$ and $R^2$ are independently selected from the group consisting of —H and alkyl. The alkyl optionally is substituted.

In some preferred embodiments, $R^1$ and $R^2$ are independently selected from the group consisting of —H, $C_1$–$C_8$-alkyl, and halo-$C_1$–$C_8$-alkyl.

In some preferred embodiments, $R^1$ and $R^2$ are independently selected from the group consisting of —H, $C_1$–$C_6$-alkyl, and halo-$C_1$–$C_6$-alkyl.

$R^3$ is —H or —OH.

$R^4$ and $R^5$ are independently selected from the group consisting of —H, alkyl, carbocyclyl, carbocyclylalkyl, heterocyclyl, and heterocyclylalkyl. Except where the member is —H, any member of this group optionally is substituted.

In some preferred embodiments, $R^4$ and $R^5$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group optionally is substituted with one or more halogen.

In some preferred embodiments, $R^4$ and $R^5$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group optionally is substituted with one or more halogen.

$R^6$ is —CN or —OH.

$R^7$ is —H, halogen, —OH, alkyl, alkoxy, or alkoxyalkyl. The alkyl, alkoxy, and alkoxyalkyl optionally are substituted.

In some preferred embodiments, $R^7$ is —H, halogen, —OH, $C_1$–$C_8$-alkyl, $C_1$–$C_8$-alkoxy, $C_1$–$C_8$-alkoxy-$C_1$–$C_8$-alkyl, halo-$C_1C_8$-alkyl, halo-$C_1$–$C_8$-alkoxy, or halogen-substituted $C_1$–$C_8$-alkoxy-$C_1$–$C_8$-alkyl.

In some preferred embodiments, $R^7$ is —H, halogen, —OH, $C_1$–$C_6$-alkyl, $C_1$–$C_6$-alkoxy, $C_1$–$C_6$-alkoxy-$C_1$–$C_6$-alkyl, halo-$C_1$–$C_6$-alkyl, halo-$C_1$–$C_6$-alkoxy, or halogen-substituted $C_1$–$C_6$-alkoxy-$C_1$–$C_6$-alkyl.

$R^8$ is —OH or alkoxy. The alkoxy optionally is substituted.

In some preferred embodiments, $R^8$ is —OH, $C_1$–$C_8$-alkoxy, or halo-$C_1$–$C_8$-alkoxy.

In some preferred embodiments, $R^8$ is —OH, $C_1$–$C_6$-alkoxy, or halo-$C_1$–$C_6$-alkoxy.

$R^9$ and $R^{10}$ are independently selected from the group consisting of —H, $C_1$–$C_8$-alkyl, $C_1$–$C_8$-alkoxycarbonyl, $C_1$–$C_8$-alkylcarbonyl, carbocyclyl-$C_1$–$C_8$-alkyl, and carbocyclyl-$C_1$–$C_8$-alkoxycarbonyl.

$R^{11}$ and $R^{12}$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group optionally is substituted with one or more halogen.

In some preferred embodiments, $R^{11}$ and $R^{12}$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group optionally is substituted with one or more halogen.

In some preferred embodiments, $R^{11}$ and $R^{12}$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group optionally is substituted with one or more halogen.

$R^{13}$ is —H, $C_1$–$C_8$-alkyl, —O—$R^{14}$, —N($R^{14}$)($R^{15}$), carbocyclyl-$C_1$–$C_8$-alkyl, heterocyclyl-$C_1$–$C_8$-alkyl, halo-$C_1$–$C_8$-alkyl, halogen-substituted carbocyclyl-$C_1$–$C_8$-alkyl, or halogen-substituted heterocyclyl-$C_1$–$C_8$-alkyl.

In some preferred embodiments, $R^{13}$ is of —H, $C_1$–$C_6$-alkyl, —O—$R^{14}$, —N($R^{14}$)($R^{15}$), carbocyclyl-$C_1$–$C_6$-alkyl, heterocyclyl-$C_1$–$C_6$-alkyl, halo-$C_1$–$C_6$-alkyl, halogen-substituted carbocyclyl-$C_1$–$C_6$-alkyl, or halogen-substituted heterocyclyl-$C_1$–$C_6$-alkyl.

$R^{14}$ and $R^{15}$ are independently selected from the group consisting of —H, $C_1$–$C_8$-alkyl, carbocyclyl, carbocyclyl-$C_1$–$C_8$-alkyl, heterocyclyl, and heterocyclyl-$C_1$–$C_8$-alkyl. Except where the member is —H, any member of this group optionally is substituted with one or more halogen.

In some preferred embodiments, $R^{14}$ and $R^{15}$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl. Except where the member is —H, any member of this group optionally is substituted with one or more halogen.

Some preferred compounds include, for example:

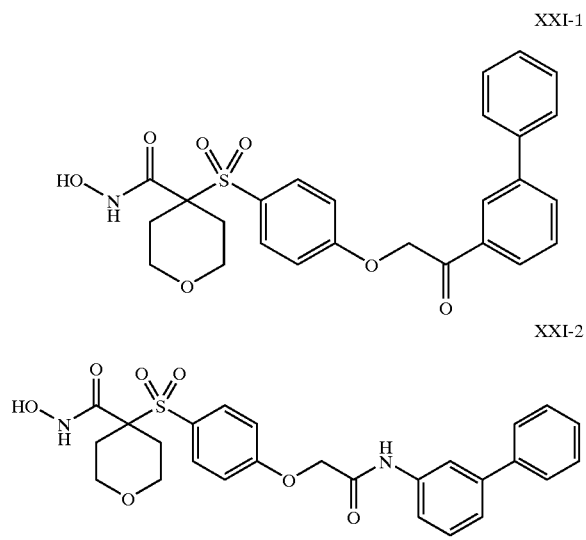

XXI-1

XXI-2

A-2. Preferred Selectivities

The hydroxamate compound or salt preferably has an inhibitory activity against MMP-1 or MMP-14 that is substantially less than its inhibitory activity against MMP-2, MMP-9, or MMP-13. In other words, the hydroxamate compound or salt preferably has an in inhibition constant ($K_i$) against at least one of MMP-2, MMP-9, and MMP-13 that is no greater than about 0.1 times its inhibition constant (s) against at least one of MMP-1 and MMP-14. The inhibition constant of a compound or salt thereof may be determined using an in vitro inhibition assay, such as the $K_i$ assay described below in Examples 55–89.

In some particularly preferred embodiments, the hydroxamate compound or salt preferably has a $K_i$ against MMP-2 that is no greater than about 0.1 (more preferably no greater than about 0.01, even more preferably no greater than about 0.001, still more preferably no greater than about 0.0001, and still even more preferably no greater than about 0.00001) times its $K_i$(s) against one or both of MMP-1 and MMP-14.

In some particularly preferred embodiments, the hydroxamate compound or salt preferably has a $K_i$ against MMP-9 that is no greater than about 0.1 (more preferably no greater than about 0.01, even more preferably no greater than about 0.001, still more preferably no greater than about 0.0001, and still even more preferably no greater than about 0.00001) times its $K_i$(s) against one or both of MMP-1 and MMP-14.

In some particularly preferred embodiments, the hydroxamate compound or salt preferably has a $K_i$ against MMP-13 that is no greater than about 0.1 (more preferably no greater than about 0.01, even more preferably no greater than about 0.001, still more preferably no greater than about 0.0001, and still even more preferably no greater than about 0.00001) times its $K_i$(s) against one or both of MMP-1 and MMP-14. It is believed that such a selectivity profile is often particularly preferred when preventing or treating, for example, a cardiovascular condition or arthritis.

In some particularly preferred embodiments, the hydroxamate compound or salt preferably has $K_i$'s against both MMP-2 and MMP-9 that are no greater than about 0.1 (more preferably no greater than about 0.01, even more preferably no greater than about 0.001, still more preferably no greater than about 0.0001, and still even more preferably no greater than about 0.00001) times its $K_i$(s) against one or both of MMP-1 and MMP-14. It is believed that such a selectivity profile is often particularly preferred when preventing or treating, for example, cancer, a cardiovascular condition, or an ophthalmologic condition.

In some particularly preferred embodiments, the hydroxamate compound or salt preferably has $K_i$'s against all of MMP-2, MMP-9, and MMP-13 that are no greater than about 0.1 (more preferably no greater than about 0.01, even more preferably no greater than about 0.001, still more preferably no greater than about 0.0001, and still even more preferably no greater than about 0.00001) times its $K_i$(s) against one or both of MMP-1 and MMP-14. It is believed that such a selectivity profile is often particularly preferred when preventing or treating, for example, cancer, a cardiovascular condition, arthritis, or an ophthalmologic condition.

In some particularly preferred embodiments, the hydroxamate compound or salt preferably has a $K_i$ against MMP-2 that is no greater than about 0.1 (more preferably no greater than about 0.01, even more preferably no greater than about 0.001, still more preferably no greater than about 0.0001, and still even more preferably no greater than about 0.00001) times its $K_i$'s against both MMP-1 and MMP-14.

In some particularly preferred embodiments, the hydroxamate compound or salt preferably has a $K_i$ against MMP-9 that is no greater than about 0.1 (more preferably no greater than about 0.01, even more preferably no greater than about 0.001, still more preferably no greater than about 0.0001, and still even more preferably no greater than about 0.00001) times its $K_i$'s against both MMP-1 and MMP-14.

In some particularly preferred embodiments, the hydroxamate compound or salt preferably has a $K_i$ against MMP-13 that is no greater than about 0.1 (more preferably no greater than about 0.01, even more preferably no greater than about 0.001, still more preferably no greater than about 0.0001, and still even more preferably no greater than about 0.00001) times its $K_i$'s against both MMP-1 and MMP-14. It is believed that such a selectivity profile is often particularly preferred when preventing or treating, for example, a cardiovascular condition or arthritis.

In some particularly preferred embodiments, the hydroxamate compound or salt preferably has $K_i$'s against both MMP-2 and MMP-9 that are no greater than about 0.1 (more preferably no greater than about 0.01, even more preferably no greater than about 0.001, still more preferably no greater than about 0.0001, and still even more preferably no greater than about 0.00001) times its $K_i$'s against both of MMP-1 and MMP-14. It is believed that such a selectivity profile is often particularly preferred when preventing or treating, for example, cancer, a cardiovascular condition, or an ophthalmologic condition.

In some particularly preferred embodiments, the hydroxamate compound or salt preferably has $K_i$'s against all of MMP-2, MMP-9, and MMP-3 that are no greater than about 0.1 (more preferably no greater than about 0.01, even more preferably no greater than about 0.001, still more preferably no greater than about 0.0001, and still even more preferably no greater than about 0.00001) times its $K_i$'s against both of MMP-1 and MMP-14. It is believed that such a selectivity profile is often particularly preferred when preventing or treating, for example, a cardiovascular condition, arthritis, or an ophthalmologic condition.

The activity and selectivity of a hydroxamate compound or salt may alternatively be determined using an in vitro $IC_{50}$ assay, such as the $IC_{50}$ assay described below in Examples 55–89. In that instance, the hydroxamate compound or salt preferably has an $IC_{50}$ value against at least one of MMP-2, MMP-9, and MMP-13 that is no greater than about 0.1 times its $IC_{50}$ value(s) against at least one of MMP-1 and MMP-14.

In some particularly preferred embodiments, the hydroxamate compound or salt preferably has an $IC_{50}$ value against MMP-2 that is no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14.

In some particularly preferred embodiments, the hydroxamate compound or salt preferably has an $IC_{50}$ value against MMP-9 that is no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14.

In some particularly preferred embodiments, the hydroxamate compound or salt preferably has an $IC_{50}$ value against MMP-13 that is no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14. It is believed that such a selectivity profile is often particularly preferred when preventing or treating, for example, a cardiovascular condition or arthritis.

In some particularly preferred embodiments, the hydroxamate compound or salt preferably has $IC_{50}$ values against both MMP-2 and MMP-9 that are no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14. It is believed that such a selectivity profile is often particularly preferred when preventing or treating, for example, cancer, a cardiovascular condition, or an ophthalmologic condition.

In some particularly preferred embodiments, the hydroxamate compound or salt preferably has $IC_{50}$ values against all of MMP-2, MMP-9, and MMP-13 that are no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14. It is believed that such a selectivity profile is often particularly preferred when preventing or treating, for example, cancer, a cardiovascular condition, arthritis, or an ophthalmologic condition.

In some particularly preferred embodiments, the hydroxamate compound or salt preferably has an $IC_{50}$ value against MMP-2 that is no greater than about 0.1 (more preferably no greater than about 0.01, even more preferably no greater than about 0.001, still more preferably no greater than about 0.0001, and still even more preferably no greater than about 0.00001) times its $IC_{50}$ values against both MMP-1 and MMP-14.

In some particularly preferred embodiments, the hydroxamate compound or salt preferably has an $IC_{50}$ value against MMP-9 that is no greater than about 0.1 (more preferably no greater than about 0.01, even more preferably no greater than about 0.001, still more preferably no greater than about 0.0001, and still even more preferably no greater than about 0.00001) times its $IC_{50}$ values against both MMP-1 and MMP-14.

In some particularly preferred embodiments, the hydroxamate compound or salt preferably has an $IC_{50}$ value against MMP-13 that is no greater than about 0.1 (more preferably no greater than about 0.01, even more preferably no greater than about 0.001, still more preferably no greater than about 0.0001, and still even more preferably no greater than about 0.00001) times its $IC_{50}$ values against both MMP-1 and MMP-14. It is believed that such a selectivity profile is often particularly preferred when preventing or treating, for example, a cardiovascular condition or arthritis.

In some particularly preferred embodiments, the hydroxamate compound or salt preferably has $IC_{50}$ values against both MMP-2 and MMP-9 that are no greater than about 0.1 (more preferably no greater than about 0.01, even more preferably no greater than about 0.001, still more preferably no greater than about 0.0001, and still even more preferably no greater than about 0.00001) times its $IC_{50}$ values against both of MMP-1 and MMP-14. It is believed that such a selectivity profile is often particularly preferred when preventing or treating, for example, cancer, a cardiovascular condition, or an ophthalmologic condition.

In some particularly preferred embodiments, the hydroxamate compound or salt preferably has $IC_{50}$ values against all of MMP-2, MMP-9, and MMP-3 that are no greater than about 0.1 (more preferably no greater than about 0.01, even more preferably no greater than about 0.001, still more preferably no greater than about 0.0001, and still even more preferably no greater than about 0.00001) times its $IC_{50}$ values against both of MMP-1 and MMP-14. It is believed that such a selectivity profile is often particularly preferred when preventing or treating, for example, cancer, a cardiovascular condition, arthritis, or an ophthalmologic condition.

B. Salts of the Compounds of this Invention

The compounds of this invention can be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. Pharmaceutically acceptable salts include salts commonly used to form alkali metal salts and to form addition salts of free acids or free bases. In general, these salts typically may be prepared by conventional means with a compound of this invention by reacting, for example, the appropriate acid or base with the compound.

Pharmaceutically-acceptable acid addition salts of the compounds of this invention may be prepared from an inorganic or organic acid. Examples of suitable inorganic acids include hydrochloric, hydrobromic acid, hydroionic, nitric, carbonic, sulfuric, and phosphoric acid. Suitable organic acids generally include, for example, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically-acceptable base addition salts of the compounds of this invention include, for example, metallic salts and organic salts. Preferred metallic salts include alkali metal (group Ia) salts, alkaline earth metal (group IIa) salts, and other physiological acceptable metal salts. Such salts may be made from aluminum, calcium, lithium, magnesium, potassium, sodium, and zinc. Preferred organic salts can be made from tertiary amines and quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$–$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), aralkyl halides (e.g., benzyl and phenethyl bromides), and others.

Particularly preferred salts of the compounds of this invention include hydrochloric acid (HCl) salts and trifluoroacetate ($CF_3COOH$ or TFA) salts.

C. Preventing or Treating Conditions Using the Compounds and Salts of this Invention One embodiment of this invention is directed to a process for preventing or treating a pathological condition associated with MMP activity in a mammal (e.g., a human, companion animal, farm animal, laboratory animal, zoo animal, or wild animal) having or disposed to having such a condition. Such a condition may be, for example, tissue destruction, a fibrotic disease, pathological matrix weakening, defective injury repair, a cardiovascular disease, a pulmonary disease, a kidney disease, a liver disease, an ophthalmologic disease, or a central nervous system disease. Specific examples of such conditions include osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermal ulceration, epidermolysis bullosa, aortic aneurysm, weak injury repair, an adhesion, scarring, congestive heart failure, post myocardial infarction, coronary thrombosis, emphysema, proteinuria, bone disease, chronic obstructive pulmonary diseases, and Alzheimer's disease.

In some particularly preferred embodiments, the condition comprises arthritis.

In some particularly preferred embodiments, the condition comprises tumor invasion, tumor metastasis, or tumor angiogenesis.

In some particularly preferred embodiments, the condition comprises periodontal disease.

In some particularly preferred embodiments, the condition comprises atherosclerosis.

In some particularly preferred embodiments, the condition comprises multiple sclerosis.

In some particularly preferred embodiments, the condition comprises dilated cardiomyopathy.

In some particularly preferred embodiments, the condition comprises post myocardial infarction.

In some particularly preferred embodiments, the condition comprises congestive heart failure.

In some particularly preferred embodiments, the condition comprises chronic obstructive pulmonary disease.

The condition may alternatively (or additionally) be associated with TNF-$\alpha$ convertase activity. Examples of such a condition include inflammation (e.g., rheumatoid arthritis), autoimmune disease, graft rejection, multiple sclerosis, a fibrotic disease, cancer, an infectious disease (e.g., malaria, mycobacterial infection, meningitis, etc.), fever, psoriasis, a cardiovascular disease (e.g., post-ischemic reperfusion injury and congestive heart failure), a pulmonary disease, hemorrhage, coagulation, hyperoxic alveolar injury, radiation damage, acute phase responses like those seen with infections and sepsis and during shock (e.g., septic shock, hemodynamic shock, etc.), cachexia, and anorexia.

The condition may alternatively (or additionally) be associated with aggrecanase activity. Examples of such a condition include inflammation diseases (e.g., osteoarthritis, rheumatoid arthritis, joint injury, reactive arthritis, acute pyrophosphate arthritis, and psoriatic arthritis) and cancer.

In this patent, the phrase "preventing a condition" means reducing the risk of (or delaying) the onset of the condition in a mammal that does not have the condition, but is predisposed to having the condition. In contrast, the phrase "treating a condition" means ameliorating, suppressing, or eradicating an existing condition. The pathological condition may be (a) the result of pathological MMP activity itself, and/or (b) affected by MMP activity (e.g., diseases associated with TNF-$\alpha$).

A wide variety of methods may be used alone or in combination to administer the hydroxamates and salt thereof described above. For example, the hydroxamates or salts thereof may be administered orally, parenterally, by inhalation spray, rectally, or topically.

Typically, a compound (or pharmaceutically acceptable salt thereof) described in this patent is administered in an amount effective to inhibit a target MMP(s). The target MMP is/are typically MMP-2, MMP-9, and/or MMP-13, with MMP-13 often being a particularly preferred target. The preferred total daily dose of the hydroxamate or salt thereof (administered in single or divided doses) is typically from about 0.001 to about 100 mg/kg, more preferably from about 0.001 to about 30 mg/kg, and even more preferably from about 0.01 to about 10 mg/kg (i.e., mg hydroxamate or salt thereof per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular hydroxamate or salt thereof employed; whether a drug delivery system is utilized; and whether the hydroxamate or salt thereof is administered as part of a drug combination. Thus, the dosage regimen actually employed can vary widely, and, therefore, can deviate from the preferred dosage regimen set forth above.

D. Pharmaceutical Compositions Containing the Compounds and Salts of this Invention This invention also is directed to pharmaceutical compositions comprising a hydroxamate or salt thereof described above, and to methods for making pharmaceutical compositions (or medicaments) comprising a hydroxamate or salt thereof described above.

The preferred composition depends on the method of administration, and typically comprises one or more conventional pharmaceutically acceptable carriers, adjuvants, and/or vehicles. Formulation of drugs is generally discussed in, for example, Hoover, John E., *Remington's Pharmaceutical Sciences* (Mack Publishing Co., Easton, Pa.: 1975). See also, Liberman, H. A. See also, Lachman, L., eds., *Pharmaceutical Dosage Forms* (Marcel Decker, New York, N.Y., 1980).

Solid dosage forms for oral administration include, for example, capsules, tablets, pills, powders, and granules. In such solid dosage forms, the hydroxamates or salts thereof are ordinarily combined with one or more adjuvants. If administered per os, the hydroxamates or salts thereof can be mixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the hydroxamate or salt thereof in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

"Parenteral administration" includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the carriers or diluents mentioned for use in the formulations for oral administration. The hydroxamates or salts thereof can be dissolved in water, polyethylene glycol, propylene glycol, ethanol, corn oil, cottonseed oil, peanut oil, sesame oil, benzyl alcohol, sodium chloride, and/or various buffers.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, such as cocoa butter; synthetic mono-, di-, or triglycerides; fatty acids; and/or polyethylene glycols "Topical administration" includes the use of transdermal administration, such as transdermal patches or iontophoresis devices.

Other adjuvants and modes of administration well-known in the pharmaceutical art may also be used.

E. Definitions

The term "alkyl" (alone or in combination with another term(s)) means a straight- or branched-chain saturated hydrocarbyl typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, isobutyl, sec-butyl, tert-butyl, pentyl, iso-amyl, hexyl, octyl, and the like.

The term "alkenyl" (alone or in combination with another term(s)) means a straight- or branched-chain hydrocarbyl containing one or more double bonds and typically from 2 to about 20 carbon atoms, more typically from about 2 to about 8 carbon atoms, and even more typically from about 2 to about 6 carbon atoms. Examples of such substituents include ethenyl (vinyl); 2-propenyl; 3-propenyl; 1,4-pentadienyl; 4-butadienyl; 1-butenyl; 2-butenyl; 3-butenyl; decenyl; and the like.

The term "alkynyl" (alone or in combination with another term(s)) means a straight- or branched-chain hydrocarbyl containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, decynyl, 1-butynyl, 2-butynyl, 3-butynyl, and the like.

The term "carbocyclyl" (alone or in combination with another term(s)) means a saturated cyclic (i.e., "cycloalkyl"), partially saturated cyclic, or aryl hydrocarbyl containing from 3 to 14 carbon ring atoms ("ring atoms" are the atoms bound together to form the ring or rings of a cyclic group). A carbocyclyl may be a single ring, which typically contains from 3 to 6 ring atoms. Examples of such single-ring carbocyclyls include cyclopropanyl, cyclobutanyl, cyclopentyl, cyclopentenyl, cyclopentadienyl, cyclohexyl, cyclohexenyl, cyclohexadienyl, and phenyl. A carbocyclyl alternatively may be 2 or 3 rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluoreneyl, decalinyl, and norpinanyl.

The term "cycloalkyl" (alone or in combination with another term(s)) means a saturated cyclic hydrocarbyl containing from 3 to 14 carbon ring atoms. A cycloalkyl may be a single carbon ring, which typically contains from 3 to 6 carbon ring atoms. Examples of single-ring cycloalkyls include cyclopropyl (or "cyclopropanyl"), cyclobutyl (or "cyclobutanyl"), cyclopentyl (or "cyclopentanyl"), and cyclohexyl (or "cyclohexanyl"). A cycloalkyl alternatively may be 2 or 3 carbon rings fused together, such as, decalinyl or norpinanyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl (e.g., alkyl, alkenyl, alkynyl, or cycloalkyl) is indicated by the prefix "$C_x$–$C_y$-", wherein x is the minimum and y is the maximum number of carbon atoms in the substituent. Thus, for example, "$C_1$–$C_6$-alkyl" refers to an alkyl containing from 1 to 6 carbon atoms. Illustrating further, $C_3$–$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "nitro" (alone or in combination with another term(s)) means —NO$_2$.

The term "cyano" (alone or in combination with another term(s)) means —CN, which also may be depicted as:

The term "keto" (alone or in combination with another term(s)) means an oxo radical, and may be depicted as =O.

The term "carboxy" (alone or in combination with another term(s)) means —C(O)—OH, which also may be depicted as:

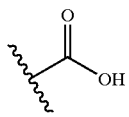

The term "amino" (alone or in combination with another term(s)) means —NH$_2$. The term "monosubstituted amino" (alone or in combination with another term(s)) means an amino wherein one of the hydrogen radicals is replaced by a non-hydrogen substituent. The term "disubstituted amino" (alone or in combination with another term(s)) means an amino wherein both of the hydrogen atoms are replaced by non-hydrogen substituents, which may be identical or different.

The term "halogen" (alone or in combination with another term(s)) means a fluorine radical (which may be depicted as —F), chlorine radical (which may be depicted as —Cl), bromine radical (which may be depicted as —Br), or iodine radical (which may be depicted as —I). Typically, a fluorine radical or chlorine radical is preferred, with a fluorine radical often being particularly preferred.

If a substituent is described as being "substituted", a non-hydrogen radical is in the place of a hydrogen radical on a carbon or nitrogen of the substituent. Thus, for example, a substituted alkyl substituent is an alkyl substituent wherein at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitutions on a substituent, each non-hydrogen radical may be identical or different (unless otherwise stated).

If a substituent is described as being "optionally substituted", the substituent may be either (1) substituted, or (2) not substituted.

This specification uses the terms "substituent" and "radical" interchangeably.

The prefix "halo" indicates that the substituent to which the prefix is attached is substituted with one or more independently selected halogen radicals. For example, haloalkyl means an alkyl wherein at least one hydrogen radical is replaced with a halogen radical. Examples of haloalkyls include chloromethyl, 1-bromoethyl, fluoromethyl, difluoromethyl, trifluoromethyl, 1,1,1-trifluoroethyl, and the like. Illustrating further, "haloalkoxy" means an alkoxy wherein at least one hydrogen radical is replaced by a halogen radical. Examples of haloalkoxy substituents include chloromethoxy, 1-bromoethoxy, fluoromethoxy, difluoromethoxy, trifluoromethoxy (also known as "perfluoromethyoxy"), 1,1,1-trifluoroethoxy, and the like. It should be recognized that if a substituent is substituted by more than one halogen radical, those halogen radicals may be identical or different (unless stated otherwise).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl wherein a fluorine radical is in the place of each hydrogen radical. Examples of perfluoroalkyl substituents include trifluoromethyl (—CF$_3$), perfluorobutyl, perfluoroisopropyl, perfluorododecyl, perfluorodecyl, and the like. To illustrate further, the term "perfluoroalkoxy" means an alkoxy wherein each hydrogen radical is replaced with a fluorine radical. Examples of perfluoroalkoxy substituents include trifluoromethoxy (—O—CF$_3$), perfluorobutoxy, perfluoroisopropoxy, perfluorododecoxy, perfluorodecoxy, and the like.

The term "carbonyl" (alone or in combination with another term(s)) means —C(O)—, which also may be depicted as:

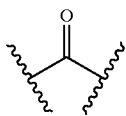

This term also is intended to encompass a hydrated carbonyl substituent, i.e., —C(OH)$_2$—.

The term "aminocarbonyl" (alone or in combination with another term(s)) means —C(O)—NH$_2$, which also may be depicted as:

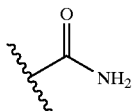

The term "oxy" (alone or in combination with another term(s)) means an ether substituent, and may be depicted as —O—.

The term "alkoxy" (alone or in combination with another term(s)) means an alkylether, i.e., —O-alkyl. Examples of such a substituent include methoxy (—O—CH$_3$), ethoxy, n-propoxy, isopropoxy, n-butoxy, iso-butoxy, sec-butoxy, tert-butoxy, and the like.

The term "alkylcarbonyl" (alone or in combination with another term(s)) means —C(O)-alkyl. For example, "ethylcarbonyl" may be depicted as:

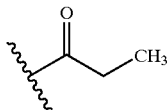

The term "aminoalkylcarbonyl" (alone or in combination with another term(s)) means —C(O)-alkyl-NH$_2$. For example, "aminomethylcarbonyl" may be depicted as:

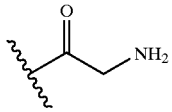

The term "alkoxycarbonyl" (alone or in combination with another term(s)) means —C(O)—O-alkyl. For example, "ethoxycarbonyl" may be depicted as:

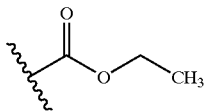

The term "carbocyclylcarbonyl" (alone or in combination with another term(s)) means —C(O)-carbocyclyl. For example, "phenylcarbonyl" may be depicted as:

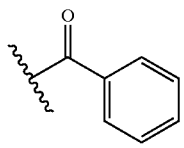

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl. For example, "phenylethylcarbonyl" may be depicted as:

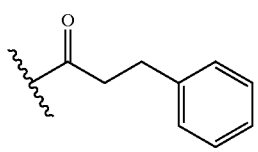

Similarly, the term "heterocyclylalkylcarbonyl" (alone or in combination with another tern(s)) means —C(O)-alkyl-heterocyclyl.

The term "carbocyclyloxycarbonyl" (alone or in combination with another term(s)) means —C(O)—O-carbocyclyl. For example, "phenyloxycarbonyl" may be depicted as:

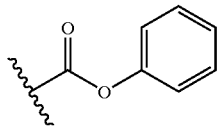

The term "carbocyclylalkoxycarbonyl" (alone or in combination with another term(s)) means —C(O)—O-alkyl-carbocyclyl. For example, "phenylethoxycarbonyl" may be depicted as:

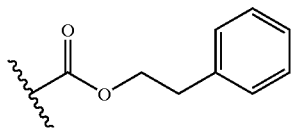

The term "thio" or "thia" (alone or in combination with another term(s)) means a thiaether, i.e., an ether substituent wherein a divalent sulfur atom is in the place of the ether oxygen atom. Such a substituent may be depicted as —S—. This, for example, "alkyl-thioalkyl" means alkyl-S-alkyl.

The term "thiol" or "sulfhydryl" (alone or in combination with another term(s)) means a sulfhydryl, and may be depicted as —SH.

The term "(thiocarbonyl)" (alone or in combination with another term(s)) means a carbonyl wherein the oxygen atom has been replaced with a sulfur. Such a substituent may be depicted as —C(S)—, and also may be depicted as:

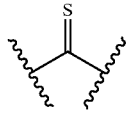

The term "alkyl(thiocarbonyl)" (alone or in combination with another term(s)) means —C(S)-alkyl. For example, "ethyl(thiocarbonyl)" may be depicted as:

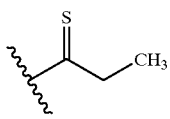

The term "alkoxy(thiocarbonyl)" (alone or in combination with another term(s)) means —C(S)—O-alkyl. For example, "ethoxy(thiocarbonyl)" may be depicted as:

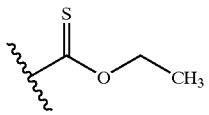

The term "carbocyclyl(thiocarbonyl)" (alone or in combination with another term(s)) means —C(S)-carbocyclyl. For example, "phenyl(thiocarbonyl)" may be depicted as:

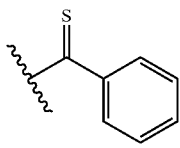

Similarly, the term "heterocyclyl(thiocarbonyl)" (alone or in combination with another term(s)) means —C(S)-heterocyclyl.

The term "carbocyclylalkyl(thiocarbonyl)" (alone or in combination with another term(s)) means —C(S)-alkyl-carbocyclyl. For example, "phenylethyl(thiocarbonyl)" may be depicted as:

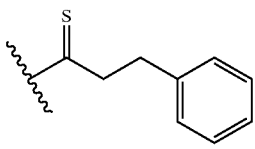

Similarly, the term "heterocyclylalkyl(thiocarbonyl)" (alone or in combination with another term(s)) means —C(S)-alkyl-heterocyclyl.

The term "carbocyclyloxy(thiocarbonyly)" (alone or in combination with another term(s)) means —C(S)—O-carbocyclyl. For example, "phenyloxy(thiocarbonyl)" may be depicted as:

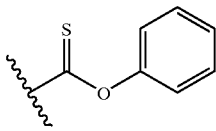

The term "carbocyclylalkoxy(thiocarbonyl)" (alone or in combination with another term(s)) means —C(S)—O-alkyl-carbocyclyl. For example, "phenylethoxy(thiocarbonyl)" may be depicted as:

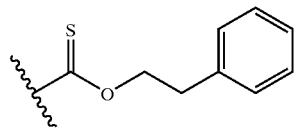

The term "sulfonyl" (alone or in combination with another term(s)) means —S(O)$_2$—, which also may be depicted as:

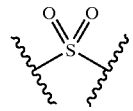

Thus, for example, "alkyl-sulfonyl-alkyl" means alkyl—S(O)$_2$-alkyl.

The term "aminosulfonyl" (alone or in combination with another term(s)) means —S(O)$_2$—NH$_2$, which also may be depicted as:

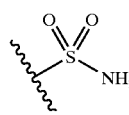

The term "sulfoxido" (alone or in combination with another term(s)) means —S(O)—, which also may be depicted as:

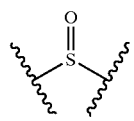

Thus, for example, "alkyl-sulfoxido-alkyl" means alkyl—S(O)-alkyl.

The term "heterocyclyl" (alone or in combination with another term(s)) means a saturated (i.e., "heterocycloalkyl"), partially saturated, or aryl (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofurnayl, tetrahydrofuranyl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4dioxazolyl), oxathiazolyl, oxathiolyl, oxathiolanyl, pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl"), or pyrazinyl (also known as "1,4diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), oxazinyl (including 1,2,3-oxazinyl, 1,3,2-oxazinyl, 1,3,6-oxazinyl (also known as "pentoxazolyl"), 1,2,6-oxazinyl, or 1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl or 1,3,5,2-oxadiazinyl), morpholinyl, azepinyl, oxepinyl, thiepinyl, and diazepinyl.

A heterocyclyl alternatively may be 2 or 3 rings fused together, such as, for example, indolizinyl, pyrindinyl, pyranopyrrolyl, 4H-quinolizinyl, purinyl, naphthyridinyl, pyridopyridinyl (including pyrido[3,4b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", or "benzothiofuranyl"), isobenzothienyl (also known as "isobenzothiophenyl", "isothionaphthenyl", or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), tetrahydroisoquinolinyl, carbazolyl, xanthenyl, and acridinyl.

The term "2-fused'ring" heterocyclyl (alone or in combination with another term(s)) means a saturated, partially saturated, or aryl heterocyclyl containing 2 fused rings. Examples of 2-fused-ring heterocyclyls include indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzolinanyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, and pyridazinyl; 5-membered ring substituents such as 1,3,5-, 1,2,4- or 1,2,3-tiiazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as 1,2-, 1,4-, 2,3- and 2,1-benzopyronyl, quinolinyl, isoquinolinyl, cinnolinyl, quinazolinyl, and 1,4-benzoxazinyl.

A carbocyclyl or heterocyclyl can optionally be substituted with, for example, one or more substituents independently selected from the group consisting of halogen, hydroxy, carboxy, keto, alkyl, alkoxy, alkoxyalkyl, alkylcarbonyl (also known as "alkanoyl"), aryl, arylalkyl, arylalkoxy, arylalkoxyalkyl, arylalkoxycarbonyl, cycloalkyl, cycloalkylalkyl, cycloalkylalkoxy, cycloalkylalkoxyalkyl, and cycloalkylalkoxycarbonyl. More typically, a carbocyclyl or heterocyclyl may optionally be substituted with, for example, one or more substituents independently selected from the group consisting of halogen, —OH, —C(O)—OH, keto, $C_1$–$C_6$-alkyl, $C_1$–$C_6$-alkoxy, $C_1$–$C_6$-alkoxy-$C_1$–$C_6$-alkyl, $C_1$–$C_6$-alkylcarbonyl, aryl, aryl-$C_1$–$C_6$-alkyl, aryl-$C_1$–$C_6$-alkoxy, aryl-$C_1$–$C_6$-alkoxy-$C_1$–$C_6$-alkyl, aryl-$C_1$–$C_6$-alkoxycarbonyl, cycloalkyl, cycloalkyl-$C_1$–$C_6$-alkyl, cycloalkyl-$C_1$–$C_6$-alkoxy, cycloalkyl-$C_1$–$C_6$-alkoxy-$C_1$–$C_6$-alkyl, and cycloalkyl-$C_1$–$C_6$-alkoxycarbonyl. The alkyl, alkoxy, alkoxyalkyl, alkylcarbonyl, aryl, arylalkyl, arylalkoxy, arylalkoxyalkyl, or arylalkoxycarbonyl substituent(s) may further be substituted with, for example, one or more halogen. The aryls or cycloalkyls are typically single-ring substituents containing from 3 to 6 ring atoms, and more typically from 5 to 6 ring atoms.

An aryl or heteroaryl can optionally be substituted with, for example, one or more substituents independently selected from the group consisting of halogen, —OH, —CN, —NO$_2$, —SH, —C(O)—OH, amino, aminocarbonyl, aminoalkyl, alkyl, alkylthio, carboxyalkylthio, alkylcarbonyl, alkylcarbonyloxy, alkoxy, alkoxyalkyl, alkoxycarbonyl, alkoxycarbonylalkoxy, alkoxyalkylthio, alkoxycarbonylalkylthio, carboxyalkoxy, alkoxycarbonylalkoxy, carbocyclyl, carbocyclylalkyl, carbocyclyloxy, carbocyclylthio, carbocyclylalkylthio, carbocyclylamino, carbocyclylalkylamino, carbocyclylcarbonylamino, carbocyclylcarbonyl, carbocyclylalkyl, carbonyl, carbocyclylcarbonyloxy, carbocyclyloxycarbonyl, carbocyclylalkoxycarbonyl, carbocyclyloxyalkoxycarbocyclyl, carbocyclylthio-alkylthiocarbocyclyl, carbocyclylthioalkoxycarbocyclyl, carbocyclyloxyalkylthiocarbocyclyl, heterocyclyl, heterocyclylalkyl, heterocyclyloxy, heterocyclylthio, heterocyclylalkylthio, heterocyclylamino, heterocyclylalkylamino, heterocyclylcarbonylamino, heterocyclylcarbonyl, heterocyclylalkylcarbonyl, heterocyclyloxycarbonyl, heterocyclylcarbonyloxy, heterocyclylalkoxycarbonyl, heterocyclyloxyalkoxy-heterocyclyl, heterocyclylthioalkylthioheterocyclyl, heterocyclylthioalkoxyheterocyclyl, and heterocyclyloxy-alkylthioheterocyclyl. More typically, an aryl or heteroaryl may, for example, optionally be substituted with one or more substituents independently selected from the group consisting of halogen, —OH, —CN, —NO$_2$, —SH, —C(O)—OH, amino, aminocarbonyl, amino-C$_1$–C$_6$-alkyl, C$_1$–C$_6$-alkyl, C$_1$–C$_6$-alkylthio, carboxy-C$_1$–C$_6$-alkylthio, C$_1$–C$_6$-alkylcarbonyl, C$_1$–C$_6$-alkylcarbonyloxy, C$_1$–C$_6$-alkoxy, C$_1$–C$_6$-alkoxy-C$_1$–C$_6$-alkyl, C$_1$–C$_6$-alkoxycarbonyl, C$_1$–C$_6$-alkoxycarbonyl-C$_1$–C$_6$-alkoxy, C$_1$–C$_6$-alkoxy-C$_1$–C$_6$-alkylthio, C$_1$–C$_6$-alkoxycarbonyl-C$_1$–C$_6$-alkylthio, carboxy-C$_1$–C$_6$-alkoxy, C$_1$–C$_6$-alkoxycarbonyl-C$_1$–C$_6$-alkoxy, aryl, aryl-C$_1$–C$_6$-alkyl, aryloxy, arylthio, aryl-C$_1$–C$_6$-alkylthio, arylamino, aryl-C$_1$–C$_6$-alkylamino, arylcarbonylamino, arylcarbonyl, aryl-C$_1$–C$_6$-alkylcarbonyl, arylcarbonyloxy, aryloxycarbonyl, aryl-C$_1$–C$_6$-alkoxycarbonyl, aryloxy-C$_1$–C$_6$-alkoxyaryl, arylthio-C$_1$–C$_6$-alkylthioaryl, arylthio-C$_1$–C$_6$-alkoxyaryl, aryloxy-C$_1$–C$_6$-alkylthioaryl, cycloalkyl, cycloalkyl-C$_1$–C$_6$-alkyl, cycloalkyloxy, cycloalkylthio, cycloalkyl-C$_1$–C$_6$-alkylthio, cycloalkylamino, cycloalkyl-C$_1$–C$_6$-alkylamino, cycloalkylcarbonylamino, cycloalkylcarbonyl, cycloalkyl-C$_1$–C$_6$-alkylcarbonyl, cycloalkylcarbonyloxy, cycloalkyloxycarbonyl, cycloalkyl-C$_1$–C$_6$-alkoxycarbonyl, heteroaryl, heteroaryl-C$_1$–C$_6$-alkyl, heteroaryloxy, heteroarylthio, heteroaryl-C$_1$–C$_6$-alkylthio, heteroarylamino, heteroaryl-C$_1$–C$_6$-alkylamino, heteroarylcarbonylamino, heteroarylcarbonyl, heteroaryl-C$_1$–C$_6$-alkylcarbonyl, heteroaryloxycarbonyl, heteroarylcarbonyloxy, and heteroaryl-C$_1$–C$_6$-alkoxycarbonyl. Here, one or more hydrogen bound to a carbon in any such substituent may, for example, optionally be replaced with halogen. In addition, the cycloalkyl, aryl, and heteroaryl are typically single-ring substituents containing 3 to 6 ring atoms, and more typically 5 or 6 ring atoms.

A prefix attached to a multi-component substituent only applies to the first component. To illustrate, the term "alkylcycloalkyl" contains two components: alkyl and cycloalkyl. Thus, the C$_1$–C$_6$-prefix on C$_1$–C$_6$-alkylcycloalkyl means that the alkyl component of the alkylcycloalkyl contains from 1 to 6 carbon atoms; the C$_1$–C$_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence. To illustrate, benzene substituted with methoxyethyl has the following structure:

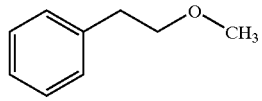

As can be seen, the ethyl is bound to the benzene, and the methoxy is the component of the substituent that is the component furthest from the benzene. As further illustration, benzene substituted with cyclohexanylthiobutoxy has the following structure:

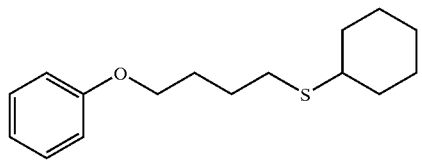

When words are used to describe a linking element between two other elements of a depicted chemical structure, the rightmost-described component of the substituent is the component that is bound to the left element in the depicted structure. To illustrate, if the chemical structure is X—L—Y and L is described as methylcyclohexanylethyl, then the chemical would be X-ethyl-cyclohexanyl-methyl-Y.

When a chemical formula is used to describe a substituent, the dash on the left side of the formula indicates the portion of the substituent that has the free valence. To illustrate, benzene substituted with —C(O)—OH has the following structure:

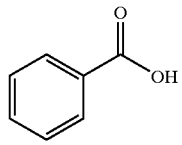

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X—L—Y and L is described as —C(O)—N(H)—, then the chemical would be:

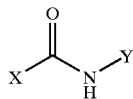

The term "pharmaceutically acceptable" is used adjectivally in this patent to mean that the modified noun is appropriate for use as a pharmaceutical product or as a part of a pharmaceutical product.

With reference to the use of the words "comprise" or "comprises" or "comprising" in this patent (including the claims), Applicants note that unless the context requires otherwise, those words are used on the basis and clear understanding that they are to be interpreted inclusively, rather than exclusively, and that Applicants intend each of those words to be so interpreted in construing this patent, including the claims below.

F. Compound Preparation

The detailed examples below illustrate preparation of compounds and salts of this invention. Other compounds and salts of this invention may be prepared using the methods illustrated in these examples (either alone or in combination with techniques generally known in the art). Such known techniques include, for example, those disclosed in Int'l Publ. No. WO 99/25687 (PCT Patent Application No. PCT/US98/23242 published on May 27, 1999) (incorporated herein by reference). Such known techniques also include, for example, those disclosed in Int'l Publ. No. WO 00/50396 (PCT Patent Application No. PCT/US00/02518 published on Aug. 31, 2000) (incorporated herein by reference). Such known techniques further include, for example, those disclosed in Int'l Publ. No. WO 00/69821 (PCT Patent Application No. PCT/US00/06719 published on Nov. 23, 2000) (incorporated herein by reference).

EXAMPLES

The following examples are merely illustrative, and not limiting to the remainder of this disclosure in any way.

Example 1

Preparation of 4-[[4-(3-aminopropoxy)-phenyl]sulfonyl]tetrahydro-2H-pyran-4-carboxylic acid 1,1-dimethylethyl ester, monohydrochloride

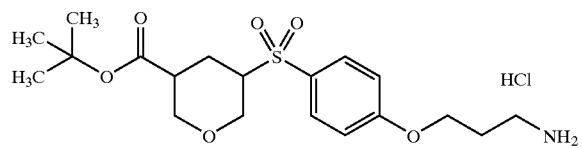

Part A

To a solution of t-butylchloroacetate (67 g, 0.44 mol) and 4-fluorothiophenol (50 g, 0.40 mol) in N,N-dimethylformamide (1 L) was added potassium carbonate (62 g, 0.45 mol), followed by dimethylaminopyridine (2 g, 0.02 mol). The mixture was stirred at ambient temperature overnight under nitrogen. Once HPLC showed that the reaction was complete, the mixture was poured into stirring 10% aqueous HCl (1 L) and extracted with ethyl acetate (4×). The combined organic layers were washed with water (2×), dried over magnesium sulfate, filtered, and concentrated in vacuo to afford 112 g (100+% crude yield) of a brown oil. $^1$H NMR confirmed the desired sulfide with no disulfide formation. This material was used without further purification.

Part B

To a solution of the product from Part A (approximately 108 g, 0.45 mol) in tetrahydrofuran (400 ml) was added water (700 ml), followed by Oxone™ (600 g, 0.98 mol). The reaction mixture was stirred overnight. Once HPLC showed completion, the reaction mixture was filtered to remove excess Oxone™, and the mother liquor was then extracted with ethyl acetate (3×). The combined organic layers were washed with water (2×), dried over magnesium sulfate, filtered, and concentrated in vacuo to afford 78.3 g (64% crude yield) of a yellow oil. Both $^{19}$F and $^1$H NMR were consistent with the desired sulfone with no starting material remaining. This material was used without further purification.

Part C

To a solution of the product from Part B (78 g, 0.28 mol) in N,N-dimethylacetamide (300 ml) was added potassium carbonate (86 g, 0.62 mol). After stirring for 5 min, 2,2'-(dibromoethyl)ether (79 g, 0.34 mol) was added, followed by 4-dimethylaminopyridine (1.7 g; 0.014 mol) and tetrabutylammonium bromide (4.5 g, 0.14 mol). The reaction mixture was stirred overnight via a mechanical stirrer. Once HPLC showed completion, the reaction mixture was slowly dumped into stirring 10% aqueous HCl (1 L). The resulting yellow solid was collected and washed with hexanes to afford 84 g (86%) of a yellow solid. $^1$H NMR confirmed the desired product.

Part D

To a solution of the product from Part C (19.8 g, 57.5 mmol) and t-butyl-N-(3-hydroxypropyl)carbamate (11.1 g, 63.3 mmol) in anhydrous N,N-dimethylformamide (300 mL) at 0° C. was added sodium hydride (2.8 g, 69.0 mmol; 60% dispersion in mineral oil). After 18 hr, the reaction was quenched with water and concentrated in vacuo. The oily residue was partitioned between ethyl acetate and saturated sodium bicarbonate solution. The layers were separated, and the organic layer was washed with brine (3×), dried over sodium sulfate, filtered, and concentrated in vacuo. The oily residue was taken up in acetonitrile and again concentrated in vacuo. The resulting solid was triturated with diethyl ether, and 15.3 g (53%/o) of the pure desired product was collected as a white powder. ESMS m/z=522 [M+Na]$^+$. The filtrate contained 11.6 g of material which was shown by HPLC to be 55% product. This material could be purified by flash chromatography to obtain more material if desired.

Part E

The product from Part D (15.3 g, 30.6 mmol) was taken up in 4N HCl in dioxane (17 mL). After 1 hr, HPLC indicated incomplete reaction, so additional 4N HCl in dioxane (2 mL) was added. After 20 min, the reaction mixture was slowly added to rapidly stirring diethyl ether (400 mL). The resulting oily solid was rinsed with more diethyl ether then dissolved in acetonitrile and concentrated in vacuo. 12.3 g (92%) of the desired hydrochloride salt was obtained as a white solid. ESMS m/z=400 [M+H]$^+$.

Additional compounds can be prepared by one skilled in the art using similar methods. Examples of such compounds include those having a structure corresponding to generic formula EX-A. Such compounds include, for example, those summarized in Table 1.

TABLE 1
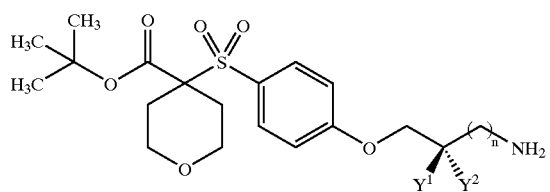
EX-A
| Ex # | structure | n | Y¹ | Y² | ESMS m/z |
|---|---|---|---|---|---|
| 2 | 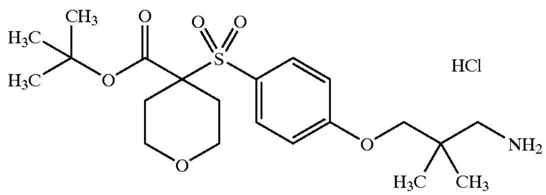 | 1 | $CH_3$ | $CH_3$ | 428 $[M+H]^+$ |
| 3 | 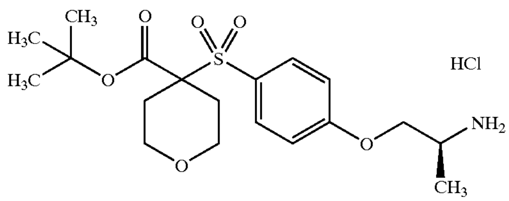 | 0 | $CH_3$ | H | 422 $[M+Na]^+$ |
| 4 | 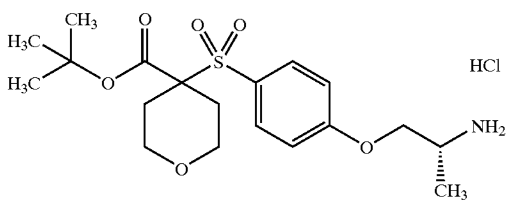 | 0 | H | $CH_3$ | 422 $[M+Na]^+$ |
| 5 | 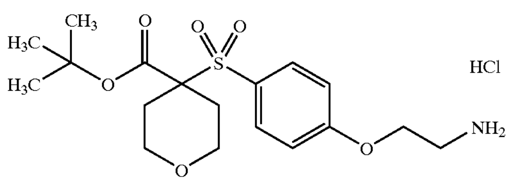 | 0 | H | H | 408 $[M+Na]^+$ |
| 6 | 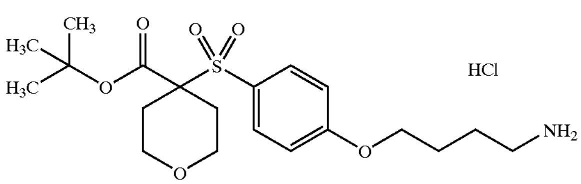 | 2 | H | H | 414 $[M+H]^+$ |

Example 7

Preparation of tetrahydro-4-[[4-[[5-(methoxymethylamino)-5oxopentyl]oxy]phenyl]sulfonyl]-N-(tetrahydro-2H-pyran-2-yl)oxy]-2H-pyran-4-carboxamide

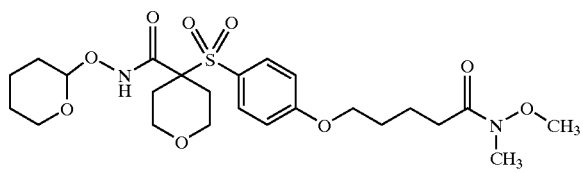

Part A

To a solution of 5-benzyloxy-1-pentanol (32.6 g, 168 mmol) in anhydrous N,N-dimethylformamide (150 mL) at 0° C. was added sodium hydride (7.7 g, 192 mmol, 60% dispersion in mineral oil). After 15 min, the reaction mixture was allowed to warm to 20° C., and then re-cooled to 0° C. A solution of 4-[(4-fluorophenyl)sulfonyl]tetrahydro-2H-pyran-4-carboxylic acid, 1,1-dimethylethyl ester (55.1 g, 160 mmol, as prepared in Example 1, Part C) in anhydrous N,N-dimethylformamide (100 mL) was added, and the cooling bath removed. After 4 hr, the reaction was concentrated in vacuo. The oily residue was partitioned between ethyl acetate and saturated sodium bicarbonate solution. The layers were separated, and the aqueous layer was back extracted with ethyl acetate (2×). The combined extracts were washed with 5% potassium hydrogensulfate, water, and brine (3×); dried over magnesium sulfate; filtered; and concentrated in vacuo. The resulting opaque oil solidified upon standing, and was subsequently purified by column chromatography using 10–20% ethyl acetate/hexanes to afford 67.6 g (81%) of the desired product as a white solid. ESMS m/z=541 [M+Na]$^+$.

Part B

The product from Part A (20.0 g, 38.6 mmol) was dissolved in tetrahydrofuran (80 mL) in a small Fisher/Porter bottle. After purging with a stream of nitrogen for 5 min, the reaction was charged with 5% palladium on carbon catalyst (4.0 g, Degussa E101 NO/W, 50% water) and pressurized to roughly ~80 psi with hydrogen. After 1.5 hr, hydrogen uptake had ceased and HPLC analysis indicated the reaction was complete. The reaction was filtered through a bed of celite and the filtrate was concentrated to yield 17.2 g (100%) of the desired alcohol as a viscous oil. This material was used without further purification.

Part C

The product from Part B (16.5 g, 38.6 mmol) was dissolved in acetonitrile (80 mL). The reaction mixture was treated with carbon tetrachloride (80 mL), water (120 mL), then sodium periodate (24.7 g, 115.7 mmol), and finally ruthenium trichloride (180 mg, 0.9 mmol). After 1 hr, HPLC analysis indicated that the reaction was complete. The reaction mixture was diluted with methylene chloride (300 mL), and the solids were removed by gravity filtration. The layers were separated, and the aqueous layer was extracted with methylene chloride (3×). The combined organic extracts were dried over magnesium sulfate, filtered, and concentrated in vacuo to yield a blue solid. This was redissolved in tetrahydrofuran, slurried with activated carbon, filtered, and concentrated in vacuo to yield 17.1 g (100%) of an off-white solid. $^1$HNMR was consistent with the desired product. This material was used without further purification.

Part D

To a solution of the product from Part C (17.1 g, 38.6 mmol) in N,N-dimethylformamide (160 ml) was added 1-hydroxybenzotriazole (7.8 g, 57.9 mmol), and then 1-(3-dimethyaminopropyl)-3-ethylcarbodiimide hydrochloride (10.3 g, 54.0 mmol). After 1.5 hr, N,O-dimethylhydroxylamine HCl (11.3 g, 115.7 mmol) and triethylamine (32.2 ml, 231.4 mmol) were added. The reaction mixture was left stirring at ambient temperature overnight. The mixture was concentrated, and the residue partitioned between ethyl acetate and saturated sodium bicarbonate solution. The aqueous layer was back extracted with ethyl acetate (2×), and the combined organic layers were washed with 5% potassium hydrogensulfate solution, water, and brine (3×), then dried over magnesium sulfate, filtered, and concentrated in vacuo. The crude solid was purified by column chromatography using 50% ethyl acetate/hexanes, and 14.7 g (79%) of the desired weinreb amide was obtained as an off-white solid. ESMS m/z=508 [M+Na]$^+$.

Part E

The product from Part D (6.24 g, 12.85 mmol) was taken up in neat trifluoroacetic acid (50 mL). After 1.5 hr, the trifluoroacetic acid was removed in vacuo at 50° C. to give the free acid as a syrupy oil. ESMS m/z=430 [M+H]$^+$. To a solution of this material in anhydrous N,N-dimethylformamide (25 mL) was added 1-hydroxybenzotriazole (2.14 g, 15.88 mmol), tetrahydro-pyranhydroxylamine (4.64 g, 39.72 mmol), and triethylamine (5.5 mL, 39.72 mmol), followed by 1-(3-dimethyaminopropyl)-3-ethylcarbodiimide hydrochloride (3.35 g, 15.83 mmol). The reaction mixture was heated at 40° C. for 3.5 hr, and then cooled to ambient temperature and stirred overnight. The reaction mixture was concentrated in vacuo at 60° C. The residue was taken up in ethyl acetate, washed with saturated sodium bicarbonate solution (2×) and brine (3×), dried over sodium sulfate, filtered, and concentrated in vacuo to give 8 g of a syrup. The crude material was purified by flash chromatography using 50–100% ethyl acetate/hexanes to give the title compound as a white solid. ESMS m/z=529 [M+H]$^+$. HRMS calculated for $C_{24}H_{36}N_2O_9S$: 529.2220. [M+H]$^+$, found: 529.2210.

Additional compounds can be prepared by one skilled in the art using similar methods. Examples of such compounds include those having a structure corresponding to generic formula EX-B. Such compounds include, for example, the compound summarized in Table 2.

TABLE 2

EX-B

| Ex # | structure | n | Calcd Mass | Observed Mass |
|---|---|---|---|---|
| 8 | 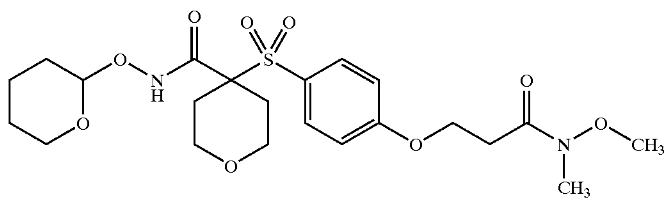 | 0 | 518.2172 | 518.2176 |
| 9 | 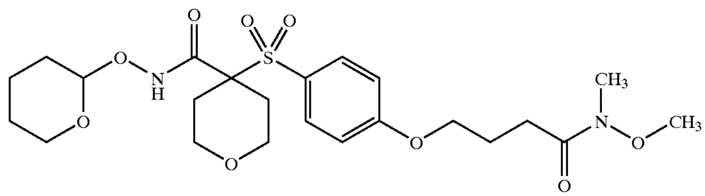 | 1 | 532.2329 | 532.2307 |

Example 10

Preparation of tetrahydro-4-[[4-[3-[(methylsulfonyl)oxy]propoxy]phenyl)sulfonyl]-N-[(tetrahydro-2H pyran-2-yl)oxy]-2H-pyran-4-carboxamide

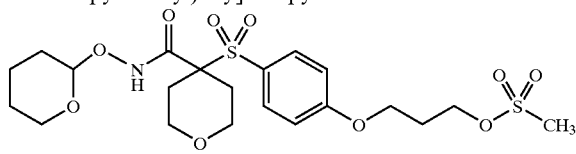

Part A

To a solution of 4-[(4-fluorophenyl)sulfonyl]-tetrahydro-2H-pyran-4-carboxylic acid, 1,1-dimethylethyl ester (5.0 g, 14.5 mmol, as prepared in Example 1, Part C) and 3-benzyloxy-1-propanol (2.3 mL, 14.5 mmol) in N,N-dimethylformamide (50 mL) at 0° C. was added NaH (696 mg, 17.4 mmol, 60% dispersion in mineral oil). The solution was stirred at ambient temperature for 5 hr. The reaction was quenched with water, and then partitioned between ethyl acetate and water. The organic layer was washed with water and brine, dried over sodium sulfate, filtered, and concentrated in vacuo to afford 7.89 g (quantitative yield) of the benzyl ether as a yellow oil. (ESMS m/z=435 [M−tBu]$^+$.

Part B

The benzyl ether of Part A (4.39 g, 8.94 mmol) was hydrolized in 1:1 trifluoroacetic acid:methylene chloride (50 mL). The solution was concentrated in vacuo to provide 3.69 g (950) of the free acid as a crude white solid. ESMS m/z=452 [M+NH4]$^+$. This material was used without purification.

Part C

To a solution of the crude acid of Part B (3.60 g, 8.29 mmol) in N,N-dimethylformamide (40 mL) was added 1-hydroxybenzotriazole (1.34 g, 9.95 mmol), triethylamine (3.5 mL, 24.9 mmol), and tetrahydropyranhydroxylamine (2.91 g, 24.9 mmol). After 30 min, 1-[3-(dimethylamino)propyl]-3-ethylcarbodiimide hydrochloride (2.23 g, 11.6 mmol) was added. The solution was stirred for 18 hr at ambient temperature. The solution was partitioned between ethyl acetate and saturated sodium bicarbonate solution. The organic layer was washed with saturated sodium bicarbonate solution and brine, and then dried over sodium sulfate. Purification by flash chromatography using ethyl acetate/hexanes provided 3.71 g (84 0) of the protected hydroxamate as a crude oil. ESMS m/z=551 (M+NH4)$^+$. HRMS calculated for $C_{27}H_{35}NO_8S \cdot NH_4$: 551.2427 (M+NH4)$^+$. Found: 551.2418.

Part D

The benzyl ether of Part C (3.52 g, 6.6 mmol) was hydrogenated over 10% palladium/carbon (3.31 g) in methanol with ammonium formate (2.5 g, 39.6 mmol) as the hydrogen source added in 3 portions and heated at reflux. The solution was filtered through celite and concentrated in vacuo to provided 2.89 g (98%) of the alcohol as a colorless oil. ESMS m/z=442 [M−H]$^+$. This material was used without purification.

Part E

To a solution of the protected hydroxamate of Part D (2.57 g, 5.8 mmol) in methylene chloride (25 mL) was added triethylamine (2.5 mL, 18.8 mmol). The solution was cooled to 0° C., and methylsulfonyl chloride (1.25 mL, 16.0 mmol) was added. After 18 hr, the reaction was washed with water, 10% citric acid, 5% sodium bicarbonate solution, and brine, and then dried over magnesium sulfate. Chromatography (on silica, ethyl acetate/hexanes) provided the title compound as a colorless oil (1.48 g, 49 0). ESMS m/z=544 (M+Na)$^+$. HRMS calculated for $C_{21}H_{31}NO_{10}S_2 \cdot NH_4$: 539.1733 (M+NH4)$^+$. Found: 539.1709.

Additional compounds can be prepared by one skilled in the art using similar methods. Examples of such compounds include those having a structure corresponding to generic formula EX—C. Such compounds include, for example, the compounds summarized in Table 3.

Oxone™ (720 g, 1.17 mmol). After 2 hr, the reaction mixture was filtered to remove the excess salts, and the filtrate was concentrated in vacuo. The resulting residue was

TABLE 3

| Ex # | structure | n | Calcd Mass | Observed Mass |
|---|---|---|---|---|
| 11 | 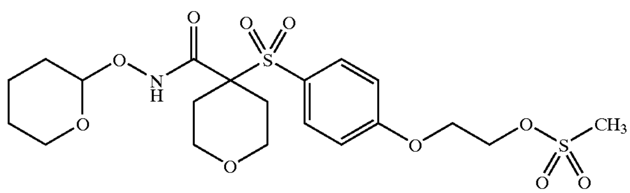 | 1 | 525.1517 | 525.1561 |
| 12 | 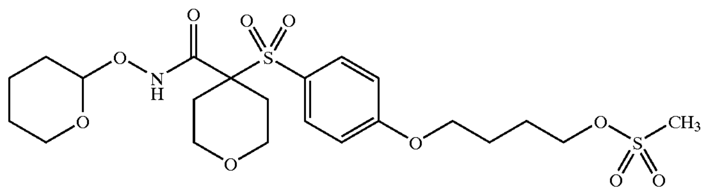 | 3 | 558.1444 | 558.1429 |
| 13 | 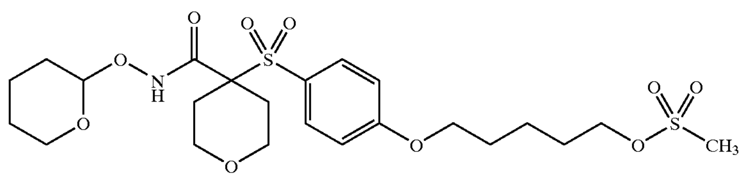 | 4 | 572.16 | 572.1583 |

Example 14

Preparation of (tetrahydro-4-[[4-(2-propenyloxy) phenyl]sulfonyl]-N-[(tetrahydro-2H-pyran-2-yl) oxy]-2H-pyran-4-carboxamide

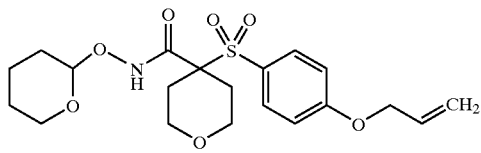

Part A

To a solution of sodium (8.97 g, 390 mmol) in methanol (1 L) at 0° C. were added 4-fluorothiophenol (50 g, 390 mmol) and methyl chloroacetate (34.2 mL, 390 mmol). After stirring at ambient temperature for 4 hr, the solution was filtered to remove salts, and the filtrate was concentrated in vacuo to provide 75.85 g (970) for the desired sulfide as a colorless oil.

Part B

To a solution of the product from Part A (75.85 g, 380 mmol) in methanol (1 L) and water (100 mL) was added dissolved in ethyl acetate and washed with water, saturated sodium bicarbonate solution, and brine, and then dried over magnesium sulfate. Concentrating in vacuo provided 82.74 g (94%) of the desired sulfone as a white solid.

Part C

To a solution of the product from Part B (28.5 g, 123 mmol) in N,N-dimethylacetamide (200 mL) were added potassium carbonate (37.3 g, 270 mmol), bis-(2-bromoethylether (19.3 mL, 147 mmol), 4-dimethylaminopyridine (750 mg, 6 mmol), and tetrabutylammonium bromide (1.98 g, 6 mmol). The resulting solution was stirred at ambient temperature for 72 hr, and then poured into 1 N HCl (300 mL). The resulting precipitate was collected by vacuum filtration. Recrystallization using ethyl acetate/hexanes provided 28.74 g (77%) of the tetrahydropyran product as a beige solid.

Part D

To a solution of the product from Part C (8.0 g, 26.5 mmol) in tetrahydrofuran (250 mL) was added potassium trimethylsilonate (10.2 g, 79.5 mmol). After 1.5 hr, the reaction mixture was quenched with water, acidified to pH 2.5, and extracted with ethyl acetate. The organic layer was washed with brine, dried over sodium sulfate, filtered, and concentrated in vacuo to afford 5.78 g (76%) of the desired acid salt as a white solid.

Part E

To a solution of the product from Part D (5.4 g, 18.7 mmol) in N,N-dimethylformamide (35 mL) were added 1-hydroxybenzotriazole (3.04 g, 22.5 mmol), N-methylmorpholine (6.2 mL, 56.2 mmol), tetrahydropyranhydroxylamine (6.8 g, 58.1 mmol) and 1-(3dimethylaminopropyl)-3-ethylcarbodiimide hydrochloride (5.0 g, 26.2 mmol). After stirring for 3 hr at ambient temperature, the solution was concentrated in vacuo, and the residue partitioned between ethyl acetate and water. The organic layer was washed with 5% aqueous potassium hydrogen sulfate, water, saturated sodium bicarbonate solution, and brine; dried over sodium sulfate; filtered; and concentrated in vacuo to provide 6.34 g (87%) of the THP protected hydroxamate as a white solid.

Part F

To a solution of the product from Part E (1.0 g, 2.58 mmol) in dimethylsulfoxide (5 mL) was added potassium carbonate (0.89 g, 6.45 mmol) and allyl alcohol (0.35 mL, 12.9 mmol). The mixture was heated to 110° C. for 72 hr. Additional allyl alcohol (0.88 mL, 13 mmol) and cesium carbonate (2.1 g, 6.45 mmol) were added, and the mixture heated at 120° C. for 6 hr. After cooling to ambient temperature, the mixture was diluted with water (50 mL), and the pH adjusted to 8–9 with 1 N HCl. The aqueous layer was extracted with ethyl acetate. The organic layer was washed brine, dried over magnesium sulfate, filtered, and concentrated in vacuo. Purification via flash column chromatography with 15% ethyl acetate/hexanes yielded 0.67 g of pure title compound as a white solid. ESMS m/z=426 [M+H]$^+$.

Additional compounds can be prepared by one skilled in the art using similar methods. Examples of such compounds include those having a structure corresponding to generic formula EX-D. Such compounds include, for example, the compounds summarized in Table 4.

Example 17

Preparation of tetrahydro-N-hydroxy-4-[[4-[3-[(4-methoxybenzoyl)amino]propoxy]phenyl]sulfonyl]-2H-pyran-4-carboxamide

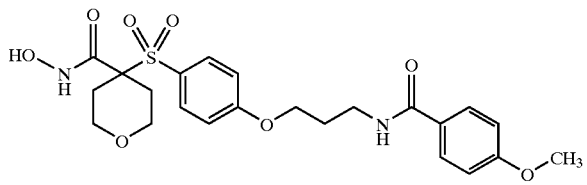

Part A

To a solution of 4-[[4-(3-aminopropoxy)-phenyl]sulfonyl] tetrahydro-2H-pyran-4-carboxylic acid 1,1-dimethylethyl ester, monohydrochloride (507 mg, 1.27 mmol, prepared as in Example 1) in anhydrous N,N-dimethylformamide (5 mL) at ambient temperature was added triethylamine (215 uL, 1.54 mmol), followed immediately by panisoyl chloride (260 mg, 1.52 mmol). After 1 hr, the reaction mixture was quenched with water (~2 mL) and concentrated in vacuo at 60° C. The crude residue was partitioned between ethyl acetate and water. The layers were separated, and the organic layer was washed with brine (3×), dried over sodium sulfate, filtered, and concentrated in vacuo to give a pale yellow oil. The crude product was partially purified by flash chromatography using 80% ethyl acetate/hexanes to provide 225 mg (33%) of the desired acylated product as a clear, colorless oil. ESMS m/z=556 M+Na]$^+$. This material was used without further purification.

Part B

The product from Part A (225 mg, 82% purity by HPLC) was taken up in neat trifluoroacetic acid (1 mL). After 3 hr, the trifluoroacetic acid was removed in vacuo at 50° C. to give the free acid as a colorless oil. ESMS m/z=478 [M+H]$^+$.

TABLE 4

| Ex. # | Structure | n | ESMS m/z |
|---|---|---|---|
| 15 | 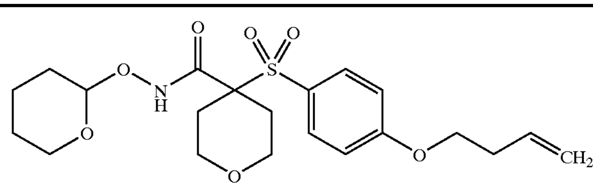 | 2 | 440 [M + H]$^+$ |
| 16 | 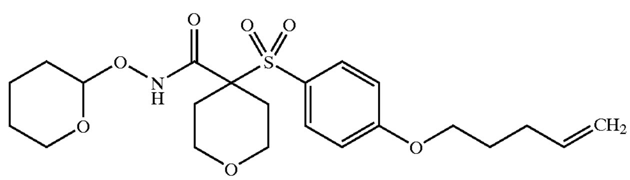 | 3 | 454 [M + H]$^+$ |

To a solution of this material in anhydrous N,N dimethylformamide (2 mL) was added 1-hyrdoxybenzotriazole (72 mg, 0.53 mmol), N-methylmorpholine (100 uL, 0.91 mmol) and tetrahydropyranhydroxylamine (78 mg, 0.67 mmol), followed by 1-(3-dimethyaminopropyl)-3-ethylcarbodiimide hydrochloride (119 mg, 0.62 mmol). The reaction mixture was stirred at ambient temperature for 72 hr, and then concentrated in vacuo at 60° C. The residue was partitioned between ethyl acetate and water. The layers were separated, and the organic layer was washed with saturated sodium bicarbonate solution and brine (2x), dried over sodium sulfate, filtered, and concentrated in vacuo to give 255 mg of the desired THP protected hydroxamate as a colorless oil. ESMS m/z=599 [M+Na]+. HRMS calculated for $C_{28}H_{36}N_2O_9S$: 577.2220 [M+H]+, found: 577.2215.

Part C

The product from Part B (255 mg, 88% purity by HPLC) was dissolved in 4N HCl in dioxane (3 mL) and methanol (300 uL). After 1 hr at ambient temperature, the reaction mixture was poured into rapidly stirring diethyl ether (50 mL). A white solid was collected and dried over $P_2O_5$ under vacuum. The title compound was obtained as a faint pink solid. ESMS m/z=493 [M+H]+. HRMS calculated for $C_{23}H_{29}N_2O_8S$: 493.1645 [M+H]+, found: 493.1636.

Additional compounds (such as those having a structure corresponding to generic Formula EX-E) can be prepared by one skilled in the art using similar methods with either the t-butyl ester or free acid of 4-[[4-(3-aminopropoxy)-phenyl]sulfonyl]tetrahydro-2H-pyran-4-carboxylic acid 1,1-dimethylethyl ester, monohydrochloride or similarly prepared starting materials. Also, one may use carboxylic acids as coupling agents in place of acid chlorides using standard peptide coupling conditions for formation of the amide bond.

EX-E

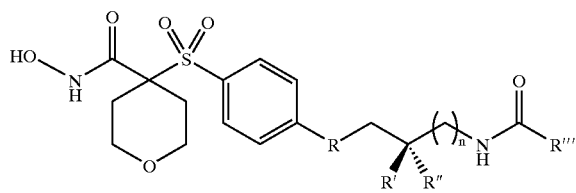

Example 18

Preparation of 1-cyclopropyl-N-hydroxy-4-[[4-[3[(4-methoxybenzoyl)amino]propoxy]phenyl]sulfonyl]-4-piperidinecarboxamide, monohydrochloride

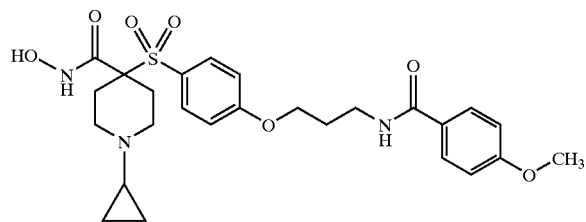

Part A to a solution of ethyl isonipecotate (15.7 g, 0.1 mol) in tetrahydrofuran (100 mL) was added a solution of di-tert-butyl dicarbonate (21.8 g, 0.1 mol) in tetrahydrofuran (5 mL) dropwise over 20 min. The solution was stirred overnight at ambient temperature and concentrated in vacuo to yield a light oil. The oil was filtered through silica gel using ethyl acetate/hexanes then concentrated in vacuo to afford 26.2 g (100%) of the desired BOC-piperidine as a clear, colorless oil.

Part B

A solution of 4-fluorothiophenol (50.29 g, 390 mmol) in dimethyl sulfoxide (500 mL) was heated to 65° C. for 6 hr. The reaction was quenched by pouring into wet ice. The resulting solid was collected by vacuum filtration to afford 34.4 g (68.9%) of the desired disulfide as a white solid.

Part C

To a solution of the product from Part A (16 g, 62 mmol) in tetrahydrofuran (300 mL) cooled to -50° C. was added lithium diisopropylamide (41.33 mL, 74 mmol). After being at 0° C. for 1.5 hr, the product from Part B (15.77 g, 62 mmol) was added. The reaction mixture was stirred at ambient temperature for 20 hr, and then quenched by the addition of water. The solution was concentrated in vacuo, and the resulting residue was partitioned between ethyl acetate and water. The organic layer was washed with 0.5 N KOH, water, and brine. Purification by column chromatography using ethyl acetate/hexanes provided 18.0 g (75%) of the desired sulfide as an oil.

Part D

To a solution of the product from Part C (16.5 g, 43 mmol) in methylene chloride (500 mL) cooled to 0° C. was added 3-chloroperbenzoic acid (18.0 g, 86 mmoL). After stirring for 20 hr, the reaction mixture was diluted with water and extracted with methylene chloride. The organic layer was washed with 10% aqueous sodium sulfite, water, and brine, dried over magnesium sulfate, filtered, and concentrated in vacuo. The crude product was purified by column chromatography using ethyl acetate/hexanes to afford 10.7 g (60%) of the desired sulfone as a solid.

Part E

Into a solution of the product from Part D (10 g, 24.0 mmol) in ethyl acetate (250 mL) was bubbled HCl gas for 10 min, followed by stirring at ambient temperature for 4 hr. Concentration in vacuo provided 7.27 g (86%) of the amine hydrochloride salt as a white solid.

Part F

To a solution of the product from Part E (10.0 g, 28.4 mmol) in methanol (100 mL) was added acetic acid (16.2 mL, 284 mmol), powdered 4A molecular sieves (9.1 g), and [(1-ethoxycyclopropyl)oxyl trimethylsilane (17.1 mL, 85.2 mmol). Sodium cyanoborohydride (4,82 g, 76.7 mmol) was then added slowly. The reaction was heated at reflux with vigorous stirring for 4.5 hr. The reaction mixture was cooled to room temperature, filtered through celite, and concentrated in vacuo. The residue was partitioned between ethyl acetate and saturated sodium bicarbonate solution. The organic layer was washed with saturated sodium bicarbonate solution (3x) and brine, dried over magnesium sulfate, filtered, and concentrated in vacuo. The crude material crystallized upon standing providing 10.9 g (100%) of the alkylated amine compound as a pale yellow oily crystal. ESMS m/z=356 (M+H)+. This material was used without purification.

Part G

The product from Part F (28.4 mmol) was hydrolized in tetrahydrofuran (65 mL) with LiOH (3.58 g, 85.2 mmol) in 35 mL of water at 60° C. over 3 days. The solution was concentrated in vacuo, diluted with water, and washed with diethyl ether. The aqueous layer was acidified with 1N HCl to a pH of ~4.5, causing a white precipitate to form. The solid was collected by filtration, washed with water, and washed with ethyl acetate. After drying over silica on a high vacuum, 8.06 g (78.2%) of the acid was obtained as a crude white solid. ESMS m/z=328 (M+H)+. HRMS calculated for $C_{15}H_{18}NO_4SF$: 328.1019 (M+H)+, found: 328.1014. This material was used without purification.

Part H

To a solution of the crude acid of Part G (7.92 g, 21.8 mmol) in N,N-dimethylformamide (48 mL) was added N-methylmorpholine (12.0 mL, 109 mmol) and PyBOP (12.5 g, 24.0 mmol). After stirring 15 min, tetrahydropyranhydroxylamine (3.07 g, 26.2 mmol) was added. The solution was stirred for 22 hr at ambient temperature. The solution was diluted with water (240 mL) and extracted with ethyl acetate (3×). The combined organics were washed with saturated aqueous sodium bicarbonate solution (2×) and brine, dried over sodium sulfate, filtered, and concentrated in vacuo to a foamy oil. The crude material was filtered through a silica plug using 1% $Et_3N$ in ethyl acetate/hexanes to afford 7.12 g (76.60) of the protected hydroxamate as a foamy oil. ESMS m/z=427 (M+H)+. HRMS calculated for $C_{20}H_{27}N_2O_5SF$: 427.1703 (M+H)+. Found: 427.1693.

Part I

To a solution of 3-(dibenzylamino)-1-propanol (4.3 g, 16.88 mmol) in anhydrous N,N-dimethylformamide (35 mL) was added sodium hydride (1.3 g, 32.35 mmol; 60% dispersion in mineral oil). The reaction mixture was stirred for 15 min, then cooled to 0° C. in an ice bath and treated with a solution of the product from Part H (6.0 g, 14.07 mmol) in anhydrous N,N-dimethylformamide (15 mL). After the addition was completed, the ice bath was removed and the reaction was allowed to stir at ambient temperature for 18 hr. The reaction was quenched with water and concentrated in vacuo. The oily residue was partitioned between ethyl acetate and saturated sodium bicarbonate solution. The layers were separated and the aqueous layer was extracted with ethyl acetate (3×). The organic extracts were combined and washed with brine (3×), dried over sodium sulfate, filtered, and concentrated in vacuo. The crude yellow solid was re-crystallized from hot acetonitrile. 6.5 g (70%) of the pure desired product was collected as a white powder. ESMS m/z=662 [M+H]+.

Part J

The product from Part I (1.0 g, 1.51 mmol) and glacial acetic acid (0.2 g, 3.02 mmol) were slurried in methanol (15 mL) in a small Fisher/Porter bottle. After purging with a stream of nitrogen for 5 min, the reaction was charged with 20% palladium on carbon catalyst (0.5 g, Degussa E169X/W, 50% water) and pressurized to 50 psi with hydrogen. After 5 hr, hydrogen uptake had ceased, and HPLC analysis indicated the reaction was complete. The reaction was filtered through a bed of celite, and the filtrate was concentrated to yield 0.8 g (1000) of the desired mono-acetate salt as a dry, white foam. ESMS m/z=481 [M+H]+.

Part K

To a solution of the product from Part J (0.7 g, 1.06 mmol) in anhydrous methylene chloride (11 mL) at ambient temperature was added triethylamine (0.73 mL, 6.35 mmol), followed by p-anisoyl chloride (0.3 g, 1.59 mmol). After 10 min, HPLC analysis showed the reaction to be complete. The reaction mixture was concentrated in vacuo, and the residue was partitioned between ethyl acetate and saturated sodium bicarbonate solution. The layers were separated, and the aqueous layer extracted with ethyl acetate (3×). The organic extracts were combined and washed with brine (3×), dried over sodium sulfate, filtered, and concentrated in vacuo to yield a tan foam. The crude product was purified by flash chromatography using 60–100% [5% (2M ammonia in methanol)ethyl acetate]/hexanes to yield 0.2 g (34%) of the desired product as a dry white foam. ESMS m/z=616 [M+H]+.

Part L

The product from Part K (0.2 g, 0.34 mmol) was slurried in 4N HCl in dioxane (2 mL). After 5 min, methanol (0.2 mL) was added. After stirring for 10 min at ambient temperature, the reaction mixture was poured into rapidly stirring diethyl ether (50 mL). A white solid was collected and dried under vacuum. The title compound (as the HCl salt) was obtained as an off-white solid. ESMS m/z=532 [M+H]+. HRMS calculated for $C_{26}H_{33}N_3O_7S$: 532.2117 [M+H]+, found: 532.2098.

Additional compounds can be prepared by one skilled in the art using similar methods. Examples of such compounds include those having a structure corresponding to generic formula EX-F.

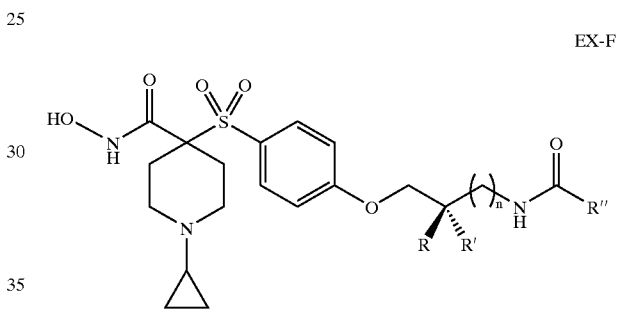

EX-F

Example 19

Preparation of 4-[[4-[3-[[4-(dimethylamino)benzoyl]methylamino]propoxy]phenyl]sulfonyl]tetrahydro-N-hydroxy-2H-pyran-4-carboxamide

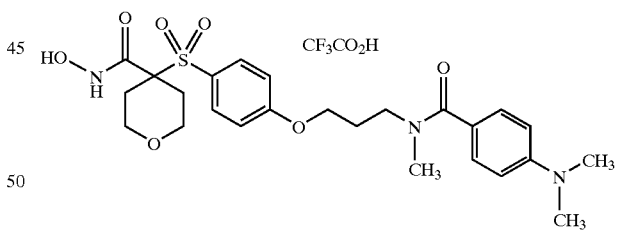

Part A

To a solution of 4-[[4-[3-[[4(dimethylamino)benzoyl]amino]propoxy]phenyl]sulfonyl]tetrahydro-2H-pyran-4-carboxylic acid, 1,1-dimethylethyl ester (prepared as in Example 17) in anhydrous N,N-dimethylformamide (3 mL) was added iodomethane (61 uL, 0.98 mmol), followed by sodium hydride (24 mg, 0.59 mmol; 60% dispersion in mineral oil). After 1 hr the reaction mixture was quenched with water, washed with brine (3×), dried over sodium sulfate, filtered, and concentrated in vacuo to yield the desired N-methylated product as a sticky solid. ESMS m/z=561 [M+H]+. HRMS calculated for $C_{29}H_{40}N_3O_7S$: 561.2634 [M+H]+, found: 561.2628.

Part B

The product from Part A (400 mg, 0.71 mmol) was taken up in neat trifluoroacetic acid (1 mL). After 1 hr, the trifluoroacetic acid was removed in vacuo at 60° C. to give the free acid as a sticky solid. ESMS m/z=505 [M+H]$^+$. To a solution of this material in anhydrous N,N-dimethylformamide (5 mL) was added 1-hydroxybenzotriazole (113 mg, 0.83 mmol), tetrahydropyranhydroxylamine (246 mg, 2.10 mmol), and triethylamine (390 uL, 2.8 mmol), followed by 1-(3dimethyaminopropyl)-3-ethylcarbodiimide hydrochloride (188 mg, 0.98 mmol). The reaction mixture was heated to 40° C. for 4 hr, and then cooled to ambient temperature. The reaction mixture was diluted with ethyl acetate, washed with saturated sodium bicarbonate solution (2×) and brine (4×), dried over sodium sulfate, filtered, and concentrated in vacuo. The crude product was de-protected and simultaneously purified by reverse phase HPLC to give 59 mg of the title compound as an off-white solid. ESMS m/z=520 [M+H]$^+$. HRMS calculated for $C_{25}H_{33}N_3O_7S$: 520.2117 [M+H]$^+$, found: 520.2120.

Additional compounds can be prepared by one skilled in the art using similar methods. Examples of such compounds include those having a structure corresponding to generic formula EX-G.

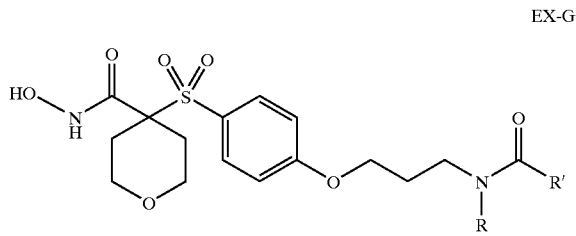

EX-G

Example 20

Preparation of 4-[[4-[[5-[[4-(dimethylamino)phenyl]amino]-5-oxopentyl]oxy]phenyl]sulfonyl]tetrahydro-N-hydroxy-2H-pyran-4-carboxamide, monohydrochloride

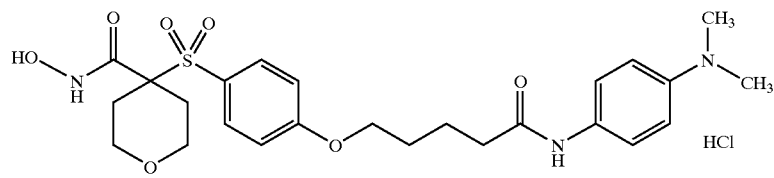

Part A

To a solution of 4-[[4-(4-carboxybutoxy)phenyl]sulfonyl]tetrahydro-2H-pyran-4-carboxylic acid, 1,1dimethylethyl ester (446 mg, 0.91 mmol, prepared as in Example 7) in anhydrous N,N-dimethylformamide (6 mL) was added 1-hydroxybenzotriazole (150 mg, 1.11 mmol), triethylamine (400 uL, 2.87 mmol), N,N-dimethyl-1,4-phenylenediamine (188 mg, 1.38 mmol), and finally 1-(3-dimethyaminopropyl)-3-ethylcarbodiimide hydrochloride (300 mg, 1.56 mmol). The reaction mixture was stirred at ambient temperature for 18 hr, and then concentrated in vacuo at 60° C. The residue was partitioned between ethyl acetate and saturated sodium bicarbonate solution. The organic layer was washed with brine (2×), dried over sodium sulfate, filtered, and concentrated in vacuo to give the desired amide. ESMS m/z=561 [M+H]$^+$. This material was taken up in neat trifluoroacetic acid (5 mL). After 3 hr the trifluoroacetic acid was removed in vacuo at 60° C. to give the free acid. ESMS m/z=505 [M+H]$^+$. To a solution of this material in anhydrous N,N-dimethylformamide (5 mL) was added 1-hydroxybenzotriazole (148 mg, 1.10 mmol), triethylamine (400 uL, 2.87 mmol), and tetrahydropyranhydroxylamine (320 mg, 2.73 mmol), followed by 1-(3-dimethyaminopropyl)-3-ethylcarbodiimide hydrochloride (262 mg, 1.37 mmol). The reaction mixture was stirred at ambient temperature overnight, and then partitioned between ethyl acetate and saturated sodium bicarbonate solution. The organic layer was washed with brine (3×), dried over sodium sulfate, filtered, and concentrated in vacuo. The crude material was purified by flash chromatography using 80% ethyl acetate/hexanes as eluant to afford the desired THP hydroxamate. ESMS m/z=604 [M+H]$^+$. HRMS calculated for $C_{30}H_{41}N_3O_8S$: 604.2693 [M+H]$^+$, found: 604.2709.

Part B

The product from Part A was dissolved in 4N HCl in dioxane (5 mL) and methanol (500 uL). After 3 hr at ambient temperature the reaction mixture was poured into rapidly stirring diethyl ether (50 mL). A purplish-pink solid was collected and subsequently purified by reverse phase HPLC. The title compound was obtained as a faint pink solid 131 mg (28% from the starting acid in part A). ESMS m/z=520 [M+H]$^+$. HRMS calculated for $C_{25}H_{33}N_3O_7SHCl$: 520.2117 [M+H]$^+$, found: 520.2127.

Additional compounds can be prepared by one skilled in the art using similar methods. Examples of such compounds include those having a structure corresponding to generic formula EX-H.

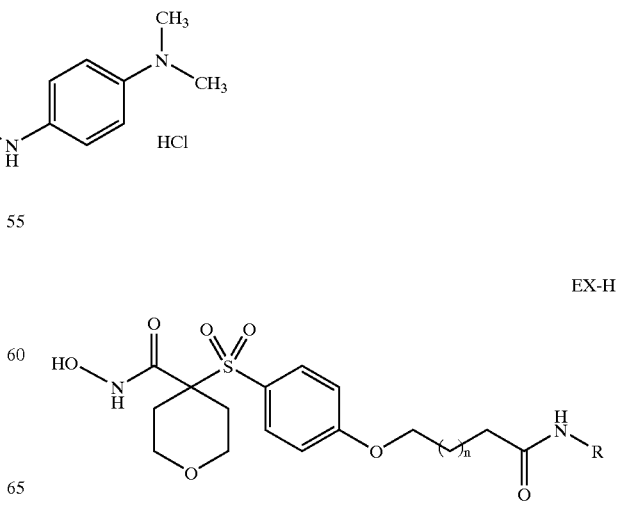

EX-H

Example 21

Preparation of 4-[[4-[3-(1,3-dihydro-1,3-dioxo-2-H-isoindol-2-yl)propoxy]phenyl]sulfonyl]tetrahydro-N-hydroxy-2H-pyran-4-carboxamide

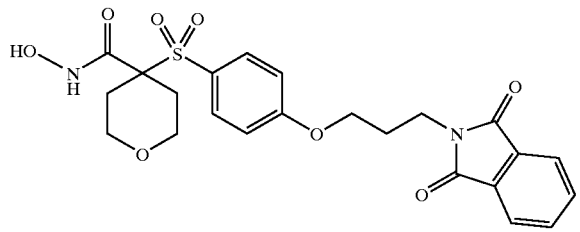

Part A

To a solution of 4-[(4-fluorophenyl)sulfonyl]tetrahydro-2H-pyran-4-carboxylic acid, 1,1-di-methylethyl ester (6.7 g, 19 mmol, as prepared in Example 1, Part C) in anhydrous N,N-dimethylformamide (40 ml) at ambient temperature was added N-(3-hydroxypropyl)phthalimide (4 g, 19 mmol), followed immediately by NaH (700 mg, 20 mmol, 60% dispersion in mineral oil). After 1.5 hr, HPLC showed less than 1% of the starting electrophile. The reaction mixture was quenched with water (60 ml). The cloudy mixture was extracted with ethyl acetate (2×100 ml). The organic layers were combined, washed with brine (1×200 ml), dried over sodium sulfate, filtered, and concentrated in vacuo to give a tan, viscous oil that crystallized from methanol (3.2 g, 520%). ESMS m/z=489 [M+H]$^+$. This material was used without further purification.

Part B

The product from Part A (3 g, 6 mmol) was dissolved in methylene chloride (304 ml) and trifluoroacetic acid (6 ml). After 12 hr, the mixture was concentrated in vacuo, and the residue was triturated with diethyl ether to form a solid which was collected and dried to afford the carboxylic acid as a beige solid (3 g, 90%). ESMS m/z=474 [M+H]$^+$. This material was used without further purification.

Part C

To a solution of the product from Part B (3 g, 6.2 mmol) in anhydrous N,N-dimethylformamide (25 ml) was added triethylamine (2 ml, 18 mmol), followed by tetrahydropyranhydroxylamine (1 g, 8 mmol), 1-hydroxybenzotriazole (0.5 g, 3 mmol), and 1-(3-dimethyaminopropyl)-3-ethylcarbodiimide hydrochloride (2 g, 8 mmol). The reaction mixture was heated at 40° C. for 0.5 hr. The reaction was monitored by RPHPLC. After 2 hr, the mixture was concentrated in vacuo, the residue was flooded with water, and the product separated as a solid. The solid was filtered, and was of sufficient purity to carry on to the next step. Mass spectral data and NMR were consistent with the desired product.

Part D

The solid from Part C (3 g) was slurried in methanol (1 mL) and diethyl ether (30 ml). To this was added 4N HCl in dioxane (10 ml) and stirred for 2 hr. RPHPLC showed complete reaction. The reaction mixture was concentrated by half, diethyl ether (100 mL) was added, and the white solid (1.5 g, 70% yield) filtered and dried under vacuum. $^1$H NMR was consistent with the desired product ESMS m/z $C_{23}H_{24}N_2O_8S$=489 [M+H]$^+$. HRMS calculated for $C_{23}H_{24}N_2O_8S$: 489.1332 [M+H]$^+$, found: 489.1298.

Example 22

Preparation of 4-[[4-[3-(1,3-dihydro-1-oxo-2H-isoindol-2-yl)propoxy]phenyl]sulfonyl]tetrahydro-N-hydroxy-2H-pyran-4-carboxamide

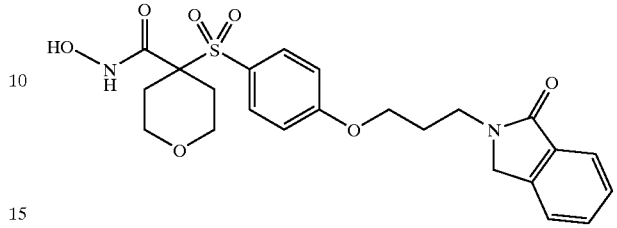

Part A

To a solution of 4-[(4-fluorophenyl)sulfonyl]tetrahydro-2H-pyran-4-carboxylic acid, 1,1-dimethylethyl ester (5.2 g, 15 mmol, as prepared in Example 1, Part C) in dimethyl sulfoxide (40 ml) at ambient temperature was added N-(3-hydroxypropyl)phthalide (3 g, 15 mmol, prepared according to J.Med.Chem., 146–157 (1996)), followed by cessium carbonate (12 g, 45 mmol). After 15 hr at 80° C., HPLC indicated complete reaction. The reaction mixture was quenched with water (60 ml). The cloudy mixture was extracted with ethyl acetate (2×100 ml). The organic layers were combined, washed with brine (1×200 ml), dried over sodium sulfate, filtered, and concentrated in vacuo to give a tan, viscous oil that crystallized from methanol (7 g, 720). ESMS m/z=516 [M+H]$^+$, NMR was consistent with desired product. This material was used without further purification.

Part B

The product from Part A (3 g, 6 mmol) was dissolved in methylene chloride (300 ml) and trifluoroacetic acid (6 ml). After 12 hr of stirring, the mixture was concentrated in vacuo and the residue was triturated with diethyl ether to form a solid which was collected and dried to afford the carboxylic acid as a beige solid (3 g, 91%). ESMS m/z=474 [M+H]$^+$. This material was used without fiber purification.

Part C

To a solution of the product from Part B (3 g, 6.2 mmol) in N,N-dimethylformamide (25 ml) was added triethylamine (2 ml, 18 mmol), followed by tetrahydropyranhydroxylamine (1.2 g, 8 mmol), 1-hydroxybenzotriazole (0.5 g, 3 mmol), and 1-(3-dimethyaminopropyl)-3-ethylcarbodiimide hydrochloride (1.5 g, 8 mmol). The reaction mixture was heated at 40° C. for 0.5 hr. The reaction was monitored by RPHPLC. After completion the mixture was concentrated and the residue was flooded with water. The resulting solid was filtered, and was of sufficient purity to carry on to the next step. Mass spectral data and NMR were consistent with the desired product.

Part D

The solid from Part C (3 g) was slurried in methanol (1 mL) and diethyl ether (30 ml). To this was added 4N HCl in dioxane (10 ml) and stirred for 2 hr. RPHPLC showed complete reaction. The reaction mixture was concentrated by half, diethyl ether (100 mL) was added, and the white solid (2.5 g, 90% yield) filtered and dried under vacuum. $^1$H NMR was consistent with the desired product. HRMS calculated for $C_{23}H_{26}N_2O_7S$: 475.1525 [M+H]$^+$, found: 475.1510.

Example 23

Preparation of 4-[[4-[[4E)-5-[-4-(dimethylamino) phenyl]-4-pentenyl]oxy]phenyl]sulfonyl]tetrahydro-N-hydroxy-2H-pyran-4-carboxamide and 4-[[4-[[4Z)-5-[-4-dimethyl-amino)phenyl]-4-pentenyl]oxy] phenyl]sulfonyl]tetrahydro-N-hydroxy-2H-pyran-4-carboxamide, monohydrochloride

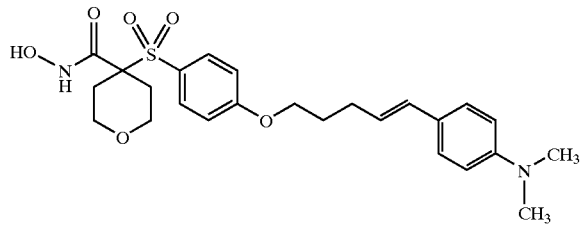

Part A

To a solution of 4-[(4-fluorophenyl)sulfonyl]tetrahydro-2H-pyran-4-carboxylic acid, 1,1-di-methylethyl ester (10.0 g, 29.0 mmol, as prepared in Example 1, Part C ) in N,N-dimethylformamide (60 ml) at ambient temperature was added 4-penten-1-ol (3.1 ml, 30.0 mmol), followed immediately by NaH (1.4 g, 34.8 mmol, 60% dispersion in mineral oil). After 1.5 hr, HPLC showed less than 1% of the starting material. The reaction mixture was quenched with water (60 ml). The cloudy mixture was extracted with ethyl acetate (3×-300 ml). The organic layers were combined; washed with 5% potassium hydrogensulfate (1×-200 ml), saturated sodium bicarbonate solution (1×-200 ml), water (1×200 ml), and brine (1×200 ml); dried over sodium sulfate; filtered; and concentrated in vacuo to give a tan oil. The crude product was partially purified by flash chromatography using 15% ethylacetate/hexanes to provide 11.7 g (98%) of the desired ether product as a clear, colorless oil. ESMS m/z=433 [M+Na]$^+$. This material was used without further purification.

Part B

To a solution of the product from Part A (2.0 g, 4.9 mmol) in N,N-dimethylformamide (3 ml) was added 4-bromo-N,N-dimethylaniline (1.2 g, 5.8 mmol), followed by triethylamine (1.4 ml, 9.8 mmol), tri-ortho-tolylphosphine (34 mg, 0.10 mmol), and palladium(II)acetate (12 mg, 0.05 mmol). The reaction was heated at 100° C. for 12 hr. The reaction was cooled and diluted with water (5 ml). The aqueous was extracted with ethyl acetate (3×15 ml). The organic extracts were dried over sodium sulfate, filtered, and concentrated in vacuo to afford a black oil (3.2 g). The black crude product was partially purified by flash chromatography using 5% ethyl acetate/hexanes to provide 1.2 g of the olefinic product as a tan oil (45% yield, trans:cis, 3:1). ESMS m/z=552 [M+Na]$^+$. This material was used without further purification.

Part C

The product from Part B (1.2 g, 2.3 mmol) was dissolved in methylene chloride (4 ml) and trifluoroacetic acid (4 ml). After 1 hr of stirring, the mixture was concentrated and the residue was triturated with diethyl ether to form a solid which was collected and dried to afford the carboxylic acid-TFA salt as a beige solid (0.73 g, 510). ESMS m/z=474 [M+H]$^+$. This material was used without further purification.

Part D

To a solution of the product from Part C (0.73 g, 1.2 mmol) in N,N-dimethylformamide (4 ml) was added triethylamine (0.9 ml, 6.2 mmol), followed by tetrahydropyranhydroxylamine (0.28 g, 2.4 mmol), 1-hydroxybenzotriazole (0.19 g, 1.4 mmol), and 1-(3-dimethyaminopropyl)-3-ethylcarbodiimide hydrochloride (0.32 g, 1.8 mmol). The reaction mixture was heated at 40° C. for 24 hr. The mixture was concentrated and the residue was purified via reverse phase chromatography (C$_{18}$, acetonitrile/water/TFA). Fractions (10 ml) were collected to separate the isomers. While analyzing, the aqueous TFA mixtures de-protected the product affording the hydroxamic acid final products. 4-[[4-[[4E)-5-[-4-(dimethylamino)phenyl]-4-pentenyl]oxy] phenyl]sulfonyl]-tetrahydro-N-hydroxy-2H-pyran-4-carboxamide, (98% trans isomer by HPLC, 0.12 g, 17% yield). HRMS calculated for C$_{23}$H$_{28}$N$_2$O$_8$S: 489.2059 [M+H]$^+$, found: 489.2067. $^1$H NMR confirmed trans isomerization (Job=15.9 Hz). 4-[[4-[[4Z)-5-[-4-(dimethyl-amino) phenyl]-4-pentenyl]oxy]phenyl]sulfonyl]tetrahydro-N-hydroxy-2H-pyran-4-carboxamide, monohydrochloride, (79% cis/17% trans by HPLC, 15 mg tan solid, 2% yield). HRMS calculated for C$_{25}$H$_{32}$N$_2$O$_6$S: 489.2059 [M+H]$^+$, found: 489.2067.

Example 24

Preparation of tetrahydro-N-hydroxy-4-[[4-[[5(4-methoxyphenyl)-5-oxopentyl]oxy]phenyl]sulfonyl]-2H-pyran-4-carboxamide

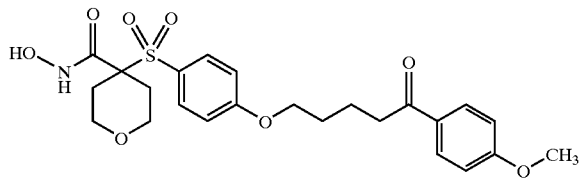

Part A

To a mixture of magnesium turnings (344 mg, 14.18 mmol) etched with iodine in anhydrous tetrahydrofuran (4 mL) at reflux was added 4-bromoanisole (1.2 mL, 9.45 mmol) dropwise over 10 min. The reaction mixture was heated at reflux for 45 min, and then cooled to ambient temperature. The prepared grignard reagent was added to a mixture of tetrahydro-4-[[4-[[5-methoxymethylamino)-5-oxopentyl]oxy]phenyl]sulfonyl]-N-[(tetrahydro-2H-pyran-2-yl)oxy]-2H-pyran-4-carboxamide (1.0 g, 1.9 mmol, as prepared in Example 7) in anhydrous tetrahydrofuran (10 mL) at 0° C. The reaction mixture was warmed to ambient temperature and left stirring overnight. The reaction was quenched with saturated ammonium chloride, and then partitioned between ethyl acetate and water. The layers were separated, and the organic layer was washed with brine, dried over sodium sulfate, filtered, and concentrated in vacuo. The crude material was purified by flash chromatography using 50–100% ethyl acetate/hexanes to afford 320 mg (29%) of the desired ketone as a white powder. ESMS m/z=593 [M+NH$_4$]$^+$. HRMS calculated for C$_{29}$H$_{37}$NO$_9$S: 593.2533 [M+NH$_4$]$^+$, found: 593.2555.

Part B

The product from Part A (300 mg, 0.52 mmol) was dissolved in 4N HCl in dioxane (3 mL) and methanol (300 uL). After 10 min at ambient temperature, the reaction mixture was poured into hexanes (75 mL), and the product precipitated out as an oil. The solvent was decanted and additional hexanes was added. The resulting solid was triturated with diethyl ether, and the title compound was obtained as an off-white solid ESMS m/z=492 [M+H]$^+$. HRMS calculated for C$_{24}$H$_{29}$NO$_8$S: 492.1692 [M+H]$^+$, found: 492.1713.

Additional compounds can be prepared by one skilled in the art using similar methods with either the t-butyl ester, THP protected hydroxamate, or resin bound hydroxamate of the weinreb amide. Examples of such compounds include those having a structure corresponding to generic formula EX-I.

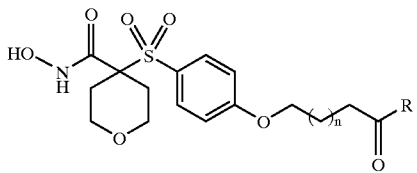

EX-I

Example 25

Preparation of tetrahydro-N-hydroxy-4-[[4-[[5-(hydroxyimino)-5-(4-methoxyphenyl)pentyl]oxy]phenyl]-sulfonyl]-2H-pyran-4-carboxamide

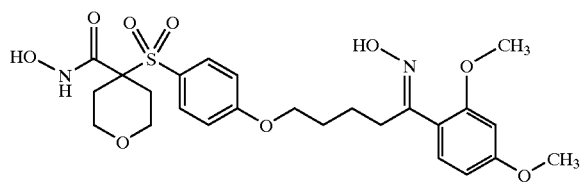

Part A

To a mixture of magnesium turnings (1.2 g, 49.4 mmol) etched with iodine in anhydrous tetrahydrofuran (4 mL) at reflux was added 1-bromo-2,4-dimethyoxybenzene (6.0 mL, 41.7 mmol) dropwise over 10 min. The reaction mixture was heated at reflux for 30 min, and then cooled to ambient temperature. The prepared grignard reagent was added to a mixture of tetrahydro-4-[[4-[3-(methoxymethyl-amino)-3-oxopropoxy]phenyl]sulfonyl]-2H-pyran-4-carboxylic acid, 1,1-dimethylethyl ester (1.0 g, 1.9 mmol, prepared as in Example 7) in anhydrous THF (10 mL) at 0° C. The reaction mixture was warned to ambient temperature, and, after 2 hr, was quenched with saturated ammonium chloride, and then partitioned between ethyl acetate and water. The layers were separated, and the organic layer was washed with brine, dried over sodium sulfate, filtered, and concentrated in vacuo. The crude material was covered with diethylether. The resulting green solid was triturated with diethyl ether. The final solid was collected to afford 2.2 g (94%) of the desired ketone as a pale green powder. ESMS m/z=585 [M+Na]$^+$. HRMS calculated for $C_{29}H_{38}NO_9S$: 563.2315 [M+H]$^+$, found: 563.2319.

Part B

The product from Part A (2.2 g, 3.91 mmol) was taken up in neat trifluoroacetic acid (6 mL). After 2 hr, the trifluoroacetic acid was removed in vacuo at 50° C. to give the free acid as a purple oil. ESMS m/z=507 [M+H]$^+$. To a solution of this material in anhydrous N,N-dimethylformamide (20 mL) was added 1-hydroxybenzotriazole (670 mg, 4.96 mmol), triethylamine (1.8 mL, 12.91 mmol), tetrahydropyranhydroxylamine (1.48 g, 12.63 mmol), and 1-(3-dimethyaminopropyl)-3-ethylcarbodiimide hydrochloride (1.13 g, 5.89 mmol). After 16 hr, the reaction mixture was concentrated in vacuo at 60° C. The crude material was partitioned between ethyl acetate and saturated sodium bicarbonate solution. The organic layer was washed with brine (2×), dried over sodium sulfate, filtered, and concentrated in vacuo to yield a yellow oil. Purification by flash chromatography using 80% ethyl acetate/hexanes afforded a mixture of THP hydroxamate/THP oxime (78%) and THP hydroxamate ketone (12%). ESMS m/z=621 [M+H]$^+$ and ESMS m/z=628 [M+H]$^+$ respectively. These products were not separated, and instead were carried forward as a mixture.

Part C

The product from Part B (540 mg, 0.77 mmol) was dissolved in 4N HCl in dioxane (5 mL) and methanol (500 uL). After 2 hr at ambient temperature the reaction mixture was poured into rapidly stirring diethyl ether. A pale pinkish/purple solid was collected and purified by reverse phase HPLC. The title compound was obtained as a white solid. ESMS m/z=537 [M+H]$^+$. HRMS calculated for $C_{25}H_{32}N_2O_9S$: 537.1907 [M+H]$^+$, found: 537.1921.

Example 26

Preparation of tetrahydro-N-hydroxy-4-[[4-[[5-(4-methyloxyphenyl)-4-methyl-5-oxopentyl]oxy]phenyl]sulfonyl]-2H-pyran-4-carboxamide

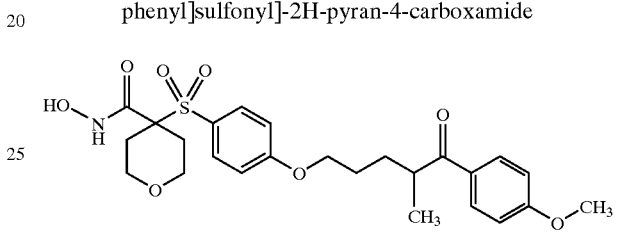

Part A

To a solution of tetrahydro-4-[[4-[[5-(4methoxyphenyl)-5-oxopentyl]oxy]phenyl]sulfonyl]-2H-pyran-4-carboxylic acid, 1,1-dimethylethyl ester (532 mg, 1.0 mmol, prepared as in Example 24) and iodomethane (623 mg, 4.4 mmol) in 5 ml N,N-dimethylformamide was added sodium hydride (125 mg, 3.1 mmol, 60% dispersion in mineral oil). The reaction was stirred 40 min then quenched with 1N HCl$_{aq}$. The reaction mixture was partitioned between ethyl acetate and 5% aqueous potassium hydrogensulfate. The organic phase was dried over sodium sulfate, filtered, and concentrated in vacuo to give a crude oil. Purification by flash chromatography using 40% ethyl acetate/hexanes afforded 370 mg (68% yield) of the desired monomethyl ketoester. ESMS m/z=547 [M+H]$^+$.

Part B

The product from Part A (370 mg, 0.68 mmol) was taken up in neat trifluoroacectic acid. After 45 min, HPLC analysis indicated that the reaction was complete. The trifluoroacetic acid was removed in vacuo, and the residue chased with acetonitrile (2×10 ml), and then vacuum dried to yield 335 mg of the free acid. ESMS m/z=491 [M+H]$^+$. To a solution of this material in anhydrous N,N-dimethylformamide (4 mL) was added 1-hydroxybenzotriazole (138 mg, 0.68 mmol) and 1-(3-dimethyaminopropyl)-3-ethylcarbodiimide hydrochloride (150 mg, 0.78 mmol), followed by triethylamine (190 uL, 1.36 mmol) and tetrahydropyranhydroxylamine (160 mg, 1.37 mmol). After 16 hr, the reaction mixture was partitioned between ethyl acetate and 5% aqueous potassium hydrogensulfate. The combined organic extracts were washed with brine, dried over sodium sulfate, filtered, and concentrated in vacuo to a crude oil. Purification by flash chromatography using 60% ethyl acetate/hexanes as eluant afforded 270 mg (67%) of the desired THP protected hydroxamate. ESMS m/z=590 [M+H]$^+$.

Part C

The product from Part B (270 mg, 0.46 mmol) was dissolved in 4N HCl in dioxane (2 mL) and methanol (500 uL). After 15 min at ambient temperature, the reaction mixture was partitioned between ethyl acetate and water. The organic layer was dried over sodium sulfate, filtered, and concentrated in vacuo to yield 200 mg (86%) of the title compound. ESMS m/z=406 [M+H]$^+$. HRMS calculated for $C_{25}H_{31}NO_8S$ 506.1849 [M+H]$^+$, found: 506.1828.

Example 27

Preparation of 4-[[4-[[4Z)-5-cyano-5-(4-methoxyphenyl)-4-pentenyl]oxy]phenyl]sulfonyl] tetrahydro-N-hydroxy-2H-pyran-4-carboxamide

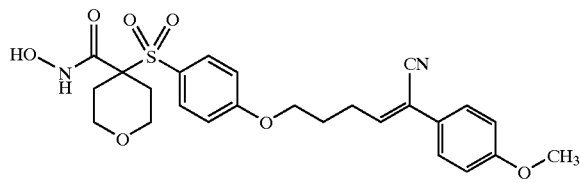

Part A

To a solution of tetrahydro-4-[[4-[[5-(4-methoxyphenyl)-5-oxopentyl]oxy]phenyl]sulfonyl]-2H-pyran-4-carboxylic acid, 1,1-dimethylethyl ester (1.0 g, 1.9 mmol, prepared as in Example 24) in 15 ml methylene chloride was added trimethylsilyl cyanide (300 uL, 2.2 mmol) and zinc iodide (660 mg, 2.1 mmol). The reaction was stirred at ambient temperature for 3 hr, and then concentrated in vacuo. The residue was partitioned between ethyl acetate and 1 N HCl$_{aq}$. The organic layer was dried over sodium sulfate, filtered, and concentrated in vacuo. The crude product was purified by flash chromatography using 25% ethyl acetate/hexanes to afford 950 mg (81%) of the silylated cyanohydrin. This material was taken up in trifluoroacetic acid (15 mL). The dark red solution showed various peaks by HPLC analysis over the first 40 min. After 1 hr, HPLC analysis indicated 1 new peak at 93%. The reaction mixture was concentrated in vacuo and chased with acetonitrile (2×10 ml). The crude solid was dissolved in methanol and added to 40 ml diethyl ether. The resulting white solid was filtered and dried to yield 630 mg of the free acid/cyano olefin. ESMS m/z=486 [M+H]$^+$.

Part B

To a solution of the product from Part A (630 mg, 1.3 mmol) in anhydrous N,N-dimethylformamide (15 mL) was added 1-hydroxybenzotriazole (285 mg, 2.1 mmol) and 1-(3-dimethyaminopropyl)-3-ethylcarbodiimide hydrochloride (285 mg, 1.5 mmol), followed by N-methylmorpholine (545 uL, 5.0 mmol) and tetrahydropyranhydroxylamine (456 mg, 3.9 mmol). After 20 hr, the reaction mixture was concentrated in vacuo, and then partitioned between ethyl acetate and 5% aqueous potassium hydrogensulfate. The combined organic extracts were washed with brine, dried over sodium sulfate, filtered, and concentrated in vacuo. Purification by flash chromatography using 80% ethyl acetate/hexanes to afford 530 mg (70%) of the desired THP protected hydroxamate. ESMS m/z=585 [M+H]$^+$.

Part C

The product from Part B (530 mg, 0.91 mmol) was dissolved in 4N HCl in dioxane (5 mL) and methanol (1 mL). After 15 min at ambient temperature, the reaction mixture was partitioned between ethyl acetate and water. The organic layer was dried over sodium sulfate, filtered, and concentrated in vacuo to yield 360 mg of the desired hydroxamate. Purification by reverse phase HPLC afforded 270 mg (59%) of the title compound. ESMS m/z=504 [M+H]$^+$. HRMS calculated for $C_{25}H_{28}N_2O_7S$: 501.1695 [M+H]$^+$, found: 501.1689.

Example 28

Preparation of tetrahydro-N-hydroxy-4-[[4[[(4E)-5-(4-methoxyphenyl)-4-hexenyl]oxy]phenyl]sulfonyl]-2H-pyran-4-carboxamide

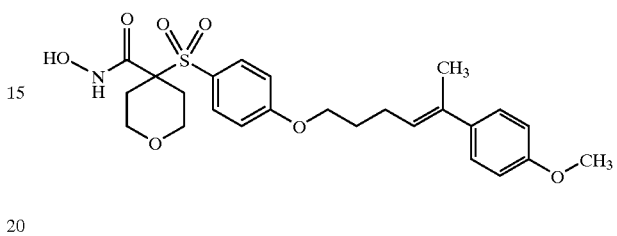

Part A

To a cooled (0° C.) solution of 4-[(4-{[5-(4-methoxyphenyl)-5-oxopentyl]oxy}phenylsulfonyl]-N-(tetrahydro-2H-pyran-2-yloxy)tetrahydro-2H-pyran-4-carboxamide (0.2 g, 0.4 mmol, as prepared in Example 24) in tetrahydrofuran (2 ml) was added a 3.0 M solution of methylmagnesium bromide (1.2 ml, 3.6 mmol). The ice bath was removed, and the reaction stirred for 2 hr at room temperature. HPLC showed less than 1% of the ketone starting material. The reaction mixture was diluted with ethyl acetate and washed with saturated ammonium chloride solution, water, and brine. After drying over sodium sulfate and filtering, the organic layer was concentrated in vacuo to afford 0.25 g (100%) of a tan oil. ESMS m/z=614 [M+Na]$^+$. This material was used without further purification.

Part B

To the product from Part A (0.24 g, 0.4 mmol) was added methanol (0.5 ml) and 4 N HCl in dioxane (4.0 ml). After stirring 2 hr, HPLC showed no remaining starting material. Diethyl ether was added to form a solid but a gummy residue developed. The mixture was concentrated and the oily residue was purified via reverse phase HPLC (C$_{18}$, acetonitrile/water/TFA) to afford 0.11 g (55%) of the desired product as a tan oil. $^1$H NMR (N.O.E) confirmed the isomerized mixture as 70% trans:30% cis. HRMS calculated for $C_{25}H_{31}NO_7S$: 490.1899 [M+H], found: 490.1898.

Additional compounds can be prepared by one skilled in the art using similar methods. Examples of such compounds include those having a structure corresponding to generic formula EX-J.

EX-J

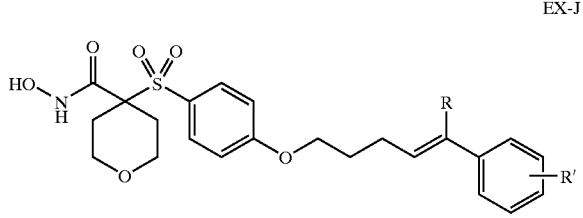

Example 29

Preparation of 3,4-dihydro-N-[3-[4-[[tetrahydro-4-[(hydroxyamino)carbonyl]-2H-pyran-4-yl]sulfonyl]-phenoxy]propyl]-2-(1H)-isoquinolinecarboxamide

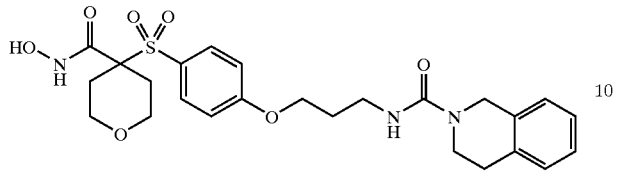

Part A

To a solution of 4-[[4-(3-aminopropoxy)-phenyl]sulfonyl]tetrahydro-2H-pyran-4-carboxylic acid 1,1-dimethylethyl ester, monohydrochloride (467 mg, 1.07 mmol, prepared in Example 1) in anhydrous chloroform (3 mL) at ambient temperature was added triethylamine (170 uL, 1.22 mmol) and 1,1'-carbonyldiimidazole (180 mg, 1.11 mmol). After 1 hr at 50° C., 1,2,3,4-tetrahydroisoquinoline (162 mg, 1.22 mmol) was added neat. After an additional 2 hr at 50° C., HPLC indicated complete reaction. The reaction mixture was partitioned between ethyl acetate and 5% aqueous potassium hydrogen sulfate. The organic layer was washed with saturated sodium bicarbonate solution and brine, dried over sodium sulfate, filtered, and concentrated in vacuo to give a yellow oil. ESMS m/z=559 [M+H]+. This material was used without further purification.

Part B

The product from Part A was taken up in neat trifluoroacetic acid (3 mL). After 13 hr, the trifluoroacetic acid was removed in vacuo at 50° C. to give the free acid. ESMS m/z=503 [M+H]+. To a solution of this material in anhydrous N,N-dimethylformamide (5 mL) was added 1-hyrdoxybenzotriazole (176 mg, 1.30 mmol), triethylamine (500 uL, 3.59 mmol), and tetrahydropyranhydroxylamine (254 mg, 2.17 mmol), followed by 1-(3-dimethyaminopropyl)-3-ethylcarbodiimide hydrochloride (310 mg, 1.62 mmol). The reaction mixture was heated at 40° C. for 4 hr, and then stirred at ambient temperature overnight. The reaction mixture was concentrated in vacuo at 60° C. The residue was partitioned between ethyl acetate and saturated sodium bicarbonate solution. The layers were separated, and the organic layer was washed with brine (3×), dried over sodium sulfate, filtered, and concentrated in vacuo. The crude product was purified by flash chromatography to give 260 mg (40% from the starting amine) of the desired THP protected hydroxamate as a white solid. ESMS m/z=624 [M+Na]+. HRMS calculated for $C_{30}H_{39}N_3O_8S$: 602.2536 [M+H]+, found: 602.2546.

Part C

The product from Part B (252 mg, 0.42 mmol) was dissolved in 4N HCl in dioxane (5 mL) and methanol (500 uL). After 1 hr at ambient temperature, the reaction mixture was poured into rapidly stirring diethyl ether. A white solid was collected and dried over P2O5 under vacuum. The title compound was obtained as a white solid. ESMS m/z=518 [M+H]+. HRMS calculated for $C_{25}H_{31}N_3O_7S$: 518.1961 [M+H]+, found: 518.1961.

Additional compounds can be prepared by one skilled in the art using similar methods (urea formation also can be achieved by coupling the starting amine with and an isocyanate). Examples of such compounds include those having a structure corresponding to generic formula EX-K.

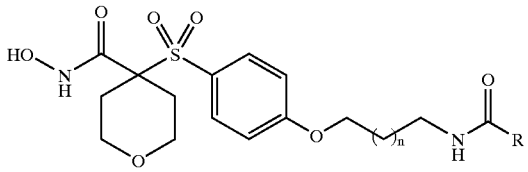

EX-K

Example 30

Preparation of tetrahydro-N-hydroxy-4-[[4-[3-[4-(4-ethoxyphenyl)-2-oxazolyl]propoxy]phenyl]sulfonyl]-2Hpyran-4-carboxamide

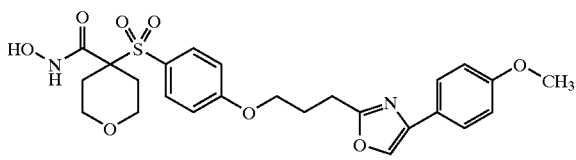

Part A

To a solution of 4-[[4-(3-carboxypropoxy)phenyl]sulfonyl]tetrahydro-2H-pyran-4-carboxylic acid, 1,1-dimethylethyl ester (3.2 g, 7.5 mmol, prepared as in Example 7) in acetone (15 mL) was added 2-bromo-4-methoxyacetophenone (1.72 g, 7.5 mmol) and potassium carbonate (1.04 g, 7.5 mmol). The reaction mixture was stirred at ambient temperature for 3 hr. The reaction mixture was filtered, and the cake washed with acetone. The acetone solution was concentrated in vacuo. Purification by flash column chromatography using ethyl acetate/hexanes provided 3.68 g (85%) of the substituted ester as a white solid. ESMS m/z=599 [M+Na]+.

Part B

The product from Part A (3.6 g, 6.25 mmol) was refluxed in acetic acid (12 mL) with ammonium acetate (2.41 g, 31.25 mmol) for 24 hr. The reaction was diluted with ethyl acetate (50 mL) and washed 2 times with water (25 mL) and filtered. The ethyl acetate filtrate was extracted with a 10% aqueous NaOH (50 mL). The basic solution was then acidified to a pH of 1, and then extracted with ethyl acetate (25 mL). The organic solution was then washed with water (25 mL), dried over sodium sulfate, filtered, and concentrated in vacuo to give 1.5 g (48%) of the carboxylic acid of the oxazole as a brown solid. ESMS m/z=502 [M+H]+.

Part C

In dry equipment under nitrogen, the carboxylic acid from Part B (1.3 g, 2.59 mmol) was dissolved in dry N,N-dimethylformamide (5 mL), and the remaining reagents were added to the solution in the following order: 1-hydroxybenzotriazole (490 mg, 3.63 mmol), triethylamine (0.43 mL, 3.11 mmol), tetrahydropyranhydroxylamine (364 mg, 3.11 mmol), and 1-(3-dimethylaminopropyl)-3-ethylcarbodiimide hydrochloride (746 mg, 3.89 mmol). After 12 hr at 40° C., the reaction was concentrated in vacuo. The residue was taken up in ethyl acetate, washed with water, saturated sodium bicarbonate solution, and brine, dried over sodium sulfate, filtered, and concentrated in vacuo. Purification by flash column chromatography using ethyl acetate/hexanes provided 0.70 g (450) of the THP hydroxamate as a white foam. ESMS m/z=601 [M+H]+.

Part D

To a solution of the product from Part C (0.6 g, 1.0 mmol) in 1,4-dioxane (1.0 mL) was added 4N HCl in dioxane (1.25 mL, 5 mmol) and methanol (0.13 mL). After 1 hr at ambient temperature, the reaction was diluted with ethyl acetate and washed with water, dried over sodium sulfate, filtered, and concentrated in vacuo. Methylene chloride (20 mL) was added, and the solution was stripped to afford 0.29 g (56%) of the title compound as a light pink solid. HRMS calculated for $C_{25}H_{28}N_2O_8S$: 517.1645 $[M+H]^+$, found: 517.1651.

Additional compounds can be prepared by one skilled in the art using similar methods. Examples of such compounds include those having a structure corresponding to generic formula EX-L.

EX-L

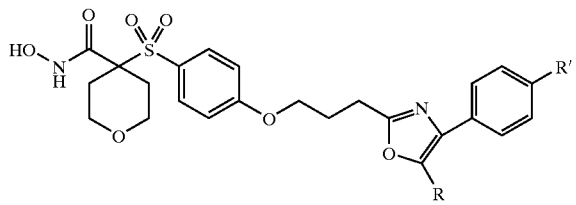

Example 31

Preparation of tetrahydro-N-hydroxy-4-[[4-[3-[3[4-(trifluoromethoxy)phenyl]-1,2,4-oxadiazol-5-yl]propoxy]phenyl]sulfonyl]-2H-pyran-4-carboxamide

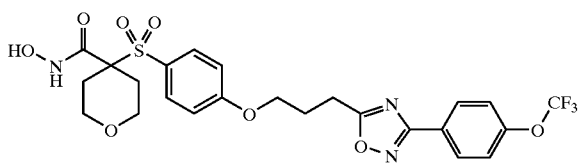

Part A

In dry equipment under nitrogen, 4-[[4-(3-carboxypropoxy)phenyl]sulfonyl]tetrahydro-2H-pyran-4-carboxylic acid, 1,1-dimethylethyl ester (2.57 g, 6.0 mmol, prepared as in Example 7) was dissolved in dry N,N-dimethylformamide (12 mL), and the remaining reagents were added to the solution in the following order: 1-hydroxybenzotriazole hydrate (1.13 g, 8.4 mmol), triethylamine (1.0 mL, 7.2 mmol), 4-(trifluoromethoxy)benzamidoxime (1.58 g, 7.2 mmol), and 1-(3-dimethylaminopropyl)-3-ethylcarbodiimide hydrochloride (1.73 g, 9.0 mmol). After 2 hr at 35° C., the reaction was concentrated in vacuo. The residue was taken up in ethyl acetate, washed with water, saturated sodium bicarbonate solution, and brine, dried over sodium sulfate, filtered, and concentrated in vacuo. Purification by flash column chromatography using ethyl acetate/hexanes afforded 3.05 g (81%) of the desired product as a clear glass. ESMS m/z= 631 $[M+Na]^+$.

Part B

The product from Part A (2.9 g, 4.60 mmol) was heated at 90° C. in toluene (15 mL) for 30 hr. The reaction was concentrated in vacuo. Purification by column chromatography using ethyl acetate/hexanes afforded 2.06 g (73%) of the oxadiazole as a white solid. ESMS m/z 635 $[M+Na]^+$.

Part C

The product from Part B (2.0 g, 3.27 mmol) was dissolved in trifluoroacetic acid (8 mL) and stirred at ambient temperature for 2 hr. The reaction was diluted with methylene chloride (10 mL) and concentrated in vacuo. Methylene chloride (10 mL) was added to the residue and concentrated in vacuo again to provide 1.8 g (99%) of the free acid as an off-white solid. ESMS m/z=557 $[M+H]^+$.

Part D

In dry equipment under nitrogen, the product from Part C (1.7 g, 3.06 mmol) was dissolved in dry N,N-dimethylformamide (6 mL), and the remaining reagents were added to the solution in the following order: 1-hydroxybenzotriazole hydrate (578 mg, 4.28 mmol), triethylamine (0.51 mL, 3.67 mmol), tetrahydropyranhydroxylamine (429 mg, 3.67 mmol), and 1-(3-dimethylaminopropyl)-3-ethylcarbodiimide hydrochloride (879 mg, 4.59 mmol). After 90 min at 40° C., the reaction was concentrated in vacuo. The residue was taken up in ethyl acetate, washed with water, saturated sodium bicarbonate solution, and brine, dried over sodium sulfate, filtered, and concentrated in vacuo. Purification by flash column chromatography using ethyl acetate/hexanes provided 1.9 g (95%) of the THP hydroxamate as a white foam. ESMS m/z=678 $[M+Na]^+$.

Part E

To a solution of the product from Part D (1.8 g, 2.75 mmol) in 1,4-dioxane (1.0 mL) was added 4N HCl in dioxane (3.5 mL, 13.7 mmol) and methanol (0.35 mL). After 2 hr at ambient temperature, the reaction was diluted with ethyl acetate and washed with water, dried over sodium sulfate, filtered, and concentrated in vacuo. Reverse phase chromatography provided 1.12 g (71%) of the title compound as a white solid. HRMS calculated for $C_{24}H_{24}N_3O_8S_1F_3$: 572.1314 $[M+H]^+$, found: 572.1290.

Example 32

Preparation of tetrahydro-N-hydroxy-4-[[4-[3-[5-(2-methylphenyl)-1,3,4-oxadiazol-2-yl]propoxy]phenyl]sulfonyl]-2H-pyran-4-carboxamide

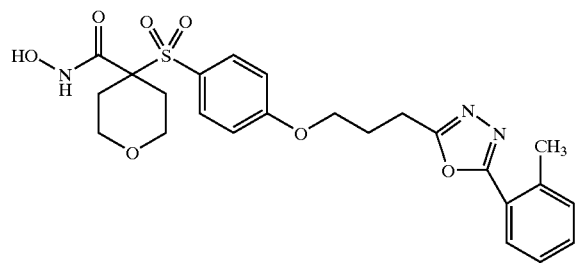

Part A

In dry equipment under nitrogen, 4-[[4-(3-carboxypropoxy)phenyl]sulfonyl]tetrahydro-2H-pyran-4-carboxylic acid, 1,1-dimethylethyl ester (2.14 g, 5.0 mmol, prepared as in Example 7) was dissolved in dry N,N-dimethylformamide (10 mL), and the remaining reagents were added to the solution in the following order: 1-hydroxybenzotriazole hydrate (945 mg, 7.0 mmol), triethylamine (0.84 mL, 6.0 mmol), o-toluic hydrazide (901 mg, 6.0 mmol), and 1-(3-dimethylaminopropyl)-3-ethylcarbodiimide hydrochloride (1.44 g, 7.5 mmol). After 2 hr at 35° C., the reaction was concentrated in vacuo. The residue was taken up in ethyl acetate; washed with water, saturated sodium bicarbonate solution, and brine; dried over sodium sulfate; filtered; and concentrated in vacuo. Purification by flash column chromatography using ethyl acetate/hexanes provided 2.32 g (83%) of the desired product as a white foam. ESMS m/z=583 $[M+Na]^+$.

Part B

The product from Part A (2.1 g, 3.75 mmol) was heated to reflux in toluene (25 mL) with p-toluenesulfonic acid (100 mg) for 4 hr. The reaction was concentrated in vacuo. Recrystalization from hot methanol provided 1.6 g (88%) of the free acid of the oxadiazole as a white solid. ESMS m/z=487 [M+Na]+.

Part C

In dry equipment under nitrogen, the product from Part B (1.5 g, 3.09 mmol) was dissolved in dry N,N-dimethylformamide (6 mL), and the remaining reagents were added to the solution in the following order: 1-hydroxybenzotriazole hydrate (578 mg, 4.28 mmol), triethylamine (0.51 mL, 3.67 mmol), tetrahydropyranhydroxylamine (429 mg, 3.67 mmol), and 1-(3dimethylaminopropyl)-3-ethylcarbodiimide hydrochloride (879 mg, 4.59 mmol). After 6 hr at 40° C., the reaction was concentrated in vacuo. The residue was taken up in ethyl acetate; washed with water, saturated sodium bicarbonate solution, and brine; dried over sodium sulfate; filtered; and concentrated in vacuo. Purification by flash column chromatography using ethyl acetate/hexanes provided 1.53 g (85%) of the THP hydroxamate as a white foam. ESMS m/z=608 [M+Na]+.

Part D

To a solution of the product from Part C (1.4 g, 2.39 mmol) in 1,4dioxane (1.0 mL) was added 4N HCl in dioxane (6 mL, 23.9 mmol) and methanol (0.6 mL). After 2 hr at ambient temperature, the reaction was diluted with ethyl acetate and washed with water, dried over sodium sulfate, filtered, and concentrated in vacuo. Reverse phase chromatography provided 1.02 g (85%) of the title compound as a white solid. HRMS calculated for $C_{24}H_{27}N_3O_7S_1$: 502.1648 [M+H]+, found: 502.1652.

Additional compounds can be prepared by one skilled in the art using similar methods. Examples of such compounds include those having a structure corresponding to generic formula EX-M.

EX-M

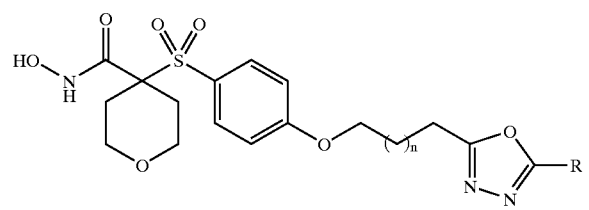

Example 33

Preparation of 4-[[4-[3-(2-benzoxazolylthio)propoxy]phenyl]sulfonyl]tetrahydro-N-N-hydroxy-2H-pyran-4-carboxamide

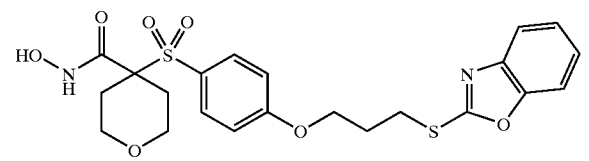

Part A

To a solution of 2-mercaptobenzoxazole (290 mg, 1.92 mmol) in N,N-dimethylformamide (5 mL) at 0° C. was added NaH (128 mg, 1.92 mmol, 60% dispersion in mineral oil). After 30 min, tetrahydro-4-[[4-[3-[(methylsulfonyl)oxy]propoxy]phenyl]sulfonyl]-N-[(tetrahydro-2H-pyran-2-yl)oxy]-2H-pyran-4-carboxamide (1.0 g, 1.92 mmol, prepared as in Example 29) was added, and the solution was stirred for 2 hr at 65° C. The solution was partitioned between ethyl acetate and water. The organic layer was washed with water and brine, dried over sodium sulfate, filtered, and concentrated in vacuo to afford 510 mg (46%) of the thiobenzoxazole as a crude dark oil. ESMS m/z=577 [M+H]+.

Part B

To a solution of the crude thiobenzoxazole of Part A (505 mg, 0.88 mmol) in 1,4-dioxane (5 mL) was added 4 N HCl in dioxane (5 mL), and was stirred for 2 hr. Purification by reverse phase HPLC ($C_{18}$, acetonitrile/water) provided 257 mg (60%) of the title compound as a white solid. ESMS m/z=493 [M+H]+. HRMS calculated for $C_{22}H_{24}N_2O_7S_2$: 493.1103, found 493.1122. Analytical calculation for $C_{22}H_{24}N_2O_7S_2 \cdot 0.3H_2O$: C, 53.06; H, 4.98; N, 5.63; S, 12.88. Found: C, 53.08; H, 5.03; N, 5.62; S 12.69.

Additional compounds can be prepared by one skilled in the art using similar methods. Examples of such compounds include those having a structure corresponding to generic formula EX-N.

EX-N

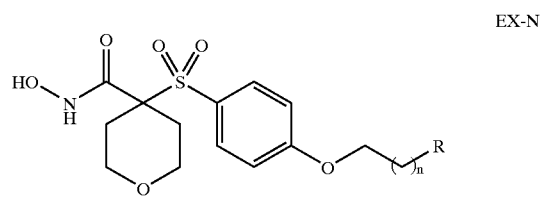

Example 34

Preparation of 4-[[4-[tetrahydro-4-[(hydroxyamino)carbonyl]-2H-pyran-4-yl]sulfonyl]cyclohexyl]oxy] butyl ester 3,4-dihydro-2(1H)-isoquinolinecarboxylic acid

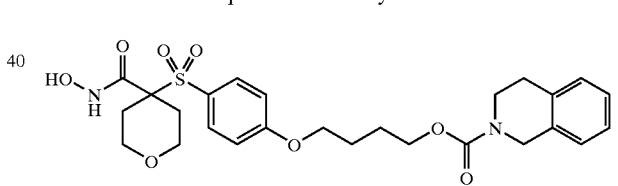

Part A

To a solution of tetrahydro-4-[[4-[4-[(methylsulfonyl)oxy]butoxy]phenyl]sulfonyl]-N-[(tetrahydro-2H-pyran-2-yl)oxy]-2H-pyran-4-carboxamide (200 mg, 0.37 mmol, synthesized in a fashion similar to Example 29) in anhydrous N,N-dimethylformamide (2 mL) was added to 1,2,3,4-tetrahydroisoquinoline (0.24 mL, 1.9 mmol) and cesium carbonate (0.62 g, 1.9 mmol). The reaction mixture was stirred at ambient temperature overnight. The crude reaction mix was poured onto a 20 mL ChemElut tube (celite) prewetted with 15 mL of water, and eluted with 1:1 ethyl acetate:methylene chloride. Purification by reverse phase HPLC (C18, acetonitrile/water), followed by treatment with 2 mL of 4N HCl in dioxane, provided 12.2 mg (6.2) of the desired product as an amorphous solid after lyophilization. ESMS m/z=531 [M+H]+. HRMS calculated for $C_{26}H_{33}N_2O_8S$: 533.1958 [M+H]+, found: 533.1943.

Additional compounds cam be prepared by one skilled in the art using similar methods. Examples of such compounds include those having a structure corresponding to generic formula EX-O.

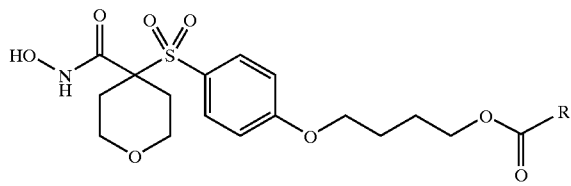

EX-O

Example 35

Preparation of 4-[[4-[4-(1,3-dihydro-1,3-dioxo-2H-isoindol-2-yl)butyl]phenyl]sulfonyl]tetrahydro-N-hydroxy-2H-pyran-4-carboxamide

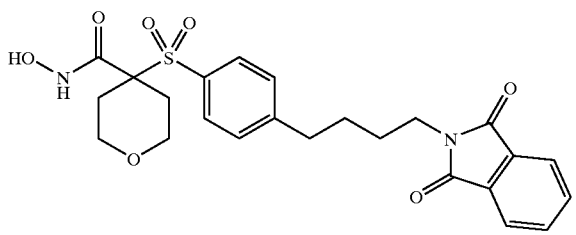

Part A

A solution of 4-bromobenzenethiol (28.5 g, 151 mmol) in N,N-dimethylformamide (250 mL) was purged with nitrogen for 10 min and then potassium carbonate (22.9 g, 166 mmol) was added. After purging for another 10 min with nitrogen, t-butyl bromoacetate (24.5 g, 166 mmol) was added, and the reaction was stirred at ambient temperature for 1 hr. The reaction was chilled to 0° C. and diluted with water (250 mL). The slurry was extracted with ethyl acetate. The organic layer was washed with water, saturated sodium bicarbonate solution, and brine; dried over sodium sulfate; filtered; and concentrated in vacuo to provide 49.8 g (100%) of the sulfide as a light yellow oil. ESMS m/z=3 2 0 [M+NH4]+.

Part B

To a solution of the product from Part A (45.67 g, 151 mmol) in tetrahydrofuran (300 mL) was added water (75 mL) and Oxone™ (278.5 g, 453 mmol) at 20° C. An exotherm to 43° C. was observed. After 3 hr, the reaction was filtered, and the cake was washed well with tetrahydrofuran. The filtrate was concentrated in vacuo to 1 third the volume. The residue was taken up in ethyl acetate, washed with brine, dried over magnesium sulfate, filtered, and concentrated in vacuo to give 51.0 g (100%) of the sulfone as a crystalline solid. ESMS m/z=335 [M+H]+.

Part C

To a solution of the product from Part B (23.45 g, 16 mmol) in N,N-dimethylformamide (140 mL) was added potassium carbonate (19.3 g, 140 mmol), bis-(2-bromoethyl) ether (9.1 mL, 70 mmol), and 18-Crown-6 (1 g). The slurry was stirred at 60° C. After 16 hr, the reaction was filtered, and the filtrate was concentrated in vacuo. The residue was taken up in ethyl acetate, washed with water (3×) and brine, dried over sodium sulfate, filtered, and concentrated in vacuo. The product was recrystallized from methanol to provide 19.79 g (70%) of the desired compound as a white solid. (ESMS m/z=405 [M+H]+.

Part D

To a solution of N-(3-buten-1-yl)phthalimide (1.2 g, 5.97 mmol) in anhydrous tetrahydrofuran (3 mL) at 0° C. was added 0.5 M 9-borobicyclononane in tetrahydrofuran (11.9 mL, 5.97 mmol) dropwise. The resultant solution was stirred with cooling for 10 min, and then the ice bath was removed. After 18 hr, the product from Part C (1 g, 2.98 mmol), tetrakis(triphenyl-phosphine)palladium(0) (172 mg, 0.15 mmol) and 2 M sodium carbonate (3 mL, 6 mmol) were added, and the reaction mixture was heated to 65° C. for 2 hr. After cooling to ambient temperature, the solution was concentrated in vacuo. The residue was partitioned between ethyl acetate (50 mL) and water (50 mL). The layers were separated, and the organic layer was washed with water (50 mL) and brine (50 mL), dried over magnesium sulfate, filtered, and concentrated in vacuo. Purification by flash column chromatography using 25–50% ethyl acetate/hexanes yielded 1.21 g of the desired compound as an off-white solid. HRMS calculated for $C_{25}H_{37}N_2O_7S$: 545.2321 [M+H]+, found: 545.2311.

Part E

To a solution of the product from Part D (1.16 g, 2.2 mmol) in anhydrous methylene chloride (20 mL) at ambient temperature was added trifluoroacetic acid (20 mL). The solution was stirred for 2 hr, and then concentrated in vacuo. The resulting residue was dissolved in methanol (50 mL) and concentrated in vacuo, and subsequently dissolved in methylene chloride (50 mL) and concentrated in vacuo. Trituration with hexanes yielded 0.98 g of the carboxylic acid as an off-white solid. HRMS calculated for $C_{28}H_{37}N_2O_7S$: 489.1695 [M+NH4], found: 489.1702.

Part F

To a solution of the product from Part E (0.95 g, 2.01 mmol) in a mixture of methylene chloride (4 mL) and N,N-dimethylformamide (4 mL) was added triethylamine (0.28 mL, 2.01 mmol), 1-hydroxybenzotriazole (0.407 g, 3.015 mmol), and 1-[3-(dimethylamino)propyl]-3-ethylcarbodiimide hydrochloride (0.538 g, 2.814 mmol). After 10 min, additional triethylamine (0.56 mL, 4.02 mmol) and tetrahydropyranhydroxylamine (0.706 g, 6.03 mmol) were added. The solution was warmed to 38° C. and stirred for 20 hr. The mixture was partitioned between ethyl acetate (50 mL) and water (50 mL). The organic layer was washed with 1 M HCl (50 mL), water, brine. After drying over magnesium sulfate, the organic layer was concentrated to give 1.31 g of an off white solid. Purification by flash column chromatography using 25–50% ethyl acetate/hexanes yielded 1.05 g of the pure product as a white solid. HRMS calculated for $C_{29}H_{34}N_2O_8SNa$: 593.1934 [M+Na], found: 593.1967.

Part G

To a solution of the product from Part F above (0.255 g, 0.446 mmol) in a mixture of methanol (3 mL) and dioxane (3 mL) was added 4 N HCl in dioxane (3 mL). The mixture was stirred at ambient temperature for 10 min, and then concentrated in vacuo. Trituration with diethyl ether/hexanes yielded 224 mg of the title compound as a white solid. HRMS calculated for $C_{24}H_{27}N_2O_7S$: 487.1539 [M+H], found: 487.1559.

Example 36

Preparation of 2H-pyran-4-carboxamide, tetrahydro-N-hydroxy-4[[4-[3-(2-naphthalenyl)propoxy]-phenyl]sulfonyl]

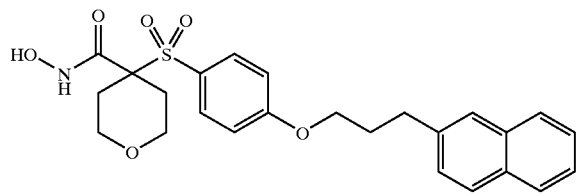

To a solution of (tetrahydro-4-[[4-(2propenyloxy)phenyl]sulfonyl]-N-[(tetrahydro-2H-pyran-2-yl)oxy]-2H-pyran-4-carboxamide (200 mg, 0.47 mmol, prepared as in Example 35) in tetrahydrofuran (1 mL) was added 0.5 M 9-borobicyclononane (0.94 mL, 0.47 mmol). The solution was stirred at ambient temperature for 16 hr. To this solution was added 2 M sodium carbonate (0.5 mL, 1 mmol), 2-bromonaphthalenylene (108 mg, 0.52 mmol), and tetrakis (triphenylphosphine)palladium(0) (54 mg, 0.047 mmol). The mixture was heated to 65° C. for 4 hr, and then cooled to ambient temperature. Saturated ammonium chloride solution (3 mL) was added to the reaction mixture. The resulting mixture was filtered through a small column of celite. The column was washed with ethyl acetate (35 mL). The eluant was concentrated in vacuo, and the residue was dissolved in methanol (3 mL), dioxane (3 mL), and 4 N HCl in dioxane. After 10 min, the solution was concentrated in vacuo, and the residue purified by preparative reverse phase HPLC (10–90% acetonitrile/0.05% TFA in water) yielding 20 mg of the title compound as a white solid. HRMS calculated for $C_{25}H_{28}NO_6S$: 470.1670 [M+H], found: 470.1614.

Additional compounds can be prepared by one skilled in the art using similar methods. Examples of such compounds include those having a structure corresponding to generic formula EX-P.

EX-P.

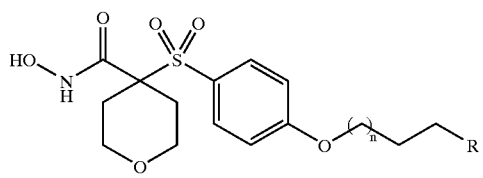

Example 37

Preparation of 4-[[4-4-[3-2-benzoxazolyl)propoxy]phenyl]sulfonyl]tetrahydro-N-hydroxy-2H-pyran-4-carboxamide

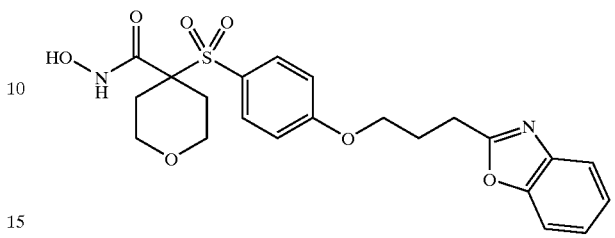

Part A

To a solution of 4-[[4-(3-carboxypropoxy)phenyl]sulfonyl]tetrahydro-2H-pyran-4-carboxylic acid, 1,1-dimethylethyl ester (3.0 g, 7.0 mmol) in N,N-dimethylformamide (14 mL) was added 1-(3-dimethylamino-propyl)-3-ethylcarbodiimide hydrochloride (1.88 g, 9.8 mmol) and 1-hydroxybenzotriazole (1.32 g, 9.8 mmol). The resulting suspension became a clear amber solution after stirring at 50° C. for 1.5 hr. The reaction was then treated with 2-aminophenol (0.76 g, 7.0 mmol), followed by N-methylmorpholine (2.3 mL, 21.0 mmol). The reaction was stirred at 50° C. overnight. After 21 hr, the reaction was partitioned between ethyl acetate (50 mL) and water (50 mL). The aqueous layer was extracted with ethyl acetate. The organic layers were combined and washed with saturated sodium bicarbonate solution, water, 1:1 solution of water:brine, and brine; dried over sodium sulfate; filtered; and concentrated in vacuo. The resulting oil was purified on silica gel using ethyl acetate/hexanes to afford 2.98 g (82%) of the amide as an amber oil. ESMS m/z=542 [M+Na]$^+$.

Part B

To a suspension of the product from Part A the (1.59 g, 3.1 mmol) toluene (50.0 mL) was added p-toluenesulfonic acid (0.12 g, 0.6 mmol), and the resulting mixture heated at reflux under Dean-Stark conditions. After 39 hr, the reaction was concentrated in vacuo, and the resulting residue was partitioned between ethyl acetate and 1 M aqueous hydrochloric acid. The organic layer was washed with 1 M aqueous hydrochloric acid, water, and brine; dried over sodium sulfate; filtered; and concentrated in vacuo to afford 1.25 g (92%) of the crude carboxylic acid benzoxazole as a tan, white solid. ESMS m/z=446 [M+H]$^+$.

Part C

To a solution of the product from Part B (0.98 g, 2.2 mmol) in N,N-dimethylformamide (10.0 mL) was added 1-(3-dimethylamino-propyl)-3-ethylcarbodiimide hydrochloride (0.59 g, 3.1 mmol) and 1-hydroxybenzotriazole (0.42 g, 3.1 mmol). The resulting suspension became a clear amber solution after stirring at 50° C. for 0.5 hr. The reaction was then treated with tetrahydropyranhydroxylamine (0.36 g, 3.1 mmol), followed by N-methylmorpholine (0.73 mL, 6.6 mmol). The reaction was stirred at 50° C. overnight. After 12 hr, the reaction was partitioned between ethyl acetate and water. The aqueous layer was extracted with ethyl acetate. The organic layers were combined and washed with saturated sodium bicarbonate solution, water, 1:1 solution of water:brine, and brine; dried over sodium sulfate;

filtered; and concentrated in vacuo. The resulting oil was purified on silica gel using ethyl acetate/hexanes as eluant to afford 1.2 g (98%) of the THP hydroxamate benzoxazole as an amber oil. ESMS m/z=545 [M+H]+.

Part D

To a solution of the product from Part C (0.104 g, 0.19 mmol) in a mixture of methanol (0.3 mL) and dioxane (2 mL) was added 4 N HCl in dioxane (0.5 mL). The mixture was stirred at ambient temperature for 30 min, concentrated in half in vacuo, and diluted with diethyl ether. Filtration afforded 17 mg (20%) of the title compound as a tan solid. HRMS calculated for $C_{22}H_{24}N_2O_7S$: 461.1382 [M+H], found: 461.1374.

Additional compounds can be prepared by one skilled in the art using similar methods. Examples of such compounds include those having a structure corresponding to generic formula EX-Q.

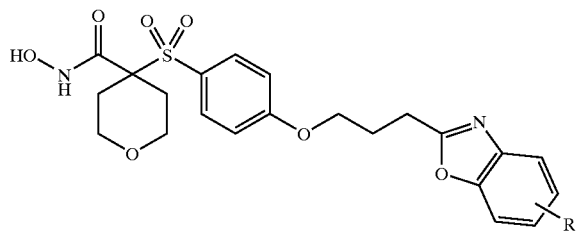

EX-Q.

Example 38
Preparation of:

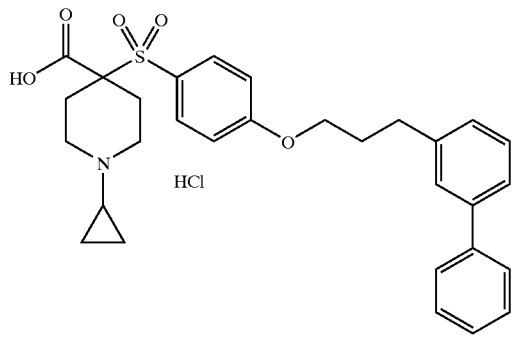

Part A
Preparation of:

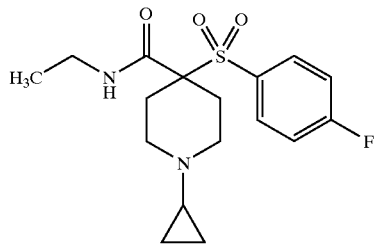

To a solution of ethyl 4-[(4-fluorophenyl)sulfonyl] piperidine-4-carboxylate hydrochloride (60.0 g, 170 mmol) in methanol (600 mL), were added acetic acid (97 mL, 1.7 mole), [(1-ethoxycyclopropyl)oxy]trimethylsilane (102 mL, 510 mmol) and 4A molecular sieves (55 g) followed by sodium cyanoborohydride (28.8 g, 459 mmol). The solution was stirred at ambient temperature overnight, then refluxed for 6 hr. The reaction mixture was filtered through celite and concentrated to solid/oil mix. Ethyl acetate and saturated sodium bicarbonate were added very carefully. When aqueous layer stayed basic, the layers were separated and the organic layer was washed 3 times with saturated sodium bicarbonate, then with brine and then dried over sodium sulfate. Concentration in vacuo and crystallization from ethyl acetate/hexane provided the n-cyclopropyl compound as an off white solid (53.8 g, 88.8%). $ESMS_{m/z}=356$ (M+H).

Part B

Preparation of:

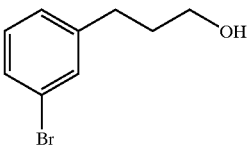

To a solution of 3-(3-bromophenyl)propionic acid (10.0 g, 43.7 mmol) in anhydrous THF (150 mL) was added 1.0 M $BH_3.THF$ (150 mL, 150 mmol) via addition funnel. After $BH_3$-THF was added, the reaction was refluxed for 18 hrs. The reaction was quenched with water (100 mL) and 1N HCl (300 mL). The solution was saturated with sodium chloride and extracted with ethyl acetate. The organic extract was washed with brine and dried over magnesium sulfate. The organic material was purified by chromatography on silica gel eluting with ethyl acetate in hexane to produce 9.39 g (100%) of the desired alcohol as a colorless oil. NMR ($CDCl_3$) δ1.82–1.89 (m, 2H), 2.67 (t, 2H), 3.64 (t, 2H), 7.11 7.15 (m, 1H), 7.29–7.31 (m, 1H), 7.34 (s, 1H).

Part C

Preparation of:

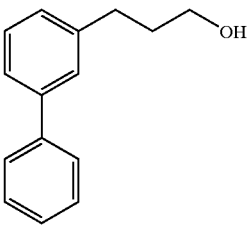

In a flask were combined the alcohol from Part B (3.43 g, 16.0 mmol), phenyl boronic acid (2.93 g, 24.0 mmol), palladium tetrakistriphenylphosphine (0.92 g, 0.8 mmol), 2M cesium carbonate (24 mL, 48 mmol) and dimethoxyethylether (48 mL). The mixture was stirred vigorously under nitrogen at reflux. After 1.5 hr the reaction was cooled to ambient temperature, diluted with water and extracted with ether 3 times. The combined organic extracts were washed with brine and dried over magnesium sulfate. 2.74 g (81% yield) purified product was obtained as a crystalline solid by chromatography (on silica, ethyl acetate/hexane). NMR ($CDCl_3$) δ1.91–1.98 (m, 2H), 2.77 (t, 2H), 3.71 (t, 2H), 7.19 (d, 1H), 7.31–7.38 (m, 2H), 7.41–7.45 (m, 4H), 7.58 (d, 2H).

Part D

Preparation of:

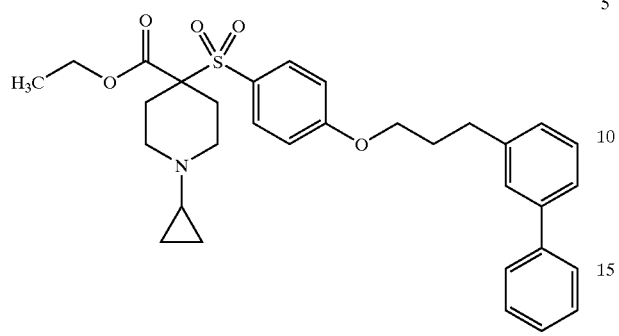

To a solution of the alcohol from Part C (2.7 g, 12.7 mmol) in anhydrous dimethylformamide (12 mL) at 0° C. was added 60% sodium hydride (0.58 g, 14.5 mmol) in portions. After that the reaction was stirred at 0° C. for 15 min and then at ambient temperature for 15 min. The reaction mixture was cooled to 0° C. and the cyclopropyl compound from Part A (4.3 g, 12.4 mmol) in anhydrous dimethylformamide (10 mL) was added slowly. Upon completion of addition, ice bath was removed and the reaction stirred at ambient temperature for 1 hr the reaction, then diluted with water and extracted with ethyl acetate 3 times. The combined organic extracts were washed with saturated NaHCO$_3$ and brine and dried over sodium sulfate. After concentration 4.63 g of material was obtained. This material was used without purification.

Part E

Preparation of:

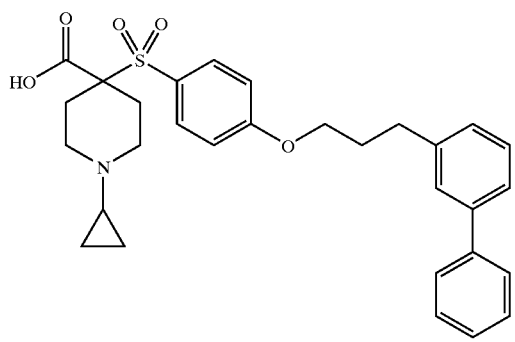

The ester of Part D (4.61 g, 8.4 mmol) was hydrolyzed in 1:1:0.56 mixture of ethanol:1,4-dioxane:6N NaOH (25.6 mL) at 60° C. The solution was concentrated in vacuo, diluted with water and extracted with ether to remove color. Acidification with 1N HCl caused precipitation of the acid which was collected by filtration, washed with water and hexane and dried under high vacuum yielding the acid as an off white solid (3.45 g, 79% yield). ESMS$_{m/z}$=520 (M+H)$^+$. This material was used without purification.

Part F

Preparation of:

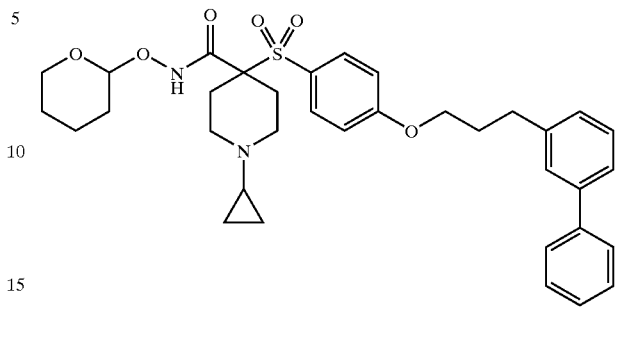

To a suspension of the crude acid of Part E (3.44 g, 6.62 mmol) in DMF (27 mL) were added HOBt (1.52 g, 9.93 mmol), N-methylmorpholine (2.2 mL, 19.9 mmol) and EDC (1.77 g, 9.27 mmol). After heating at 40° C., acid slowly went into solution. When reaction was clear, it was cooled to ambient temperature and THP-hydroxylamine (1.16 g, 9.93 mmol) was added. The solution was stirred for 18 hr at ambient temperature. The solution was partitioned between ethyl acetate and water. The organic layer was washed with water and brine and dried over magnesium sulfate. Chromatography (on silica, ethyl acetate/hexanes) provided the protected hydroxamate as a crystalline solid (3.20 g, 74%). NMR δ0.36 (d, 4H), 1.50–1.92 (m, 8H), 2.05–2.21 (m, 3H), 2.32 (s, 2H), 2.86 (t, 2H), 2.98 (s, 2H), 3.69 (d, 1H), 3.96–4.07 (m, 3H), 5.00 (s, 1H), 6.95 (d, 2H), 7.17 (d, 1H), 7.30–7.43 (m, 6H), 7.54 (d, 2H), 7.73 (d, 2H), 9.41 (s, 1H).

Part G

Preparation of:

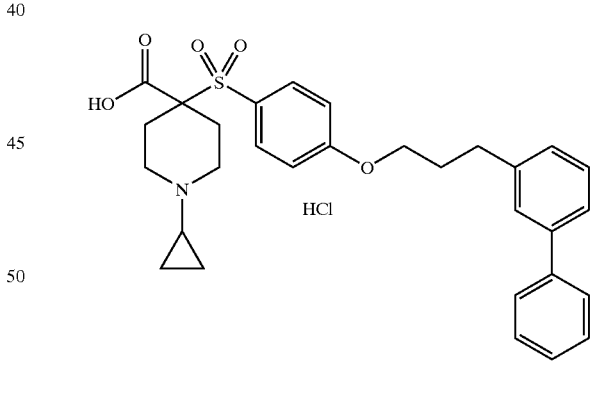

To the semi pure product from Part F (3.03 g, 4.89 mmol) in methanol (10 mL) and 1,4-dioxane (10 mL) was added 4M hydrochloric acid in 1,4-dioxane (10 mL) and after stirring 20–30 min the product began to crystallize out. Reverse phase chromatography (on C$_{18}$, acetonitrile/water) to remove color followed by conversion to HCl salt with methanol and 4N HCl/dioxane then recrystallization from methanol/iso propanol provided 1.95 g (70%) of the title compound as a hydrochloric acid salt that was colorless. ESMS$_{m/z}$=535 (M+H)$^+$. HRMS calcd. for C$_{30}$H$_{35}$N$_{20}$O$_5$S H: 535.2261 (M+H)$^+$. Found: 535.2270.

Example 39

Preparation of:

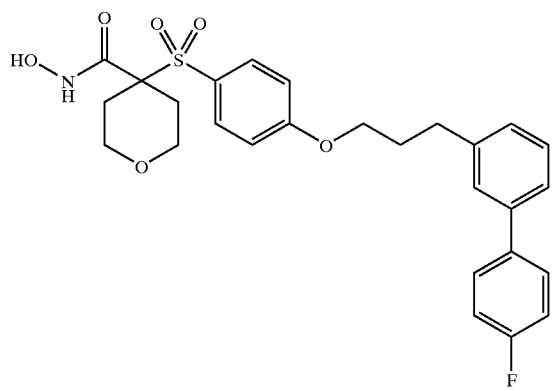

Part A
Preparation of:

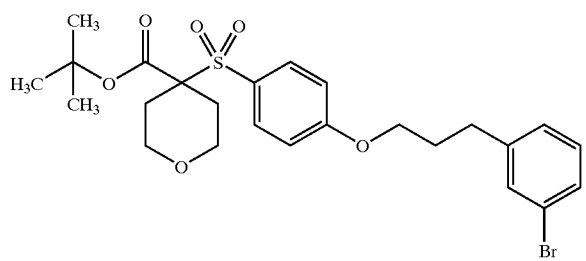

A solution of the alcohol from Part B, Example 38 (4.4 g, 20.4 mmol), tert-butyl 4-[(4-fluorophenyl)sulfonyl] tetrahydro-2H-pyran-4-carboxylate (5.0 g, 14.6 mmol) and $Cs_2CO_3$ (9.5 g, 29.2 mmol) in anhydrous dimethylformamide (30 mL) was stirred at 80° C. for 30 hr. The reaction was diluted with water (300 mL) and extracted with ethyl acetate (3 times). The combined organic extracts were washed with brine and dried over magnesium sulfate. Crystallization from methylene chloride/hexane gave 6.95 g (88%) of the product as a colorless solid. $ESMS_{m/z}$=556 $(M+NH_4)^+$. HRMS calcd. for $C_{25}H_{35}BrNO_6S$ H: 556.1368 $(M+NH_4)^+$. Found: 556.1318.

Part B
Preparation of:

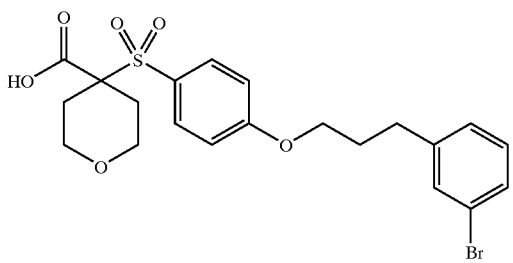

The ester of Part A (6.81 g, 12.6 mmol) was hydrolyzed in 1:1 TFA:methylene chloride (50 mL) at ambient temperature for 1.5 hr. The solution was concentrated in vacuo, taken up in toluene, concentrated to a colorless solid and dried under high vacuum yielding the acid as an impure white solid (6.28 g, 100% yield). $ESMS_{m/z}$=500 $(M+NH_4)^+$. HRMS calcd. for $C_{21}H_{23}BrO_6SNH_4$: 500.0742 $(M+NH_4)^+$. Found: 500.0761.

Part C

Preparation of:

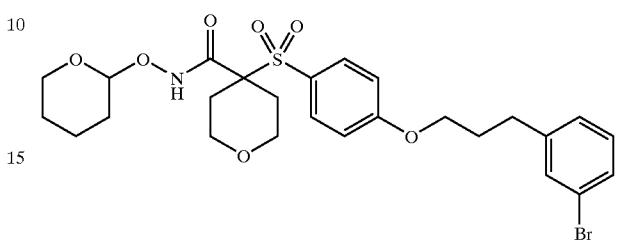

To a suspension of the impure acid of Part B (theoretically 12.5 mmol) in anhydrous DMF (25 mL) were added HOBt (2.0 g, 15 mmol), triethylamine (5.2 mL, 37.5 mmol) and EDC (3.4 g, 17.5 mmol). After heating at 40° C. for 1 hr, THP hydroxylamine (4.4 g, 37.5 mmol) was added. The solution was stirred for 18 hr at ambient temperature, then at 40° C. for 3 hr. The reaction was diluted with water (150 mL) and extracted with ethyl acetate (3 times). The combined organic extracts were washed with brine and dried over magnesium sulfate. Chromatography (on silica, ethyl acetate/hexanes) provided the protected hydroxamate as a viscous oil (4.32 g, 60%). $ESMS_{m/z}$=601 $(M+NH_4)^+$. HRMS calcd. for $C_{26}H_{32}BrNO_7SNH_4$: 601.1410 $(M+NH_4)^+$. Found: 601.1448.

Part D

Preparation of:

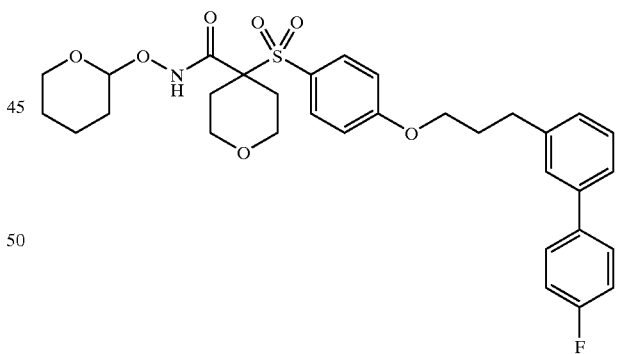

In a vial were combined the aryl bromide from Part C (0.20 g, 0.34 mmol) in 1 mL of dimethoxyethyl ether, 4-fluorobenzeneboronic acid (74 mg, 0.53 mmol), palladium tetrakistriphenylphosphine (23 mg, 0.02 mmol) in 0.5 mL of dimethoxyethyl ether and 2M cesium carbonate (0.51 mL, 1.02 mmol). The mixture stirred vigorously at 65° C. for 18 hr. The eaction mixture was poured onto 5 mL Chem-Elut tube pre-wetted with 3 mL of water and eluted with 10% ethyl acetate/methylene chloride. Concentration under nitrogen gave 254 mg of crude product that was carried on as is.

Part E

Preparation of:

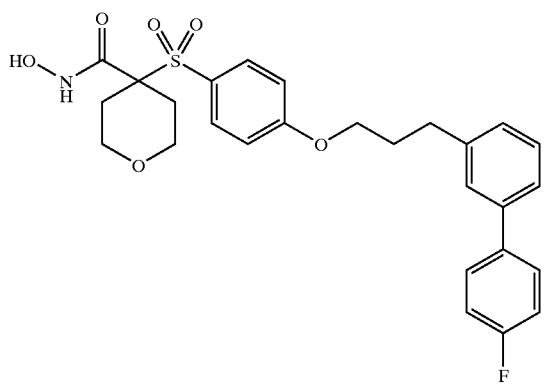

The crude product from Part D (254 mg) was taken up in 4M hydrochloric acid in 1,4-dioxane (2 mL) and methanol (1–2 mL) and stirred for 2 hr then concentrated. Material purified by reverse phase chromatography (on $C_{18}$, acetonitrile/water). Product crystallized upon concentration yielding 108.5 mg (62%) of the title compound as colorless solid. $ESMS_{m/z}$=514 (M+H)$^+$. HRMS calcd. for $C_{27}H_{29}FNOS$: 514.1700 (M+H)$^+$. Found: 514.1694.

Example 40

Preparation of:

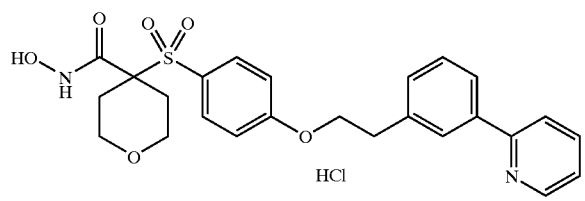

Part A

Preparation of:

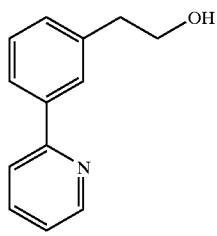

3-bromophenethyl alcohol (5.0 g, 24.9 mmol) and 2-(tributylstannyl)pyridine (13.6 g, 37.4 mmol) were combined in a round bottom flask with $PdCl_2(PPh_3)_2$ (0.84 g, 1.2 mmol), CuI (0.23 g, 1.2 mmol) and anhydrous THF (100 mL) and heated to reflux. After refluxing overnight, additional $PdCl_2(PPh_3)_2$ (0.84 g, 1.2 mmol) and CuI (0.23 g, 1.2 mmol) were added and the reaction refluxed overnight. The reaction was cooled to ambient temperature, Norit A charcoal added, the mixture stirred and then filtered through a bed of celite. Chromatography (on silica, ethyl acetate/hexanes) provided the alcohol as an orange oil (2.76 g, 55.8%). $ESMS_{m/z}$=200 (M+H)$^+$.

Part B

Preparation of:

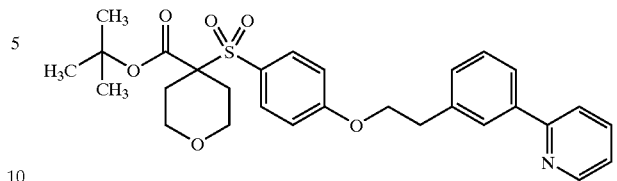

To a solution of the alcohol from Part A (2.75 g, 13.8 mmol) in anhydrous dimethylformamide (13 mL) at 0° C. was added 60% sodium hydride (0.58 g, 14.4 mmol). in portions. After completion of the addition, the reaction was stirred at 0° C. for 30 min. tert-butyl 4-[(4-fluorophenyl)sulfonyl]tetrahydro-2H-pyran-4-carboxylate (4.51 g, 13.1 mmol) in anhydrous dimethylformamide (10 mL) was added over 15 min. Upon completion of addition, the ice bath was removed and the reaction stirred at ambient temperature. After 1.5 hr the reaction was diluted with water and extracted with ethyl acetate 3 times. The combined organics were washed with saturated NaCl and dried over magnesium sulfate. Chromatography (on silica, ethyl acetate/hexanes) provided the product as an off white solid (5.44 g, 79%). $ESMS_{m/z}$=524 (M+H)$^+$.

Part C

Preparation of:

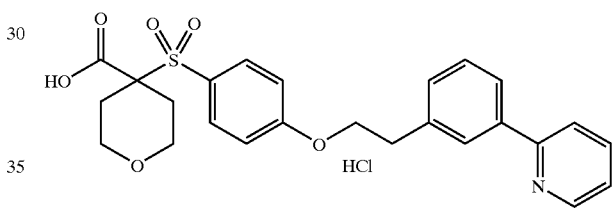

The ester of Part B (5.45 g, 10.4 mmol) was hydrolyzed in 1:1 mixture of TFA:methylene chloride (30 mL) at ambient temperature for 8 hr. The solution was concentrated in vacuo, taken up in methanol and 4N HCl in dioxane and concentrated. This was repeated to give a viscous oil (6.25 g, >100% yield). This material was used without further purification.

Part D

Preparation of:

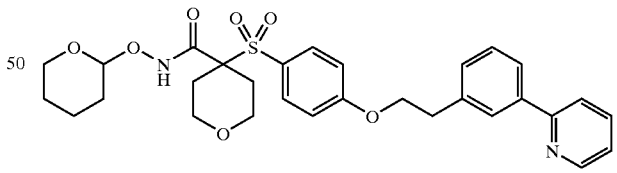

To a suspension of the crude acid of Part C (assume 10.4 mmol) in NMP (40 mL) were added HOBt (2.39 g, 15.6 mmol), N-methylmorpholine (3.4 mL, 31.2 mmol) and EDC (2.79 g, 14.6 mmol). After heating at 40° C. overnight, HPLC still showed acid to be present so additional added HOBt (2.39 g, 15.6 mmol), N-methylmorpholine (3.4 mL, 31.2 mmol) and EDC (2.79 g, 14.6 mmol) were added. After 1 hr at 40° C., THP hydroxylamine (3.66 g, 31.2 mmol) was added. After 1 hr, the solution was diluted with water and extracted with ethyl acetate 3 times. The combined organic layers were washed with brine and dried over magnesium sulfate. Chromatography (on silica, ethyl acetate/hexanes)

provided the protected hydroxamate as a colorless foam (5.05 g, 85.7). ESMS$_{m/z}$=567 (M+H)$^+$.

Part E

Preparation of:

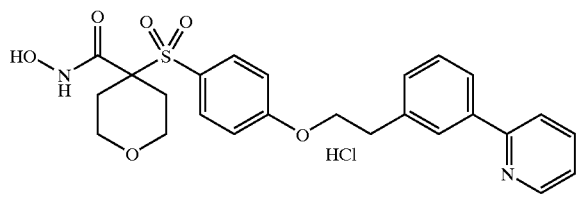

To the product from Part D (5.05 g, 8.91 mmol) in methanol (15 mL) and 1,4-dioxane (15 mL) was added 4M hydrochloric acid in 1,4dioxane (15 mL) and after stirring 1 hr reaction was complete. Concentration followed by crystallization from methanol/isopropanol provided 3.88 g (84%) of the title compound as a hydrochloric acid salt that was colorless. ESMS$_{m/z}$=483 (M+H)$^+$. HRMS calcd. for $C_{25}H_{27}N_2O_6S$ H: 483.1584 (M+H)$^+$. Found: 483.1585.

Example 41

Preparation of 1-ethyl-N-hydroxy 4-{[4-(3-{3-[4-(trifluoromethoxy)phenyl]-1,2,4-oxadiazol-5-yl}propoxy)phenyl]sulfonyl}piperidine-4-carboxamide hydrochloride

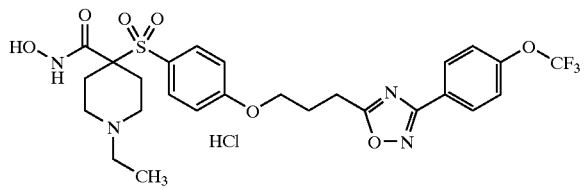

Part A

To a slurry of ethyl 4-[(4-fluorophenyl)sulfonyl]-4-piperidinecarboxylate, monohydrochloride (14.06 g, 40 mmol) in dimethylacetamide (80 mL) were added potassium carbonate (13.82 g, 100 mmol) and iodoethane (3.36 mL, 42 mmol). The slurry was stirred at ambient temperature. After 3 hr the reaction was concentrated in vacuo. The residue was taken up in ethyl acetate, washed with water three times, saturated sodium chloride solution, dried over $Na_2SO_4$, filtered, and concentrated in vacuo. Chromatography (on silica, methylene chloride/hexanes) provided the N-ethyl piperidine as a white solid (13.05 g, 95%).

Part B

In dry equipment under nitrogen, potassium trimethylsilanolate (10.52 g, 73.8 mmol) was dissolved in dimethylsulfoxide (40 mL) and gamma-butyrolactone (4.26 mL, 55.4 mmol) was added over 5 min while the reaction temperature rose to 49 C. After stirring at ambient temperature for 90 min. sodium hydride (2.2 g of a 60% oil dispersion, 55.4 mmol) was added portion wise over 20 min and the reaction temperature rose to 38° C. Gas evolution was also observed. After stirring at ambient temperature for 40 min, a solution of the N-ethyl piperidine from Part A (12.66 g, 36.9 mmol) in dimethylsulfoxide (10 mL) was added over 10 min as the reaction rose to 8° C. The reaction was stirred at ambient temperature for t30 min. The slurry was slowly poured into ice water (400 mL) and then extracted with hexanes (100 mL) two times followed by a diethyl ether extraction (100 mL). The aqueous layer was chilled to 5° C. and the pH adjusted to 7 with concentrated hydrochloric acid. The aqueous solution was extracted with methylene chloride (150 mL) until there was no UV activity in the extract. The combined methylene chloride extracts were washed with saturated sodium chloride solution, dried over $Na_2SO_4$, filtered, and concentrated in vacuo. The solid was recrystallized from isopropanol (65 mL) to give the butyric acid as a white solid (8.2 g, 52%). LCMS$_{m/z}$=428 [M+H]$^+$.

Part C

In dry equipment under nitrogen, the butyric acid from Part B (5.12 g, 12.0 mmol) was dissolved in dry dimethylacetamide (20 mL) and the remaining reagents were added to the solution in the following order: N-hydroxybenzotriazole hydrate (2.43 g, 18.0 mmol), triethylamine (3.34 mL, 24.0 mmol), 4-(trifluoromethoxy)benzamidoxime (3.96 g, 18.0 mmol), and 1-(3-dimethylaminopropyl)-3-ethylcarbodiimide hydrochloride (4.6 g, 24.0 mmol). After 24 hr at 70° C., the reaction was concentrated in vacuo. The residue was taken up in ethyl acetate, washed with water, saturated $NaHCO_3$, saturated sodium chloride solution, dried over $Na_2SO_4$, filtered, and concentrated in vacuo. Chromatography (on silica, ethyl acetate/methanol/hexanes) provided the oxadiazole as a light yellow solid (5.05 g, 69%). LCMS$_{m/z}$=612 [M+H]$^+$.

Part D

A slurry of the oxadiazole from Part C (4.9 g, 8.02 mmol), 2.5N sodium hydroxide (9.6 mL, 24.06 mmol) and sodium hydroxide (1.28 g, 32.08 mmol) in isopropanol (40 ml) were stirred at 70° C. for 7 hr. The heat was removed and the reaction diluted with water (100 ml) and chilled to 5° C. The pH was adjusted to 7 with concentrated hydrochloric acid. The solids were filtered, washed with hexanes, and dried in vacuo to give the carboxylic acid as a white solid (4.54 g, 97%). LCMS$_{m/z}$=584 [M+H]$^+$.

Part E

In dry equipment under nitrogen, the carboxylic acid from Part D (4.5 g, 7.72 mmol) was dissolved in dry dimethylacetamide (15 ml) and the remaining reagents were added to the solution in the following order: N-hydroxybenzotriazole hydrate (1.56 g, 11.6 mmol), triethylamine (3.22 mL, 23.2 mmol), O-(tetrahydro-2H-pyran-2-yl)hydroxylamine (1.35 g, 11.6 mmol), and 1-(3-diethylaminopropyl)-3-ethylcarbodiimide hydrochloride (2.96 g, 15.4 mmol). After 29 hr at 50° C., the reaction was concentrated in vacuo. The residue was taken up in ethyl acetate, washed with water, saturated $NaHCO_3$, saturated sodium chloride solution, dried over $Na_2SO_4$, filtered, and concentrated in vacuo. Chromatography (on silica, ethyl acetate/methanol/hexanes) provided the THP hydroxamate as a light yellow solid (2.4 g, 46%). LCMS$_{m/z}$=683 [M+H]$^+$.

Part F

To the THP hydroxamate from Part E (2.3 g, 3.37 mmol) was added 4N HCl dioxane solution (8.4 mL, 33.7 mmol) and methanol (0.84 mL). The slurry became very thick. Diethyl ether (50 ml) was added to and after 1 hr at ambient temperature the reaction was filtered under nitrogen. The solids were washed with diethyl ether (150 ml) under nitrogen and dried in vacuo over phosphorus pentoxide to give the title compound as a white solid (1.92 g, 91%). HRMS (ES+) M+H$^+$ calculated for $C_{26}H_{29}N_4O_7S_1F_3$: 599.1787, found 599.1766.

Example 42

Preparation of:

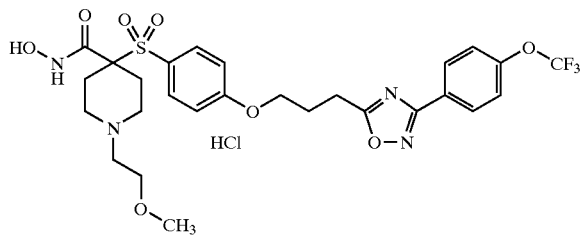

Part A

In dry equipment under nitrogen, potassium trimethylsilanolate (42.76 g, 0.3 mol) was dissolved in dimethylsulfoxide (170 mL) and gamma-butyrolactone (17.31 mL, 0.225 mol) was added over 5 min while the reaction temperature rose to 49 C. After stirring at ambient temperature for 90 min, sodium hydride (9.0 g of a 60% oil dispersion, 0.225 mol) was added portion wise over 20 min and the reaction temperature rose to 38° C. Gas evolution was also observed. After stirring at ambient temperature for 40 min. a solution of ethyl 4-[(4-fluorophenyl)sulfonyl]-1-(2-methoxyethyl)piperidine-4-carboxylate (56 g, 0.15 mol) in dimethylsulfoxide (20 mL) was added over 10 mins as the reaction rose to 38° C. The reaction was stirred at ambient temperature for 30 min. The slurry was slowly poured into ice water (1.1 L) and then extracted with hexanes (300 mL) two times followed by a diethyl ether extraction (200 mL). The aqueous layer was chilled to 5° C. and the pH adjusted to 7 with concentrated hydrochloric acid. The aqueous solution was extracted with methylene chloride (150 mL) until there was no UV activity in the extract. The combined methylene chloride extracts were washed with saturated sodium chloride solution, dried over $Na_2SO_4$, filtered, and concentrated in vacuo. The solid was recrystallized from methanol (200 mL) to give the butyric acid as a white solid (34.8 g, 51%). $LCMS_{m/z}$=458 [M+H]$^+$.

Part B

In dry equipment under nitrogen, the butyric acid from Part A (19.19 g, 42.0 mmol) was dissolved in dry dimethylformamide (100 mL) and the remaining reagents were added to the solution in the following order: N-hydroxybenzotriazole hydrate (8.5 g, 63.0 mmol), triethylamine (11.7 mL, 84.0 mmol), 4-(trifluoromethoxy)benzamidoxime (13.9 g, 63.0 mmol), and 1-(3-dimethylaminopropyl)-3-ethylcarbodiimide hydrochloride (16.1 g, 84.0 mmol). After 24 hr at 70° C., the reaction was concentrated in vacuo. The residue was taken up in ethyl acetate, washed with water, saturated $NaHCO_3$, saturated sodium chloride solution, dried over $Na_2SO_4$, filtered, and concentrated in vacuo. The solid was recrystallized from methanol (35 mL) to give the oxadiazole as an off white solid (17.86 g, 66%). $LCMS_{m/z}$=642 [M+H]$^+$.

Part C

A slurry of the oxaziazole from Part B (16.9 g, 26.4 mmol), 2.5N sodium hydroxide (31.6 mL, 79.1 mmol) and sodium hydroxide (4.22 g, 105.5 mmol) in isopropanol (30 mL) were stirred at 70° C. for 7 hr. The heat was removed and the reaction diluted with water (150 mL) and chilled to 5° C. The pH was adjusted to 7 with concentrated hydrochloric acid. The solids were filtered, washed with hexanes, and dried in vacuo to give the carboxylic acid as a white solid (15.78 g, 98%). $LCMS_{m/z}$=614 [M+H]$^+$.

Part D

In dry equipment under nitrogen, the carboxylic acid from Part C (15.7 g, 25.6 mmol) was dissolved in dry dimethylformamide (70 mL) and the remaining reagents were added to the solution in the following order: N-hydroxybenzotriazole hydrate (5.19 g, 38.4 mmol), triethylamine (10.7 mL, 76.8 mmol), O-(tetrahydro-2H-pyran-2-yl)hydroxylamine (5.99 g, 51.2 mmol), and 1-(3-dimethylaminopropyl)-3-ethylcarbodiimide hydrochloride (10.8 g, 56.3 mmol). After 12 hr at 40° C., the reaction was concentrated in vacuo. The residue was taken up in ethyl acetate, washed with water, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white foam (14.94 g, 82%). $LCMS_{m/z}$=713 [M+H]$^+$.

Part E

To the THP hydroxamate from Part D (14.88 g, 20.9 mmol) was added 4N HCl dioxane solution (52 mL, 209.0 mmol) and methanol (5.2 mL). The slurry became very thick. Dioxanes (50 mL) and diethyl ether (100 mL) were added to facilitate stirring. After 1 hr at ambient temperature the reaction was filtered under nitrogen. The solids were washed with acetonitrile (100 mL) under nitrogen and dried in vacuo over phoshorus pentoxide to give the title compound as a white solid (13.25 g, 95%). HRMS (ES+) M+H$^+$ calculated for $C_{27}H_{31}N_4O_8S_1F_3$: 629.1893, found 629.1913.

Example 43

Preparation of 4-({4-[3-(1,3-benzoxazol-2-ylthio)propoxy]phenyl]sulfonyl)-N-hydroxy-1-(2-methoxyethyl)piperidine-4-carboxamide hydrochloride

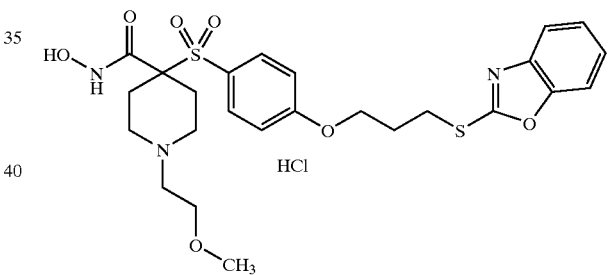

Part A

A solution of 1-benzyl 4-tert-butyl 4-[(4-fluorophenyl)sulfonyl]piperidine-1,4-dicarboxylate (16.0 g, 33.5 mmol) in methanol/tetrahydropyran was hydrogenated for 1 hr at 5 psi in the presence of 5% Pd/C. The solution was filtred to remove the catalyst and concentrated in vacuo. 11.0 g (95% yield) of the amine was obtained as a white solid.

Part B

The solution of the amine of Part A (11.0 g, 32.1 mmol) in N,N-dimethylformamide (100 mL) was cooled to 0° C. on an ice bath. Potassium carbonate (13.3 g, 96.4 mmol) and 2-bromoethylmethyl ether (7.54 mL, 80.2 mmol) were added to the chilled solution. The solution was stirred for 72 hr at ambient temperature and partitioned between ethyl acetate and water. The organic layer was washed with water and saturated sodium chloride and dried over sodium sulfate. 14.5 g of the desired alkylated amine was obtained as an orange oil by concentration in vacuo.

Part C

To a solution of propanediol (10.44 mL, 144 mmol) in 1-methyl-2-pyrrolidinone (40 mL) cooled to 0° C. was added sodium hydride (60% suspension in mineral oil, 3.85 g, 96.3 mmol). The alkylated amine from Part B (14.5 g, 32.1 mmol) was dissolved into 1-methyl-2-pyrrolidinone (50 mL) and added dropwise to the cooled solution. The solution was stirred at ambient temperature for 1 hr. The reaction was quenched by adding water and partitioned between ethyl acetate and water. The organic layer was washed with water and saturated sodium chloride and dried over sodium sulfate. The desired alcohol was obtained as an orange oil by concentration in vacuo. MS(CI) MH$^+$ calculated for $C_{22}H_{35}NO_7S$: 457, found 457.

Part D

To a solution of the alcohol of Part C (32.1 mmol) in methylene chloride (100 mL) was added triethylamine (4.92 mL, 35.3 mmol). The solution was cooled to 0° C. and methanesulfonyl choride (2.56 mL, 33.0 mmol) was added dropwise. After 1 hr the reaction was concentrated in vacuo. The residue was dissolved into ethyl actate and washed with water, saturated sodium bicarbonate and saturated sodium chloride and dried over sodium sulfate. The solution was concentrated in vacuo to provide 17.5 g of the desired mesylate. MS(CI) MH$^+$ calculated for $C_{23}H_{37}NO_9S_2$: 536, found 536.

Part E

To a solution of 2-mercaptobenzoxazole (4.86 g, 32.1 mmol) in N,N-dimethylformamide (30 mL) cooled to 0° C. was added sodium hydride (60% suspension in mineral oil, 1.54 g, 38.5 mmol). After 30 min the mesylate of Part D (17.5 g, 32.1 mmol) in N,N-dimethylformamide (30 mL) was added dropwise. The solution was heated at 60° C. for 4 hr and at 45° C. for 18 hr. The solution was returned to ambient temperature and partitioned between ethyl acetate and water. The organic layer was washed with water and saturated sodium chloride and dried over sodium sulfate. Chromotography (ethyl acetate, on silica) provided the mercaptobenzoxazole as a colorless oil (7.3 g, 39% yield over four steps). MS(CI) MH$^+$ calculated for $C_{29}H_{38}N_2O_7S_2$: 591, found 591.

Part F

To a solution of the mercaptobenzoxazole of Part E (7.3 g, 12.4 mmol) was added trifluoroacetic acid (20 mL) and the solution stirred for 3 hr. The solution was concentrated in vacuo and azotroped with toluene to provide the acid as an oil. The material was carried on without additional purification. MS(CI) MH$^+$ calculated for $C_{25}H_{30}N_2O_7S_2$: 535, found 535.

Part G

To a solution of the acid of Part F (12.4 mmol) in N,N-dimethylformamide (50 mL) were added 1-hydroxybenztriazole (2.01 g, 14.9 mmol), 4-methylmorpholine (6.82 mL, 62 mmol) and tetrahydropyranylamine (2.18 g, 18.6 mmol). After 30 min 1-(3-dimethylaminopropyl)-3-ethylcarbodiimide hydrochloride (3.33 g, 17.4 mmol) was added. The solution was heated to 65° C. for 2 hr. The solution was partitioned between ethyl acetate and water. The organic layer was washed with water and saturated sodium chloride and dried over sodium sulfate. Chromatography (ethyl acetate/methanol, on silica) provided the protected hydroxamate as a colorless oil (3.9 g, 50% yield). MS(CI) MH$^+$ calculated for $C_{30}H_{39}N_3O_8S_2$: 634, found 634.

Part H

To a solution of the protected hydroxamate of Part G (3.9 g, 6.2 mmol) in 1,4-dioxane (10 mL) was added 4M hydrochloric acid in 1,4-dioxane (10 mL). The reaction was complete after 1 hr. The solution was concentrated in vacuo. The residue was purified via reverse phase chromatography (acetonitrile/water, on silica) to provide the title compound as a white solid (1.49 g, 41% yield). MS(CI) MH$^+$ calculated for $C_{25}H_{31}N_3O_7S_2$: 550, found 550. HRMS calculated for $C_{25}H_{31}N_3O_7S_2$: 550.1682, found 550.1668. Analytical calculation for $C_{25}H_{31}N_3O_7S_2 \cdot HCl \cdot H_2O$: C, 49.70; H, 5.67; N, 696; S, 10.62; Cl, 5.87. Found: C, 49.91; H, 6.03; N, 6.74; S, 10.75; Cl, 6.35.

Example 44

Preparation of:

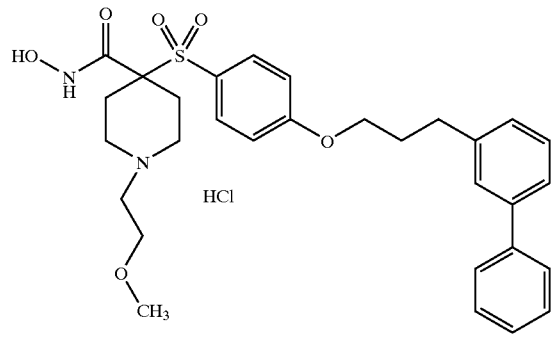

Part A

Preparation of:

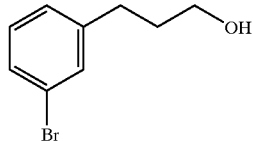

To a solution of 3-(3-bromophenyl)propionic acid (15.0 g, 65.5 mmol) in anhydrous THF (200 mL) at 5° C. was added, via addition funnel, 1.0 M BH$_3$.THF (200 mL, 200 mmol). The reaction temperature was kept below 14° C. during the addition of the BH$_3$.THF. After all the BH$_3$.THF was added, the reaction was refluxed for 22 hr and then quenched with water (100 mL) and 1N HCl (300 mL). The solution was saturated with sodium chloride and extracted with ethyl acetate (3×300 mL). The organic extract was washed with brine, dried over magnesium sulfate, and concentrated providing 14.4 g (100%) of crude alcohol as a colorless oil. NMR(CDCl$_3$) δ1.82–1.89 (m, 2H), 2.67 (t, 2H), 3.64 (t, 2H), 7.11–7.15 (m, 1H), 7.29–7.31 (m, 1H), 7.34 (s, 1H).

Part B

Preparation of:

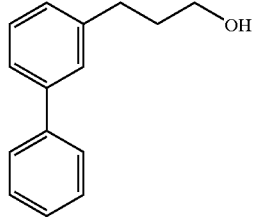

In a flask were combined the alcohol from Part A (65.5 mmol), phenyl boronic acid (12.0 g, 98.2 mmol), palladium tetrakistriphenylphosphine (3.8 g, 3.3 mmol), 2M cesium carbonate (98 mL, 196 mmol) and dimethoxyethylether (100 mL). The mixture was stirred vigorously under nitrogen at reflux overnight. The reaction was cooled to ambient temperature, poured into water (300 mL) and extracted 3 times with ethyl acetate. The combined organic extracts were washed with brine and dried over magnesium sulfate. Chromatography (on silica, ethyl acetate/hexane) provided the coupled product as a golden oil (11.95 g, 86.0%). NMR(CDCl₃) δ1.91–1.98 (m, 2H), 2.77 (t, 2H), 3.71 (t, 2H), 7.19 (d, 1H), 7.31–7.38 (m, 2H), 7.41–7.45 (m, 4H), 7.58 (d, 2H).

Part C

Preparation of:

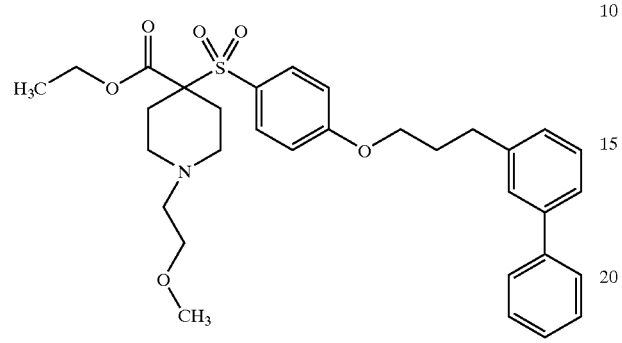

To a solution of the alcohol from Part B (11.9 g, 56.1 mmol) in anhydrous dimethylformamide (56 mL) at 0° C. was added 60% sodium hydride (2.55 g, 63.8 mmol) in portions. After completion of the addition, the reaction was stirred at 0° C. for 15 min then ambient temperature for 15 min. The reaction was cooled to 0° C. and ethyl 4-[(4-fluorophenyl)sulfonyl]-1-(2-methoxyethyl)piperidine-4-carboxylate (19.0 g, 51 mmol) in anhydrous dimethylformamide (60 mL) was added slowly. Upon completion of addition, the ice bath was removed and the reaction stirred at ambient temperature overnight. Reaction was poured into water (1 L) and extracted with ethyl acetate (800 mL). The combined organics were washed with water (2×500 mL) and brine and dried over magnesium sulfate. Concentration gave 34.4 g of crude material. This material was used without purification.

Part D

Preparation of:

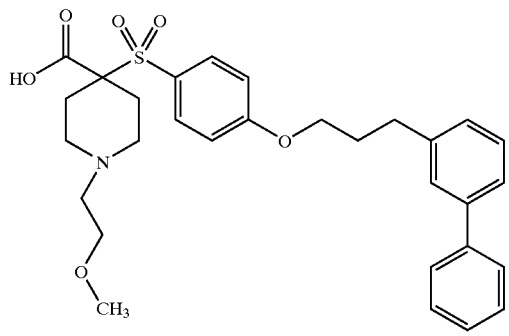

The impure ester of Part C (34.4 g, 51 mmol theoretical) was hydrolyzed in 41 mL of ethanol, 41 mL of 1,4-dioxane and 26.5 mL of 6 N NaOH at 60° C. The solution was poured into water and extracted with ether to remove color. Acidification with 1N HCl caused precipitation of the acid which was collected by filtration and washed with water, ethyl acetate and hexane then dried under high vacuum yielding the acid as an off white solid (18.8 g, 68.6% yield). NMR (CD₃OD w/K₂CO₃) δ1.98 (t, 2H), 2.07–2.19 (m, 4H), 2.32 (d, 2H), 2.48 (t, 2H), 2.85–2.95 (m, 4H), 3.25 (s, 3H), 4.06 (t, 2H), 7.04 (d, 2H), 7.20 (d, 1H), 7.27–7.48 (m, 5H), 7.54 (d, 2H), 7.78 (d, 2H). ESMS m/z=538 (M+H)⁺.

Part E

Preparation of:

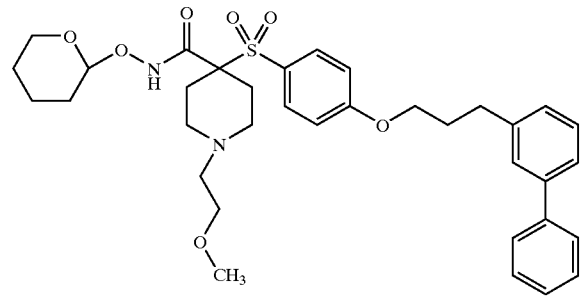

To the acid of Part D (12.7 g, 23.6 mmol), HOBt (5.42 g, 35.4 mmol), EDC (6.30 g, 3.30 mmol) in a flask under N₂ was added 70 mL anhydrous DMF. The mixture was heated to 60° C. and triethylamine (9.85 mL, 70.8 mmol) was added. After heating at 60° C. for 1 hr, THP-hydroxylamine (4.14 g, 35.4 mmol) was added. The solution was stirred for 16.5 hr at 60° C. The solution was partitioned between ethyl acetate (300 mL) and water (500 mL). The organic layer was washed with brine and dried over magnesium sulfate. Concentration provided the protected hydroxamate as an oil (14.86 g, 98.7%). NMR(CDCl₃) δ1.55–1.90 (m, 6H), 2.09–2.27 (m, 8H), 2.50 (t, 2H), 2.87 (t, 2H), 2.90–2.98 (m, 2H), 3.32 (s, 3H), 3.42 (t, 2H), 3.7.1 (d, 1H), 3.98 (d, 1H), 4.05 (t, 2H), 4.99 (s, 1H), 6.97 (d, 2H), 7.19 (d, 1H), 7.30–7.46 (m, 6H), 7.57 (d, 2H), 7.77 (d, 2H), 9.42 (s, 1H). ESMS m/z=637 (M+H)⁺.

Part F

Preparation of:

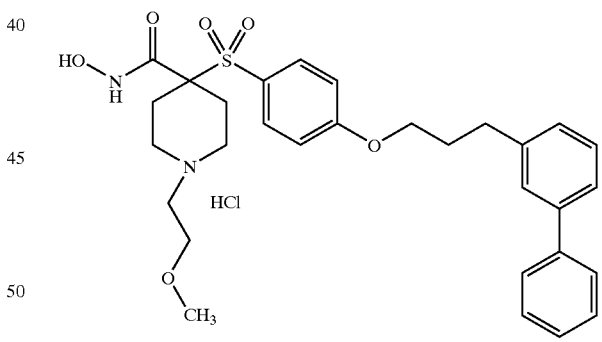

To the product from Part E (14.7 g, 23.1 mmol) in methanol (23 mL) and 1,4-dioxane (23 mL) was added 4M hydrochloric acid in 1,4-dioxane (23 mL) and after stirring 1 hr, material dripped in to stirring IPA, let stand overnight. Collection of solid under N₂ followed by washing with IPA and hexane then drying on high vacuum over P₂O₅ provided 12.5 g (91.8%) of the title compound as a hydrochloric acid salt that was colorless. NMR(DMSO) δ2.05–2.25 (m, 4H), 2.74, (t, 2H), 2.81 (t, 2H), 3.18–3.26 (m, 4H), 3.39 (s, 3H), 3.51–3.61 (m, 4H), 4.09 (t, 2H), 7.15 (d, 2H), 7.22 (d, 1H), 7.29–7.49 (m, 6H), 7.58 (d, 2H), 7.45 (d, 2H). ESMS m/z=553 (M+H)⁺. HRMS calcd. for C₃₀H₃₅N₂O₅S H: 553.2369 (M+H)⁺. Found: 553.2372.

Example 45

Preparation of:

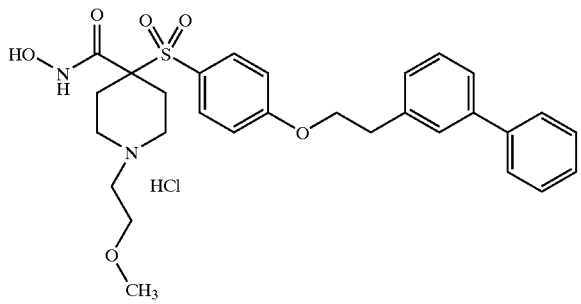

Part A
Preparation of:

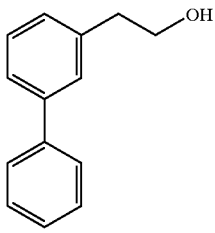

In a flask were combined the 3-bromophenethyl alcohol (17.5 g, 87.1 mmol), phenyl boronic acid (12.7 g, 104.5 mmol), palladium tetrakistriphenylphosphine (2.0 g, 1.74 mmol), 2M cesium carbonate (105 mL, 210 mmol) and dimethoxyethylether (105 mL). Mixture stirred vigorously under nitrogen at reflux overnight. After cooling to ambient temperature, poured mixture into water (400 mL) and extracted with ethyl acetate (2×400 mL). Combined organics were washed with brine and dried over magnesium sulfate. Silica gel chromotography (ethyl acetate/hexane) provided the coupled product as a crystalline solid (15.04 g, 87.3%). NMR(CDCl$_3$) δ2.95 (t, 2H), 3.93 (q, 2H), 7.19–18 (m, 2H), 7.31–7.51 (m, 5H), 7.58 (d, 2H). GCMS EI+198 (M+).

Part B
Preparation of:

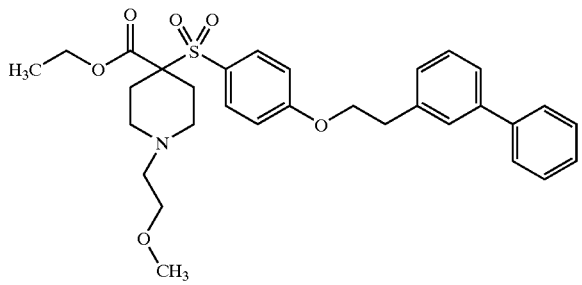

To a solution of the alcohol from Part A (14.9 g, 75.2 mmol) in anhydrous dimethylformamide (70 mL) at 0° C. was added 60% sodium hydride (3.0 g, 75.2 mmol) in portions. After completion of the addition, the reaction was stirred at 0° C. for 30 min. ethyl 4-[(4fluorophenyl)sulfonyl]-1-(2-methoxyethyl)piperidine-4-carboxylate (33.6 g, 90.2 mmol) in anhydrous dimethylformamide (50 mL) at 5° C. was added slowly. Upon completion of addition let reaction slowly warm up overnight. Reaction was poured into water (700 mL) and extracted with ethyl acetate (3×500 mL). The combined organics were washed with brine and dried over sodium sulfate. Concentration gave 50.6 g of crude material. This material was used without purification. ESMS m/z=552 (M+H)$^+$.

Part C

Preparation of:

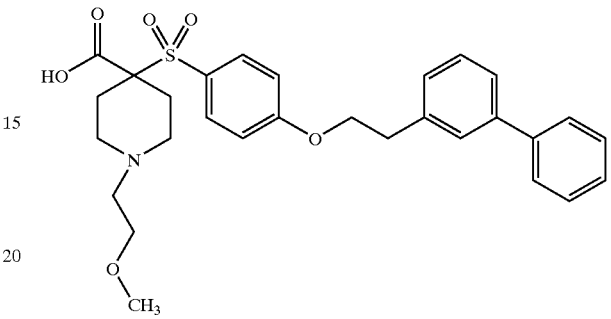

The impure ester of Part B (75.2 mmol theoretical) was hydrolyzed in 75 mL of ethanol, 75 mL of 1,4-dioxane and 50 mL of 6 N NaOH at 60 C. for 2.5 hr. The solution was poured into water and extracted with ether to remove color. Acidification with 1N HCl caused precipitation of the acid which was collected by filtration and washed with water, ethyl acetate and diethyl ether then dried under high vacuum yielding the acid as a white solid (31.7 g, 80.6% yield). ESMS m/z=524 (M+H)$^+$. HRMS calcd. for C$_{29}$H$_{34}$NO$_6$S: 524.2101 (M+H)$^+$. Found: 524.2075.

Part D

Preparation of:

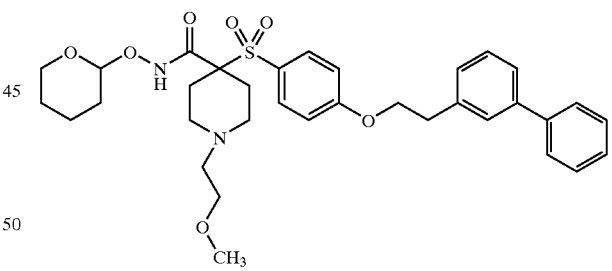

The acid of Part C (31.6 g, 60.4 mmol), HOBt (13.9 g, 90.6 mmol), EDC (16.2 g, 84.6 mmol), triethylamine (25.2 mL, 181 mmol) and TBP-hydroxylamine (10.6 g, 90.6 mmol) were stirred in anhydrous dimethylformamide (200 mL) under N$_2$ at 60° C. overnight. After cooling to room temperature solution was poured into 1.6 L of ice water and extracted with ethyl acetate (2×1 L). The organic layer was washed with brine and dried over sodium sulfate. Silica gel chromatography (2.0M NH$_3$ in MeOH/ethyl acetate/hexane) gave the desired product as a colorless foam (30.89 g, 82%). ESMS m/z=623 (M+H)$^+$. HRMS calcd. for C$_{34}$H$_{43}$N$_2$O$_7$S: 623.2786 (M+H)$^+$. Found: 623.2793.

Part E
Preparation of:

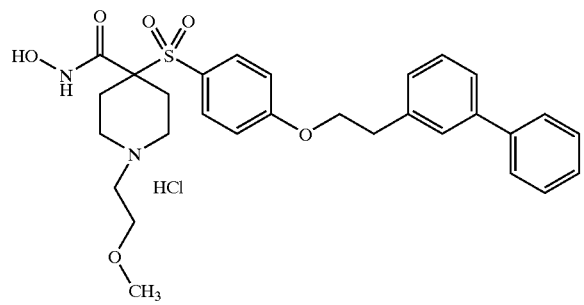

To the product from Part D (30.7 g, 49.3 mmol) in methanol (49 mL) and 1,4-dioxane (49 mL) was added 4N HCl in dioxane (50 mL). Material concentrated after 1 hr and crystallized from methanol providing the desired product as a colorless crystalline solid (25.6 g, 90.2%). ESMS m/z=539 (M+H)$^+$. HRMS calcd. for $C_{29}H_{35}N_2O_6S$: 539.2210 (M+H)$^+$. Found: 539.2187.

Example 46

Preparation of:

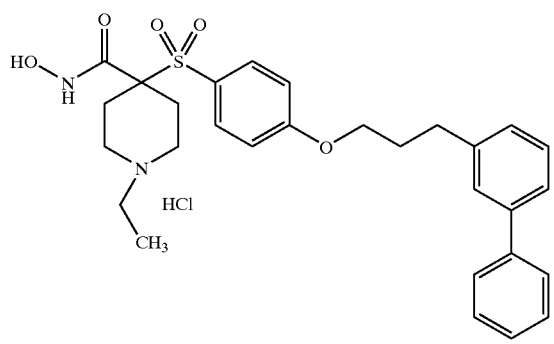

Part A
Preparation of:

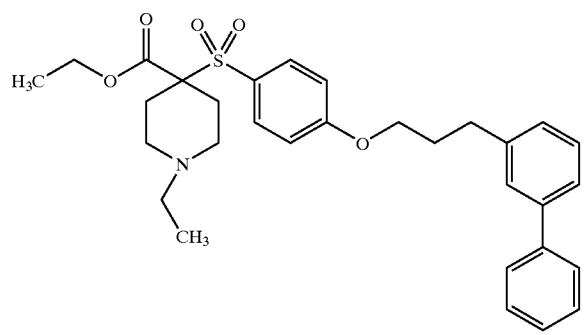

To a solution of the alcohol from Example 38, Part B (12.0 g, 56.1 mmol) in anhydrous dimethylformamide (50 mL) at 0° C. was added 60% sodium hydride (2.58 g, 64.5 mmol) in portions. After completion of the addition, the reaction was stirred at 0° C. for 15 min then ambient temperature for 15 min. The reaction was cooled to 0° C. and ethyl 1-ethyl-4-[(4-fluorophenyl)sulfonyl]piperidine-4-carboxylate (17.7 g, 51.6 mmol) in anhydrous dimethylformamide (60 mL) was added slowly. Upon completion of addition, ice bath was removed and reaction stirred at ambient temperature overnight. Reaction was poured into water and extracted with ethyl acetate 2 times. The combined organics were washed with water 2 times and brine and dried over sodium sulfate. Concentration gave 34.4 g of crude material. This material was used without purification. ESMS m/z=536 (M+H)$^+$.

Part B
Preparation of:

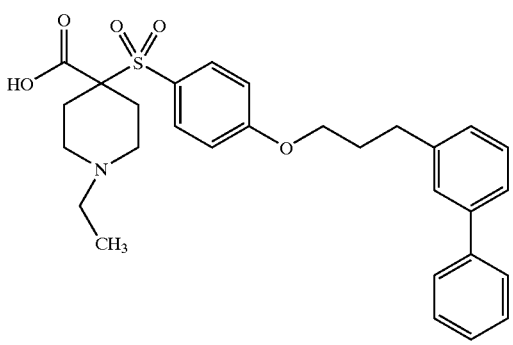

The impure ester of Part A (51.6 mmol theoretical) was hydrolyzed in 50 mL of ethanol, 50 mL of 1,4-dioxane and 34.4 mL of 6 N NaOH at 60° C. After cooling to room temperature, the solution was poured into water (500 mL) and extracted with ether (2×250 mL) to remove color. Acidification with 1N HCl caused precipitation of the acid which was collected by filtration and washed with water, ethyl acetate and hexane then dried under high vacuum yielding the acid as an off white solid (18.4 g, 70% yield). ESMS m/z=508 (M+H)$^+$. HRMS calcd. for $C_{29}H_{34}NO_5S$ H: 508.2152 (M+H)$^+$. Found: 508.2176.

Part C
Preparation of:

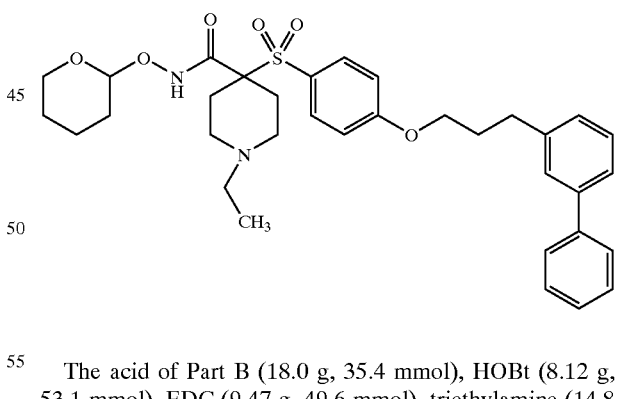

The acid of Part B (18.0 g, 35.4 mmol), HOBt (8.12 g, 53.1 mmol), EDC (9.47 g, 49.6 mmol), triethylamine (14.8 mL, 106.2 mmol) and THP-hydroxylamine (6.21 g, 53.1 mmol) were stirred in anhydrous dimethylformamide (110 mL) under $N_2$ at 60° C. overnight. After cooling to room temperature, the solution was poured into water (600 mL) and extracted with ethyl acetate. The organic layer was washed with water and brine and dried over sodium sulfate. Silica gel chromatography (2.0M $NH_3$ in MeOH/ethyl acetate/hexane) gave the desired product as a colorless foam (11.0 g, 51%). ESMS m/z=607 (M+H)$^+$. HRMS calcd. for $C_{34}H_{43}N_2O_6S$: 607.2836 (M+H)$^+$. Found: 607.2829

Part D
Preparation of:

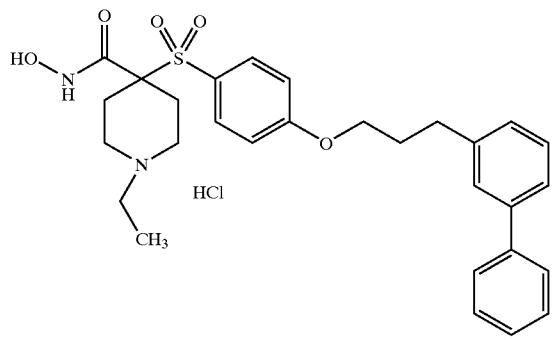

To the product from Part C (10.8 g, 17.8 mmol) in methanol (18 mL) and 1,4-dioxane (18 mL) was added 4M hydrochloric acid in 1,4-dioxane (18 mL) and after stirring 1 hr, material concentrated. Co-crystallized with another batch from MeOH/4N HCl/dioxane. Collection of solid followed by washing with methanol then drying on high vac provided 11.51 g (88%) of the title compound as a hydrochloric acid salt that was colorless. ESMS m/z=523 (M+H)$^+$. HRMS calcd. for $C_{29}H_{35}N_2O_5S$ H: 523.2261 (M+H)$^+$. Found: 523.2224.

Example 47

Preparation of 4-[(4-{3-[4-(2,4-difluorophenyl)thien-2-1]propoxy}phenyl)sulfonyl]-N-hydroxy-1-(2-methoxyethyl)piperidine-4-carboxamide hydrochloride

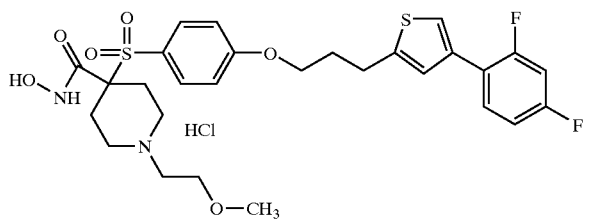

Part A
A round bottom flask was charged with 4-bromo-2-thiophene carboxaldehyde (Aldrich, 55.8 g, 292 mmol), 2,4difluorophenyl boronic acid (Aldrich, 60.0 g, 380 mmol), tetrakis-triphenylphosphine palladium (Aldrich, 16.9 g, 14.6 mmol), 2 M $Na_2CO_3._{aq}$ (190 ml, 380 mmol), and ethylene glycol-dimethyl ether (Aldrich, 500 ml). The reaction was heated to 80° C. and stirred for 5 hr. The reaction suspension was then poured into a mixture of methylene chloride (500 ml) and ice water (500 ml). The organic layer was separated and washed with water (2×-200 ml) and brine (1×300 ml) then dried over $Na_2SO_4$ and concentrated to afford the thiophene phenyl adduct as a brown oil. Silica gel purification (hexanes/ethyl acetate) yielded a white solid (34.2 g, 52% yield). $^1$H NMR showed the desired compound.

Part B
A solution of triethyl phosphonoacetate (Aldrich, 24.2 g, 108 mmol) in tetrahydrofuran (100 ml) was cooled to −78° C. A 1.6 M n-butyllithium solution in hexanes (68 ml, 108 mmol) was slowly dripped in then the reaction stirred for 30 min at −78° C. A solution of the thiophene phenyl carboxaldehyde product from Part A in tetrahydrofuran (100 ml) was slowly dripped in. The dry ice bath was removed and the reaction stirred as it came to ambient temperature overnight. The mixture was diluted with water (200 ml) to quench. The organic layer was separated and washed with water (2×-200 ml) and brine (1×-300 ml) then dried over $Na_2SO_4$ and concentrated to afford a tan solid. This solid was recrystallized from warm methanol to yield a light yellow solid (16.1 g, 56% yield). $^1$H NMR showed the desired compound.

Part C
A solution of the ethyl ester olefin of Part B (16 g, 54.4 mmol) in methylene chloride was cooled to 0° C. A 1.0 M solution of lithium aluminum hydride was dripped in slowly, then the reaction continued stirring for 45 min at 0° C. A saturated solution of $NH_4Cl._{aq}$ was dripped in to quench, followed by a solution of sodium, potassium tartrate$_{aq}$ (10 ml). After stirring for 30 min, $Na_2SO_4$ (40 g) was added. The mixture was filtered and concentrated to afford a yellow oil (16.8 g, 100$^+$% yield). $^1$H NMR showed the desired compound along with impurities.

Part D
A hydrogenation flask was charged with the crude hydroxy olefin residue from Part C (~54.4 mmol) was dissolved in tetrahydrofuran (125 ml) and methanol (20 ml). Nitrogen gas was bubbled through for 15 min then 10% Pd/C catalyst (Aldrich, 50% water, 2.7 g) was added. A hydrogenation head was attached and the vessel was purged with nitrogen (3×), followed by hydrogen (3×). The vessel was left at 50 psi of hydrogen. After 1 hr of stirring, the reaction was complete by LCMS. The mixture was filtered through a Celite pad and concentrated to afford a black oil that was purified on silica gel (hexanes/ethyl acetate). Collected fractions gave the product as a clear oil (8.6 g, 62% yield).). $^1$H NMR showed the desired compound.

Part E
The saturated alcohol from Part D (7.6 g, 30.0 mmol) was dissolved in dimethylsulfoxide (60 ml). Sodium hydride (Aldrich, 60% in oil dispersion, 1.3 g, 32.6 mmol) was added portion wise over 30 min. After stirring for 1 hr, the aryl-fluoride, SC 84087, was added and the reaction was stirred overnight at ambient temperature. The reaction was quenched with saturated $NH_4Cl._{aq}$ (100 ml) then extracted with ethyl acetate (3×-125 ml). The combined organics were washed with water (2×-200 ml) and brine (1×-200 ml) then dried over $Na_2SO_4$ filtered and concentrated to a brown oil. The residue was purified on silica gel (hexanes/ethyl acetate) to afford the product as a tan solid (14.0 g, 81% yield).). $^1$H NMR showed the desired compound at 90% purity.

Part F
The t-butyl ester from Part E (9.5 g, 15.0 mmol) was dissolved in methylene chloride (30 ml) after which, trilfluoroacetic acid (Aldrich, 30 ml) was added. The reaction stirred for 4 hr then was concentrated to one-third volume via a nitrogen stream. The slightly viscous residue was then dripped into stirring diethyl ether to form a solid that was filtered and dried to give the product as a tan solid (6.9 g, 66% yield).). $^1$H NMR showed the desired compound.

Part G
To a solution of the carboxylic acid of Part F (6.9 g, 9.9 mmol) in N,N-dimethylformamide (20 ml) was added triethylamine (Aldrich, 4.2 ml, 30.0 mmol) followed by N-hydroxybenzotriazole hydrate (Aldrich, 2.7 g, 20.0 mmol), O-(tetrahydro-2H-pyran-2-yl) hydroxylamine (2.34 g, 20.0 mmol), and, lastly, 1-(3-dimethylaminopropyl)-3-ethylcarbodiimide hydrochloride (Sigma, 4.18 g, 21.8 mmol). The reaction stirred at room temperature for 18 hr. The mixture was diluted with water (30 ml) then extracted with ethyl acetate (3×-100 ml). The organics were combined and washed with saturated $NaHCO_3._{aq}$ (3×-100 ml), water (2×-100 ml), and brine (1×-150 ml). After drying over Na₂SO₄, the mixture was filtered and concentrated for a tan oil. The oil was tritiated with ethanol (3×) and methanol (3×) to afford a tan oil (8.1 g, 100⁺% yield). ¹H NMR showed the desired compound with trace impurities.

Part H

The crude protected hydroxamic acid of Part G (~9.9 mmol) was slurried in methanol (4 ml) and stirred with 4 N HCl in dioxane (20 ml) for 1 hr. The solvent volume was reduced in half then diethylether was added, providing a gummy solid that was purified by Reverse Phase LC ($C_{18}$, acetonitrile/water). The resulting partial TFA salt was dissolved in 4 N HCl in dioxane (20 ml) and stirred for 1 hr. The solvent volume was again reduced in half then diethyl ether was added, providing a white solid. The solid was collected and dried to afford the desired hydrochloride salt as a white powder (3.35 g, 54% yield). ¹H NMR showed the desired compound.

Example 48

Preparation of:

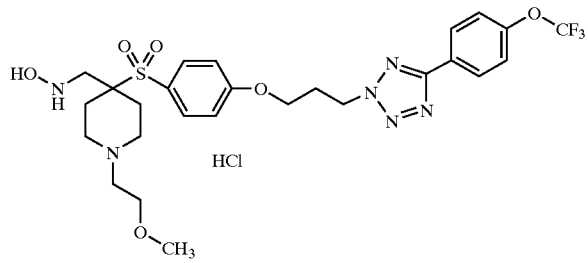

Part A

Preparation of:

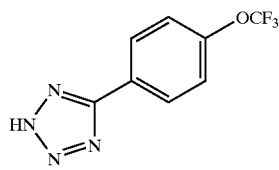

A mixture of lithium chloride (1.71 g, 40.3 mmol), trifluoromethoxy-benzonitrile (5.00 g, 26.7 mmol), and sodium azide (1.75 g, 26.7 mmol) in 2-methoxyethanol (26 mL) under an $N_2$ atmosphere was refluxed for 4 hr. The ambient mixture was poured into a mixture of ice (84 g) and concentrated HCl (8.4 mL) and stirred until the ice melted. The white solid was collected by filtration, washed with water, and dried for 2 hr in a 40° C. vacuum oven to produce the tetrazole in the form of an off white solid (4.86 g, 79% yield). MS MH⁺ calcd. for $C_8H_6N_4OF_3$ 231, found 231.

Part B

Preparation of:

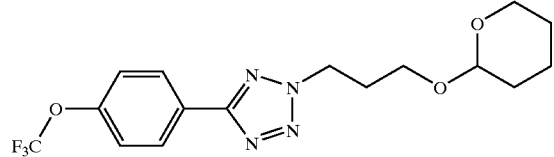

A solution of the tetrarole of Part A (2.00 g, 8.69 mmol) in NMP (12 mL) was added dropwise to an ambient mixture of 95% sodium hydride (0.438 g, 18.2 mmol) in NMP (12 mL) under an $N_2$ atmosphere. After an 1 hr of stirring, 2-(3-chloropropoxy)tetrahydro-2H-pyran (1.58 mL, 9.56 mmol) was added dropwise. The mixture was stirred at ambient temperature for 18 hr and then at 70° C. for 2 hr. The mixture was diluted with a solution of water (200 mL) and saturated NaHCO₃ (100 mL), and extracted with ethyl acetate (3×100 mL). The organic layer was washed with water (2×100 mL) and brine (100 mL), dried over MgSO₄, and concentrated in vacuo to produce a yellow liquid. Flash chromatography purification (ethyl acetate-hexane/silica gel) provided the pyran in the form of a white solid (1.46 g, 45% yield). Anal. Calcd. for $C_{16}H_{19}N_4O_3F_3$: C,56.34; H, 5.98; N, 7.73; S, 4.42. Found C,56.13; H, 6.08; N, 7.65; S, 4.75.

Part C

Preparation of:

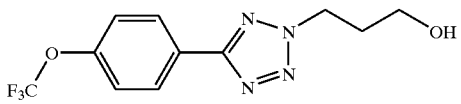

To an ambient solution of the pyran of Part B (1.40 g, 3.76 mmol) in MeOH (13.5 mL) was added a solution of acetyl chloride (0.896 mL, 13.1 mmol) in MeOH (13.5 mL). After 15 min, the solution was concentrated in vacuo to provide the alcohol in the form of a solid (1.02 g, 94% yield). MS MH⁺ calcd. for $C_{11}H_{12}N_4O_2F_3$ 289, found 289.

Part D

Preparation of:

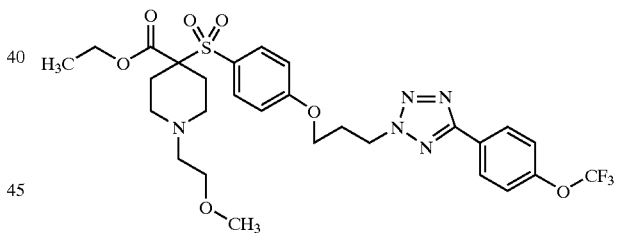

To an ambient mixture of 95% sodium hydride (0.110 g, 3.58 mmol) in NMP (2.5 mL) under an $N_2$ atmosphere was added dropwise a solution of the alcohol of Part C (1.00 g, 3.47 mmol) in NMP (3.2 mL), and then the mixture was heated at 55° C. for 30 min. A solution of ethyl 4-[(4fluorophenyl)sulfonyl]-1-(2-methoxyethyl)piperidine-4-carboxylate (1.22 g, 3.27 mmol) in NMP (3.2 mL) was added dropwise to the 55° C. reaction mixture. After 1 hr at 55° C., the ambient mixture was diluted with a solution of water (600 mL) and NaHCO₃ (100 mL), and extracted with ethyl acetate (3×200 mL). The organic layer was washed with water (2×150 mL) and brine (150 mL), dried over MgSO₄, and concentrated in vacuo to form a yellow oil (1.96 g). Flash chromatography purification (MeOH-EA/silica gel) provided the sulfone in the form of a yellow oil (1.48 g, 70% yield). MS MH⁺ calcd. for $C_{28}H_{35}N_5O_7SF_3$ 642, found 642.

Part E

Preparation of:

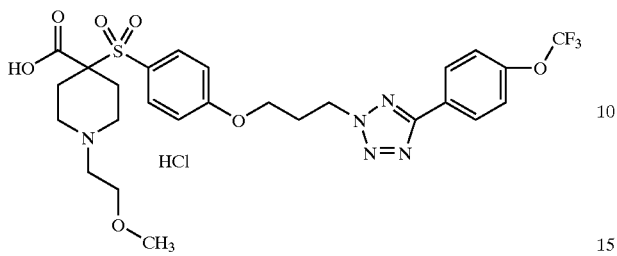

A mixture of the sulfone of Part D (1.44 g, 2.24 mmol) and 50% aqueous NaOH (1.08 g, 22.4 mmol) in a solution of THF (23 mL) and EtOH (11 mL) was stirred at ambient temperature for 3 hr and then 60° C. for 15 min. The mixture was concentrated in vacuo, diluted with a solution of acetonitrile and water, acidified to a pH of approximately 2 with concentrated HCl, and concentrated in vacuo to provide the acid (containing NaCl) as a crude tan foam (2.77 g). MS MH+ calcd. for $C_{26}H_{31}N_5O_7SF_3$ 614, found 614.

Part F

Preparation of:

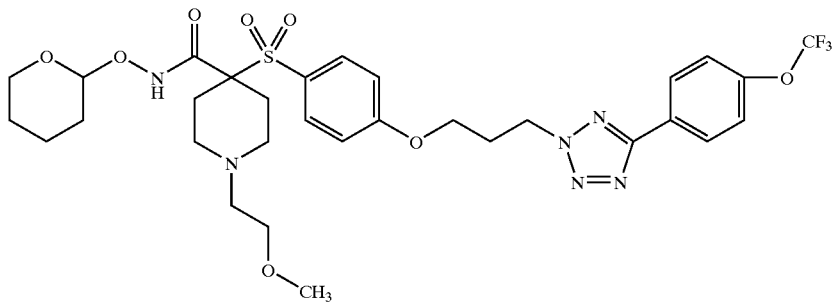

A mixture of the crude acid of Part E (2.24 mmol), 1-hydroybenzotriazole hydrate (0,534 g, 3.95 mmol), triethylamine (3.62 mL, 25.9 mmol), O-(tetrahydro-2H-pyran-2-yl)hydroxylamine (0.542 g, 4.63 mmol), and 1-(3-dimethylaminopropyl)-3-ethylcarbodimide hydrochloride (0.888 g, 4.63 mmol) in DMF (23 mL) under an $N_2$ atmosphere was stirred at ambient temperature for 40 hr. The mixture was diluted with water (400 mL) and extracted with ethyl acetate (3×100 mL). The organic layer was washed with water (2×100 mL) and brine (100 mL), dried over $MgSO_4$, and concentrated in vacuo to form a white foam (1.37 g). Chromatography purification (MeOH-EA/silica gel) produced the O-protected hydroxamate in the form of a white foam (1.04 g, 65% based on the ester of Part ID). MS MH+ calcd. for $C_{31}H_{40}N_6O_8F_3S$ 713, found 713. Anal. Calcd. for $C_{31}H_{39}N_6O_8F_3S$: C,52.24; H, 5.52; N,11.79. Found C,52.47; H, 5.73; N, 11.64.

Part G

Preparation of:

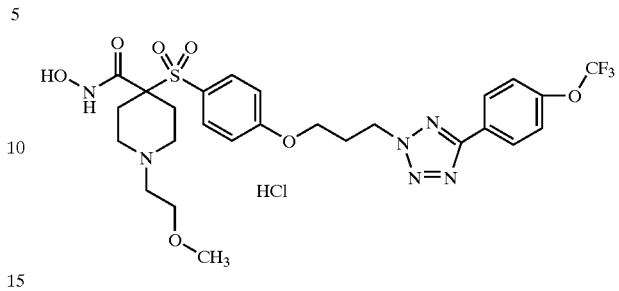

A solution of the O-protected hydroxamate of Part F (0.960 g, 1.35 mmol) and acetyl chloride (0.493 g, 6.53 mmol) in methanol (15 mL) was stirred at ambient temperature for 1 hr. The solution was concentrated in vacuo to a white solid. The solid was triturated with ether and concentrated in vacuo to provide the title compound in the form of a white solid (0.66 g, 74% yield). Anal. Calcd. for $C_{26}H_{31}N_6O_7F_3S.HCl$: C, 46.95; H, 4.85; N, 12.64; Cl, 5.33; S, 4.82. Found C, 46.59; H, 5.07; N, 12.64; Cl, 5.36; S, 5.20. MS MH+ calcd. for $C_{26}H_{32}N_6O_7F_3S$ 629, found 629.

Example 49

Preparation of:

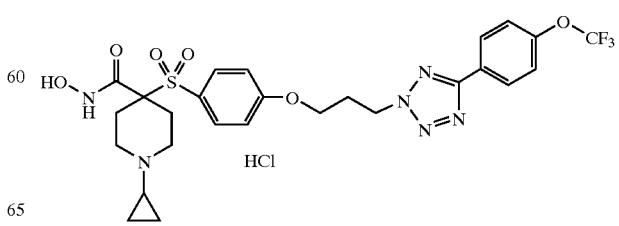

Part A

Preparation of:

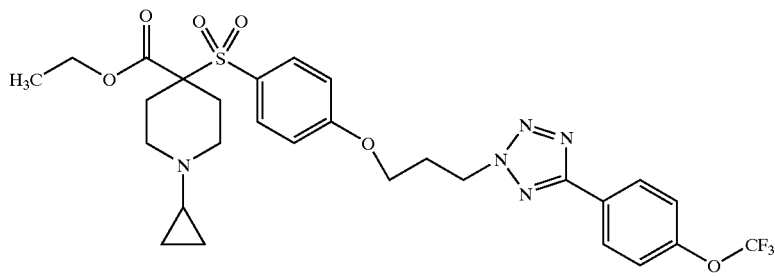

To an ambient mixture of 95% sodium hydride (0.397 g, 16.5 mmol) in NMP (7 mL) under an $N_2$ atmosphere was added dropwise a solution of the alcohol of Part C of Example 48 (3.44 g, 11.9 mmol) in NMP (7 mL). The mixture was then stirred at ambient temperature for 45 min. The ethyl 1-cyclopropyl-4-[(4-fluorophenyl)sulfonyl] piperidine-4-carboxylate (4.00 g, 11.3 mmol) was added in one portion, and the mixture was heated to 60° C. After heating for 24 hr at 60° C. and adding 2 more portions of 95% sodium hydride (0.10 g, 4.0 mmol and 0.08 g, 3.0 mmol), the mixture was diluted with water (300 mL) and extracted with ethyl acetate (3×100 mL). The organic layer was washed with water (2×100 mL) and brine (100 mL), dried over $MgSO_4$, and concentrated in vacuo to form a yellow oil (5.81 g). Flash chromatography purification (Hexane-EA/silica gel) produced the sulfone in the form of a yellow oil (3.10 g, 44% yield). The proton NMR ($CDCl_3$) spectrum was consistent with the desired sulfone product.

Part B

Preparation of:

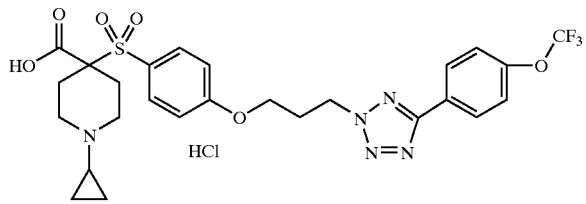

A mixture of the sulfone of Part A (3.00 g, 4.81 mmol) and 50% aqueous NaOH (3.85 g, 48.1 mmol) in a solution of THF (50 mL) and EtOH (24 mL) was stirred for 2.5 hr at 60° C. The mixture was concentrated in vacuo, diluted with a solution of acetonitrile and water, acidified to a pH of approximately 2 with concentrated HCl, and concentrated in vacuo. The crude acid was purified by reverse phase HPLC ($H_2O$—$CH_3CN$) to produce the acid in the form of a white solid (1.86 g, 55% yield). MS $MH^+$ calcd. for $C_{26}H_{29}N_5O_6F_3S$ 596, found 596.

Part C

Preparation of:

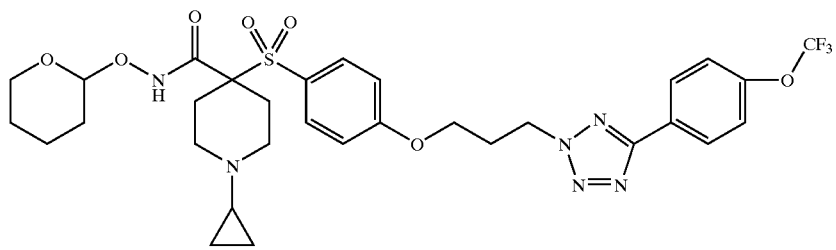

A mixture of the acid of Part B (1.80 g, 2.85 mmol), 1-hydroybenzotriazole hydrate (0.679 g, 5.02 mmol), triethylamine (4.61 mL, 33.1 mmol), O-(tetrahydro-2H-pyran-2-yl)hydroxylamine (0.692 g, 5.91 mmol), and 1-(3-diethylaminopropyl)-3-ethylcarbodiimide hydrochloride (1.13 g, 5.91 mmol) in DMF (29 mL) under an $N_2$ atmosphere was stirred at ambient temperature for 24 hr and 57° C. for 6.5 hr. The mixture was concentrated in vacuo, diluted with water (300 mL), and extracted with ethyl acetate (3×100 mL). The organic layer was washed with water (2×100 mL) and brine (100 mL), dried over $MgSO_4$, and concentrated in vacuo to form a yellow oil (1.80 g). Flash chromatography purification (MeOH—$CH_2Cl_2$/silica gel) produced the O-protected hydroxamate in the form of a white foam (0.89 g, 45% yield). MS $MH^+$ calcd. for $C_{31}H_{38}N_6O_7F_3S$ 695, found 695. Anal. Calcd. for $C_{31}H_{37}N_6O_7F_3S$: C,53.59; H, 5.37; N,12.10; S, 4.62. Found C,53.30; H, 5.43; N, 12.05; S, 4.73.

Part D

Preparation of:

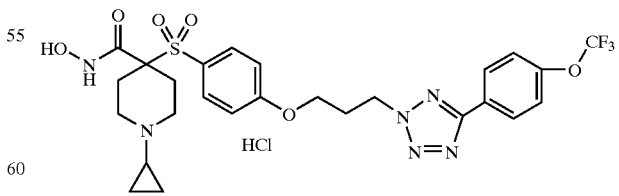

A solution of the O-protected hydroxamate of Part C (0.870 g, 1.25 mmol) and acetyl chloride (0.456 g, 6.04 mmol) in methanol (14 mL) was stirred at ambient temperature for 30 min. The mixture was poured into diethyl ether (250 mL). The white solid was isolate by filtration and dried in a 40° C. vacuum oven to produce the title compound in the form of a white solid (0.56 g, 69% yield). MS MH+ calcd. for $C_{26}H_{30}N_6O_6F_3S$ 611, found 611.

Example 50

Preparation of:

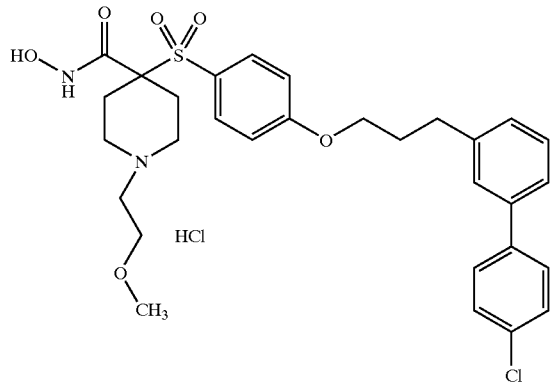

Part A
Preparation of:

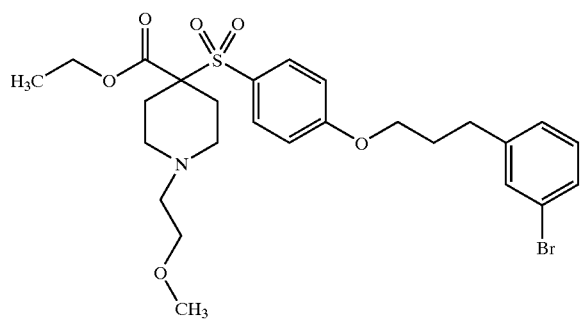

To a solution of the alcohol from Part B of Example 38 (3.65 g, 17.0 mmol) in anhydrous dimethylformamide (17 mL) at 5° C. was added 60% sodium hydride (0.77 g, 19.3 mmol) in portions. After completion of the addition, the reaction was stirred at 5° C. for 15 min and then at ambient temperature for 15 min. The reaction was cooled to 5° C. and ethyl 4-[(4-fluorophenyl)sulfonyl]-1-(2-methoxyethyl) piperidine-4-carboxylate (6.0 g, 16.1 mmol) in anhydrous dimethylformamide (15 mL) was added slowly. Reaction stirred at room temperature for 2 hr. then was diluted with water (250 mL) and extracted with ethyl acetate (3×150 mL). The combined organics were washed with brine and dried over magnesium sulfate. Silica Gel chromatography (ethyl acetate/hexane) gave the product as a colorless oil (8.06 g, 88%). NMR(CDCl$_3$) δ1.20–1.26 (m, 3H), 1.88–2.02 (m, 2H), 2.06–2.27 (m, 4H), 2.43 (d, 2H), 2.53 (bs, 2H), 2.78 (t, 2H), 2.97–3.08 (m, 2H), 3.32 (s, 3H), 3.47 (bs, 2H), 4.00 (t, 2H), 4.18 (q, 2H), 6.95 (d, 2H), 709–7.18 (m, 2H), 7.34 (d, 2H), 7.68 (d, 2H).

Part B
Preparation of:

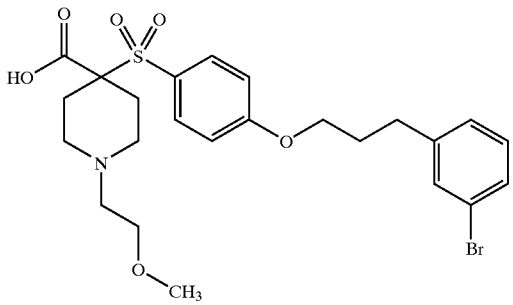

The impure ester of Part A (8.06 g, 14.2 mmol theoretical) was hydrolyzed in 15 mL of ethanol, 15 mL of 1,4-dioxane and 9.5 mL of 6 N NaOH at 60° C. The solution was poured into water and extracted with ether to remove color. Acidification with 1N HCl caused precipitation of the acid which was collected by filtration and washed with water and hexane then dried under high vacuum yielding the acid as an off white solid (5.90 g, 76.8% yield). NMR (CD$_3$OD w/K$_2$CO$_3$) δ2.00 (q, 2H), 2.07–2.19 (m, 4H), 2.32 (d, 2H), 2.48 (t, 2H), 2.79 (d, 2H), 2.91 (d, 2H), 3.45 (t, 2H), 4.06 (t, 2H), 7.04 (d, 2H), 7.20 (d, 2H), 7.29–7.35 (m, 1H), 7.40 (s, 1H), 7.78 (d, 2H).

Part C
Preparation of:

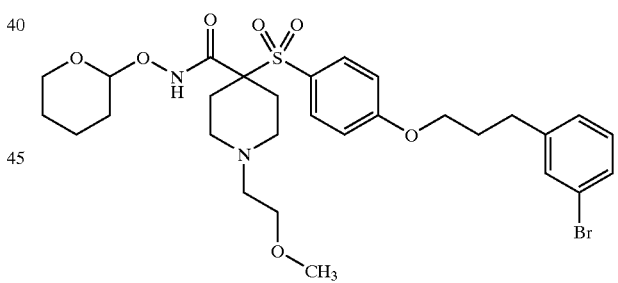

To the acid of Part B (5.90, 10.9 mmol), EDC (2.9 g, 15.3 mmol), and HOBt (2.5 g, 16.4 mmol) in anhydrous NMP (33 mL) was added triethylamine (4.5 mL, 32.7 mmol). After heating at 60° C. for 1 hr, THP-hydroxylamine (1.9 g, 16.4 mmol) was added. The solution was stirred for 18 hr at 60° C., additional EDC (2.9 g, 15.3 mmol), HOBt (2.5 g, 16.4 mmol), triethylamine (4.5 mL, 32.7 mmol) and THP-hydroxylamine (1.9 g, 16.4 mmol) were added. After 2 hr, the reaction was diluted with water (300 mL) and extracted with ethyl acetate (3×150 mL). The combined organics were washed with brine and dried over magnesium sulfate. Silica gel Chromatography (ethyl acetate/hexanes) provided the protected hydroxamate as a viscous impure colorless oil (5.70 g). ESMS m/z=641 (M+H)+.

Part D

Preparation of:

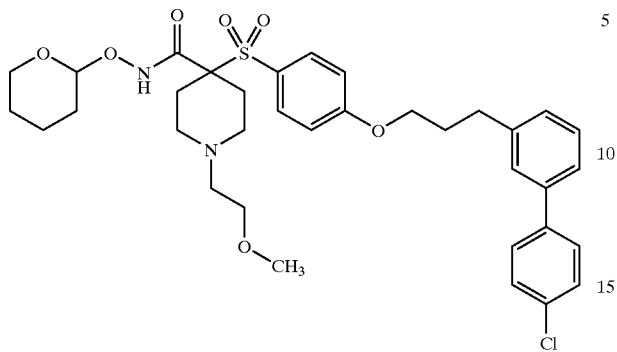

In a vial were combined the aryl bromide from Part C (0.50 g, 0.78 mmol) in 3 mL of dimethoxyethyl ether, 4-chlorobenzeneboronic acid (185 mg, 1.17 mmol), palladium tetrakistriphenylphosphine (~45 mg, 0.04 mmol) and 2M cesium carbonate (1.17 mL, 2.34 mmol). Mixture stirred vigorously at 80° C. for 18 hr. Reaction poured onto 2 mL Chem-Elut tube prewetted with 3 mL of water and eluted with ethyl acetate and methylene chloride. Purification by reverse phase chromatography (acetonitrile/water/0.05% TFA) gave the TFA salt of the deprotected material (239.6 mg) which was carried on as is.

Part E

Preparation of:

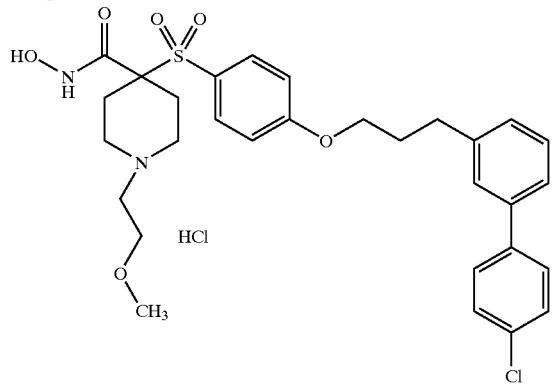

The product from Part D (239.6 mg) was taken up in 4M hydrochloric acid in 1,4-dioxane (2 mL) and methanol (1–2 mL) and stirred for 0.5 hr then concentrated. This was repeated. Product crashed out of solution, was collected by filtration, washed with diethyl ether and dried under high vacuum yielding the title compound as colorless solid (170.5 mg, 35% over two steps). ESMS m/z=587 (M+H)$^+$. HRMS calcd. for $C_{30}H_{36}ClN_2O_6S$: 587.1977 (M+H)$^+$. Found: 587.1979.

Example 51

Preparation of 1-cyclopropyl-N-hydroxy-4-{[4-(3-{3-[4-(trifluoromethoxy)phenyl]-1,2,4-oxadiazol-5yl}propoxy)phenyl]sulfonyl}piperidine-4-carboxamide hydrochloride

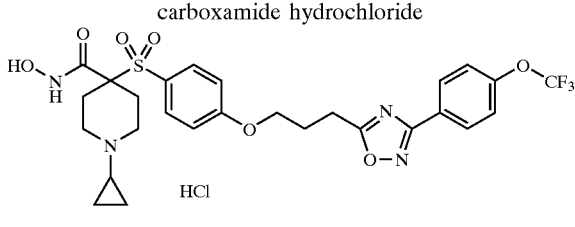

Part A

In dry equipment under nitrogen, potassium trimethylsilanolate (35.9 g, 0.28 mol) was dissolved in dimethylsulfoxide (250 mL) and gamma-butyrolactone (16.14 mL, 0.21 mol) was added over 10 min while the reaction temperature rose to 38° C. After stirring at ambient temperature for 40 min, sodium hydride (8.4 g of a 60% oil dispersion, 0.21 mol) was added portion wise over 20 min and the reaction temperature rose to 43° C. Gas evolution was also observed. After stirring at ambient temperature for 50 min, a solution of ethyl 1-cyclopropyl-4-[(4-fluorophenyl)sulfonyl]-4-piperidinecarboxylate (49.7 g, 0.14 mol) in dimethylsulfoxide (50 mL) was added over 10 min as the reaction temperature rose to 38° C. The reaction was stirred at ambient temperature for 30 min. The slurry was slowly poured into ice water (1.5 L) and then extracted with hexanes (150 mL) 3 times followed by a diethyl ether extraction (300 mL). The aqueous layer was chilled to 5° C. and the pH adjusted to 6 with concentrated hydrochloric acid. The slurry was filtered and the cake washed with 500 mL water two times. The solid was dried in vacuo to give the butyric acid as a white solid (47.5 g, 77%). LCMS m/z=440 [M+H]$^+$.

Part B

In dry equipment under nitrogen, the butyric acid from Part A (3.07 g, 7.0 mmol) was dissolved in dry dimethylacetamide (15 mL) and the remaining reagents were added to the solution in the following order: N-hydroxybenzotriazole hydrate (1.42 g, 10.5 mmol), triethylamine (1.95 mL, 14.0 mmol), 4-(trifluoromethoxy)benzamidoxime (2.31 g, 10.5 mmol), and 1-(3-dimethylaminopropyl)-3-ethylcarbodiimide hydrochloride (2.68 g, 14.0 mmol). Additional dry dimethylacetamide (5 mL) was added. After 24 hr at 70° C., the reaction was concentrated in vacuo. The residue was taken up in ethyl acetate, washed with water, saturated NaHCO$_3$, saturated sodium chloride solution, dried over Na$_2$SO$_4$, filtered, and concentrated in vacuo. Chromatography (on silica, ethyl acetate/methanol/hexanes) provided the oxadiazole as a light white solid (3.38 g, 78%). LCMS m/z=624[M+H]$^+$.

Part C

A slurry of the oxadiazole from Part B (3.36 g, 5.39 mmol), 2.5N sodium hydroxide (6.5 mL, 16.2 mmol) and sodium hydroxide (0.86 g, 21.6 mmol) in isopropanol (27 mL) was stirred at 75° C. for 5 hr. The heat was removed and the reaction diluted with water (50 mL) and chilled to 5° C. The pH was adjusted to 7 with concentrated hydrochloric acid. The solids were filtered, washed with hexanes, and dried in vacuo to give the carboxylic acid as a white solid (3.1 g, 97). LCMS m/z=596 [M+H]$^+$.

Part D

In dry equipment under nitrogen, the carboxylic acid from Part C (2.9 g, 4.87 mmol) was dissolved in dry dimethylacetamide (10 mL) and the remaining reagents were added to the solution in the following order: N-hydroxybenzotriazole hydrate (0.99 g, 7.3 mmol), triethylamine (2.03 mL, 14.6 mmol), O-(tetrahydro-2H-pyran-2-yl)hydroxylamine (0.86 g, 7.31 mmol), and 1-(3-dimethylaminopropyl)-3-ethylcarbodiimide hydrochloride (1.87 g, 9.75 mmol). Additional dry dimethylacetamide (5 mL) was added. After 29 hr at 40° C., the reaction was concentrated in vacuo. The residue was taken up in ethyl acetate, washed with water, saturated NaHCO$_3$, saturated sodium chloride solution, dried over Na$_2$SO$_4$, filtered, and concentrated in vacuo. Chromatography (on silica, ethyl acetate/methanol/hexanes) provided the THP hydroxamate as a white foam (1.48 g, 44%). LCMS m/z=695 [M+H]$^+$.

Part E

To the THP hydroxamate from Part D (1.4 g, 2.02 mmol) was added 4N HCl dioxane solution (5 mL, 20.2 mmol) and methanol (0.5 mL). The slurry became very thick. Diethyl ether (50 mL) was added to and after 1 hr at ambient temperature the reaction was filtered under nitrogen. The solids were washed with diethyl ether (150 mL) under nitrogen and dried in vacuo over phosphorus pentoxide to give the title compound as a white solid (1.4 g, 100%). HRMS (ES+) M+H$^+$ calculated for C$_{27}$H$_{29}$N$_4$O$_7$S$_1$F$_3$ 611.1787, found 611.1773.

Example 52

Preparation of:

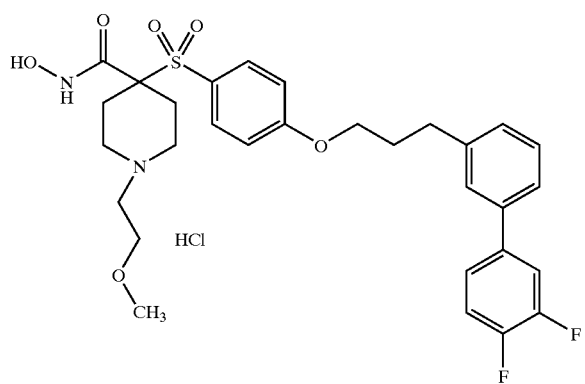

Part A

In a vial were combined the aryl bromide from Part C of Example 50 (0.50 g, 0.78 mmol) in 3 mL of dimethoxyethyl ether, 3,4-difluorobenzeneboronic acid (185 mg, 1.17 mmol), palladium tetrakistriphenylphosphine (~45 mg, 0.04 mmol) and 2M cesium carbonate (1.17 mL, 2.34 mmol). Mixture stirred vigorously at 80° C. for 18 hr. Reaction poured onto 2 mL Chem-Elut tube prewetted with 3 mL of water and eluted with ethyl acetate and methylene chloride. Purification by reverse phase chromatography (acetonitrile/water/0.05% TFA) gave the TFA salt of the deprotected material (354.8 mg) which was carried on as is.

Part B

The product from Part D (354.8 mg) was taken up in 4M hydrochloric acid in 1,4-dioxane (2 mL) and methanol (1–2 mL) and stirred for 30 min and then concentrated. This was repeated. Product crashed out of solution, was collected by filtration, washed with diethyl ether and dried under high vacuum yielding the title compound as a colorless solid (298.0 mg, 61% over two steps). ESMS m/z=589 (M+H)$^+$. HRMS calcd. for C$_{30}$H$_{35}$F$_2$N$_2$O$_6$S: 589.2178 (M+H)$^+$. Found: 589.2192.

Example 53

Preparation of:

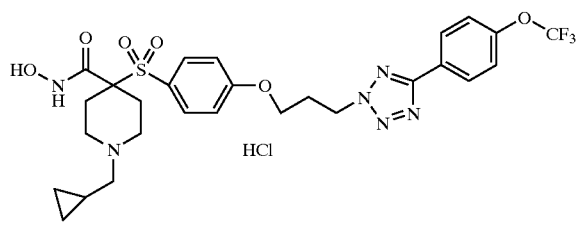

Part A

Preparation of:

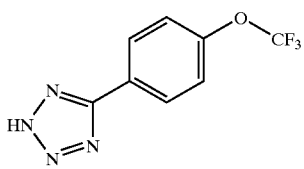

A mixture of lithium chloride (1.71 g, 40.3 mmol), trifluoromethoxy-benzonitrile(5.00 g, 26.7 mmol), and sodium azide(1.75 g, 26.7 mmol) in 2-methoxyethanol(26 mL) under an N$_2$ atmosphere was refluxed for 4 hr. The ambient mixture was poured into a mixture of ice (84 g) and concentrated hydrochloric acid (8.4 mL), and then stirred until the ice melted. The resulting white solid was collected by filtration, washed with water, and dried for 2 hr in a 40° C. vacuum oven to provide the tetrazole in the form of an off white solid (4.86 g, 79% yield). MS MH$^+$ calcd. for C$_8$H$_6$N$_4$OF$_3$ 231, found 231.

Part B

Preparation of:

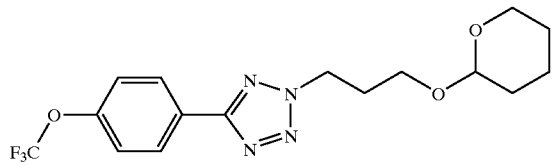

A solution of the tetrazole of Part A (2.00 g, 8.69 mmol) in NMP (12 mL) was added dropwise to an ambient mixture of 95% sodium hydride (0.438 g, 18.2 mmol) in NMP (12 mL) under an $N_2$ atmosphere. After an 1 hr of stirring, 2-(3-chloropropoxy)tetrahydro-2H-pyran(1.58 mL, 9.56 mmol) was added dropwise. The mixture was stirred at ambient temperature for 18 hr and then at 70° C. for 2 hr. The mixture was diluted with a solution of water (200 mL) and saturated $NaHCO_3$ (100 mL), and extracted with ethyl acetate (3×100 mL). The organic layer was washed with water (2×100 mL) and brine(100 mL), dried over $MgSO_4$, and concentrated in vacuo to give a yellow liquid. Flash chromatography purification (ethyl acetate-hexane/silica gel) provided the pyran in the form of a white solid (1.46 g, 45% yield). Anal. Calcd. for $C_{16}H_{19}N_4O_3F_3$: C,56.34; H, 5.98; N, 7.73; S, 4.42. Found C,56.13; H, 6.08; N, 7.65; S, 4.75.

To an ambient mixture of 95% sodium hydride (0.923 g, 38.5 mmol) in NMP (16 mL) under an $N_2$ atmosphere was added dropwise a solution of the alcohol of Part C (8.00 g, 27.7 mmol) in NMP(16 mL), and the mixture was stirred at ambient temperture for 35 minutes. A solution of 1-benzyl 4-tert-butyl 4-[(4-fluorophenyl)sulfonyl]piperidine-1,4-dicarboxylate (12.5 g, 26.3 mmol) in NMP (16 mL) was added dropwise to the reaction mixture. After 3 hr at 55° C., the ambient mixture was diluted with water (700 mL) and extracted with ethyl acetate (3×150 mL). The organic layer was washed with water (2×100 mL) and brine (100 mL), dried over $MgSO_4$, and concentrated in vacuo to produce a yellow oil (18.6 g). Chromatography purification (hexane-EA/silica gel) provided the sulfone as a yellow oil (10.1 g, 52% yield). MS $MH^+$ calcd. for $C_{35}H_{39}N_5O_8SF_3$ 746, found 746. Anal. Calcd. for $C_{35}H_{38}N_5O_8SF_3$ C,56.37; H, 5.14; N, 9.39; S, 4.30. Found C,56.22; H, 4.96; N, 9.22; S, 4.37.

Part E
Preparation of:

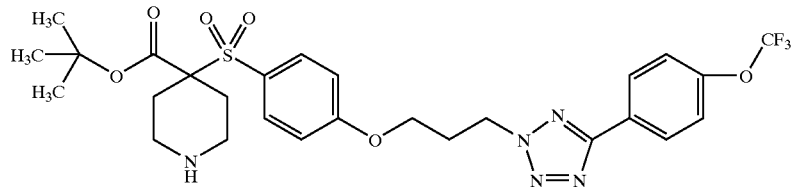

Part C
Preparation of:

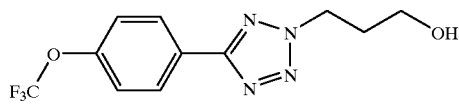

To an ambient solution of the pyran of Part B (1.40 g, 3.76 mmol) in MeOH (13.5 mL) was added a solution of acetyl chloride (0.896 mL, 13.1 mmol) in MeOH (13.5 mL). After 15 min, the solution was concentrated in vacuo to provide the alcohol in the form of a solid (1.02 g, 94% yield). MS $MH^+$ calcd. for $C_{11}H_{12}N_4O_2F_3$ 289, found 289.

Part D
Preparation of:

A mixture of the sulfone of Part D (10.0 g, 13.4 mmol) and 10% palladium on carbon (1.43 g, 1.34 mmol) in methanol (50 mL) was placed under an $H_2$ atmosphere with a balloon at ambient temperature for 20 hr. The mixture was filtered through a bed of celite and concentrated in vacuo to provide the piperidine in the form of a pale yellow oil (7.57 g, 92%). The proton NMR spectrum was consistent for the desired compound.

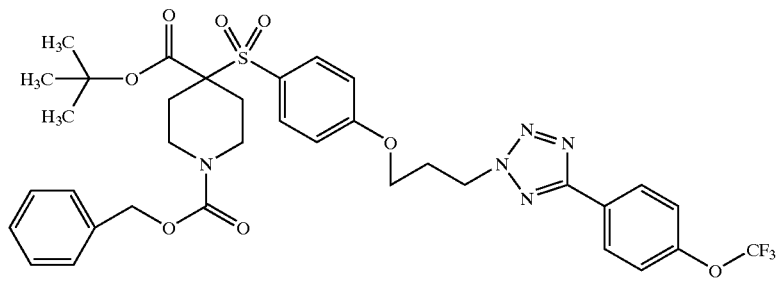

Part F
  Preparation of:

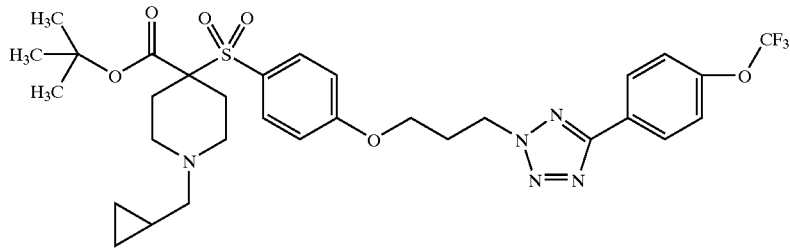

A mixture of the piperidine of Part E (3.50 g, 5.72 mmol), (bromomethyl)cyclopropane (0.67 mL, 6.87 mmol), and potassium carbonate (2.38 g, 17.2 mmol) in DMF (15 mL) was stirred at ambient temperature for 20 hr under an $N_2$ atmosphere. The mixture was diluted with water (700 mL) and extracted with ethyl acetate (3×100 mL). The organic layer was washed with water (2×75 mL) and brine (75 mL), dried over $MgSO_4$, and concentrated in vacuo to produce a yellow oil. Flash chromatography purification (hexane-EA/silica gel) provided the alkylpiperidine in the form of a colorless oil (2.08 g, 55% yield): MS MH+ calcd. for $C_{31}H_{39}N_5O_6SF_3$ 666, found 666. Anal. Calcd. for $C_{31}H_{38}N_5O_6SF_3$: C, 55.93; H, 5.75; N, 10.52; S, 4.82. Found C, 55.85; H, 5.91; N, 10.25; S, 4.99.

Part G
  Preparation of:

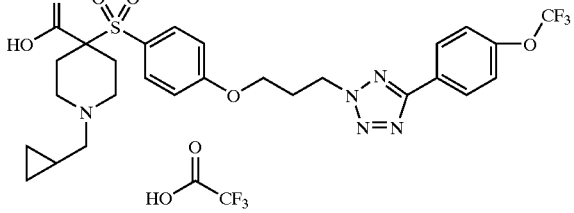

A solution of the alkylpiperidine of Part F (2.00 g, 3.00 mmol) in trifluoroacetic acid (10 mL, 130 mmol) was stirred at ambient temperature for 1.7 hr. The mixture was concentrated in vacuo, triturated twice with ether, and dried in a 40° C. vacuum to provide the acid as a white solid (2.21 g, 102%). MS MH+ calcd. for $C_{27}H_{31}N_5O_6SF_3$ 610, found 610.

Part H
  Preparation of:

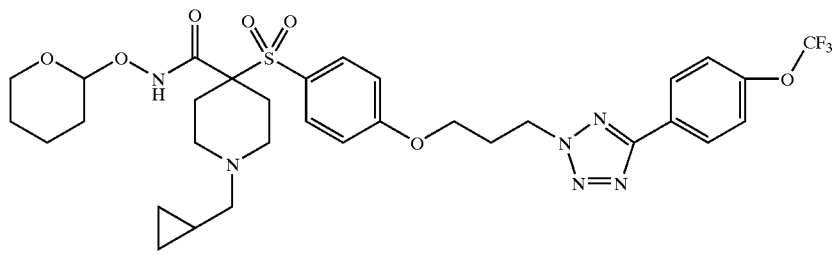

A mixture of the crude acid of Part G (2.10 g, 3.44 mmol), 1-hydroybenzotriazole hydrate(0.820 g, 6.07 mmol), triethylamine(5.57 mL, 39.9 mmol), O-(tetrahydro-2H-pyran-2-yl)hydroxylamine(0.835 g, 7.13 mmol), and 1-(3-dimethylaminopropyl)-3-ethylcarbodiimide hydrochloride (1.37 g, 7.13 mmol) in DMF (35 mL) under an $N_2$ atmosphere was stirred at ambient temperature for 20 hr. The mixture was diluted with water (700 mL) and extracted with ethyl acetate (3×200 mL). The organic layer was washed with water (2×100 mL) and brine (100 mL), dried over $MgSO_4$, and concentrated in vacuo to produce a yellow foam. Chromatography purification (MeOH—$CH_2Cl_2$/silica gel) produced the O-protected hydroxamate in the form of a white foam (1.60 g, 66%). MS $MH^+$ calcd. for $C_{32}H_{40}N_6O_7F_3S$ 709, found 709.

Part I

Preparation of:

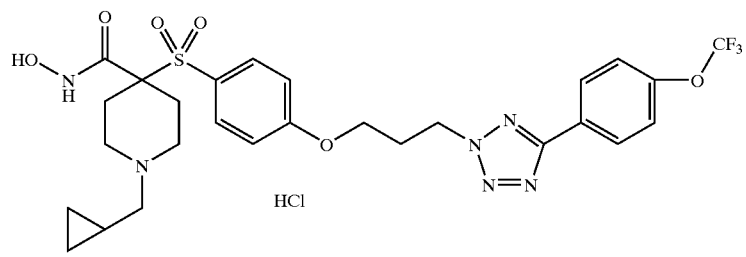

A solution of the O-protected hydroxamate of Part H (1.50 g, 2.12 mmol) and acetyl chloride(0.677 mL, 10.2 mmol) in methanol (23 mL) was stirred at ambient temperature for 1 hr. The solution was diluted with ether and a solid formed. The solid was isolated by filtration, washed with ether, and dried in a 40° C. vacuum oven to produce the title compound as a white solid (1.55 g, 82% yield). Anal. Calcd. for $C_{27}H_{31}N_6O_6F_3S$·HCl: C, 49.05; H, 4.88; N, 12.71; Cl, 5.36; S, 4.85. Found C, 48.94; H, 4.72; N, 12.71; Cl, 5.29; S, 4.94

Example 54

Preparation of:

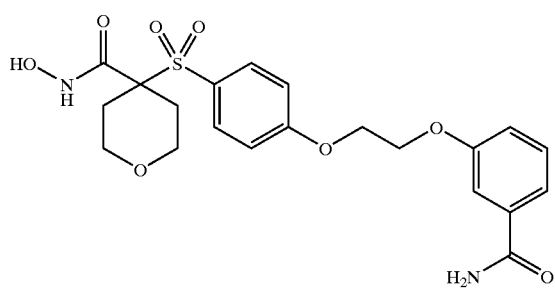

Part A

Preparation of:

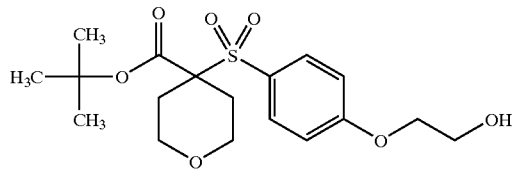

To a solution of tert-butyl 4-[(4-fluorophenyl)sulfonyl] tetrahydro-2H-pyran-4-carboxylate (5.0 g, 14.6 mmol) and cesium carbonate (14.3 g, 43.8 mmol) in anhydrous DMSO (30 mL) was added ethylene glycol (8.1 mL, 146 mmol). The resulting reaction mixture was stirred at 80° C. for 3 hr. After cooling to room temperature, the mixture was poured into water (350 mL) and extracted with ethyl acetate (3×). The organics were washed with brine and dried over magnesium sulfate. Silica gel chromatography (ethyl acetate/methylene chloride) provided the alcohol as a colorless solid (2.33 g, 41%). NMR(CDCl$_3$) δ1.45 (s, 9H), 2.13–2.20 (m, 4H), 3.22–3.33 (m, 2H), 3.94–4.03 (m, 2H), 4.16 (q, 2H), 7.02 (d, 2H), 7.73 (d, 2H). ESMS m/z=404 $(M+NH4)^+$. HRMS calcd. for $C_{18}H_{26}O_7S$ $NH_4$: 404.1743 $(M+NH_4)^+$. Found: 404.1734.

Part B

Preparation of:

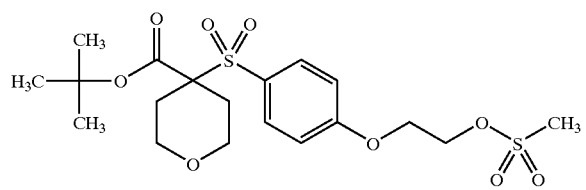

To a solution of the alcohol from Part A (0.50 g, 1.3 mmol) in $CH_2Cl_2$ (2.5 mL) was added triethylamine (0.24 mL g, 1.7 mmol), followed by mesyl chloride. The resulting mixture was stirred at room temperature for 1.5 hr. The mixture was diluted with methylene chloride and washed with 10% citric acid, washed with 5% sodium bicarbonate, washed with brine, and dried over $MgSO_4$. Concentration produced the desired compound in the form of a tan solid (0.62 g, 100%). NMR(CDCl$_3$) 1.45 (s, 9H), 2.13–2.22 (m, 4H), 3.07 (s, 3H), 3.22–3.37 (m, 2H), 4.00 (dt, 2H), 4.32–4.37 (m, 2H), 4.58–4.62 (m, 2H), 7.02 (d, 2H), 7.75 (d, 2H). ESMS m/z=482 $(M+NH4)^+$.

307

Part C

Preparation of:

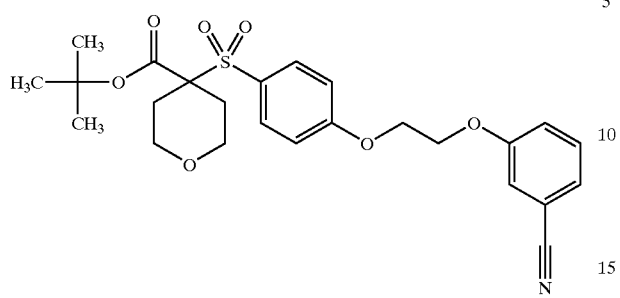

To a solution of 60% sodium hydride (39 mg, 0.98 mmol) in anhydrous dimethylformamide (2.5 mL) was added 3-cyanophenol (108 mg, 0.91 mmol). After stirring for 15 min, solution was clear. The mesylate from Part B (0.30 g, 0.65 mmol) in anhydrous dimethylformamide (1 mL) was added. After completion of the addition, the mixture as stirred at ambient temperature overnight. The next morning, the mixture was poured onto a 10 mL Chem-Elut tube, prewetted with 5 mL of water, and eluted with ethyl acetate and $CH_2Cl_2$. Chromatography (silica gel with ethyl acetate/hexane) produced the desired ester (0.27 g, 85%). NMR ($CDCl_3$) δ1.46 (s, 9H), 2.17–2.21 (m, 4H), 3.22–3.36 (m, 2H), 3.98 (dt, 2H), 4.35–4.43 (m, 4H), 7.04 (d, 2H), 7.15–7.20 (m, 2H), 7.28 (dt, 1H), 7.39 (t, 1H), 7.74 (d, 2H). ESMS m/z=505 $(M+NH4)^+$. HRMS calcd. for $C_{25}H_{33}N_2O_2O_7S$: 505.2008 $(M+NH_4)^+$. Found: 505.2019.

Part D

Preparation of:

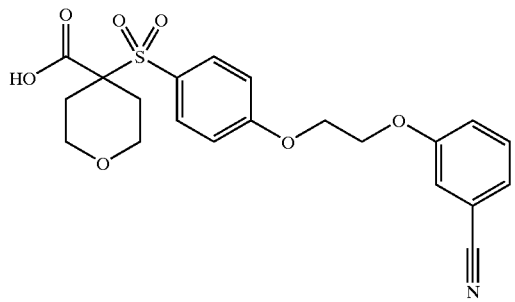

The ester of Part C (0.24 g, 0.49 mmol) was hydrolyzed in 5 mL of methylene chloride and 5 mL of trifluoroacetic acid. Concentration and drying under high vacuum produced the desired acid (0.21 g, 100%). NMR ($CD_3OD$ w/$K_2CO_3$) δ2.01–2.11 (m, 2H), 2.20 (d, 2H), 3.32–3.42 (m, 2H), 3.95 (dt, 2H), 4.38–4.45 (m, 4H), 7.13 (d, 2H), 7.26–7.34 (m, 3H), 7.45 (t, 1H), 7.76 (d, 2H). ESMS m/z=449 $(M+NH4)^+$. HRMS calcd. for $C_{21}H_{21}NO_7S$ $NH_4$: 449.1382 $(M+NH_4)^+$. Found: 449.1407.

308

Part E

Preparation of:

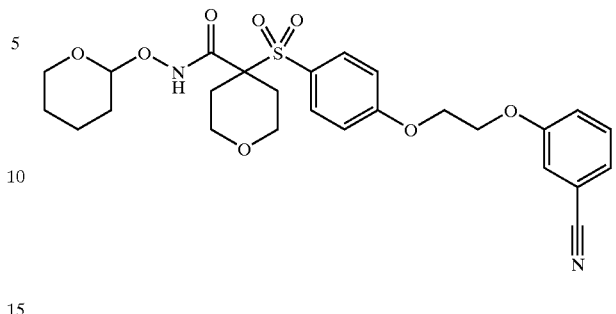

To a slurry of the acid of Part D (0.20 g, 0.46 mmol), HOBt (76 mg, 0.55 mmol), and EDC (130 mg, 0.68 mmol) was added triethylamine (1.4 mmol) and THP-hydroxylamine (167 mg, 1.4 mmol) in a flask under $N_2$ in 2 mL anhydrous DMF. The resulting mixture was stirred at 40° C. overnight. The next morning, the mixture was poured onto 10 mL Chem-Elut tube prewetted with 6 mL of water and eluted with ethyl acetate and $CH_2Cl_2$. Chromatography (silica gel, ethyl acetate/hexane) produced the product as a colorless oil (0.18 g, 74).

Part F

Preparation of:

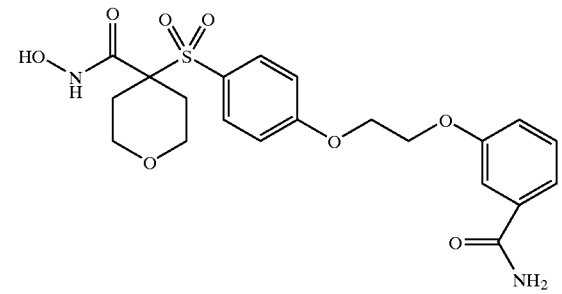

To the product from Part E (0.18 g, 0.34 mmol) in methanol (1–2 mL) was added 4M HCl in 1,4-dioxane (2.5 mL). The resulting mixture was stirred overnight. Reverse phase chromatography (water/acetonitrile/0.05% TFA) produced the desired compound as a colorless crystalline solid (25.0 mg 16%). NMR(DMSO) δ1.82–1.98 (m, 2H), 2.15–2.30 (m, 2H), 3.15, (t, 2H), 3.86 (d, 2H), 4.44 (d, 4H), 7.10–7.25 (m, 3H), 7.38 (t, 1H), 7.44–7.52 (m, 2H), 7.68 (d, 2H).ESMS m/z=465 $(M+H)^+$. HRMS calcd. for $C_{21}H_{25}N_2O_8S$: 465.1332 $(M+H)^+$. Found: 465.1354.

Examples 55–89

In Vitro MMP Inhibition Analysis

Several hydroxamates and salts thereof were analyzed in in vitro assays to determine their ability to inhibit the MM cleavage of peptide substrates. Inhibition ($K_i$) and $IC_{50}$ constants were calculated from the assayed hydroxamate-MMP interactions.

Human recombinant MMP-1, MMP-2, MMP-9, MMP-13, and MMP-14 were used in this assay. All enzymes were prepared in Assignee's laboratories following usual laboratory procedures. Protocols for the preparation and use of these enzymes are available in the scientific literature. See, e.g., *Enzyme Nomenclature* (Academic Press, San Diego, Calif., 1992) (and the citations therein). See also, Frije et al., *J Biol. Chem.*, 26(24), 16766–73 (1994).

The MMP-1 proenzyme was purified from the spent media of MMP-1-transfected HT-1080 cells provided by Dr.

Harold Welgus of Washington University (St. Louis, Mo.). The protein was purified on a zinc chelating column.

The MMP-2 proenzyme was purified by gelatin Sepharose chromatography from MMP-2-transfected p2AHT2 cells provided by Dr. Gregory Goldberg of Washington University (St. Louis, Mo.).

The MMP-9 proenzyme was purified by gelatin Sepharose chromatography from spent media of MMP-9-transfected HT1080 cells provided by Dr. Howard Welgus of Washington University (St. Louis, Mo.).

The MMP-13 was obtained as a proenzyme from a full-length cDNA clone using baculovirus, as described by V. A. Luckow, "Insect Cell Expression Technology," *Protein Engineering: Principles and Practice*, pp. 183–218 (edited by J. L. Cleland et al., Wiley-Liss, Inc., 1996). The expressed proenzyme was first purified over a heparin agarose column, and then over a chelating zinc chloride column. The proenzyme was then activated by APMA for use in the assay. Further details on baculovirus expression systems may be found in, for example, Luckow et al., *J. Virol.*, 67, 4566–79 (1993). See also, O'Reilly et al, *Baculovirus Expression Vectors: A Laboratory Manual* (W. H. Freeman and Co., New York, N.Y., 1992). See also, King et al., *The Baculovirus Expression System: A Laboratory Guide* (Chapman & Hall, London, England, 1992).

The MMP-14 full length cDNA was provided by Dr. Gregory Goldberg of Washington University (St. Louis, Mo.). The catalytic domain enzyme was expressed in *E. coli* inclusion bodies, solubilized in urea, purified on a preparative C-14 reverse phase HPLC column, and then refolded in the presence of zinc acetate and purified for use.

All MMPs were activated using 4-aminophenylmercuric acetate ("APMA", Sigma Chemical, St. Louis, Mo.) or trypsin. MMP-9 also was activated using human recombinant MMP-3 (purified in Assignee's laboratory following standard cloning and purification techniques).

Two fluorogenic, methoxycoumarin-containing polypeptide substrates were used in the MMP inhibition assays:

MCA-ProLeuGlyLeuDpaAlaArgNH$_2$     (I)

MCA-ArgProLeuGlyLeuDpaAlaArgGluArgNH$_2$     (II)

Here, "Dpa" is 3-(2,4-dinitrophenyl)-L-2,3-diaminopropionyl group, and "MCA" is 7-methoxycoumarin-4-yl acetyl. Substrate (I) was purchased from Baychem (Redwood City, Calif.), and substrate II was prepared Assignee's laboratory. Substrate I was used in the IC$_{50}$ determination assays, while substrate II was used in the K$_i$ determination assays. In the absence of MMP inhibitory activity, either substrate is cleaved at the Gly-Leu peptide bond. This cleavage separates the highly fluorogenic peptide from the 2,4-dinitrophenyl quencher, thus resulting in increase of fluorescent intensity.

The stock solutions of the assayed hydroxamates (or salts thereof) were prepared in 1% dimethyl sulfoxide (DMSO). These stock solutions were diluted in Buffer A (100 mM Tris-HCl, 100 mNM NaCl, 10 mM CaCl$_2$, 0.05% polyoxyethylene 23 lauryl ether, pH 7.5) to obtain solutions with different hydroxamate concentrations, i.e., assay solutions with different concentrations of the assayed MMP inhibitory compound. The experiment controls contained the same amount of Buffer A/DMSO as the assayed sample, but contained no hydroxamate (or salt thereof).

The assays from which the IC$_{50}$ determinations were made were performed as follows. The MMPs were activated with either trypsin or APMA (4-aminophenylmercuric acetate, Sigma Chemical, St. Louis, Mo.). The assayed hydroxamate samples were incubated in Microfluor™ White Plates (Dynatech, Chantilly, Va.) and analyzed on a Perkin Elmer L550 plate reader (Norwalk, Conn.). The excitation wavelength was 328 nm, and the emission wavelength—415 nm. All samples (assayed hydroxamates and controls) were incubated in separate plates at room temperature in the presence of 4 µM of MMP substrate (I). As stated in the previous paragraph, samples containing varying concentrations of the same assayed hydroxamate were prepared. Inhibition was measured as a reduction in fluorescent intensity as a function of MMP inhibitor concentration.

The assays from which the K$_i$ determinations were made were performed as follows. The assayed hydroxamate samples were incubated in separate wells of untreated white polystyrene plates (Nunc Nalgene International, Rochester, N.Y.), and analyzed on a Tecan SpectraFlour Plus plate reader. The excitation wavelength was 330 nm, and the emission wavelength—420 nm. All samples (assayed hydroxamates and controls) were incubated in separate plate wells at room temperature for 1 hr in the presence of 4 µM of MMP substrate (II). In the absence of MMP inhibitory activity, substrate II was cleaved at the Gly-Leu bond resulting in an increase of relative fluorescence. Inhibition was observed as a reduced rate of this increase in relative fluorescence. The various hydroxamates were analyzed using a single low enzyme concentration with a single substrate concentration fixed at or below the K$_m$. This protocol is a modification of method by Knight et al., *FEBS Lett.*, 296(3), 263–266 (1992). Apparent inhibitory constants were determined by non-linear regression of reaction velocity as a function of inhibitor and enzyme concentration using Morrison's equation, as described by Kuznic, Anal. Biochem. 286, 45–50 (2000). Modifications were made in the non-linear regression method to allow a common control reaction rate and effective enzyme concentration to be shared between all dose-response relationships on a given assay plate. Since the substrate concentration was chosen to be at or below the K$_m$, the apparent K$_i$'s from this analysis were reported as K$_i$'s without correction for the influence of substrate.

The above protocols were used to determine IC50 constants and K$_i$ values values for several of the compounds in Examples 1–52 above. The results are shown in Table 5. All values in Table 5 are given in nM units. The K$_i$ measurements are in parenthesis.

TABLE 5

| Ex. # | Compound | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
| --- | --- | --- | --- | --- | --- | --- |
| 55 | Example 17 | | 550 | | 1.6 | |
| 56 | Example 18 | >10000 | 537 | 6000 | 1.8 | >10000 |
| 57 | Example 19 | >10000 | 9000 | 5190 | 15 | >10000 |
| 58 | Example 20 | >10000 | 1.8 | 498 | 1.8 | >10000 |

TABLE 5-continued

| Ex. # | Compound | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|
| 59 | Example 21 | >10000 | 450 | >10000 | 3.5 | >10000 |
| 60 | Example 22 | >10000 | 1000 | >10000 | 4.9 | >10000 |
| 61 | Example 25 | >10000 | 247.2 | 8498 | 1.8 | >10000 |
| 62 | Example 26 | >10000 | 52.0 | 4429 | 3.4 | >10000 |
| 63 | Example 27 | >10000 | 83.9 | 9366 | 0.2 | >10000 |
| 64 | Example 28 | >10000 | 76.4 | 3710 | 7.0 | >10000 |
| 65 | Example 30 | >10000 | 22.6 | 809 | 1.3 | >10000 |
| 66 | Example 31 | >10000 (>10000) | 346.3 (412.93) | 5651 (1596.8) | 2.1 (1.503) | >10000 (>10000) |
| 67 | Example 32 | >10000 | 217.7 | 4076 | 0.8 | >10000 |
| 68 | Example 33 | >10000 | 16 | 7.9 | 1 | 4936 |
| 69 | Example 34 | 429 | 36.6 | >10000 | 3.0 | >10000 |
| 70 | Example 35 | >10000 | 600 | >10000 | 3 | >10000 |
| 71 | Example 36 | | 95 | | 2.4 | |
| 72 | Example 37 | 8708 | 30.3 | 449 | 1.4 | >10000 |
| 73 | Example 38 | >10000 (>10000) | 157.5 | 1026.3 (369.98) | 0.9 (6.55) | >10000 (4451.2) |
| 74 | Example 39 | (>10000) | 1299 (1640) | (2360) | 0.9 (3.04) | (>10000) |
| 75 | Example 40 | >10000 (>10000) | 112.4 (215.98) | 413 (585.44) | 0.5 (0.58) | >10000 (>10000) |
| 76 | Example 41 | >10000 (>10000) | 357.5 (414.99) | 1597 (1465.7) | 2.0 (1.056) | >10000 (>10000) |
| 77 | Example 42 | >10000 (>10000) | 100.3 (186.28) | 382.5 (661.7) | 0.3 (0.486) | >10000 (>10000) |
| 78 | Example 43 | >10000 | 4.8 | 1.0 | 1.0 | 2084 |
| 79 | Example 44 | >10000 | 133.2 | 154.5 | 1.4 | 4976 |
| 80 | Example 45 | (>10000) | (224.78) | (499.18) | (0.62) | (>10000) |
| 81 | Example 46 | >10000 (>10000) | 320.9 (786.36) | 1966 (417.51) | 3.1 (2.29) | >10000 (>10000) |
| 82 | Example 47 | (>10000) | 18.2 (19.15) (46.49) | (118.75) (308.77) | 0.2 (0.304) (0.423) | (3317.66) (5293) |
| 83 | Example 48 | <10000 (<10000) | 104.6 (227.54) | 4450.3 (159.2) | 0.2 (0.127) | <10000 (<10000) |
| 84 | Example 49 | <10000 (<10000) | 273.9 (1947.90) | 4056 (0.439) | 0.3 (<10000) | <10000 |
| 85 | Example 50 | (<10000) | (1127.89) | (304.41) | (0.60) | (<10000) |
| 86 | Example 51 | <10000 (5160.20) | 251.6 (93.68) | 7983 (98.72) | 0.2 (1.697) | <10000 (687.93) |
| 87 | Example 52 | (<10000) | (542.89) | (617.14) | (0.81) | (<10000) |
| 88 | Example 53 | >10000 (>10000) | 383.5 (697) | 75.5 (2900) | 1.0 (0.662) | >10000 (>10000) |
| 89 | Example 54 | (>10000) | 35.5 (64.8) | (388) | 10.5 | (4120) |

Example 90

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, *A Model of Angiogenesis in the Mouse Cornea;* Kenyon, B M, et al., Investigative Ophthalmology & Visual Science, July 1996, Vol. 37, No. 8.

In this assay, uniformLy sized Hydron™ pellets containing bFGF and sucralfate are prepared and surgically implanted into the stroma mouse cornea adjacent to the temporal limbus. The pellets are formed by making a suspension of 20 μL sterile saline containing 10 μg recombinant bFGF, 10 mg of sucralfate and 10 μL of 12 percent Hydron™ in ethanol. The slurry is then deposited on a 10×10 mm piece of sterile nylon mesh. After drying, the nylon fibers of the mesh are separated to release the pellets.

The corneal pocket is made by anesthetizing a 7 week old C57B1/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet is placed on the corneal surface at the base of the pocket with a jeweler's forceps. The pellet is then advanced to the temporal end of the pocket. Antibiotic ointment is then applied to the eye.

Mice are dosed on a daily basis for the duration of the assay. Dosing of the animals is based on bioavailability and overall potency of the compound. An exemplary dose is 10 or 50 mg/kg (mpk) bid, po. Neovascularization of the corneal stroma is permitted to continue under the influence of the assayed compound for 2 days. At that point, the degree of angiogenic inhibition is scored by viewing the neovascular progression with a slit lamp microscope.

The mice are anesthetized and the studied eye is once again proptosed. The maximum vessel length of neovascularization, extending from the limbal vascular plexus toward the pellet is measured. In addition, the contiguous circumferential zone of neovascularization is measured as clock hours, where 30 degrees of arc equals one clock hour. The area of angiogenesis is calculated as follows.

$$\text{area} = (0.4 \times \text{clock hours} \times 3.14 \times \text{vessel length (in mm)})$$

Five to six mice should be utilized for each compound in each study. The studied mice are thereafter compared to control mice and the difference in the area of neovascularization is recorded as an averaged value. Each group of mice so studied constitutes an "n" value of one, so that "n" values greater than one represent multiple studies whose averaged result is provided in the table. A contemplated compound typically exhibits about 25 to about 75 percent inhibition, whereas the vehicle control exhibits zero percent inhibition.

Example 91

Tumor Necrosis Factor Assays

Cell Culture

The cells used in the assay are the human moncytic line U-937 (ATCC CRL-1593). The cells are grown in RPMI w/10% FCS and PSG supplement (R-10) and are not permitted to overgrow. The assay is carried out as follows:

1. Count, then harvest cells by centrifugation. Resuspend the pellet in R-10 supplement to a concentration of $1.540 \times 10^6$ cells/mL.

2. Add test compound in 65 uL R-10 to the appropriate wells of a 96-well flat bottom tissue culture plate. The initial dilution from a DMSO stock (100 mM compound) provides a 400 uM solution, from which five additional three-fold serial dilutions are made. Each dilution of 65 ul (in triplicate) yields final compound test concentrations of 100 $\mu$M, 33.3 $\mu$M, 11.1 $\mu$M, 3.7 $\mu$M, 1.2 $\mu$M and 0.4 $\mu$M 3. The counted, washed and resuspended cells (200,000 cells/well) in 130 $\mu$L are added to the wells.

4. Incubation is for 45 min to 1 hr at 37° C. in 5% $CO_2$ in a water saturated container.

5. R-10 (65 uL)containing 160 ng/mL PMA (Sigma) is added to each well.

6. The test system is incubated at 37° C. in 5% CO2 overnight (18–20 hr) under 100% humidity.

7. Supernatant, 150 $\mu$L, is carefully removed from each well for use in the ELISA assay.

8. For toxicity, a 50 $\mu$L aliquot of working solution containing 5 mL R-10, 5 mL MTS solution [CellTiter 96 AQueous One Solution Cell Proliferation Assay Cat.#G358/0,1 (Promega Biotech)] and 250 ul PMS solution are added to each well containing the remaining supernatant and cells and the cells incubated at 37° C. in 5% $CO_2$ until the color develops. The system is excited at 570 nm and read at 630 nm.

TNF Receptor II ELISA Assay

1. Plate 100 $\mu$L/well 2 ug/mL mouse anti-human TNFrII antibody (R&D Systems #MAB226) in 1×PBS (pH 7.1, Gibco) on NUNC-Immuno Maxisorb plate. Incubate the plate at 4° C. overnight (about 18–20 hr).

2. Wash the plate with PBS-Tween (1×PBS w/0.05% Tween).

3. Add 200 $\mu$L 5% BSA in PBS and block at 37° C. in a water saturated atmosphere for 2 hr.

4. Wash the plate with PBS-Tween.

5. Add sample and controls (100 ul of each) to each well. The standards are 0, 50, 100, 200, 300 and 500 pg recombinant human TNFrII (R&D Systems #226B2) in 100 $\mu$L 0.5% BSA in PBS. The assay is linear to between 400–500 pg of standard.

6. Incubate at 37° C. in a saturated atmosphere for 1.5 hr.

7. Wash the plate with PBS-Tween.

8. Add 100 $\mu$L goat anti-human TNFrII polyclonal (.5 $\mu$g/mL R&D Systems #AB226-PB in 0.5% BSA in PBS).

9. Incubate at 37° C. in a saturated atmosphere for 1 hr.

10. Wash the plate with PBS-Tween.

11. Add 100 $\mu$L anti-goat IgG-peroxidase (1:50,000 in 0.5% BSA in PBS, Sigma #A5420).

12. Incubate at 37° C. in a saturated atmosphere for 1 hr.

13. Wash the plate with PBS-Tween.

14. Add 10 $\mu$L KPL TMB developer, develop at room temperature (usually about 10 min), then terminate with phosphoric acid and excite at 450 nm and read at 570 nm.

TNFαELISA Assay

Coat Immulon® 2 plates with 0.1 mL/well of 1 ug/mL Genzyme mAb in 0.1 M NaHCO3 pH 8.0 buffer overnight (about 18–20 hr) at 4° C., wrapped tightly in Saran® wrap.

Flick out coating solution and block plates with 0.3 mL/well blocking buffer overnight at 4° C., wrapped in Saran® wrap.

Wash wells thoroughly 4× with wash buffer and completely remove all wash buffer. Add 0.1 mL/well of either samples or rhTNFα standards. Dilute samples if necessary in appropriate diluant (e.g. tissue culture medium). Dilute standard in same diluant. Standards and samples should be in triplicates.

Incubate at 37° C. for 1 hr in humified container.

Wash plates as above. Add 0.1 mL/well of 1:200 dilution of Genzyme rabbit anti-hTNFα.

Repeat incubation.

Repeat wash. Add 0.1 mL/well of 1 $\mu$g/mL Jackson goat anti-rabbit IgG (H+L)-peroxidase.

Incubate at 37° C. for 30 min.

Repeat wash. Add 0.1 mL/well of peroxide-ABTS solution.

Incubate at room temperature for 5–20 min.

Read OD at 405 nm.

12 Reagents are:

Genzyme mouse anti-human TNF monoclonal (Cat.# 80-3399-01)

Genzyme rabbit anti-human TNF polyclonal (Cat.#IP-300)

Genzyme recombinant human TNF (Cat.#TNF-H).

Jackson Immunoresearch peroxide-conjugated goat anti-rabbit IgG (H+L) (Cat.#111-035-144).

Kirkegaard/Perry peroxide ABTS solution (Cat#50-66-01).

Immulon 2 96-well microtiter plates.

Blocking solution is 1 mg/mL gelatin in PBS with 1×thimerasol.

Wash buffer is 0.5 mL Tween® 20 in 1 liter ofPBS.

Example 92

In Vitro Aggrecanase Inhibition Analysis

Assays for measuring the potency ($IC_{50}$) of a compound toward inhibiting aggrecanase are known in the art.

One such assay, for example, is reported in European Patent Application Publ. No. EP 1 081 137 Al. In that assay, primary porcine chondrocytes from articular joint cartilage are isolated by sequential trypsin and collagenase digestion followed by collagenase digestion overnight and are plated at $2 \times 10^5$ cells per well into 48 well plates with 5 $\mu$Ci/ml$^{35}$S (1000 Ci/mmol) sulphur in type 1 collagen coated plates.

Cells are allowed to incorporate label into their proteoglycan matrix (approximately 1 week) at 37° C. under an atmosphere of 5% $CO_2$. The night before initiating the assay, chondrocyte monolayers are washed 2 times in DMEM/1% PSF/G and then allowed to incubate in fresh DMEM/1% FBS overnight. The next morning, chondrocytes are washed once in DMEM/1% PSF/G. The final wash is allowed to sit on the plates in the incubator while making dilutions. Media and dilutions are made as described in the following Table 6:

TABLE 6

| | |
|---|---|
| control media | DMEM alone |
| IL-1 media | DMEM + IL-1 (5 ng/ml) |
| drug dilutions | Make all compound stocks at 10 mM in DMSO. Make a 100 µM stock of each compound in DMEM in 96-well plate. Store in freezer overnight. The next day, perform serial dilutions in DMEM with IL-1 to 5 µM, 500 µM, and 50 µM. Aspirate final wash from wells and add 50 µM of compound from above dilutions to 450 µL of IL-1 media in appropriate wells of the 48 well plates. Final compound concentrations equal 500 nM, 50 nM, and 5 nM. All samples completed in triplicate with control and IL-1 alone on each plate. |

Plates are labeled and only the interior 24 wells of the plate are used. On one of the plates, several columns are designated as IL-1 (no drug) and control (no IL-1, no drug). These control columns are periodically counted to monitor 35S-proteoglycan release. Control and IL-1 media are added to wells (450 µL) followed by compound (50 µL) so as to initiate the assay. Plates are incubated at 37° C. with 5% $CO_2$ atmosphere. At 40–50% release (when CPM from IL-1 media is 4–5 times control media) as assessed by liquid scintillation counting (LSC) of media samples, the assay is terminated (about 9 to about 12 hours). Media is removed from all wells and placed into scintillation tubes. Scintillate is added and radioactive counts are acquired (LSC). To solubilize cell layers, 500 µL of papain digestion buffer (0.2 M Tris, pH 7.0, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC). The percent of released counts from the total present in each well is determined. Averages of the triplicates are made with control background subtracted from each well. The percent of compound inhibition is based on IL-1 samples as 0% inhibition (100% of total counts).

Another assay for measuring aggrecanase inhibition is reported in WIPO Int'l Publ. No. WO 00/59874. That assay reportedly uses active aggrecanase accumulated in media from stimulated bovine cartilage (BNC) or related cartilage sources and purified cartilage aggrecan monomer or a fragment thereof as a substrate. Aggrecanase is generated by stimulation of cartilage slices with interleukin-1 (IL-1), tumor necrosis factor alpha (TNF-α), or other stimuli. To accumulate BNC aggrecanase in culture media, cartilage reportedly is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. To decrease the amounts of matrix metalloproteinases released into the media during aggrecanase accumulation, agents which inhibit MMP-1, -2, -3, and -9 biosynthesis are included during stimulation. This BNC conditioned media containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, et al., Biochem J, 306:799–804 (1995)). This antibody reportedly recognizes aggrecan fragments with the N-terminus, 374ARGSVIL, generated upon cleavage by aggrecanase. The BC-3 antibody reportedly recognizes this neoepitope only when it is at the N-terminus and not when it is present internally within aggrecan fragments or within the aggrecan protein core. Only products produced upon cleavage by aggrecanase reportedly are detected. Kinetic studies using this assay reportedly yield a Km of 1.5+/−0.35 µM for aggrecanase. To evaluate inhibition of aggrecanase, compounds are prepared as 10 mM stocks in DMSO, water, or other solvents and diluted to appropriate concentrations in water. Drug (50 µL) is added to 50 µL of aggrecanase-containing media and 50 µL of 2 mg/ml aggrecan substrate and brought to a final volume of 200 µL in 0.2 M Tris, pH 7.6, containing 0.4 M NaCl and 40 mM $CaCl_2$. The assay is run for 4 hr at 37° C., quenched with 20 mM EDTA, and analyzed for aggrecanase-generated products. A sample containing enzyme and substrate without drug is included as a positive control and enzyme incubated in the absence of substrate serves as a measure of background. Removal of the glycosaminoglycan side chains from aggrecan reportedly is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 µGAG) for 2 hr at 37° C. and then with keratanase (0.1 units/10 µg GAG) and keratanase II (0.002 units/10 µg GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 gL of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

Examples 93–645

Additional hydroxamate compounds (and salts thereof) can be prepared by one skilled in the art using methods similar to those described in Examples 1–54 alone or in combination with techniques well known in the art. Such compounds include, for example, the compounds summarized in the following Table 7. Table 7 also summarizes in vitro MMP inhibition results obtained by Applicants with the listed hydroxamates. As with Table 5, all in vitro $K_i$ and $IC_{50}$ results in Table 7 are given in nM units. The Ki measurements are in parenthesis.

TABLE 7

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 93 | 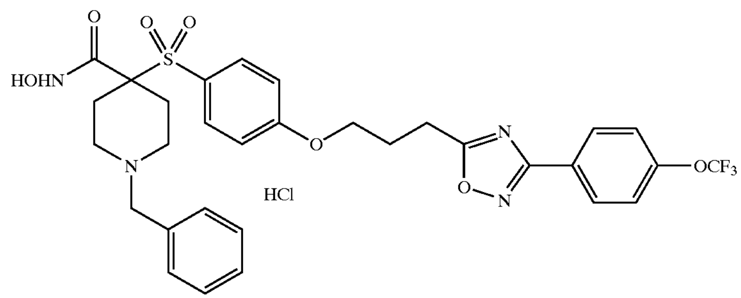 | | | (>10000) | 746.6 (676) | (1120) | 15.5 (9.29) | (>10000) |
| 94 | 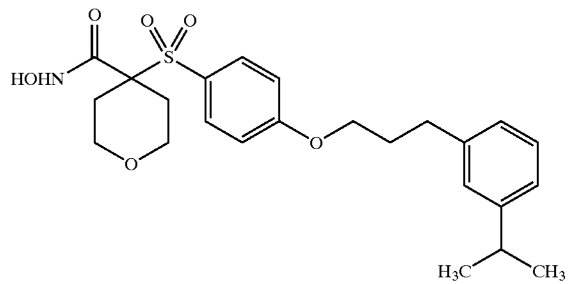 | | | | 17.8 | | 3.7 | |
| 95 | 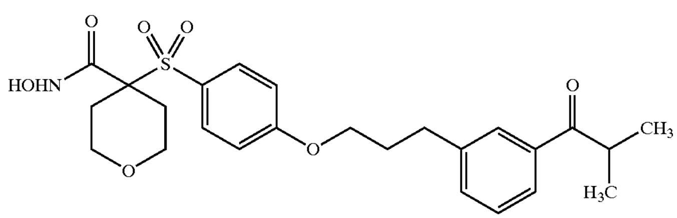 | | | >10000 (>10000) | 91.4 (149) | 1204.6 (788) | 2.7 | >10000 (5410) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 96 | 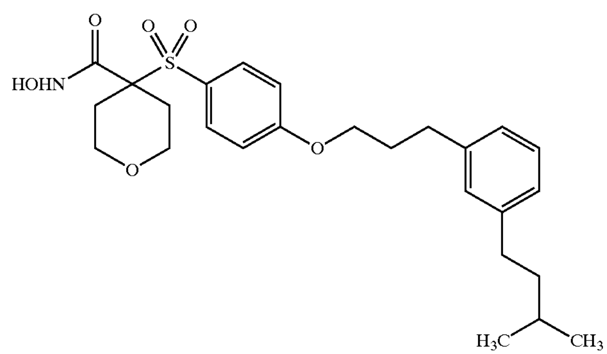 | | | | 39.1 | | 15.3 | |
| 97 | 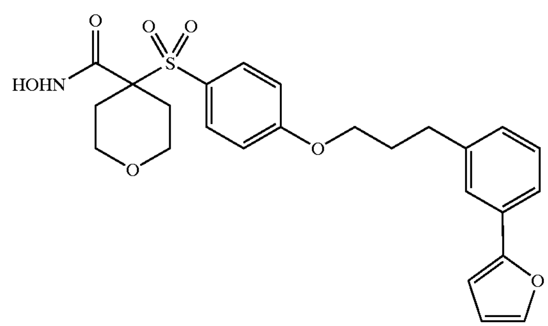 | 486.1586 | 486.1602 | (7360) | 185.0 (295) | (473) | 3.3 (5.57) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 98 | 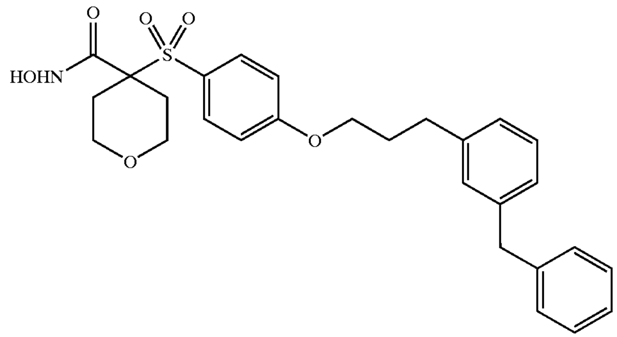 | 510.1950 | 510.1947 | >10000 (>10000) | 316.2 (625) | 2418 (1450) | 1.8 (9.15) | >10000 (>10000) |
| 99 | 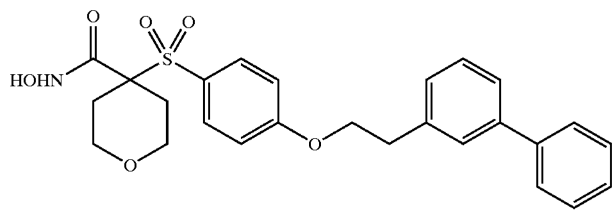 | 482.1637 | 482.1661 | >10000 | 245.8 | 3435 | 0.4 | >10000 |
| 100 | 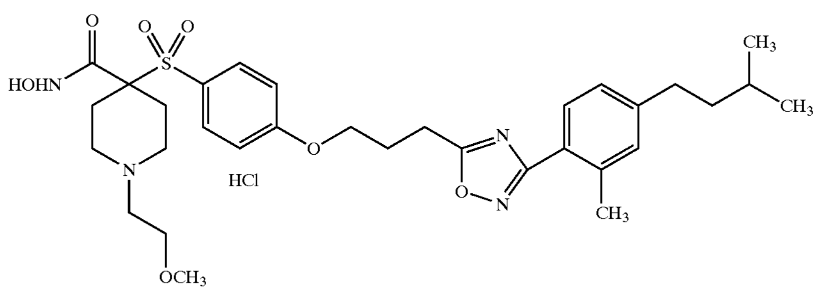 | | | | 1691.4 | | 152.6 | |

TABLE 7-continued

| Ex # | Structure | Calc. Mass | Observed Mass | MMP-1 IC₅₀ (Ki) | MMP-2 IC₅₀ (Ki) | MMP-9 IC₅₀ (Ki) | MMP-13 IC₅₀ (Ki) | MMP-14 IC₅₀ (Ki) |
|---|---|---|---|---|---|---|---|---|
| 101 | 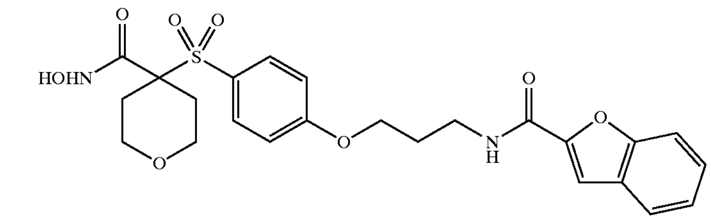 | 503.1480 | 503.1465 | | 18.2 | | 0.2 | |
| 102 | 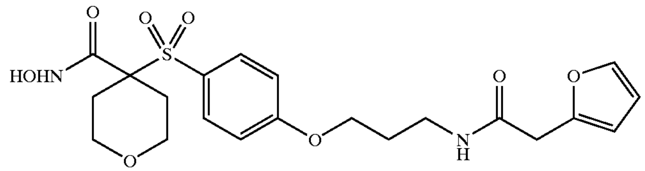 | 483.1260 | 483.1264 | | 12.4 | | 1.2 | |
| 103 | 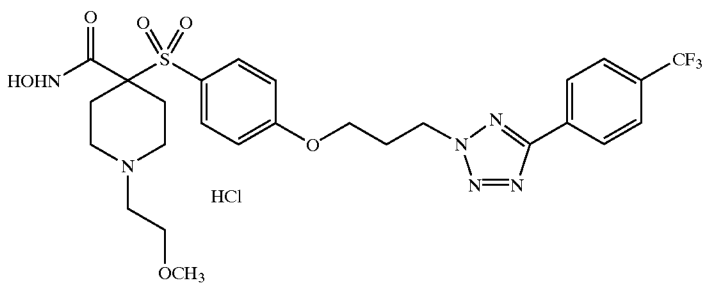 | 613 | 613 | >10000 | 85.8 | 1134 | 0.4 | >10000 |
| 104 | 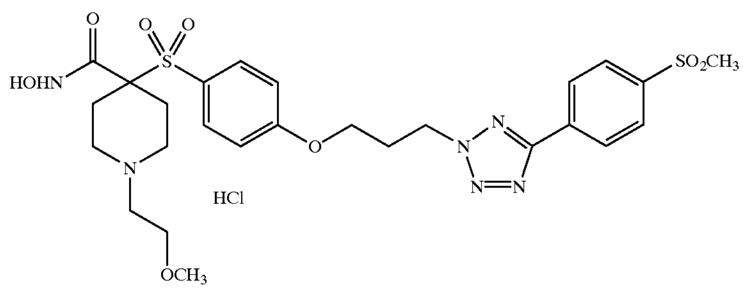 | | | | 44.2 | | 0.8 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 105 | 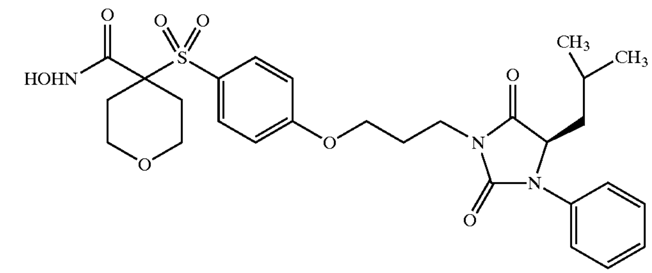 | | | >10000 | 1368.8 | 7694 | 9.7 | >10000 |
| 106 | 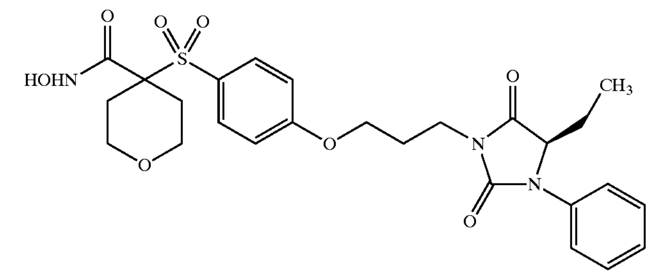 | | | >10000 | 1046.6 | >10000 | 3.5 | >10000 |
| 107 | 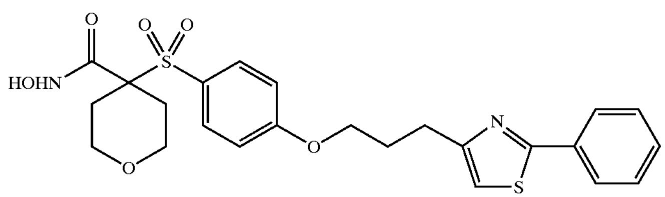 | | | | 34.0 | | 5.5 | |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 108 | 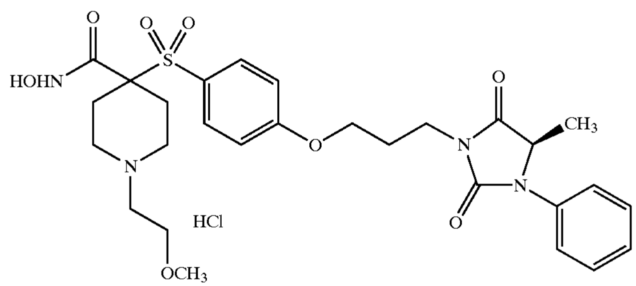 | | | | 433.7 | | 20.0 | |
| 109 | 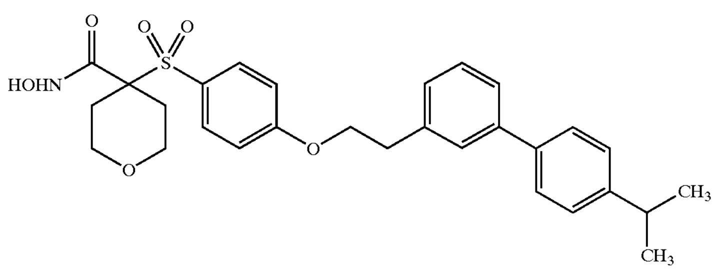 | 542.2107 | 524.2136 | (>10000) | 5410.3 (8100) | (>10000) | 152.1 (93.1) | (>10000) |
| 110 | 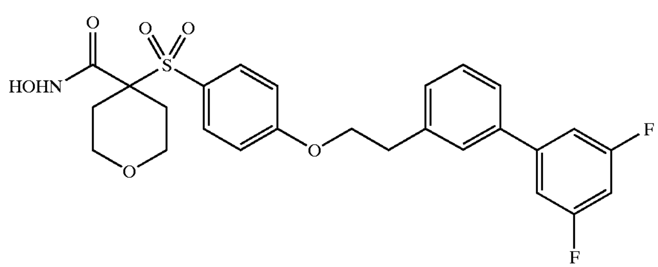 | 518.1449 | 518.1505 | (>10000) | 1198.5 (1120) | (4340) | 7.6 (11.4) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 111 | 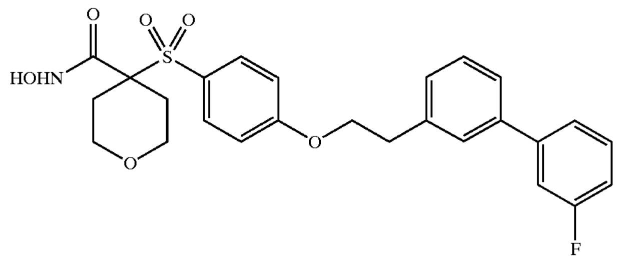 | 500.1543 | 500.1561 | (>10000) | 559.4 (769) | (2680) | 2.0 (6.39) | (>10000) |
| 112 | 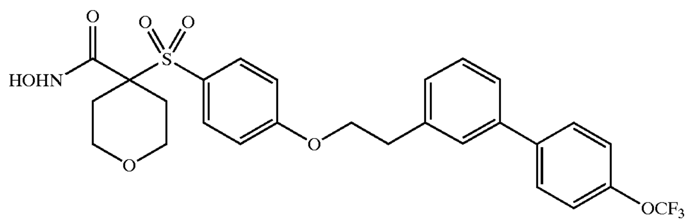 | 566.1460 | 566.1500 | (>10000) | 66.4 (3970) | (8850) | 37.9 (51.2) | (>10000) |
| 113 | 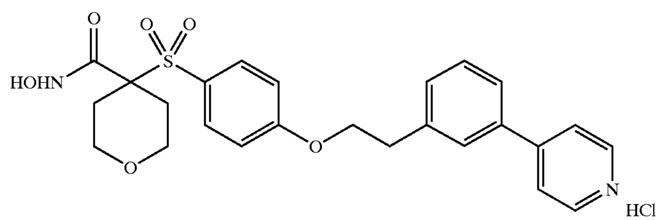 | 483.1590 | 483.1597 | >10000 (>10000) | 20.3 (42.30) | 1980.5 (161.22) | 0.2 (0.312) | 7725 (3481.8) |
| 114 | 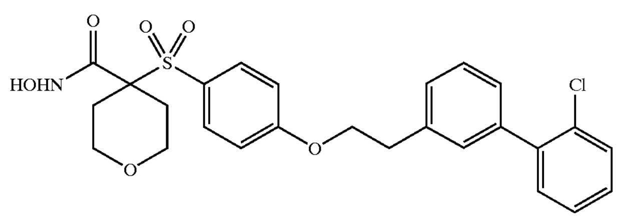 | 516.1248 | 516.1259 | (>10000) | 1010.6 (1500) | (4870) | 5.2 (4.2) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 115 | 2'-F biphenyl structure | 500.1543 | 500.1550 | >10000 (>10000) | 311.9 (807) | >10000 (1980) | 0.9 (2.24) | >10000 (>10000) |
| 116 | 2'-CH$_3$ biphenyl structure | 496.1794 | 496.1811 | (>10000) | 1053.2 (1250) | (5550) | 11.2 (5.1) | (>10000) |
| 117 | 3',4'-diCH$_3$ biphenyl structure | 510.1950 | 510.1965 | (>10000) | 1744.7 (3640) | (9910) | 16.0 (21) | (>10000) |
| 118 | 4'-Cl-3'-CH$_3$ biphenyl structure | 530.1404 | 530.1418 | (>10000) | 1862.0 (2650) | (>10000) | 29.8 (18.8) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 119 | 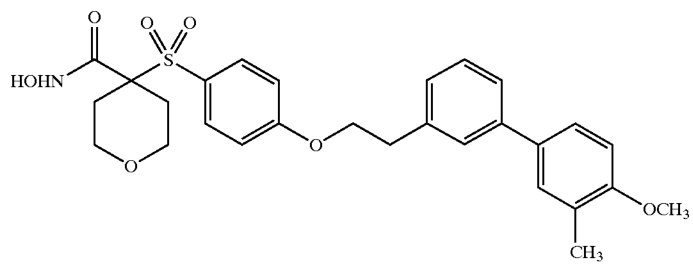 | 526.1899 | 526.1920 | (>10000) | 1187.6 (1680) | (3950) | 18.3 (31.4) | (>10000) |
| 120 | 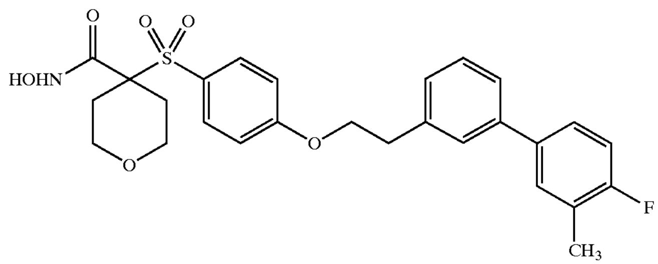 | 514.1700 | 514.1724 | >10000 | 1171.6 | >10000 | 5.8 | >10000 |
| 121 | 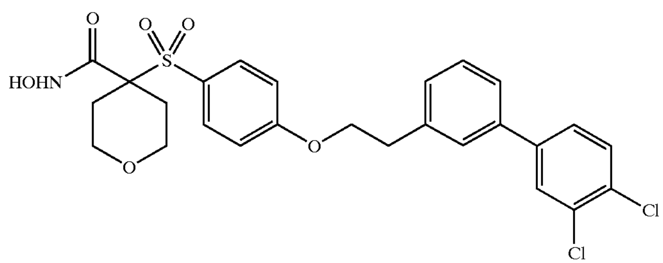 | 550.0858 | 550.0846 | (>10000) | 2469.3 (4620) | (>10000) | 21.6 (26.9) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 122 | 3,4-difluorobiphenyl derivative | 518.1449 | 518.1470 | >10000 | 759.7 | 7668 | 1.9 | >10000 |
| 123 | 4-fluorobiphenyl derivative | 500.1543 | 500.1545 | >10000 (>10000) | 383.0 (793) | >10000 (2130) | 1.4 (7.35) | >10000 (>10000) |
| 124 | 2,4-dichlorobiphenyl derivative | 550.0858 | 550.0896 | (>10000) | 2151.5 (5730) | (>10000) | 21.9 (20.1) | (>10000) |
| 125 | pyridyl-phenyl derivative·HCl | | | 2937 (3584.24) | 27.3 (51.34) | 962.9 (146.43) | 0.2 (0.17) | 5825 (1666.65) |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 126 | 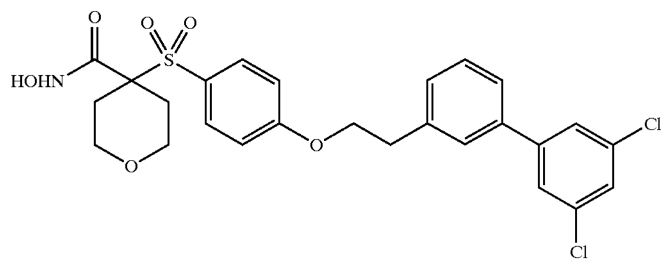 | 550.0858 | 550.0881 | (>10000) | 3260.4 (6360) | (>10000) | 349.0 (81.3) | (>10000) |
| 127 | 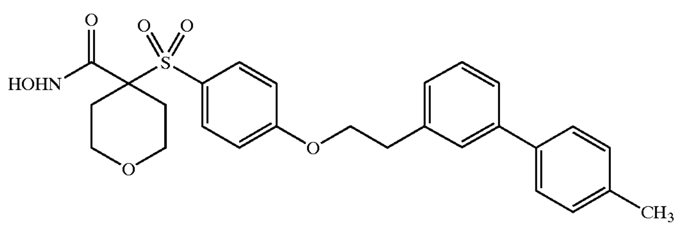 | 496.1794 | 496.1800 | >10000 (>10000) | 1380.0 (2160) | >10000 (4230) | 5.5 (16.2) | >10000 (>10000) |
| 128 | 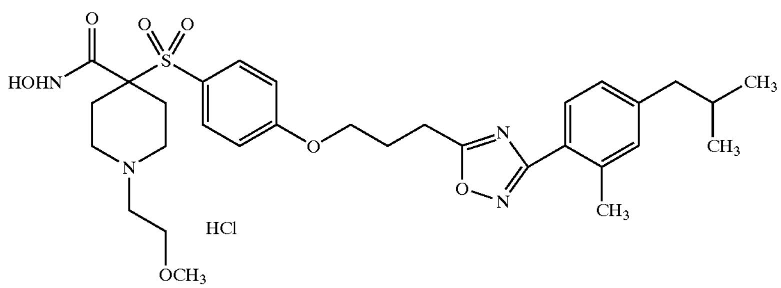 | 615.2902 | 615.2852 | (>10000) | 658.7 (1130) | (3550) | 23.7 (13.8) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 129 | 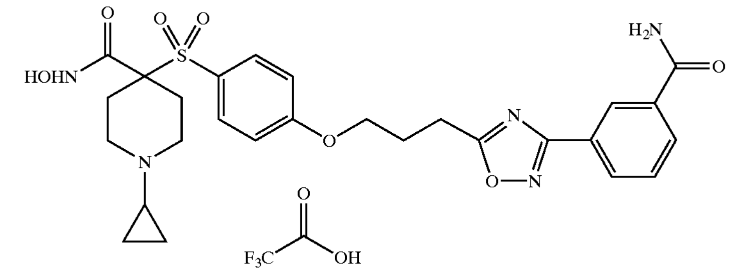 | | | (>10000) | 41.4 (50) | (110) | 1.9 (0.27) | (>10000) |
| 130 | 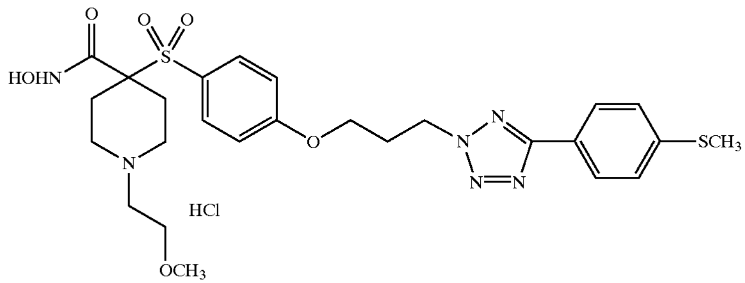 | | | 4611 | 4.7 | 50.2 | 0.3 | 499.8 |
| 131 | 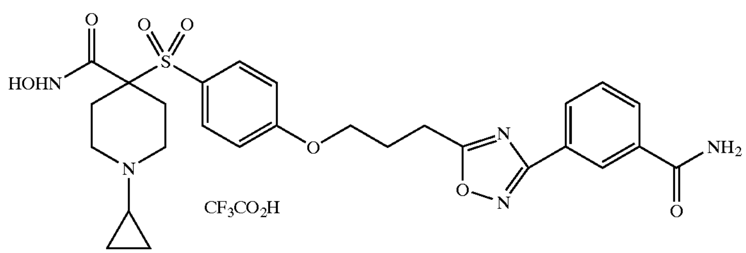 | | | | 107.9 | | 4.5 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 132 | 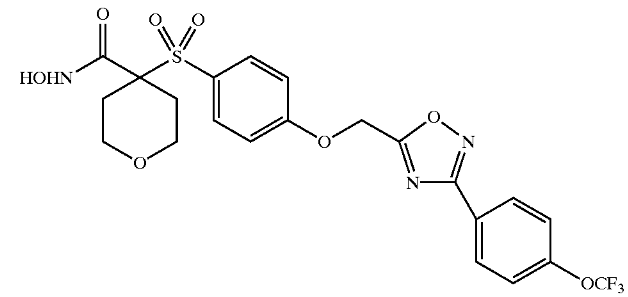 | | | | 61.7 | | 3.7 | |
| 133 | 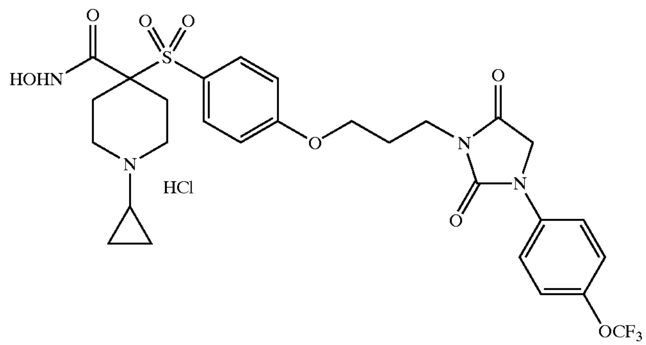 | | | | 84.4 | | 4.3 | |
| 134 | 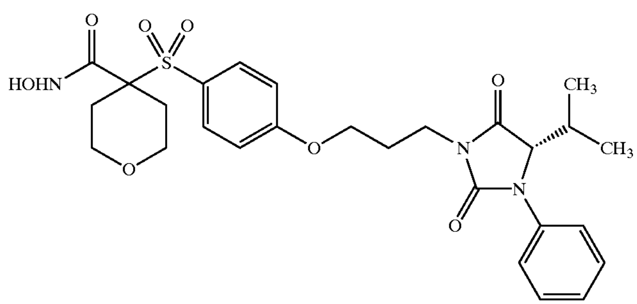 | | | >10000 | 2382 | >10000 | 7.7 | >10000 |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 135 | 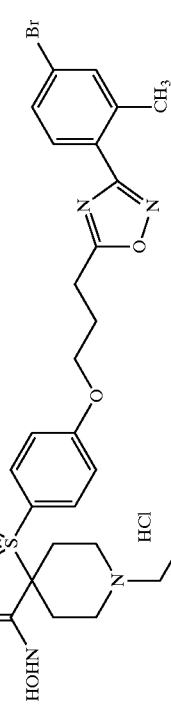 | 637.1332 | 637.1315 | (>10000) | 24.3 (58.5) | (457) | 2.9 (0.761) | (9510) |
| 136 | 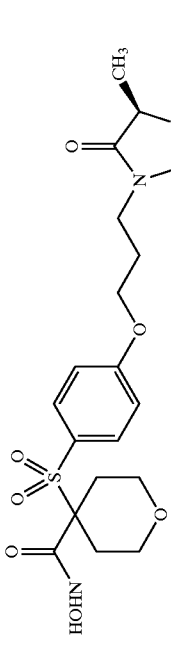 | | | | 229.4 | | 4.4 | |
| 137 | 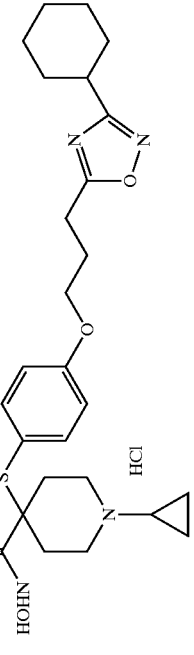 | | | (>10000) | 20.4 (36.6) | (604) | 7.0 (0.976) | (>10000) |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 138 | 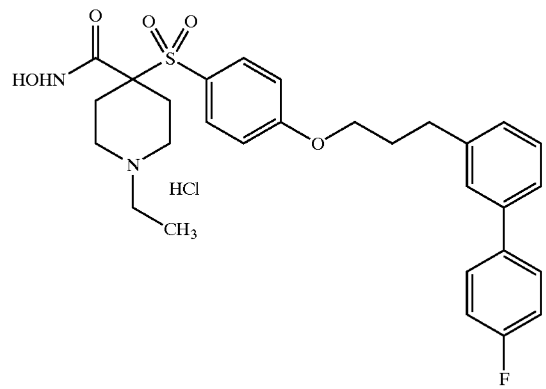 | | | >10000 | 247.3 | 1896 | 2.1 | >10000 |
| 139 | 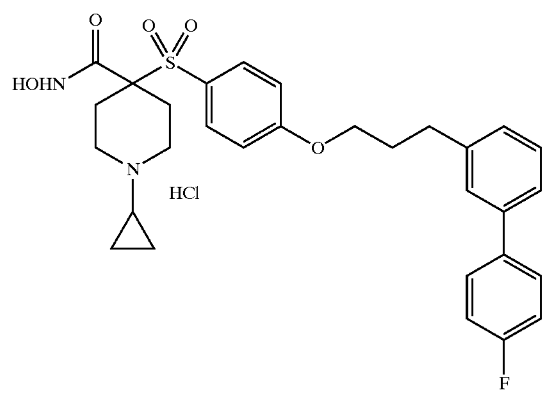 | 553.2172 | 553.2176 | >10000 (>10000) | 207.7 (1410) | 4514 (1390) | 0.4 (2.89) | >10000 (>10000) |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 140 | 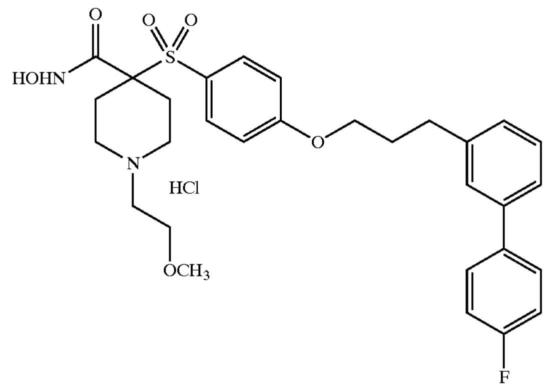 | | | >10000 (>10000) | 48.0 (708) | 1692 (754) | 0.5 (0.895) | >10000 (>10000) |
| 141 | 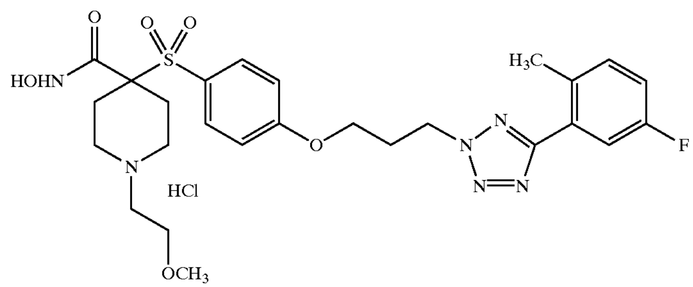 | 577 | 577 | | 32.5 | | 3.6 | |
| 142 | 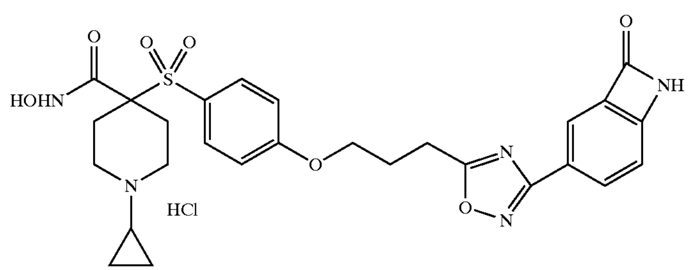 | | | (>10000) | 58.6 (96.4) | (310) | 7.5 (1.34) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 143 | 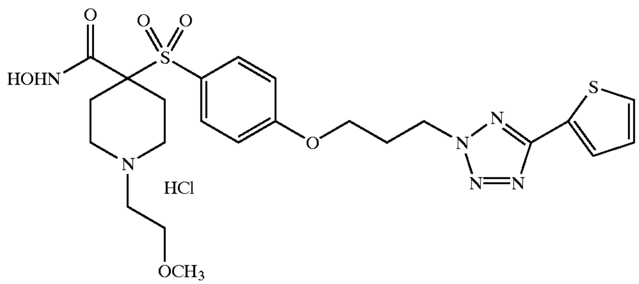 | | | | 4.9 | | 1.4 | |
| 144 | 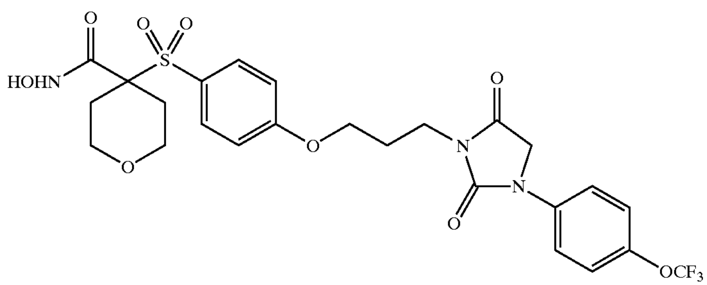 | | | >10000 | 238.6 | 5989 | 2.5 | >10000 |
| 145 | 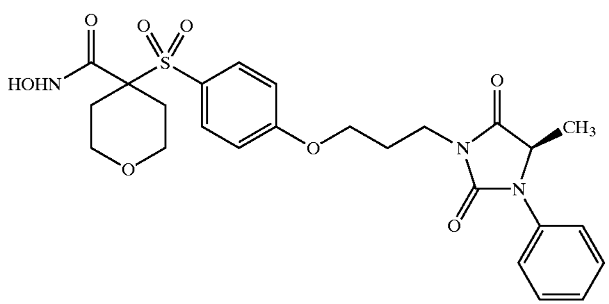 | | | >10000 | 816.9 | 9438 | 2.0 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 146 | 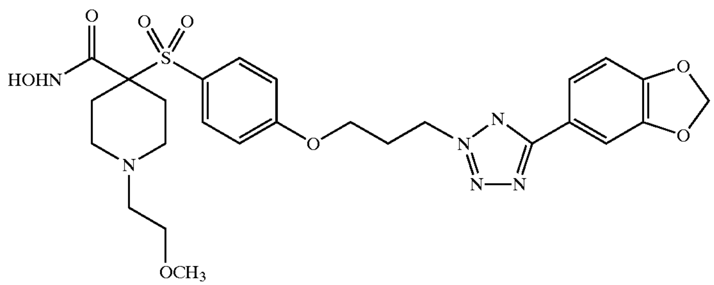 | | | | 11.1 | | 0.4 | |
| 147 | 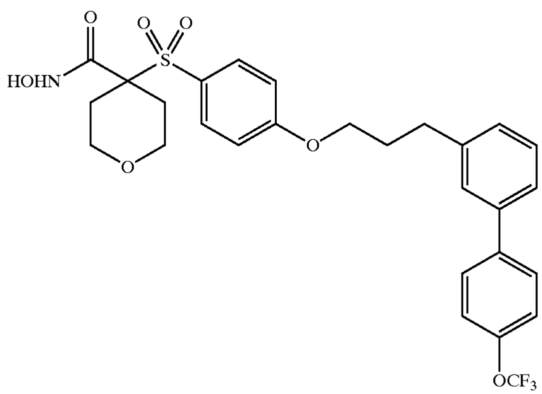 | 580.1617 | 580.1620 | (>10000) | 4746.8 (>10000) | (7970) | 28.3 (23.9) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 148 | 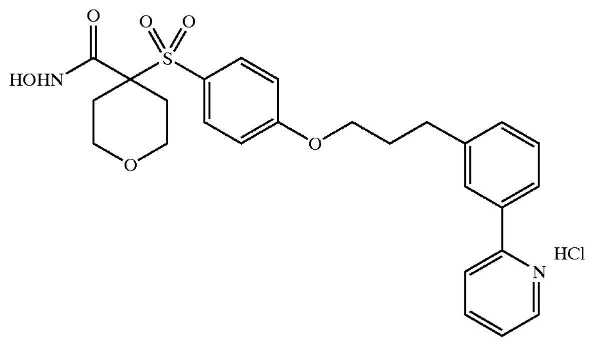 | | | (8790) | 272.0 (213) | (427) | 3.1 (1.72) | (5150) |
| 149 | 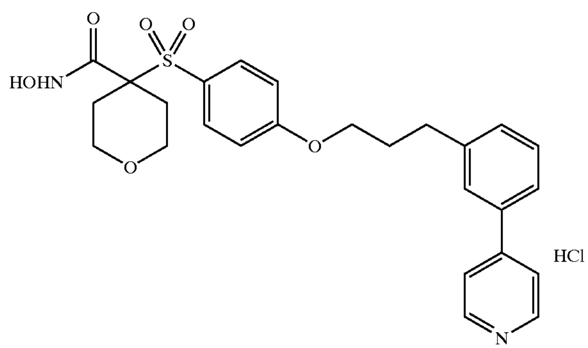 | | | (>10000) | 77.1 (84.1) | (94.5) | 1.3 (1.18) | (2530) |

TABLE 7-continued
| Ex # | Structure | Calc. Mass | Ob- served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 150 | 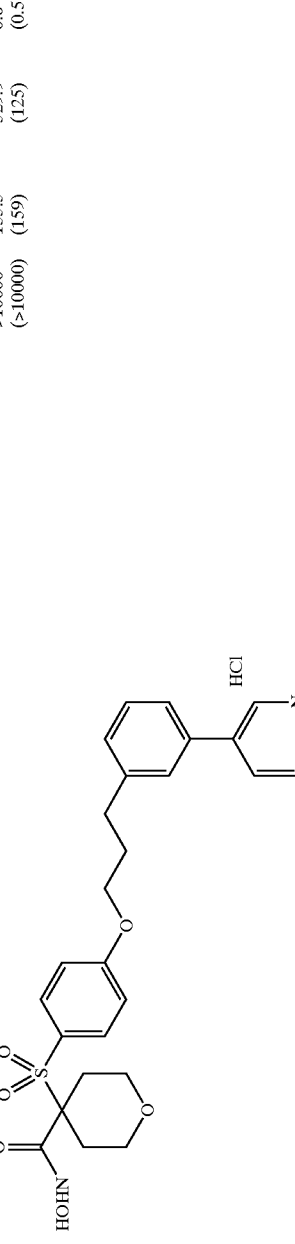 | | | >10000 (>10000) | 135.5 (159) | 529.9 (125) | 0.6 (0.587) | 6630 (5510) |
| 151 | 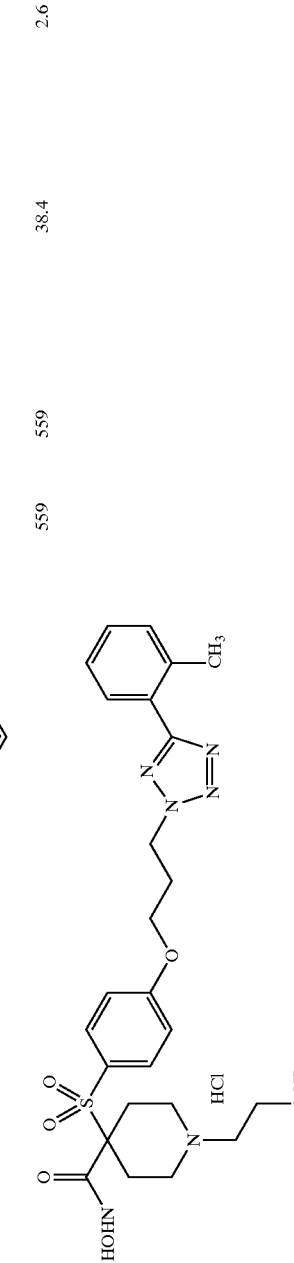 | 559 | 559 | | 38.4 | | 2.6 | |
| 152 | 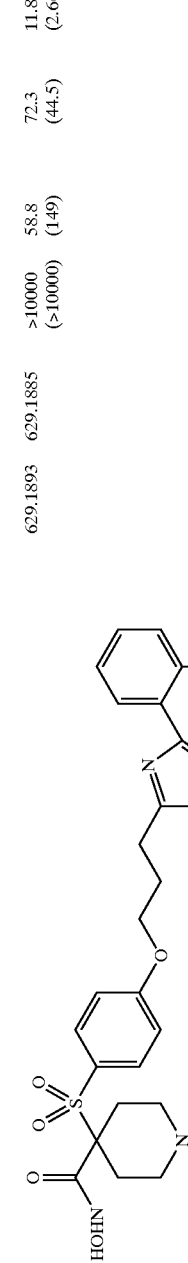 | 629.1893 | 629.1885 | >10000 (>10000) | 58.8 (149) | 72.3 (44.5) | 11.8 (2.66) | >10000 (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 153 | 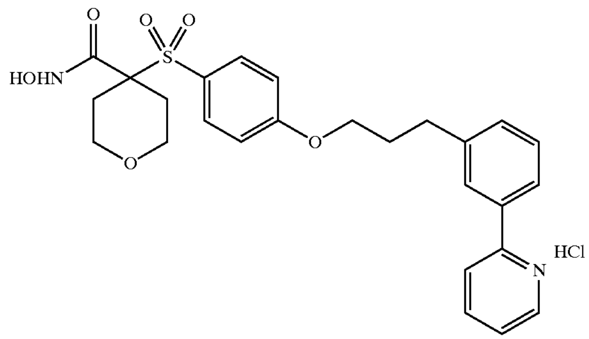 | | | | 192.5 | | 7.6 | |
| 154 | 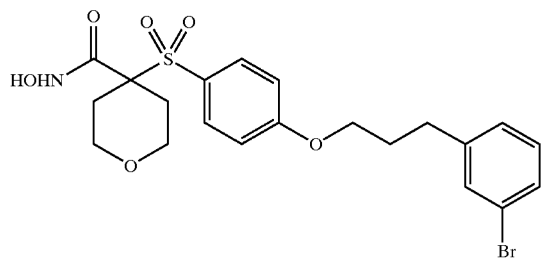 | 498.0586 | 498.0591 | >10000 (>10000) | 10.9 (33.9) | 111 (151) | 0.8 (0.95) | 9123 (3910) |
| 155 | 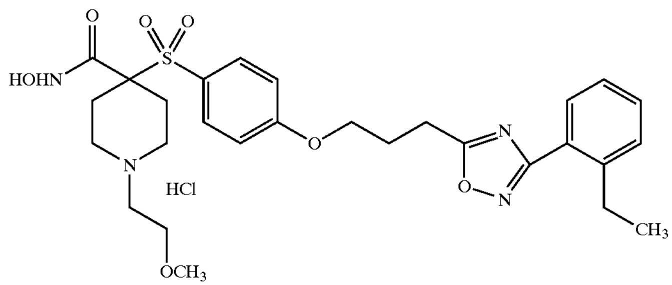 | 573.2383 | 573.2413 | >10000 (>10000) | 13.8 (37.9) | 1173.7 (172) | 9.7 (1.58) | >10000 (9370) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 156 | 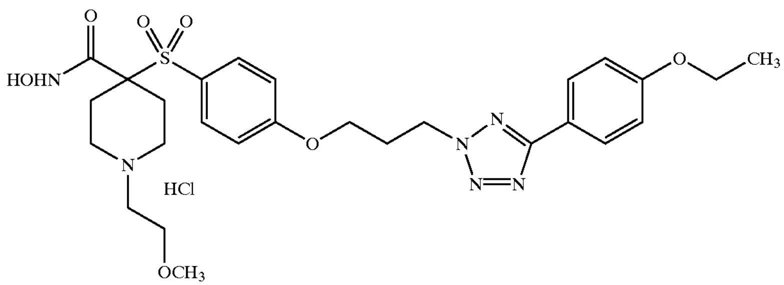 | | | | 32.1 | | 1.0 | |
| 157 | 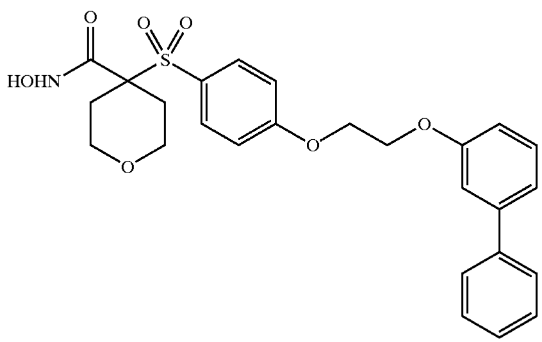 | | | >10000 (>10000) | 182.1 (419) | 2473 (1390) | 3.5 (4.01) | >10000 (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 158 | 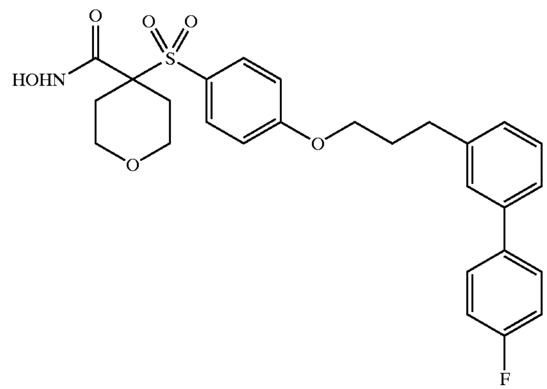 | 530.1404 | 530.1446 | >10000 (>10000) | 2184 (2730) | 5630 (3950) | 3.6 (5.1) | >10000 (>10000) |
| 159 | 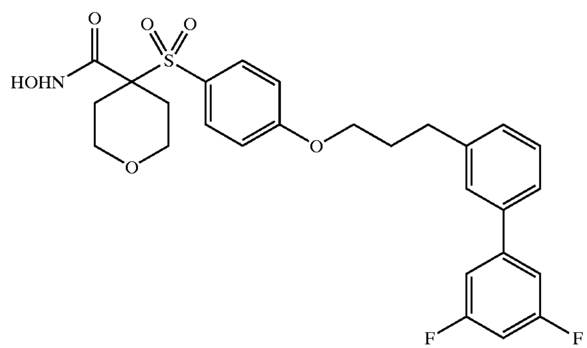 | 532.1605 | 532.1632 | | 1368.6 | | 24.4 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 160 | 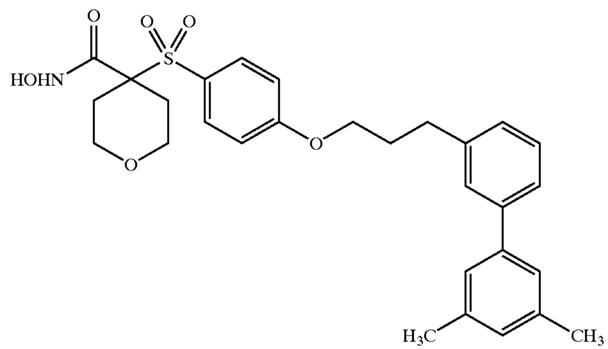 | 538.2263 | 538.2275 | >10000 (>10000) | >10000 (>10000) | (>10000) | 505.1 | (>10000) |
| 161 | 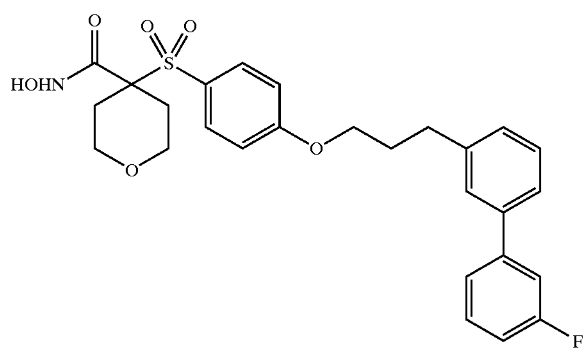 | 514.1700 | 514.1708 | >10000 (>10000) | 1001.1 (1760) | 2625 (1730) | 2.6 (20.3) | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 162 | 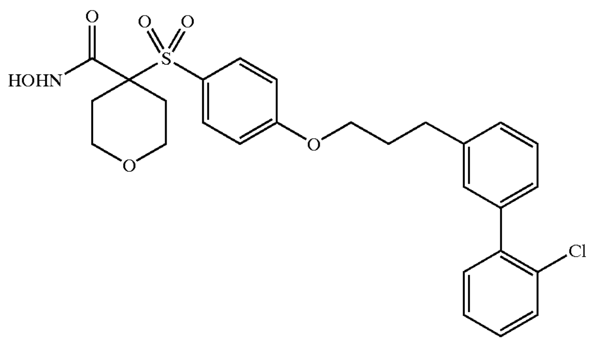 | 530.1404 | 530.1428 | >10000 (>10000) | 1596.6 (2370) | (3150) | 15.6 (12) | (>10000) |
| 163 | 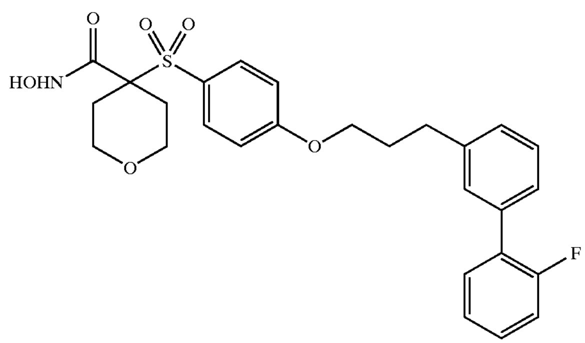 | 514.1700 | 514.1680 | >10000 (>10000) | 1370.7 (1010) | 2880 (2500) | 2.5 (11.6) | >10000 (>10000) |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 164 | 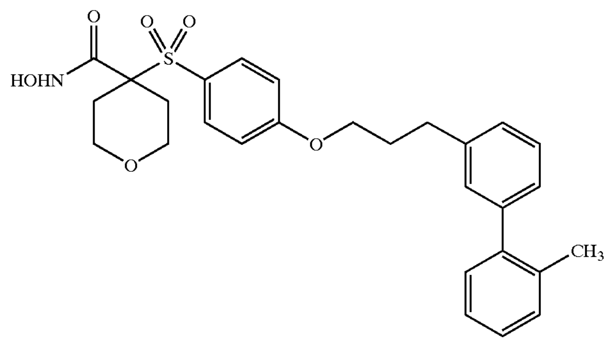 | 510.1950 | 510.1940 | (>10000) | 1073.2 (978) | (2720) | 20.0 (6.85) | (>10000) |
| 165 | 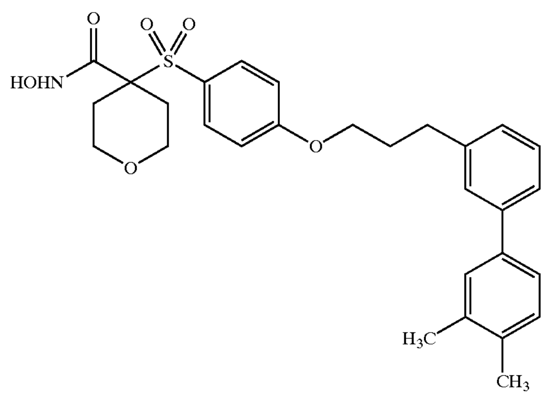 | 524.2107 | 524.2112 | (>10000) | 3396.2 (>10000) | (9750) | 146.9 (144) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 166 | 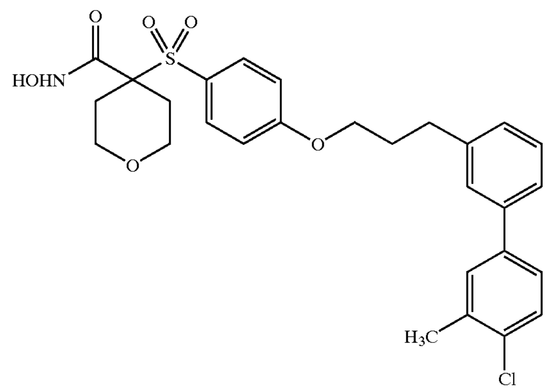 | 544.1561 | 644.1606 | (>10000) | 3081.7 (8090) | (8690) | 135.9 (63.4) | (>10000) |
| 167 | 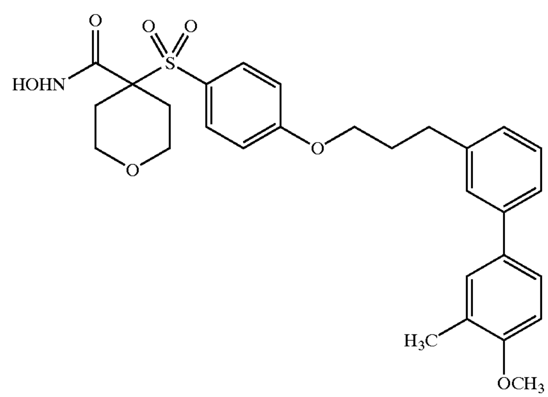 | 540.2056 | 540.2029 | (>10000) | 3739.4 (128) | (68.1) | 147.0 (78.9) | (>10000) |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 168 | 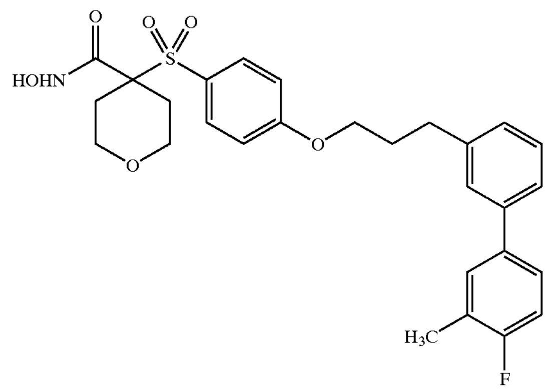 | 528.1856 | 528.1863 | (>10000) | 3428.2 (5500) | (6500) | 34.3 (27.3) | (>10000) |
| 169 | 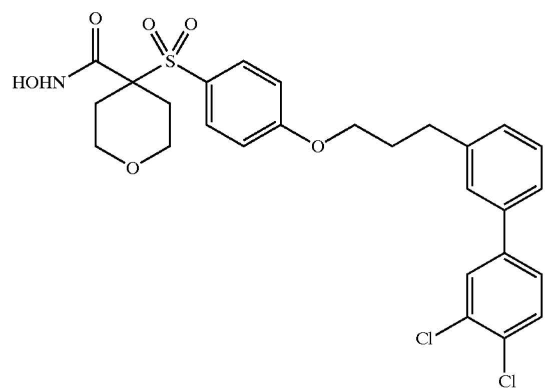 | 564.1014 | 564.1026 | (>10000) | 4363.5 (5360) | (6500) | 70.7 (20.4) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 170 | 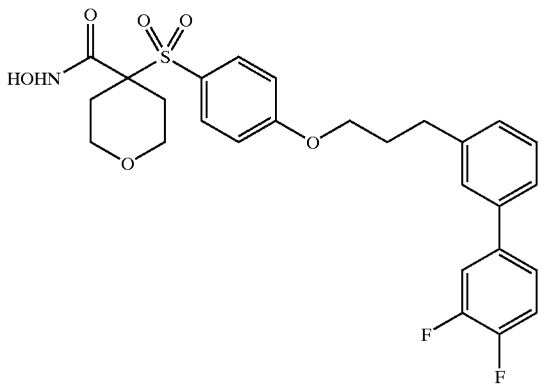 | 532.1605 | 532.1618 | (>10000) | 1608.7 (1410) | (1500) | 3.3 (6.79) | (>10000) |
| 171 | 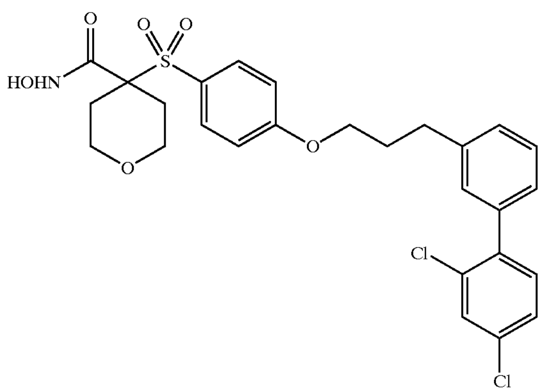 | 564.1014 | 564.1028 | (>10000) | 2288.8 (3190) | (6600) | 62.8 (12.5) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 172 | 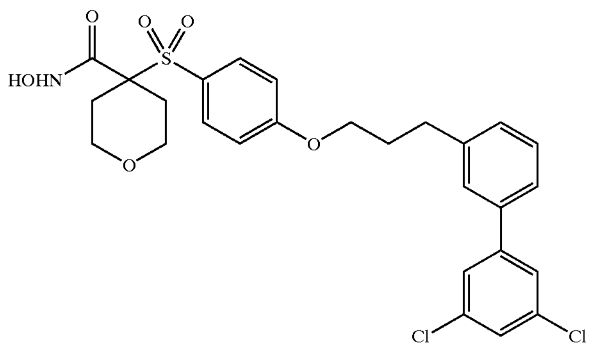 | 564.1014 | 564.1032 | (>10000) | 5163.1 (>10000) | (9440) | 377.0 (71.1) | (>10000) |
| 173 | 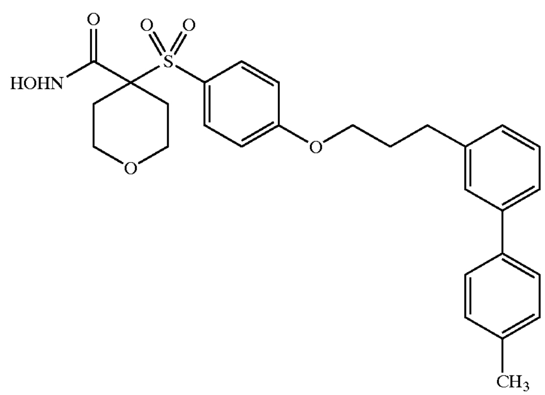 | 509.1950 | 509.1954 | (>10000) | 2120.4 (4090) | (3480) | 12.2 (11.5) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 174 | 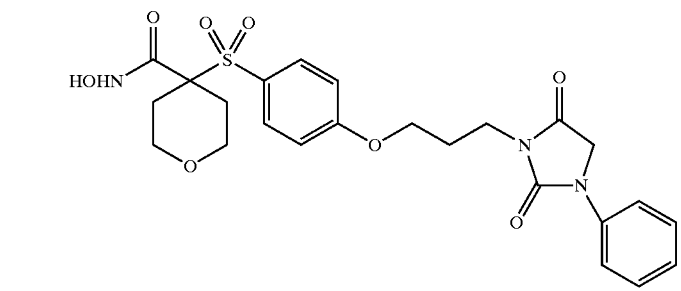 | | | (>10000) | 708.6 | 4017 | 5.2 | >10000 |
| 175 | 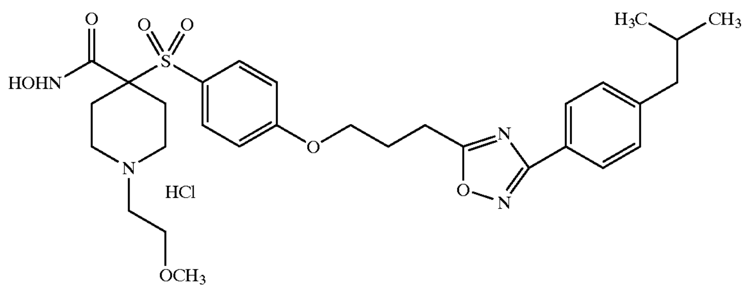 | 601.2696 | 601.2657 | >10000 (>10000) | 438.0 (872) | 7296.6 (1390) | 1.4 (2.01) | >10000 (>10000) |
| 176 | 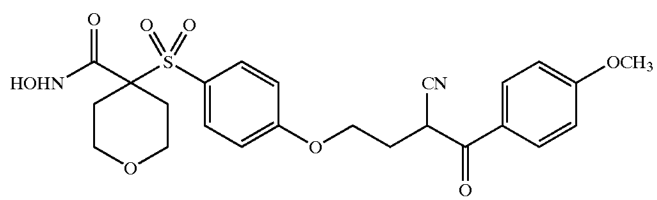 | | | | 108.9 | | 7.8 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 177 | 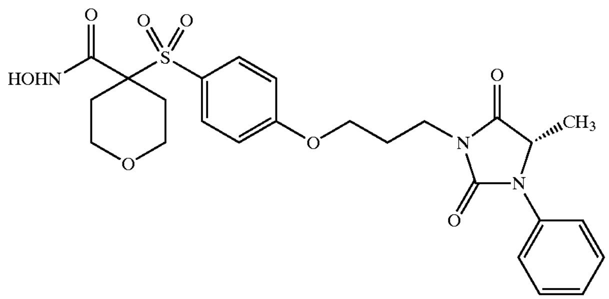 | | | | 333.2 | | 17.0 | |
| 178 | 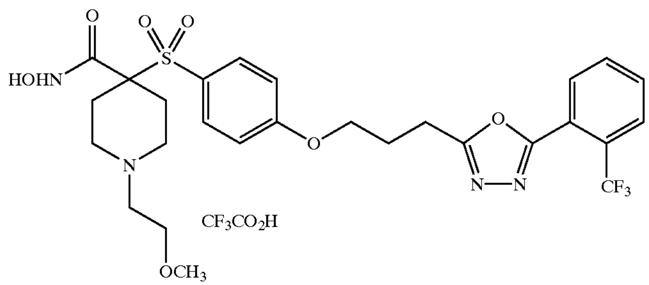 | | | >10000 (>10000) | 28.4 (39.3) | 1166.4 (306) | 7.8 (1.71) | >10000 (>10000) |
| 179 | 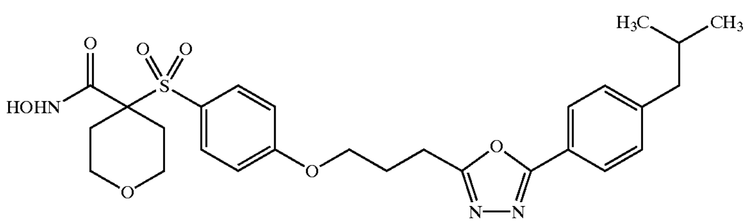 | | | | 246.9 | | 1.1 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 180 | 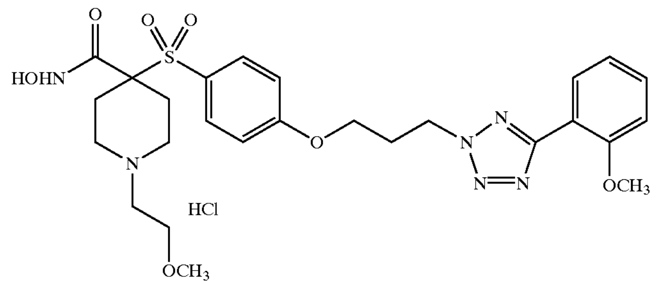 | | | | 443.0 | | 17.0 | |
| 181 | 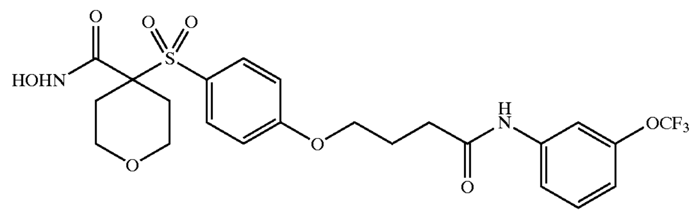 | | | >10000 (1850) | 13.9 (15.8) | 26.4 (40.5) | 0.3 (0.27) | 8059 (4830) |
| 182 | 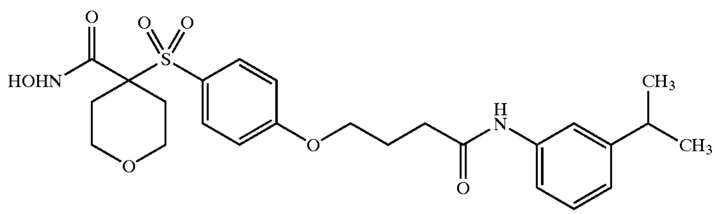 | | | >10000 (6540) | 33.1 (34.3) | 62.1 (85.4) | 0.5 (0.212) | >10000 (5850) |
| 183 | 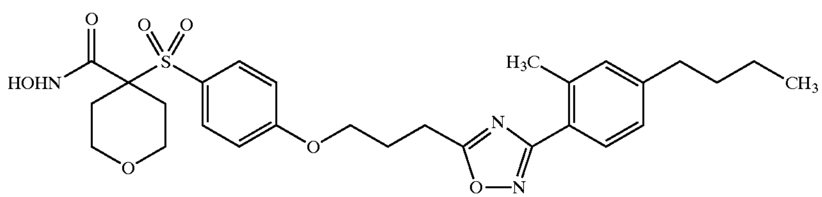 | | | (>10000) | 708.0 (643) | (2510) | 21.0 (15.1) | (>10000) |

TABLE 7-continued

| Ex # | Structure | Calc. Mass | Observed Mass | MMP-1 IC₅₀ (Ki) | MMP-2 IC₅₀ (Ki) | MMP-9 IC₅₀ (Ki) | MMP-13 IC₅₀ (Ki) | MMP-14 IC₅₀ (Ki) |
|---|---|---|---|---|---|---|---|---|
| 184 | 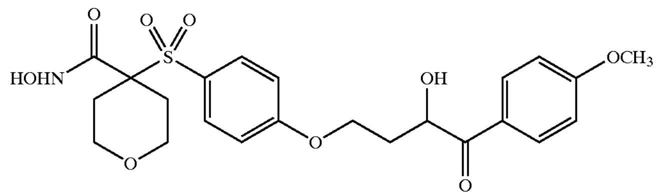 | | | 1528.7 | 30.4 | 103.5 | 3.9 | 2715.4 |
| 185 | 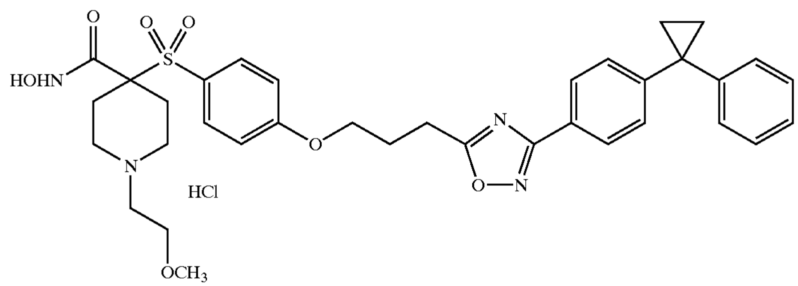 | | | (>10000) | 84.7 (116) | (220) | 12.4 (3.73) | (>10000) |
| 186 | 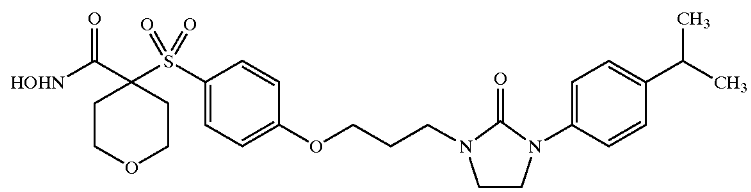 | | | | 609.9 | | 13.5 | |
| 187 | 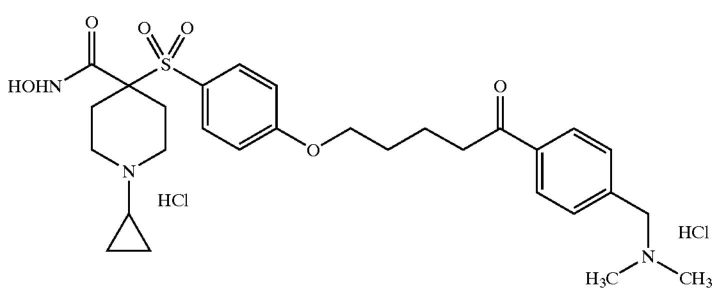 | | | 3868 | 3.6 | 11.2 | 1.8 | 1425 |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 188 | 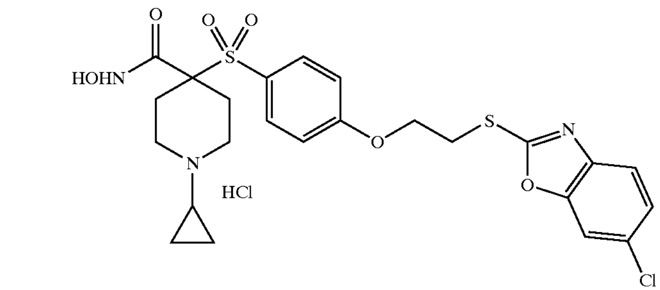 | | | >10000 | 4.7 | 48.2 | 0.3 | 3537.7 |
| 189 | 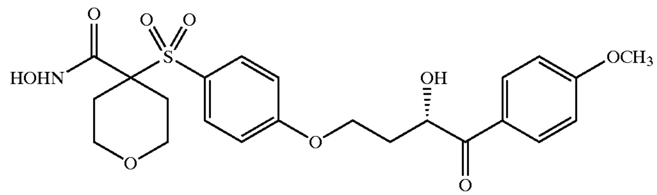 | | | 1070 | 19.3 | 24.1 | 1.9 | 4316 |
| 190 | 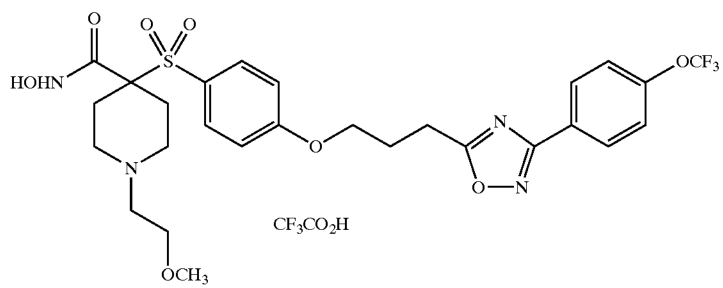 | | | >10000 (>10000) | 165.9 (283) | 1742.6 (669) | 0.5 (0.6) | >10000 (>10000) |
| 191 | 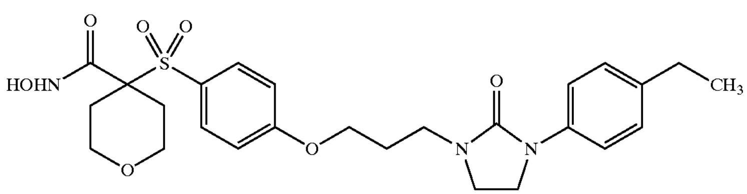 | | | 6956 | 341.2 | 383.4 | 9.5 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 192 | 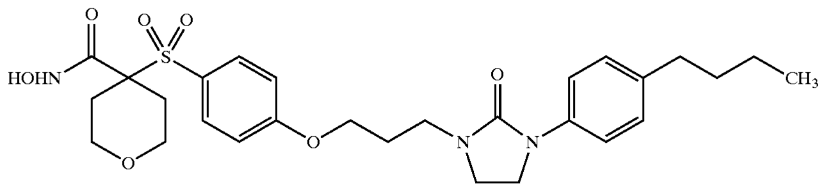 | | | | 1256.4 | | 15.4 | |
| 193 | 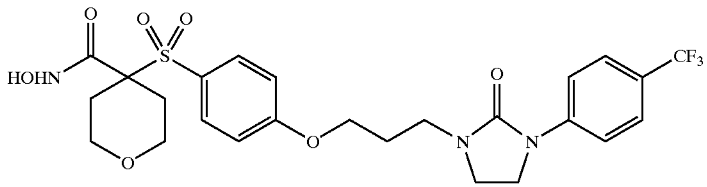 | | | 5931.6 | 312.3 | 272.5 | 6.8 | >10000 |
| 194 | 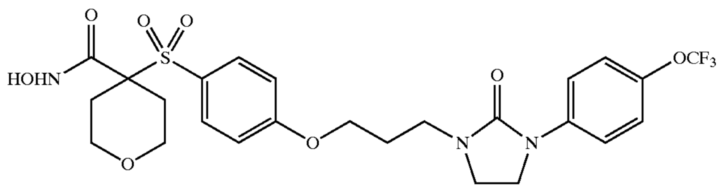 | | | >10000 | 221.6 | 515.7 | 6.2 | >10000 |
| 195 | 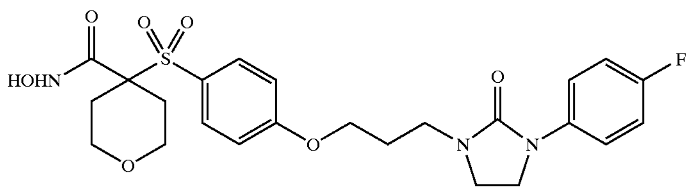 | | | 4381.7 | 20.6 | 45.8 | 7.5 | 2741.5 |
| 196 | 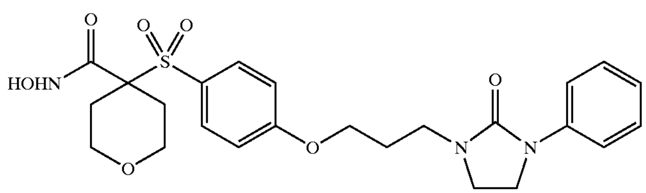 | | | | 32.2 | | 11.4 | |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 197 | 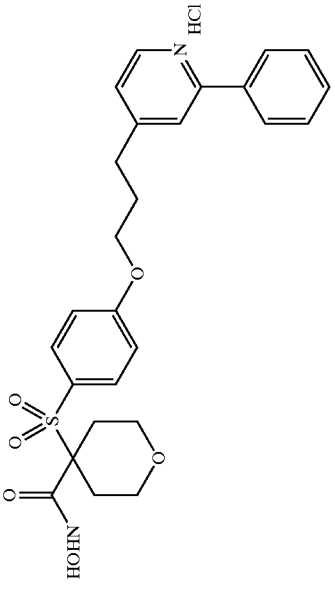 | | | >10000 (>10000) | 13.2 (30.7) | 432.2 (334) | 0.5 (0.37) | >10000 (>10000) |
| 198 | 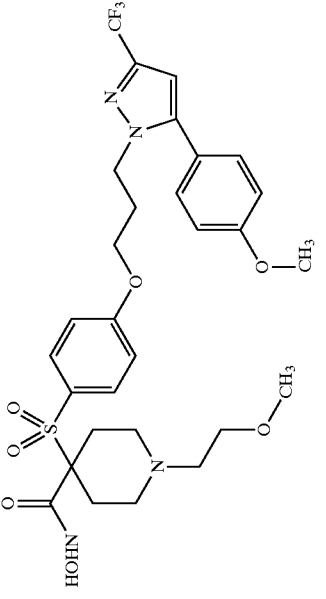 | | | | 4527.4 | | 834.9 | |
| 199 | 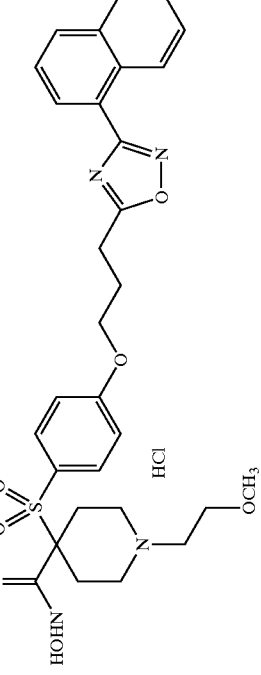 | | | (>10000) | 133.2 (228) | (59.5) | 7.4 (3.09) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 200 | 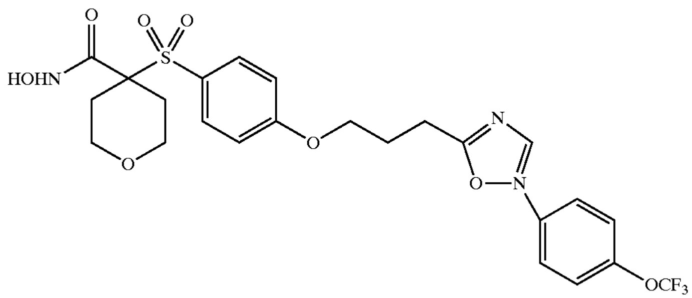 | | | 7498 | 84.0 | 1207.2 | 0.6 | >10000 |
| 201 | 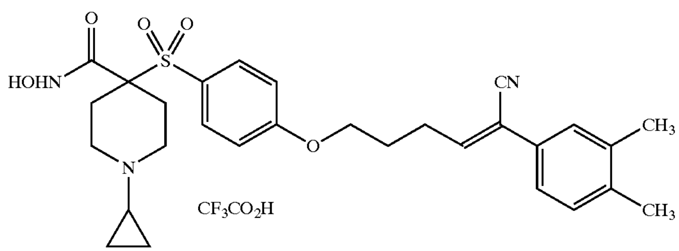 | 538.2376 | 538.2362 | >10000 | 127.7 | 4509.5 | 0.7 | >10000 |
| 202 | 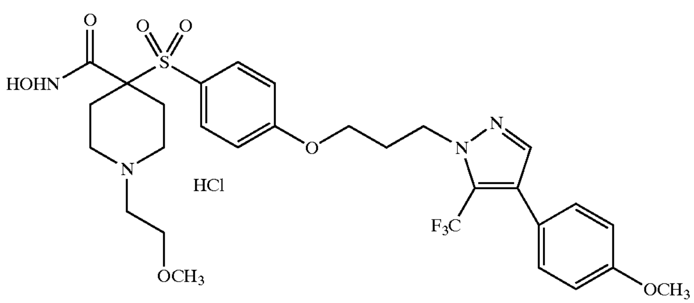 | | | | 1604.4 | | 41.9 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 203 | 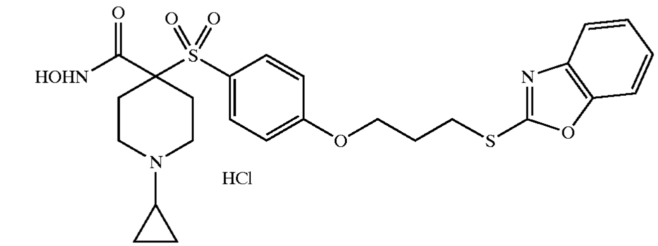 | | | >10000 | 4.2 | 6.0 | 1.0 | >10000 |
| 204 | 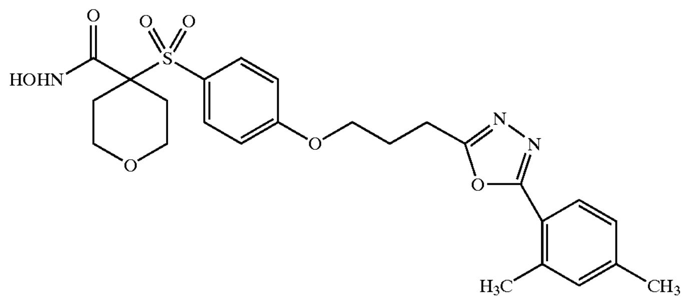 | | | >10000 | 145.7 | 1824.8 | 0.6 | >10000 |
| 205 | 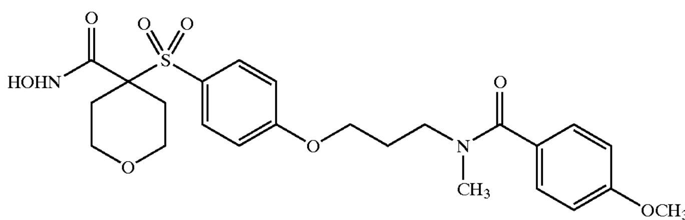 | | | | 4780.2 | | 17.6 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 206 | 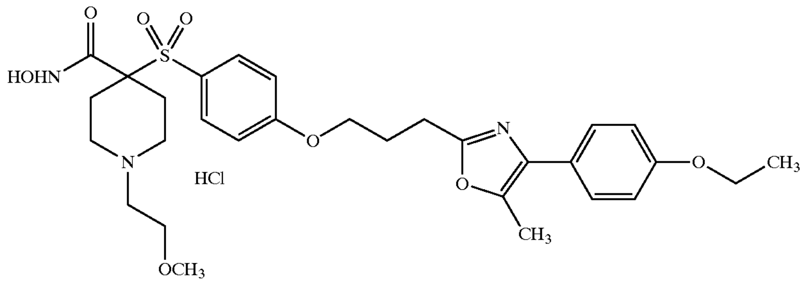 | | | >10000 | 92.6 | 59.4 | 15.8 | 3112 |
| 207 | 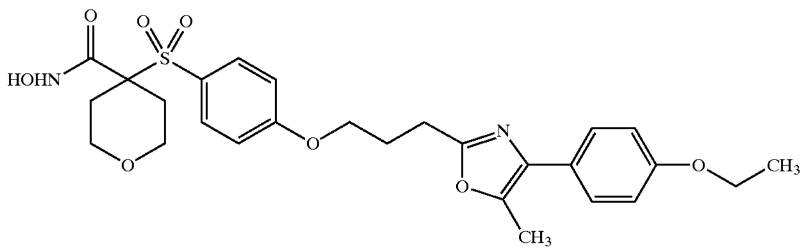 | | | >10000 | 114.3 | 126.7 | 3.7 | >10000 |
| 208 | 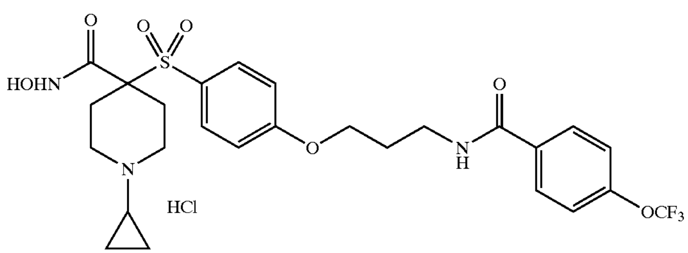 | | | >10000 | 230.2 | 6587.6 | 0.6 | >10000 |

TABLE 7-continued
| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 209 | 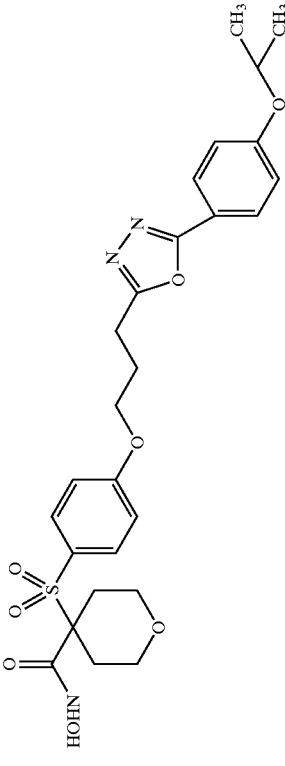 | | | >10000 | 172.5 | 905.6 | 1.4 | >10000 |
| 210 | 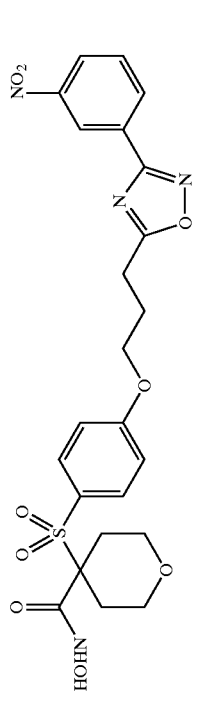 | | | >10000 | 6.9 | 284.6 | 1.3 | >10000 |
| 211 | 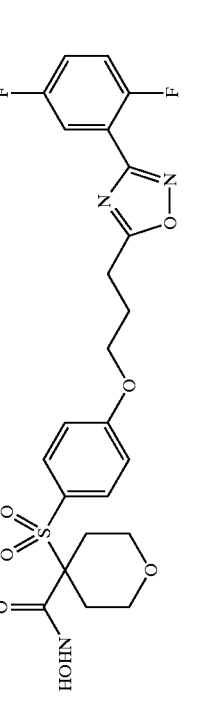 | | | 9653 | 26.2 | 863.5 | 0.4 | >10000 |
| 212 | 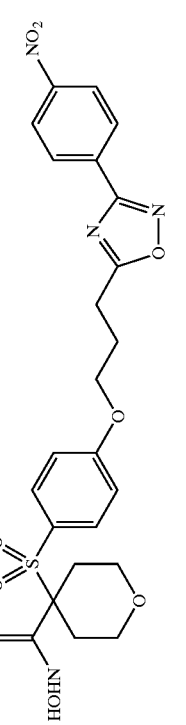 | | | 1408 | 4.1 | 212.2 | 0.3 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 213 | 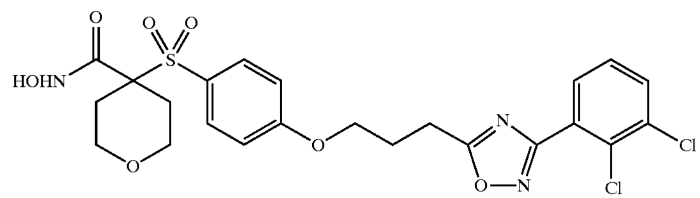 | | | >10000 | 54.8 | 2204 | 2.2 | >10000 |
| 214 | 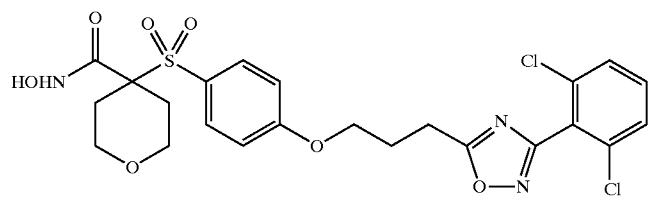 | | | >10000 | 15.8 | 4239 | 3.3 | >10000 |
| 215 | 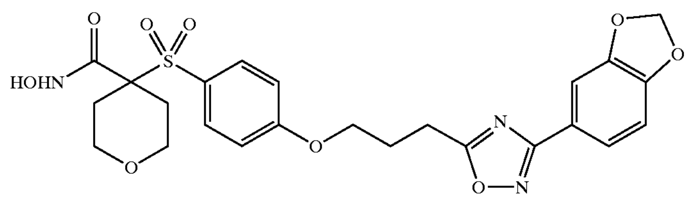 | | | >10000 | 20.3 | 767.9 | 0.3 | >10000 |
| 216 | 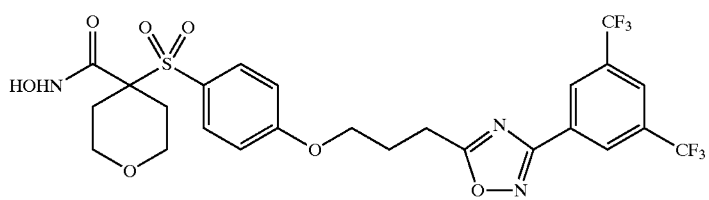 | | | | 1952.2 | | 51.2 | |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 217 | 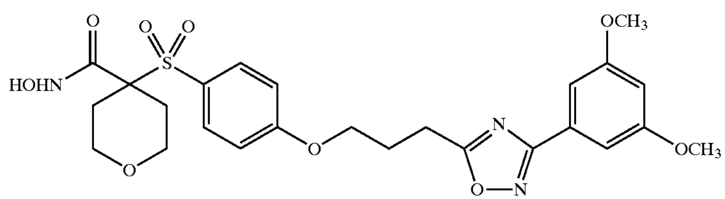 | | | >10000 | 48.9 | 5179 | 4.6 | >10000 |
| 218 | 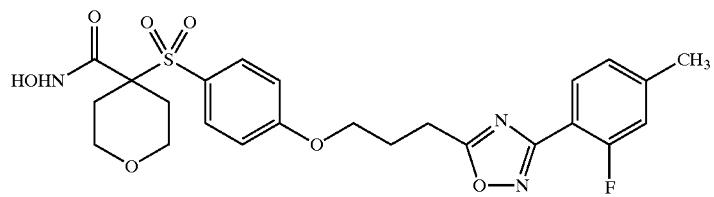 | | | >10000 | 40.4 | 2973 | 1.4 | >10000 |
| 219 | 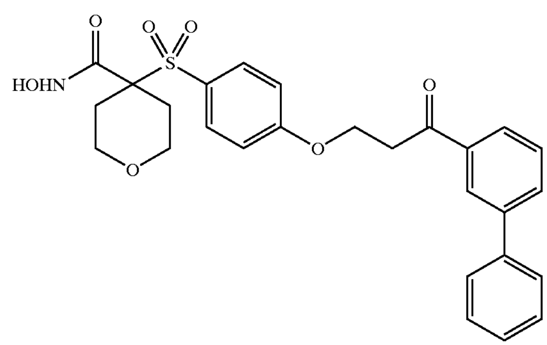 | | | >10000 (5600) | 60.8 (105) | 77.7 (59.5) | 0.4 (0.355) | >10000 (7940) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 220 | 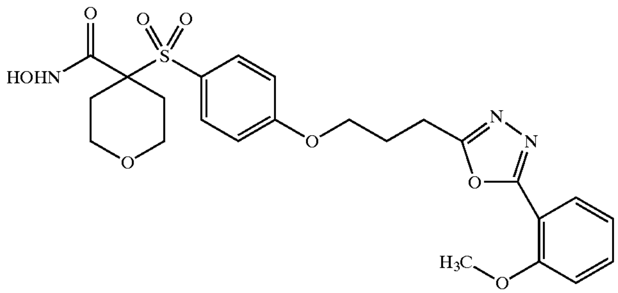 | | | >10000 | 409.7 | 1466.8 | 5.7 | >10000 |
| 221 | 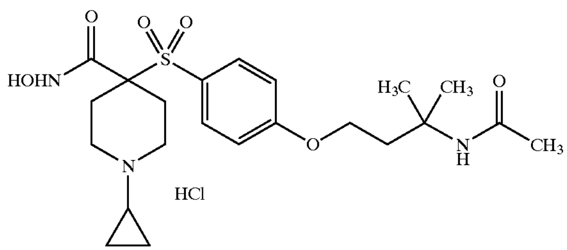 | | | | 8796.4 | | 243.8 | |
| 222 | 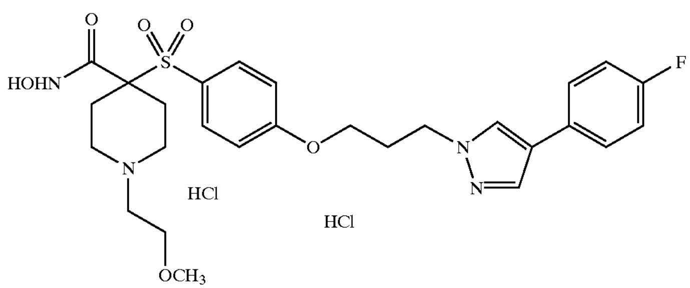 | | | | 138.1 | | 13.3 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 223 | 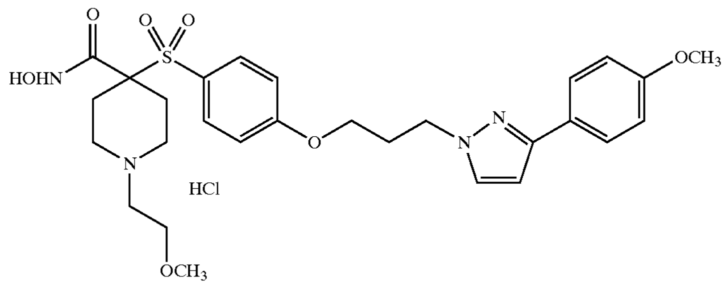 | | | | 69.7 | | 11.9 | |
| 224 | 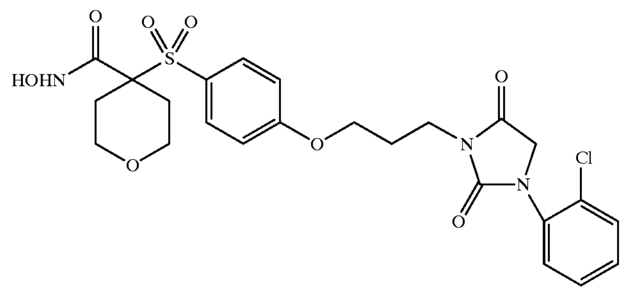 | | | >10000 | 193.5 | 1466.8 | 4.7 | >10000 |
| 225 | 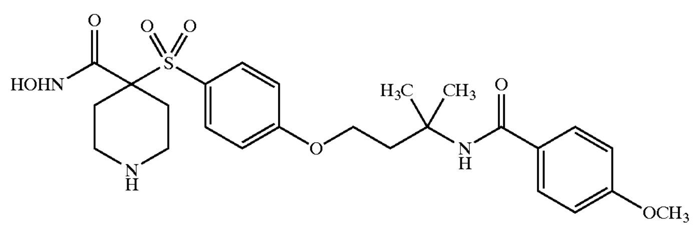 | | | | 2332.3 | | 17.8 | |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 226 | 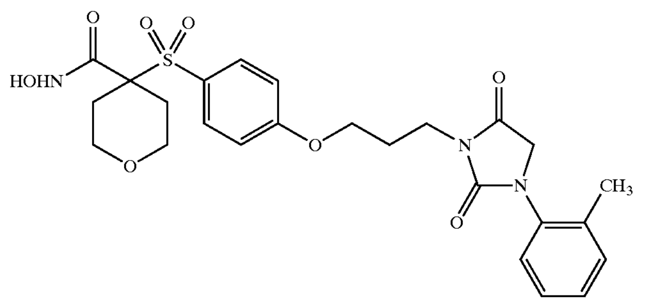 | | | >10000 | 222.0 | 2144.0 | 4.3 | >10000 |
| 227 | 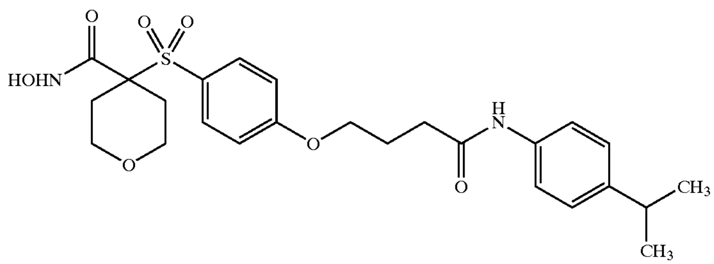 | | | | 2.7 | | 0.2 | |
| 228 | 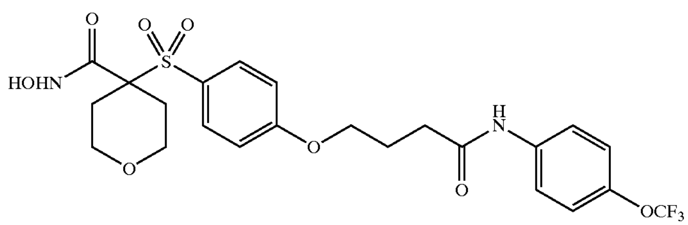 | | | 6871 (3940) | 11.4 (22.4) | 180.4 (247) | 0.2 (0.324) | >10000 (6290) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 229 | 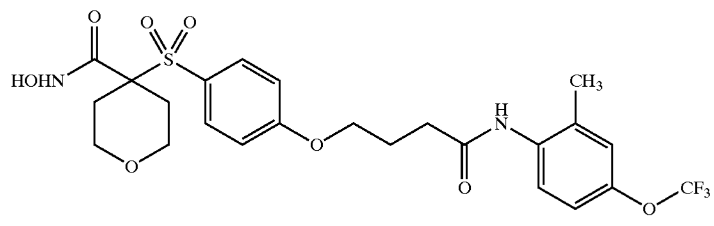 | | | 5033 (955) | 12.2 (10.4) | 293.7 (281) | 1.7 (0.27) | >10000 (7870) |
| 230 | 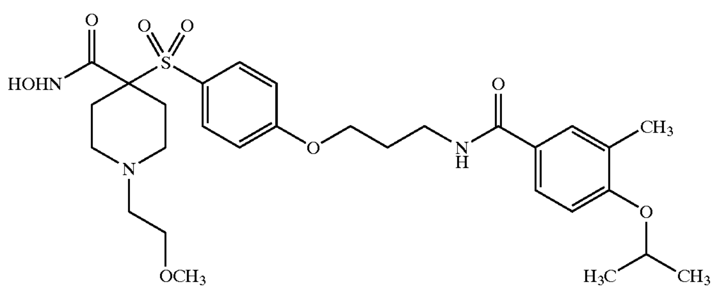 | | | >10000 | 555.2 | 1017.7 | 1.1 | >10000 |
| 231 | 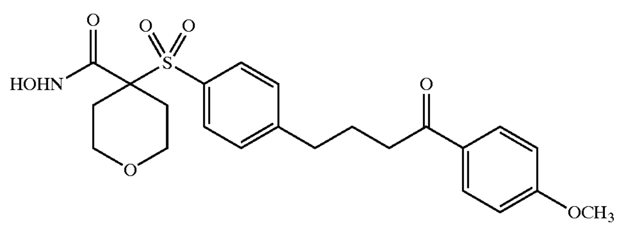 | | | >10000 | 1.6 | 10.2 | 0.2 | 641.7 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 232 | 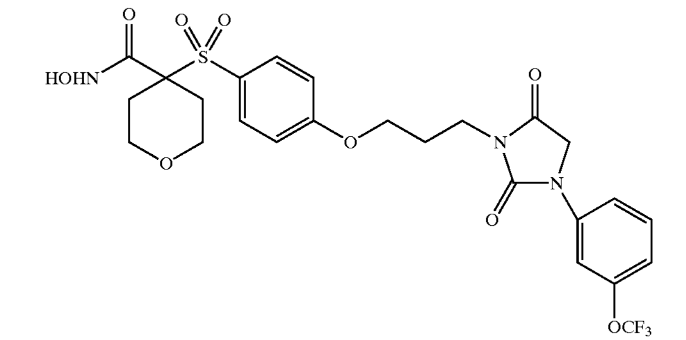 | | | >10000 | 74.2 | 877.7 | 5.6 | >10000 |
| 233 | 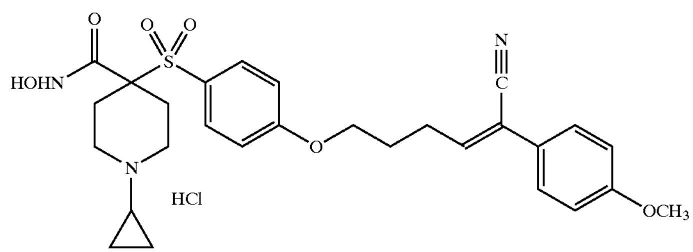 | | | >10000 (>10000) | 25.5 (60.18) | 831.8 (509.42) | 0.1 (0.137) | >10000 (>10000) |
| 234 | 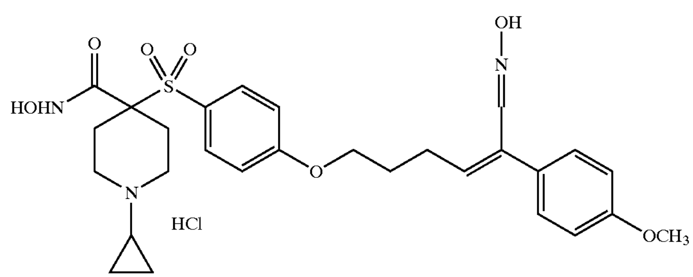 | 596.2430 | 596.2441 | | 213.4 | | 10.3 | |

TABLE 7-continued

| Ex # | Structure | Calc. Mass | Ob- served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 235 | 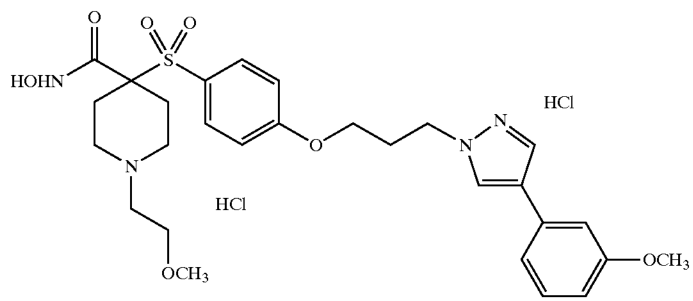 | | | | 421.7 | | 26.0 | |
| 236 | 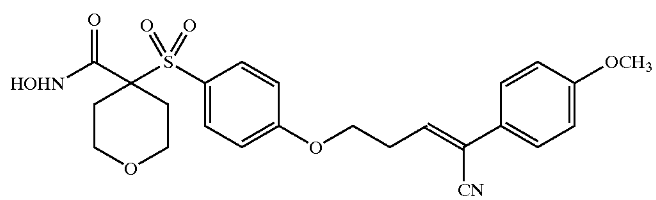 | | | | 7.6 | | 3.4 | |
| 237 | 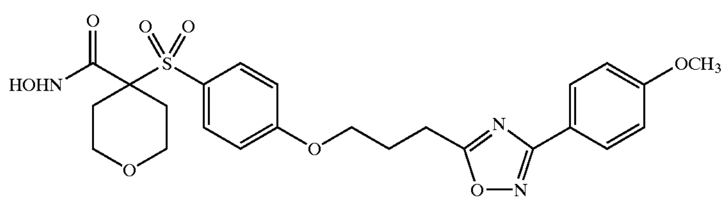 | | | >10000 | 42.5 | 1111 | 0.7 | >10000 |

TABLE 7-continued
| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 238 | 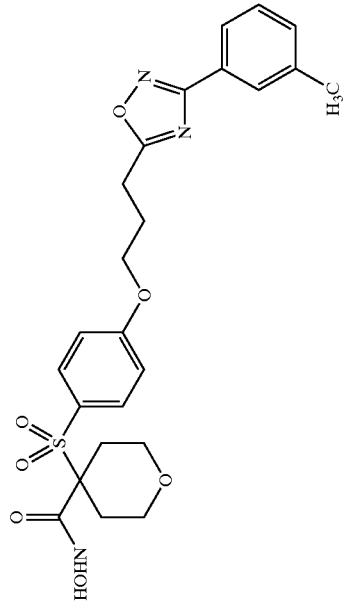 | | | >10000 | 78.7 | 1186.1 | 1.2 | >10000 |
| 239 | 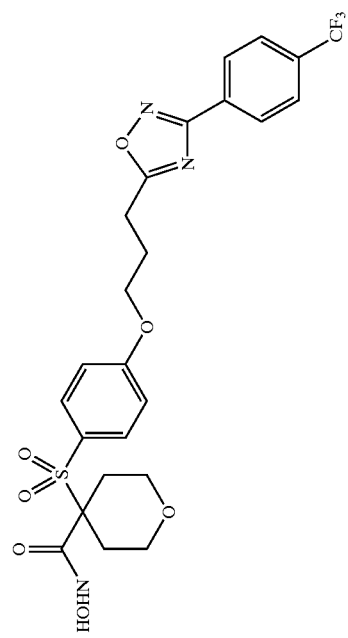 | | | | 236.9 | | 2.5 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 240 | 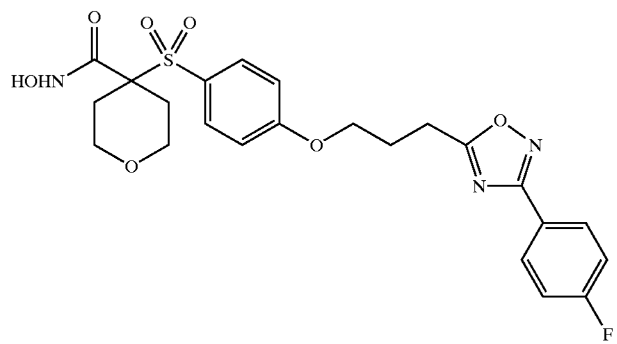 | | | >10000 | 84.0 | 1428.4 | 0.7 | >10000 |
| 241 | 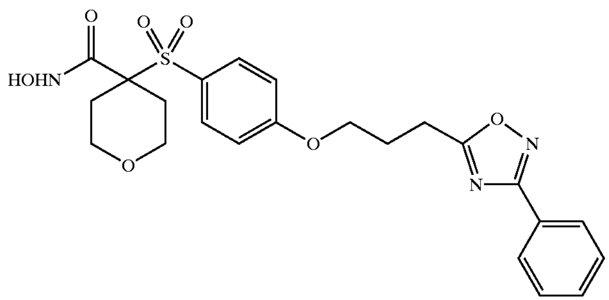 | | | >10000 | 60.2 | 944.2 | 1.3 | >10000 |
| 242 | 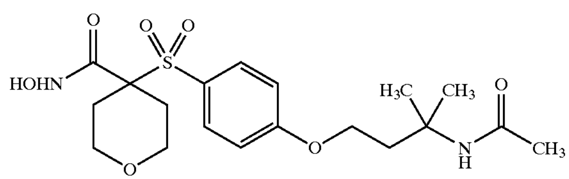 | | | | 2720.2 | | 203.0 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 243 | 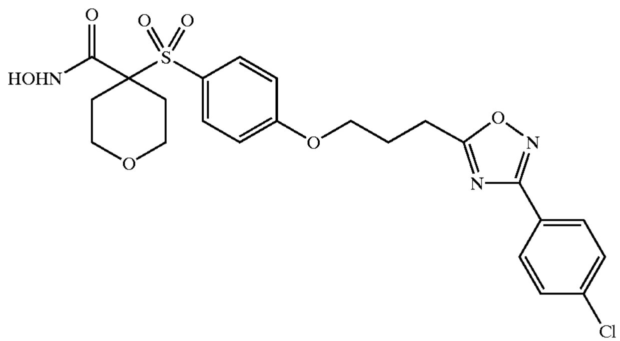 | | | 9313.6 | 49.4 | 2101.9 | 0.5 | >10000 |
| 244 | 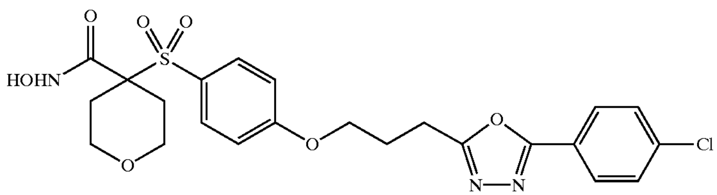 | | | 3250.6 | 18.8 | 108.2 | 0.7 | >10000 |
| 245 | 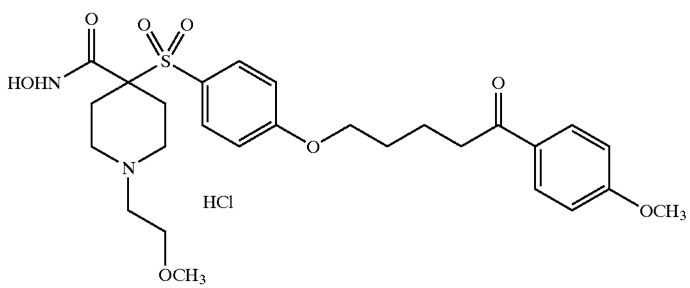 | | | >10000 | 8.6 | 61.1 | 0.2 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 246 | 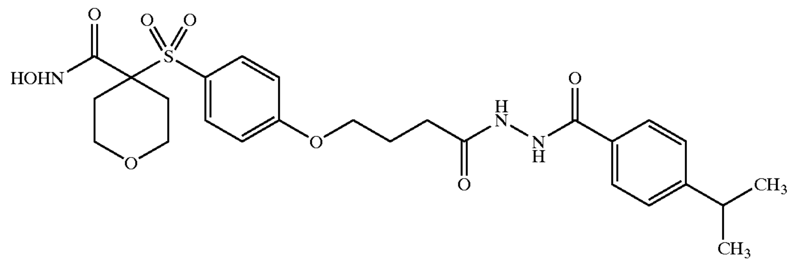 | | | 1166.7 | 7.5 | 104.7 | 3.0 | >10000 |
| 247 | 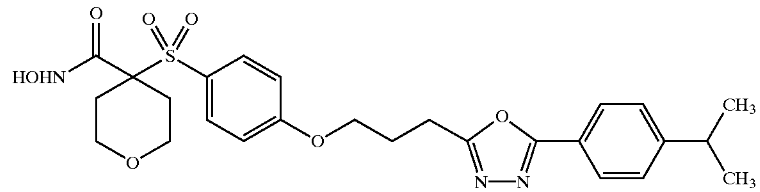 | | | 3610.8 | 445.1 | 341.1 | 1.1 | >10000 |
| 248 | 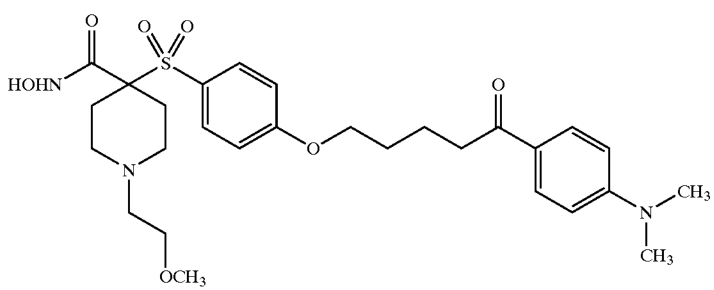 | | | >10000 | 15.7 | 105.6 | 0.2 | 1704.1 |
| 249 | 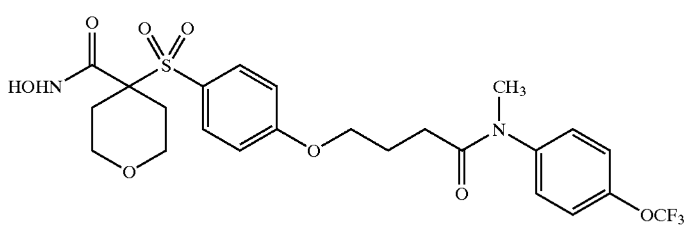 | | | >10000 (>10000) | 226 (333) | 3628.6 (1490) | 5.09 (1.49) | >10000 (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 250 | 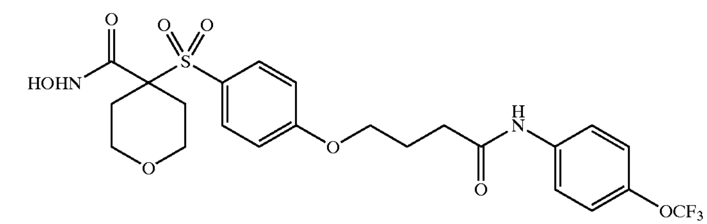 | | | 4406.1 (1440) | 2.5 (3.12) | 22.5 (12.5) | 0.3 (0.127) | 7630.2 (1700) |
| 251 | 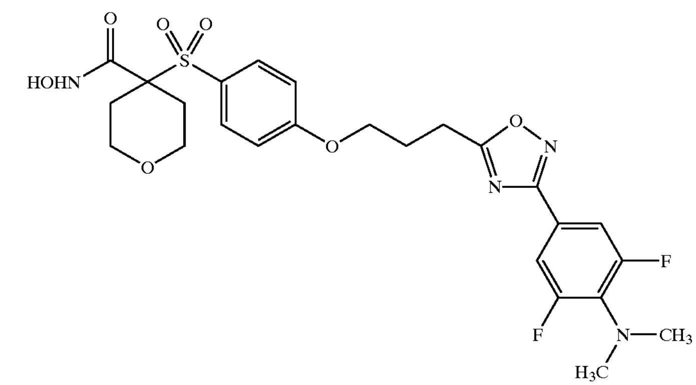 | | | | 182.4 | | 5.4 | |
| 252 | 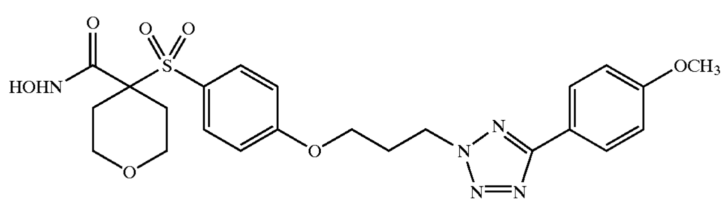 | | | 5602.7 | 47.9 | 1052.4 | 0.2 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 253 | 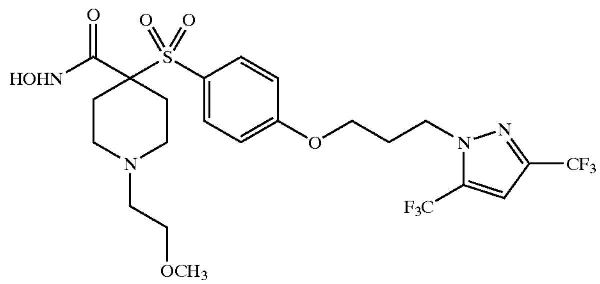 | | | | 1448.2 | | 32.4 | |
| 254 | 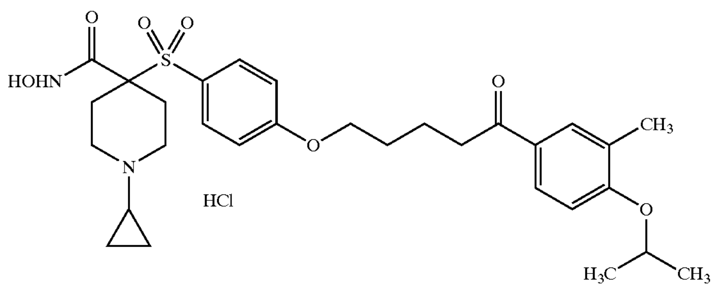 | | | >10000 | 138.3 | 968.2 | 1.7 | >10000 |
| 255 | 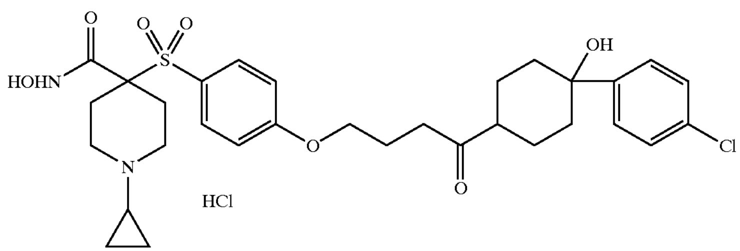 | | | | 51.3 | | 1.9 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 256 | 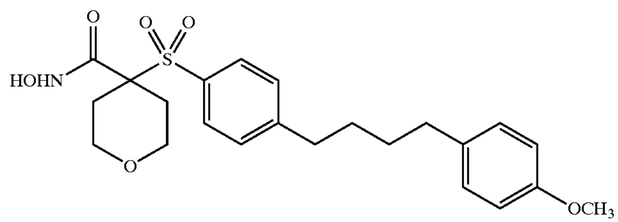 | | | >10000 | 0.1 | 37.9 | <0.1 | >10000 |
| 257 | 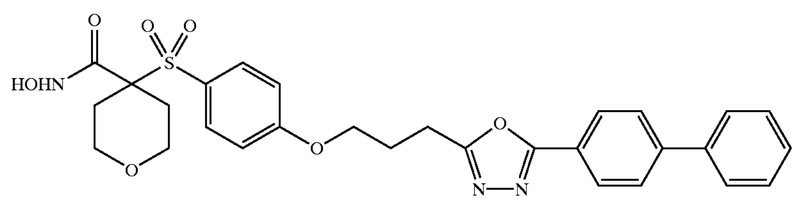 | | | >10000 | 173.8 | 6227 | 0.5 | >10000 |
| 258 | 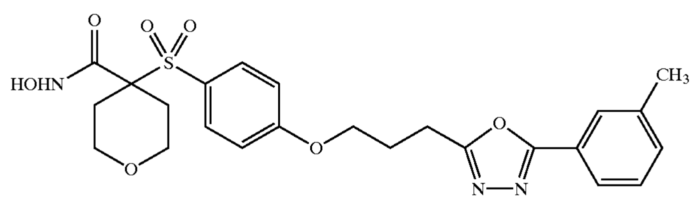 | | | >10000 | 173.5 | 1956 | 1.7 | >10000 |
| 259 | 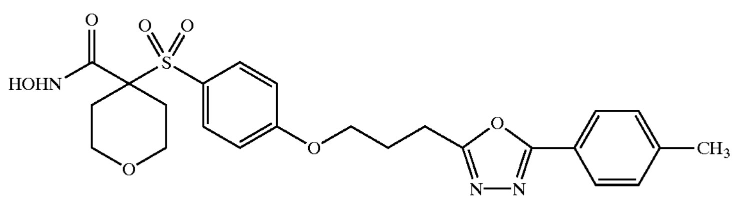 | | | 7256 | 201.1 | 1876 | 0.7 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 260 | 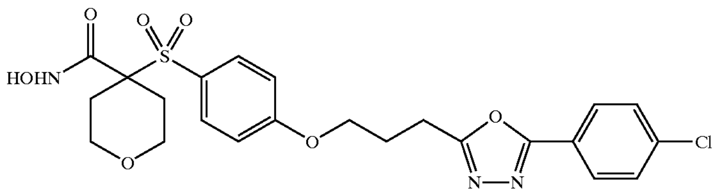 | | | 1159 | 13.2 | 391.0 | 1.8 | >10000 |
| 261 | 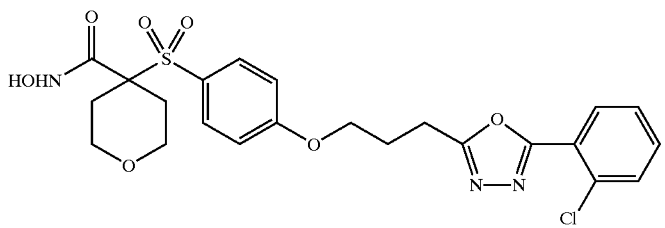 | | | >10000 | 178.3 | 1185.0 | 1.9 | >10000 |
| 262 | 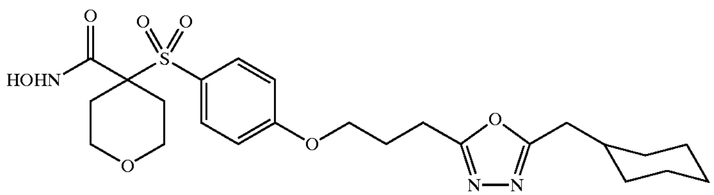 | | | >10000 | 118.3 | 1702.3 | 3.0 | >10000 |
| 263 | 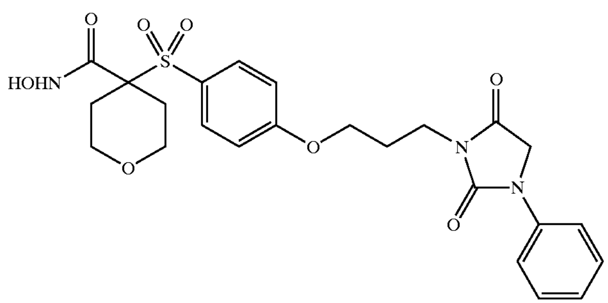 | | | >10000 | 87.7 | 3267.5 | 3.8 | >10000 |

TABLE 7-continued
| Ex # | Structure | Calc. Mass | Observed Mass | MMP-1 IC50 (Ki) | MMP-2 IC50 (Ki) | MMP-9 IC50 (Ki) | MMP-13 IC50 (Ki) | MMP-14 IC50 (Ki) |
|---|---|---|---|---|---|---|---|---|
| 264 | 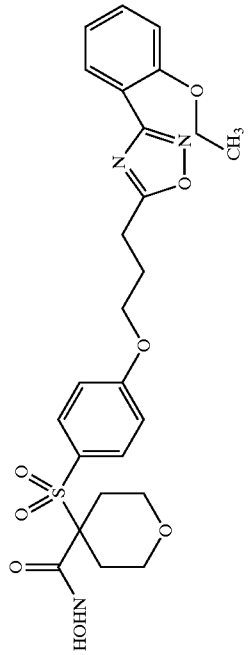 | | | >10000 | 162.8 | 287.1 | 5.3 | >10000 |
| 265 | 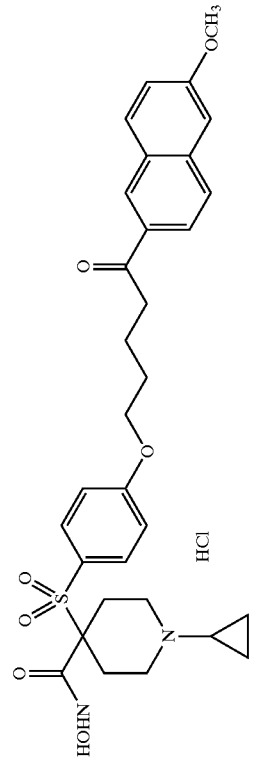 | | | | 40.0 | | 0.2 | |
| 266 | 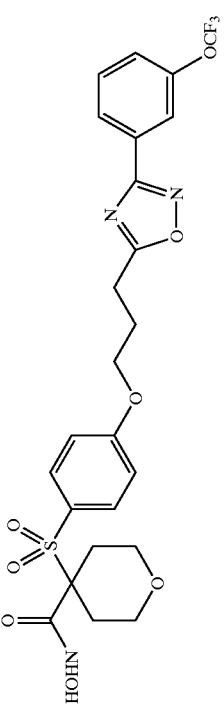 | | | >10000 | 391.2 | 202.6 | 9.1 | >10000 |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 267 | 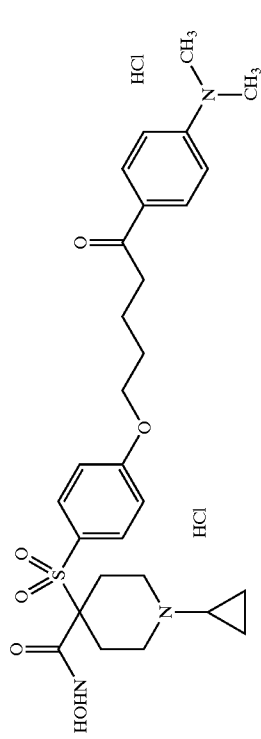 | | | >10000 | 18.5 | 106.7 | | >10000 |
| 268 | 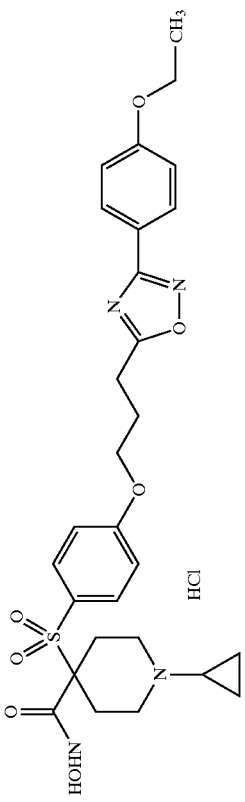 | | | >10000 | 125.9 | 674.0 | 2.5 | >10000 |
| 269 | 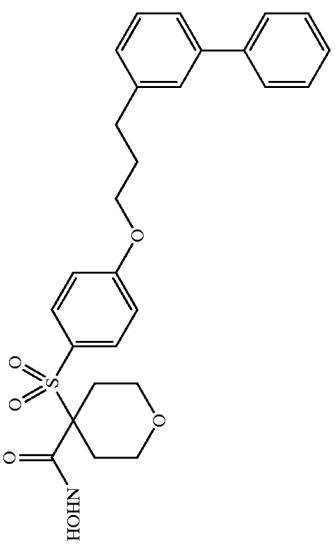 | | | >10000 | 897.9 | 2755 | 1.8 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 270 | 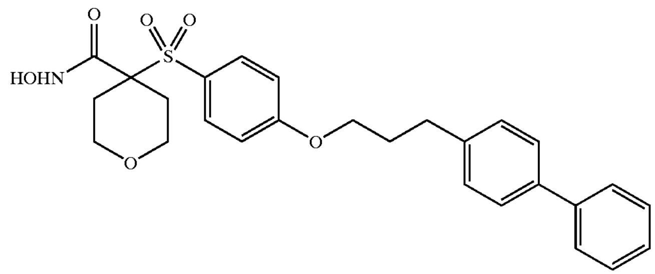 | | | | 521.8 | | 8.1 | |
| 271 | 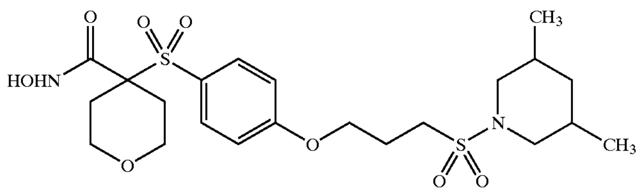 | | | >10000 | 8.7 | 531.8 | 2.9 | >10000 |
| 272 | 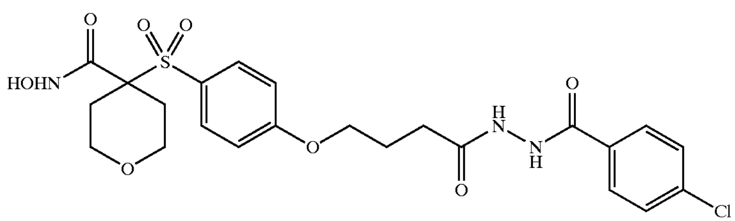 | | | 399 | 4.2 | 152.1 | 2.8 | >10000 |
| 273 | 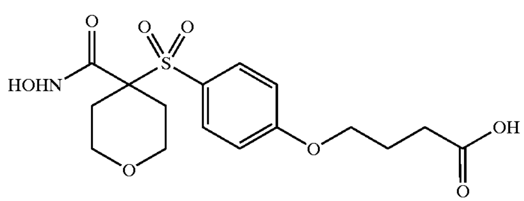 | 405.1332 | 405.1335 | | 1010.7 | | 304.0 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 274 | 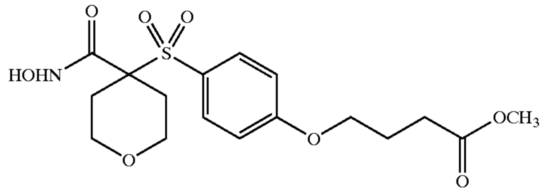 | 402.1223 | 402.1225 | 9864 | 15.4 | 33.6 | 4.1 | >10000 |
| 275 | 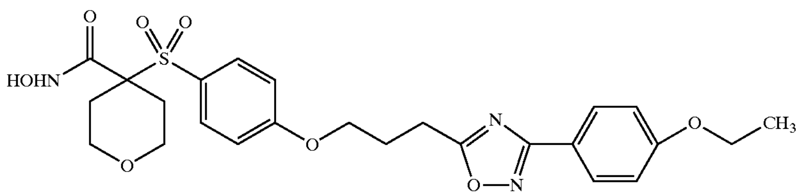 | | | | 115.2 | | 1.7 | |
| 276 | 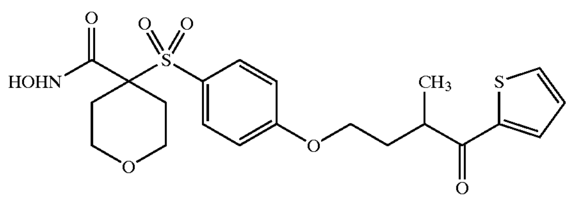 | | | 6670.4 | 17.4 | 196.3 | 2.8 | 7019.9 |
| 277 | 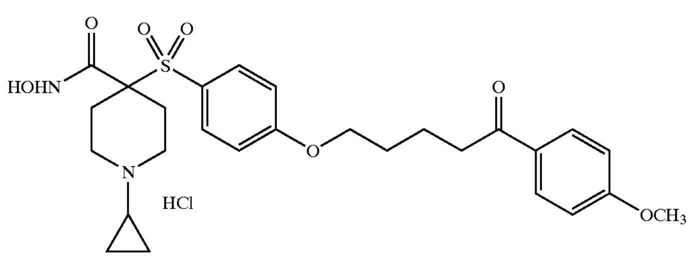 | | | >10000 | 3.5 | 41.5 | 0.2 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 278 | 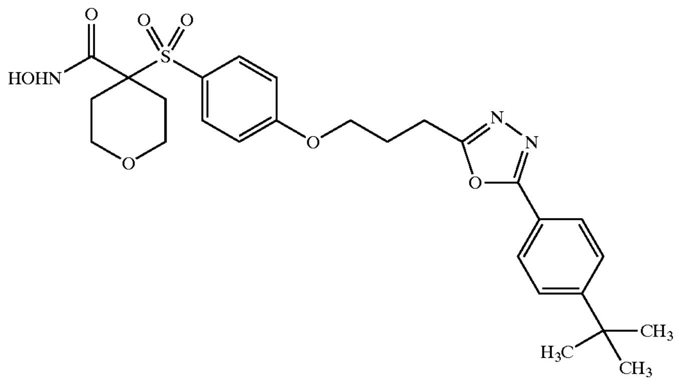 | 544.2117 | 544.2104 | >10000 | 207.9 | 494 | 3.7 | >10000 |
| 279 | 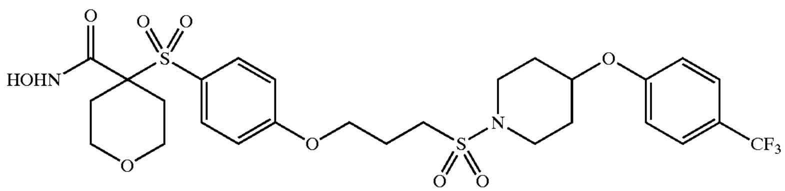 | 518.1597 | 518.1578 | | 15.9 | | 9.4 | |
| 280 | 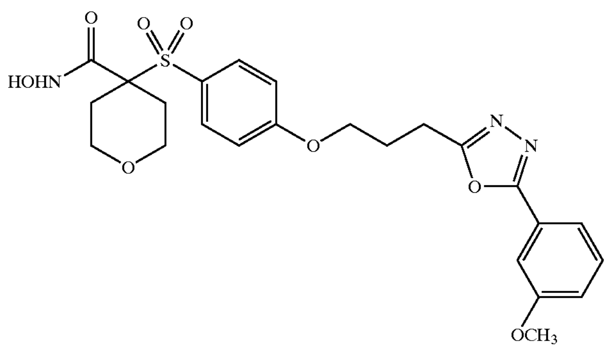 | | | >10000 | 170.1 | 2034 | 1.5 | >10000 |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 281 | 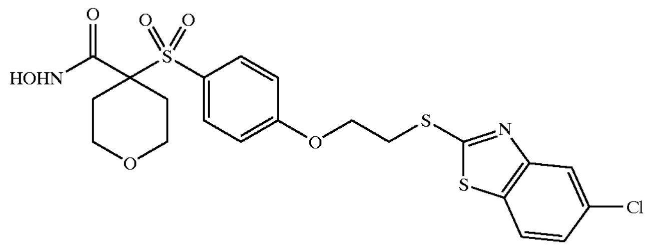 | 529.0329 | 529.0353 | >10000 | 70.4 | 276.1 | 1.3 | >10000 |
| 282 | 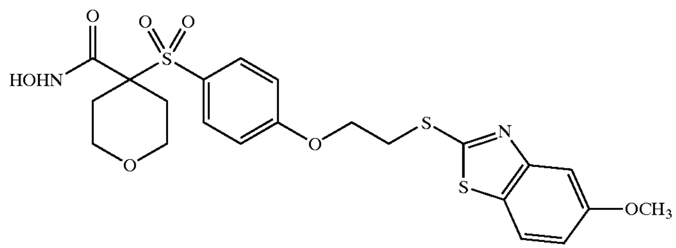 | 525.0824 | 525.0827 | >10000 | 43.3 | 704.3 | 2.6 | >10000 |
| 283 | 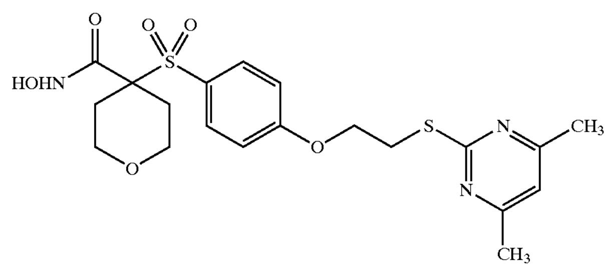 | 468.1263 | 468.1257 | | 186.2 | | 29.3 | |
| 284 | 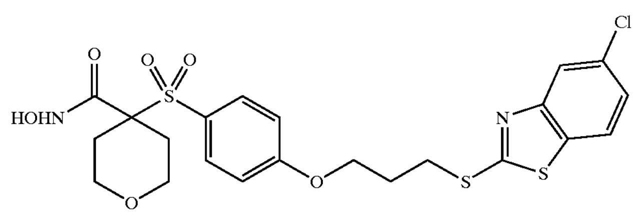 | 543.0485 | 543.0500 | >10000 | 10.1 | 18.5 | 1.1 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 285 | 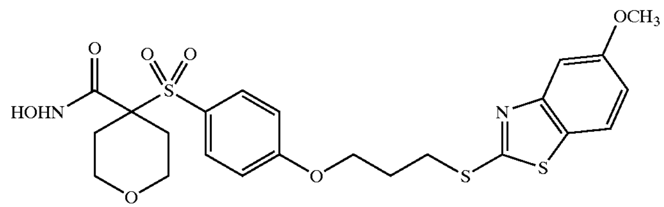 | 539.0980 | 539.0978 | >10000 | 16.7 | 23.6 | 1.8 | >10000 |
| 286 | 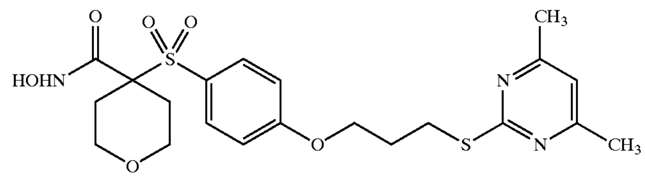 | 482.1420 | 482.1421 | >10000 | 74.9 | 1134.5 | 4.0 | >10000 |
| 287 | 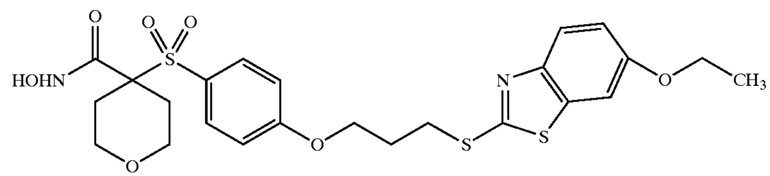 | 553.1137 | 553.1137 | >10000 | 3.6 | 16.4 | 0.8 | >10000 |
| 288 | 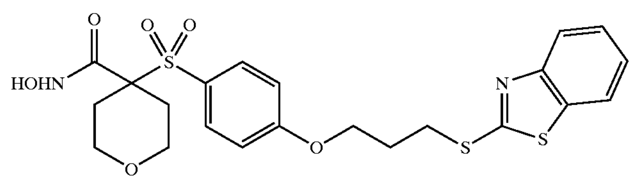 | 509.0875 | 509.0880 | >10000 | 2.3 | 10.6 | 0.8 | >10000 |
| 289 | 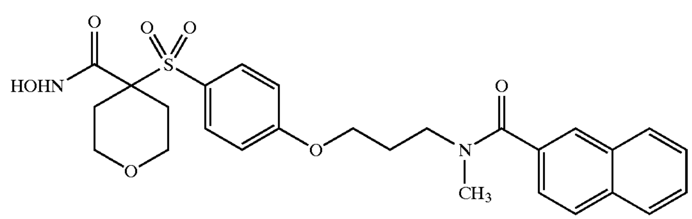 | 527.1852 | 527.1838 | >10000 | 2720.2 | >10000 | 10.1 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 290 | 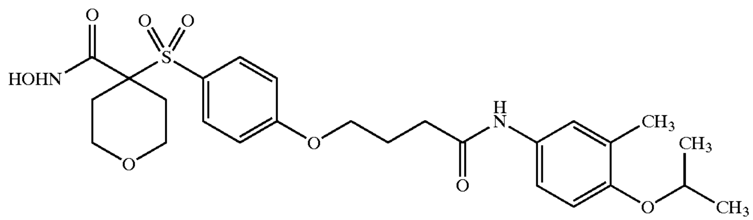 | | | >10000 (>10000) | 590.2 (1009.04) | >10000 (>10000)3 | 1.1 (0.547) | >10000 (>10000) |
| 291 | 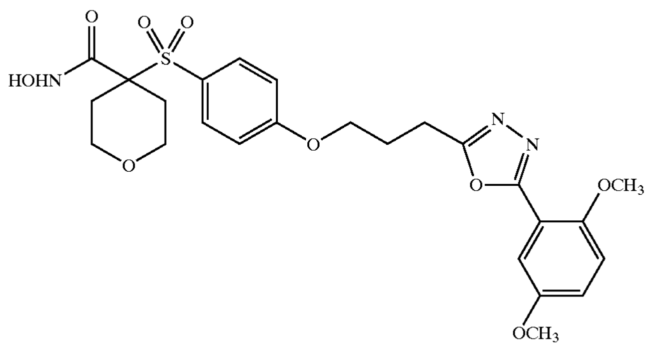 | | | | 100 | | 8.0 | |
| 292 | 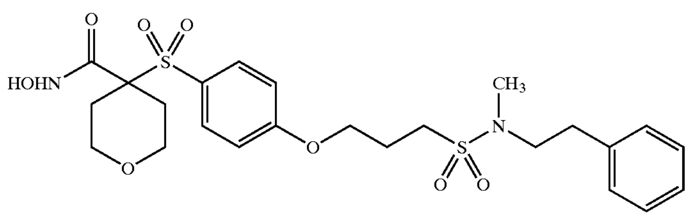 | | | 970 | 14.4 | 163.5 | 2.4 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 293 | 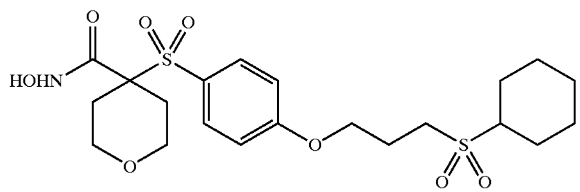 | | | 6147 | 2.3 | 447.9 | 2.6 | >10000 |
| 294 | 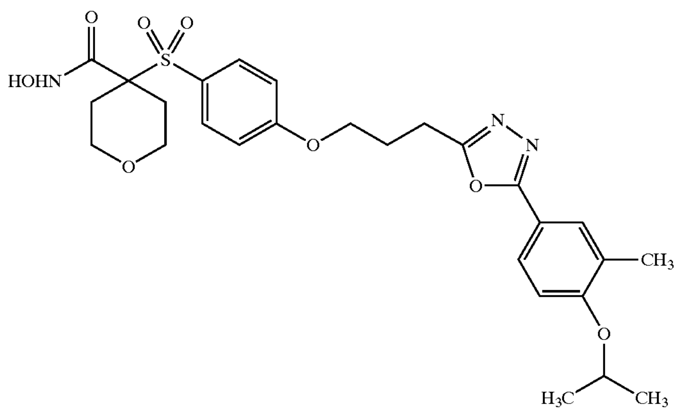 | | | 4623 | 100.0 | 447.9 | 4.3 | >10000 |
| 295 | 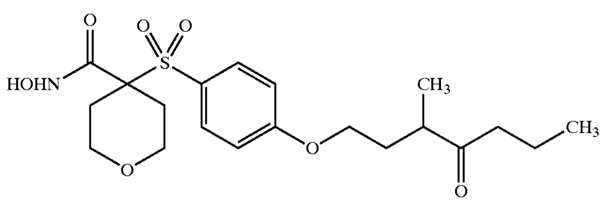 | | | >10000 | 15.6 | 172.1 | 2.6 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 296 | 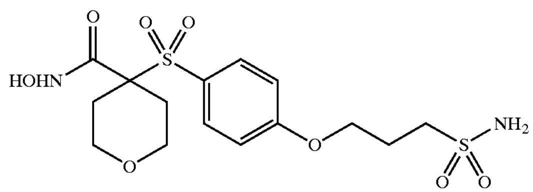 | | | | 1335.9 | | 564.8 | |
| 297 | 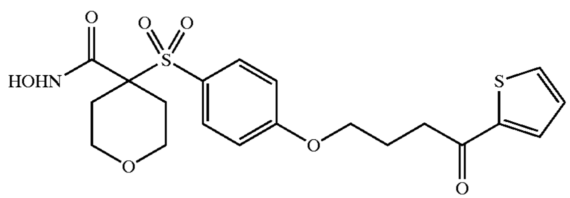 | 454.0944 | 454.0986 | 6812 | 8.1 | 64.6 | 0.5 | 6562 |
| 298 | 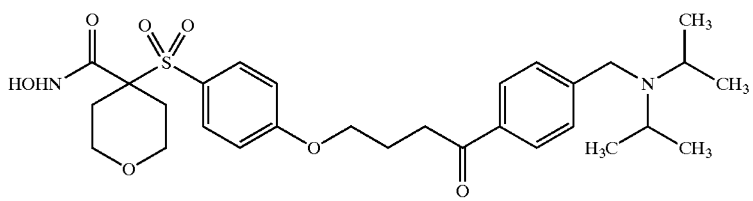 | 561.2634 | 561.2641 | | 11.9 | | 18.1 | |
| 299 | 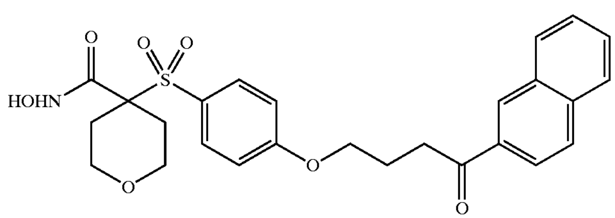 | 498.1586 | 498.1588 | | 3.2 | | 0.1 | |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 300 | 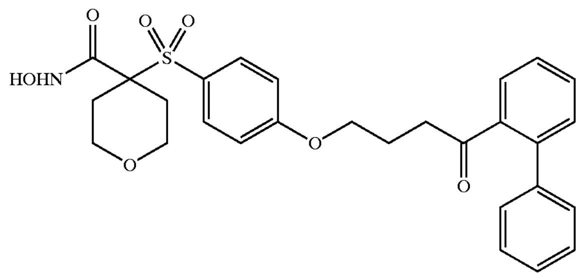 | 524.1743 | 524.1729 | | 12.5 | | 6.7 | |
| 301 | 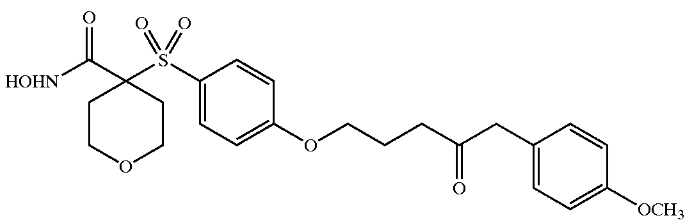 | 492.1692 | 492.1687 | 3655.3 | 0.2 | 9.1 | <0.1 | 319.9 |
| 302 | 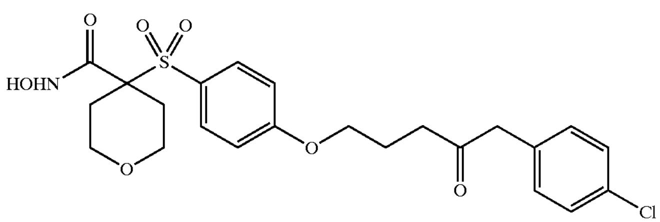 | 496.1197 | 496.1192 | 2728.9 | 0.2 | 2.9 | 0.1 | 94.9 |

TABLE 7-continued

| Ex # | Structure | Calc. Mass | Observed Mass | MMP-1 IC₅₀ (Ki) | MMP-2 IC₅₀ (Ki) | MMP-9 IC₅₀ (Ki) | MMP-13 IC₅₀ (Ki) | MMP-14 IC₅₀ (Ki) |
|---|---|---|---|---|---|---|---|---|
| 303 | 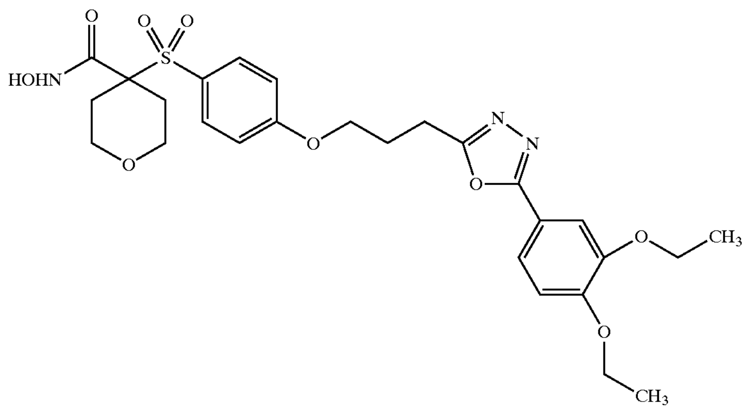 | 576.2016 | 576.2198 | | 50.0 | | 9.9 | |
| 304 | 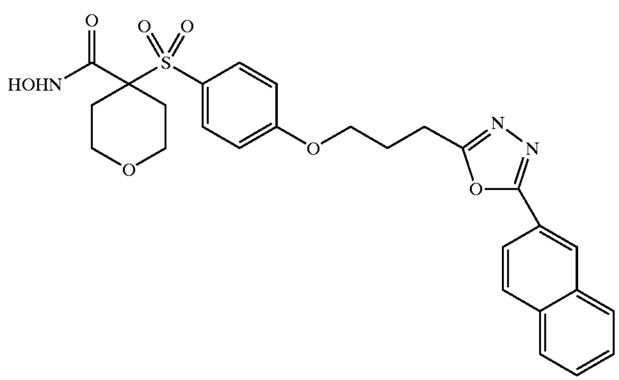 | 538.1648 | 538.1629 | | 138.6 | | 0.2 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 305 | 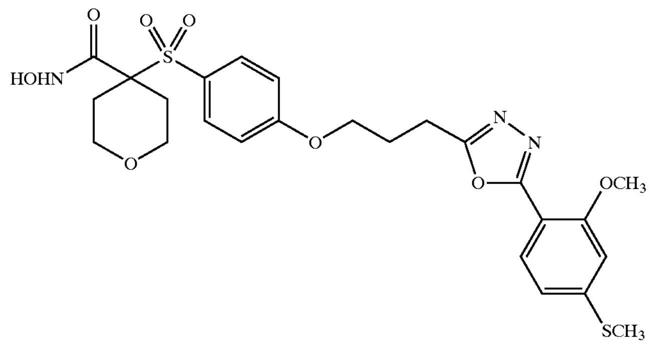 | 569.1474 | 569.1444 | | 175.9 | | 3.9 | |
| 306 | 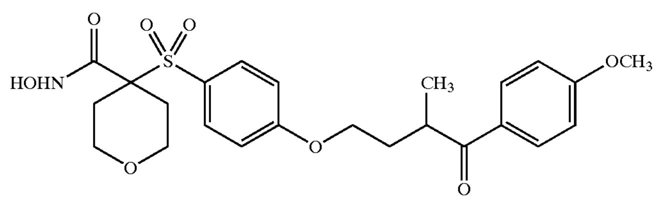 | | | >10000 | 92.9 | 185.2 | 1.7 | >10000 |
| 307 | 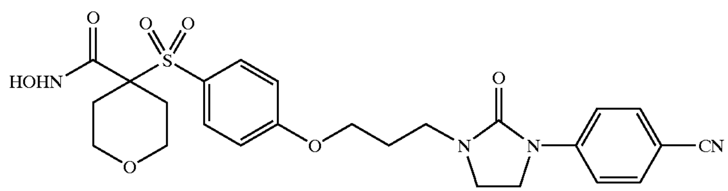 | | | 8135 | 135 | 139.5 | 4.5 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 308 | 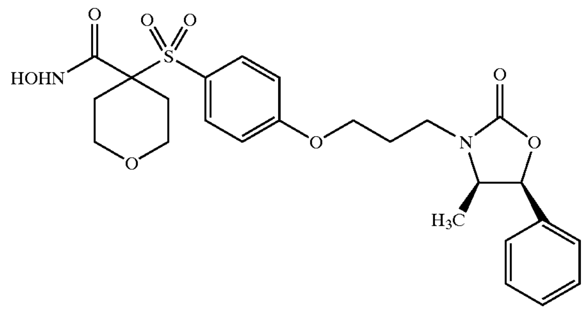 | 519.1801 | 519.1780 | >10000 | 175.8 | 1601.1 | 3.7 | >10000 |
| 309 | 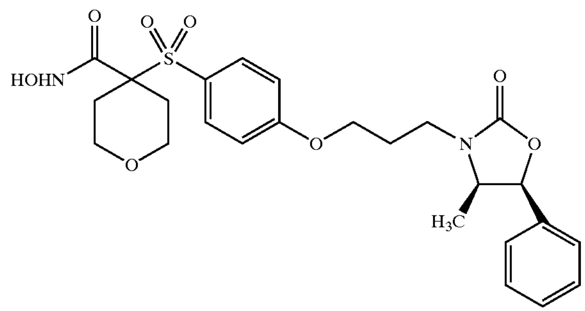 | 519.1801 | 519.1772 | >10000 | 135.3 | 1557.8 | 1.8 | >10000 |
| 310 | 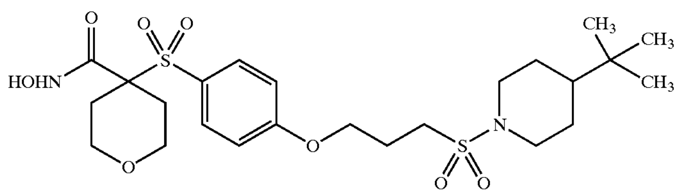 | | | >10000 | 32.0 | 1980.5 | 3.0 | >10000 |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 311 | 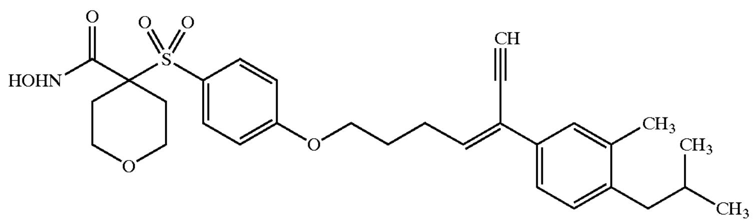 | 543.2165 | 543.2165 | | 25.6 | | 2.6 | |
| 312 | 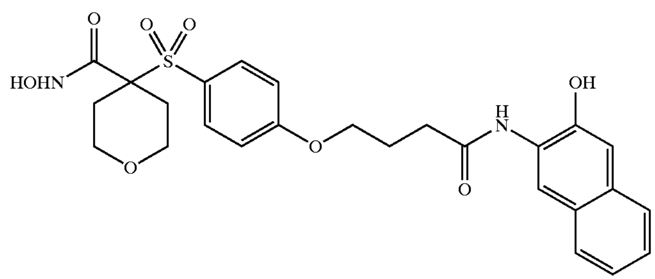 | 529.1645 | 529.1635 | | 9.1 | | 0.2 | |
| 313 | 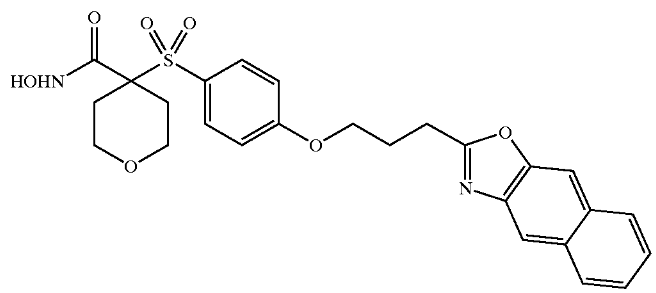 | 511.1539 | 511.1535 | | 18.1 | | <0.1 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 314 | 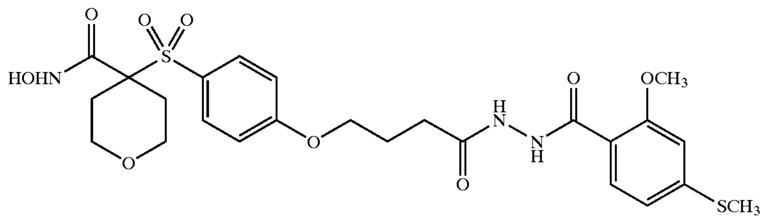 | | | | 7.8 | | 2.5 | |
| 315 | 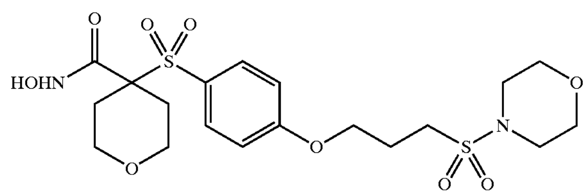 | | | | 12.8 | | 12.7 | |
| 316 | 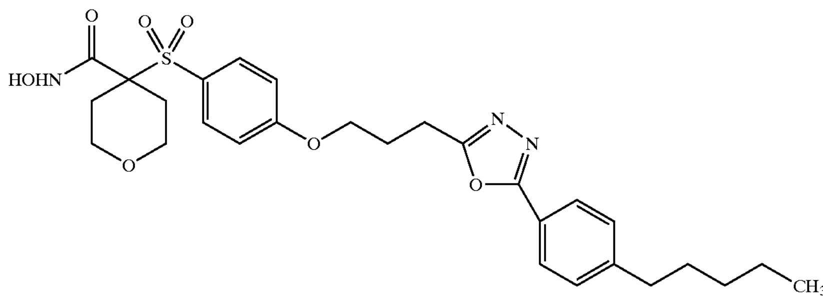 | 558.2274 | 558.2274 | 2678 | 2842 | 692.0 | 13.6 | >10000 |
| 317 | 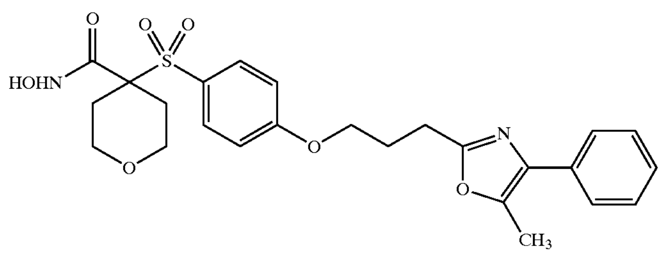 | 501.1695 | 501.1693 | >10000 | 120.4 | 244.3 | 3.1 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 318 | 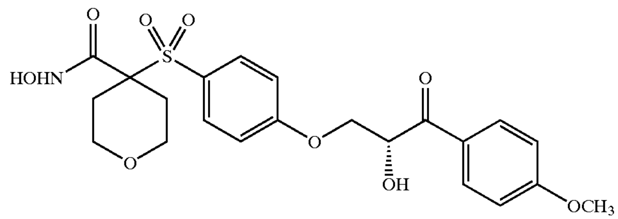 | | | | 615 | | 97.3 | |
| 319 | 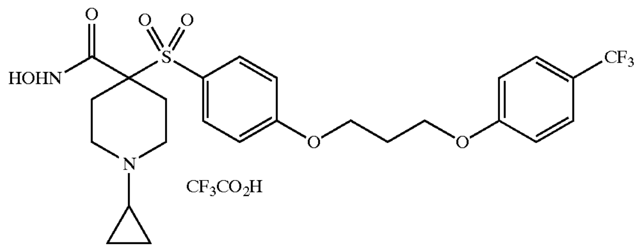 | | | >10000 | 5.8 | 258 | 1.0 | 4225 |
| 320 | 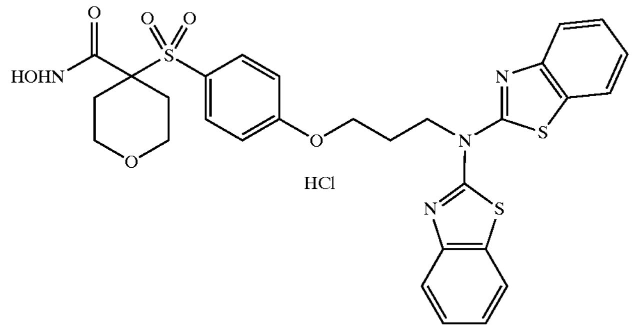 | | | | 5864 | | 6110 | |
| 321 | 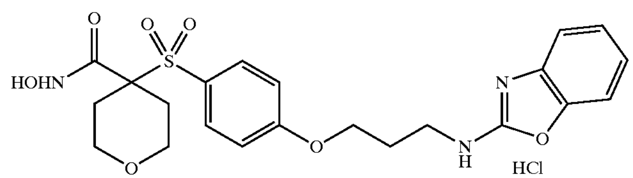 | | | >10000 | 1701 | 625.6 | 3.7 | >10000 |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 322 | 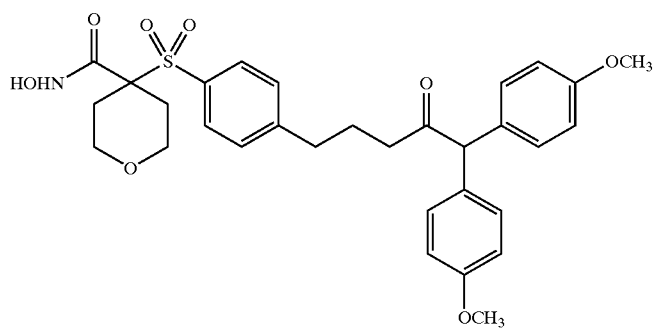 | 601.2220 | 601.2226 | | 354 | | 233 | |
| 323 | 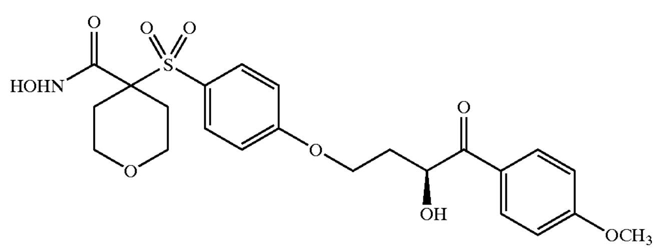 | 468.1151 | 468.1148 | | 358.8 | | 108 | |
| 324 | 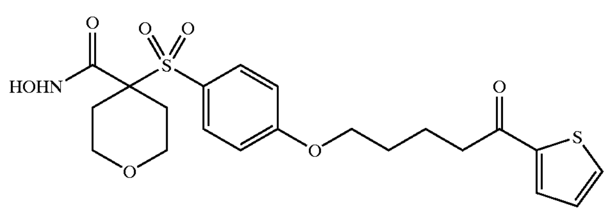 | | | 2990 | 4.2 | 500 | 0.5 | 8002 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 325 | 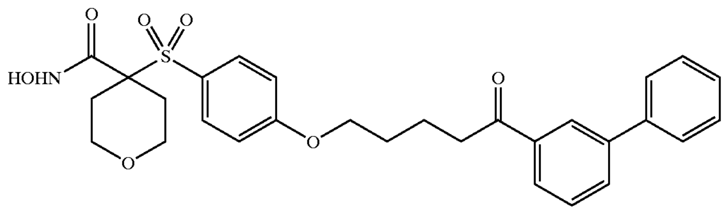 | 538.1899 | 538.1918 | >10000 | 11.0 | 4042 | 0.5 | >10000 |
| 326 | 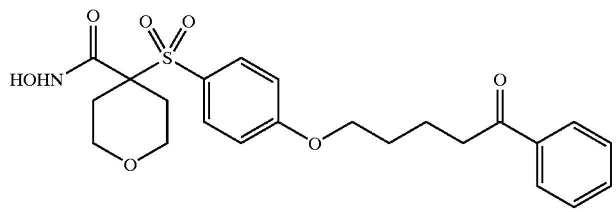 | 462.1586 | 462.1582 | >10000 | 7.4 | 263 | 0.3 | 8316 |
| 327 | 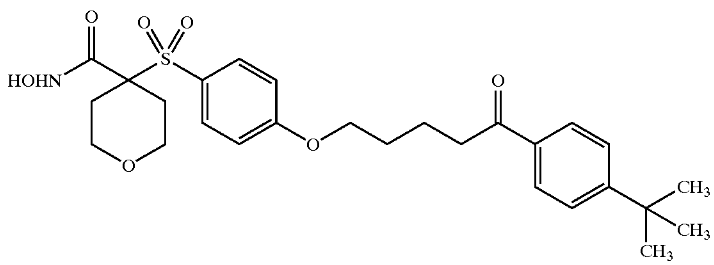 | 518.2212 | 518.2203 | >10000 | 50.7 | 5284 | 0.9 | >10000 |
| 328 | 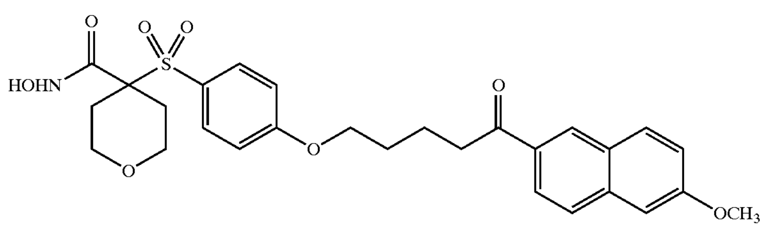 | 542.1849 | 542.1866 | | 61.3 | | <0.1 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 329 | 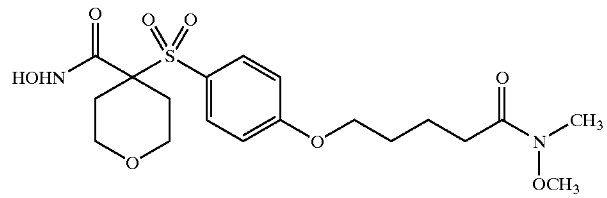 | | | | 103.1 | | 8.6 | |
| 330 | 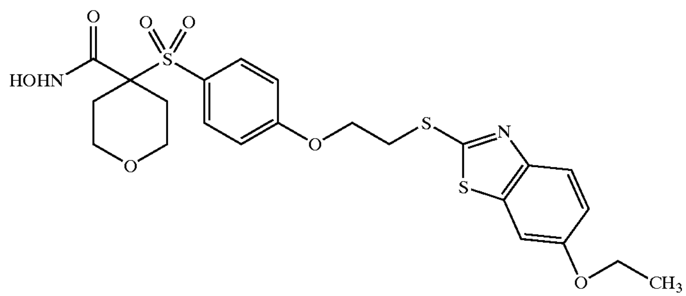 | 539.0980 | 539.0985 | >10000 | 261.7 | 216 | 16.0 | 592 |
| 331 | 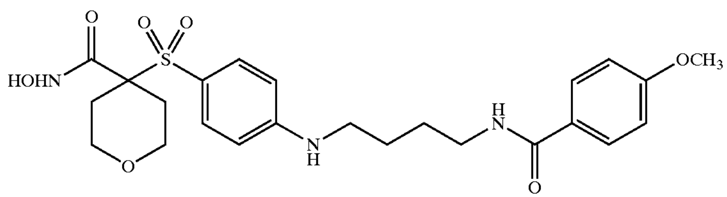 | 506.1961 | 506.1954 | | 386 | | 261.4 | |
| 332 | 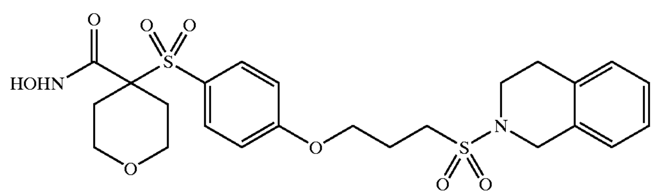 | | | 2459 | 3.6 | 132.4 | 2.6 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 333 | 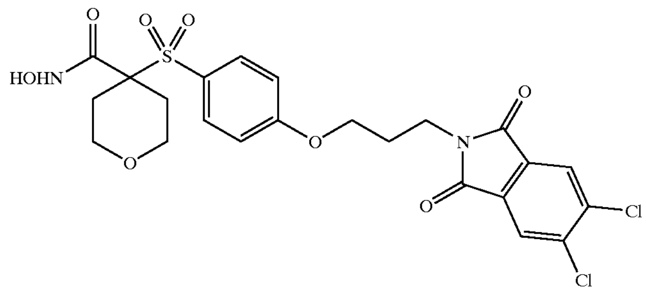 | 557.0552 | 557.0562 | >10000 | 656.3 | 3240 | 1.8 | >10000 |
| 334 | 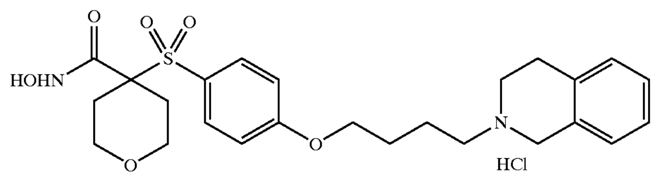 | 489.2059 | 489.2073 | >10000 | 16.4 | 866 | 5.1 | 2876 |
| 335 | 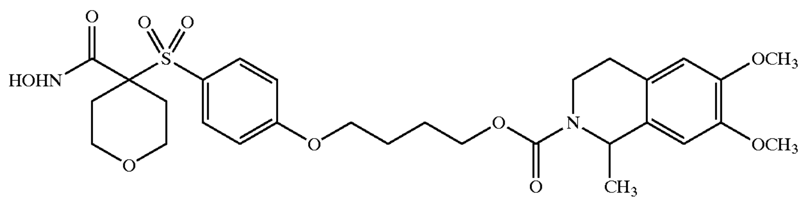 | 607.2325 | 607.233 | >10000 | 2.3 | 172.3 | 6.5 | >10000 |
| 336 | 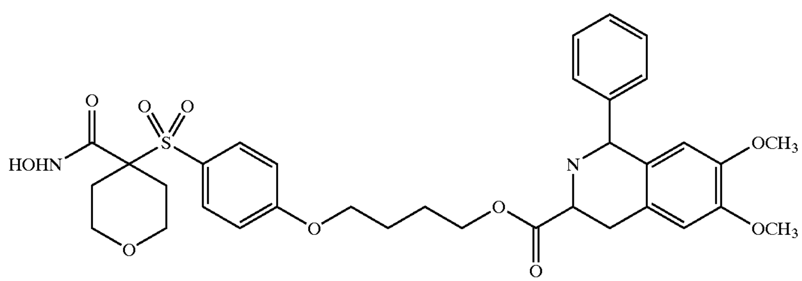 | 669.2482 | 669.2463 | | 300.6 | | 19.8 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 337 | 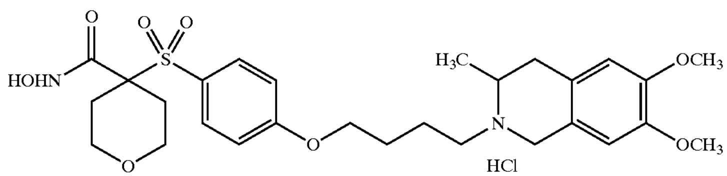 | 563.2427 | 563.2414 | | 41.9 | | 12.2 | |
| 338 | 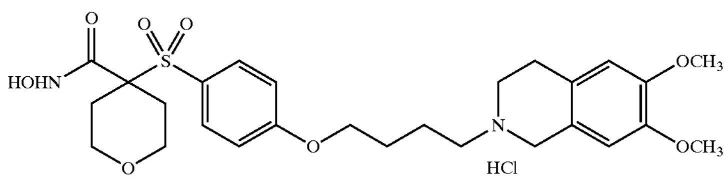 | 549.2271 | 549.2242 | | 20.6 | | 137.7 | |
| 339 | 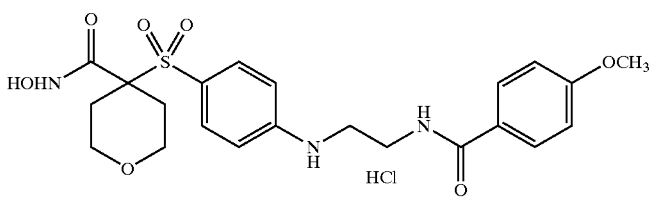 | 478.1648 | 478.1631 | | 1205.8 | | 932.9 | |
| 340 | 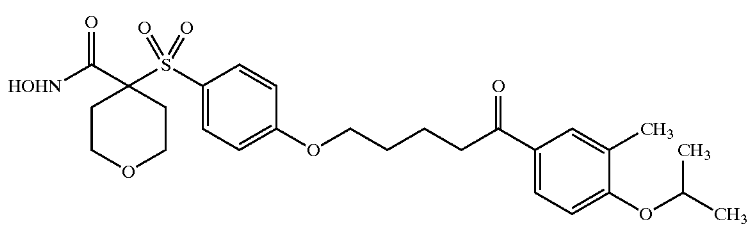 | 534.2162 | 534.2161 | >10000 | 253.0 | 5590 | 1.9 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 341 | 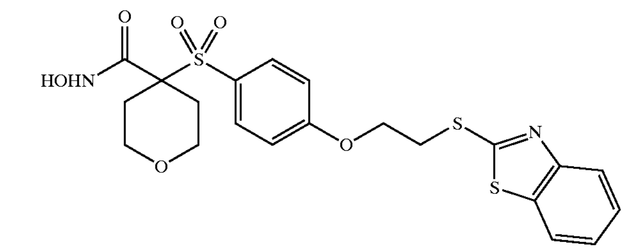 | 495.0718 | 495.0689 | >10000 | 16.8 | 1122 | 0.5 | 6400 |
| 342 | 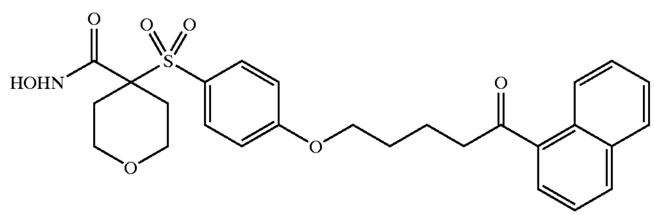 | 512.1743 | 512.1769 | >10000 | 41.2 | 2165 | 2.0 | >10000 |
| 343 | 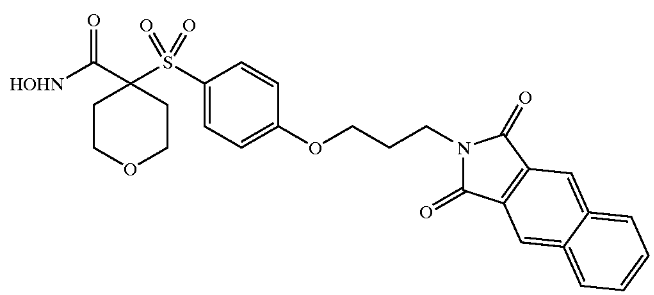 | | | | 7702.4 | | 2.4 | |

TABLE 7-continued

| Ex # | Structure | Calc. Mass | Ob- served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 344 | 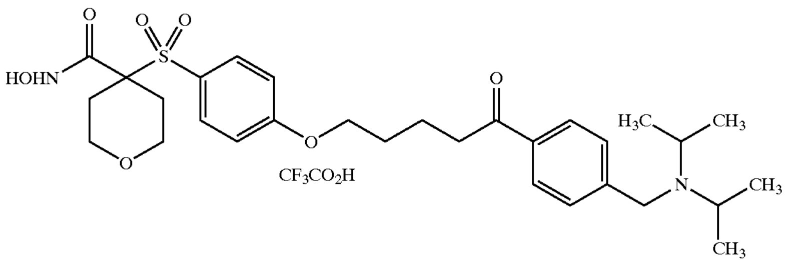 | 575.2791 | 575.2819 | | 12.7 | | 4.6 | |
| 345 | 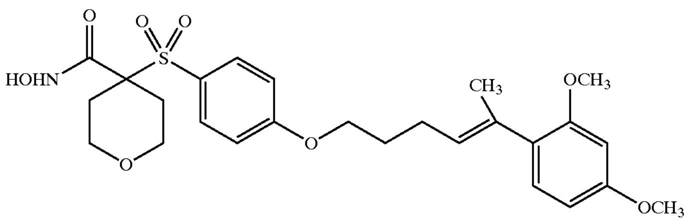 | 520.2005 | 520.1988 | | 271.1 | | 14.3 | |
| 346 | 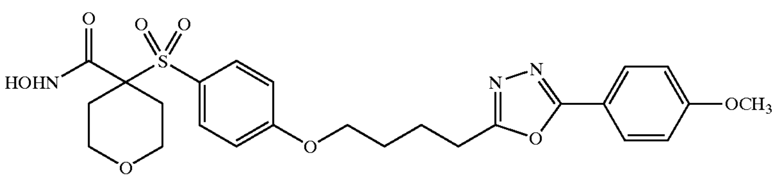 | 532.1754 | 532.171 | >10000 | 2.6 | 2010 | 0.9 | >10000 |
| 347 | 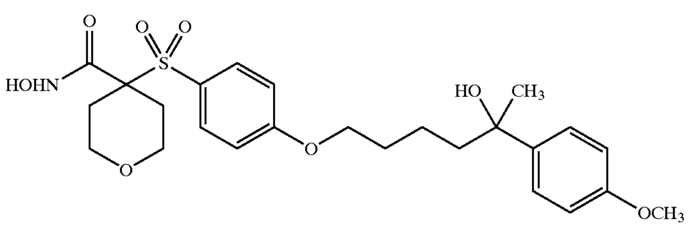 | | | | 10.3 | | 1.8 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 348 | 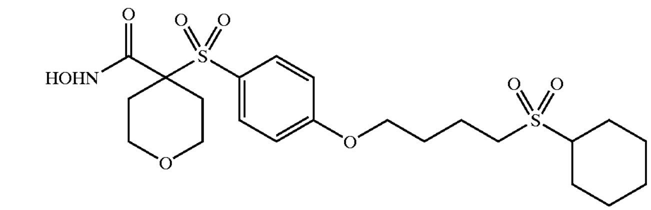 | | | >10000 | 61.8 | >10000 | 4.4 | >10000 |
| 349 | 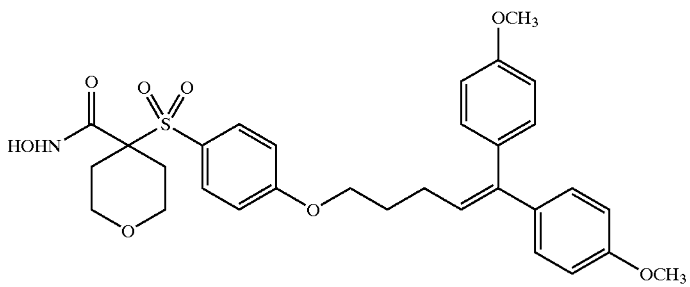 | | | | 505.3 | | 39.0 | |
| 350 | 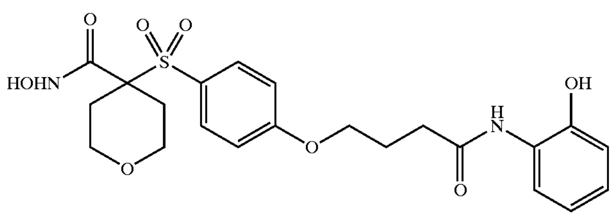 | 479.1488 | 479.1484 | 3283 | 2.6 | 271 | 0.5 | 2670 |
| 351 | 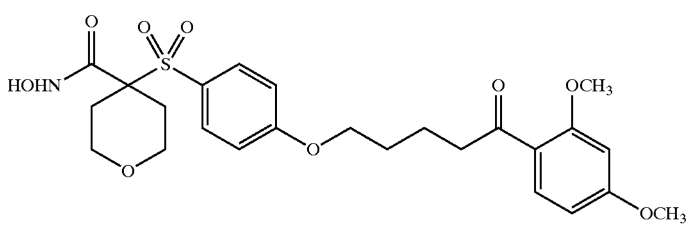 | 522.1798 | 522.1791 | >10000 | 34.1 | 2225 | 1.0 | >10000 |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 352 | 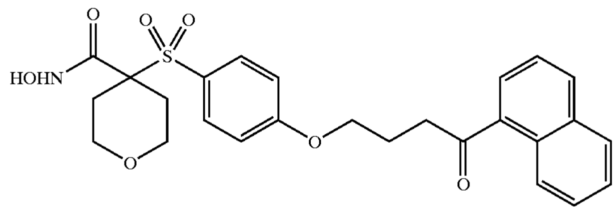 | 498.1586 | 498.1576 | >10000 | 33.6 | 3601 | 2.0 | 6238 |
| 353 | 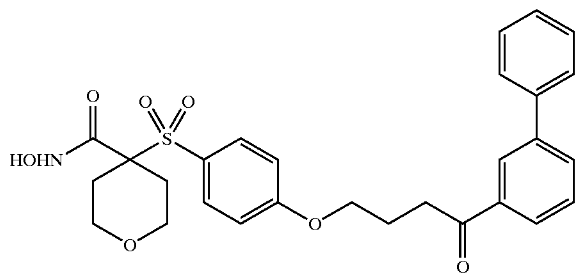 | 524.1743 | 524.1703 | >10000 | 25.1 | 1152 | 1.8 | >10000 |
| 354 | 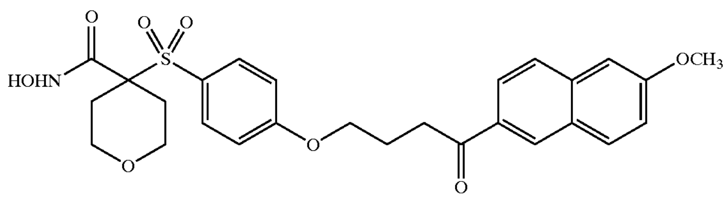 | 528.1692 | 528.1658 | | | | | |
| 355 | 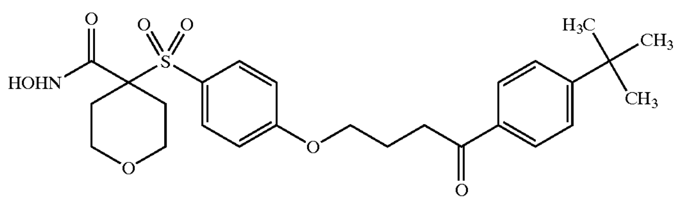 | 504.2056 | 504.2017 | >10000 | 17.4 | 1072 | 1.1 | 36.22 |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 356 | 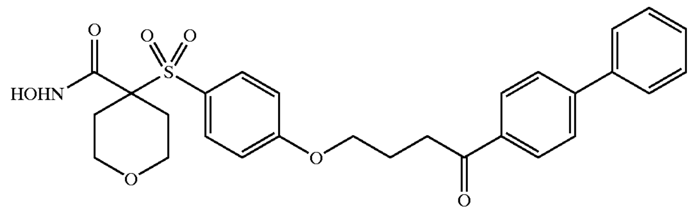 | 524.1743 | 524.1731 | >10000 | 33.1 | 1650 | 0.8 | >10000 |
| 357 | 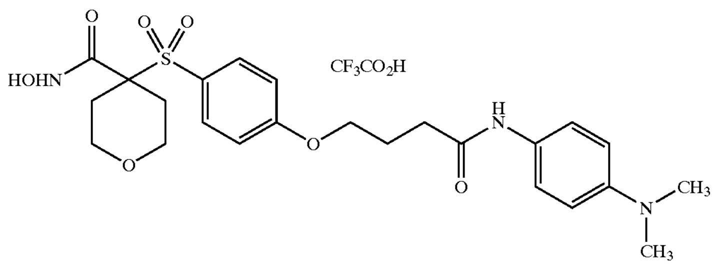 | 506.1961 | 506.1964 | >10000 | 10.2 | 952 | 1.7 | >10000 |
| 358 | 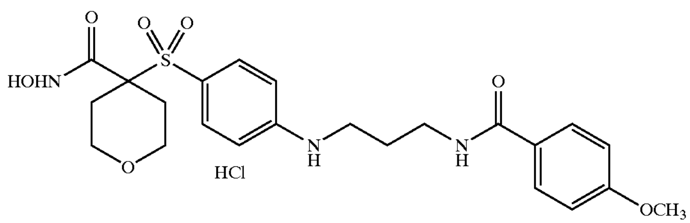 | 492.1804 | 492.1813 | | 768.4 | | 14.6 | |
| 359 | 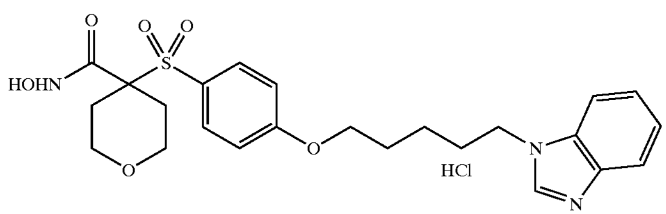 | 488.1855 | 488.1862 | >10000 | 2.3 | 1183 | 1.0 | 7956 |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 360 | 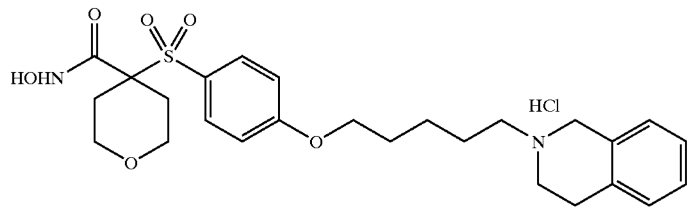 | 503.2216 | 503.2226 | >10000 | 9.7 | 547 | 6.4 | 962 |
| 361 | 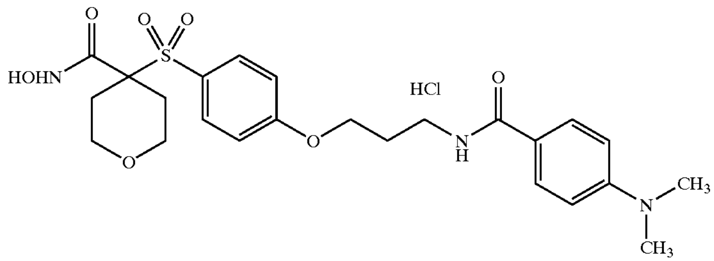 | 506.1961 | 516.1965 | 6000 | 5000 | >10000 | 0.5 | >10000 |
| 362 | 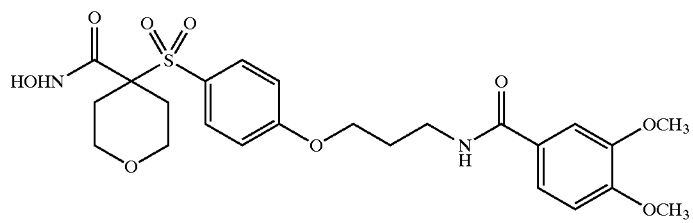 | 523.1750 | 523.1763 | | 347 | | 3.7 | |
| 363 | 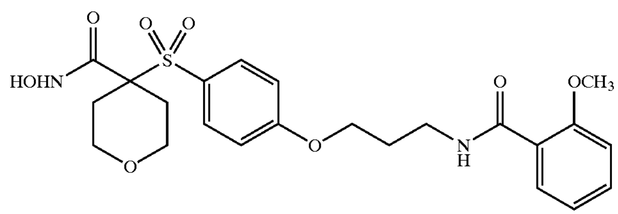 | 493.1645 | 493.1660 | | 430 | | 7 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 364 | 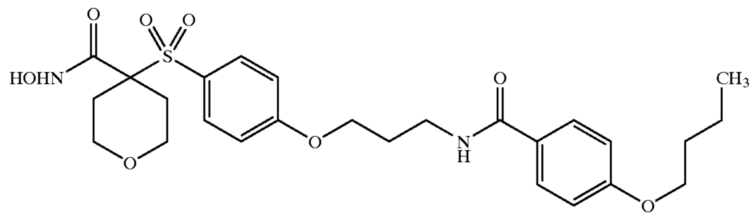 | 535.2114 | 535.2105 | >10000 | 250 | >10000 | 1.8 | >10000 |
| 365 | 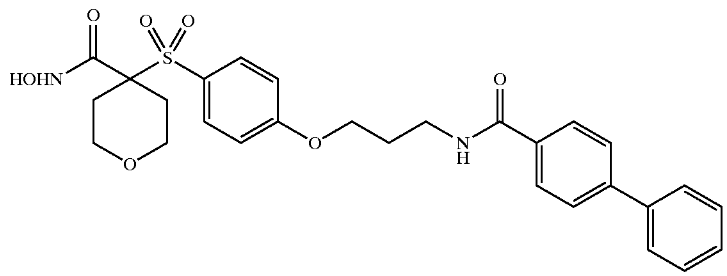 | 539.1852 | 539.1846 | | 21 | | 0.6 | |
| 366 | 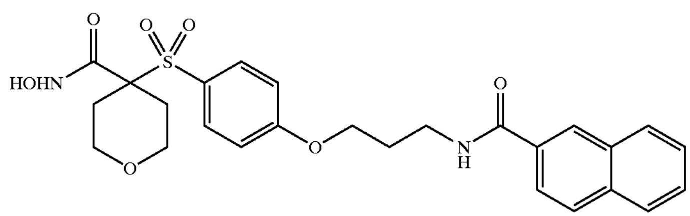 | 513.1695 | 513.1699 | | 347 | | 0.3 | |
| 367 | 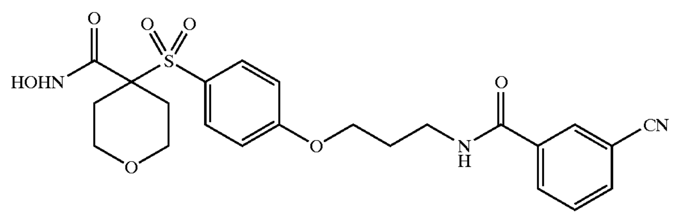 | 488.1491 | 488.1496 | | 235 | | 4.5 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 368 | 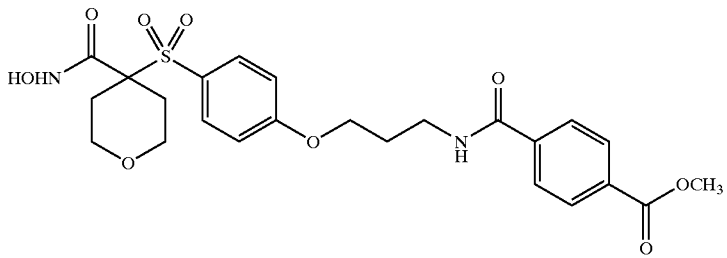 | 521.1594 | 521.1594 | >10000 | 150 | 9000 | 0.8 | >10000 |
| 369 | 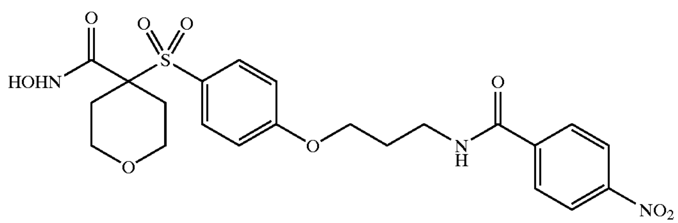 | 508.1390 | 508.1390 | | 155 | | 1.5 | |
| 370 | 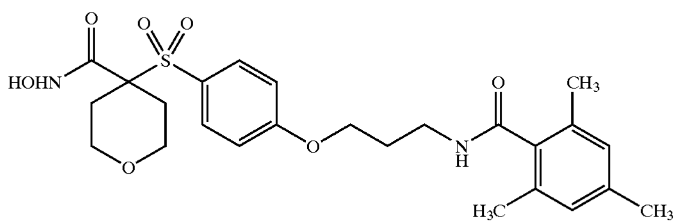 | 505.2008 | 505.1990 | | 900 | | 37 | |
| 371 | 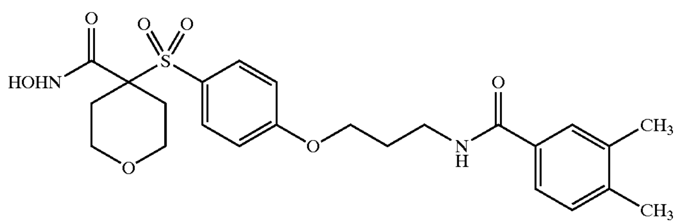 | 491.1852 | 491.1894 | >10000 | 1100 | 9600 | 2.4 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 372 | 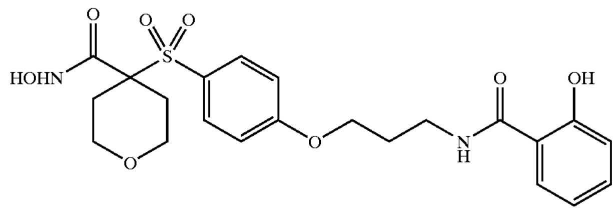 | 479.1488 | 479.1491 | | 210 | | 6 | |
| 373 | 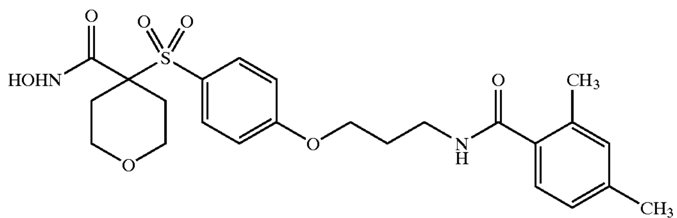 | 491.1852 | 491.1843 | >10000 | 940 | 3945 | 7 | >10000 |
| 374 | 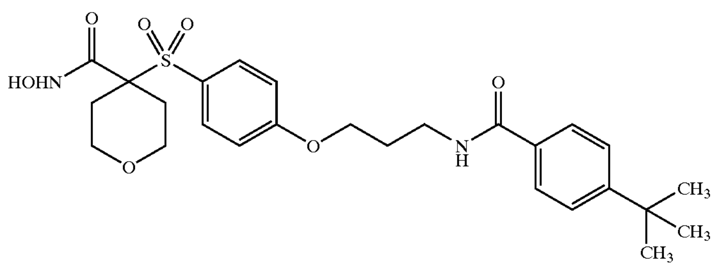 | 519.2165 | 519.2148 | | 800 | | 8 | |
| 375 | 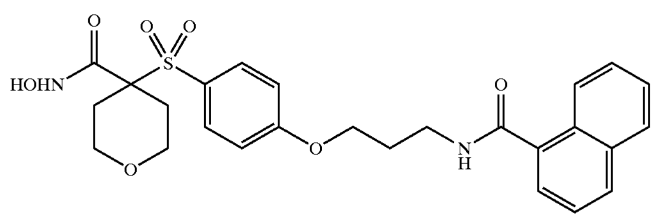 | 513.1695 | 513.1695 | | 425 | | 17 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 376 | 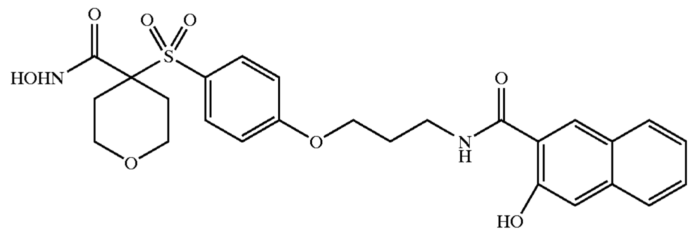 | 529.1645 | 529.1625 | >10000 | 360 | >10000 | 0.8 | >10000 |
| 377 | 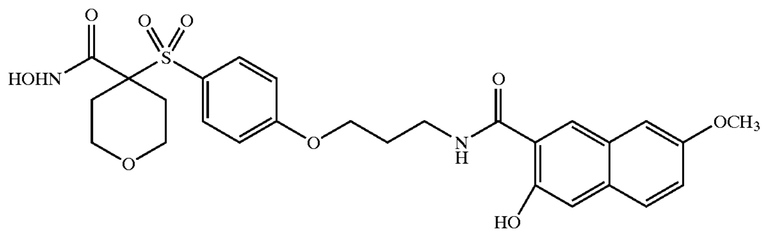 | 559.1750 | 559.1761 | | 1271 | | 5.9 | |
| 378 | 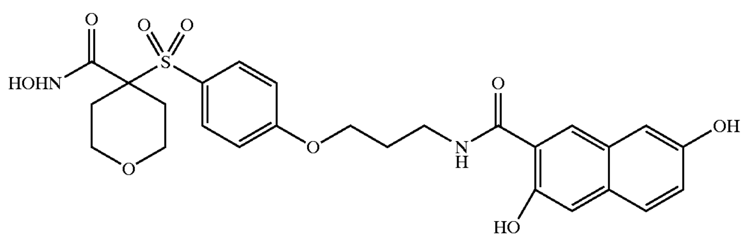 | 545.1594 | 545.1596 | | 655 | | 2.7 | |
| 379 | 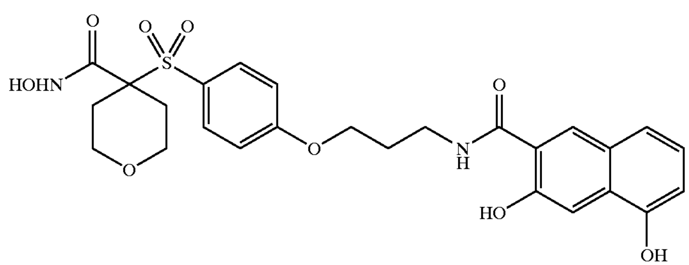 | 545.1594 | 545.1585 | | 258 | | 10 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 380 | 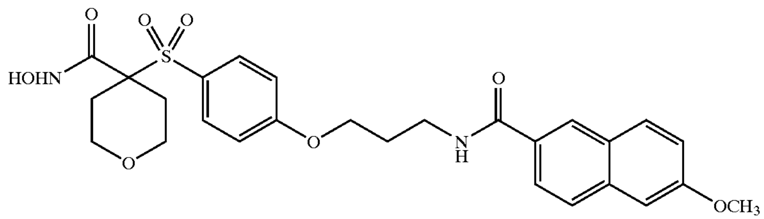 | 543.1801 | 543.1835 | | 450 | | 0.2 | |
| 381 | 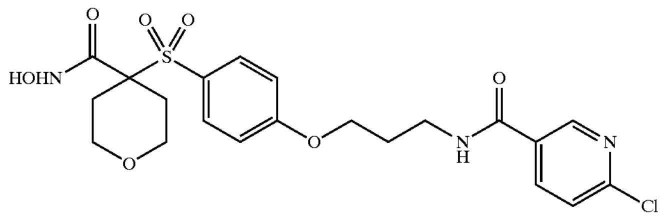 | 498.1102 | 498.1090 | | 193 | | 1.4 | |
| 382 | 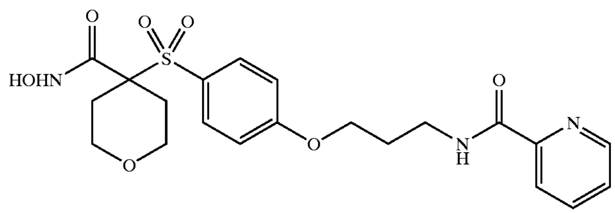 | 464.1491 | 464.1475 | | 59 | | 1.7 | |
| 383 | 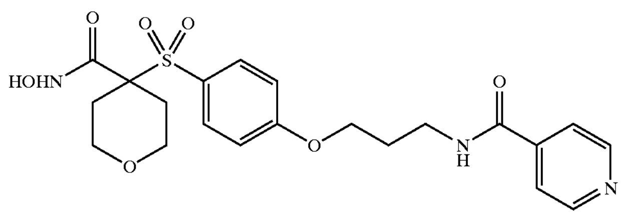 | 464.1491 | 464.1487 | | 351 | | 7.5 | |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 384 | 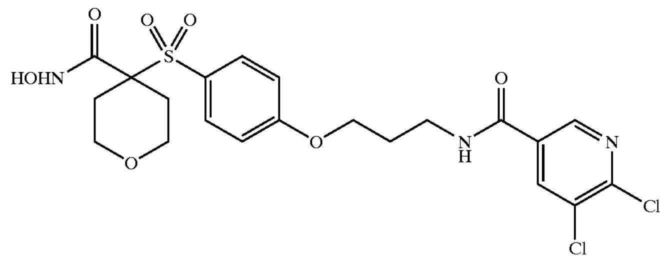 | 532.0712 | 532.0709 | >10000 | 176 | 2628 | 0.8 | >10000 |
| 385 | 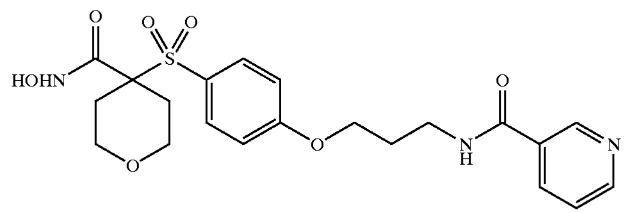 | 464.1491 | 464.1490 | 4341 | 253 | >10000 | 3.3 | |
| 386 | 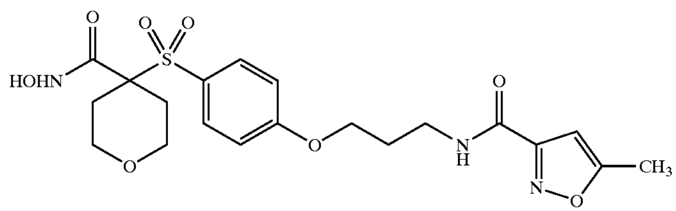 | 468.1441 | 468.1459 | >10000 | 131 | 35.3 | 1.2 | 9725 |
| 387 | 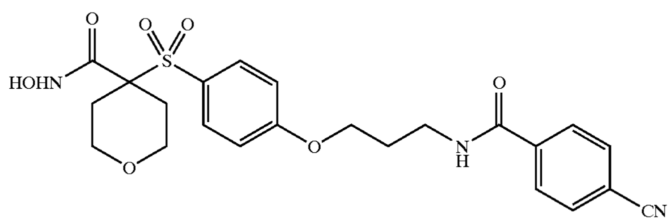 | 488.1491 | 488.1508 | | 83 | | 2.2 | |

TABLE 7-continued
| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 388 | 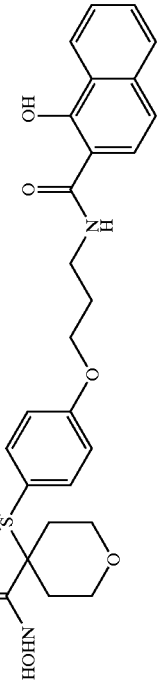 | 529.1645 | 529.1640 | | 185 | | 2 | |
| 389 | 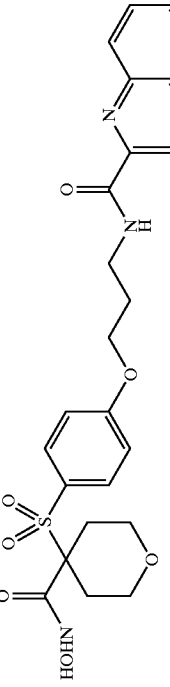 | 514.1648 | 514.1623 | | 47 | | 0.5 | |
| 390 | 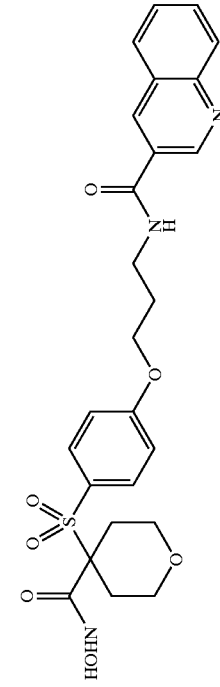 | 514.1648 | 514.1641 | >10000 | 907 | >10000 | 2.7 | >10000 |
| 391 | 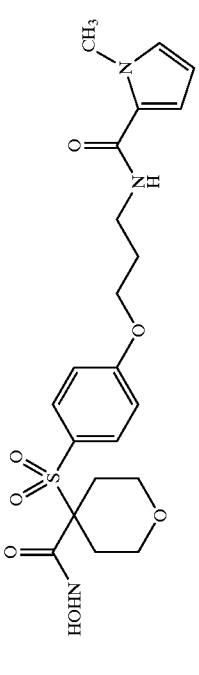 | 466.1648 | 466.1647 | | 900 | | 7 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 392 | 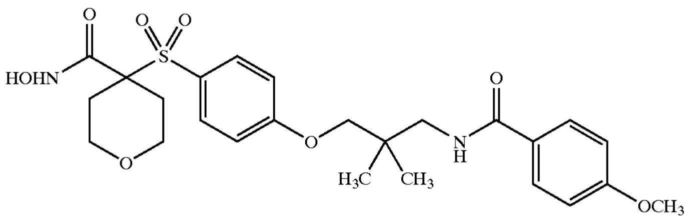 | 521.1958 | 521.1947 | >10000 | >10000 | >10000 | 40 | >10000 |
| 393 | 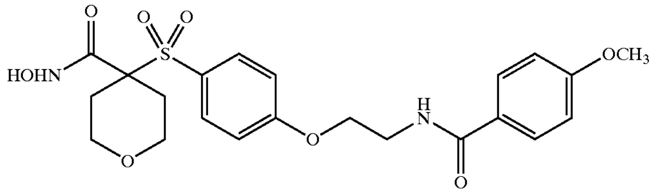 | 479.1488 | 479.1497 | | 50 | | 45 | |
| 394 | 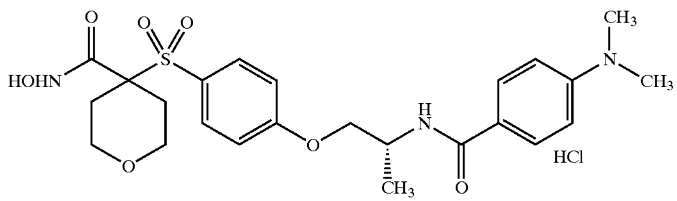 | 506.1961 | 506.1961 | | 3200 | | 1900 | |
| 395 | 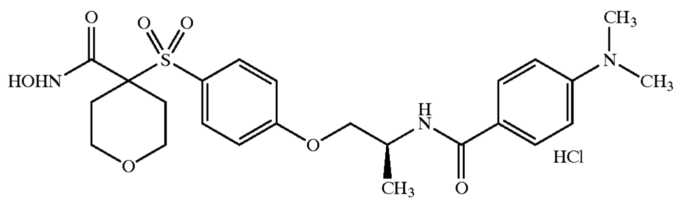 | 506.1961 | 506.1947 | | 6000 | | 305 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 396 | 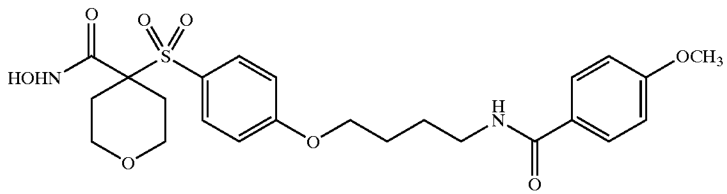 | 507.1801 | 507.1807 | 4 | 4 | | 4 | |
| 397 | 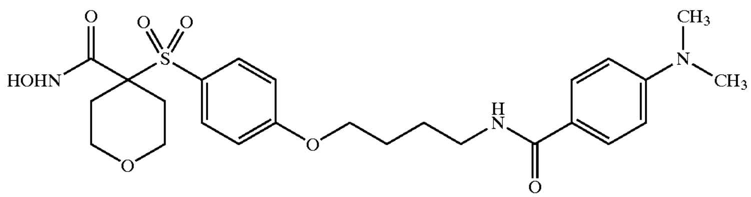 | 520.2117 | 520.2093 | | 3 | | 14 | |
| 398 | 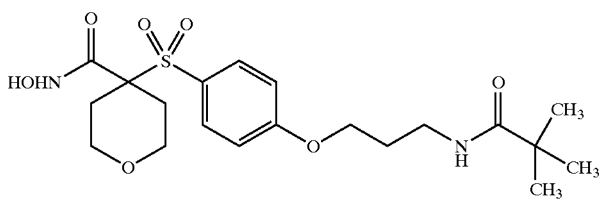 | 433 | 433 | | 730 | | 22 | |
| 399 | 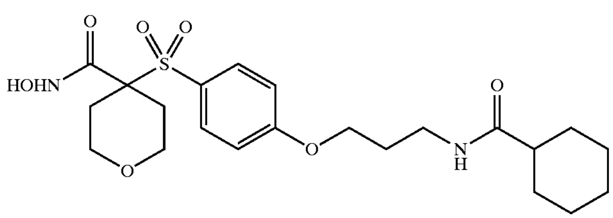 | 469.2008 | 469.1988 | | 650 | | 8 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 400 | 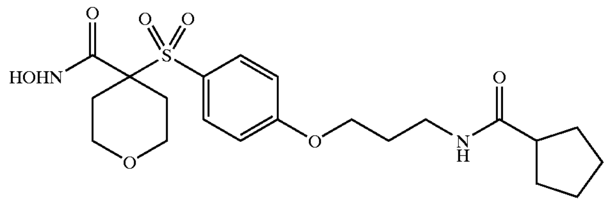 | 455.1852 | 455.1843 | | 326 | | 9 | |
| 401 | 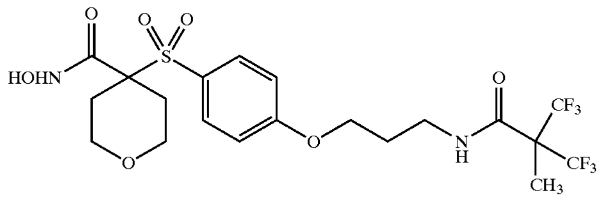 | 551.1287 | 551.1264 | | 700 | | 25 | |
| 402 | 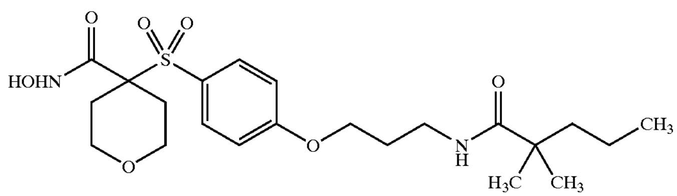 | 471.2165 | 471.2144 | | 454 | | 30 | |
| 403 | 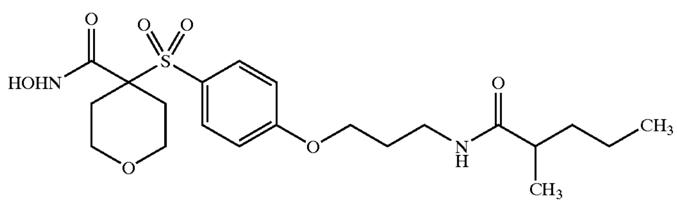 | 457.2008 | 457.1997 | >10000 | 454 | >10000 | 5.2 | >10000 |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 404 | 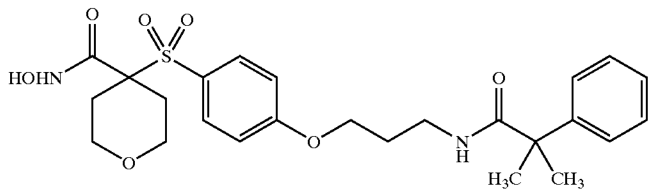 | 505.2008 | 505.1992 | | 254 | | 15 | |
| 405 | 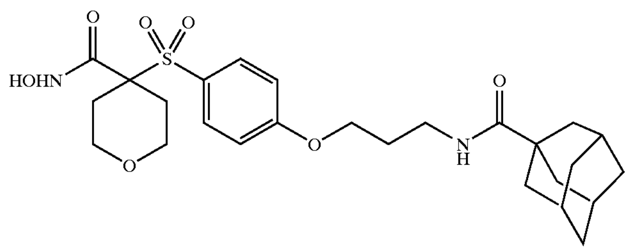 | 521.5321 | 521.2323 | >10000 | 2352 | >10000 | 1.9 | >10000 |
| 406 | 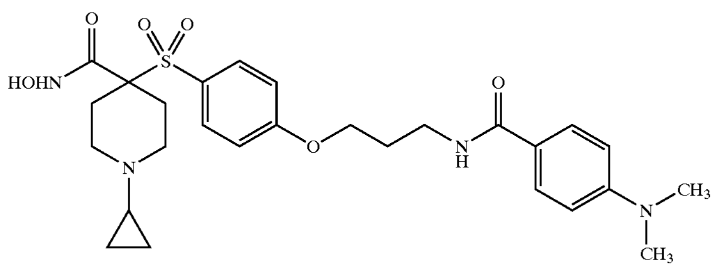 | 545.2434 | 545.2441 | >10000 | 2200 | >10000 | 4 | >10000 |
| 407 | 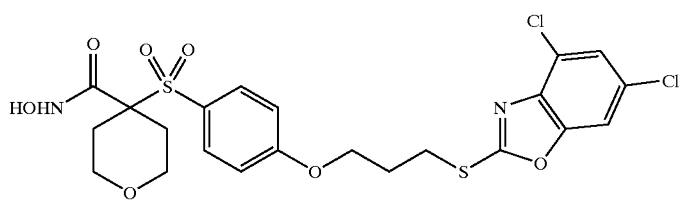 | 561.0324 | 561.0366 | | 285 | | 25 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 408 | 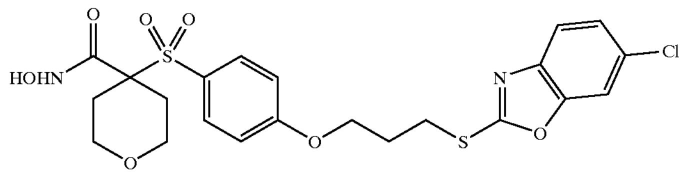 | 527.0713 | 527.0694 | >10000 | 90 | 49 | 2.5 | 6813 |
| 409 | 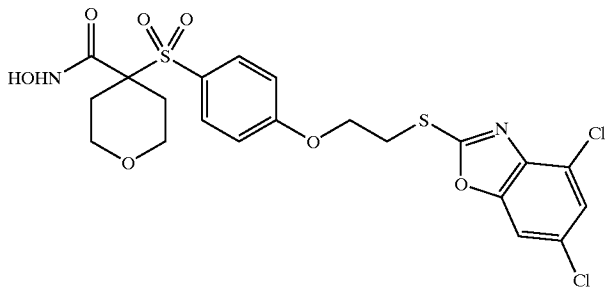 | 547.0167 | 547.0196 | >10000 | 23 | 160 | 1 | 5644 |
| 410 | 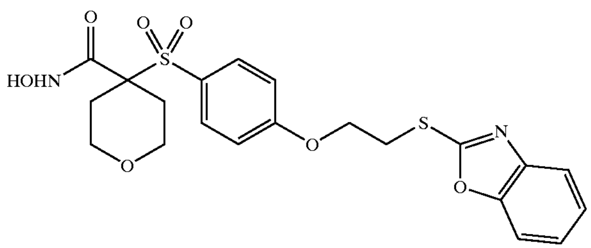 | 479.0947 | 479.0978 | 4700 | 12 | 202 | 1.1 | 515 |
| 411 | 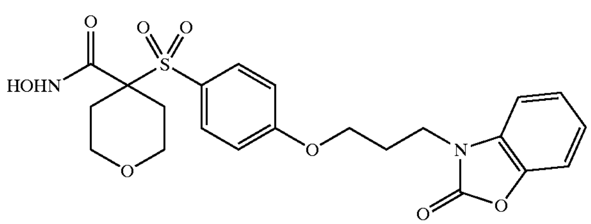 | 463.1175 | 463.1204 | >10000 | 1517 | >10000 | 587 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 412 | 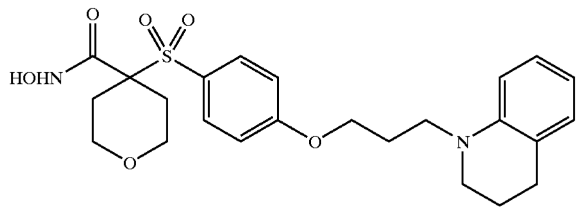 | 475.1903 | 475.0916 | | 313 | | 41 | |
| 413 | 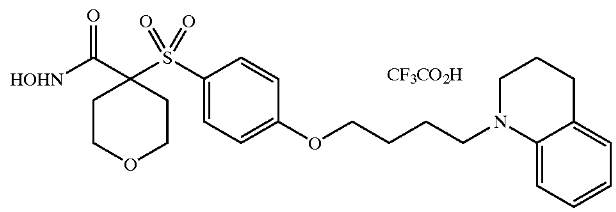 | 489.2059 | 489.2068 | | 61 | | 8 | |
| 414 | 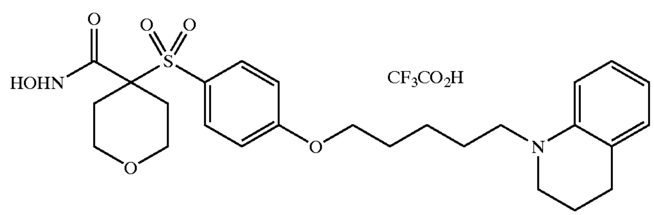 | 503.2216 | 203.2215 | | 37 | | 14 | |
| 415 | 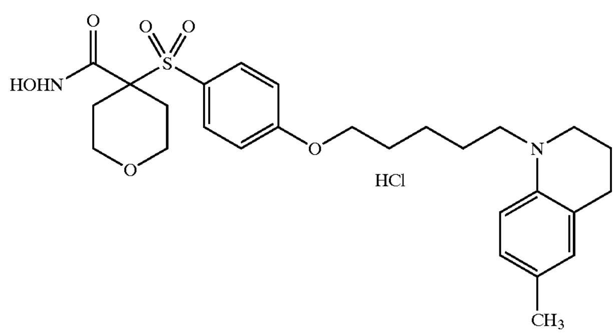 | 517.2372 | 517.2377 | >10000 | 51 | 1784 | 15 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 416 | 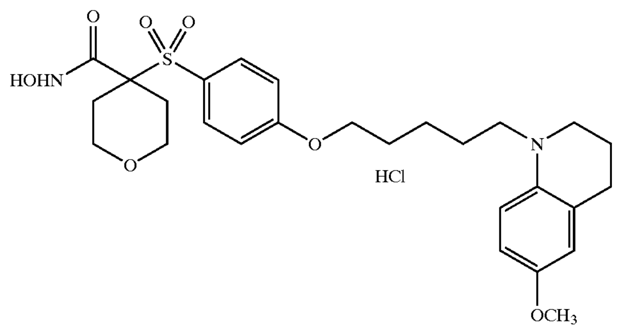 | 533.2321 | 533.2314 | | 17 | | 8.6 | |
| 417 | 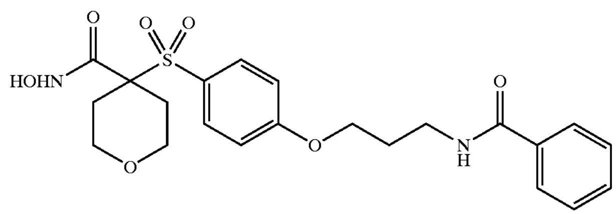 | 463.1539 | 463.1546 | | 315 | | 2.6 | |
| 418 | 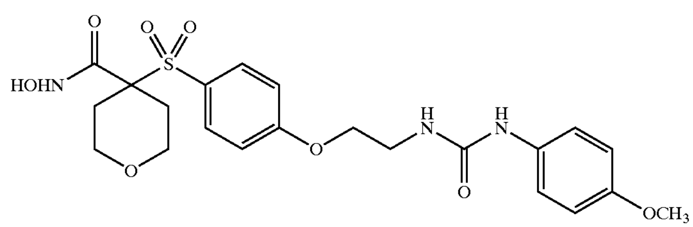 | | | >10000 | 1500 | >10000 | 64 | >10000 |

TABLE 7-continued

| Ex # | Structure | Calc. Mass | Ob- served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 419 | 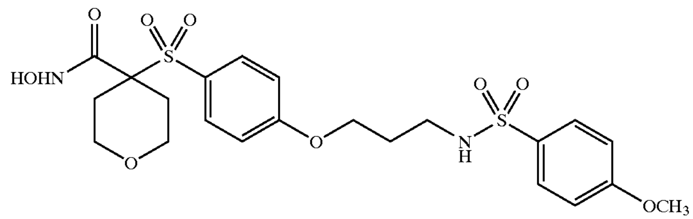 | | | | 120 | | 4 | |
| 420 | 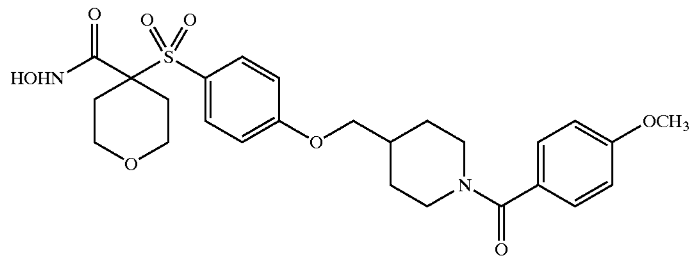 | | | >10000 | 67 | >10000 | 4 | >10000 |
| 421 | 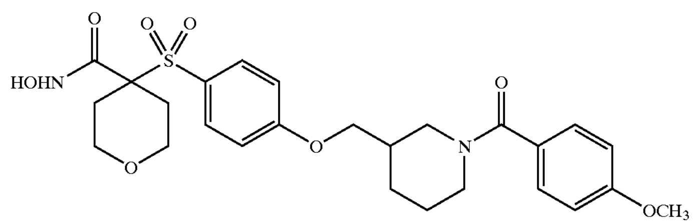 | | | | 649 | | 256 | |
| 422 | 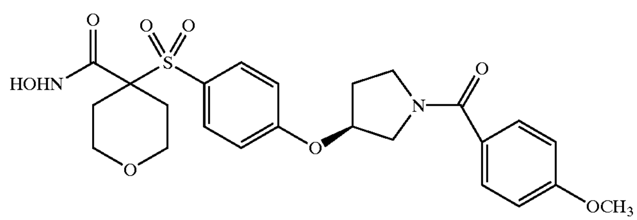 | | | | 7200 | | 1484 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 423 | 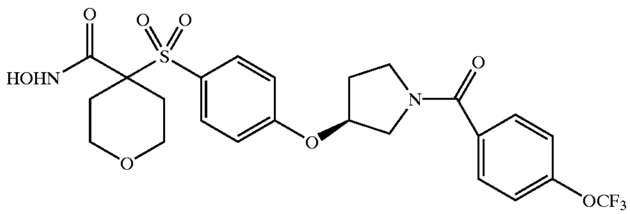 | | | | 9000 | | 1585 | |
| 424 | 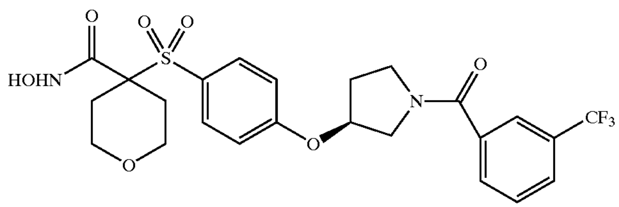 | | | | 485 | | 192 | |
| 425 | 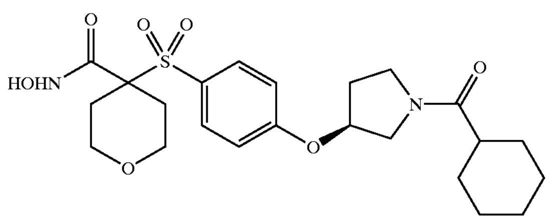 | | | | >10000 | | 3308 | |
| 426 | 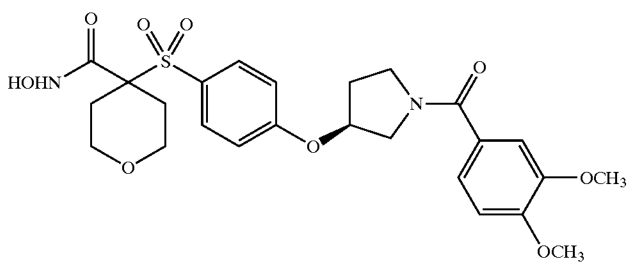 | | | | >10000 | | 5151 | |

TABLE 7-continued

| Ex # | Structure | Calc. Mass | Observed Mass | MMP-1 IC₅₀ (Ki) | MMP-2 IC₅₀ (Ki) | MMP-9 IC₅₀ (Ki) | MMP-13 IC₅₀ (Ki) | MMP-14 IC₅₀ (Ki) |
|---|---|---|---|---|---|---|---|---|
| 427 | 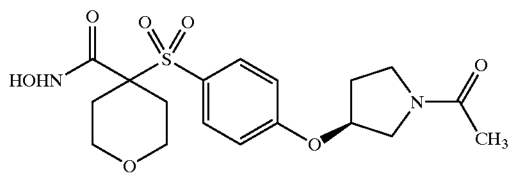 | | | | 251 | | 114 | |
| 428 | 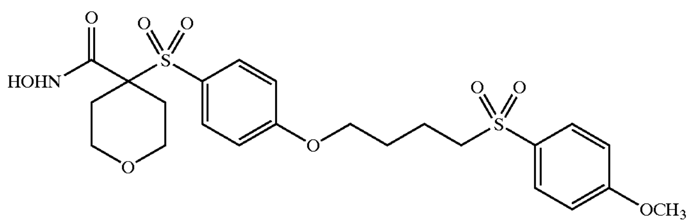 | | | | 20 | | 1.4 | |
| 429 | 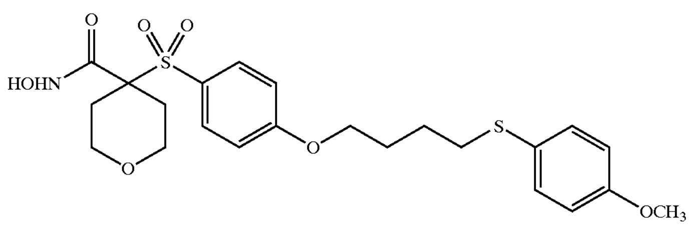 | | | | 6.5 | >10000 | 0.5 | >10000 |
| 430 | 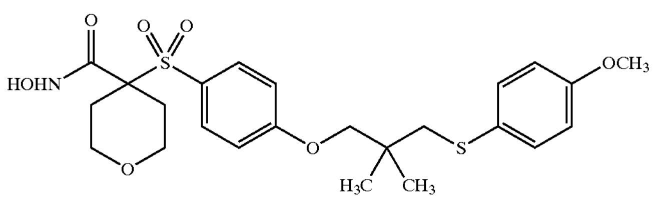 | | | | 2700 | | 195 | |

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 431 | 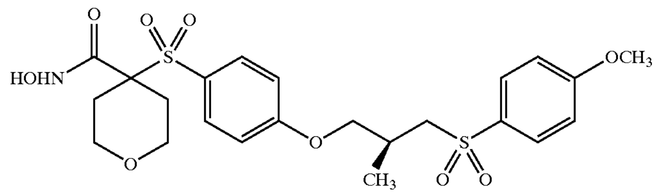 | | | | 115 | | 4 | |
| 432 | 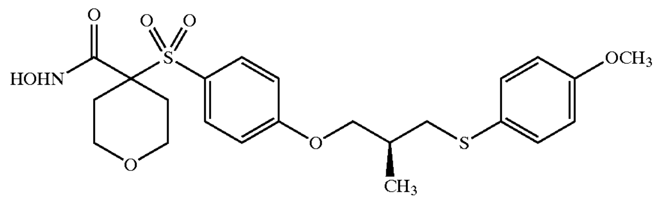 | | | | 7 | | 1.5 | |
| 433 | 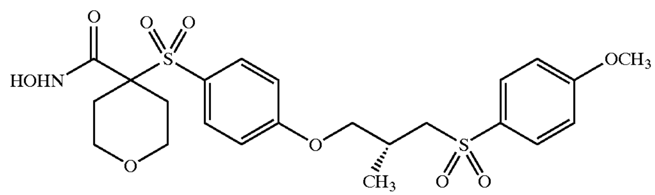 | | | | 220 | | 7 | |
| 434 | 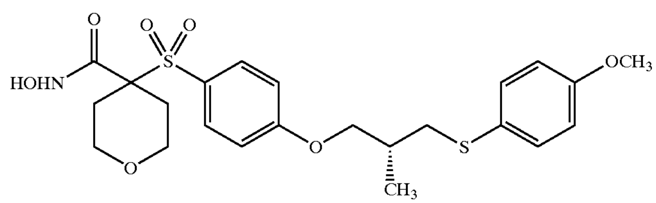 | | | | 1.1 | | 0.6 | |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 435 | 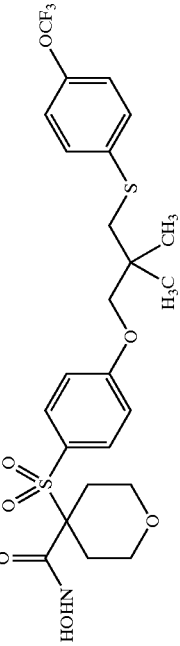 | | | >10000 | >10000 | | 500 | |
| 436 | 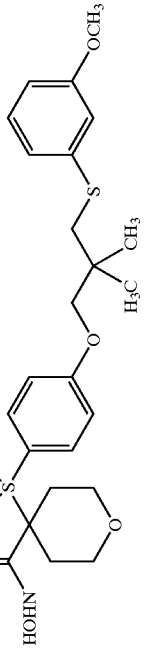 | | | >10000 | 1500 | | 100 | |
| 437 | 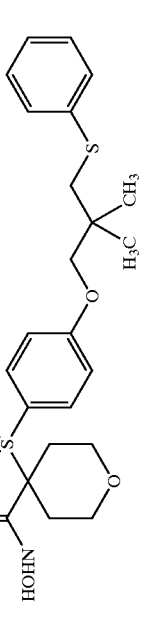 | | | >10000 | >10000 | >10000 | 90 | >10000 |
| 438 | 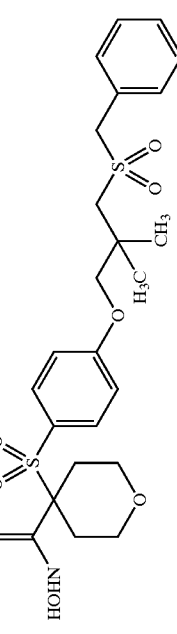 | | | >10000 | 505 | 3800 | 11 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 439 | 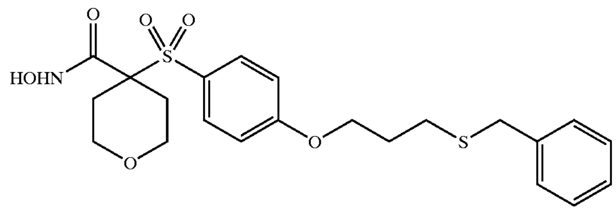 | | | >10000 | 2000 | 6000 | 25 | >10000 |
| 440 | 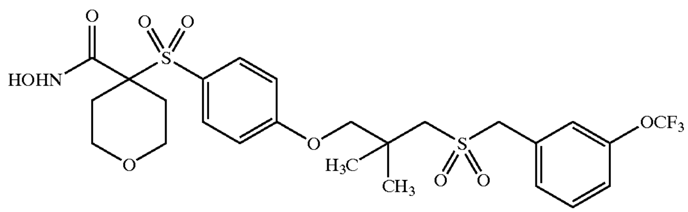 | | | >10000 | 4 | 140 | 1 | 2500 |
| 441 | 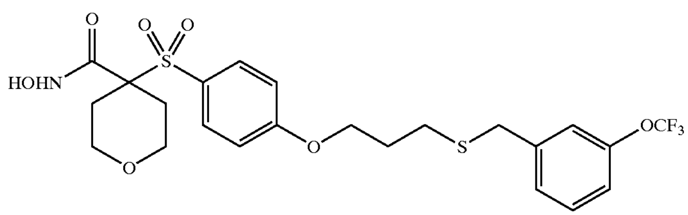 | | | 9000 | 13 | 110 | 2 | 2290 |
| 442 | 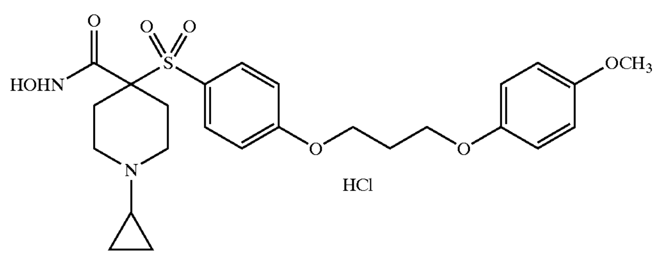 | | | >10000 | 6.2 | 5.4 | 1.8 | 997 |

TABLE 7-continued

| Ex # | Structure | Calc. Mass | Observed Mass | MMP-1 IC50 (Ki) | MMP-2 IC50 (Ki) | MMP-9 IC50 (Ki) | MMP-13 IC50 (Ki) | MMP-14 IC50 (Ki) |
|---|---|---|---|---|---|---|---|---|
| 443 | 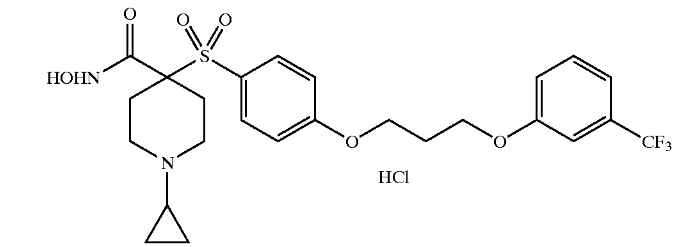 | | | >10000 | 25 | 375 | 3.5 | 2429 |
| 444 | 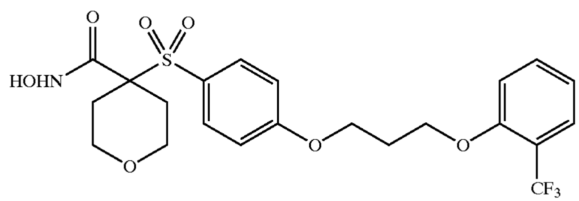 | | | | 8.9 | | 7.6 | |
| 445 | 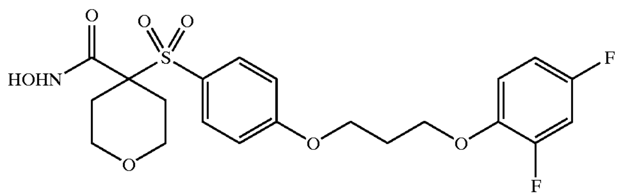 | | | 3325 | 2.2 | 44 | 0.5 | 546 |
| 446 | 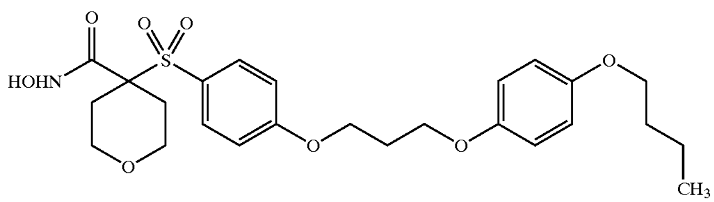 | | | | 76 | | 6.6 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 447 | 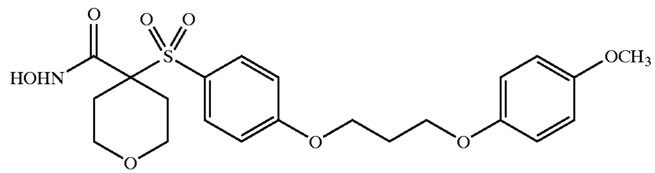 | | | >10000 | 8.9 | 12.2 | 2 | 1360 |
| 448 | 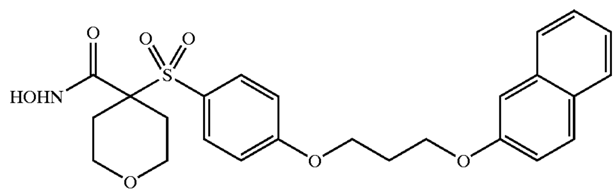 | | | 3080 | 9 | 116 | 2.7 | 832 |
| 449 | 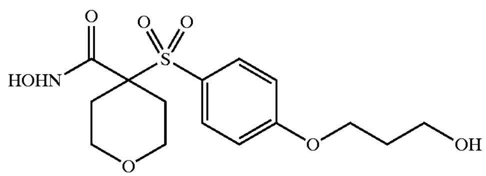 | | | 1929 | 3.7 | 41 | 7 | 58 |
| 450 | 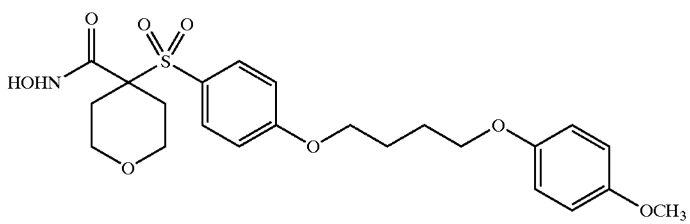 | | | >10000 | 6.6 | 44 | 0.9 | 4937 |
| 451 | 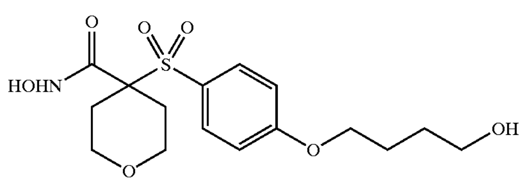 | | | | 4.7 | | 9 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 452 | 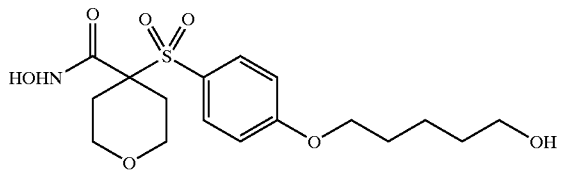 | | | | 2.2 | | 14.8 | |
| 453 | 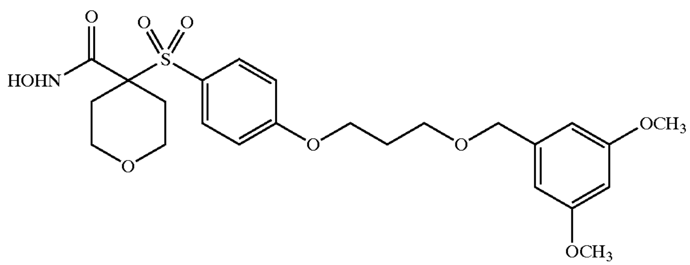 | | | >10000 | 13 | 800 | 3 | 5000 |
| 454 | 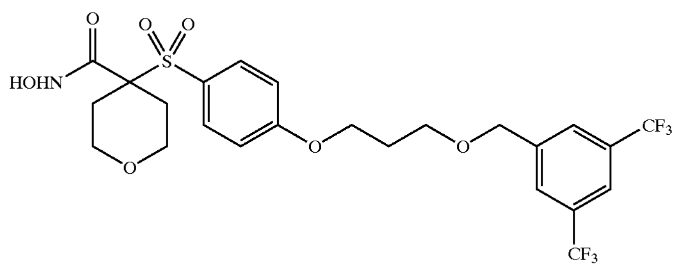 | | | >10000 | 165 | | 27 | |
| 455 | 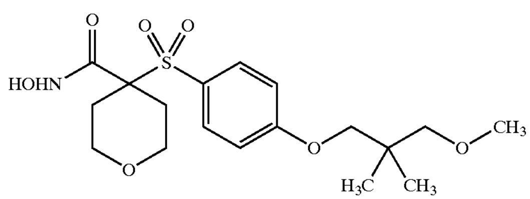 | | | | 900 | | 690 | |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 456 | 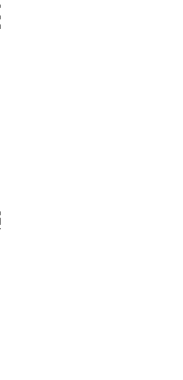 | | | | 425 | | 350 | |
| 457 | 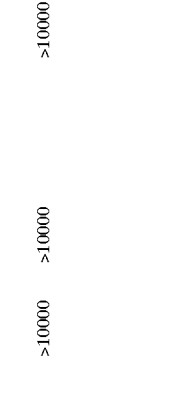 | | | >10000 | >10000 | | >10000 | |
| 458 | 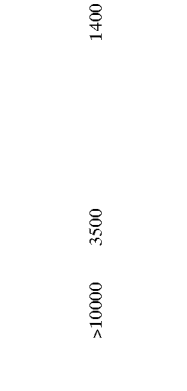 | | | >10000 | 3500 | | 1400 | |
| 459 | 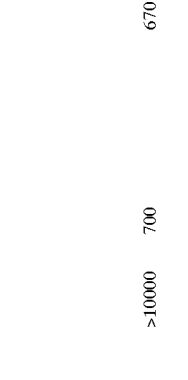 | | | >10000 | 700 | | 670 | |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 460 | 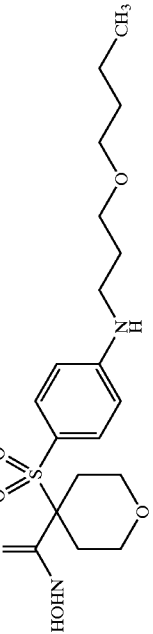 | | | >10000 | 145 | 700 | 25 | >10000 |
| 461 | 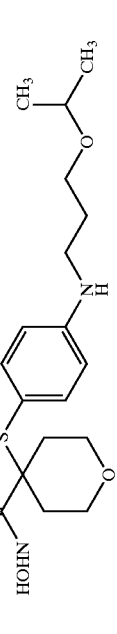 | | | >10000 | 2200 | | 590 | |
| 462 | 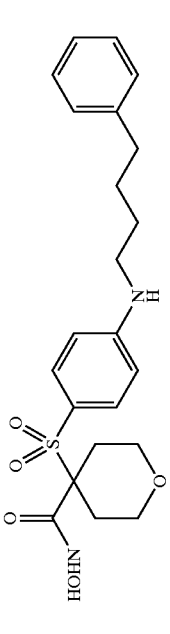 | | | >10000 | 11 | 18 | 7 | 6500 |
| 463 | 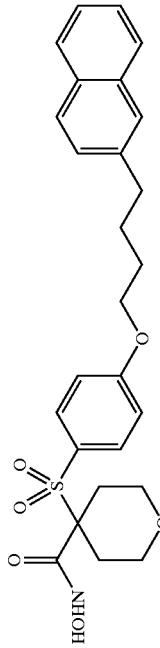 | 484.1794 | 484.1776 | | 17 | | 7 | |
| 464 | 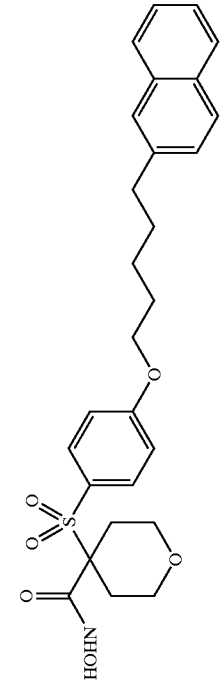 | 498.195 | 498.1925 | | 46 | | 1.4 | |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 465 | 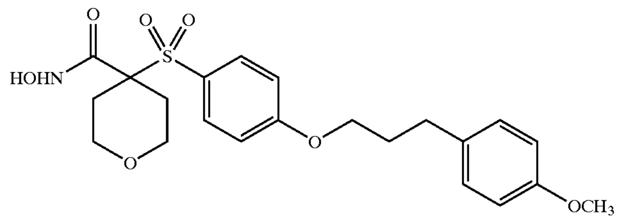 | 450.1586 | 450.1577 | >10000 | 4 | 180 | 0.3 | 1800 |
| 466 | 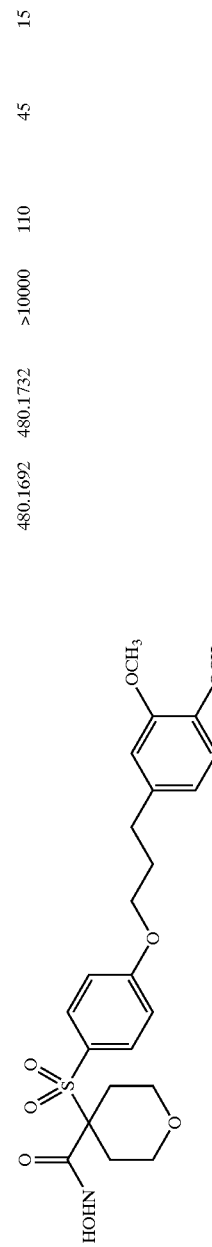 | 480.1692 | 480.1732 | >10000 | 110 | 45 | 15 | >10000 |
| 467 | 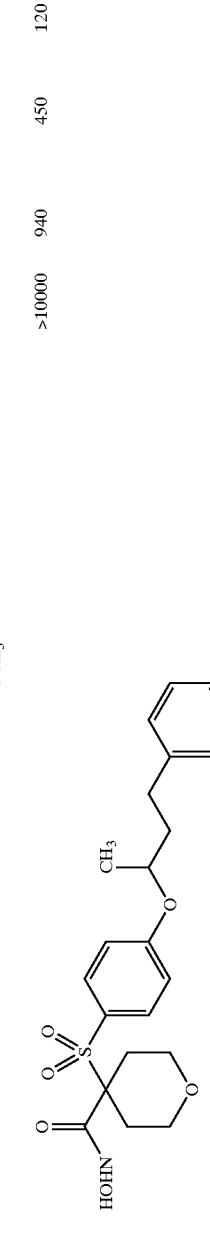 | | | >10000 | 940 | 450 | 120 | >10000 |
| 468 | 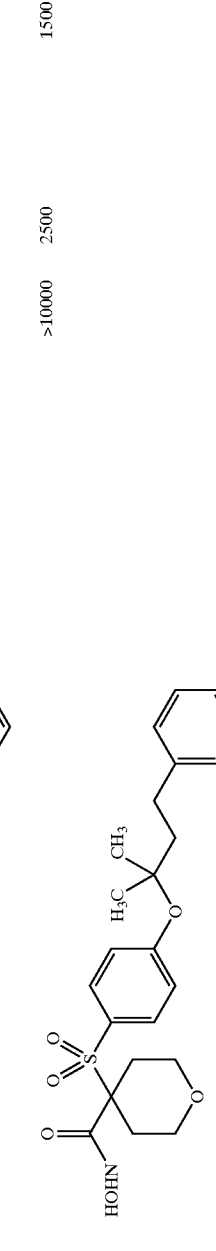 | | | >10000 | 2500 | | 1500 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 469 | 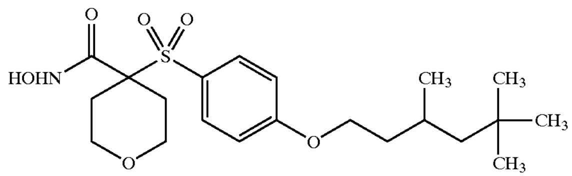 | | | >10000 | 145 | | 60 | |
| 470 | 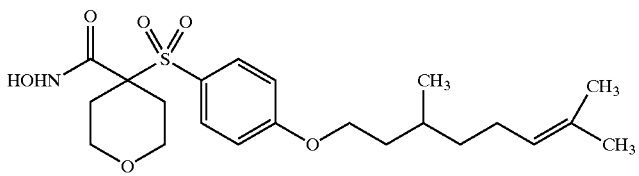 | | | | 7 | | 3 | |
| 471 | 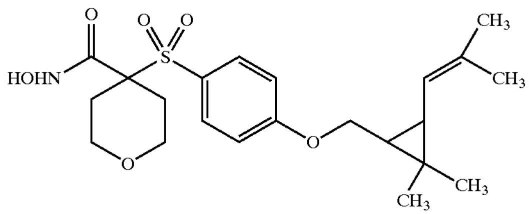 | | | >10000 | 270 | | 120 | |
| 472 | 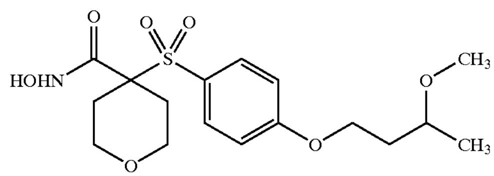 | | | >10000 | 3 | 40 | 6 | 400 |
| 473 | 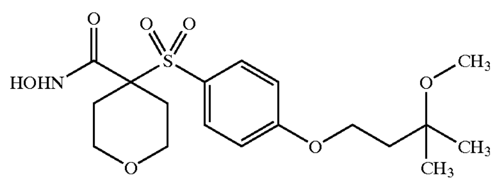 | | | >10000 | 5 | 45 | 5 | 600 |

TABLE 7-continued

| Ex # | Structure | Calc. Mass | Observed Mass | MMP-1 IC₅₀ (Ki) | MMP-2 IC₅₀ (Ki) | MMP-9 IC₅₀ (Ki) | MMP-13 IC₅₀ (Ki) | MMP-14 IC₅₀ (Ki) |
|---|---|---|---|---|---|---|---|---|
| 474 | 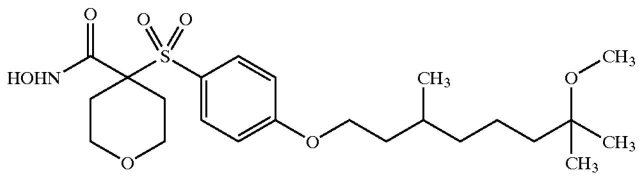 | | | >10000 | 12 | | 3 | |
| 475 | 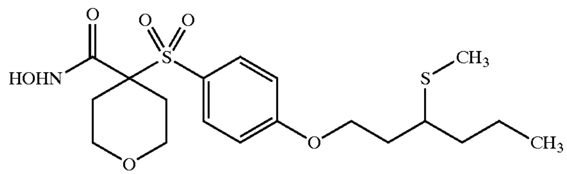 | | | | 30 | 120 | 2 | 3600 |
| 476 | 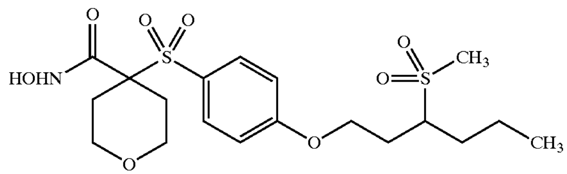 | | | >10000 | 2500 | >10000 | 230 | >10000 |
| 477 | 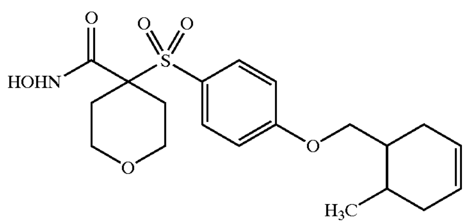 | | | 1300 | 1.5 | | 2 | |
| 478 | 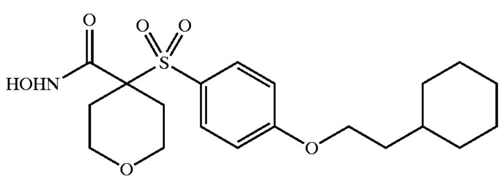 | | | >10000 | 1 | 34 | 5 | 1450 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 479 | 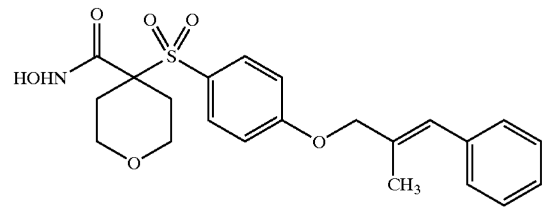 | | | 2700 | 4 | 14 | 3 | 2000 |
| 480 | 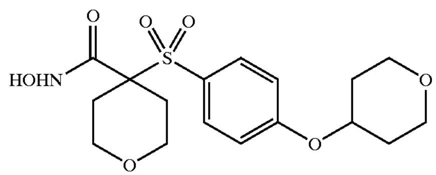 | | | 4200 | 18 | 60 | 11 | 1400 |
| 481 | 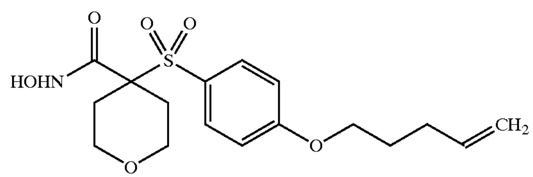 | | | | 1.3 | | 2 | |
| 482 | 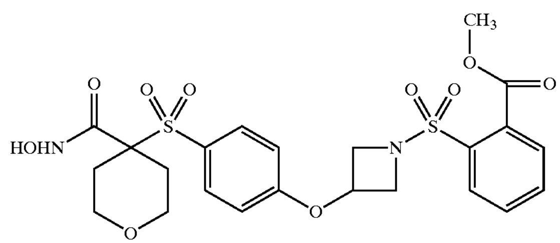 | | | | 3300 | | 40 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 483 | 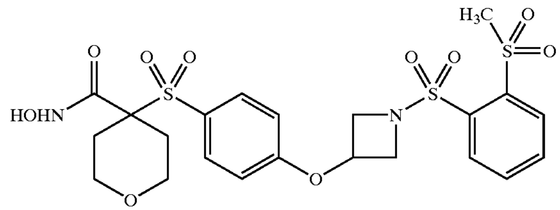 | | | | 2000 | | 29 | |
| 484 | 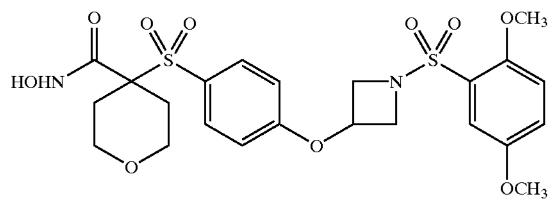 | | | | 640 | | 12 | |
| 485 | 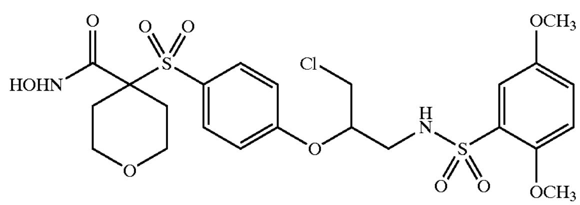 | | | | 4000 | | 64 | |
| 486 | 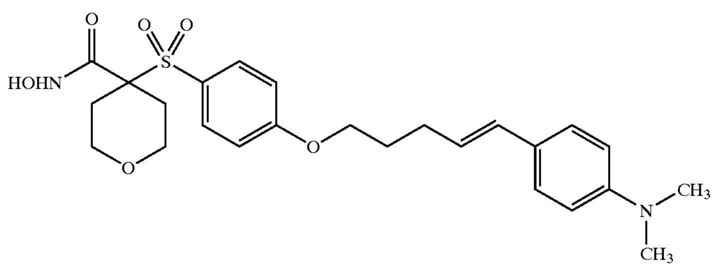 | | | >10000 | 106 | 255 | 4.6 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 487 | 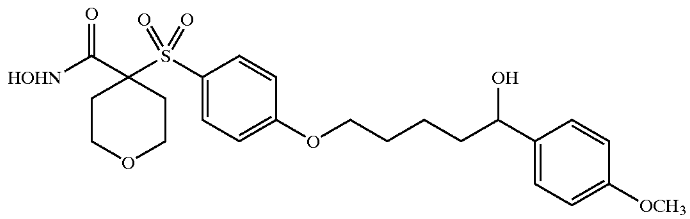 | | | >10000 | 3.1 | 169 | 0.5 | 1570 |
| 488 | 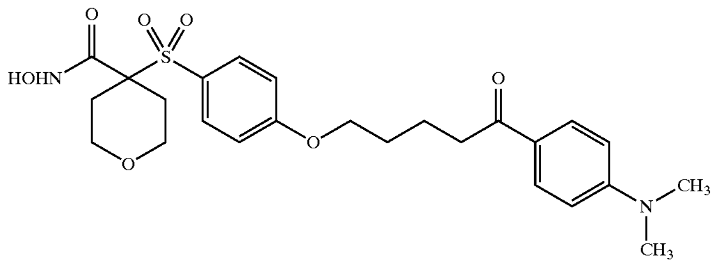 | 505.2008 | 505.1991 | | | | | |
| 489 | 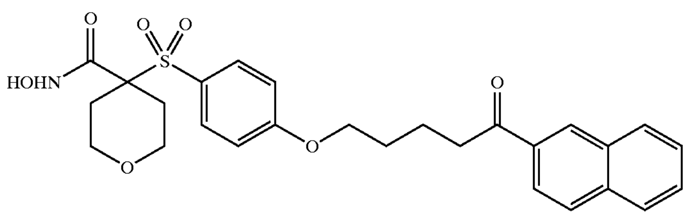 | 512.1743 | 512.1766 | >10000 | 58.2 | >10000 | 0.4 | >10000 |
| 490 | 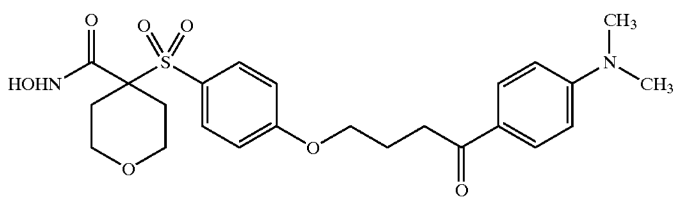 | 491.1852 | 491.1856 | >10000 | 18.2 | 928 | 0.2 | 5630 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 491 | 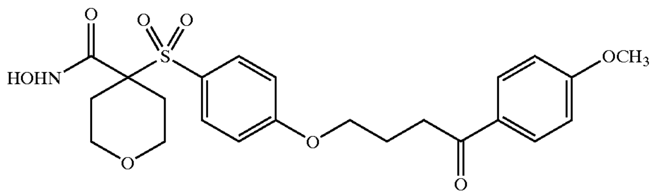 | 478.1536 | 478.1540 | 7310 | 6.8 | 94.2 | 0.8 | 981 |
| 492 | 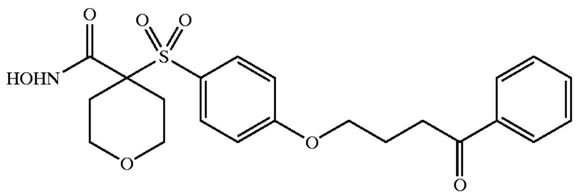 | 448.1430 | 448.1428 | 3550 | 3.5 | 67.3 | 0.7 | 574 |
| 493 | 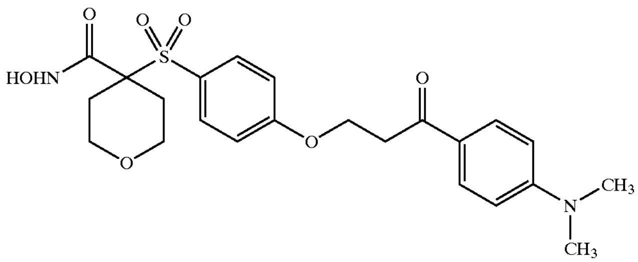 | 471.1695 | 471.1695 | 4770 | 15.9 | 752 | 0.9 | 3230 |
| 494 | 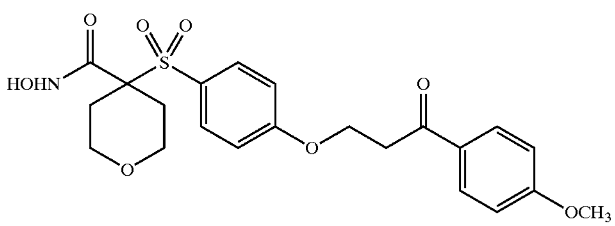 | 464.1392 | 464.1379 | 1520 | <0.1 | 13.6 | <0.1 | 197 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 495 | 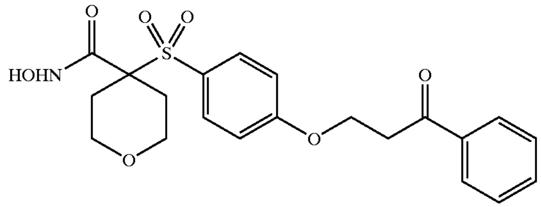 | 434.1273 | 434.1277 | 815 | 1.9 | 25.8 | 1.7 | 505 |
| 496 | 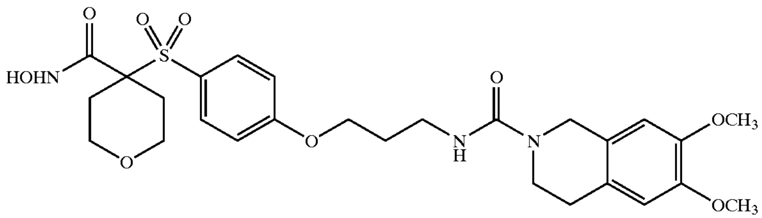 | 578.2172 | 578.2164 | | 242 | | 8.4 | |
| 497 | 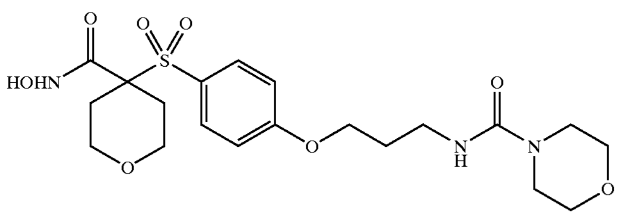 | 472.1754 | 472.1769 | | 1450 | | 23.5 | |
| 498 | 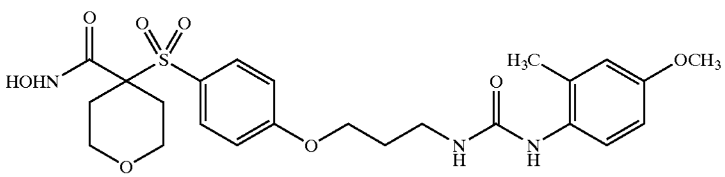 | 522.191 | 522.1915 | | 160 | | 14.8 | |

TABLE 7-continued

| Ex # | Structure | Calc. Mass | Observed Mass | MMP-1 IC₅₀ (Ki) | MMP-2 IC₅₀ (Ki) | MMP-9 IC₅₀ (Ki) | MMP-13 IC₅₀ (Ki) | MMP-14 IC₅₀ (Ki) |
|---|---|---|---|---|---|---|---|---|
| 499 | 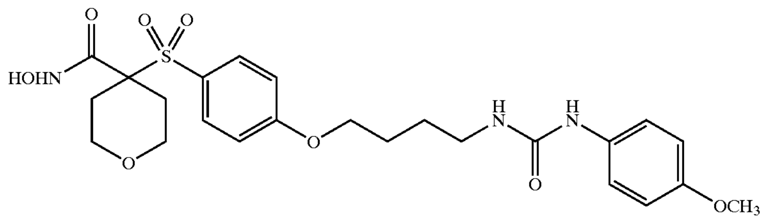 | 508.1754 | 508.1753 | | 56.2 | 7.0 | | |
| 500 | 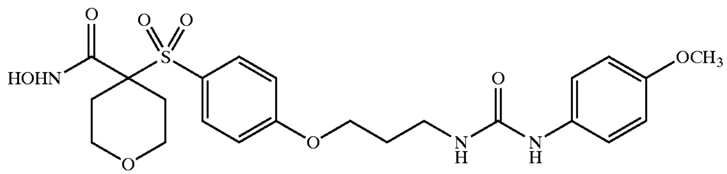 | 494.1597 | 494.1596 | 2390 | 1, 9 | 63.2 | 8.5 | 2960 |
| 501 | 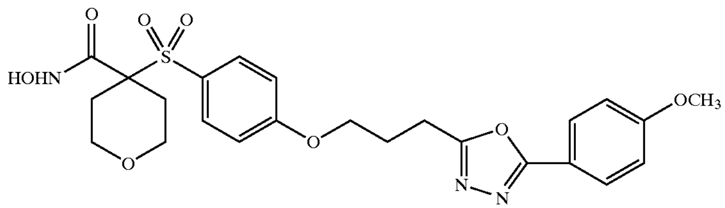 | 518.1597 | 518.158 | >10000 | 184 | 7710 | 1.4 | >10000 |
| 502 | 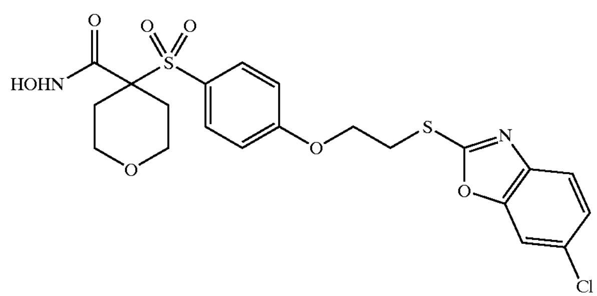 | 513.0557 | 513.0574 | >10000 | 22.7 | 160 | 1.0 | 5640 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 503 | 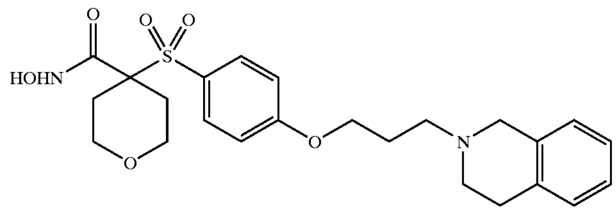 | 475.1903 | 475.1907 | | | | | |
| 504 | 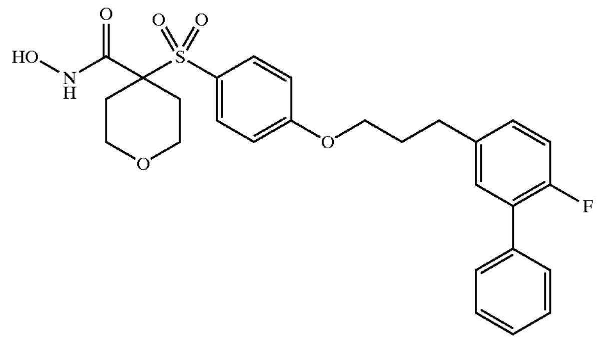 | 514.1700 | 514.1735 | (>10000) | (434) | (2310) | (4.65) | (>10000) |
| 505 | 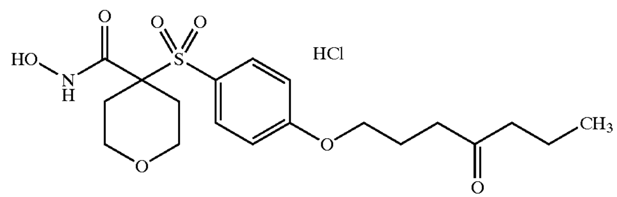 | 414.1581 | 414.1586 | (850) | (2.56) | (10.2) | (0.81) | (962) |
| 506 | 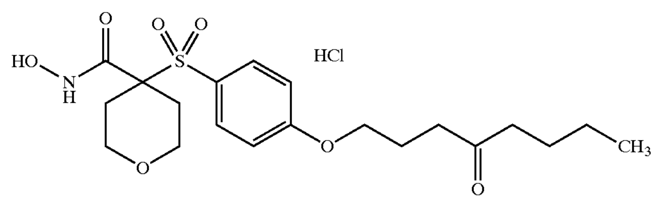 | 428.1738 | 428.1751 | (1465) | (1.92) | (11.4) | (0.23) | (681) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 507 | 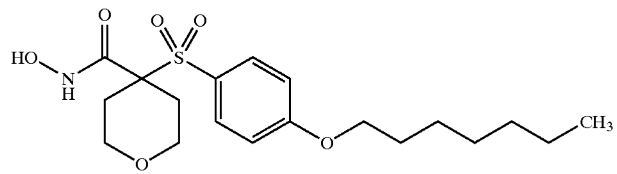 | 400.1767 | 400.1788 | (3590) | (0.84) | (0.44) | (0.19) | (444) |
| 508 | 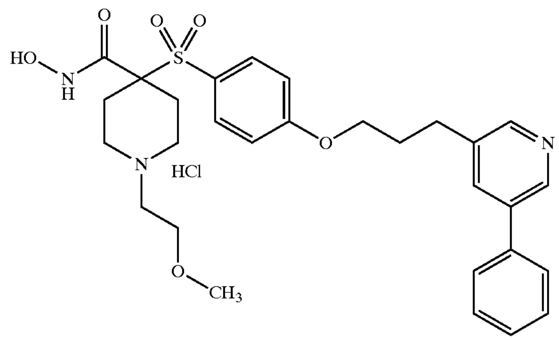 | 554.2319 | 554.2347 | (4850) | (22.8) | (160) | (0.141) | (2790) |
| 509 | 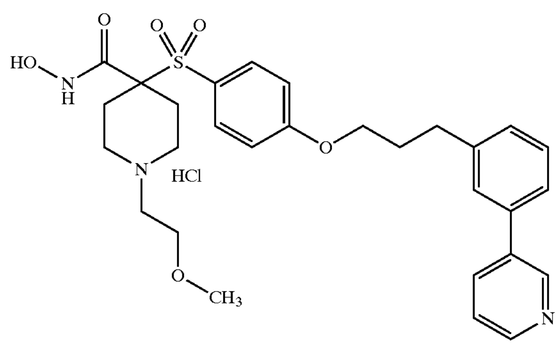 | 554.2319 | 554.2308 | (>10000) | (89.26) | (50.85) | (0.297) | (4158.92) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 510 | 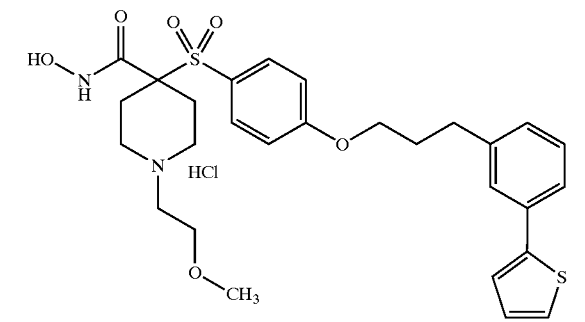 | | | (>10000) | (7.85) | (39.82) | (0.25) | (2183.66) |
| 511 | 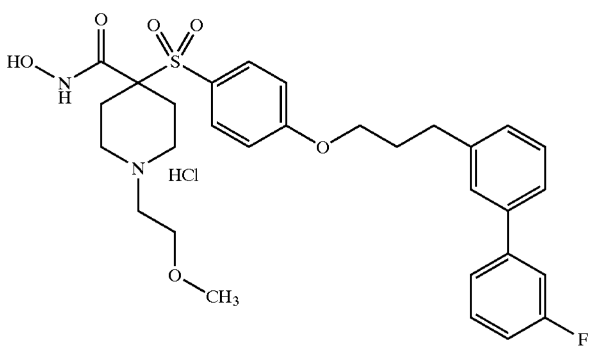 | 571.2273 | 571.2255 | (>10000) | (525.78) | (38.53) | (1.36) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 512 | 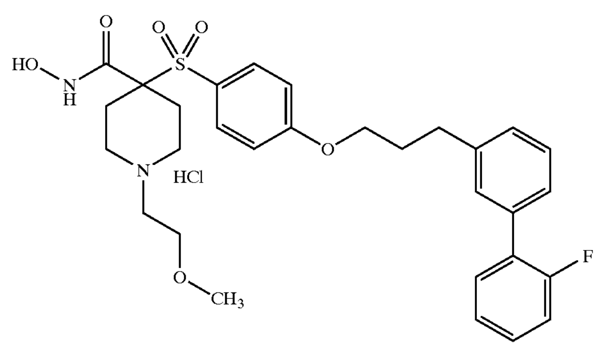 | 571.2273 | 571.2281 | (>10000) | (757.99) | (25.71) | (1.07) | (>10000) |
| 513 | 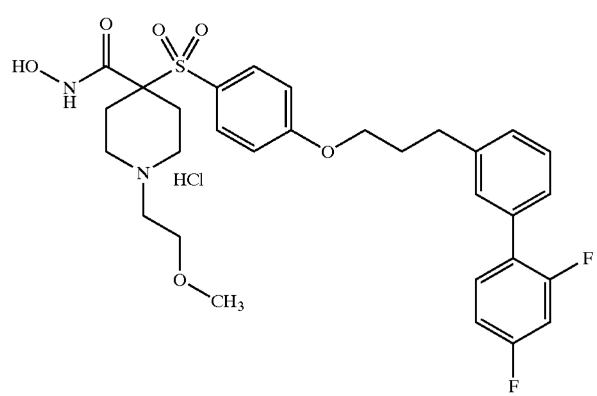 | 589.2178 | 589.2193 | (>10000) | (879.71) | (254.58) | (0.98) | (9274.4) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 514 | 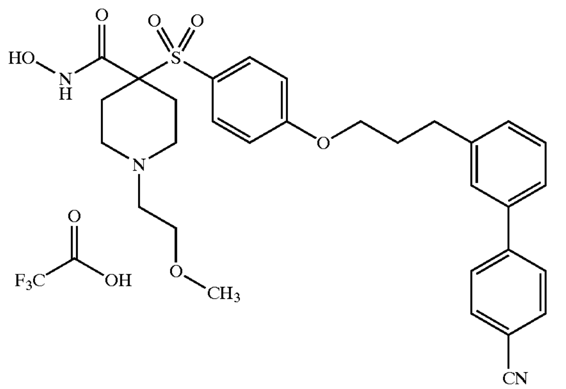 | 578.2319 | 578.2305 | (>10000) | (292.63) | (223.53) | (0.28) | (4082.05) |
| 515 | 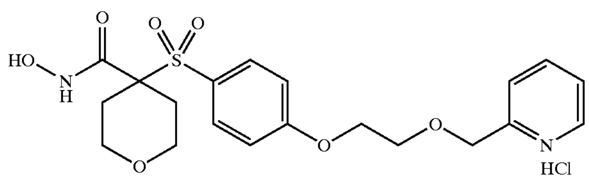 |  |  | >10000 | 89.76 | 154.32 | 24.23 | >10000 |
| 516 | 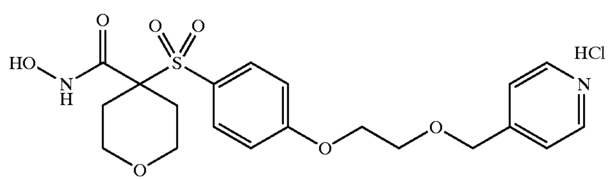 |  |  | >10000 | 41.94 | 119.72 | 9.55 | 9434.24 |
| 517 | 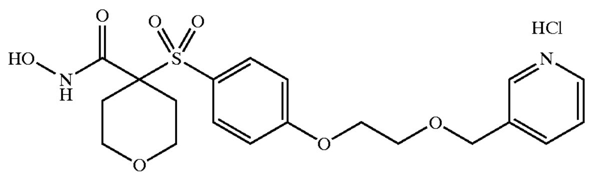 |  |  | >10000 | 34.66 | 137.63 | 6.19 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 518 | 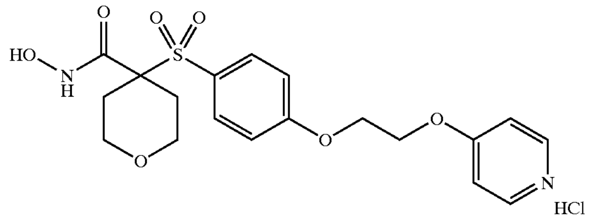 | | | >10000 | 26.35 | 115.39 | 169.48 | 967.13 |
| 519 | 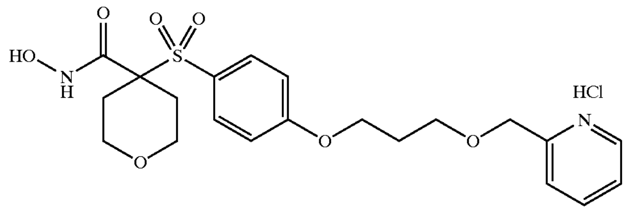 | | | | 170.25 | 421.64 | 2.18 | >10000 |
| 520 | 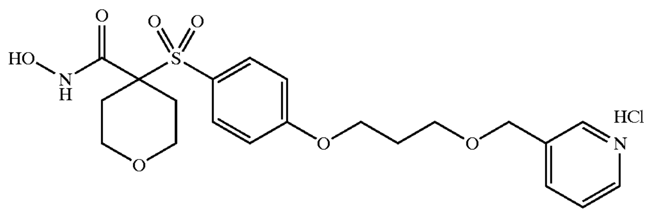 | | | >10000 | 54.24 | 36.38 | 0.62 | 4296.13 |
| 521 | 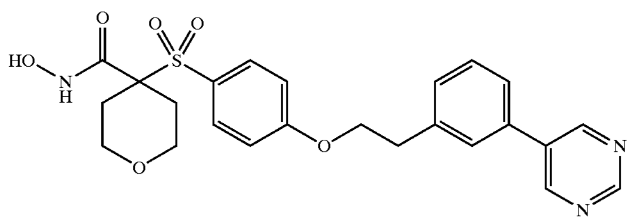 | | | | 62.0 | | 5.8 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 522 | 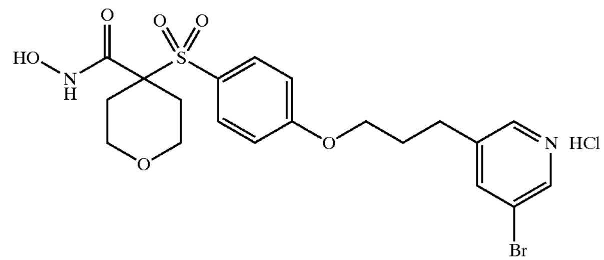 | | | (>10000) | 12.9 (32.1) | (135) | 0.3 | (6290) |
| 523 | 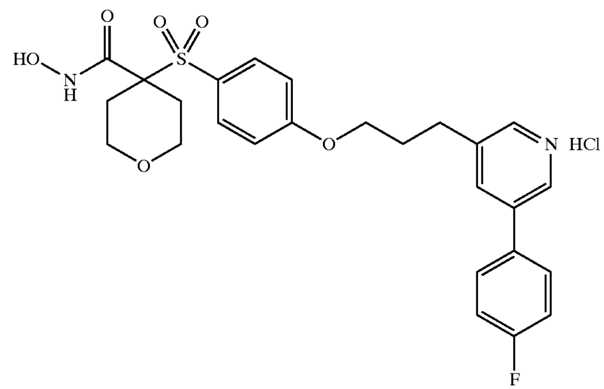 | 515.1647 | 515.1690 | 8069 (3213) | 161.6 (196.7) | 1647.2 (1253) | 0.3 (0.234) | >10000 (>10000) |
| 524 | 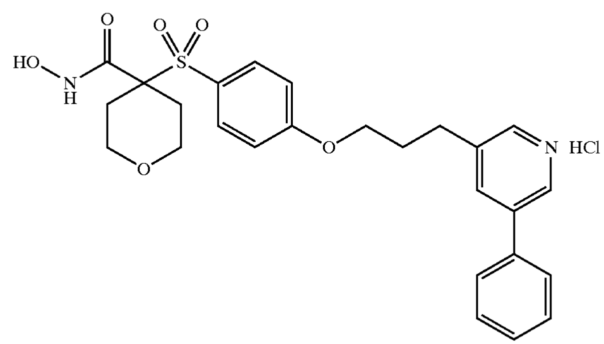 | 497.1741 | 497.1763 | >10000 | 38.3 (51.8) | 1841.5 (739.5) | 0.2 (0.244) | >10000 (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 525 | 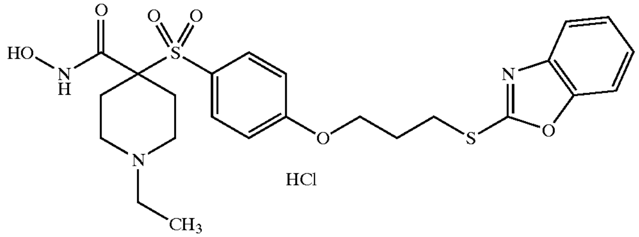 | 420.1576 | 520.1581 | | 7.5 | | 1.5 | |
| 526 | 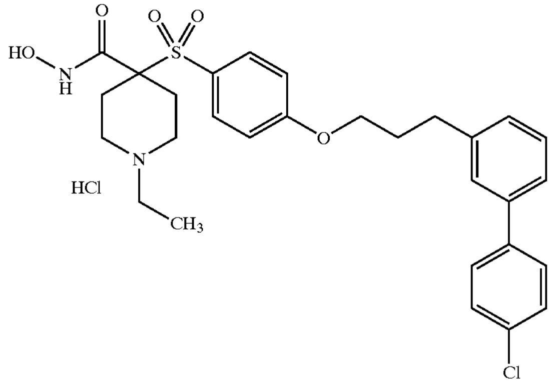 | 557.1871 | 557.1863 557.1843 | (>10000) | (1680) | (2070) | (3.96) | (>10000) |
| 527 | 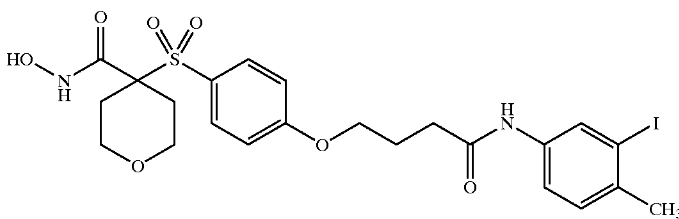 | | | (5100) | (21.3) | (30.4) | (.044) | (1360) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 528 | 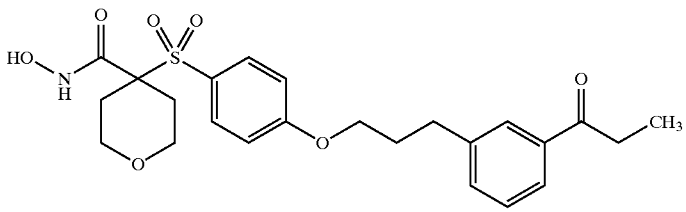 | | | (>10000) | (83.5) | (238) | (2.57) | (5700) |
| 529 | 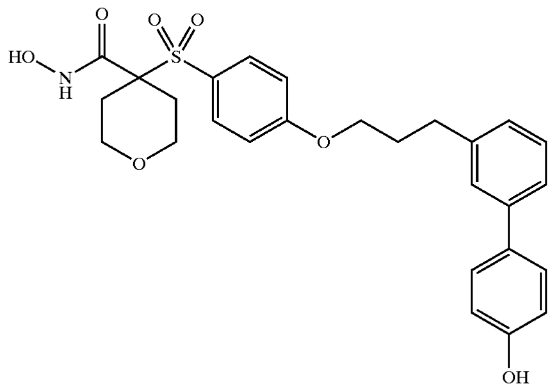 | 529.2003 | 529.1982 | (>10000) | (3550) | (1870) | (20.2) | (>10000) |
| 530 | 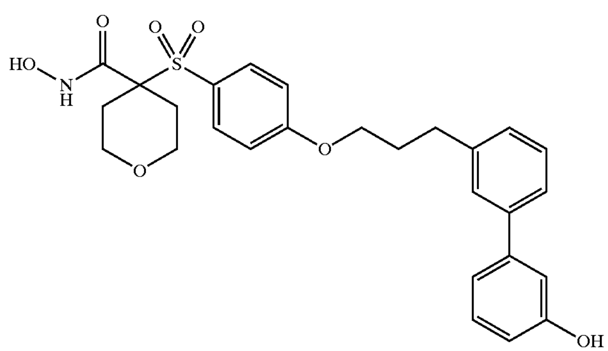 | 512.1738 | 512.1774 | (>10000) | (699) | (220) | (7.33) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 531 | 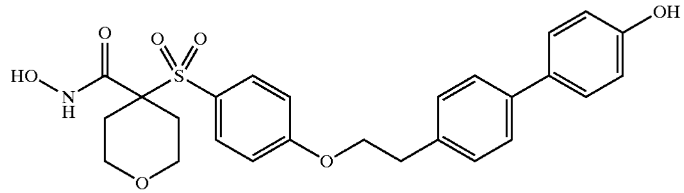 | 498.1581 | 498.1614 | (>10000) | (337) | (774) | (2.72) | (>10000) |
| 532 | 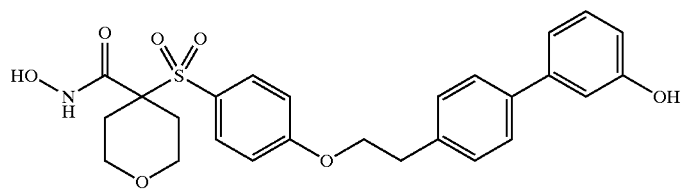 | 498.1581 | 498.1610 | (>10000) | (739) | (1320) | (1.02) | (>10000) |
| 533 | 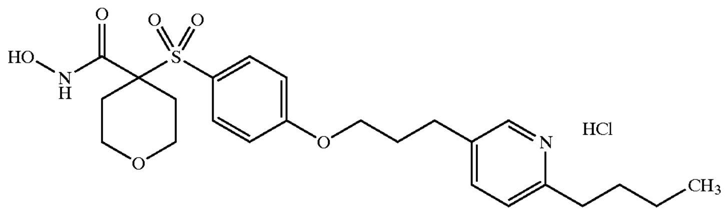 | | | (>10000) | (29.3) | (141) | (0.226) | (6680) |
| 534 | 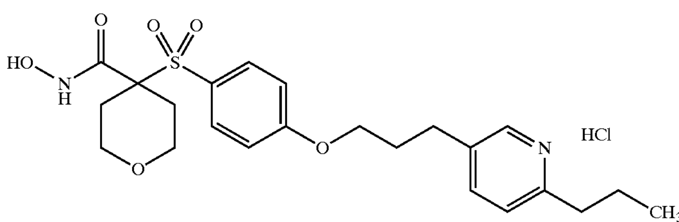 | | | (>10000) | (25.4) | (324) | (0.493) | (6810) |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 535 | 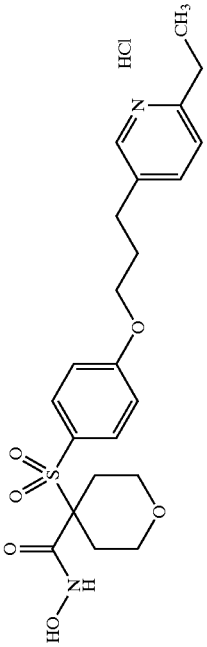 | | | (>10000) | (23.2) | (128) | (0.261) | (3870) |
| 536 | 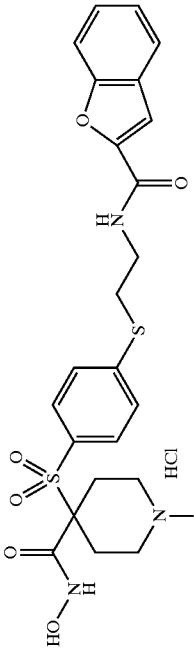 | | | (>10000) | (744) | (3400) | (3.4) | (>10000) |
| 537 | 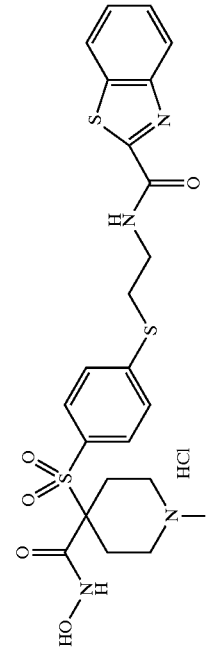 | 535.1138 | 535.1160 | (>10000) | (985) | (900) | (0.657) | (>10000) |
| 538 | 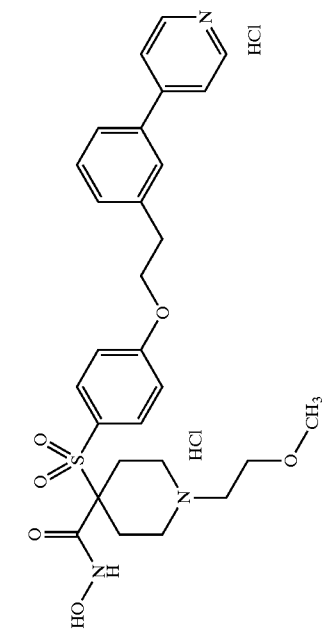 | 540.2163 | 540.2142 | (>10000) | (24.6) | (117) | (0.184) | (1700) |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 539 | 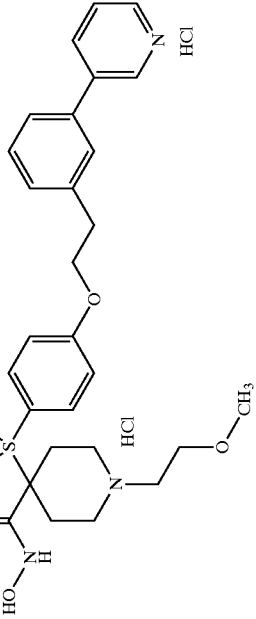 | 540.2163 | 540.2160 | (9130) | (38.6) | (85.5) | (0.21) | (1180) |
| 540 | 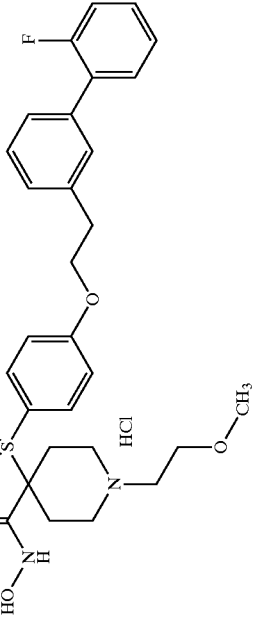 | 557.2116 | 557.2132 | (>10000) | (270) | (689) | (0.58) | (>10000) |
| 541 | 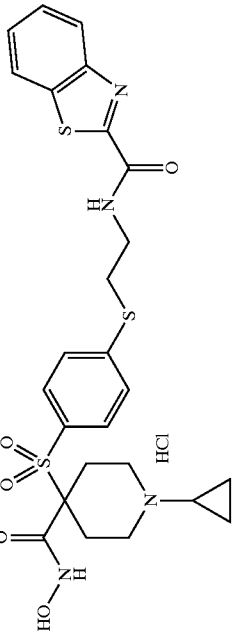 | 561.1295 | 561.1266 | (>10000) | (302.15) | (269.03) | (0.24) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 542 | 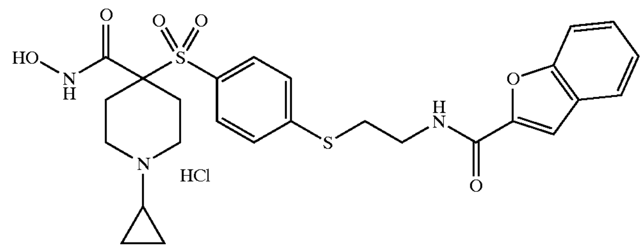 | 544.1571 | 544.1566 | (>10000) | (234.13) | (921.73) | (0.86) | (>10000) |
| 543 | 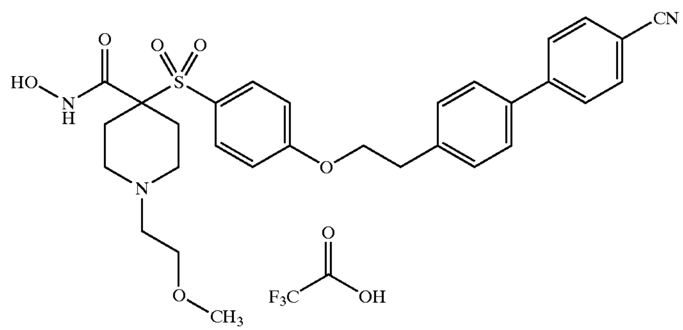 | 564.2163 | 564.2192 | (>10000) | (124.15) | (207.41) | (0.23) | (3094.73) |
| 544 | 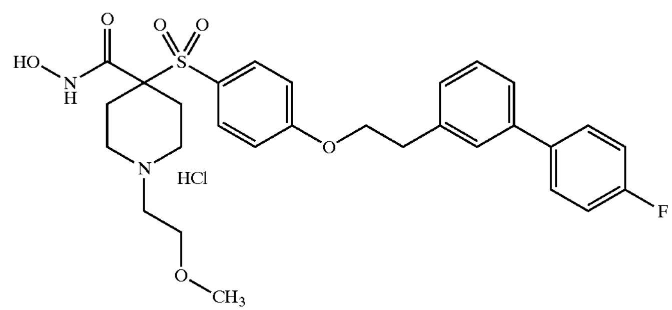 | 557.2116 | 557.2087 | (>10000) | (302.23) | (787.01) | (0.898) | (>10000) |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 545 | 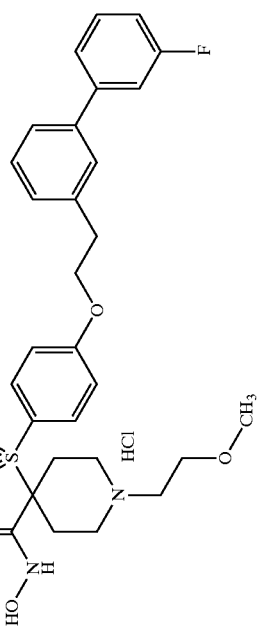 | 557.2116 | 557.2101 | (>10000) | (309.81) | (922.55) | (1.11) | (>10000) |
| 546 | 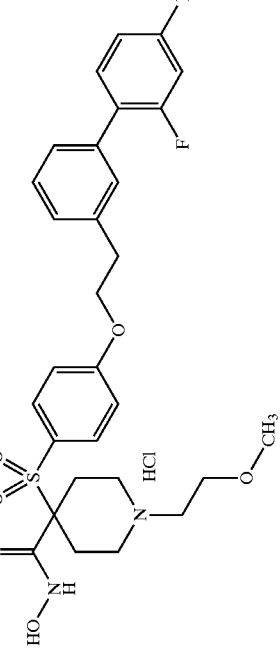 | 575.2022 | 557.5023 | (>10000) | (426.17) | (1269.5) | (1.06) | (>10000) |
| 547 | 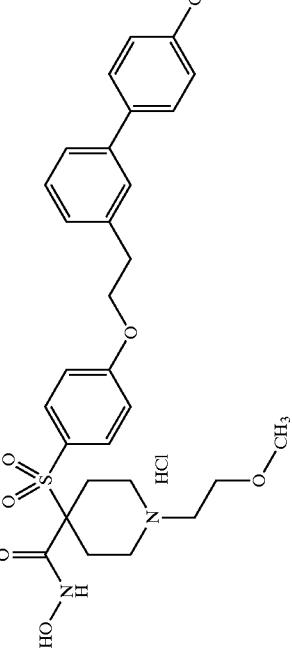 | 573.1821 | 573.1848 | (>10000) | (727.08) | (1863.44) | (2.28) | (>10000) |

TABLE 7-continued
| Ex # | Structure | Calc. Mass | Ob- served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 548 | 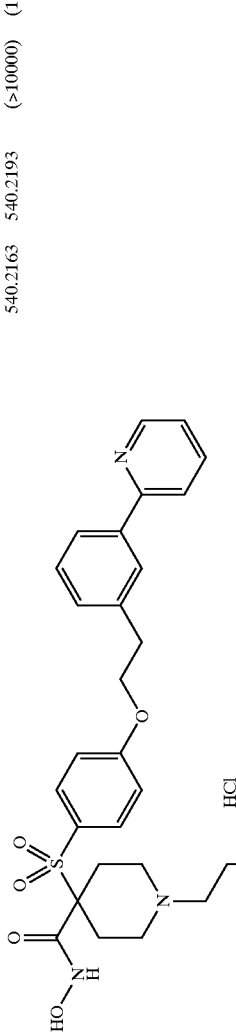 | 540.2163 | 540.2193 | (>10000) | (1.58) | (278.57) | (0.38) | (7415.08) |
| 549 | 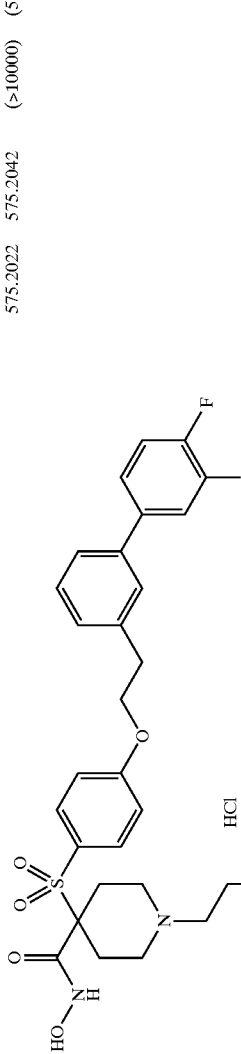 | 575.2022 | 575.2042 | (>10000) | (503.95) | (1770.79) | (1.87) | (>10000) |
| 550 | 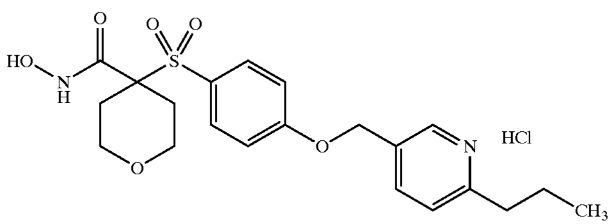 | | | (>10000) | (5.49) | (7.51) | (0.52) | (2180) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 551 | 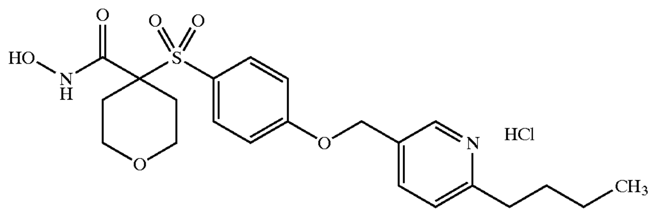 | | | (>10000) | (5.07) | (48.2) | (0.62) | (2055) |
| 552 | 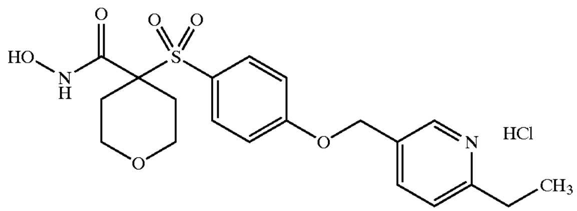 | | | | (4.94) | (2.22) | (1.78) | (2440) |
| 553 | 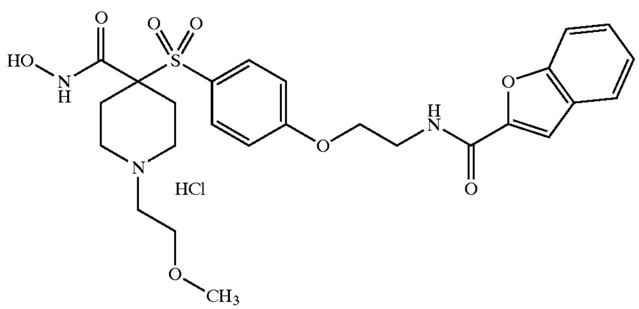 | 546.1905 | 546.1896 | (>10000) | (7.797) | (71.205) | (0.259) | (2257.112) |
| 554 | 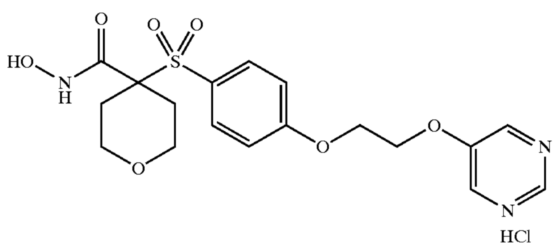 | | | (>10000) | (61.27) | (442.07) | (14.50) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 555 | 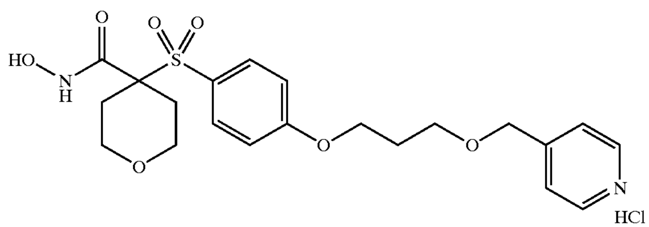 | | | (>10000) | (3.383) | (50.012) | (0.261) | (688.63) |
| 556 | 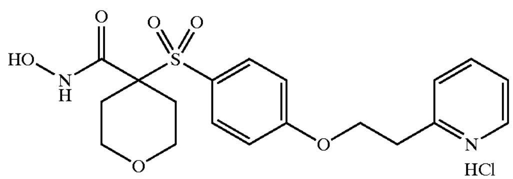 | | | (8972.84) | (68.058) | (211.92) | (53.22) | (3496.68) |
| 557 | 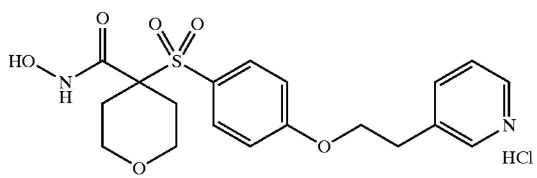 | | | (>10000) | (6.46) | (33.57) | (3.68) | (52.23) |
| 558 | 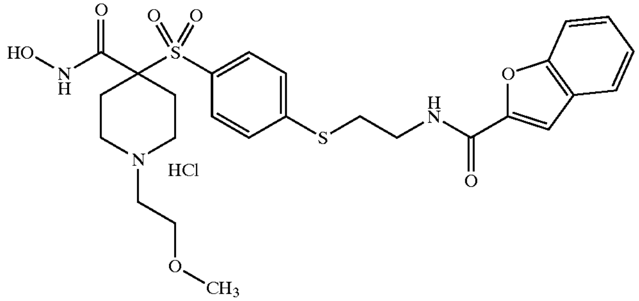 | 562.1676 | 562.1714 | (>10000) | (352.06) | (1357.7) | (2.163) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 559 | 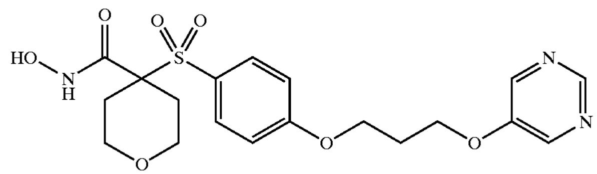 | | | (>10000) | (11.65) | (57.56) | (1.51) | (845.5) |
| 560 | 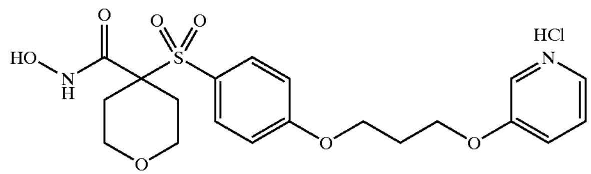 | | | (>10000) | (10.26) | (7.17) | (0.616) | (549.16) |
| 561 | 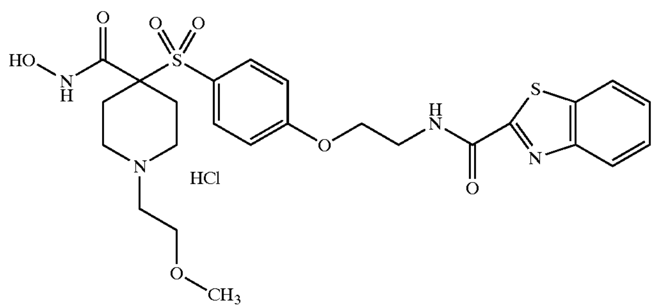 | 579.1400 | 579.1389 | (>10000) | (336.04) | (467.44) | (0.31) | (>10000) |
| 562 | 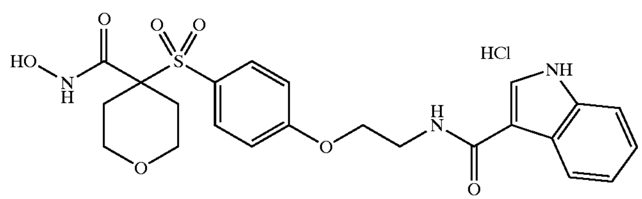 | 488.1486 | 488.1476 | (2738.33) | (241.03) | (785.83) | (2.97) | (9265.67) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 563 | 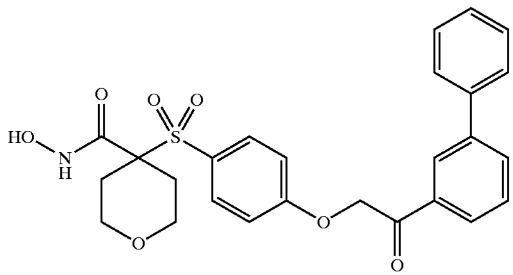 | 496.1425 | 496.1453 | (>10000) | 73.5 (70.11) | (132.06) | 1.1 (0.70) | (4400.5) |
| 564 | 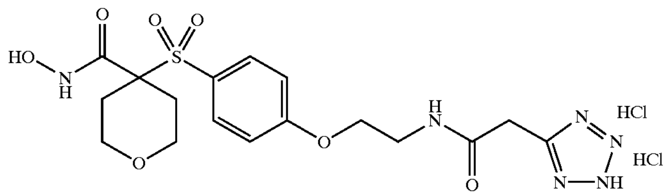 | 455.1343 | 455.1345 | | 144.9 | | 19.4 | |
| 565 | 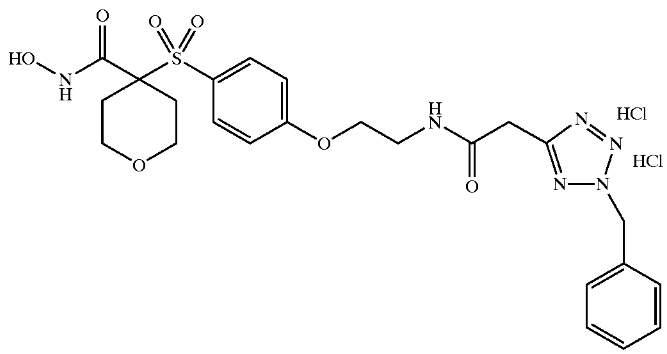 | 545.1813 | 545.1825 | | 14.0 | | 1.6 | |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 566 | 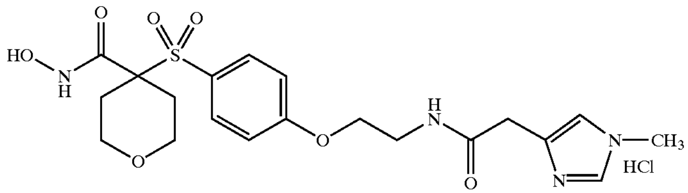 | 467.1595 | 467.1643 | | 65.7 | | 18.8 | |
| 567 | 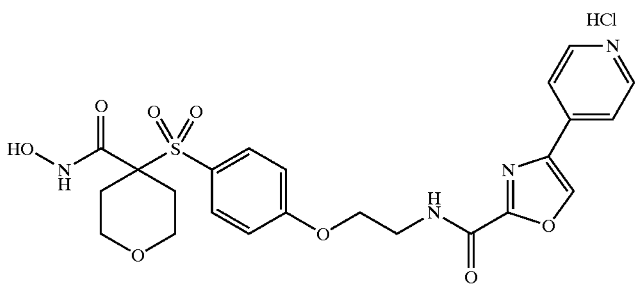 | 549.0931 | 549.0955 | | 660.5 | | 21.9 | |
| 568 | 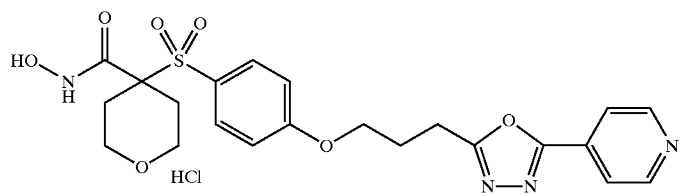 | 489.1438 | 489.1435 | | 21.0 | | 1.5 | |
| 569 | 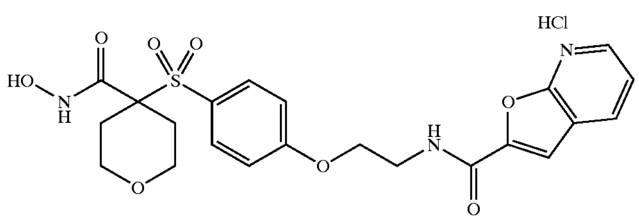 | 506.1050 | 506.1028 | | 1405 | | 171.8 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 570 | 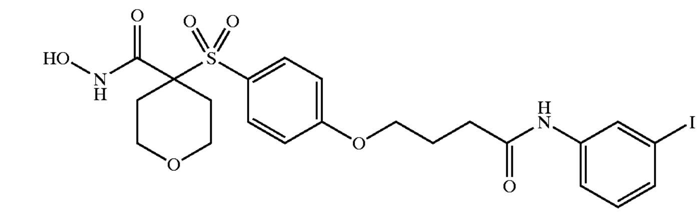 | | | (3061.49) | 4.8 (10.09) | (6.15) | 0.2 (0.142) | (1357.46) |
| 571 | 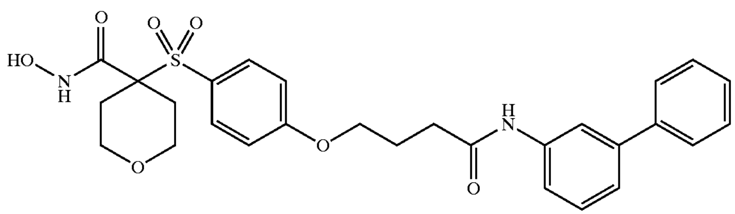 | | | | 11.9 | | 1.6 | |
| 572 | 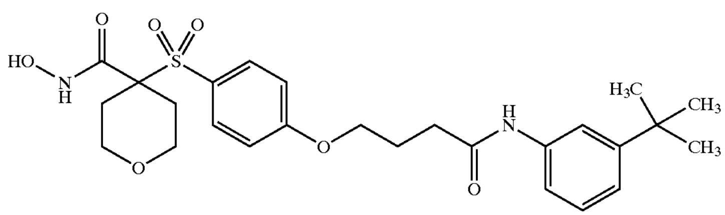 | | | | 37.3 | | 4.7 | |
| 573 | 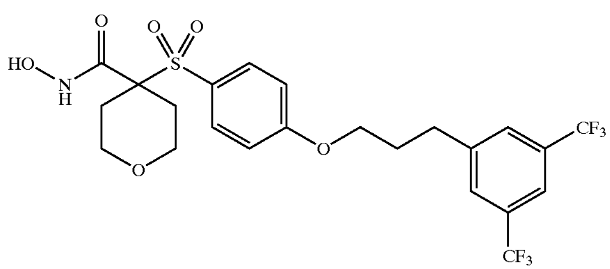 | 556.1223 | 556.1214 | | 1707.7 | | 75.1 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 574 | 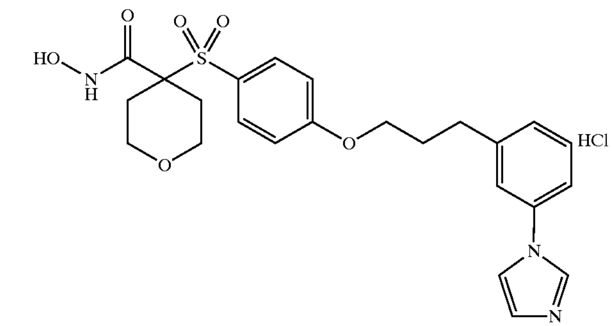 | | | (>10000) | 29.4 (112.25) | (83.02) | 0.7 (1.32) | (5386.06) |
| 575 | 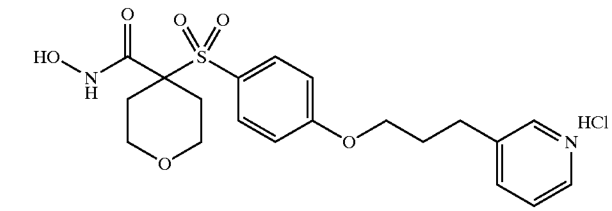 | | | | 8.4 | | 2.0 | |
| 576 | 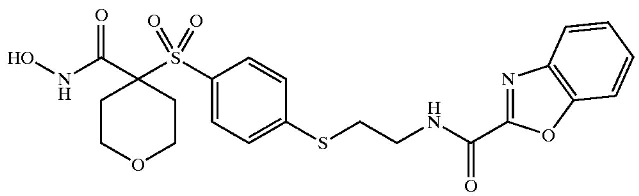 | 506.1050 | 506.1069 | >10000 | 232.7 | 397.0 | 0.3 | >10000 |
| 577 | 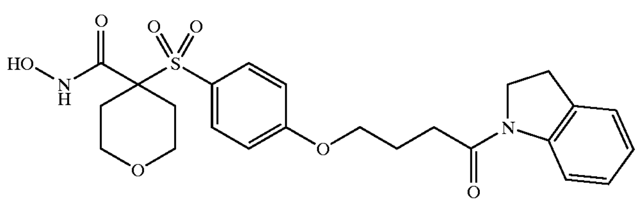 | | | | 48.2 | | 1.2 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 578 | | | 489.1438 | 489.1428 | (>10000) | 20.5 (72.1) | (578) | 2.9 (1.72) | (>10000) |
| 579 | 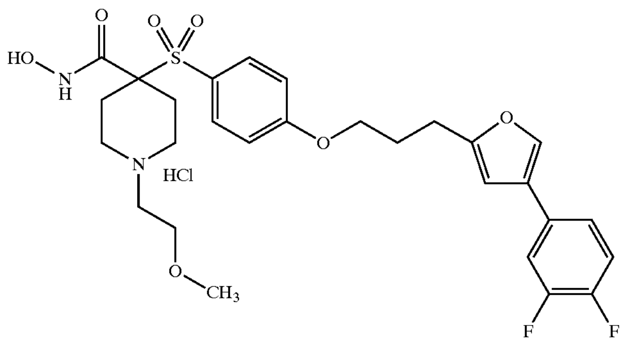 | 595.1743 | 595.1767 | >10000 | 37.8 | 136.0 | 0.4 | >10000 |
| 580 | 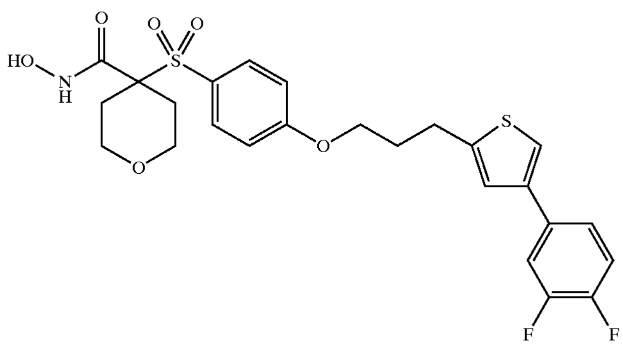 | 555.1430 | 555.1454 | >10000 | 136.0 | 417.2 | 0.6 | >10000 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 581 | 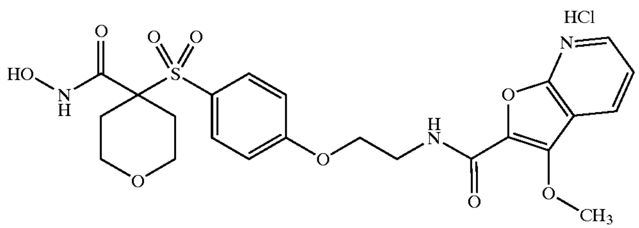 | 536.1156 | 536.1173 | | 2534.3 | | 29.8 | |
| 582 | 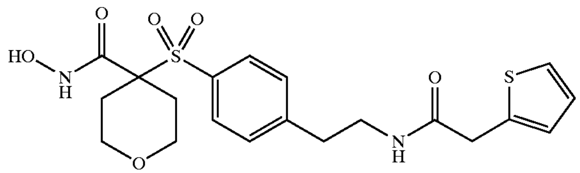 | 460.1571 | 460.1573 | | 55.7 | | 25.3 | |
| 583 | 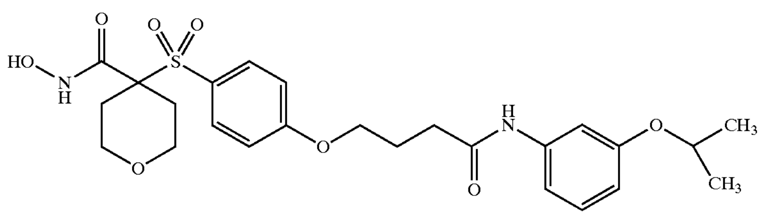 | | | | 15.7 | | 1.6 | |
| 584 | 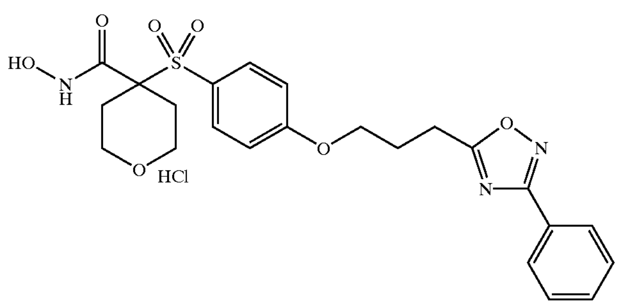 | | | (2760) | 72.9 (20.8) | (12.6) | 3.6 (0.944) | (6630) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 585 | 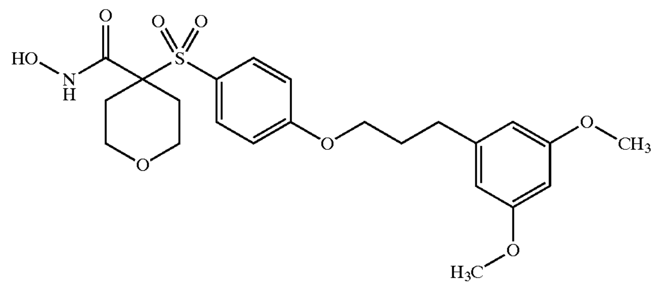 | | | | 85.4 | | 4.0 | |
| 586 | 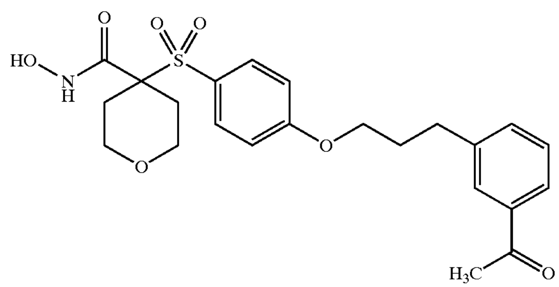 | | | | 10.1 | | 0.6 | |
| 587 | 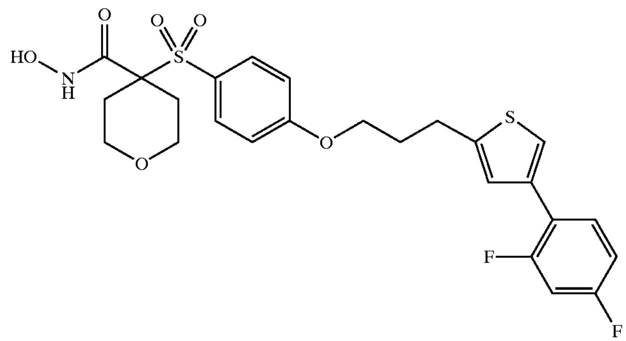 | 538.1164 | 538.1191 | >10000 (>10000) | 81.7 (124.9) | 1372.9 (8180) | 0.1 (1.424) | >10000 (4154) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 588 | 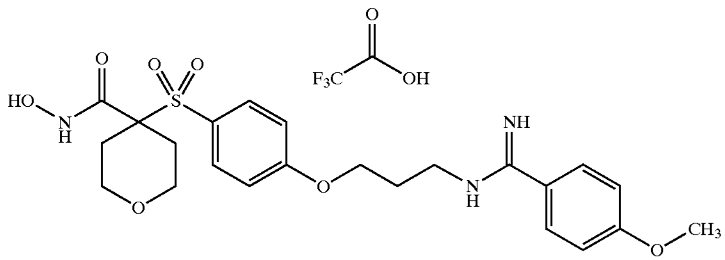 | 492.1804 | 492.1773 | | 94.9 | | 15.0 | |
| 589 | 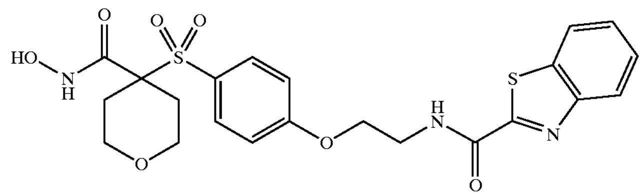 | 506.1050 | 506.1054 | | 9.9 | | 0.4 | |
| 590 | 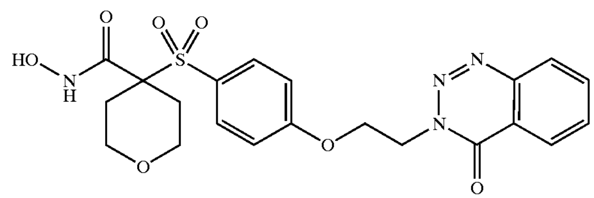 | | | | 857.7 | | 48.0 | |
| 591 | 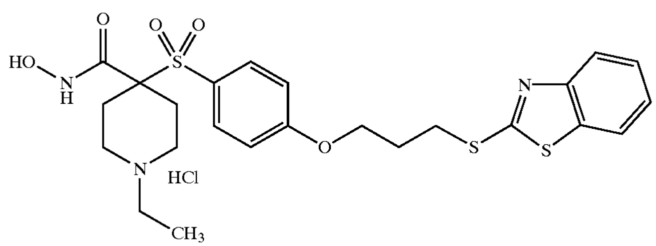 | 536.1348 | 536.1372 | >10000 (>10000) | 3.5 (4.4) | 12.0 (4.22) | 0.3 (0.19) | >10000 (8742.7) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 592 | 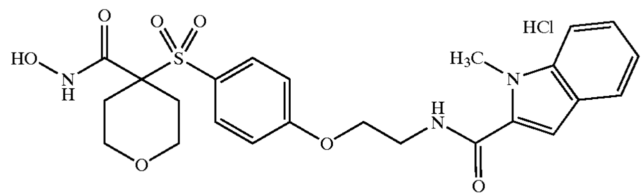 | 502.1648 | 502.1639 | | 336.4 | | 38.7 | |
| 593 | 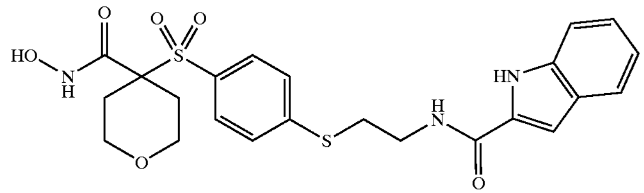 | 504.1263 | 504.1254 | | 6.5 | | 15.6 | |
| 594 | 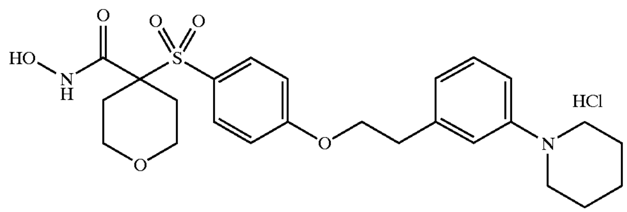 | | | | 140.1 | | 3.8 | |
| 595 | 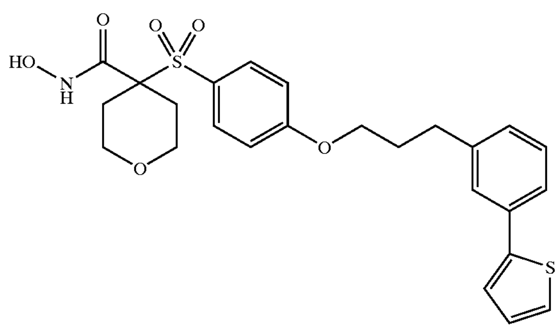 | 502.1353 | 502.1359 | >10000 (>10000) | 482.5 (586.2) | 1733 (2056.6) | 1.0 (7.245) | >10000 (>10000) |

TABLE 7-continued

| Ex # | Structure | Calc. Mass | Ob- served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 596 | 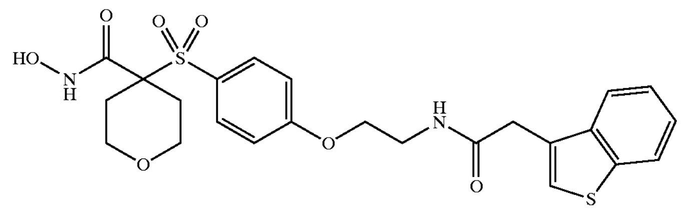 | 519.1260 | 519.1265 | >10000 (>10000) | 10.3 (11.2) | 194.5 (307.7) | 2.7 (0.398) | 2491 (1160) |
| 597 | 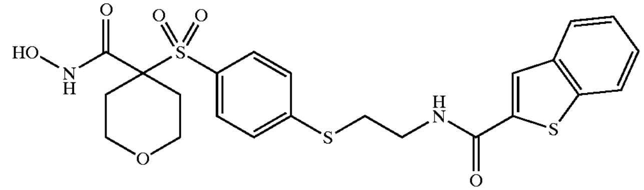 | 521.0875 | 521.0910 | | 471.1 | | 12.1 | |
| 598 | 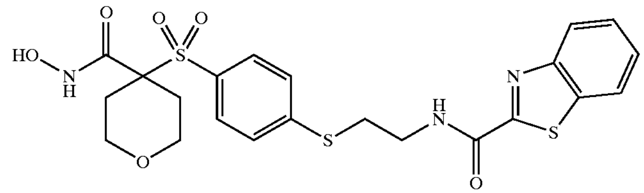 | 522.0827 | 522.0932 | (>10000) | (599.35) | (705.33) | (0.27) | (>10000) |
| 599 | 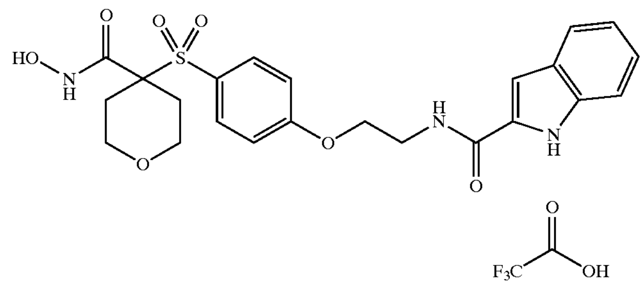 | 488.1491 | 488.1491 | >10000 (>10000) | <0.1 (0.38) | 11.6 (11.34) | 0.1 (0.24) | 57.01 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 600 | 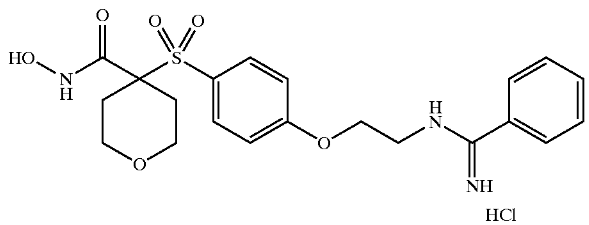 | 448.1542 | 448.1542 | | 205.7 | | 214.4 | 2062 |
| 601 | 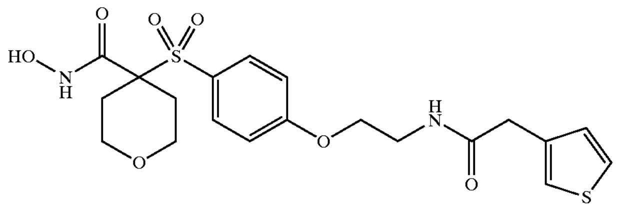 | 469.1103 | 469.1093 | 4916 | 1.9 | 42.6 | 1.3 | |
| 602 | 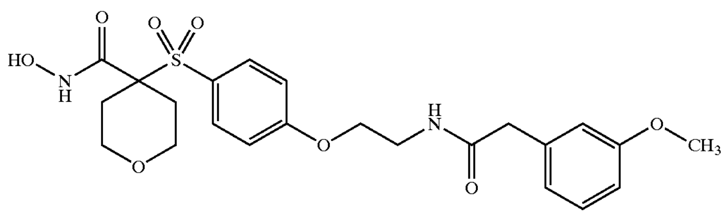 | 493.1639 | 493.1608 | | 13.7 | | 3.6 | |
| 603 | 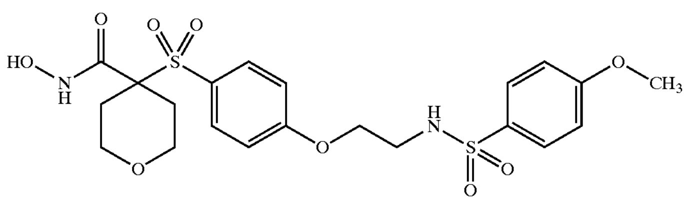 | 515.1158 | 515.1145 | | 34.0 | | 2.4 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 604 | 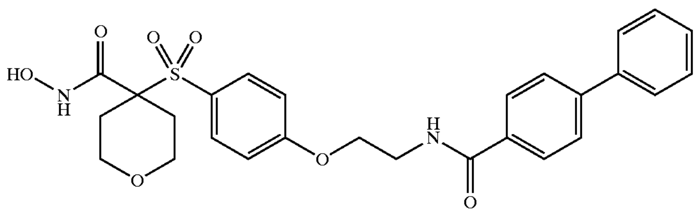 | | | | 36.6 | | 3.3 | |
| 605 | 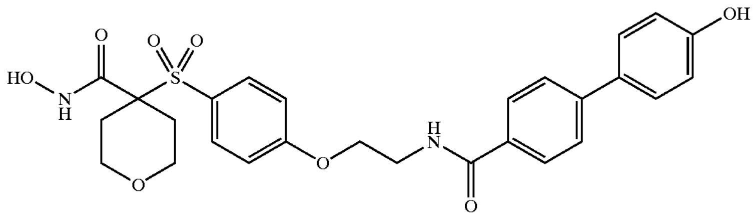 | | | | 44.0 | | 3.8 | |
| 606 | 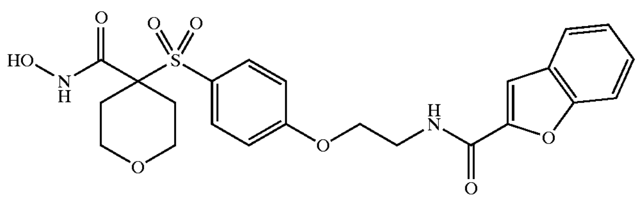 | 489.1332 | 489.1326 | >10000 (>10000) | 5.0 (11.574) | 234.0 (105.89) | 0.4 (0.432) | 2566 (2053.20) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 607 | 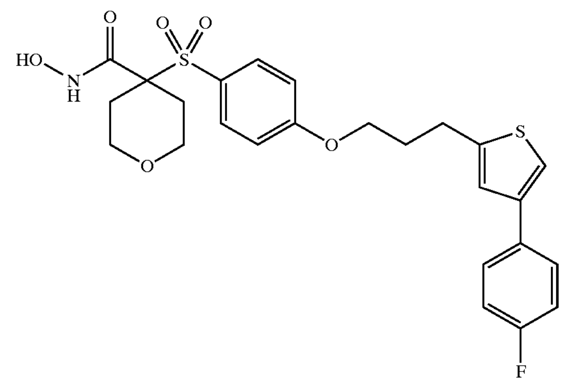 | 520.1264 | 520.1297 | >10000 | 45.2 | 2298 | 0.1 | >10000 |
| 608 | 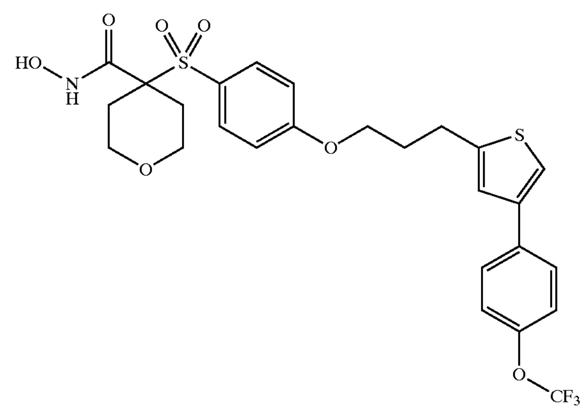 | 586.1181 | 586.1160 | >10000 (>10000) | 342.1 (723.95) | 1794 (1368.3) | 6.6 (9.34) | >10000 (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 609 | 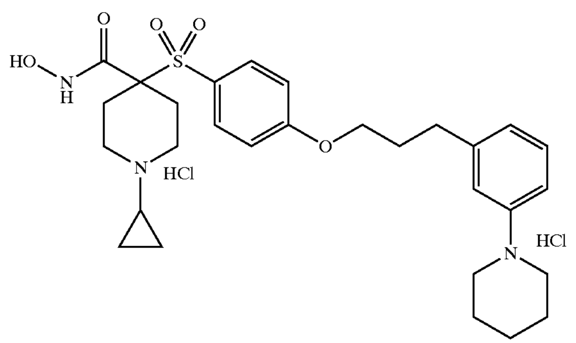 | | | >10000 | 579.9 | 6887 | 7.7 | >10000 |
| 610 | 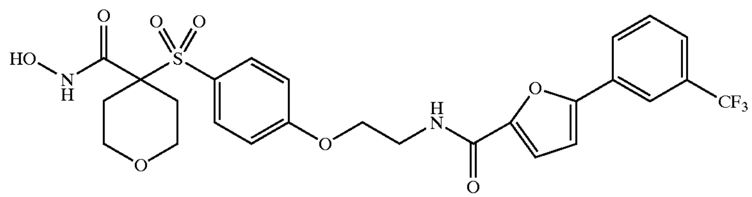 | | | | 488.3 | | 4.1 | |
| 611 | 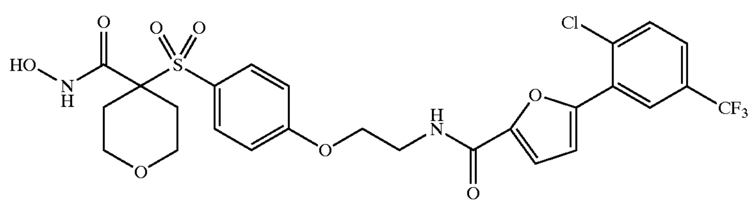 | | | | 733.2 | | 13.6 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 612 | 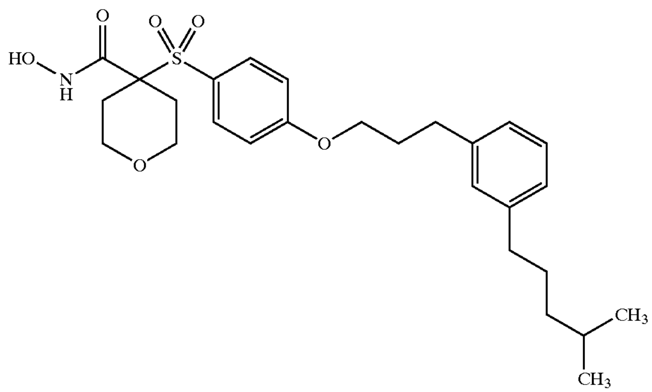 | 504.2414 | 504.2413 | | 1232.2 | | 16.1 | |
| 613 | 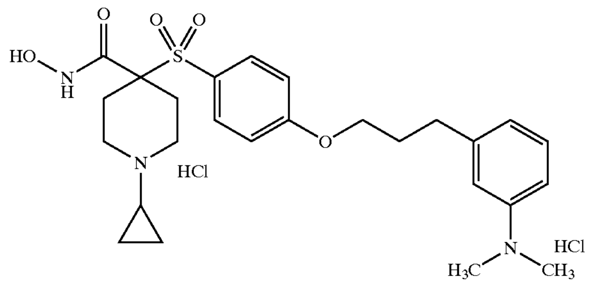 | 562.1504 | 562.1516 | | 34.3 | | 6.6 | |
| 614 | 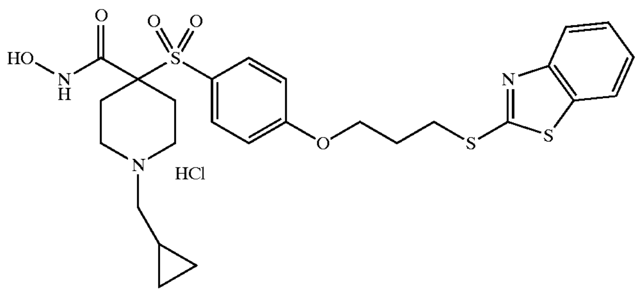 | | | >10000 | 1.8 | 8.5 | 0.7 | 9440 |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 615 | 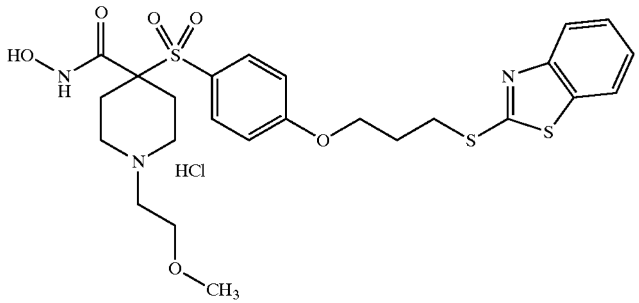 | 566.1443 | 566.1453 | >10000 | 1.1 | 3.6 | 0.4 | 6696 |
| 616 | 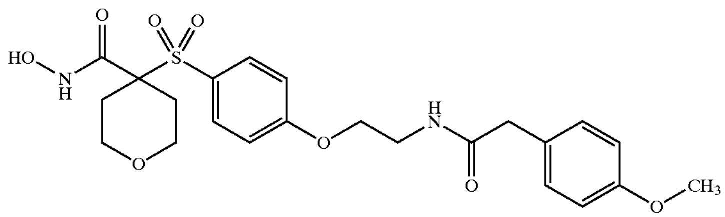 | 493.1645 | 493.1617 | 1584 | 5.3 | 54.8 | 2.0 | 1969 |
| 617 | 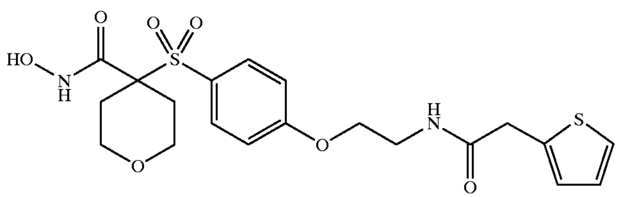 | 469.1103 | 469.1086 | 2074 1112 | 0.8 | 413 | 0.6 | 4133 |
| 618 | 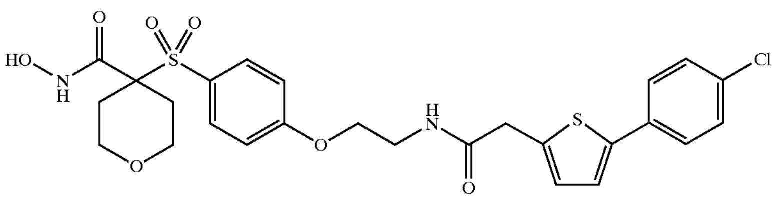 | | | | 822.1 | | 27.5 | |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 619 | 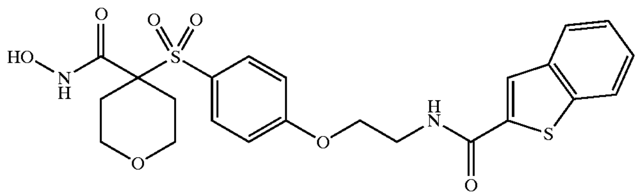 | | | | 66.2 | | 1.5 | |
| 620 | 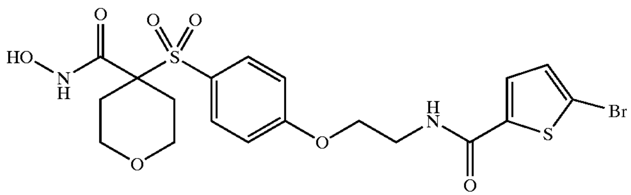 | 488.1491 | 488.1489 | | 16.2 | | 4.1 | |
| 621 | 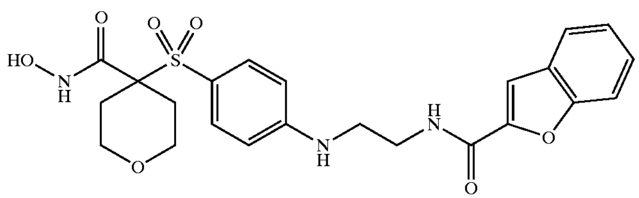 | 505.1103 | 505.1120 | | 367.7 | | 17.8 | |
| 622 | 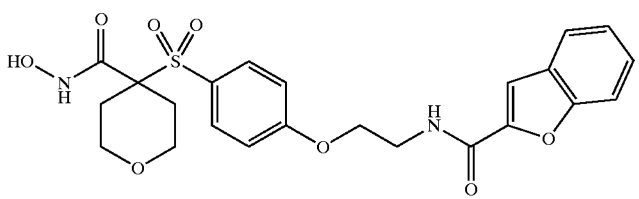 | | | >10000 (>10000) | 273.1 (450.85) | 1756 (2077.1) | 1.5 (2.68) | >10000 (>10000) |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 623 | 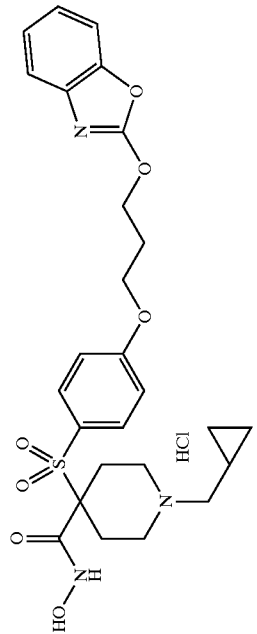 | 546.1733 | 546.1728 | >10000 | 5.2 | 3.1 | 1.2 | 5520 |
| 624 | 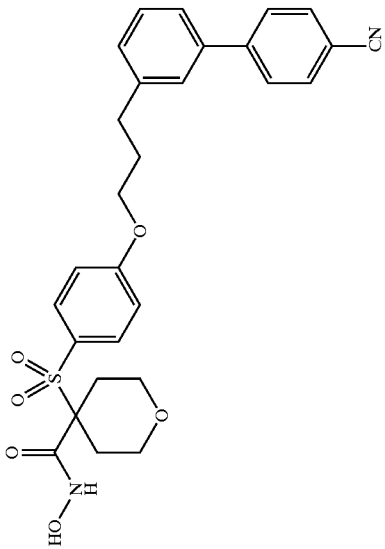 | 521.1746 | 521.1753 | >10000 (>10000) | 214.4 (623) | 1029 (443) | 0.3 (0.9) | >10000 (7580) |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 625 | 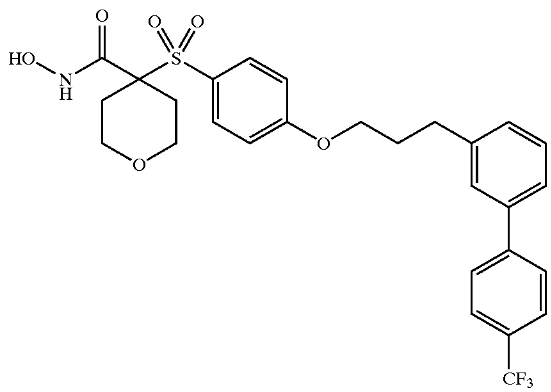 | 564.1668 | 564.1643 | (>10000) | 3499.5 (6860) | (4600) | 33.6 (43.6) | (>10000) |
| 626 | 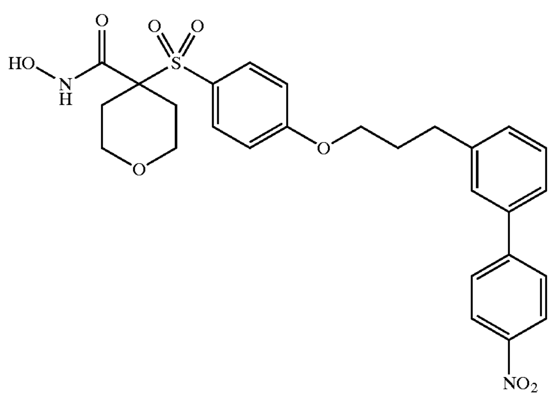 | 558.191 | 558.1925 | >10000 (>10000) | 142.8 (645) | 885 (1100) | 0.4 (7.5) | >10000 (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 627 | 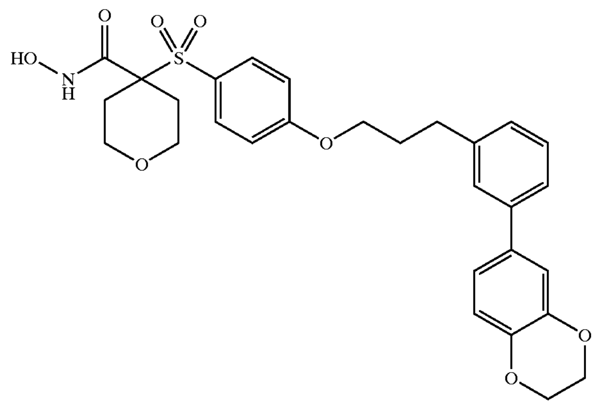 | 554.1849 | 554.1884 | (>10000) | 2072.7 (3950) | (3150) | 14.9 (40.9) | (>10000) |
| 628 | 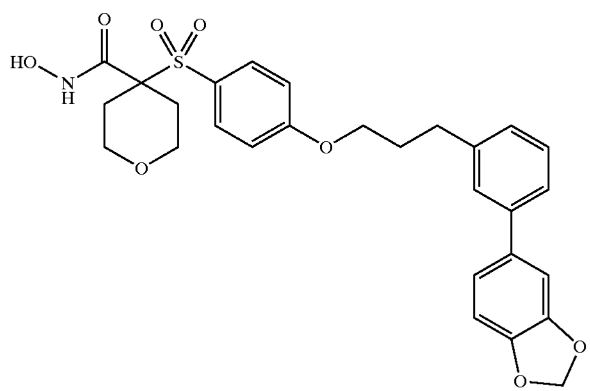 | 540.1692 | 540.1712 | >10000 (>10000) | 1701.3 (2750) | 1754 (1930) | 3.3 (19.8) | >10000 (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 629 | 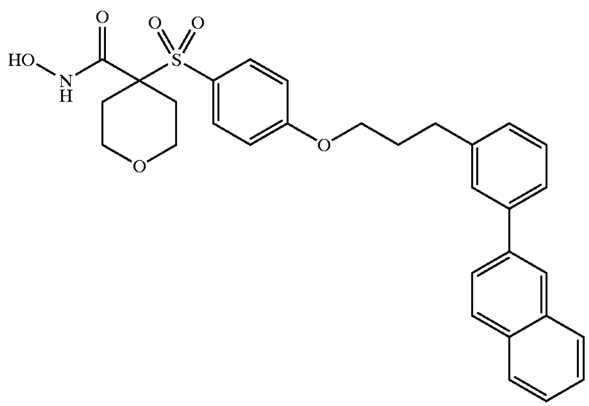 | 546.1950 | 546.1965 | >10000 (>10000) | 536.8 (1020) | (1300) | 78.6 (89.1) | (>10000) |
| 630 | 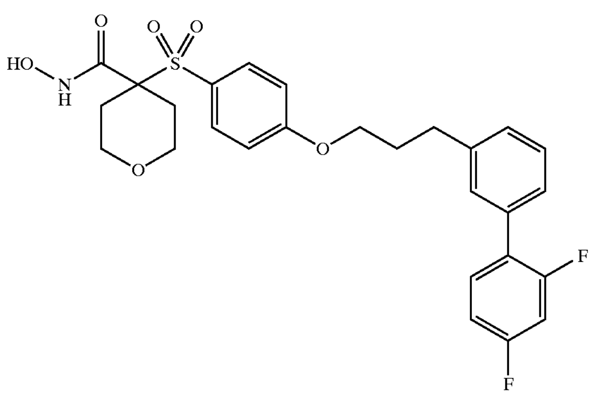 | 532.1605 | 532.1598 | >10000 (>10000) | 1166.6 (2070) | 5990 (2280) | 0.4 (6.02) | >10000 (>10000) |

TABLE 7-continued

| Ex # | Structure | Calc. Mass | Ob- served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 631 | 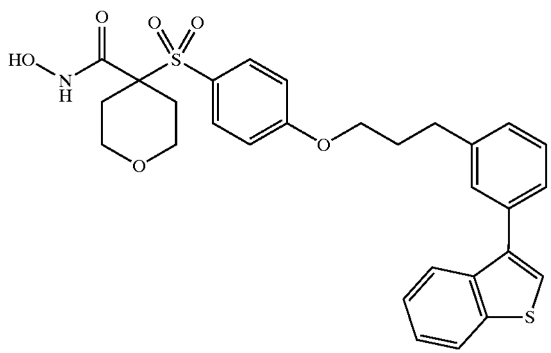 | 552.1515 | 552.1520 | (>10000) | 2143.2 (4960) | (5810) | 117.7 (57.6) | (>10000) |
| 632 | 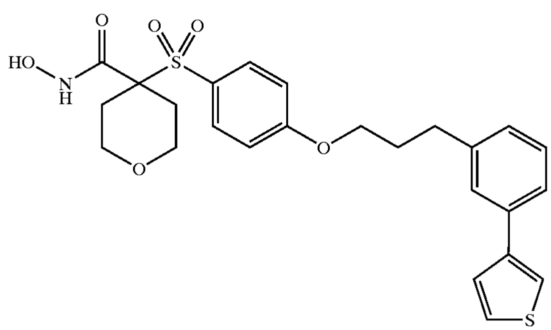 | 502.1358 | 502.1387 | >10000 (>10000) | 91.0 (279) | 411 (716) | 1.6 (6.54) | >10000 (>10000) |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 633 | 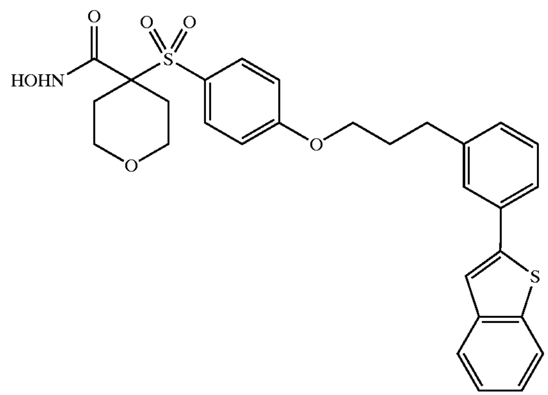 | 552.1515 | 552.1510 | (>10000) | 2828.1 (4580) | (6780) | 117.0 (92.4) | (>10000) |
| 634 | 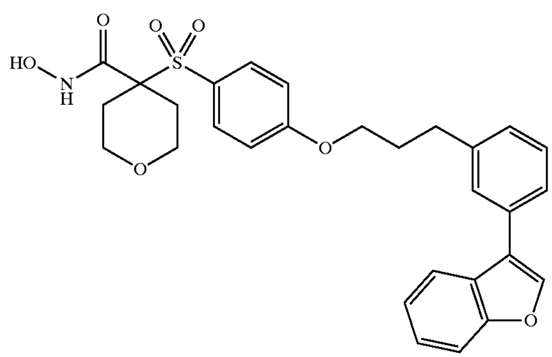 | 536.1743 | 536.1730 | (>10000) | 486.4 (983) | (1300) | 16.3 (19.4) | (>10000) |

TABLE 7-continued

| Ex # | Structure | Calc. Mass | Ob-served Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 635 | 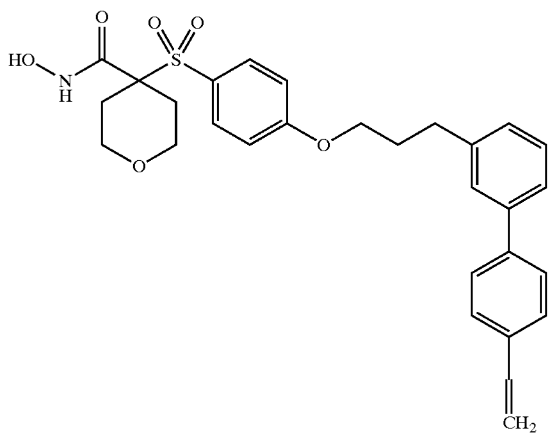 | 522.1950 | 522.1973 | (>10000) | 2309.5 (4680) | (4830) | 20.0 (26.2) | (>10000) |
| 636 | 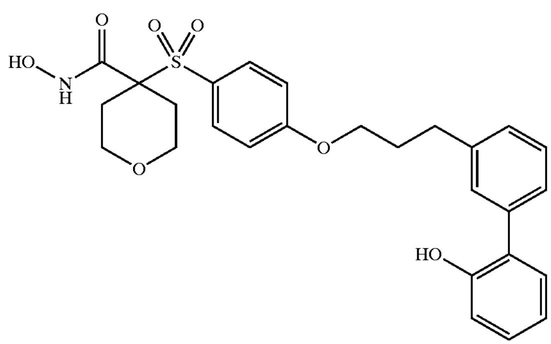 | 512.1743 | 512.1755 | (>10000) | 195.0 (527) | (763) | 3.2 (3.21) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 637 | 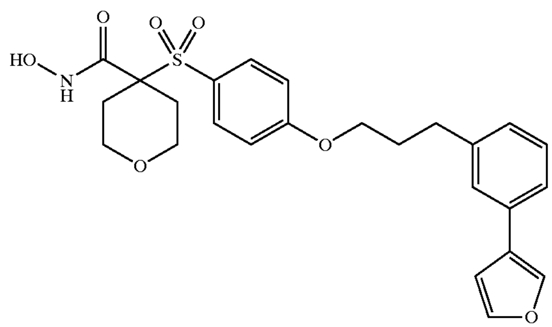 | 486.1586 | 486.1576 | >10000 (>10000) | 137.6 (498) | 830 (881) | 1.8 (4.63) | >10000 (>10000) |
| 638 | 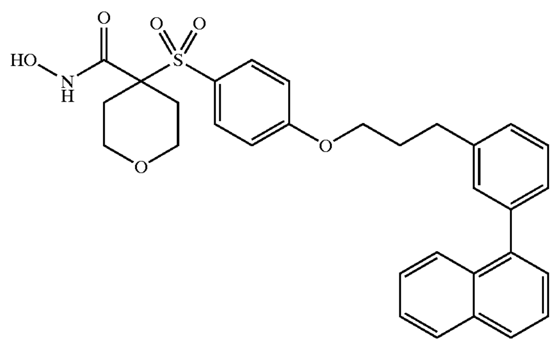 | 546.1950 | 546.1950 | (>10000) | 4400.9 (8120) | (8770) | 400.4 (68.1) | (>10000) |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 639 | 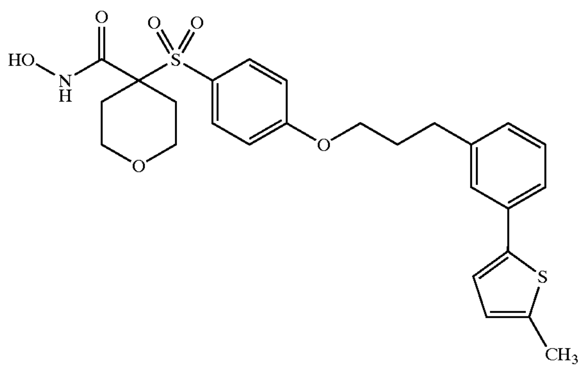 | 516.1515 | 516.1501 | (>10000) | 247.1 (505) | (688) | 4.3 (12.5) | (>10000) |
| 640 | 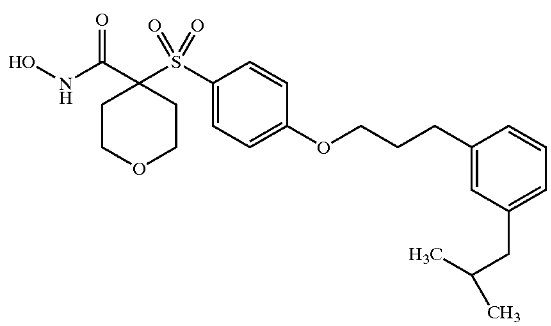 | 476.2101 | 476.2114 | | 324.5 | | 10.4 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 641 | 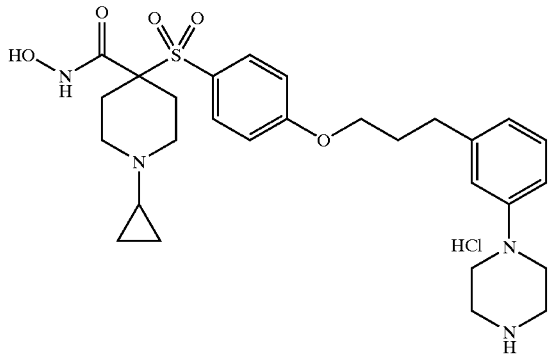 | | | | 134.7 | | 5.0 | |
| 642 | 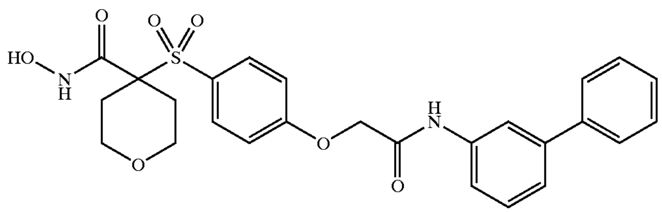 | 528.1799 | 528.1771 | | 2889.0 | | 36.9 | |
| 643 | 4-[(4-{3-[[(1-adamantylcarbonyl)amino]propoxy]phenyl}sulfonyl]-1-cyclopropyl-N-hydroxypiperidine-4-carboxamide hydrochloride | 560.2794 | 560.2793 | | 1134.1 | | 11.4 | |

TABLE 7-continued

| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 644 | 4-[(4-{3-[(1-adamantylcarbonyl)(methyl)amino]propoxy}phenyl)sulfonyl]-1-cyclopropyl-N-hydroxypiperidine-4-carboxamide hydrochloride | 574.2951 | 574.2943 | | 2633.4 | | 20.9 | |
| 645 | 4-[(4-{3-[(2-adamantylamino)sulfonyl]propoxy}phenyl)sulfonyl]-N-hydroxytetrahydro-2H-pyran-4-carboxamide | 557 | 557 | 9283 | 22.9 | 1729 | 4.3 | >10000 |

TABLE 7-continued
| Ex # | Structure | Calc. Mass | Observed Mass | MMP-1 IC$_{50}$ (Ki) | MMP-2 IC$_{50}$ (Ki) | MMP-9 IC$_{50}$ (Ki) | MMP-13 IC$_{50}$ (Ki) | MMP-14 IC$_{50}$ (Ki) |
|---|---|---|---|---|---|---|---|---|
| 646 | 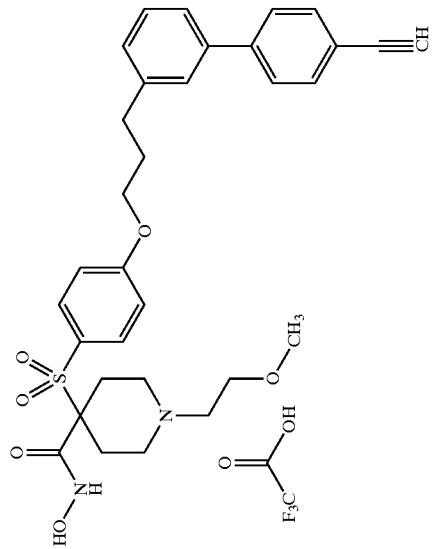 | | | (>10000) | (288.84) | (76.21) | (0.16) | (4296.95) |

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A compound or salt thereof, wherein: the compound corresponds in structure to Formula 122-1:

(122-1)

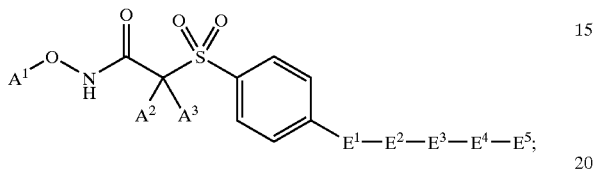

and $A^1$ is selected from the group consisting of —H, alkylcarbonyl, alkoxycarbonyl, carbocyclylcarbonyl, carbocyclylalkylcarbonyl, heterocyclylcarbonyl, heterocyclylalkylcarbonyl, carbocyclyloxycarbonyl, carbocyclylalkoxycarbonyl, aminoalkylcarbonyl, alkyl(thiocarbonyl), alkoxy(thiocarbonyl), carbocyclyl(thiocarbonyl), carbocyclylalkyl(thiocarbonyl), heterocyclyl(thiocarbonyl), heterocyclylalkyl(thiocarbonyl), carbocyclyloxy(thiocarbonyl), carbocyclylalkoxy(thiocarbonyl), and aminoalkyl(thiocarbonyl), wherein any member of such group optionally is substituted; and $A^2$ and $A^3$, together with the carbon atom to which they are both attached, form an optionally-substituted heterocyclyl containing from 5 to 8 ring members; and $E^1$ is selected from the group consisting of —O—, —S(O)$_2$—, and —S(O)—; and $E^2$ is alkyl, wherein the alkyl optionally is substituted; and $E^2$ forms a link of at least 2 carbon atoms between $E^1$ and $E^3$; and $E^3$ is heterocyclyl, wherein the heterocyclyl has 5 or 6 ring members and optionally is substituted; and $E^4$ is selected from the group consisting of a bond, alkyl, alkenyl, —O—, and, —N(R$^3$)—, wherein the alkyl or alkenyl optionally is substituted; and $E^5$ is selected from the group consisting of carbocyclyl and heterocyclyl, wherein the carbocyclyl or heterocyclyl optionally is substituted; and $R^3$ is selected from the group consisting of —H and alkyl, wherein the alkyl optionally is substituted.

2. A compound or salt thereof according to claim 1, wherein:

$A^1$ is selected from the group consisting of —H, $C_1$–$C_8$-alkylcarbonyl, $C_1$–$C_8$-alkoxycarbonyl, carbocyclylcarbonyl, carbocyclyl-$C_1$–$C_8$-alkylcarbonyl, heterocyclylcarbonyl, heterocyclyl-$C_1$–$C_8$-alkylcarbonyl, carbocyclyloxycarbonyl, carbocyclyl-$C_1$–$C_8$-alkoxycarbonyl, N(R$^4$)(R$^5$)—$C_1$–$C_8$-alkylcarbonyl, $C_1$–$C_8$-alkyl(thiocarbonyl), $C_1$–$C_8$-alkoxy(thiocarbonyl), carbocyclyl(thiocarbonyl), carbocyclyl-$C_1$–$C_8$-alkyl(thiocarbonyl), heterocyclyl(thiocarbonyl), heterocyclyl-$C_1$–$C_8$-alkyl(thiocarbonyl), carbocyclyloxy(thiocarbonyl), carbocyclyl-$C_1$–$C_8$-alkoxy(thiocarbonyl), and N(R$^4$)(R$^5$)—$C_1$–$C_8$-alkyl(thiocarbonyl); and $E^2$ is $C_2$–$C_{20}$-alkyl, wherein the $C_2$–$C_{20}$-alkyl optionally is substituted with one or more substituents independently selected from the group consisting of halogen, $C_1$–$C_6$-alkyl, and halo-$C_1$–$C_6$-alkyl; and $E^3$ is heterocyclyl, wherein the heterocyclyl:
has 5 or 6 ring members, and
optionally is substituted with one or more substituents independently selected from the group consisting of halogen, —OH, keto, $C_1$–$C_8$-alkyl, $C_1$–$C_8$-alkoxy, $C_1$–$C_8$-alkoxy-$C_1$–$C_8$-alkyl, carbocyclyl, carbocyclyl-$C_1$–$C_8$-alkyl, heterocyclyl, and heterocyclyl-$C_1$–$C_8$-alkyl, wherein:
any such substituent optionally is substituted with one or more substituents independently selected from the group consisting of halogen, —OH, $C_1$–$C_8$-alkyl, $C_1$–$C_8$-alkoxy, $C_1$–$C_8$-alkoxy-$C_1$–$C_8$-alkyl, $C_1$–$C_8$-alkylthio, halo-$C_1$–$C_8$-alkyl, halo-$C_1$–$C_8$-alkoxy, halo-$C_1$–$C_8$-alkylthio, and halogen-substituted $C_1$–$C_8$-alkoxy-$C_1$–$C_8$-alkyl; and $E^4$ is selected from the group consisting of a bond, —O—, —N(R$^3$)—, $C_1$–$C_{20}$-alkyl, and $C_2$–$C_{20}$-alkenyl, wherein the $C_2$–$C_{20}$-alkyl or $C_2$–$C_{20}$-alkenyl optionally is substituted with one or more substituents independently selected from the group consisting of:
halogen, and
carbocyclyl optionally substituted with one or more substituents independently selected from the group consisting of halogen, —OH, —NO$_2$, —CN, $C_1$–$C_8$-alkyl, $C_1$–$C_8$-alkoxy, $C_1$–$C_8$-alkoxy-$C_1$–$C_8$-alkyl, carbocyclyl, carbocyclyl-$C_1$–$C_8$-alkyl, halo-$C_1$–$C_8$-alkyl, halo-$C_1$–$C_8$-alkoxy, halocarbocyclyl, halogen-substituted carbocyclyl-$C_1$–$C_8$-alkyl, and halogen-substituted $C_1$–$C_8$-alkoxy-$C_1$–$C_8$-alkyl; and $E^5$ is selected from the group consisting of carbocyclyl and heterocyclyl, wherein the carbocyclyl or heterocyclyl optionally is substituted with one or more substituents independently selected from the group consisting of halogen, —OH, —NO$_2$, —CN, keto, $C_1$–$C_8$-alkyl, $C_2$–$C_8$-alkenyl, $C_2$–$C_8$-alkynyl, $C_1$–$C_8$-alkoxy, $C_1$–$C_8$-alkoxy-$C_1$–$C_8$-alkyl, —N(R$^6$)(R$^7$), —C(O)(R$^8$), —S—R$^6$, —S(O)$_2$—R$^6$, carbocyclyl, carbocyclyl-$C_1$–$C_8$-alkyl, halo-$C_1$–$C_8$-alkyl, halo-$C_1$–$C_8$-alkoxy, halogen-substituted $C_1$–$C_8$-alkoxy-$C_1$–$C_8$-alkyl, halocarbocyclyl, and halogen-substituted carbocyclyl-$C_1$–$C_8$-alkyl; and $R^3$ is selected from the group consisting of —H, $C_1$–$C_8$-alkyl, and halo-$C_1$–$C_8$-alkyl; and $R^4$ and $R^5$ are independently selected from the group consisting of —H, $C_1$–$C_8$-alkyl, $C_1$–$C_8$-alkoxycarbonyl, $C_1$–$C_8$-alkylcarbonyl, carbocyclyl-$C_1$–$C_8$-alkyl, and carbocyclyl-$C_1$–$C_8$-alkoxycarbonyl; and $R^6$ and $R^7$ are independently selected from the group consisting of —H, $C_1$–$C_8$-alkyl, carbocyclyl, carbocyclyl-$C_1$–$C_8$-alkyl, heterocyclyl, heterocyclyl-$C_1$–$C_8$-alkyl, halo-$C_1$–$C_8$-alkyl, halocarbocyclyl, halogen-substituted carbocyclyl-$C_1$–$C_8$-alkyl, haloheterocyclyl, and halogen-substituted heterocyclyl-$C_1$–$C_8$-alkyl; and $R^8$ is selected from the group consisting of —H, $C_1$–$C_8$-alkyl, —O—R$^9$, —N(R$^9$)(R$^{10}$), carbocyclyl-$C_1$–$C_8$- alkyl, heterocyclyl-$C_1$–$C_8$-alkyl, halo-$C_1$–$C_8$-alkyl, halogen-substituted carbocyclyl-$C_1$–$C_8$-alkyl, and halogen-substituted heterocyclyl-$C_1$–$C_8$-alkyl; and $R^9$ and $R^{10}$ are independently selected from the group consisting of —H, $C_1$–$C_8$-alkyl, carbocyclyl, carbocyclyl-$C_1$–$C_8$-alkyl, heterocyclyl, heterocyclyl-$C_1$–$C_8$-alkyl, halo-$C_1$–$C_8$-alkyl, halocarbocyclyl, halogen-substituted carbocyclyl-$C_1$–$C_8$-alkyl, haloheterocyclyl, and halogen-substituted heterocyclyl-$C_1$–$C_8$-alkyl.

3. A compound or salt thereof according to claim 2, wherein $A^1$ is —H.

4. A compound or salt thereof according to claim 3, wherein:

$E^2$ is $C_2$–$C_6$-alkyl optionally substituted with one or more halogen; and $E^3$ is heterocyclyl, wherein the heterocyclyl:
  has 5 or 6 ring members, and
  optionally is substituted with one or more substituents independently selected from the group consisting of halogen, —OH, keto, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl, wherein:
    any such substituent optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio; and $E^4$ is selected from the group consisting of a bond, —O—, —N($R^3$)—, $C_1$–$C_3$-alkyl, and $C_2$–$C_3$-alkenyl, wherein the $C_1$–$C_3$-alkyl or $C_2$–$C_3$-alkenyl optionally is substituted with one or more substituents independently selected from the group consisting of:
  halogen, and
  carbocyclyl optionally substituted with one or more substituents independently selected from the group consisting of halogen, —OH, —$NO_2$, —CN, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halocarbocyclyl, and halogen-substituted carbocyclyl-$C_1$–$C_6$-alkyl; and $E^5$ is selected from the group consisting of carbocyclyl and heterocyclyl, wherein the carbocyclyl or heterocyclyl optionally is substituted with one or more substituents independently selected from the group consisting of halogen, —OH, —$NO_2$, —CN, keto, $C_1$–$C_6$-alkyl, $C_2$–$C_8$-alkenyl, $C_2$–$C_8$-alkynyl, $C_1$–$C_6$-alkoxy, $C_1$–$C_6$-alkoxy-$C_1$–$C_6$-alkyl, —N($R^6$)($R^7$), —C(O)($R^8$), —S—$R^6$, —S(O)$_2$—$R^6$, carbocyclyl, carbocyclyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halocarbocyclyl, and halogen-substituted carbocyclyl-$C_1$–$C_6$-alkyl; and $R^3$ is selected from the group consisting of —H, $C_1$–$C_6$-alkyl, and halo-$C_1$–$C_6$-alkyl; and $R^6$ and $R^7$ are independently selected from the group consisting of —H, $C_1$–$C_6$-alkyl, carbocyclyl, carbocyclyl-$C_1$–$C_6$-alkyl, heterocyclyl, and heterocyclyl-$C_1$–$C_6$-alkyl, wherein any member of such group optionally is substituted with one or more halogen; and $R^8$ is selected from the group consisting of —H, $C_1$–$C_6$-alkyl, —O—$R^9$, —N($R^9$)($R^{10}$), carbocyclyl-$C_1$–$C_6$-alkyl, heterocyclyl-$C_1$–$C_6$-alkyl, halo-$C_1$–$C_6$-alkyl, halogen-substituted carbocyclyl-$C_1$–$C_6$-alkyl, and halogen-substituted heterocyclyl-$C_1$–$C_6$-alkyl; and $R^9$ and $R^{10}$ are independently selected from the group consisting of —H, $C_1$–$C_6$-alkyl, carbocyclyl, carbocyclyl-$C_1$–$C_6$-alkyl, heterocyclyl, heterocyclyl-$C_1$–$C_6$-alkyl, halo-$C_1$–$C_6$-alkyl, halocarbocyclyl, halogen-substituted carbocyclyl-$C_1$–$C_6$-alkyl, haloheterocyclyl, and halogen-substituted heterocyclyl-$C_1$–$C_6$-alkyl.

5. A compound or salt thereof according to claim 4, wherein $A^2$ and $A^3$, together with the carbon atom to which they both are attached, form an optionally-substituted heterocyclyl containing either 5 or 6 ring members.

6. A compound or salt thereof according to claim 5, wherein:

the compound corresponds in structure to a formula selected from the group consisting of:

(127-1)

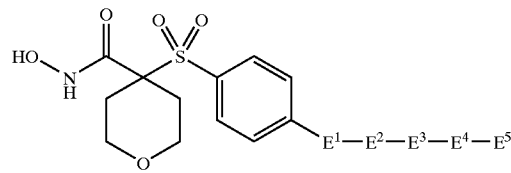

and (127-2)

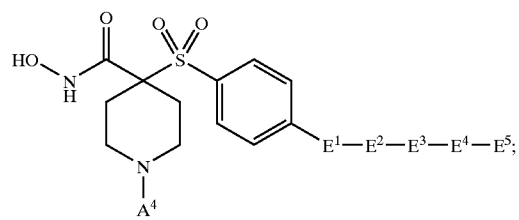

and $A^4$ is selected from the group consisting of —H, alkyl, alkylcarbonyl, alkylcarbonylalkyl, alkylcarbonylalkylcarbonyl, alkoxycarbonyl, alkoxycarbonylalkyl, alkoxycarbonylalkylcarbonyl, alkylsulfonyl, alkyliminocarbonyl, alkenyl, alkynyl, alkoxyalkyl, alkylthioalkyl, alkylsulfonylalkyl, alkylsufoxidoalkyl, alkylthioalkenyl, alkylsulfoxidoalkenyl, alkylsulfonylalkenyl, carbocyclyl, carbocyclylalkyl, carbocyclylalkoxyalkyl, carbocyclylcarbonyl, carbocyclylsulfonyl, carbocycyliminocarbonyl, carbocyclyloxycarbonyl, carbocylylthioalkyl, carbocylylsulfoxidoalkyl, carbocylylsulfonylalkyl, carbocyclylthioalkenyl, carbocyclylsulfoxidoalkenyl, carbocyclylsulfonylalkenyl, heterocyclyl, heterocyclylalkyl, heterocyclylalkoxyalkyl, heterocyclylcarbonyl, heterocyclylthioalkyl, heterocyclylsulfoxidoalkyl, heterocyclylsulfonylalkyl, heterocyclylthioalkenyl, heterocyclylsulfoxidoalkenyl, heterocyclylsulfonylalkenyl, heterocyclylsulfonyl, heterocyclyliminocarbonyl, heterocyclylalkylcarbonyl, heterocyclylcarbonylalkylcarbonyl, heterocyclylsulfonyl, heterocyclylcarbonylalkyl, aminoalkylcarbonyl, aminocarbonyl, aminocarbonylalkylcarbonyl, aminosulfonyl, aminosulfonylalkyl, aminoalkyl, aminocarbonylalkyl, and aminoalkylsulfonyl, wherein:
  any member of such group optionally is substituted.

7. A compound or salt thereof according to claim 6, wherein:
  $A^4$ is selected from the group consisting of —H, $C_1$–$C_8$-alkyl, $C_1$–$C_8$-alkylcarbonyl, $C_1$–$C_8$-alkylcarbonyl-$C_1$–$C_8$-alkyl, $C_1$–$C_8$-alkylcarbonyl-$C_1$–$C_8$-alkylcarbonyl, $C_1$–$C_8$-alkoxycarbonyl, $C_1$–$C_8$-alkoxycarbonyl-$C_1$–$C_8$-alkyl, $C_1$–$C_8$-alkoxycarbonyl-$C_1$–$C_8$-alkylcarbonyl, $C_1$–$C_8$-alkylsulfonyl, $C_1$–$C_8$-alkyliminocarbonyl, $C_2$–$C_8$-alkenyl, $C_2$–$C_8$-alkynyl, $C_1$–$C_8$-alkoxy-$C_1$–$C_8$-alkyl, $C_1$–$C_8$-alkylthio-$C_1$–$C_8$-alkyl, $C_1$–$C_8$-alkylthio-$C_2$–$C_8$-alkenyl, $C_1$–$C_8$-alkylsulfoxido-$C_1$–$C_8$-alkyl, $C_1$–$C_8$-alkylsulfoxido-$C_2$–$C_8$-alkenyl, $C_1$–$C_8$-alkylsulfonyl-$C_1$–$C_8$-alkyl, $C_1$–$C_8$-alkylsulfonyl-$C_2$–$C_8$-alkenyl, carbocyclyl, carbocyclyl-$C_1$–$C_8$-alkyl, carbocyclyl-$C_1$–$C_8$-alkoxy-$C_1$–$C_8$-alkyl, carbocyclylcarbonyl, carbocyclylsulfonyl, carbocyclyliminocarbonyl, carbocyclyloxycarbonyl, carbocyclylthio-$C_1$–$C_8$-alkyl, carbocyclylthio-$C_2$–$C_8$-alkenyl, carbocyclylsulfoxido-$C_1$–$C_8$-alkyl, carbocyclylsulfoxido-$C_2$–$C_8$-alkenyl, carbocyclylsulfonyl-$C_1$–$C_8$-alkyl, carbocyclylsulfonyl-$C_2$–$C_8$-alkenyl, heterocyclyl, heterocyclyl-$C_1$–$C_8$-alkyl, heterocyclyl-$C_1$–$C_8$-alkoxy-$C_1$–$C_8$-alkyl, heterocyclylcarbonyl, heterocyclylthio-$C_1$–$C_8$-alkyl, heterocyclylsulfoxido-$C_1$–$C_8$-alkyl, heterocyclylsulfonyl-$C_1$–$C_8$-alkyl, heterocyclylthio-$C_2$–$C_8$-alkenyl, heterocyclylsulfoxido-$C_2$–$C_8$-alkenyl, heterocyclylsulfonyl-$C_2$–$C_8$-alkenyl, heterocyclylsulfonyl, heterocyclyliminocarbonyl, heterocyclyl-$C_1$–$C_8$-alkylcarbonyl, heterocyclylcarbonyl-$C_1$–$C_8$-alkylcarbonyl, heterocyclylsulfonyl, heterocyclylcarbonyl-$C_1$–$C_8$-alkyl, $N(R^{11})(R^{12})$—$C_1$–$C_8$-alkylcarbonyl, $N(R^{11})(R^{12})$-carbonyl, $N(R^{11})(R^{12})$-carbonyl-$C_1$–$C_8$-alkylcarbonyl, $N(R^{11})(R^{12})$-sulfonyl, $N(R^{11})(R^{12})$-sulfonyl-$C_1$–$C_8$-alkyl, $N(R^{11})(R^{12})$—$C_1$–$C_8$-alkyl, $N(R^{11})(R^{12})$-carbonyl-$C_1$–$C_8$-alkyl, and $N(R^{11})(R^{12})$—$C_1$–$C_8$-alkylsulfonyl, wherein:
    any member of such group optionally is substituted with one or more substituents independently selected from the group consisting of halogen, —OH, —CN, —C(O)—OH, —SH, —$SO_3H$, and $NO_2$; and
  $R^{11}$ and $R^{12}$ are independently selected from the group consisting of —H, —OH, $C_1$–$C_8$-alkyl, $C_1$–$C_8$-alkylcarbonyl, $C_1$–$C_8$-alkoxy-$C_1$–$C_8$-alkyl, $C_2$–$C_8$-alkenyl, $C_2$–$C_8$-alkynyl, $C_1$–$C_8$-alkyl-thio-$C_1$–$C_8$-alkyl, $C_1$–$C_8$-alkyl-sulfoxido-$C_1$–$C_8$-alkyl, $C_1$–$C_8$-alkyl-sulfonyl-$C_1$–$C_8$-alkyl, carbocyclyl, carbocyclyl-$C_1$–$C_8$-alkyl, carbocyclylcarbonyl, carbocyclyl-$C_1$–$C_8$-alkoxy-$C_1$–$C_8$-alkyl, carbocyclylthio-$C_1$–$C_8$-alkyl, carbocyclylsulfoxido-$C_1$–$C_8$-alkyl, carbocyclylsulfonyl-$C_1$–$C_8$-alkyl, heterocyclyl, heterocyclyl-$C_1$–$C_8$-alkyl, heterocyclyl-$C_1$–$C_8$-alkoxy-$C_1$–$C_8$-alkyl, heterocyclylcarbonyl, heterocyclylthio-$C_1$–$C_8$-alkyl, heterocyclylsulfoxido-$C_1$–$C_8$-alkyl, heterocyclylsulfonyl-$C_1$–$C_8$-alkyl, aminocarbonyl-$C_1$–$C_8$-alkyl, $C_1$–$C_8$-alkyloxycarbonylamino-$C_1$–$C_8$-alkyl, and amino-$C_1$–$C_8$-alkyl, wherein:
    any member of such group optionally is substituted with one or more substituents independently selected from the group consisting of halogen, —OH, —CN, —C(O)—OH, —SH, —$SO_3H$, and $NO_2$, and
    the nitrogen of the amino-$C_1$–$C_8$-alkyl optionally is substituted with 1 or 2 substituents independently selected from the group consisting of $C_1$–$C_8$-alkyl, $C_1$–$C_8$-alkylcarbonyl, carbocyclyl, and carbocyclyl-$C_1$–$C_8$-alkyl, and
  no greater than one of $R^{11}$ or $R^{12}$ is —OH.

8. A compound or salt thereof according to claim 7, wherein $A^4$ is selected from the group consisting of —H, $C_1$–$C_6$-alkyl, $C_1$–$C_6$-alkoxy-$C_1$–$C_6$-alkyl, carbocyclyl, carbocyclyl-$C_1$–$C_6$-alkyl, $C_1$–$C_6$-alkylsulfonyl, $C_3$–$C_6$-alkenyl, $C_3$–$C_6$-alkynyl, wherein any member of such group optionally is substituted with halogen.

9. A compound or salt thereof according to claim 8, wherein $A^4$ is selected from the group consisting of —H, $C_1$–$C_4$-alkyl, $C_1$–$C_2$-alkoxy-$C_1$–$C_3$-alkyl, $C_3$–$C_6$-cycloalkyl, $C_3$–$C_6$-cycloalkyl-$C_1$–$C_3$-alkyl, phenyl, phenyl-$C_1$–$C_3$-alkyl, $C_1$–$C_2$-alkylsulfonyl, $C_3$–$C_4$-alkenyl, $C_3$–$C_4$-alkynyl, wherein any member of such group optionally is substituted with halogen.

10. A compound or salt thereof according to claim 9, wherein $A^4$ is selected from the group consisting of —H, ethyl, methoxyethyl, cyclopropyl, cyclopropylmethyl, benzyl, methylsulfonyl, $C_3$-alkenyl, and $C_3$-alkynyl, wherein any member of such group optionally is substituted with halogen.

11. A compound or salt thereof according to claim 10, wherein $A^4$ is selected from the group consisting of —H, ethyl, methoxyethyl, cyclopropyl, cyclopropylmethyl, and benzyl, wherein any member of such group optionally is substituted with halogen.

12. A compound or salt thereof according to claim 7, wherein the salt comprises an acid selected from the group consisting of HCl and $CF_3COOH$.

13. A compound or salt thereof according to claim 7, wherein $E^2$ is $C_2$–$C_5$-alkyl optionally substituted with one or more halogen.

14. A compound or salt thereof according to claim 13, wherein $E^2$ is —$(CH_2)_m$—, and m is from 2 to 5.

15. A compound or salt thereof according to claim 14, wherein $E^4$ is a bond.

16. A compound or salt thereof according to claim 7, wherein $E^3$ is heterocyclyl optionally substituted with one or more substituents independently selected from the group consisting of halogen, —OH, keto, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, heterocyclyl-$C_1$–$C_6$-alkyl, halo-$C_1$–$C_6$-alkyl, halo-$C_1$–$C_6$-alkoxy, and halogen-substituted $C_1$–$C_6$-alkoxy-$C_1$–$C_6$-alkyl, wherein:
  any such substituent optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio.

17. A compound or salt thereof according to claim 16, wherein $E^3$ is selected from the group consisting of furanyl, tetrahydropyranyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, dioxazolyl, oxathiazolyl, oxathiolyl, oxathiolanyl, pyranyl, dihydropyranyl, pyridinyl, piperidinyl, diazinyl, piperazinyl, triazinyl, oxazinyl, isoxazinyl, oxathiazinyl, oxadiazinyl, morpholinyl, azepinyl, oxepinyl, thiepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl, wherein any member of such group optionally is substituted with one or more substituents independently selected from the group consisting of halogen, —OH, keto, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, heterocyclyl-$C_1$–$C_6$-alkyl, halo-$C_1$–$C_6$-alkyl, halo-$C_1$–$C_6$-alkoxy, and halogen-substituted $C_1$–$C_6$-alkoxy-$C_1$–$C_6$-alkyl, wherein:

any such substituent optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio.

18. A compound or salt thereof according to claim 16, wherein $E^3$ contains no greater than one heteroatom ring member.

19. A compound or salt thereof according to claim 18, wherein $E^3$ is selected from the group consisting of furanyl, tetrahydropyranyl, dihydrofuranyl, tetrahydrofuranyl, thiophenyl, dihydrothiophenyl, tetrahydrothiophenyl, pyrrolinyl, pyrrolyl, isopyrrolyl, pyrrolidinyl, pyridinyl, piperidinyl, pyranyl, dihydropyranyl, and tetrahydropyranyl, wherein:

any member of such group optionally is substituted with one or more substituents independently selected from the group consisting of halogen, —OH, keto, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

20. A compound or salt thereof according to claim 18, wherein $E^3$ is pyridinyl optionally substituted with one or more substituents independently selected from the group consisting of halogen, —OH, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

21. A compound or salt thereof according to claim 20, wherein $E^5$ is phenyl optionally substituted with one or more substituents independently selected from the group consisting of halogen, —OH, —$NO_2$, —CN, $C_1$–$C_6$-alkyl, $C_2$–$C_6$-alkenyl, $C_2$–$C_6$-alkynyl, $C_1$–$C_6$-alkoxy, $C_1$–$C_6$-alkoxy-$C_1$–$C_6$-alkyl, —N($R^6$)($R^7$), —C(O)($R^8$), —S—$R^6$, —S(O)$_2$—$R^6$, phenyl phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl.

22. A compound or salt thereof according to claim 22, wherein the compound corresponds in structure to a formula selected from the group consisting of:

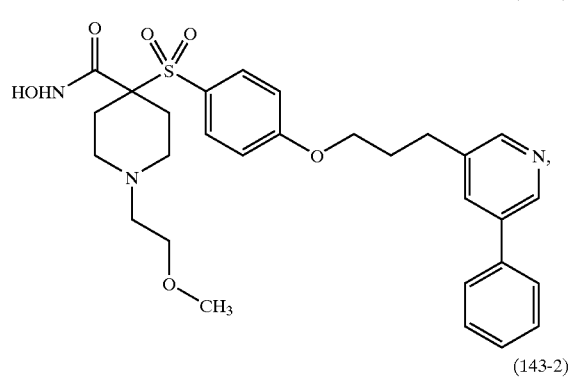

(143-1)

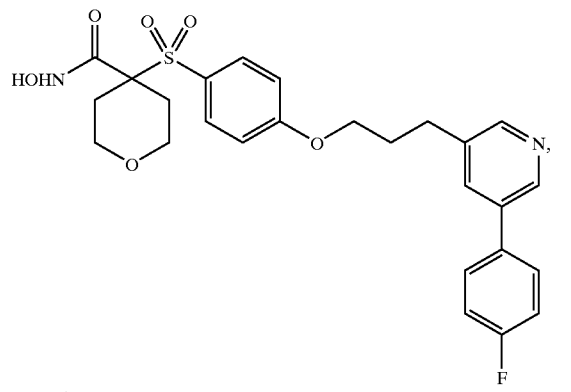

(143-2)

and

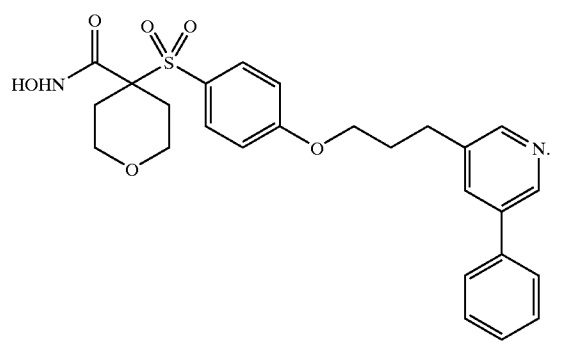

(143-3)

23. A compound or salt thereof according to claim 21, wherein the compound corresponds in structure to the following formula:

24. A compound or salt thereof according to claim 18, wherein:

E³ is selected from the group consisting of:

(144-1), (145-1), (145-2), (145-3), (145-4), (145-5), (145-6), (145-7), (145-8), (145-9), (145-10), (145-11), (145-12), (145-13), (145-14), (145-15), (145-16), and (145-17);

and any member of such group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl, wherein:

any such substituent optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio; and $R^{14}$ is selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl, wherein any member of such group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio.

25. A compound or salt thereof according to claim 24, wherein E³ is furanyl optionally substituted with one or more substituents independently selected from the group consisting of halogen, —OH, keto, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

26. A compound or salt thereof according to claim 25, wherein the compound corresponds in structure to the following formula:

(147-1)

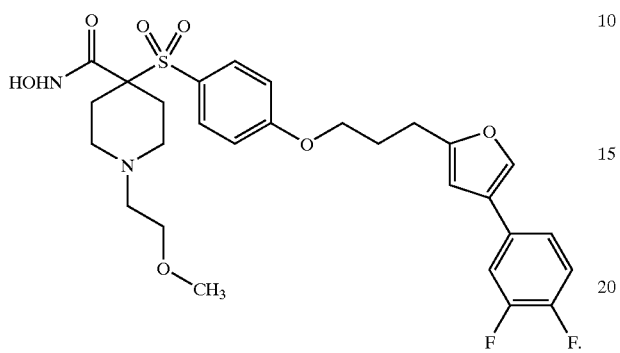

27. A compound or salt thereof according to claim 24, wherein $E^3$ is thienyl optionally substituted with one or more substituents independently selected from the group consisting of halogen, —OH, keto, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

28. A compound or salt thereof according to claim 27, wherein the compound corresponds in structure to a formula selected from the group consisting of:

(149-1)

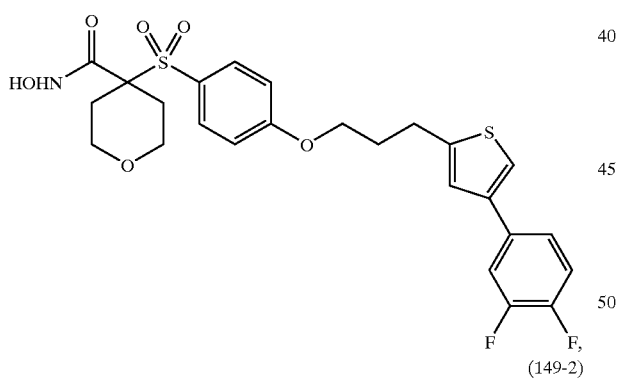

(149-2)

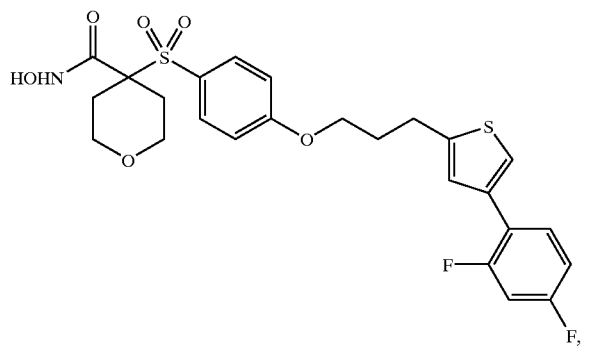

-continued (149-3)

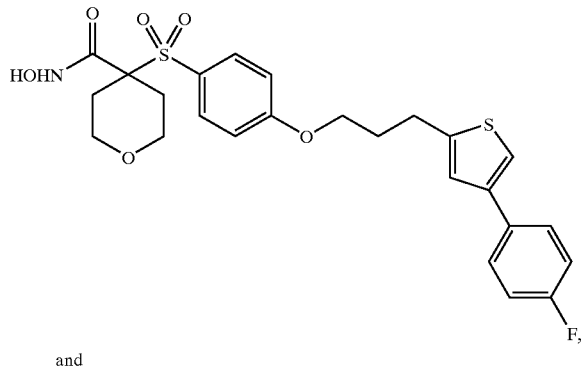

and (149-4)

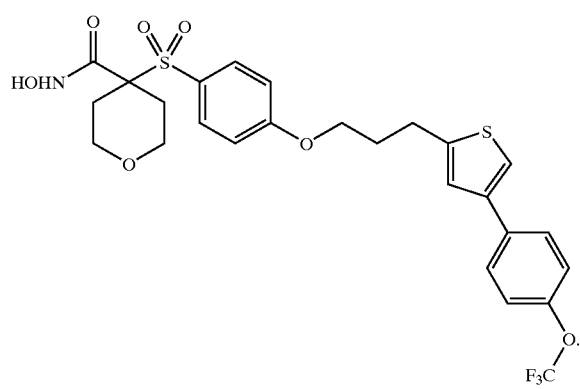

29. A compound or salt thereof according to claim 27, wherein the compound corresponds in structure to the following formula:

(150-1)

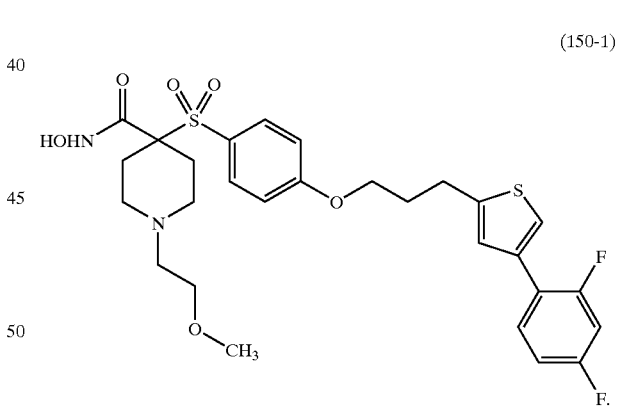

30. A compound or salt thereof according to claim 24, wherein $E^3$ is pyrrolidinyl optionally substituted with one or more substituents independently selected from the group consisting of halogen, —OH, keto, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

31. A compound or salt thereof according to claim 30, wherein $E^5$ is phenyl optionally substituted with one or more substituents independently selected from the group consisting of halogen, —OH, —NO$_2$, —CN, $C_1$–$C_6$-alkyl, $C_2$–$C_6$-alkenyl, $C_2$–$C_6$-alkynyl, $C_1$–$C_6$-alkoxy, $C_1$–$C_6$-alkoxy- $C_1$–$C_6$-alkyl, —N($R^6$)($R^7$), —C(O)($R^8$), —S—$R^6$, —S(O)$_2$—$R^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl.

32. A compound or salt thereof according to claim 31, wherein the compound corresponds in structure to a formula selected from the group consisting of:

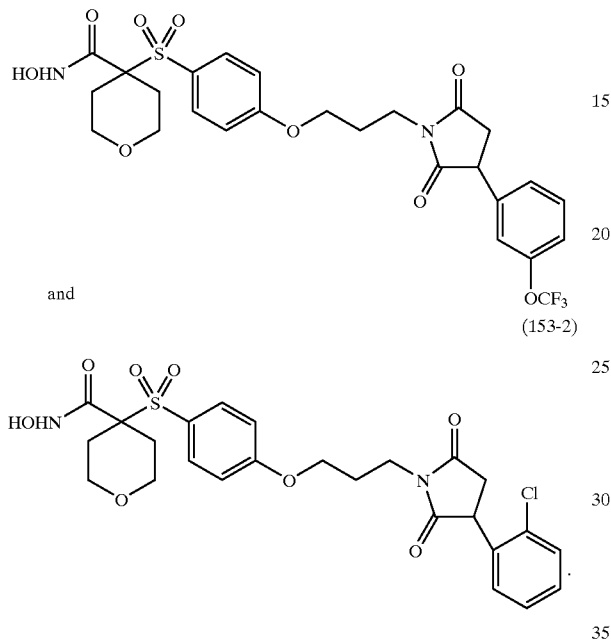

(153-1)

and (153-2)

33. A compound or salt thereof according to claim 16, wherein $E^3$ contains no greater and no less than two heteroatom ring members.

34. A compound or salt thereof according to claim 33, wherein $E^3$ is selected from the group consisting of pyrazolyl, pyrazolinyl, pyrazolidinyl, imidazolyl, isoimidazolyl, imidazolinyl, imidazolidinyl, dithiolyl, thiazolyl, isothiazolyl, thiazolinyl, isothiazolinyl, thiazolidinyl, isothiazolidinyl, oxathiolyl, oxathiolanyl, oxazolyl, isoxazolyl, oxazolidinyl, isoxazolidinyl, pyridinyl, piperazinyl, pyrimidinyl, pyridazinyl, oxazinyl, and morpholinyl, wherein:

any member of such group optionally is substituted with one or more substituents independently selected from the group consisting of halogen, —OH, keto, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

35. A compound or salt thereof according to claim 33, wherein:

$E^3$ is selected from the group consisting of:

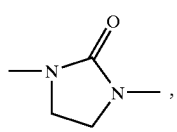

(156-1)

-continued

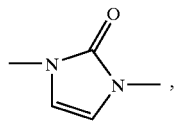

(156-2)

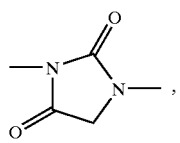

(156-3)

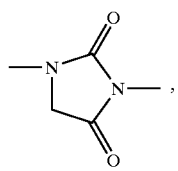

(156-4)

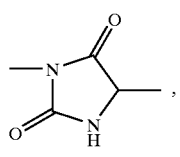

(156-5)

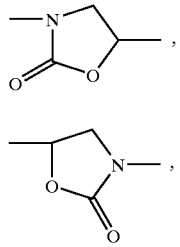

(156-6)

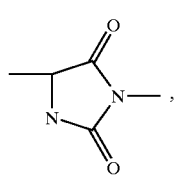

(156-7)

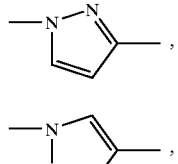

(156-8)

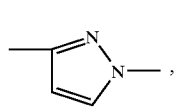

(156-9)

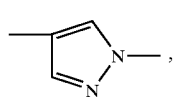

(156-10)

(156-11)

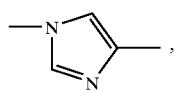

(156-12)

(156-13)

-continued

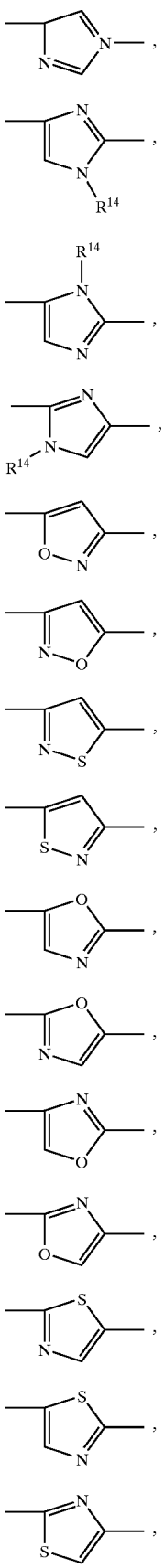

and

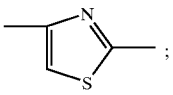

and any member of such group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl, wherein:

any such substituent optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio; and $R^{14}$ is selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl, wherein:

any member of such group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio.

36. A compound or salt thereof according to claim 35, wherein $E^3$ is selected from the group consisting of oxazolyl and isoxazolyl, wherein:

the oxazolyl or isoxazolyl is optionally substituted with one or more substituents independently selected from the group consisting of halogen, —OH, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

37. A compound or salt thereof according to claim 36, wherein $E^5$ is phenyl optionally substituted with one or more substituents independently selected from the group consisting of halogen, —OH, —NO$_2$, —CN, $C_1$–$C_6$-alkyl, $C_2$–$C_6$-alkenyl, $C_2$–$C_6$-alkynyl, $C_1$–$C_6$-alkoxy, $C_1$–$C_6$-alkoxy-$C_1$–$C_6$-alkyl, —N(R$^6$)(R$^7$), —C(O)(R$^8$), —S—R$^6$, —S(O)$_2$—R$^6$, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl.

38. A compound or salt thereof according to claim 37, wherein the compound corresponds in structure to a formula selected from the group consisting of:

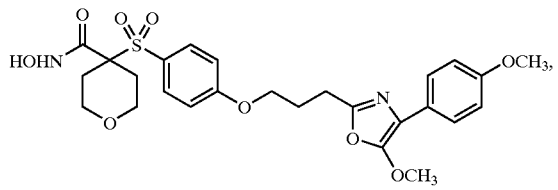
(159-1)

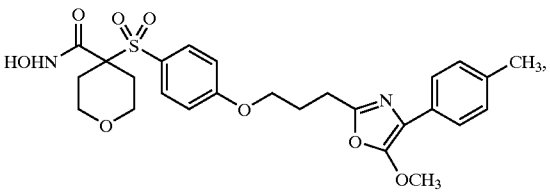
(159-2)

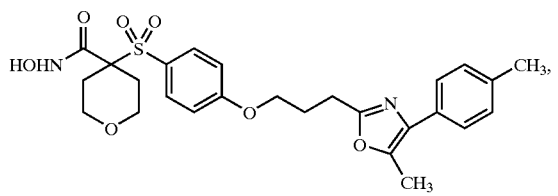
(159-3)

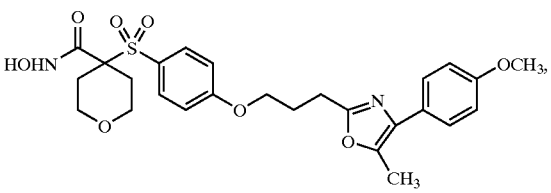
(159-4)

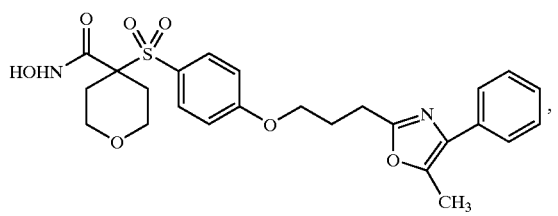
(159-5)

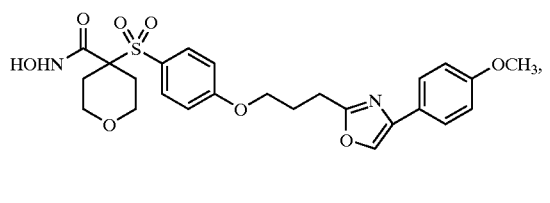
(159-6)

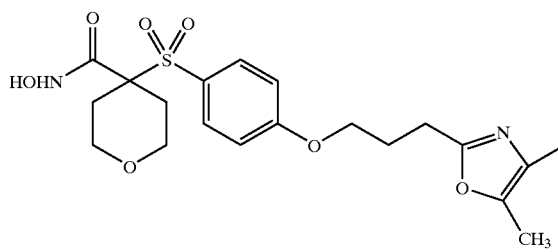
(159-7)

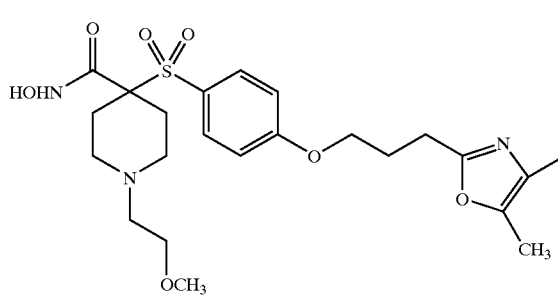
(159-8)

and

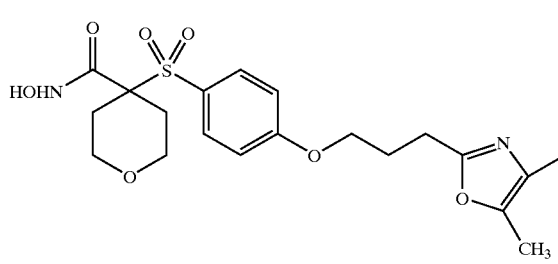
(159-9)

39. A compound or salt thereof according to claim 35, wherein $E^3$ is selected from the group consisting of pyrazolyl and isoimidazolyl, wherein:

the pyrazolyl and isoimidazolyl optionally is substituted with one or more substituents independently selected from the group consisting of halogen, —OH, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

40. A compound or salt thereof according to claim 39, wherein $E^5$ is phenyl optionally substituted with one or more substituents independently selected from the group consisting of halogen, —OH, —NO$_2$, —CN, C$_1$–C$_6$-alkyl, C$_2$–C$_6$-alkenyl, C$_2$–C$_6$-alkynyl, C$_1$–C$_6$-alkoxy, C$_1$–C$_6$-alkoxy-C$_1$–C$_6$-alkyl, —N(R$^6$)(R$^7$), —C(O)(R$^8$), —S—R$^6$, —S(O)$_2$—R$^6$, phenyl phenyl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, halophenyl, and halogen-substituted phenyl-C$_1$–C$_6$-alkyl.

41. A compound or salt thereof according to claim 40, wherein the compound corresponds in structure to a formula selected from the group consisting of:

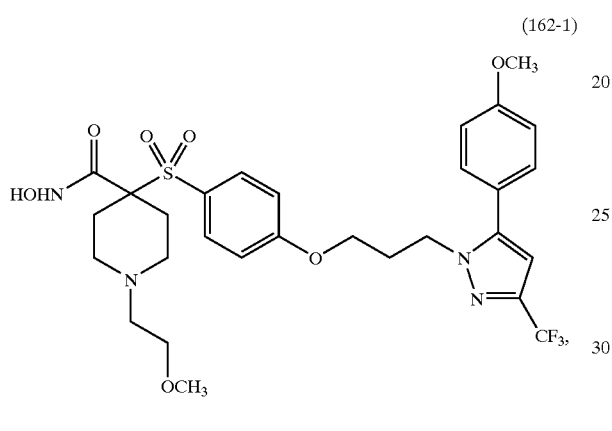

(162-1)

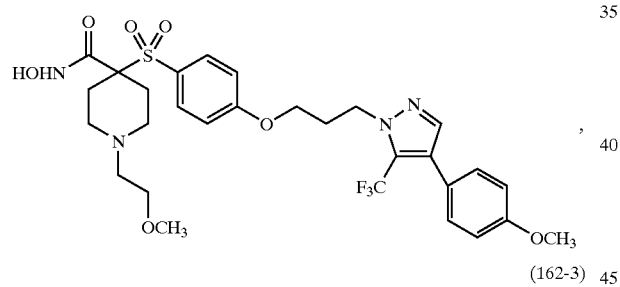

(162-2)

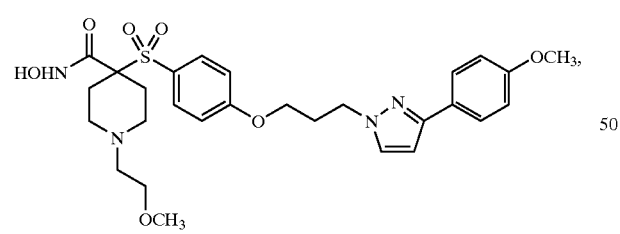

(162-3)

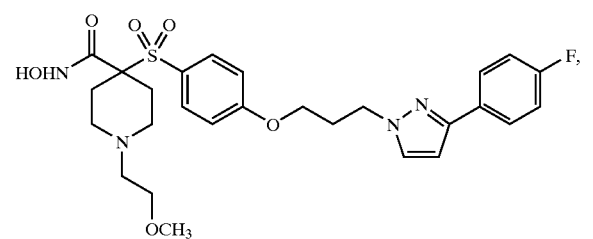

(162-4)

and

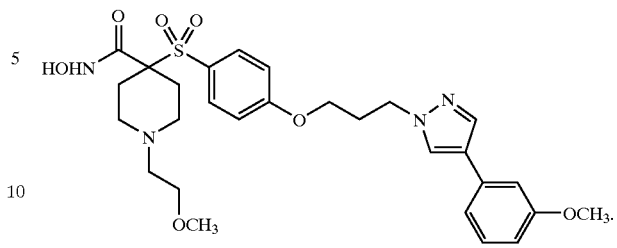

(162-5)

42. A compound or salt thereof according to claim 35, wherein $E^3$ is selected from the group consisting of thiazolyl and isothiazolyl, wherein:
  the thiazolyl and isothiazolyl optionally is substituted with one or more substituents independently selected from the group consisting of halogen, —OH, C$_1$–C$_6$-alkyl, C$_1$–C$_6$-alkoxy, and C$_1$–C$_6$-alkoxy-C$_1$–C$_6$-alkyl, wherein:
    any such substituent optionally is substituted with one or more substituents independently selected from the group consisting of halogen and —OH.

43. A compound or salt thereof according to claim 42, wherein $E^5$ is phenyl optionally substituted with one or more substituents independently selected from the group consisting of halogen, —OH, —NO$_2$, —CN, C$_1$–C$_6$-alkyl, C$_2$–C$_6$-alkenyl, C$_2$–C$_6$-alkynyl, C$_1$–C$_6$-alkoxy, C$_1$–C$_6$-alkoxy-C$_1$–C$_6$-alkyl, —N(R$^6$)(R$^7$), —C(O)(R$^8$), —S—R$^6$, —S(O)$_2$—R$^6$, phenyl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, halophenyl, and halogen-substituted phenyl-C$_1$–C$_6$-alkyl.

44. A compound or salt thereof according to claim 43, wherein the compound corresponds in structure to the following formula:

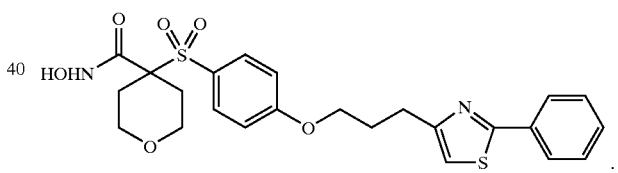

(165-1)

45. A compound or salt thereof according to claim 44, wherein $E^3$ is selected from the group consisting of pyrazolidinyl and imidazolidinyl, wherein:
  the pyrazolidinyl and imidazolidinyl optionally is substituted with one or more substituents independently selected from the group consisting of halogen, —OH, keto, C$_1$–C$_6$-alkyl, C$_1$–C$_6$-alkoxy, and C$_1$–C$_6$-alkoxy-C$_1$–C$_6$-alkyl, wherein:
    any such substituent optionally is substituted with one or more substituents independently selected from the group consisting of halogen and —OH.

46. A compound or salt thereof according to claim 45, wherein $E^5$ is phenyl optionally substituted with one or more substituents independently selected from the group consisting of halogen, —OH, —NO$_2$, —CN, C$_1$–C$_6$-alkyl, C$_2$–C$_6$-alkenyl, C$_2$–C$_6$-alkynyl, C$_1$–C$_6$-alkoxy, C$_1$–C$_6$-alkoxy-C$_1$–C$_6$-alkyl, —N(R$^6$)(R$^7$), —C(O)(R$^8$), —S—R$^6$, —S(O)$_2$—R$^6$, phenyl, phenyl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, halophenyl, and halogen-substituted phenyl-C$_1$–C$_6$-alkyl.

47. A compound or salt thereof according to claim 46, wherein the compound corresponds in structure to a formula selected from the group consisting of:

(168-1) 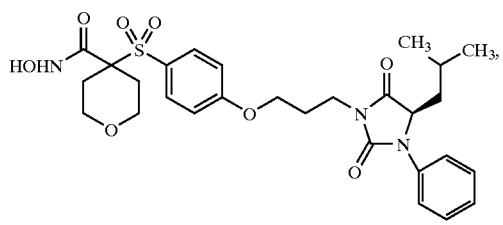
(168-2) 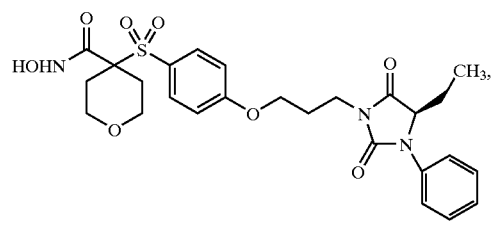
(168-3) 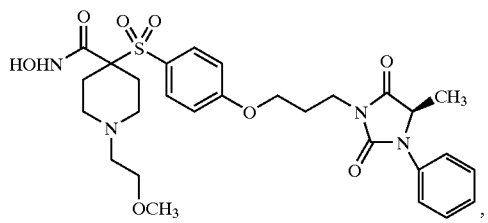
(168-4) 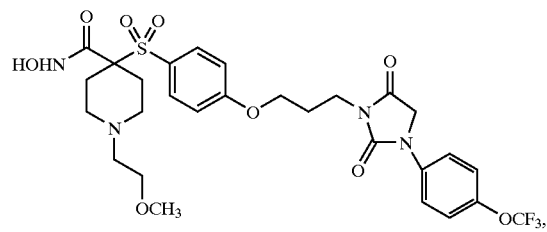
(168-5) 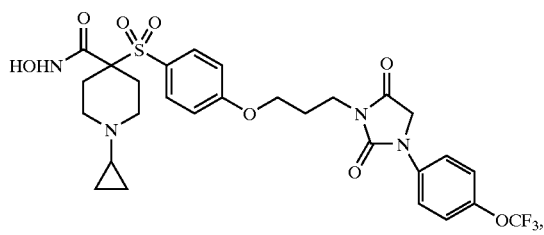
(168-6) 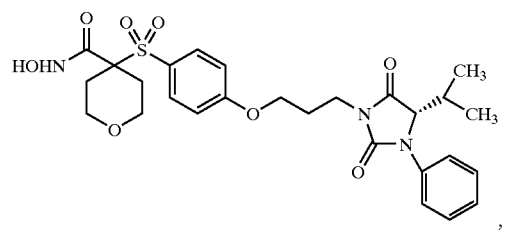
(168-7) 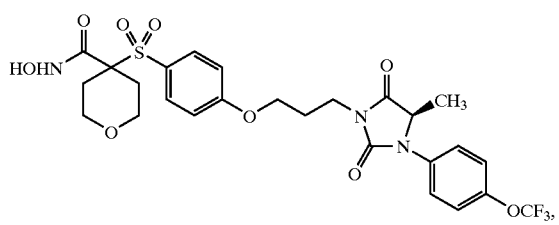
(168-8) 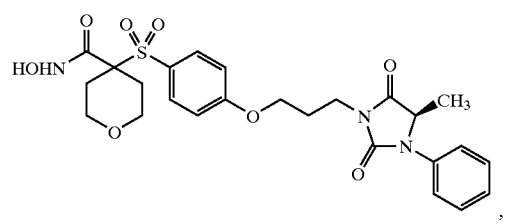
(168-9) 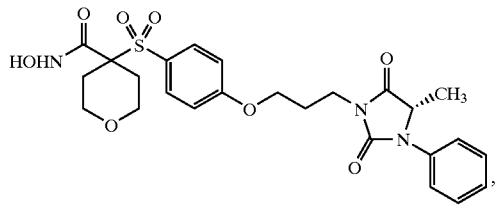
(168-10) 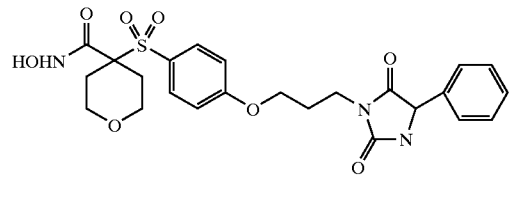
(168-11) 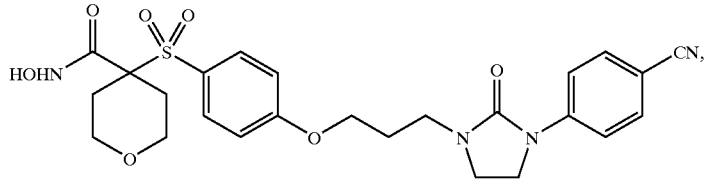

(168-12)
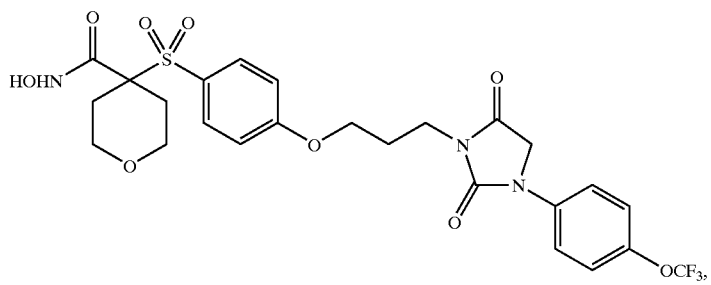
(168-13)
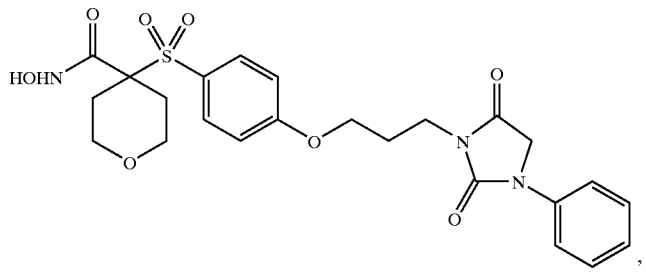
(168-14)
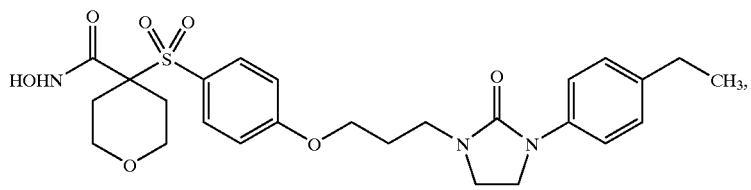
(168-15)
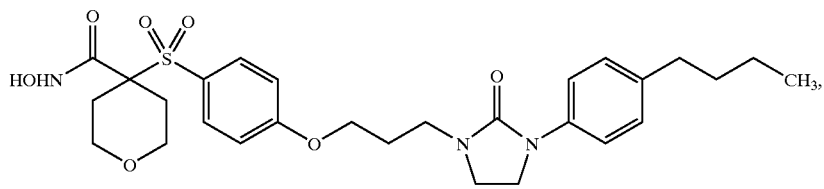
(168-16)
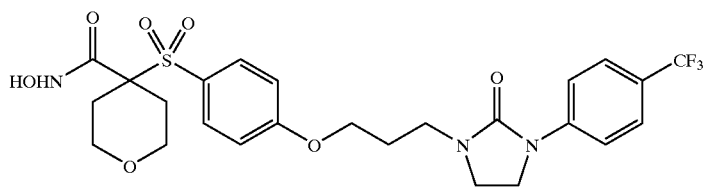
(168-17)
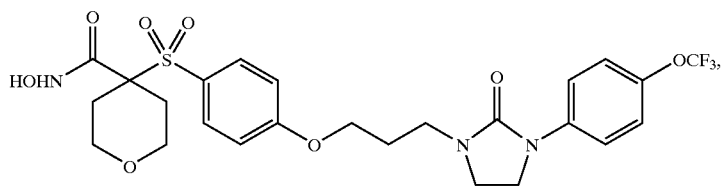
(168-18)
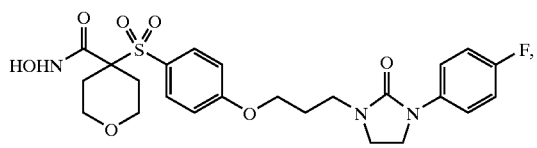
(168-19)
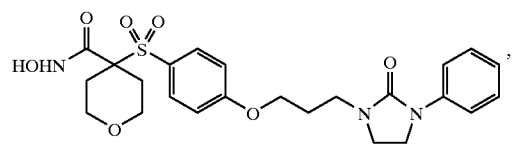

-continued

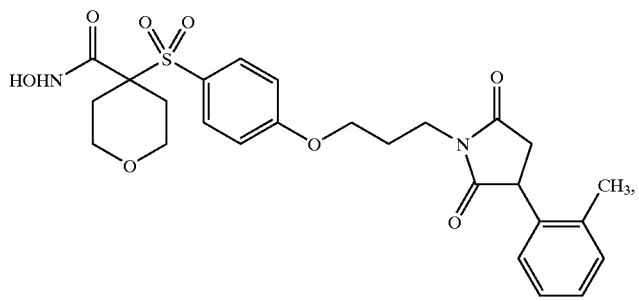
(168-20)

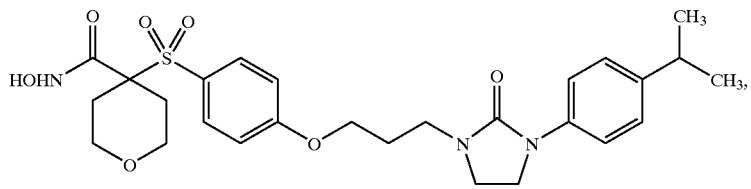
(168-21)

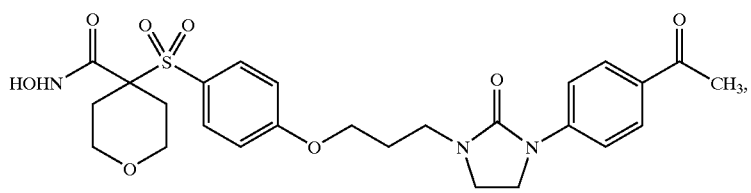
(168-22)

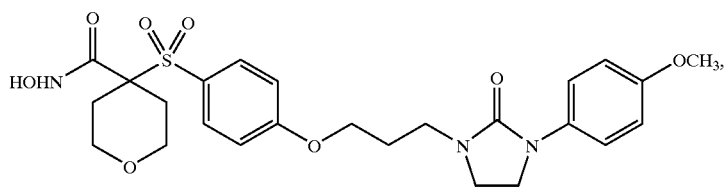
(168-23)

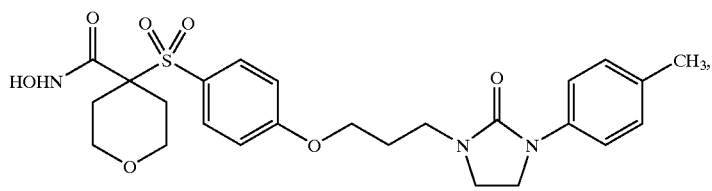
(168-24)

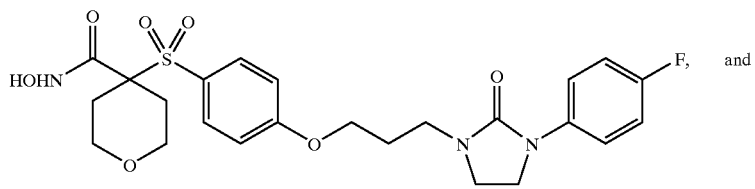
(168-25)

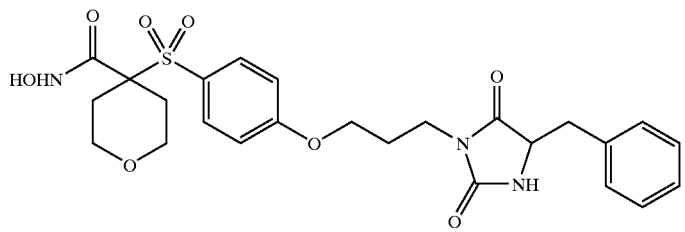
(168-26)

48. A compound or salt thereof according to claim 45, wherein $E^5$ is $C_5$–$C_6$-cycloalkyl optionally substituted with one or more substituents independently selected from the group consisting of halogen, —OH, —NO$_2$, —CN, $C_1$–$C_6$-alkyl, $C_2$–$C_6$-alkenyl, $C_2$–$C_6$-alkynyl, $C_1$–$C_6$-alkoxy, $C_1$–$C_6$-alkoxy-$C_1$–$C_6$-alkyl, —N($R^6$)($R^7$), —C(O)($R^8$), —S—$R^6$, —S(O)$_2$—$R^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl.

49. A compound or salt thereof according to claim 48, wherein the compound corresponds in structure to the following formula:

(170-1).

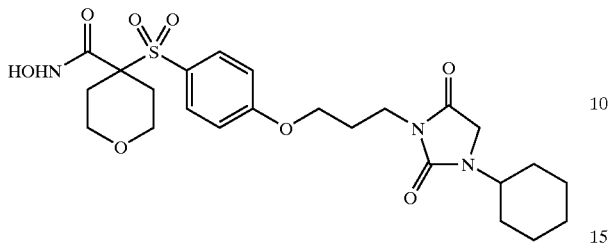

50. A compound or salt thereof according to claim 35, wherein $E^3$ is oxazolidinyl optionally substituted with one or more substituents independently selected from the group consisting of halogen, —OH, keto, $C_1$–$C_6$-alkyl, $C_1$–$C_6$-alkoxy, and $C_1$–$C_6$-alkoxy-$C_1$–$C_6$-alkyl, wherein:

any such substituent optionally is substituted with one or more substituents independently selected from the group consisting of halogen and —OH.

51. A compound or salt thereof according to claim 50, wherein $E^5$ is phenyl optionally substituted with one or more substituents independently selected from the group consisting of halogen, —OH, —NO$_2$, —CN, $C_1$–$C_6$-alkyl, $C_2$–$C_6$-alkenyl, $C_2$–$C_6$-alkynyl, $C_1$–$C_6$-alkoxy, $C_1$–$C_6$-alkoxy-$C_1$–$C_6$-alkyl, —N(R$^6$)(R$^7$), —C(O)(R$^8$), —S—R$^6$, —S(O)$_2$—R$^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl.

52. A compound or salt thereof according to claim 51, wherein the compound corresponds in structure to a formula selected from the group consisting of:

(173-1),

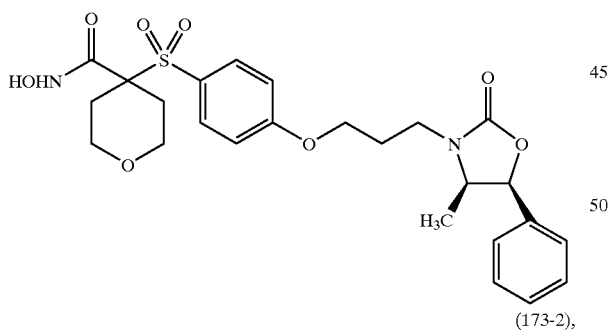

(173-2),

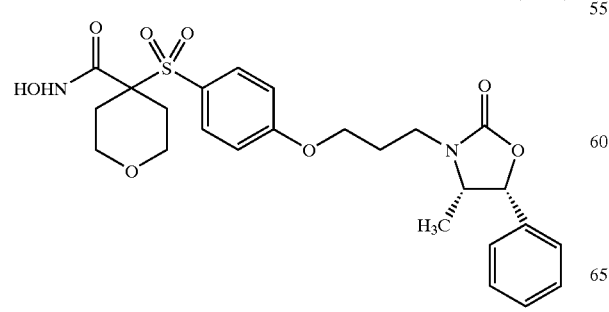

-continued (173-3),

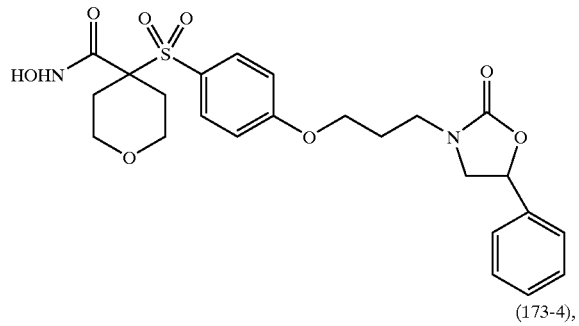

(173-4),

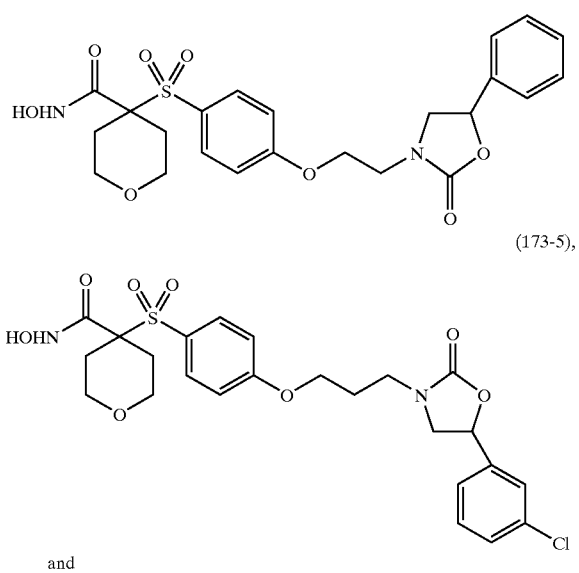

(173-5), and (173-6).

53. A compound or salt thereof according to claim 16, wherein $E^3$ contains no greater and no less than 3 heteroatoms.

54. A compound or salt thereof according to claim 53, wherein $E^3$ is selected from the group consisting of oxadiazolyl, thiadiazolyl, and triazolyl, wherein:

the triazolyl optionally is substituted with a substituent selected from the group consisting of halogen, —OH, $C_1$–$C_6$-alkyl, $C_1$–$C_6$-alkoxy, and $C_1$–$C_6$-alkoxy-$C_1$–$C_6$-alkyl, any such substituent optionally is substituted with one or more substituents independently selected from the group consisting of halogen and —OH.

55. A compound or salt thereof according to claim 53, wherein:

$E^3$ is selected from the group consisting of:

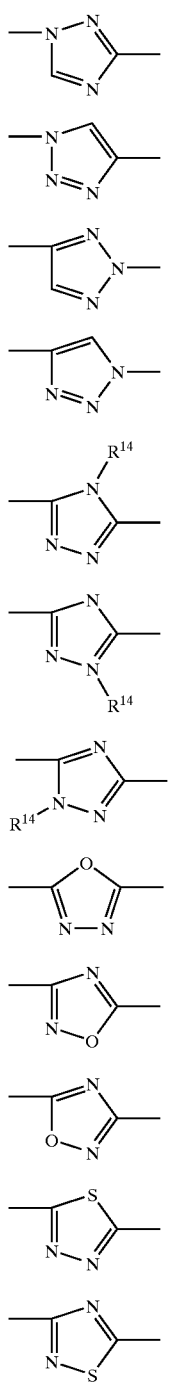

(176-1), (176-2), (176-3), (176-4), (176-5), (176-6), (176-7), (176-8), (176-9), (176-10), (176-11), (176-12), and

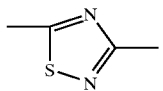

(176-13);

and any member of such group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl, wherein:

any such substituent optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio; and $R^{14}$ is selected from the group consisting of halogen, —OH, $C_1$–$C_6$-alkyl, $C_1$–$C_6$-alkoxy, $C_1$–$C_6$-alkoxy-$C_1$–$C_6$-alkyl, carbocyclyl, carbocyclyl-$C_1$–$C_6$-alkyl, heterocyclyl, and heterocyclyl-$C_1$–$C_6$-alkyl, wherein:

any member of such group optionally is substituted with one or more substituents independently selected from the group consisting of halogen, —OH, $C_1$–$C_6$-alkyl, $C_1$–$C_6$-alkoxy, $C_1$–$C_6$-alkoxy-$C_1$–$C_6$-alkyl, $C_1$–$C_6$-alkylthio, halo-$C_1$–$C_6$-alkyl, halo-$C_1$–$C_6$-alkoxy, halogen-substituted $C_1$–$C_6$-alkoxy-$C_1$–$C_6$-alkyl, and halo-$C_1$–$C_6$-alkylthio.

56. A compound or salt thereof according to claim 55, wherein $E^3$ is oxadiazolyl.

57. A compound or salt thereof according to claim 56, wherein $E^5$ is phenyl optionally substituted with one or more substituents independently selected from the group consisting of halogen, —OH, —$NO_2$, —CN, $C_1$–$C_6$-alkyl, $C_2$–$C_6$-alkenyl, $C_2$–$C_6$-alkynyl, $C_1$–$C_6$-alkoxy, $C_1$–$C_6$-alkoxy-$C_1$–$C_6$-alkyl, —N($R^6$)($R^7$), —C(O)($R^8$), —S—$R^6$, —S(O)$_2$—$R^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl.

58. A compound or salt thereof according to claim 57, wherein the compound corresponds in structure to a formula selected from the group consisting of:

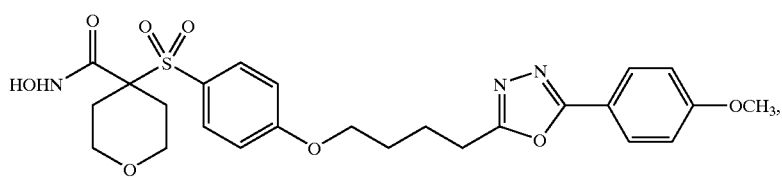

(179-1)

(179-2)
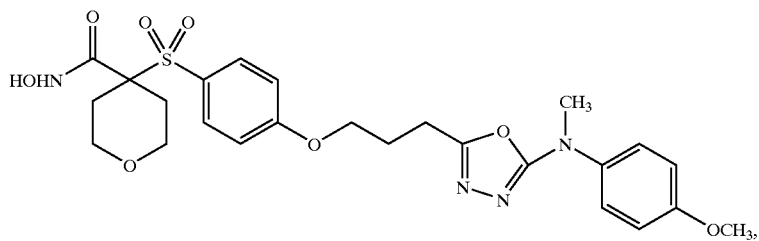
(179-3)
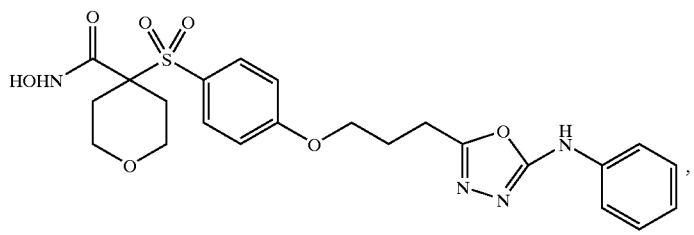
(179-4)
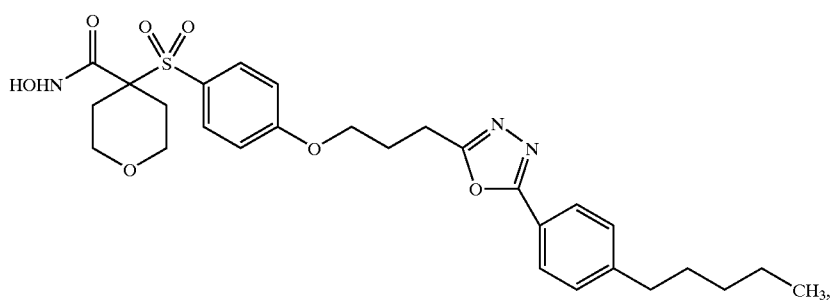
(179-5)
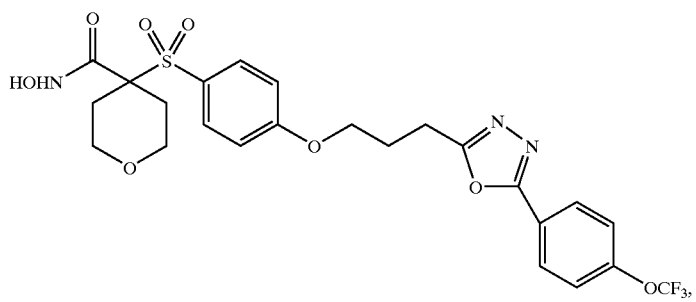
(179-6)
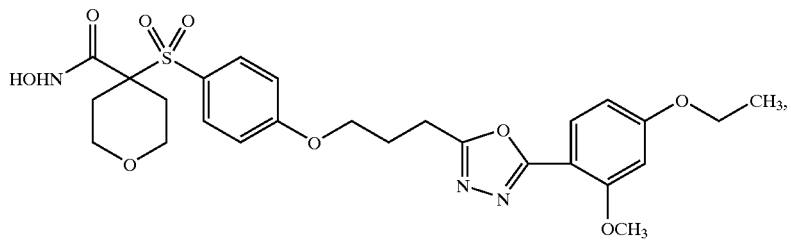
(179-7)
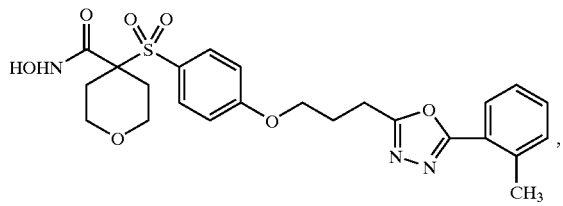

-continued
(179-8)
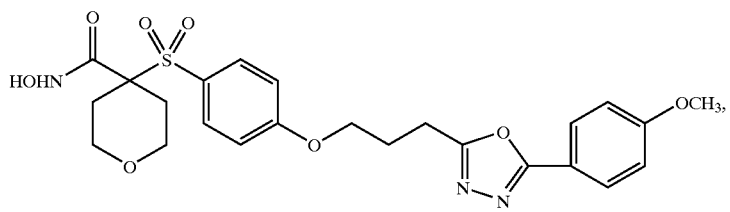
(179-9)
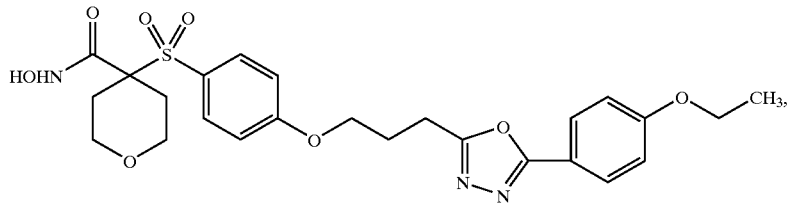
(179-10)
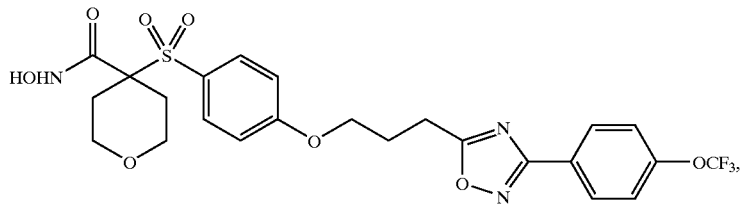
(179-11)
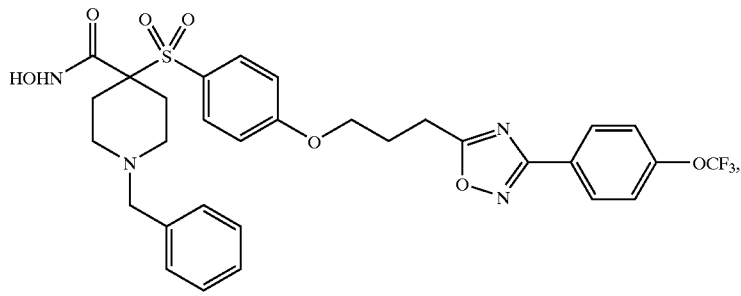
(179-12)
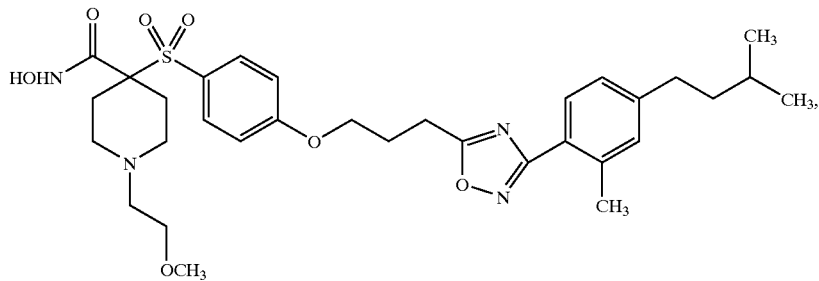
(179-13)
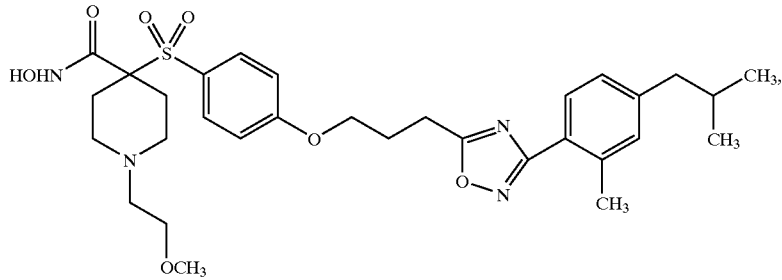

-continued
(179-14)
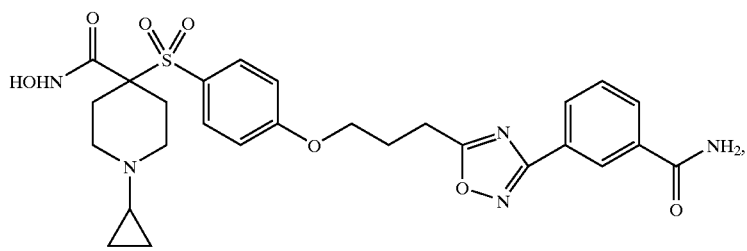
(179-15)
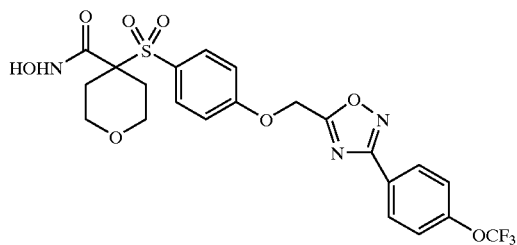
(179-16)
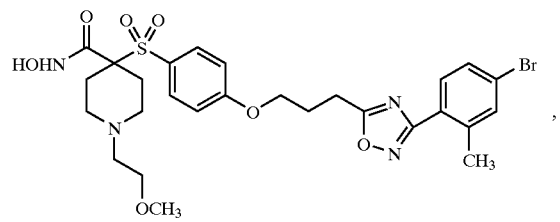
(179-18)
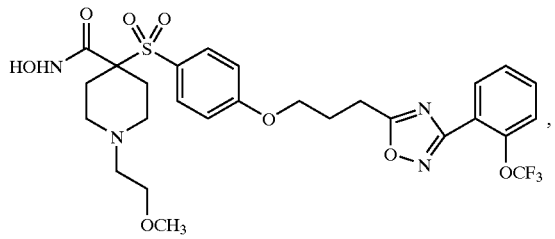
(179-19)
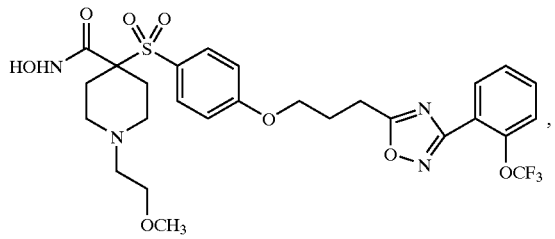
(179-20)
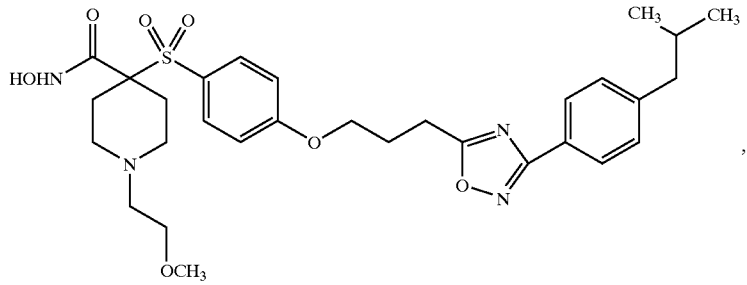
(179-21)
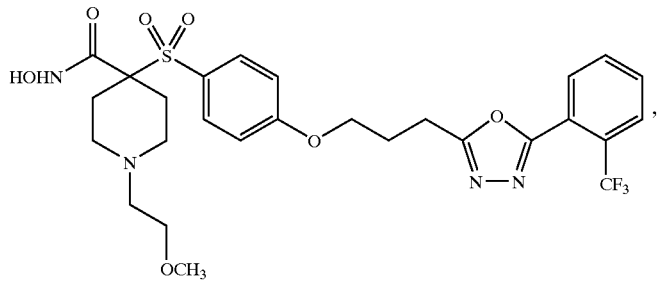
(179-22)
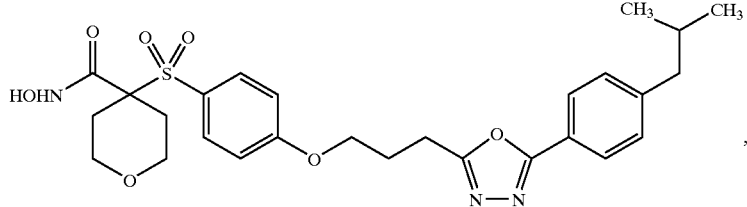

-continued
(179-23)
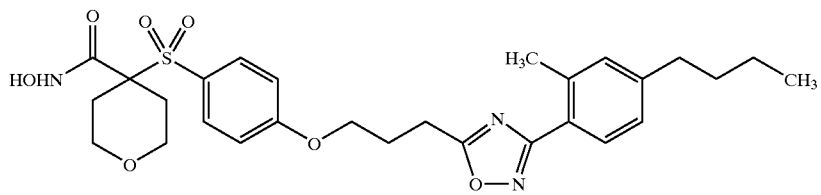
(179-24)
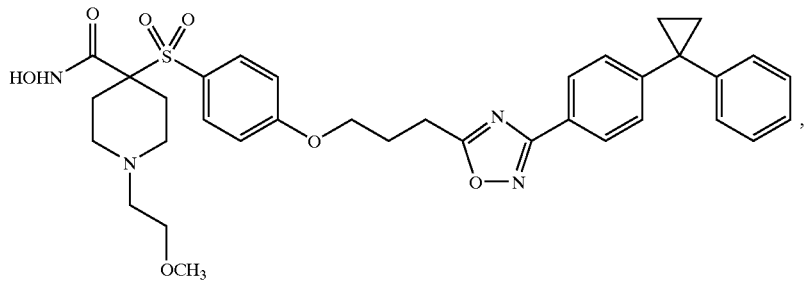
(179-25)
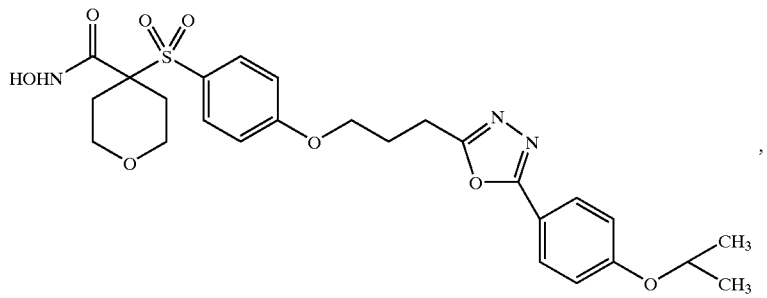
(179-26)
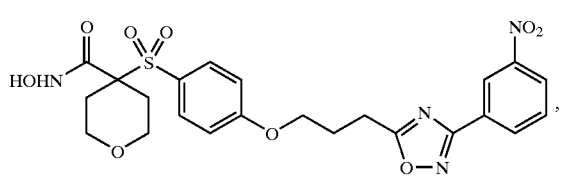
(179-27)
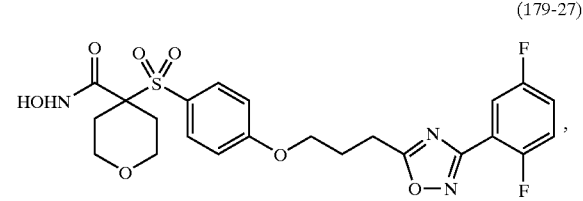
(179-28)
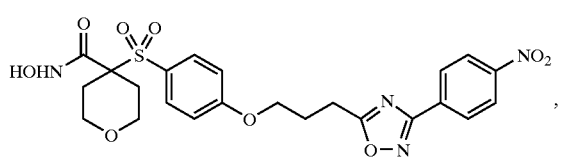
(179-29)
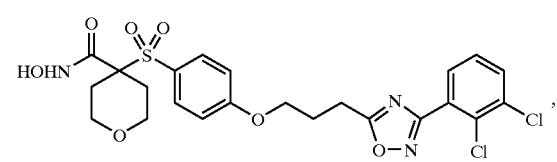
(179-30)
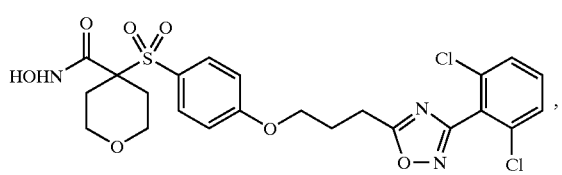
(179-31)
(179-32)
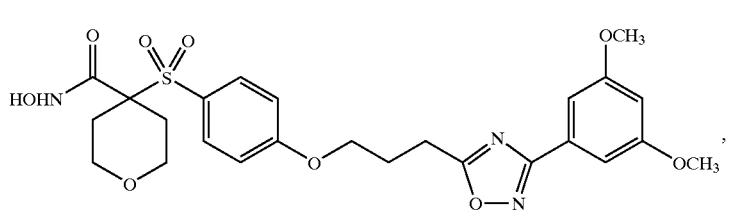

-continued
(179-33)
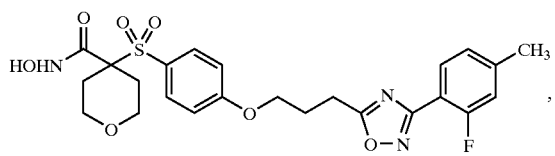
(179-34)
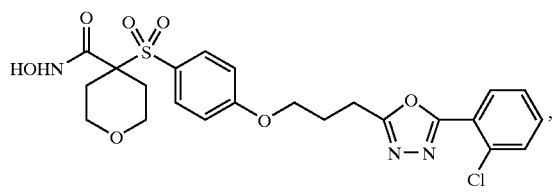
(179-35)
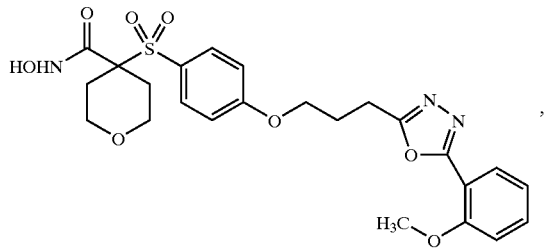
(179-36)
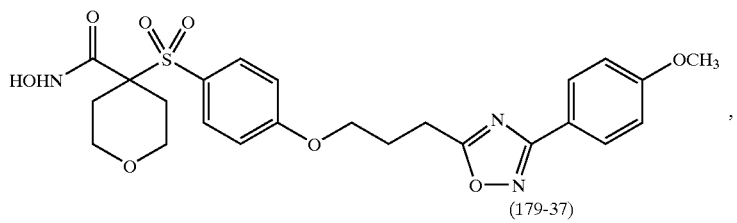
(179-37)
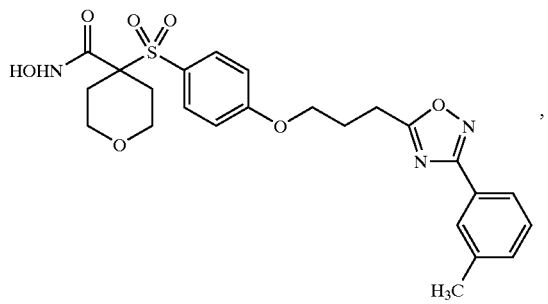
(179-38)
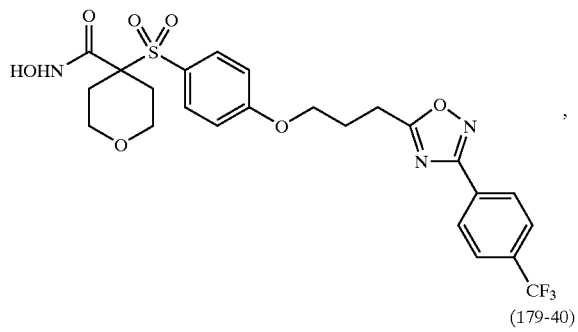
(179-39)
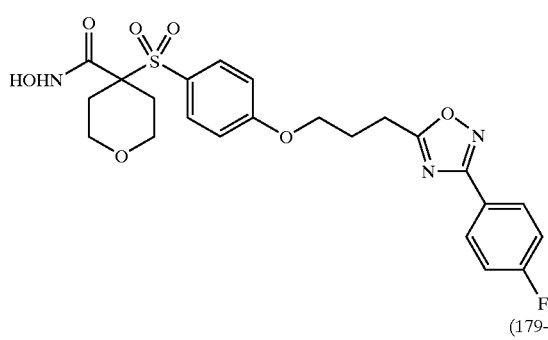
(179-40)
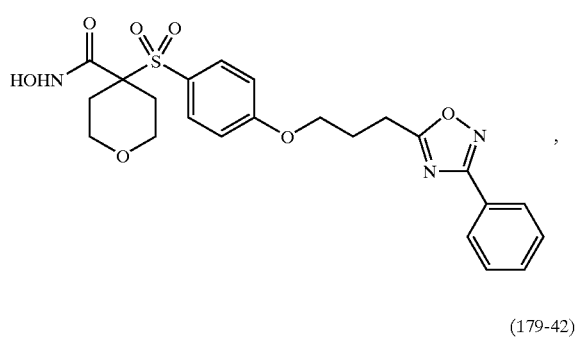
(179-41)
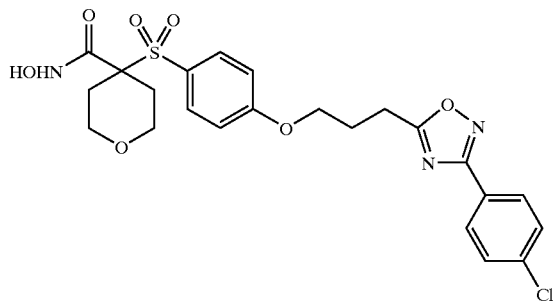
(179-42)
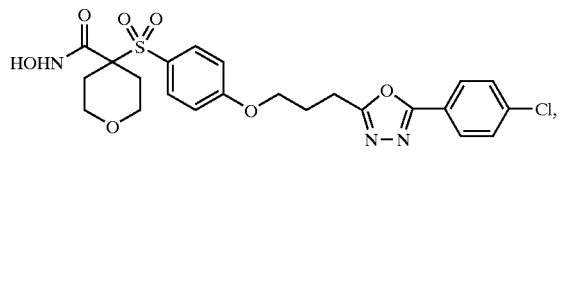

(179-43)
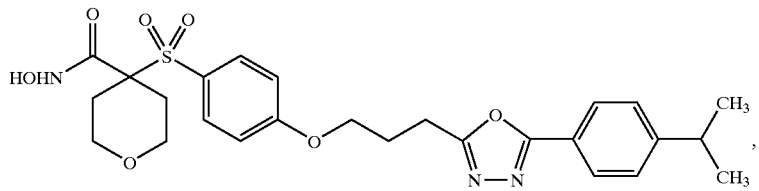
(179-44)
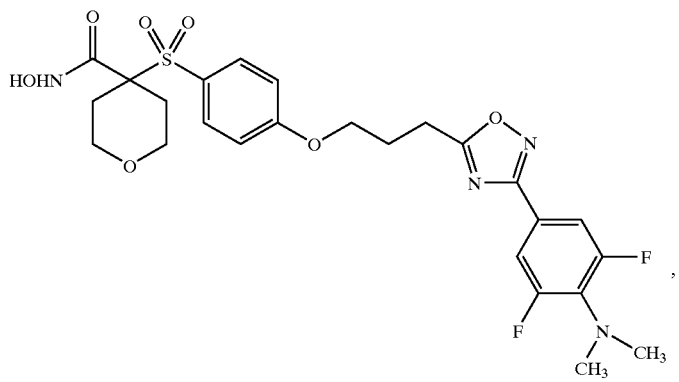
(179-45)
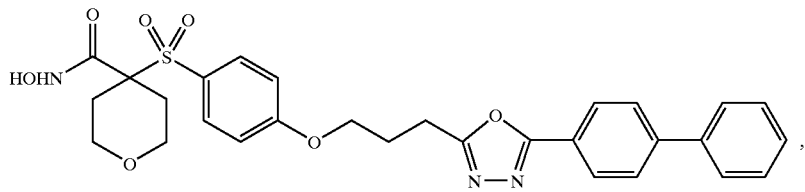
(179-46)
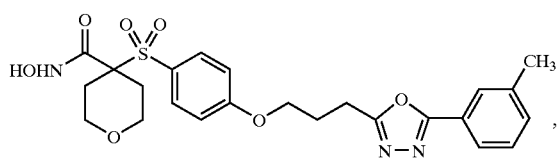
(179-47)
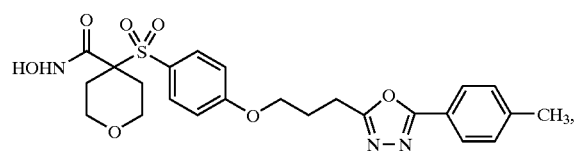
(179-48)
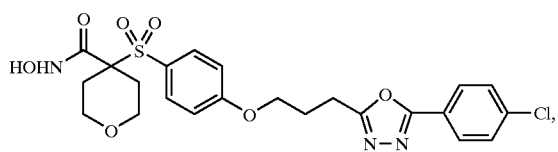
(179-49)
(179-50)
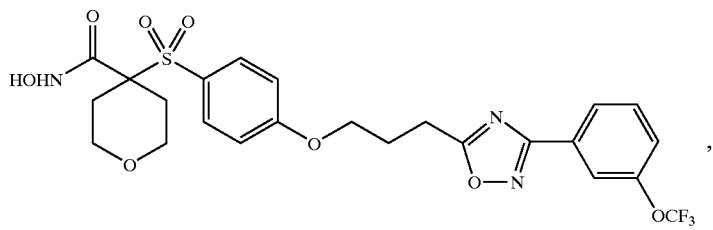

(179-51)
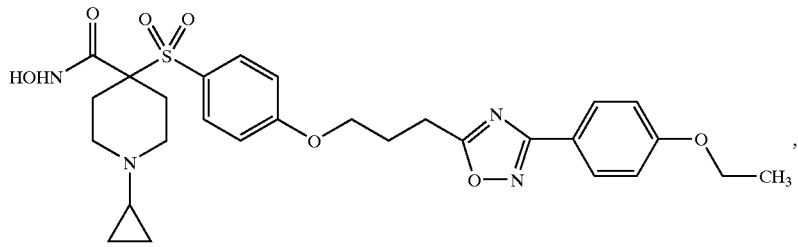
(179-52)
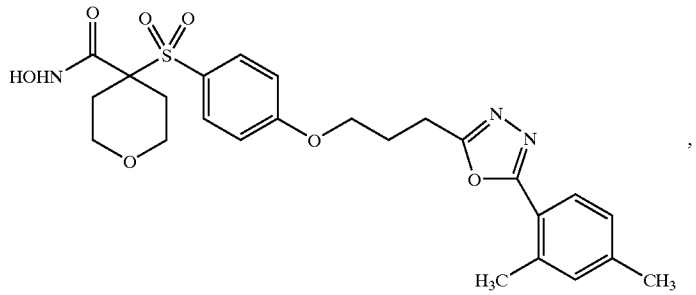
(179-53)
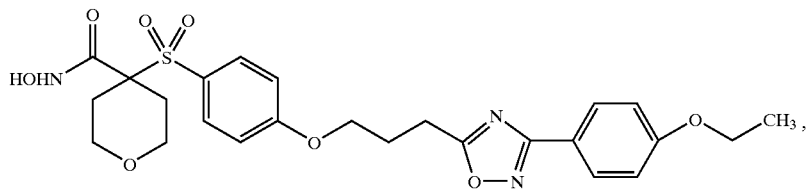
(179-54)
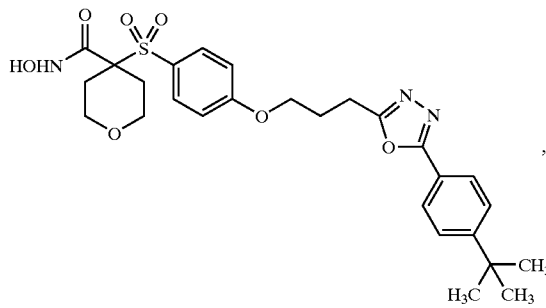
(179-55)
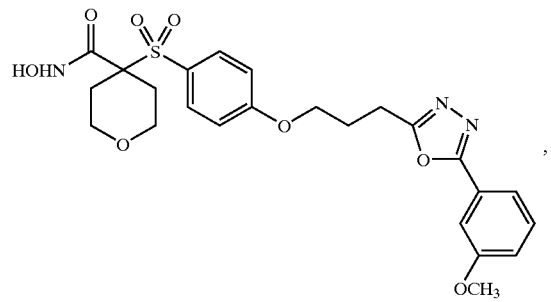
(179-56)
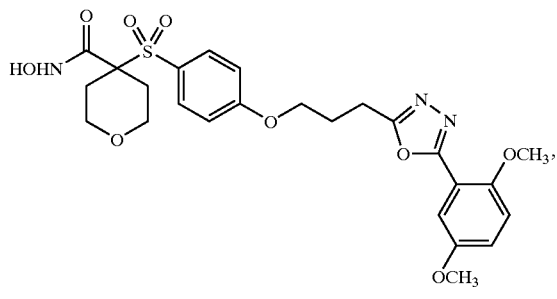
(179-57)
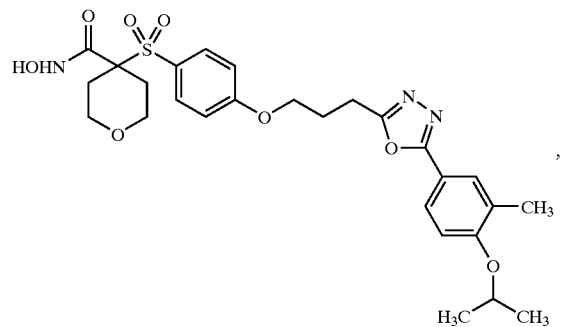

(179-58)
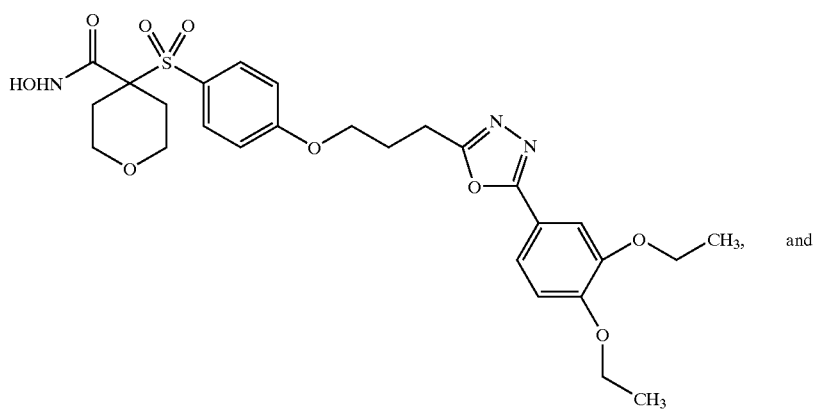
(179-59)
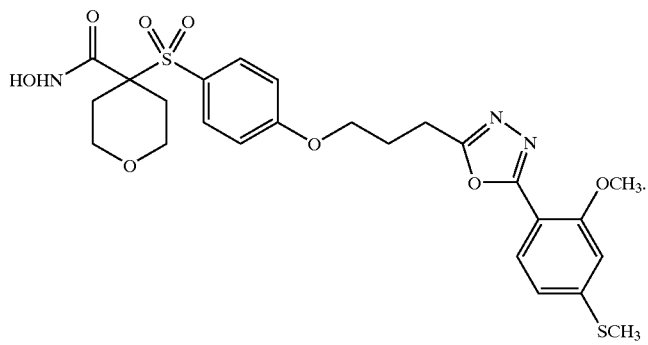
59. A compound or salt thereof according to claim 57, wherein the compound corresponds in structure to a formula selected from the group consisting of:
(180-1)
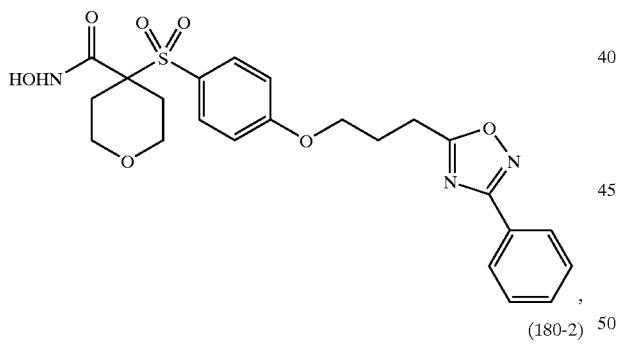
(180-2)
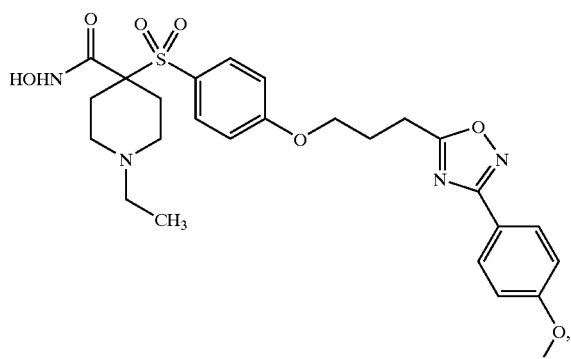
and
-continued
(180-3)
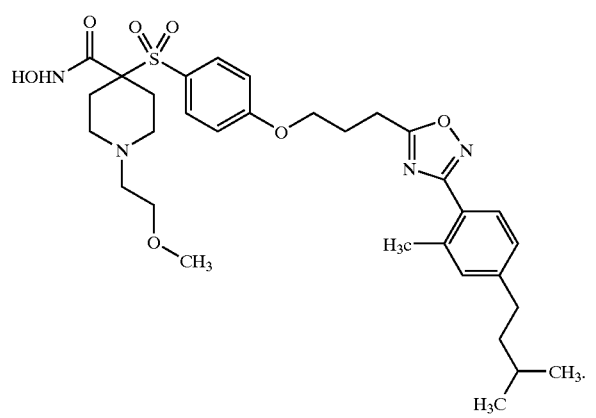
60. A compound or salt thereof according to claim 57, wherein the compound corresponds in structure to the following formula:
181-1
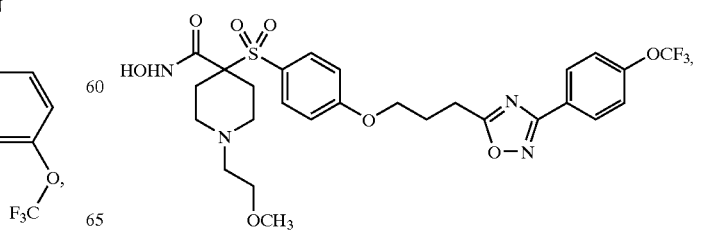

61. A compound or salt thereof according to claim 57, wherein the compound corresponds in structure to the following formula:

(182-1)

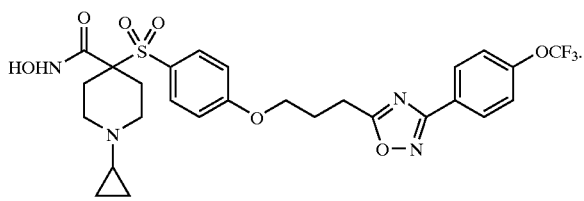

62. A compound or salt thereof according to claim 56, wherein $E^5$ is naphthalenyl optionally substituted with one or more substituents independently selected from the group consisting of halogen, —OH, —NO$_2$, —CN, C$_1$–C$_6$-alkyl, C$_2$–C$_6$-alkenyl, C$_2$–C$_6$-alkynyl, C$_1$–C$_6$-alkoxy, C$_1$–C$_6$-alkoxy-C$_1$–C$_6$-alkyl, —N(R$^6$)(R$^7$), —C(O)(R$^8$), —S—R$^6$, —S(O)$_2$—R$^6$, phenyl, phenyl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, halophenyl, and halogen-substituted phenyl-C$_1$–C$_6$-alkyl.

63. A compound or salt thereof according to claim 62, wherein the compound corresponds in structure to a formula selected from the group consisting of:

(184-1)

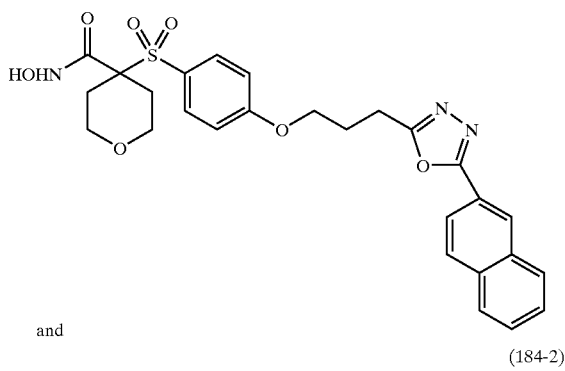

and (184-2)

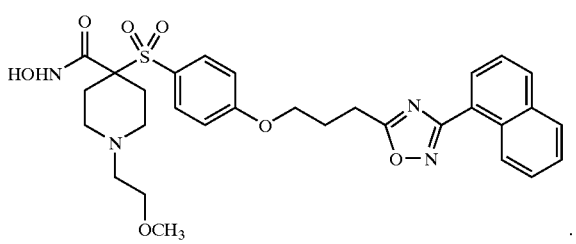

64. A compound or salt thereof according to claim 56, wherein $E^5$ is C$_5$–C$_6$-cycloalkyl optionally substituted with one or more substituents independently selected at from the group consisting of halogen, —OH, —NO$_2$, —CN, C$_1$–C$_6$-alkyl, C$_2$–C$_6$-alkenyl, C$_2$–C$_6$-alkynyl, C$_1$–C$_6$-alkoxy, C$_1$–C$_6$-alkoxy-C$_1$–C$_6$-alkyl, —N(R$^6$)(R$^7$), —C(O)(R$^8$), —S—R$^6$, —S(O)$_2$—R$^6$, phenyl, phenyl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, halophenyl, and halogen-substituted phenyl-C$_1$–C$_6$-alkyl.

65. A compound or salt thereof according to claim 64, wherein the compound corresponds in structure to a formula selected from the group consisting of:

(186-1)

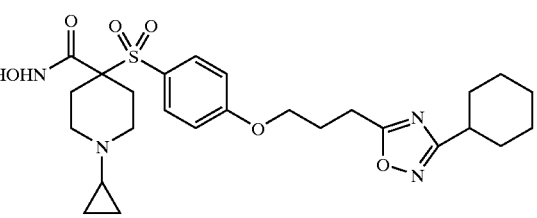

and (186-2)

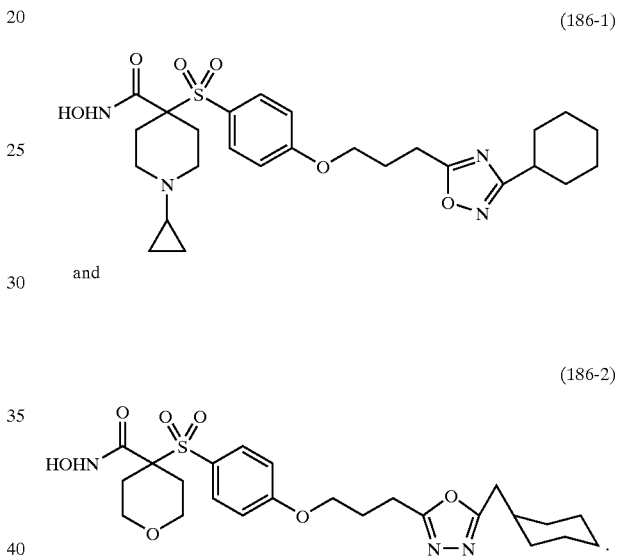

66. A compound or salt thereof according to claim 56, wherein $E^5$ is heterocyclyl optionally substituted with one or more substituents independently selected from the group consisting of halogen, —OH, —NO$_2$, —CN, keto, C$_1$–C$_6$-alkyl, C$_2$–C$_6$-alkenyl, C$_2$–C$_6$-alkynyl, C$_1$–C$_6$-alkoxy, C$_1$–C$_6$-alkoxy-C$_1$–C$_6$-alkyl, —N(R$^6$)(R$^7$), —C(O)(R$^8$), —S—R$^6$, —S(O)$_2$—R$^6$, phenyl, phenyl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, halophenyl, and halogen-substituted phenyl-C$_1$–C$_6$-alkyl.

67. A compound or salt thereof according to claim 66, wherein the compound corresponds in structure to a formula selected from the group consisting of:

(188-1)

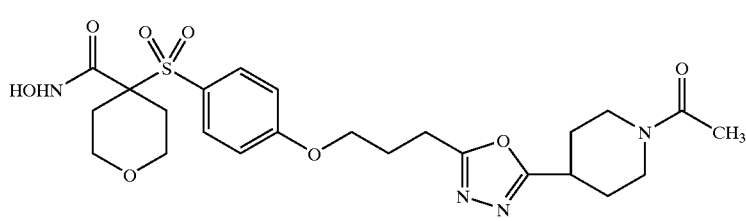

-continued

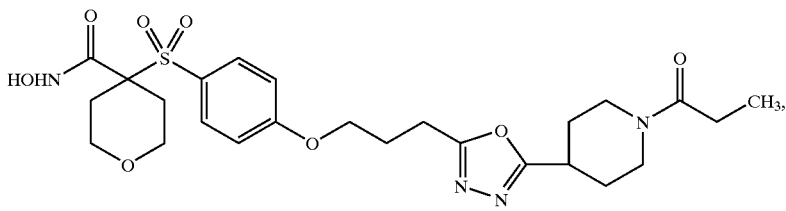
(188-2)

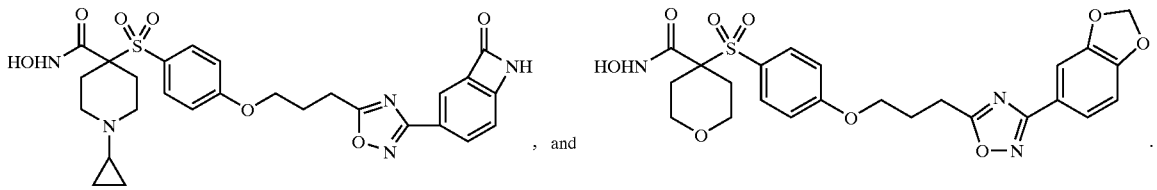
(188-4)

68. A compound or salt thereof according to claim 66, wherein the compound corresponds in structure to a formula selected from the group consisting of:

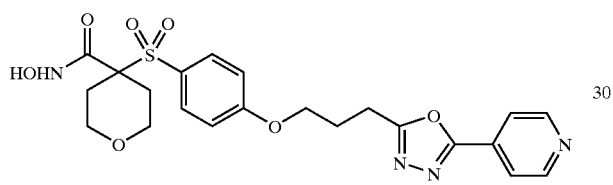
(189-1)

and

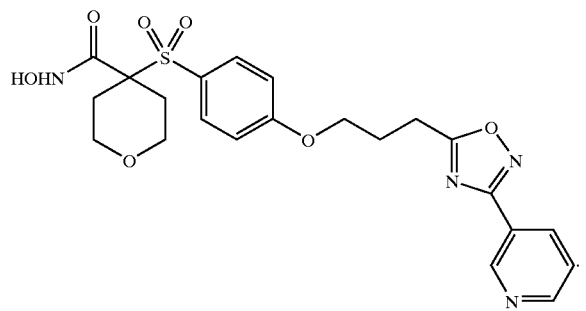
(189-2)

69. A compound or salt thereof according to claim 16, wherein $E^3$ contains at least 4 heteroatom ring members.

70. A compound or salt thereof according to claim 69, wherein $E^3$ is selected from the group consisting of:

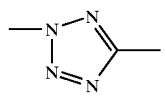
(191-1),

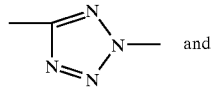
(191-2), and

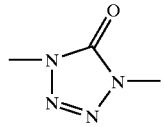
(191-3).

71. A compound or salt thereof according to claim 70, wherein $E^5$ is phenyl optionally substituted with one or more substituents independently selected from the group consisting of halogen, —OH, —NO$_2$, —CN, C$_1$–C$_6$-alkyl, C$_2$–C$_6$-alkenyl, C$_2$–C$_6$-alkynyl, C$_1$–C$_6$-alkoxy, C$_1$–C$_6$-alkoxy-C$_1$–C$_6$-alkyl, —N(R$^6$)(R$^7$), —C(O)(R$^8$), —S—R$^6$, —S(O)$_2$—R$^6$, phenyl, phenyl-C$_1$–C$_6$-alkyl, halo-C$_1$–C$_6$-alkyl, halo-C$_1$–C$_6$-alkoxy, halogen-substituted C$_1$–C$_6$-alkoxy-C$_1$–C$_6$-alkyl, halophenyl, and halogen-substituted phenyl-C$_1$–C$_6$-alkyl.

72. A compound or salt thereof according to claim 71, wherein the compound corresponds in structure to a formula selected from the group consisting of:

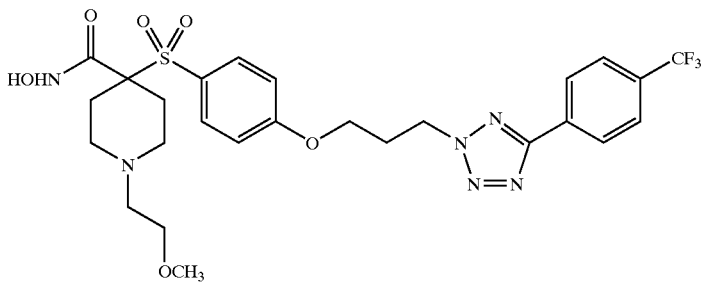
(193-1),

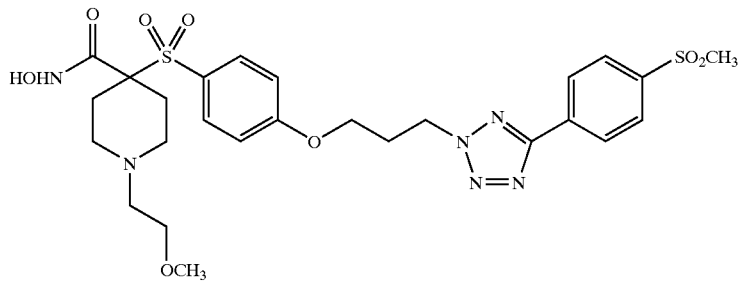
(193-2),
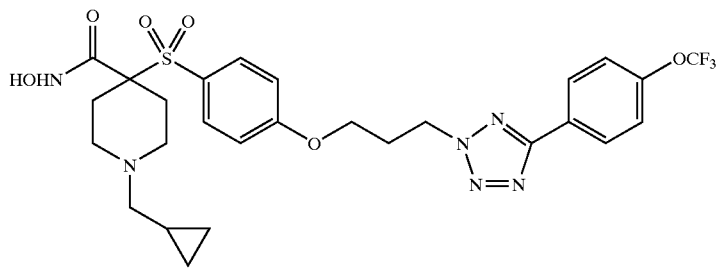
(193-3),
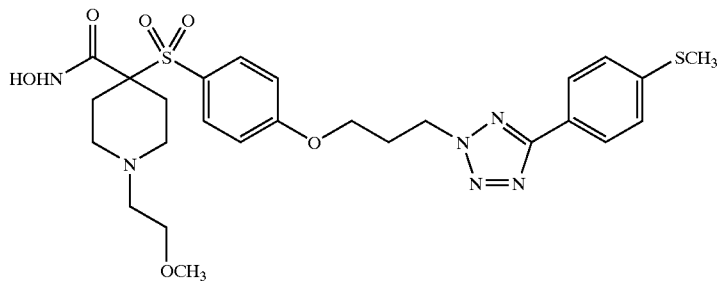
(193-4),
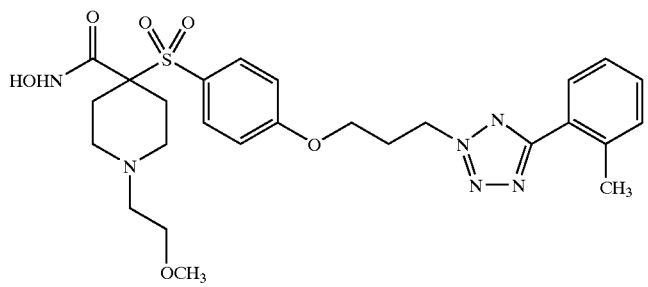
(193-5),
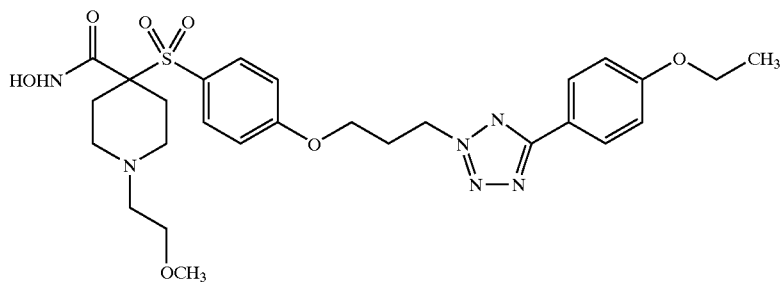
(193-6), -continued
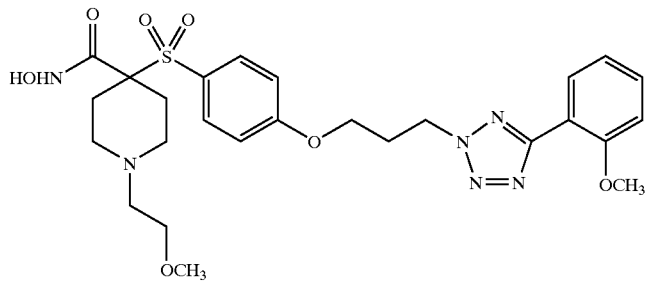
(193-7),
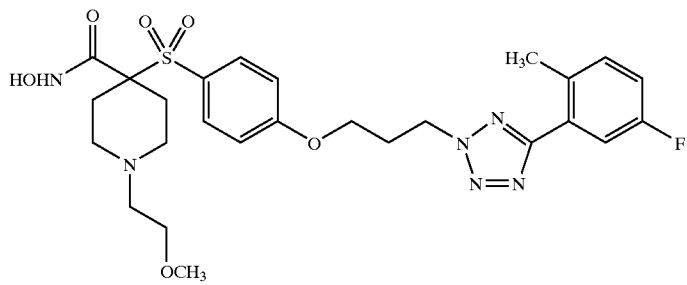
(193-8),
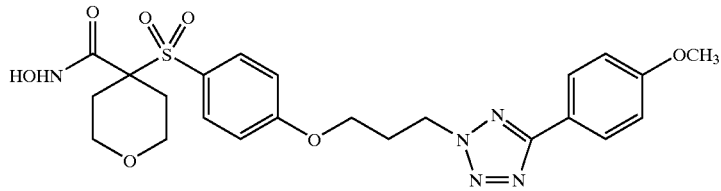
(193-9),
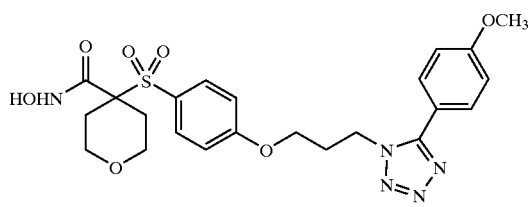
(193-10),
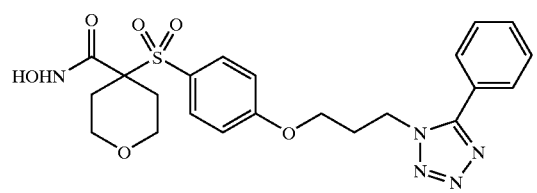
(193-11),
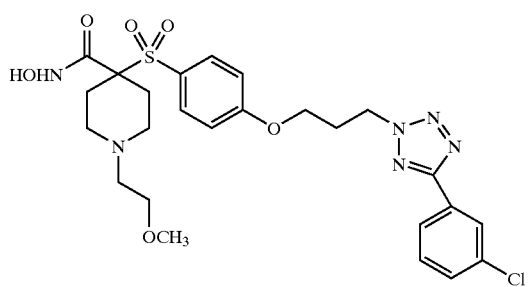
(193-12),
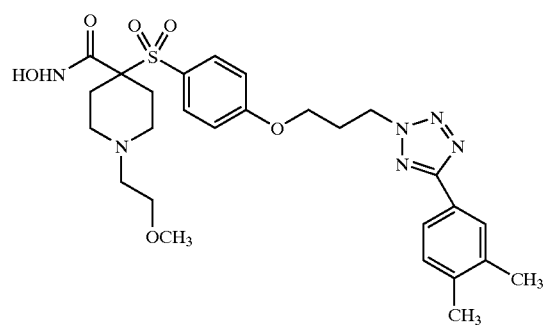
(193-13), (193-14),

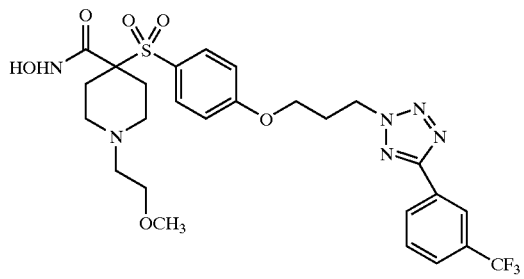

(193-15),

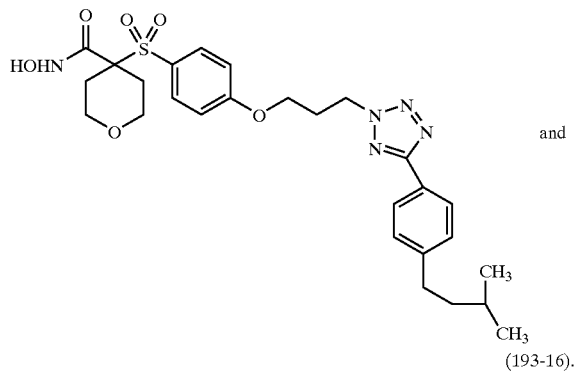

and

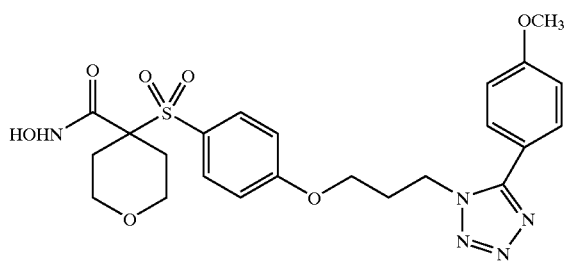

(193-16).

73. A compound or salt thereof according to claim 71, wherein the compound corresponds in structure to the following formula:

(194-1).

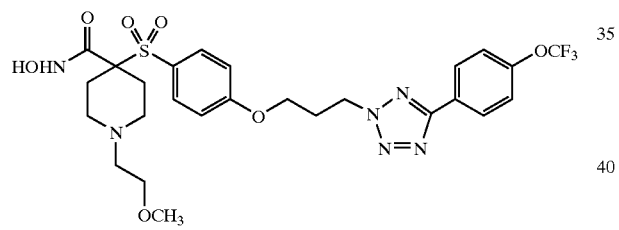

74. A compound or salt thereof according to claim 71, wherein the compound corresponds in structure to the following formula:

(195-1).

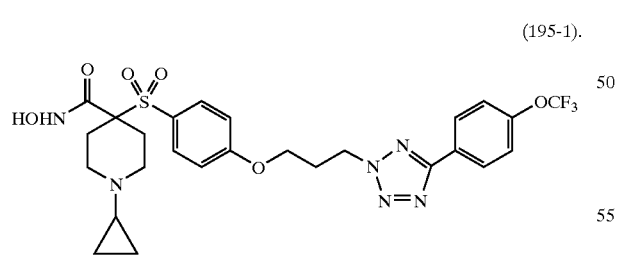

75. A compound or salt thereof according to claim 70, wherein $E^5$ is heterocyclyl optionally substituted with one or more substituents independently selected from the group consisting of halogen, —OH, —NO$_2$, —CN, keto, $C_1$–$C_6$-alkyl, $C_2$–$C_6$-alkenyl, $C_2$–$C_6$-alkynyl, $C_1$–$C_6$-alkoxy, $C_1$–$C_6$-alkoxy-$C_1$–$C_6$-alkyl, —N(R$^6$)(R$^7$), —C(O)(R$^8$), —S—R$^6$, —S(O)$_2$—R$^6$, phenyl, phenyl-$C_1$–$C_6$-alkyl, halo-$C_1$–$C_6$-alkyl, halo-$C_1$–$C_6$-alkoxy, halogen-substituted $C_1$–$C_6$-alkoxy-$C_1$–$C_6$-alkyl, halophenyl, and halogen-substituted phenyl-$C_1$–$C_6$-alkyl.

76. A compound or salt thereof according to claim 75, wherein the compound corresponds in structure to a formula selected from the group consisting of:

(197-1)

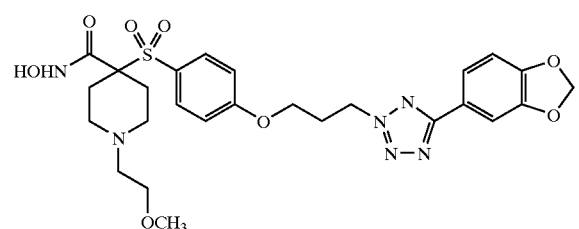

and (197.2).

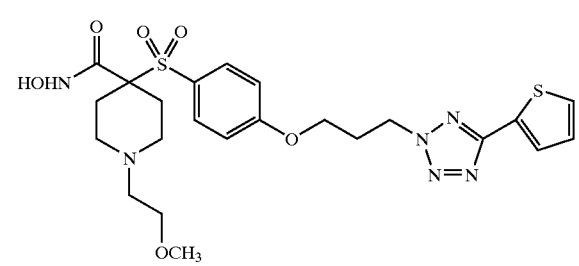

77. A method for preventing or treating a condition associated with pathological matrix metalloprotease activity in a mammal having the condition or predisposed to having the condition, wherein:

the method comprises administering a compound or a pharmaceutically acceptable salt thereof in a therapeutically-effective amount to the mammal; and the compound is selected from the group of compounds recited in claim 1.

78. A method according to claim 77, wherein the compound or salt inhibits the activity of one or more of MMP-2, MMP-9, and MMP-13, while exhibiting substantially less inhibitory activity against both MMP-1 and MMP-14.

79. A method according to claim 78, wherein the compound or salt inhibits the activity of MMP-13, while exhibiting substantially less inhibitory activity against both MMP-1 and MMP-14.

80. A method according to claim 79, wherein the pathological condition comprises arthritis or a cardiovascular condition.

81. A method according to claim 78, wherein the compound or salt inhibits the activity of both MMP-2 and MMP-9, while exhibiting substantially less inhibitory activity against both MMP-1 and MMP-14.

82. A method according to claim 81, wherein the pathological condition comprises cancer, an opthalmologic condition, or a cardiovascular condition.

83. A method for preventing or treating a pathological condition in a mammal having the pathological condition or predisposed to having the pathological condition, wherein:

the method comprises administering a compound or a pharmaceutically acceptable salt thereof in a therapeutically-effective amount to the mammal; and the compound is selected from the group of compounds recited in claim 1; and the pathological condition is selected from the group consisting of tissue destruction, a fibrotic disease, matrix weakening, defective injury repair, a cardiovascular disease, a pulmonary disease, a kidney disease, a liver disease, an ophthalmologic disease, and a central nervous system disease.

84. A method for preventing or treating a pathological condition in a mammal having the pathological condition or predisposed to having the pathological condition, wherein:

the method comprises administering a compound or a pharmaceutically acceptable salt thereof in a therapeutically-effective amount to the mammal; and the compound is selected from the group of compounds recited in claim 1; and the pathological condition is selected from the group consisting of osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermal ulceration, epidermolysis bullosa, aortic aneurysm, defective injury repair, an adhesion, scarring, congestive heart failure, post myocardial infarction, coronary thrombosis, emphysema, proteinuria, Alzheimer's disease, bone disease, and chronic obstructive pulmonary disease.

85. A method for preventing or treating a pathological condition associated with pathological TNF-α convertase activity in a mammal having the pathological condition or predisposed to having the condition, wherein:

the method comprises administering a compound or a pharmaceutically acceptable salt thereof in a therapeutically-effective amount to the mammal; and the compound is selected from the group of compounds recited in claim 1.

86. A method according to claim 85, wherein the pathological condition is selected from the group consisting of inflammation, a pulmonary disease, a cardiovascular disease, an autoimmune disease, graft rejection, a fibrotic disease, multiple sclerosis, cancer, an infectious disease, fever, psoriasis, hemorrhage, coagulation, radiation damage, acute-phase responses of shock and sepsis, anorexia, and cachexia.

87. A method for preventing or treating a pathological condition associated with pathological aggrecanase activity in a mammal having the pathological condition or predisposed to having the condition, wherein:

the method comprises administering a compound or a pharmaceutically acceptable salt thereof in a therapeutically-effective amount to the mammal; and the compound is selected from the group of compounds recited in claim 1.

88. A method according to claim 87, wherein the condition comprises an inflammation condition or cancer.

89. A method according to claim 87, wherein the method further comprises administering the compound or salt thereof to prevent or treat a condition associated with matrix metalloprotease activity.

90. A pharmaceutical composition comprising a therapeutically-effective amount of a compound or a pharmaceutically-acceptable salt thereof, wherein the compound is selected from the group of compounds recited in claim 1.

* * * * *